(12) United States Patent
Chaudhari et al.

(10) Patent No.: US 9,718,817 B2
(45) Date of Patent: Aug. 1, 2017

(54) ARYL AND HETEROARYL ETHER COMPOUNDS AS ROR GAMMA MODULATORS

(71) Applicant: Glenmark Pharmaceuticals S.A., La Chaux-de-Fonds (CH)

(72) Inventors: Sachin S. Chaudhari, Navi Mumbai (IN); Abraham Thomas, Navi Mumbai (IN); Ashok B. Kadam, Navi Mumbai (IN); Sachin V. Dhone, Usmanabad (IN); Bharat G. Adik, Ahmednagar (IN); Neelima Khairatkar-Joshi, Thane (IN); Daisy M. Shah, Mumbai (IN); Malini Bajpai, Lucknow (IN)

(73) Assignee: Glenmark Pharmaceuticals S.A. (CH)

( * ) Notice: Subject to any disclaimer, the term of this patent is extended or adjusted under 35 U.S.C. 154(b) by 0 days.

(21) Appl. No.: 14/778,892

(22) PCT Filed: Apr. 15, 2015

(86) PCT No.: PCT/IB2015/052745
§ 371 (c)(1),
(2) Date: Sep. 21, 2015

(87) PCT Pub. No.: WO2015/159233
PCT Pub. Date: Oct. 22, 2015

(65) Prior Publication Data
US 2017/0022195 A1 Jan. 26, 2017

(30) Foreign Application Priority Data

Apr. 16, 2014 (IN) .......................... 1376/MUM/2014
Aug. 22, 2014 (IN) .......................... 2696/MUM/2014
Feb. 20, 2015 (IN) ............................ 545/MUM/2015

(51) Int. Cl.
| | |
|---|---|
| C07D 213/75 | (2006.01) |
| C07D 209/12 | (2006.01) |
| C07D 309/10 | (2006.01) |
| C07D 211/44 | (2006.01) |
| C07D 235/12 | (2006.01) |
| C07D 401/12 | (2006.01) |
| C07D 405/12 | (2006.01) |
| C07D 471/04 | (2006.01) |
| C07D 271/06 | (2006.01) |
| C07D 309/12 | (2006.01) |
| C07D 211/46 | (2006.01) |
| C07D 213/61 | (2006.01) |
| C07D 305/08 | (2006.01) |
| C07C 317/44 | (2006.01) |
| C07C 317/24 | (2006.01) |
| C07D 211/52 | (2006.01) |

(52) U.S. Cl.
CPC .......... *C07D 471/04* (2013.01); *C07C 317/24* (2013.01); *C07C 317/44* (2013.01); *C07D 209/12* (2013.01); *C07D 211/44* (2013.01); *C07D 211/46* (2013.01); *C07D 211/52* (2013.01); *C07D 213/61* (2013.01); *C07D 213/75* (2013.01); *C07D 235/12* (2013.01); *C07D 271/06* (2013.01); *C07D 305/08* (2013.01); *C07D 309/10* (2013.01); *C07D 309/12* (2013.01); *C07D 401/12* (2013.01); *C07D 405/12* (2013.01); *C07C 2101/02* (2013.01); *C07C 2101/04* (2013.01); *C07C 2101/08* (2013.01); *C07C 2101/14* (2013.01)

(58) Field of Classification Search
CPC .. C07D 213/75; C07D 209/12; C07D 309/10; C07D 211/44; C07D 235/12; C07D 401/12; C07D 405/12; C07D 471/04; C07D 271/06
See application file for complete search history.

(56) References Cited

FOREIGN PATENT DOCUMENTS

| WO | WO-2012027965 A1 | 3/2012 |
|---|---|---|
| WO | WO-2012028100 A1 | 3/2012 |
| WO | WO-2012064744 A2 | 5/2012 |
| WO | WO-2012100732 A1 | 8/2012 |
| WO | WO-2012100734 A1 | 8/2012 |
| WO | WO-2012139775 A1 | 10/2012 |
| WO | WO-2013171729 A2 | 11/2013 |

OTHER PUBLICATIONS

Claremon et al., 2015, caplus an 2015:1284297.*

* cited by examiner

*Primary Examiner* — Sun Jae Yoo
(74) *Attorney, Agent, or Firm* — Blank Rome LLP

(57) ABSTRACT

The present disclosure is directed to compounds of formula (I) and pharmaceutically acceptable salts thereof, wherein Ring A, Ring B, R, $R^2$, $R^3$, n, and p are as defined herein, which are active as modulators of retinoid-related orphan receptor gamma t (RORγt). These compounds prevent, inhibit, or suppress the action of RORγt and are therefore useful in the treatment of RORγt mediated diseases, disorders, syndromes or conditions such as, e.g., pain, inflammation, COPD, asthma, rheumatoid arthritis, colitis, multiple sclerosis, psoriasis, neurodegenerative diseases and cancer.

(I)

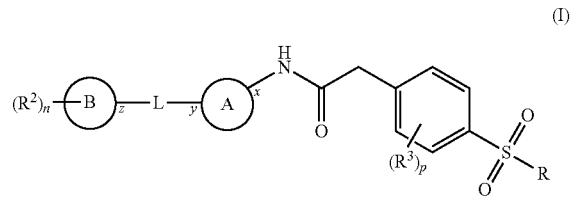

28 Claims, No Drawings

ARYL AND HETEROARYL ETHER COMPOUNDS AS ROR GAMMA MODULATORS

RELATED APPLICATIONS

This application is the U.S. national phase of International Application No. PCT/IB2015/052745, filed Apr. 15, 2015, which claims the benefit of Indian Provisional Application Nos. 1376/MUM/2014 filed on Apr. 16, 2014; 2696/MUM/2014 filed on Aug. 22, 2014; and 545/MUM/2015 filed on Feb. 20, 2015, each of which is hereby incorporated by reference in its entirety.

TECHNICAL FIELD

The present patent application is directed to aryl and heteroaryl ether compounds which may be useful as retinoid-related orphan receptor gamma t (RORγt) modulators.

BACKGROUND OF THE INVENTION

Retinoid-related orphan receptors (RORs) are transcription factors which belong to the steroid hormone nuclear receptor super family. The ROR family consists of three members, ROR alpha (RORα), ROR beta (RORβ) and ROR gamma (RORγ), also known as NR1F1, NR1F2 and NR1F3 respectively (and each encoded by a separate gene RORA, RORB and RORC, respectively). RORs contain four principal domains shared by the majority of nuclear receptors: an N-terminal A/B domain, a DNA-binding domain, a hinge domain, and a ligand binding domain. Each ROR gene generates several isoforms which differ only in their N-terminal A/B domain. Two isoforms of RORγ, RORγ1 and RORγt (also known as RORγ2) have been identified.

RORγt is a truncated form of RORγ, lacking the first N-terminal 21 amino acids and is exclusively expressed in cells of the lymphoid lineage and embryonic lymphoid tissue inducers (Sun et al., *Science*, 2000, 288, 2369-2372; Eberl et al., *Nat Immunol.*, 2004, 5: 64-73) in contrast to RORγ which is expressed in multiple tissues (heart, brain, kidney, lung, liver and muscle).

RORγt has been identified as a key regulator of Th17 cell differentiation. Th17 cells are a subset of T helper cells which produce IL-17 and other proinflammatory cytokines and have been shown to have key functions in several mouse autoimmune disease models including experimental autoimmune encephalomyelitis (EAE) and collagen-induced arthritis (CIA). In addition, Th17 cells have also been associated in the pathology of a variety of human inflammatory and autoimmune disorders including multiple sclerosis, rheumatoid arthritis, psoriasis, Crohn's disease and asthma (Jetten et al., *Nucl. Recept. Signal*, 2009, 7:e003; Manel et al., *Nat. Immunol.*, 2008, 9, 641-649). The pathogenesis of chronic autoimmune diseases including multiple sclerosis and rheumatoid arthritis arises from the break in tolerance towards self-antigens and the development of auto-aggressive effector T cells infiltrating the target tissues. Studies have shown that Th17 cells are one of the important drivers of the inflammatory process in tissue-specific auto-immunity (Steinman et al., *J. Exp. Med.*, 2008, 205: 1517-1522; Leung et al., *Cell. Mol. Immunol.*, 2010 7: 182-189). Th17 cells are activated during the disease process and are responsible for recruiting other inflammatory cells types, especially neutrophils, to mediate pathology in the target tissues (Korn et al., *Annu. Rev. Immunol.*, 2009, 27:485-517) and RORγt has been shown to play a critical role in the pathogenic responses of Th17 cells (Ivanov et al., *Cell*, 2006 126: 1121-1133). RORγt deficient mice have shown no Th17 cells and also resulted in amelioration of EAE. The genetic disruption of RORγ in a mouse colitis model also prevented colitis development (Buonocore et al., *Nature*, 2010, 464: 1371-1375). The role of RORγt in the pathogenesis of autoimmune or inflammatory diseases has been well documented in the literature. (Jetten et al., *Adv. Dev. Biol.*, 2006, 16:313-355; Meier et al. *Immunity*, 2007, 26:643-654; Aloisi et al., *Nat. Rev. Immunol.*, 2006, 6:205-217; Jager et al., *J. Immunol.*, 2009, 183:7169-7177; Serafmi et al., *Brain Pathol.*, 2004, 14: 164-174; Magliozzi et al., *Brain*, 2007, 130: 1089-1104; Barnes et al., *Nat. Rev. Immunol.*, 2008, 8: 183-192).

In addition, RORγt is also shown to play a crucial role in other non-Th17 cells, such as mast cells (Hueber et al., *J Immunol.*, 2010, 184: 3336-3340). RORγt expression and secretion of Th17-type of cytokines has also been reported in NK T-cells (Eberl et al., *Nat. Immunol.*, 2004, 5: 64-73) and gamma-delta T-cells (Sutton et al, *Nat. Immunol.*, 2009, 31: 331-341; Louten et al., *J Allergy Clin. Immunol.*, 2009, 123: 1004-1011), suggesting an important function for RORγt in these cells.

PCT Publication Nos. WO 2012/139775, WO 2012/027965, WO 2012/028100, WO 2012/100732, WO 2012/100734, WO2012/064744 and WO 2013/171729 disclose heterocyclic compounds which are modulators of retinoid-related orphan receptor gamma (RORγ) receptor activity.

In view of the above, a need exists for new therapeutic agents that modulate the activity of RORγt and thus will provide new methods for treating diseases or condition associated with the modulation of RORγt.

The present application is directed to compounds that are modulators of the RORγt receptor.

SUMMARY OF THE INVENTION

In one aspect, the present invention relates to compound of formula (I)

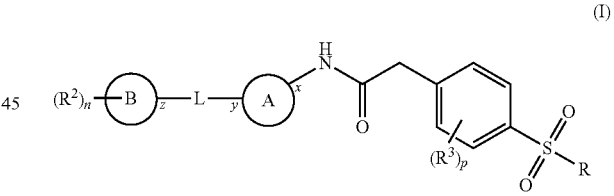

or a pharmaceutically acceptable salt thereof,
wherein,
Ring A is

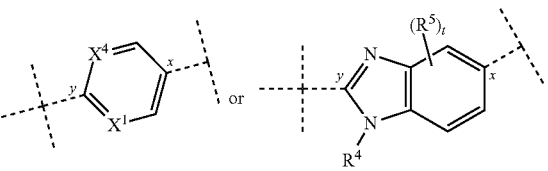

$X^1$ and $X^4$, which may be same or different, are each independently selected from N, CH and $CR^1$;

Ring B is selected from phenyl, pyridinyl, benzimidazolyl, indolyl, [1,2,4]triazolo[4,3-a]pyridinyl and [1,2,4]oxadiazolyl;

is selected from

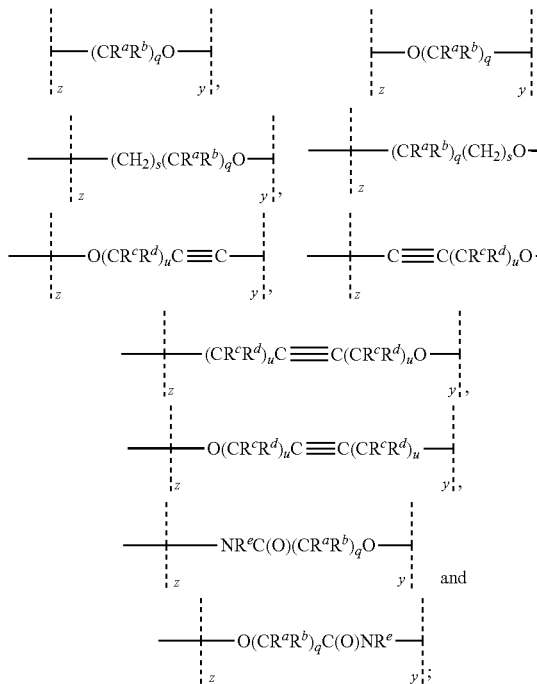

x, y and z represents point of attachment;

R is selected from $C_{1-8}$alkyl and halo$C_{1-8}$alkyl;

each occurrence of $R^1$ is independently selected from halogen, cyano, hydroxyl and $C_{1-8}$alkyl;

each occurrence of $R^2$ is independently selected from halogen, cyano, hydroxyl, $C_{1-8}$alkyl, $C_{1-8}$alkoxy, halo$C_{1-8}$alkyl, halo$C_{1-8}$alkoxy, hydroxy$C_{1-8}$alkyl, $C_{3-6}$cycloalkyl, $C_{3-6}$cycloalkyl$C_{1-8}$alkyl and 4-chloro-phenyl;

each occurrence of $R^3$ is independently selected from halogen, cyano, hydroxyl and $C_{1-4}$alkyl;

$R^4$ is independently selected from hydrogen, —(CH$_2$)$_2$N(CH$_3$)$_2$, $C_{1-8}$alkyl, halo$C_{1-8}$alkyl, $C_{3-6}$cycloalkyl and $C_{3-6}$cycloalkyl$C_{1-8}$alkyl;

each occurrence of $R^5$ is independently selected from halogen, cyano, hydroxyl and $C_{1-8}$alkyl;

$R^a$ and $R^b$, which may be same or different, are each independently selected from halogen, $C_{1-8}$alkyl, halo$C_{1-8}$alkyl and $C_{1-8}$alkoxy; or $R^a$ and $R^b$ together with the carbon atom to which they are attached, form a cyclopropyl, cyclobutyl, cyclopentyl, cyclohexyl, tetrahydro-2H-pyran-4-yl, oxetan-3-yl, N-methyl-piperidin-4-yl or piperidin-4-yl ring;

$R^c$ and $R^d$, which may be same or different, are each independently selected from hydrogen, $C_{1-8}$alkyl, halo$C_{1-8}$alkyl and $C_{1-8}$alkoxy; or $R^c$ and $R^d$ together with the carbon atom to which they are attached, form a $C_{3-6}$cycloalkyl ring;

$R^e$ is independently selected from $C_{1-8}$alkyl, halo$C_{1-8}$alkyl and $C_{3-6}$cycloalkyl;

'n' is 0, 1, 2 or 3;

'p' is 0, 1 or 2;

'q' is 1 or 2;

's' is 1, 2 or 3;

't' is 0, 1 or 2; and

'u' is 1 or 2.

The compounds of formula (I) may involve one or more embodiments. Embodiments of formula (I) include compounds of formula (II), (III) and (IV) as described hereinafter. It is to be understood that the embodiments below are illustrative of the present invention and are not intended to limit the claims to the specific embodiments exemplified. It is also to be understood that the embodiments defined herein may be used independently or in conjunction with any definition, any other embodiment defined herein. Thus the invention contemplates all possible combinations and permutations of the various independently described embodiments. For example, the invention provides compounds of formula (I) as defined above wherein ring B is phenyl, pyridin-2-yl, benzimidazol-2-yl, indol-1-yl, [1,2,4]triazolo[4,3-a]pyridin-3-yl or [1,2,4]oxadiazol-3-yl (according to an embodiment defined below), $R^2$ is —F, —Cl, —CH$_3$, —CH$_2$CH$_3$, —CH(CH$_3$)$_2$, —CF$_3$, —OCF$_2$, —OCF$_3$, —CN or 4-chlorophenyl (according to another embodiment defined below), 'n' is 1, 2 or 3 (according to yet another embodiment defined below) and 'p' is 0 (according to yet another embodiment defined below).

According to one embodiment, specifically provided are compounds of formula (I), in which $X^1$ is N, CH or CR$^1$.

According to another embodiment, specifically provided are compounds of formula (I), in which $X^4$ is CH or CR$^1$.

According to yet another embodiment, specifically provided are compounds of formula (I), in which $X^1$ and $X^4$ are CH.

According to yet another embodiment, specifically provided are compounds of formula (I), in which $X^1$ is N, CH or CR$^1$; and $X^4$ is CH or CR$^1$.

According to yet another embodiment, specifically provided are compounds of formula (I), in which $R^1$ is halogen (e.g. F, Cl, Br or I) or $C_{1-4}$alkyl (e.g. methyl or ethyl).

According to yet another embodiment, specifically provided are compounds of formula (I), in which $R^1$ is F.

According to yet another embodiment, specifically provided are compounds of formula (I), in which $X^1$ is N, CH or CR$^1$; and $X^4$ is CH or CR$^1$. In this embodiment, $R^1$ is halogen (e.g. F, Cl, Br or I).

According to yet another embodiment, specifically provided are compounds of formula (I), in which $X^1$ is N, CH or CF; and $X^4$ is CH or CF.

According to yet another embodiment, specifically provided are compounds of formula (I), in which $R^4$ is hydrogen, $C_{1-8}$alkyl (e.g. methyl, ethyl, propyl, isopropyl or isobutyl), halo$C_{1-8}$alkyl (e.g. 2-fluoroethyl), $C_{3-6}$cycloalkyl (e.g. cyclopropyl), $C_{3-6}$cycloalkyl$C_{1-8}$alkyl (e.g. cyclopropylmethyl) or —(CH$_2$)$_2$N(CH$_3$)$_2$.

According to yet another embodiment, specifically provided are compounds of formula (I), in which $R^4$ is —H, —CH$_3$, —CH$_2$CH$_3$, —CH$_2$CH$_2$CH$_3$, —CH(CH$_3$)$_2$, —CH$_2$CH(CH$_3$)$_2$, —CH$_2$CH$_2$F, —(CH$_2$)$_2$N(CH$_3$)$_2$, cyclopropyl or cyclopropylmethyl.

According to yet another embodiment, specifically provided are compounds of formula (I), in which ring A is

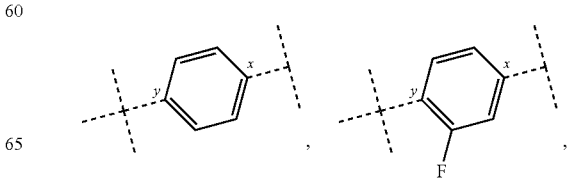

-continued

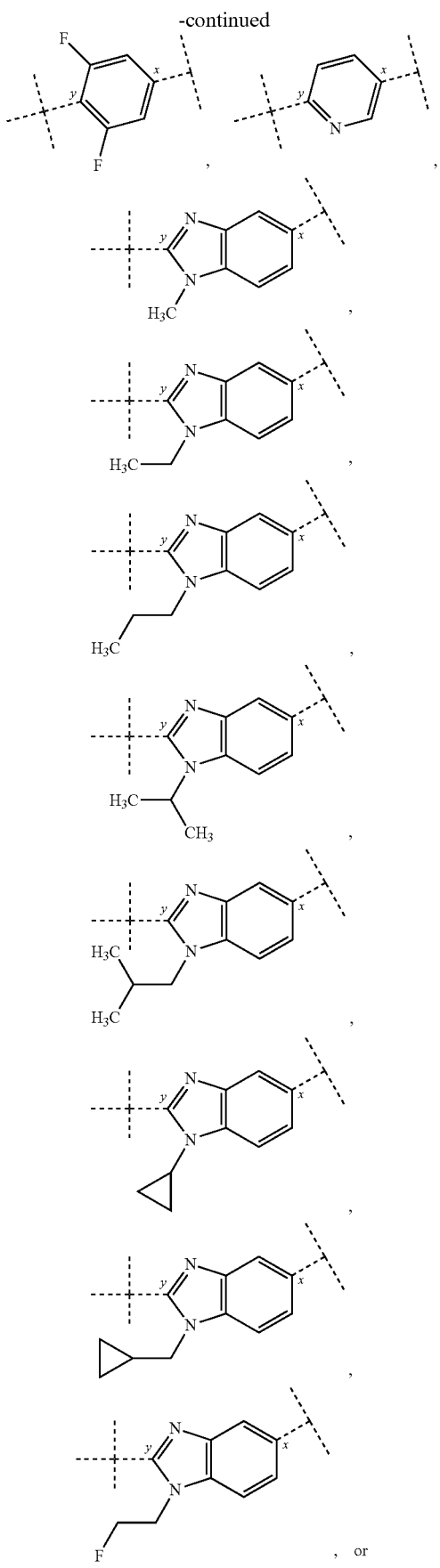

-continued

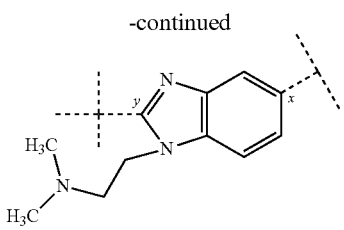

According to yet another embodiment, specifically provided are compounds of formula (I), in which ring B is phenyl, pyridin-2-yl, benzimidazol-2-yl, indol-1-yl, [1,2,4]triazolo[4,3-a]pyridin-3-yl or [1,2,4]oxadiazol-3-yl.

According to yet another embodiment, specifically provided are compounds of formula (I), in which $R^2$ is cyano, halogen (e.g. F, Cl, Br or I), $C_{1-8}$alkyl (e.g. methyl, ethyl or isopropyl), halo$C_{1-8}$alkyl (e.g. trifluoromethyl), halo$C_{1-8}$ alkoxy (e.g. difluoromethoxy or trifluoromethoxy) or 4-chloro-phenyl.

According to yet another embodiment, specifically provided are compounds of formula (I), in which $R^2$ is —F, —Cl, —CH$_3$, —CH$_2$CH$_3$, —CH(CH$_3$)$_2$, —CF$_3$, —OCF$_2$, —OCF$_3$, —CN or 4-chlorophenyl.

According to yet another embodiment, specifically provided are compounds of formula (I), in which $R^2$ is cyano, halogen (e.g. F, Cl, Br or I), $C_{1-8}$alkyl (e.g. methyl, ethyl or isopropyl), halo$C_{1-8}$alkyl (e.g. trifluoromethyl), halo$C_{1-8}$ alkoxy (e.g. difluoromethoxy or trifluoromethoxy) or 4-chloro-phenyl; and 'n' is 1, 2 or 3.

According to yet another embodiment, specifically provided are compounds of formula (I), in which $R^2$ is —F, —Cl, —CH$_3$, —CH$_2$CH$_3$, —CH(CH$_3$)$_2$, —CF$_3$, —OCF$_2$, —OCF$_3$, —CN or 4-chlorophenyl; and 'n' is 1, 2 or 3.

According to yet another embodiment, specifically provided are compounds of formula (I), in which 'n' is 1, 2 or 3.

According to yet another embodiment, specifically provided are compounds of formula (I), in which ring B is phenyl, pyridin-2-yl, benzimidazol-2-yl, indol-1-yl, [1,2,4]triazolo[4,3-a]pyridin-3-yl or [1,2,4]oxadiazol-3-yl; $R^2$ is —F, —Cl, —CH$_3$, —CH$_2$CH$_3$, —CH(CH$_3$)$_2$, —CF$_3$, —OCF$_2$, —OCF$_3$, —CN or 4-chlorophenyl; and 'n' is 1, 2 or 3.

According to yet another embodiment, specifically provided are compounds of formula (I), in which Ring

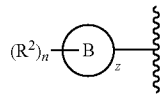

is 4-chlorophenyl, 4-fluorophenyl, 4-(trifluoromethyl)phenyl, 4-trifluoromethoxy-phenyl, 4-difluoromethoxy-phenyl, 4-cyano-phenyl, 2,4-dichlorophenyl, 3,4-dichlorophenyl, 3,5-dichlorophenyl, 2,4-difluorophenyl, 2,5-difluorophenyl, 3,4-difluorophenyl, 2-chloro-4-fluorophenyl, 3-chloro-4-fluorophenyl, 4-chloro-2-fluorophenyl, 4-chloro-3-fluorophenyl, 3-fluoro-4-trifluoromethyl-phenyl, 4-fluoro-3-trifluoromethyl-phenyl, 2,3,4-trifluorophenyl, 3,4,5-trifluorophenyl, 2,4,6-trifluorophenyl, 2,4,5-trifluorophenyl, 4-chloro-2,6-difluoro-phenyl, 5-chloro-pyridin-2-yl, 3,5-dichloro-pyridin-2-yl, 1-ethyl-6-fluoro-1H-benzimidazol-2-yl, 1-ethyl-5-fluoro-1H-benzoimidazol-2-yl, 5-chloro-1-ethyl-1H-benzimidazol-2-yl, 5-chloro-1-methyl-1H-benzimidazol-2-yl, 6-chloro-1-ethyl-1H-benzimidazol-2-yl, 6-chloro-1-methyl-1H-benzoimidazol-2-yl, 7-chloro-1-ethyl-1H-benzimidazol-2-yl, 5-fluoro-1-isopropyl-1H-benzoimidazol-2-yl, 6-chloro-[1,2,4]triazolo[4,3-a]pyridin-3-yl, 5-chloro-1H-indol-1-yl, 5-chloro-1-ethyl-1H-indol-2-yl, 5-fluoro-2-methyl-1H-indol-1-yl, or 4-chloro-phenyl-[1,2,4]oxadiazol-3-yl.

According to yet another embodiment, specifically provided are compounds of formula (I), in which $R^a$ and $R^b$ are independently selected from halogen (e.g. F, Cl, Br or I) and $C_{1-8}$alkyl (e.g. methyl or ethyl); or $R^a$ and $R^b$ together with the carbon atom to which they are attached, form a cyclopropyl, cyclobutyl, cyclopentyl, cyclohexyl, tetrahydro-2H-pyran-4-yl, oxetan-3-yl, N-methyl-piperidin-4-yl or piperidin-4-yl ring.

According to yet another embodiment, specifically provided are compounds of formula (I), in which $R^a$ and $R^b$ are independently selected from fluoro, methyl and ethyl; or $R^a$ and $R^b$ together with the carbon atom to which they are attached, form a cyclopropyl, cyclobutyl, cyclopentyl, cyclohexyl, tetrahydro-2H-pyran-4-yl, oxetan-3-yl, N-methyl-piperidin-4-yl or piperidin-4-yl ring.

According to yet another embodiment, specifically provided are compounds of formula (I), in which 's' is 1.

According to yet another embodiment, specifically provided are compounds of formula (I), in which 'q' is 1.

According to yet another embodiment, specifically provided are compounds of formula (I), in which $R^c$ and $R^d$ are independently selected from hydrogen and $C_{1-8}$alkyl (e.g. methyl or ethyl).

According to yet another embodiment, specifically provided are compounds of formula (I), in which $R^c$ and $R^d$ are independently selected from hydrogen and methyl.

According to yet another embodiment, specifically provided are compounds of formula (I), in which $R^e$ is selected from hydrogen and $C_{1-8}$alkyl (e.g. methyl or ethyl).

According to yet another embodiment, specifically provided are compounds of formula (I), in which $R^e$ is selected from methyl and ethyl.

According to yet another embodiment, specifically provided are compounds of formula (I), in which 'u' is 1.

According to yet another embodiment, specifically provided are compounds of formula (I), in which

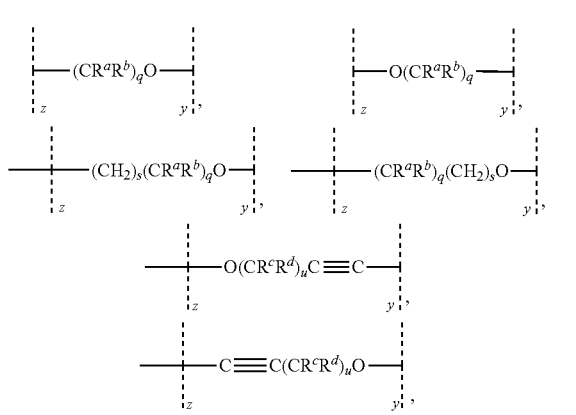

is

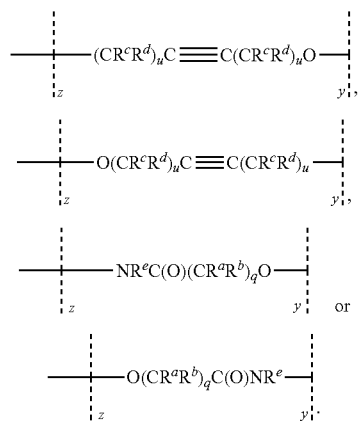

In this embodiment, $R^a$ and $R^b$ are independently selected from fluoro, methyl and ethyl; or $R^a$ and $R^b$ together with the carbon atom to which they are attached, form a cyclopropyl, cyclobutyl, cyclopentyl, cyclohexyl, tetrahydro-2H-pyran-4-yl, oxetan-3-yl, N-methyl-piperidin-4-yl or piperidin-4-yl ring; $R^c$ and $R^d$ are independently selected from hydrogen and methyl; $R^e$ is selected from methyl and ethyl; 's' is 1; 'q' is 1; and 'u' is 1.

According to yet another embodiment, specifically provided are compounds of formula (I), in which

is

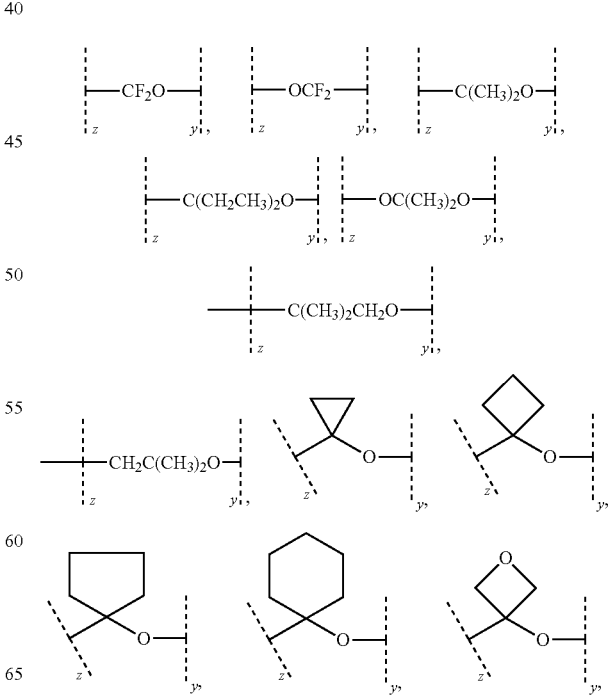

-continued

[Chemical structures: tetrahydropyran-4-yl, piperidin-4-yl (NH), and N-methyl-piperidin-4-yl ether linkers]

[Chemical structures: —OCH₂C≡C—, —OC(CH₃)₂C≡C—, —C≡CCH₂O—, —C≡C(CH₃)₂O—]

[Chemical structures: —N(CH₃)—C(O)—C(CH₃)₂O—, —N(CH₂CH₃)—C(O)—C(CH₃)₂O— or —OC(CH₃)₂—C(O)—N(CH₂CH₃)—]

According to yet another embodiment, specifically provided are compounds of formula (I), in which R is $C_{1-8}$alkyl (e.g. methyl or ethyl).

According to yet another embodiment, specifically provided are compounds of formula (I), in which R is —$C_2H_5$.

According to yet another embodiment, specifically provided are compounds of formula (I), in which 'p' is 0.

According to yet another embodiment, specifically provided are compounds of formula (I), in which 't' is 0.

According to yet another embodiment, specifically provided are compounds of formula (I), in which Ring A is

[Chemical structures: pyridine-type ring with $X^1$, $X^4$; and benzimidazole with $(R^5)_t$ and $R^4$]

$X^1$ is N, CH or $CR^1$;
$X^4$ is CH or $CR^1$;
ring B is phenyl, pyridin-2-yl, benzimidazol-2-yl, indol-1-yl, [1,2,4]triazolo[4,3-a]pyridin-3-yl or [1,2,4]oxadiazol-3-yl;
$R^1$ is —F;
$R^2$ is —F, —Cl, —$CH_3$, —$CH_2CH_3$, —$CH(CH_3)_2$, —$CF_3$, —$OCF_2$, —$OCF_3$, —CN or 4-chlorophenyl;
$R^4$ is —H, —$CH_3$, —$CH_2CH_3$, —$CH_2CH_2CH_3$, —$CH(CH_3)_2$, —$CH_2CH(CH_3)_2$, —$(CH_2)_2N(CH_3)_2$, —$CH_2CH_2F$, cyclopropyl or cyclopropylmethyl;

[Linker L between z and y]

is

[Chemical linkers: —(CRᵃRᵇ)_qO—, —O(CRᵃRᵇ)_q—, —(CH₂)_s(CRᵃRᵇ)_qO—, —(CRᵃRᵇ)_q(CH₂)_s O—]

[—O(CRᶜRᵈ)_uC≡C—, —C≡C(CRᶜRᵈ)_uO—]

[—(CRᶜRᵈ)_uC≡C(CRᶜRᵈ)_uO—]

[—O(CRᶜRᵈ)_uC≡C(CRᶜRᵈ)_u—]

[—NRᵉC(O)(CRᵃRᵇ)_qO— or —O(CRᵃRᵇ)_qC(O)NRᵉ—]

$R^a$ and $R^b$ are independently selected from fluoro, methyl and ethyl; or $R^a$ and $R^b$ together with the carbon atom to which they are attached, form a cyclopropyl, cyclobutyl, cyclopentyl, cyclohexyl, tetrahydro-2H-pyran-4-yl, oxetan-3-yl, N-methyl-piperidin-4-yl or piperidin-4-yl ring;
$R^c$ and $R^d$ are independently selected from hydrogen and methyl;
$R^e$ is selected from methyl and ethyl;
's' is 1;
'q' is 1;
'u' is 1;
'n' is 1, 2 or 3;
'p' is 0;
't' is 0; and
R is $C_2H_5$.

According to yet another embodiment, specifically provided are compounds of formula (I), in which ring A is

[Chemical structures: para-substituted phenyl and fluoro-substituted phenyl]

-continued

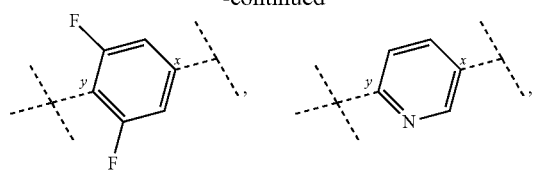

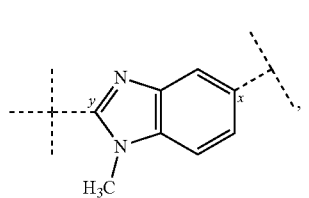

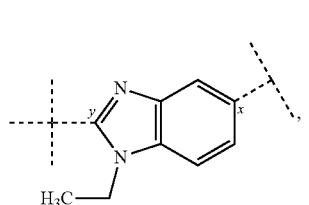

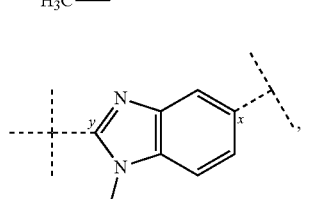

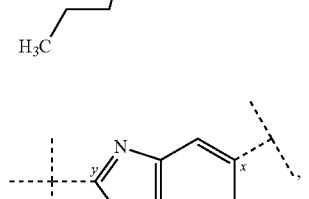

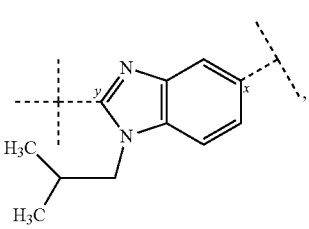

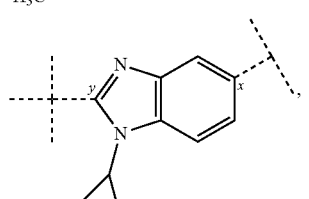

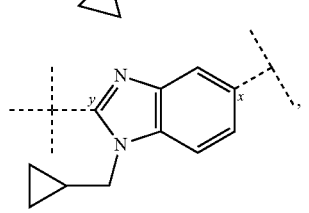

-continued

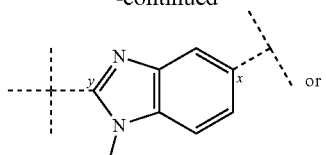 or

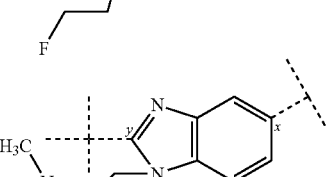

Ring

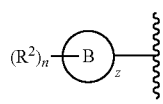

is 4-chlorophenyl, 4-fluorophenyl, 4-(trifluoromethyl)phenyl, 4-trifluoromethoxy-phenyl, 4-difluoromethoxy-phenyl, 4-cyano-phenyl, 2,4-dichlorophenyl, 3,4-dichlorophenyl, 3,5-dichlorophenyl, 2,4-difluorophenyl, 2,5-difluorophenyl, 3,4-difluorophenyl, 2-chloro-4-fluorophenyl, 3-chloro-4-fluorophenyl, 4-chloro-2-fluorophenyl, 4-chloro-3-fluorophenyl, 3-fluoro-4-trifluoromethyl-phenyl, 4-fluoro-3-trifluoromethyl-phenyl, 2,3,4-trifluorophenyl, 3,4,5-trifluorophenyl, 2,4,6-trifluorophenyl, 2,4,5-trifluorophenyl, 4-chloro-2,6-difluoro-phenyl, 5-chloro-pyridin-2-yl, 3,5-dichloro-pyridin-2-yl, 1-ethyl-6-fluoro-1H-benzimidazol-2-yl, 1-ethyl-5-fluoro-1H-benzoimidazol-2-yl, 5-chloro-1-ethyl-1H-benzimidazol-2-yl, 5-chloro-1-methyl-1H-benzimidazol-2-yl, 6-chloro-1-ethyl-1H-benzimidazol-2-yl, 6-chloro-1-methyl-1H-benzoimidazol-2-yl, 7-chloro-1-ethyl-1H-benzimidazol-2-yl, 5-fluoro-1-isopropyl-1H-benzoimidazol-2-yl, 6-chloro-[1,2,4]triazolo[4,3-a]pyridin-3-yl, 5-chloro-1H-indol-1-yl, 5-chloro-1-ethyl-1H-indol-2-yl, 5-fluoro-2-methyl-1H-indol-1-yl, or 4-chloro-phenyl-[1,2,4]oxadiazol-3-yl;

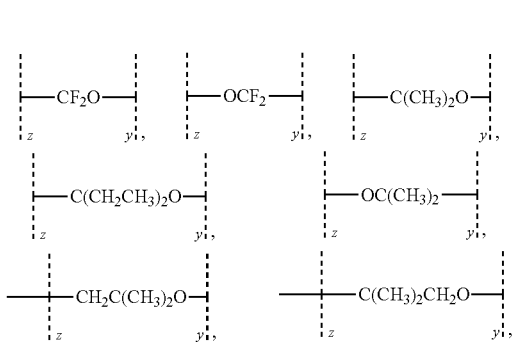

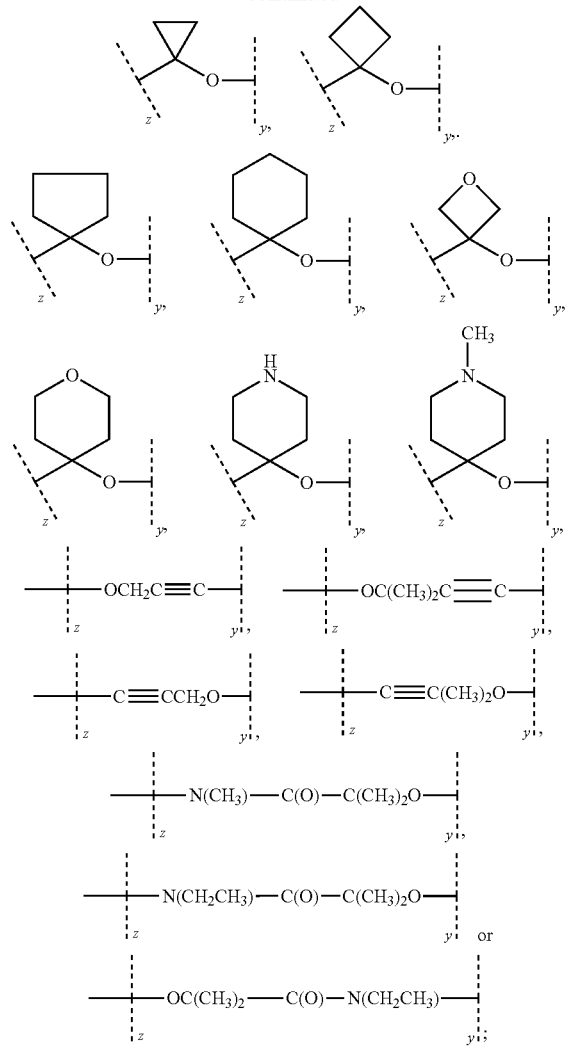

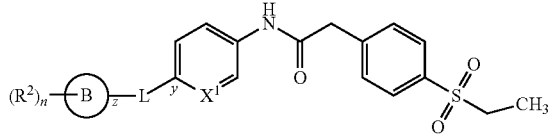

or a pharmaceutically acceptable salt thereof,
wherein, $X^1$ is selected from N, CH and $CR^1$;

Ring B is selected from phenyl, pyridinyl, benzimidazolyl, indolyl, [1,2,4]triazolo[4,3-a]pyridinyl and [1,2,4]oxadiazolyl;

is selected from

[structures showing various linker groups L including:
—(CR$^a$R$^b$)$_q$O—, —O(CR$^a$R$^b$)$_q$—,
—(CH$_2$)$_s$(CR$^a$R$^b$)$_q$O—, —(CR$^a$R$^b$)$_q$(CH$_2$)$_s$O—,
—O(CR$^c$R$^d$)$_u$C≡C—, —C≡C(CR$^c$R$^d$)$_u$O—,
—(CR$^c$R$^d$)$_u$C≡C(CR$^c$R$^d$)$_u$O—,
—O(CR$^c$R$^d$)$_u$C≡C(CR$^c$R$^d$)$_u$—,
—NR$^e$C(O)(CR$^a$R$^b$)$_q$O—, and
—O(CR$^a$R$^b$)$_q$C(O)NR$^e$—];

y and z represents point of attachment;

$R^1$ is independently selected from halogen, cyano, hydroxyl and $C_{1-8}$alkyl;

each occurrence of $R^2$ is independently selected from halogen, cyano, hydroxyl, $C_{1-8}$alkyl, $C_{1-8}$alkoxy, halo$C_{1-8}$alkyl, halo$C_{1-8}$alkoxy, hydroxy$C_{1-8}$alkyl, $C_{3-6}$cycloalkyl, $C_{3-6}$cycloalkyl$C_{1-8}$alkyl and 4-chloro-phenyl;

$R^a$ and $R^b$, which may be same or different, are each independently selected from halogen, $C_{1-8}$alkyl, halo$C_{1-8}$alkyl and $C_{1-8}$alkoxy; or $R^a$ and $R^b$ together with the carbon atom to which they are attached, form a cyclopropyl, cyclobutyl, cyclopentyl, cyclohexyl, tetrahydro-2H-pyran-4-yl, oxetan-3-yl, N-methyl-piperidin-4-yl or piperidin-4-yl ring;

'p' is 0; and
R is $C_2H_5$.

According to an embodiment, specifically provided are compounds of formula (I) with an $IC_{50}$ value of less than 500 nM, preferably less than 100 nM, more preferably less than 50 nM, with respect to RORγt activity.

Further embodiments relating to groups L, R, $R^2$, $R^3$, p, n, ring A, ring B (and groups defined therein) are described hereinafter in relation to the compounds of formula (II), Formula (III) or Formula (IV). It is to be understood that these embodiments are not limited to use in conjunction with formula (II), Formula (III), or Formula (IV) but apply independently and individually to the compounds of formula (I). For example, in an embodiment described hereinafter, the invention specifically provides compounds of formula (II), Formula (III) or Formula (IV) in which 'n' is 1, 2 or 3 and consequently there is also provided a compound of the formula (I) in which 'n' is 1, 2 or 3.

The invention also provides a compound of formula (II), which is an embodiment of a compound of formula (I).

Accordingly the invention provides a compound of formula (II)

$R^c$ and $R^d$, which may be same or different, are each independently selected from hydrogen, $C_{1-8}$alkyl, halo$C_{1-8}$alkyl and $C_{1-8}$alkoxy; or $R^c$ and $R^d$ together with the carbon atom to which they are attached, form a $C_{3-6}$cycloalkyl ring;

$R^e$ is independently selected from $C_{1-8}$alkyl, halo$C_{1-8}$alkyl and $C_{3-6}$cycloalkyl;

'n' is 0, 1, 2 or 3;

'q' is 1 or 2;

's' is 1, 2 or 3; and

'u' is 1.

The compounds of formula (II) may involve one or more embodiments. It is to be understood that the embodiments below are illustrative of the present invention and are not intended to limit the claims to the specific embodiments exemplified. It is also to be understood that the embodiments defined herein may be used independently or in conjunction with any definition, any other embodiment defined herein. Thus the invention contemplates all possible combinations and permutations of the various independently described embodiments. For example, the invention provides compounds of formula (II) as defined above wherein ring B is phenyl, pyridin-2-yl, benzimidazol-2-yl, indol-1-yl, [1,2,4]triazolo[4,3-a]pyridin-3-yl or [1,2,4]oxadiazol-3-yl (according to an embodiment defined below), $R^2$ is —F, —Cl, —CH$_3$, —CH$_2$CH$_3$, —CH(CH$_3$)$_2$, —CF$_3$, —OCF$_2$, —OCF$_3$, —CN or 4-chlorophenyl (according to another embodiment defined below) and 'n' is 1, 2 or 3 (according to yet another embodiment defined below).

According to one embodiment, specifically provided are compounds of formula (II), in which $X^1$ is N, CH or CR$^1$. In this embodiment R$^1$ is halogen (e.g. F, Cl, Br or I) or $C_{1-8}$alkyl (e.g. methyl or ethyl).

According to another embodiment, specifically provided are compounds of formula (II), in which R$^1$ is halogen (e.g. F, Cl, Br or I) or $C_{1-8}$alkyl (e.g. methyl or ethyl).

According to yet another embodiment, specifically provided are compounds of formula (II), in which R$^1$ is F.

According to yet another embodiment, specifically provided are compounds of formula (II), in which $X^1$ is N, CH or CF.

According to yet another embodiment, specifically provided are compounds of formula (II), in which ring B is phenyl, pyridin-2-yl, benzimidazol-2-yl, indol-1-yl, [1,2,4]triazolo[4,3-a]pyridin-3-yl or [1,2,4]oxadiazol-3-yl.

According to yet another embodiment, specifically provided are compounds of formula (II), in which R$^2$ is cyano, halogen (e.g. F, Cl, Br or I), $C_{1-8}$alkyl (e.g. methyl, ethyl or isopropyl), halo$C_{1-8}$alkyl (e.g. trifluoromethyl), halo$C_{1-8}$alkoxy (e.g. difluoromethoxy or trifluoromethoxy) or 4-chloro-phenyl.

According to yet another embodiment, specifically provided are compounds of formula (II), in which R$^2$ is —F, —Cl, —CH$_3$, —CH$_2$CH$_3$, —CH(CH$_3$)$_2$, —CF$_3$, —OCF$_2$, —OCF$_3$, —CN or 4-chlorophenyl.

According to yet another embodiment, specifically provided are compounds of formula (II), in which R$^2$ is cyano, halogen (e.g. F, Cl, Br or I), $C_{1-8}$alkyl (e.g. methyl, ethyl or isopropyl), halo$C_{1-8}$alkyl (e.g. trifluoromethyl), halo$C_{1-8}$alkoxy (e.g. difluoromethoxy or trifluoromethoxy) or 4-chloro-phenyl; and 'n' is 1, 2 or 3.

According to yet another embodiment, specifically provided are compounds of formula (II), in which R$^2$ is —F, —Cl, —CH$_3$, —CH$_2$CH$_3$, —CH(CH$_3$)$_2$, —CF$_3$, —OCF$_2$, —OCF$_3$, —CN or 4-chlorophenyl; and 'n' is 1, 2 or 3.

According to yet another embodiment, specifically provided are compounds of formula (II), in which 'n' is 1, 2 or 3.

According to yet another embodiment, specifically provided are compounds of formula (II), in which ring B is phenyl, pyridin-2-yl, benzimidazol-2-yl, indol-1-yl, [1,2,4]triazolo[4,3-a]pyridin-3-yl or [1,2,4]oxadiazol-3-yl; R$^2$ is —F, —Cl, —CH$_3$, —CH$_2$CH$_3$, —CH(CH$_3$)$_2$, —CF$_3$, —OCF$_2$, —OCF$_3$, —CN or 4-chlorophenyl; and 'n' is 1, 2 or 3.

According to yet another embodiment, specifically provided are compounds of formula (II), in which Ring

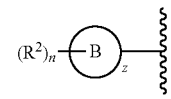

is 4-chlorophenyl, 4-fluorophenyl, 4-(trifluoromethyl)phenyl, 4-trifluoromethoxy-phenyl, 4-difluoromethoxy-phenyl, 4-cyano-phenyl, 2,4-dichlorophenyl, 3,4-dichlorophenyl, 3,5-dichlorophenyl, 2,4-difluorophenyl, 2,5-difluorophenyl, 3,4-difluorophenyl, 2-chloro-4-fluorophenyl, 3-chloro-4-fluorophenyl, 4-chloro-2-fluorophenyl, 4-chloro-3-fluorophenyl, 3-fluoro-4-trifluoromethyl-phenyl, 4-fluoro-3-trifluoromethyl-phenyl, 2,3,4-trifluorophenyl, 3,4,5-trifluorophenyl, 2,4,6-trifluorophenyl, 2,4,5-trifluorophenyl, 4-chloro-2,6-difluoro-phenyl, 5-chloro-pyridin-2-yl, 3,5-dichloro-pyridin-2-yl, 1-ethyl-6-fluoro-1H-benzimidazol-2-yl, 1-ethyl-5-fluoro-1H-benzoimidazol-2-yl, 5-chloro-1-ethyl-1H-benzimidazol-2-yl, 5-chloro-1-methyl-1H-benzimidazol-2-yl, 6-chloro-1-ethyl-1H-benzimidazol-2-yl, 6-chloro-1-methyl-1H-benzoimidazol-2-yl, 7-chloro-1-ethyl-1H-benzimidazol-2-yl, 5-fluoro-1-isopropyl-1H-benzoimidazol-2-yl, 6-chloro-[1,2,4]triazolo[4,3-a]pyridin-3-yl, 5-chloro-1H-indol-1-yl, 5-chloro-1-ethyl-1H-indol-2-yl, 5-fluoro-2-methyl-1H-indol-1-yl, or 4-chloro-phenyl-[1,2,4]oxadiazol-3-yl.

According to yet another embodiment, specifically provided are compounds of formula (II), in which R$^a$ and R$^b$ are independently selected from halogen (e.g. F, Cl, Br or I) and $C_{1-8}$alkyl (e.g. methyl or ethyl); or R$^a$ and R$^b$ together with the carbon atom to which they are attached, form a cyclopropyl, cyclobutyl, cyclopentyl, cyclohexyl, tetrahydro-2H-pyran-4-yl, oxetan-3-yl, N-methyl-piperidin-4-yl or piperidin-4-yl ring.

According to yet another embodiment, specifically provided are compounds of formula (II), in which R$^a$ and R$^b$ are independently selected from fluoro, methyl and ethyl; or R$^a$ and R$^b$ together with the carbon atom to which they are attached, form a cyclopropyl, cyclobutyl, cyclopentyl, cyclohexyl, tetrahydro-2H-pyran-4-yl, oxetan-3-yl, N-methyl-piperidin-4-yl or piperidin-4-yl ring.

According to yet another embodiment, specifically provided are compounds of formula (II), in which 's' is 1.

According to yet another embodiment, specifically provided are compounds of formula (II), in which 'q' is 1.

According to yet another embodiment, specifically provided are compounds of formula (II), in which R$^c$ and R$^d$ are independently selected from hydrogen and $C_{1-8}$alkyl (e.g. methyl or ethyl).

According to yet another embodiment, specifically provided are compounds of formula (II), in which R$^c$ and R$^d$ are independently selected from hydrogen and methyl.

According to yet another embodiment, specifically provided are compounds of formula (II), in which 'u' is 1.

According to yet another embodiment, specifically provided are compounds of formula (II), in which R$^e$ is selected from hydrogen and $C_{1-8}$alkyl (e.g. methyl or ethyl).

According to yet another embodiment, specifically provided are compounds of formula (II), in which $R^e$ is selected from methyl and ethyl.

According to yet another embodiment, specifically provided are compounds of formula (II), in which

is

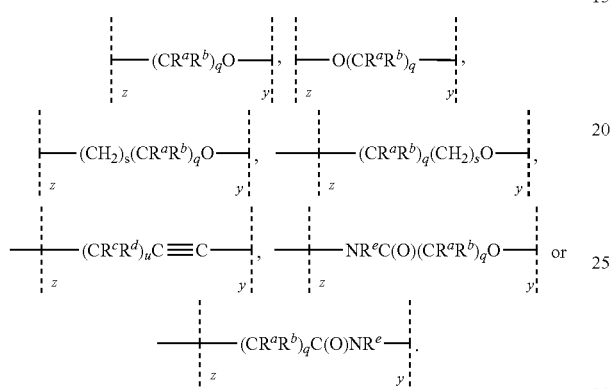

In this embodiment, $R^a$ and $R^b$ are independently selected from fluoro, methyl and ethyl; or $R^a$ and $R^b$ together with the carbon atom to which they are attached, form a cyclopropyl, cyclobutyl, tetrahydro-2H-pyran-4-yl, oxetan-3-yl, N-methyl-piperidin-4-yl or piperidin-4-yl ring; $R^c$ and $R^d$ are independently selected from hydrogen and methyl; $R^e$ is selected from methyl and ethyl; 's' is 1; 'q' is 1; and 'u' is 1.

According to yet another embodiment, specifically provided are compounds of formula (II), in which

is

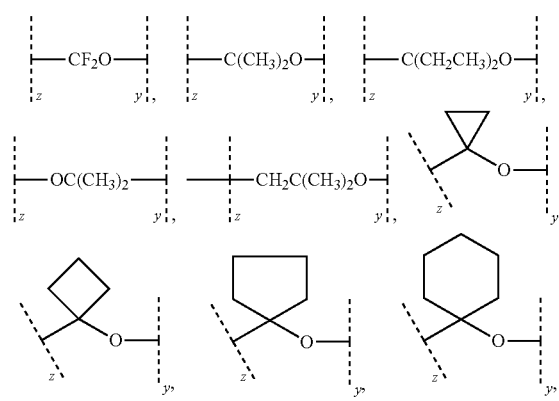

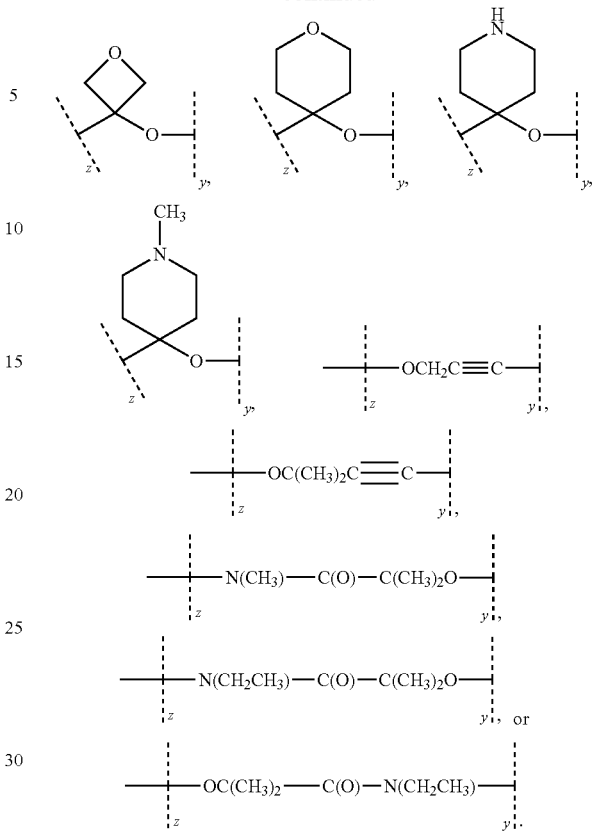

According to yet another embodiment, specifically provided are compounds of formula (II), in which $X^1$ is N, CH or $CR^1$;

ring B is phenyl, pyridin-2-yl, benzimidazol-2-yl, indol-1-yl, [1,2,4]triazolo[4,3-a]pyridin-3-yl or [1,2,4]oxadiazol-3-yl;

$R^1$ is F;

$R^2$ is —F, —Cl, —$CH_3$, —$CH_2CH_3$, —$CH(CH_3)_2$, —$CF_3$, —$OCF_2$, —$OCF_3$, —CN or 4-chlorophenyl;

is

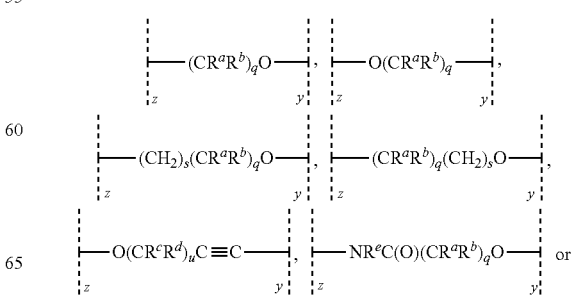

-continued

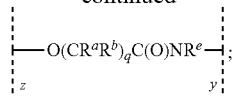

$R^a$ and $R^b$ are independently selected from fluoro, methyl and ethyl; or $R^a$ and $R^b$ together with the carbon atom to which they are attached, form a cyclopropyl, cyclobutyl, cyclopentyl, cyclohexyl, tetrahydro-2H-pyran-4-yl, oxetan-3-yl, N-methyl-piperidin-4-yl or piperidin-4-yl ring;

$R^c$ and $R^d$ are independently selected from hydrogen and methyl;

$R^e$ is selected from methyl and ethyl;

's' is 1;
'q' is 1;
'u' is 1; and
'n' is 1, 2 or 3.

According to yet another embodiment, specifically provided are compounds of formula (II), in which
$X^1$ is N, CH or CF;
Ring

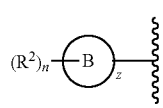

is 4-chlorophenyl, 4-fluorophenyl, 4-(trifluoromethyl)phenyl, 4-trifluoromethoxy-phenyl, 4-difluoromethoxy-phenyl, 4-cyano-phenyl, 2,4-dichlorophenyl, 3,4-dichlorophenyl, 3,5-dichlorophenyl, 2,4-difluorophenyl, 2,5-difluorophenyl, 3,4-difluorophenyl, 2-chloro-4-fluorophenyl, 3-chloro-4-fluorophenyl, 4-chloro-2-fluorophenyl, 4-chloro-3-fluorophenyl, 3-fluoro-4-trifluoromethyl-phenyl, 4-fluoro-3-trifluoromethyl-phenyl, 2,3,4-trifluorophenyl, 3,4,5-trifluorophenyl, 2,4,6-trifluorophenyl, 2,4,5-trifluorophenyl, 4-chloro-2,6-difluoro-phenyl, 5-chloro-pyridin-2-yl, 3,5-dichloro-pyridin-2-yl, 1-ethyl-6-fluoro-1H-benzimidazol-2-yl, 1-ethyl-5-fluoro-1H-benzoimidazol-2-yl, 5-chloro-1-ethyl-1H-benzimidazol-2-yl, 5-chloro-1-methyl-1H-benzimidazol-2-yl, 6-chloro-1-ethyl-1H-benzimidazol-2-yl, 6-chloro-1-methyl-1H-benzoimidazol-2-yl, 7-chloro-1-ethyl-1H-benzimidazol-2-yl, 5-fluoro-1-isopropyl-1H-benzoimidazol-2-yl, 6-chloro-[1,2,4]triazolo[4,3-a]pyridin-3-yl, 5-chloro-1H-indol-1-yl, 5-chloro-1-ethyl-1H-indol-2-yl, 5-fluoro-2-methyl-1H-indol-1-yl, or 4-chloro-phenyl-[1,2,4]oxadiazol-3-yl; and

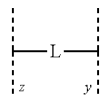

is

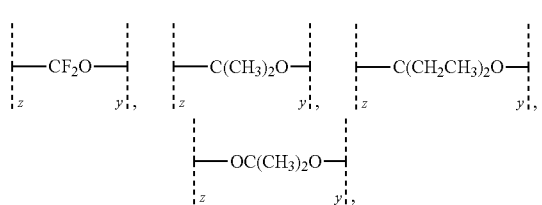

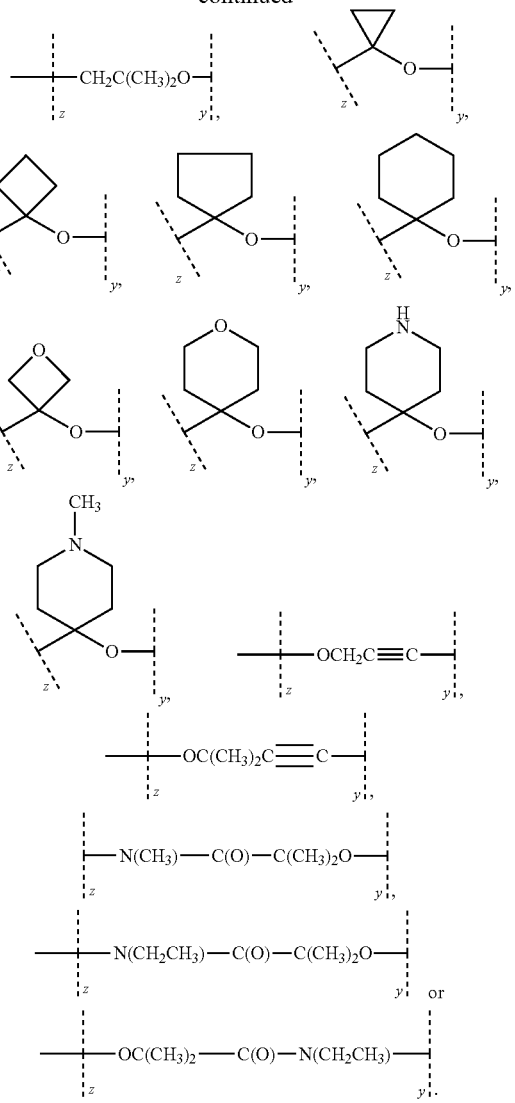

According to an embodiment, specifically provided are compounds of formula (II) with an $IC_{50}$ value of less than 500 nM, preferably less than 100 nM, more preferably less than 50 nM, with respect to RORγt activity.

The invention also provides a compound of formula (III), which is an embodiment of a compound of formula (I) or (II).

Accordingly the invention provides a compound of formula (III)

(III)

or a pharmaceutically acceptable salt thereof, wherein,
$X^1$ is selected from N, CH and $CR^1$;
Ring B is selected from phenyl and pyridinyl;
$R^1$ is independently selected from halogen, cyano, hydroxyl and $C_{1-8}$alkyl;

each occurrence of $R^2$ is independently selected from halogen, cyano, hydroxyl, $C_{1-8}$alkyl, $C_{1-8}$alkoxy, halo$C_{1-8}$alkyl, halo$C_{1-8}$alkoxy, hydroxy$C_{1-8}$alkyl and $C_{3-6}$cycloalkyl;

$R^c$ and $R^d$, which may be same or different, are each independently selected from hydrogen, $C_{1-8}$alkyl, halo$C_{1-8}$alkyl and $C_{1-8}$alkoxy; or $R^c$ and $R^d$ together with the carbon atom to which they are attached, form a $C_{3-6}$cycloalkyl ring;

z represent point of attachment; and

'n' is 0, 1, 2 or 3.

The compounds of formula (III) may involve one or more embodiments. It is to be understood that the embodiments below are illustrative of the present invention and are not intended to limit the claims to the specific embodiments exemplified. It is also to be understood that the embodiments defined herein may be used independently or in conjunction with any definition, any other embodiment defined herein. Thus the invention contemplates all possible combinations and permutations of the various independently described embodiments. For example, the invention provides compounds of formula (III) as defined above wherein ring B is phenyl (according to an embodiment defined below), $R^2$—F, —Cl, —$CF_3$, —$OCF_2$, —$OCF_3$ or —CN (according to another embodiment defined below) and 'n' is 1, 2 or 3 (according to yet another embodiment defined below).

According to one embodiment, specifically provided are compounds of formula (III), in which $X^1$ is N, CH or $CR^1$. In this embodiment $R^1$ is halogen (e.g. F, Cl, Br or I) or $C_{1-8}$alkyl (e.g. methyl or ethyl).

According to another embodiment, specifically provided are compounds of formula (III), in which $R^1$ is halogen (e.g. F, Cl, Br or I) or $C_{1-8}$alkyl (e.g. methyl or ethyl).

According to yet another embodiment, specifically provided are compounds of formula (III), in which $R^1$ is F.

According to yet another embodiment, specifically provided are compounds of formula (III), in which $X^1$ is N, CH or CF.

According to yet another embodiment, specifically provided are compounds of formula (III), in which ring B is phenyl.

According to yet another embodiment, specifically provided are compounds of formula (III), in which $R^2$ is cyano, halogen (e.g. F, Cl, Br or I), $C_{1-8}$alkyl (e.g. methyl or ethyl or isopropyl), halo$C_{1-8}$alkyl (e.g. trifluoromethyl) or halo$C_{1-8}$ alkoxy (e.g. difluoromethoxy or trifluoromethoxy).

According to yet another embodiment, specifically provided are compounds of formula (III), in which $R^2$—F, —Cl, —$CF_3$, —$OCF_2$, —$OCF_3$ or —CN.

According to yet another embodiment, specifically provided are compounds of formula (III), in which 'n' is 1, 2 or 3.

According to yet another embodiment, specifically provided are compounds of formula (III), in which $R^2$—F, —Cl, —$CF_3$, —$OCF_2$, —$OCF_3$ or —CN; and 'n' is 1, 2 or 3.

According to yet another embodiment, specifically provided are compounds of formula (III), in which Ring

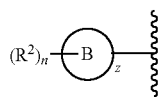

is 4-chlorophenyl, 4-fluorophenyl, 4-(trifluoromethyl)phenyl, 2,4-dichlorophenyl, 3,4-dichlorophenyl, 3,5-dichlorophenyl, 2,4-difluorophenyl, 2,5-difluorophenyl, 3,4-difluorophenyl, 2-chloro-4-fluorophenyl, 3-chloro-4-fluorophenyl, 4-chloro-2-fluorophenyl, 4-chloro-3-fluorophenyl, 3-fluoro-4-trifluoromethyl-phenyl, 2,3,4-trifluorophenyl, 3,4,5-trifluorophenyl, 2,4,6-trifluorophenyl, 2,4,5-trifluorophenyl or 4-chloro-2,6-difluoro-phenyl.

According to yet another embodiment, specifically provided are compounds of formula (III), in which $R^c$ and $R^d$ are independently selected from hydrogen, halogen (e.g. F, Cl, Br or I) and $C_{1-8}$alkyl (e.g. methyl or ethyl).

According to yet another embodiment, specifically provided are compounds of formula (III), in which $R^c$ and $R^d$ are independently selected from hydrogen and methyl.

According to yet another embodiment, specifically provided are compounds of formula (III), in which
$X^1$ is N, CH or CF;
ring B is phenyl;
$R^2$ is —F, —Cl, —$CF_3$, —$OCF_2$, —$OCF_3$ or —CN;
'n' is 1, 2 or 3; and
$R^c$ and $R^d$ are independently selected from hydrogen and methyl.

According to yet another embodiment, specifically provided are compounds of formula (III), in which
$X^1$ is N, CH or CF;
Ring

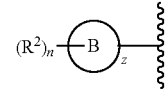

is 4-chlorophenyl, 4-fluorophenyl, 4-(trifluoromethyl)phenyl, 2,4-dichlorophenyl, 3,4-dichlorophenyl, 3,5-dichlorophenyl, 2,4-difluorophenyl, 2,5-difluorophenyl, 3,4-difluorophenyl, 2-chloro-4-fluorophenyl, 3-chloro-4-fluorophenyl, 4-chloro-2-fluorophenyl, 4-chloro-3-fluorophenyl, 3-fluoro-4-trifluoromethyl-phenyl, 2,3,4-trifluorophenyl, 3,4,5-trifluorophenyl, 2,4,6-trifluorophenyl, 2,4,5-trifluorophenyl or 4-chloro-2,6-difluoro-phenyl; and
$R^c$ and $R^d$ are independently selected from hydrogen and methyl.

According to an embodiment, specifically provided are compounds of formula (III) with an $IC_{50}$ value of less than 500 nM, preferably less than 100 nM, more preferably less than 50 nM, with respect to RORγt activity.

The invention also provides a compound of formula (IV), which is an embodiment of a compound of formula (I).

Accordingly the invention provides compound of formula (IV)

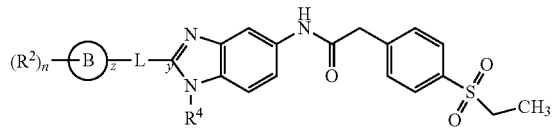

(IV)

or a pharmaceutically acceptable salt thereof,
wherein,
Ring B is selected from phenyl and pyridinyl;

is selected from

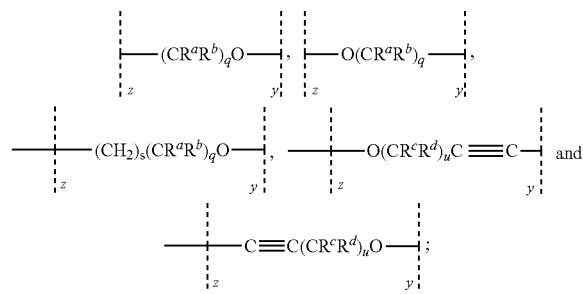

y and z represents point of attachment;

each occurrence of $R^2$ is independently selected from halogen, cyano, hydroxyl, $C_{1-8}$alkyl, $C_{1-8}$alkoxy, halo$C_{1-8}$alkyl, halo$C_{1-8}$alkoxy, hydroxy$C_{1-8}$alkyl and $C_{3-6}$cycloalkyl;

$R^4$ is independently selected from hydrogen, —$(CH_2)_2N(CH_3)_2$, $C_{1-8}$alkyl, halo$C_{1-8}$alkyl, $C_{3-6}$cycloalkyl and $C_{3-6}$cycloalkyl$C_{1-8}$alkyl;

$R^a$ and $R^b$, which may be same or different, are each independently selected from halogen, $C_{1-8}$alkyl, halo$C_{1-8}$alkyl and $C_{1-8}$alkoxy; or $R^a$ and $R^b$ together with the carbon atom to which they are attached, form a cyclopropyl, cyclobutyl, cyclopentyl, or cyclohexyl ring;

$R^c$ and $R^d$, which may be same or different, are each independently selected from hydrogen, $C_{1-8}$alkyl, halo$C_{1-8}$alkyl and $C_{1-8}$alkoxy; or $R^c$ and $R^d$ together with the carbon atom to which they are attached, form a $C_{3-6}$cycloalkyl ring;

'n' is 0, 1, 2 or 3;
'q' is 1 or 2;
's' is 1, 2 or 3; and
'u' is 1.

The compounds of formula (IV) may involve one or more embodiments. It is to be understood that the embodiments below are illustrative of the present invention and are not intended to limit the claims to the specific embodiments exemplified. It is also to be understood that the embodiments defined herein may be used independently or in conjunction with any definition, any other embodiment defined herein. Thus the invention contemplates all possible combinations and permutations of the various independently described embodiments. For example, the invention provides compounds of formula (IV) as defined above wherein ring B is phenyl or pyridin-2-yl (according to an embodiment defined below), $R^2$ is F, Cl or $CF_3$ (according to another embodiment defined below), and 'n' is 1, 2 or 3 (according to yet another embodiment defined below).

According one embodiment, specifically provided are compounds of formula (IV), in which ring B is phenyl or pyridin-2-yl.

According to another embodiment, specifically provided are compounds of formula (IV), in which $R^2$ is halogen (e.g. F, Cl, Br or I), $C_{1-8}$alkyl (e.g. methyl or ethyl), halo$C_{1-8}$alkyl (e.g. trifluoromethyl) or halo$C_{1-8}$alkoxy (e.g. difluoromethoxy or trifluoromethoxy).

According to yet another embodiment, specifically provided are compounds of formula (IV), in which $R^2$ is F, Cl or $CF_3$.

According to yet another embodiment, specifically provided are compounds of formula (IV), in which 'n' is 1, 2 or 3.

According to yet another embodiment, specifically provided are compounds of formula (IV), in which $R^2$ is F, Cl or $CF_3$; and 'n' is 1, 2 or 3.

According to yet another embodiment, specifically provided are compounds of formula (IV), in which ring B is phenyl or pyridin-2-yl; $R^2$ is F, Cl or $CF_3$; and 'n' is 1, 2 or 3.

According yet another embodiment, specifically provided are compounds of formula (IV), in which

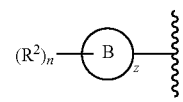

is chlorophenyl, 4-fluorophenyl, 4-(trifluoromethyl)phenyl, 2,4-dichlorophenyl, 3,4-dichlorophenyl, 3,5-dichlorophenyl, 2,4-difluorophenyl, 2,5-difluorophenyl, 3,4-difluorophenyl, 2-chloro-4-fluorophenyl, 4-chloro-2-fluorophenyl, 4-chloro-3-fluoro-phenyl, 3-fluoro-4-trifluoromethyl-phenyl, 2,3,4-trifluorophenyl, 3,4,5-trifluorophenyl, 2,4,6-trifluorophenyl, 2,4,5-trifluorophenyl, 4-chloro-2,6-difluorophenyl or 5-chloro-pyridin-2-yl.

According to yet another embodiment, specifically provided are compounds of formula (IV), in which $R^4$ is hydrogen, $C_{1-8}$alkyl (e.g. methyl, ethyl, propyl, isopropyl or isobutyl), halo$C_{1-8}$alkyl (e.g. 2-fluoroethyl), $C_{3-6}$cycloalkyl (e.g. cyclopropyl), $C_{3-6}$cycloalkyl$C_{1-8}$alkyl (e.g. cyclopropylmethyl) or —$(CH_2)_2N(CH_3)_2$.

According to yet another embodiment, specifically provided are compounds of formula (IV), in which $R^4$ is —H, —$CH_3$, —$CH_2CH_3$, —$CH_2CH_2CH_3$, —$CH(CH_3)_2$, —$CH_2CH(CH_3)_2$, —$(CH_2)_2N(CH_3)_2$, —$CH_2CH_2F$, cyclopropyl or cyclopropylmethyl.

According to yet another embodiment, specifically provided are compounds of formula (IV), in which

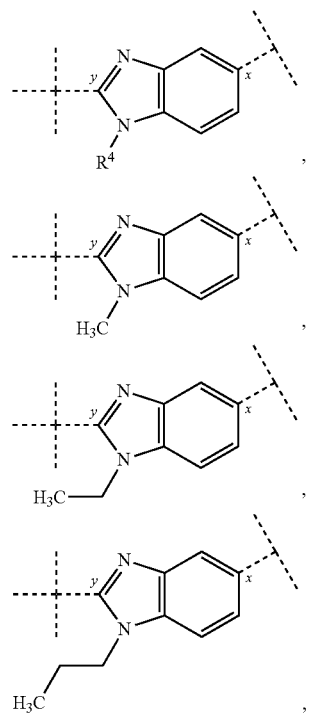

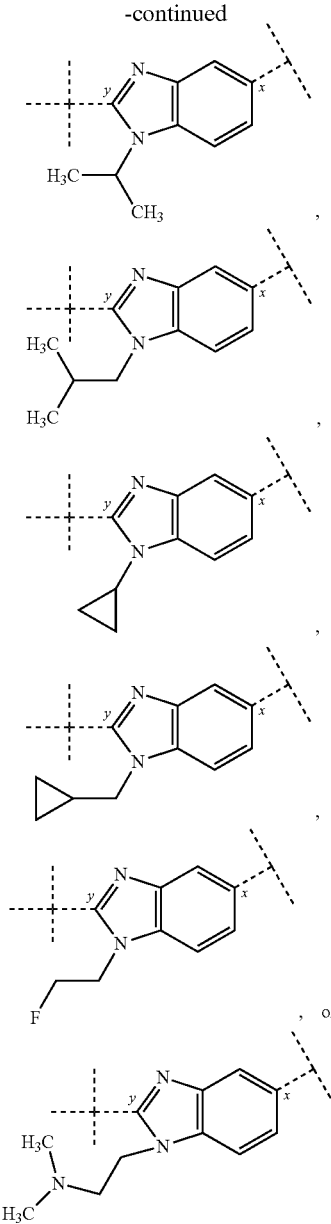

According to yet another embodiment, specifically provided are compounds of formula (IV), in which $R^a$ and $R^b$ are halogen (e.g. F, Cl, Br or I) or $C_{1-8}$alkyl (e.g. methyl or ethyl); or $R^a$ and $R^b$ together with the carbon atom to which they are attached, form a cyclopropyl, or cyclobutyl ring.

According to yet another embodiment, specifically provided are compounds of formula (IV), in which $R^a$ and $R^b$ are F or $CH_3$.

According to yet another embodiment, specifically provided are compounds of formula (IV), in which $R^c$ and $R^d$ are hydrogen or methyl.

According to yet another embodiment, specifically provided are compounds of formula (IV), in which 's' is 1.

According to yet another embodiment, specifically provided are compounds of formula (IV), in which 'q' is 1.

According to yet another embodiment, specifically provided are compounds of formula (IV), in which

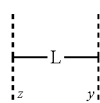

is

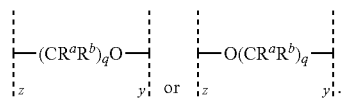

In this embodiment, $R^a$ and $R^b$ are F or methyl; or $R^a$ and $R^b$ together with the carbon atom to which they are attached, form a cyclopropyl, or cyclobutyl ring; 's' is 1; and 'q' is 1.

According to yet another embodiment, specifically provided are compounds of formula (IV), in which

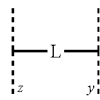

is

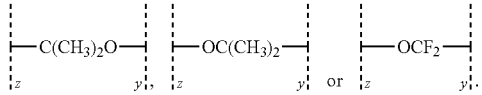

According to yet another embodiment, specifically provided are compounds of formula (IV), in which ring B is phenyl or pyridin-2-yl;

$R^2$ is F, Cl or $CF_3$;

$R^4$ is —H, —$CH_3$, —$CH_2CH_3$, —$CH_2CH_2CH_3$, —CH($CH_3$)$_2$, —$CH_2CH(CH_3)_2$, —$(CH_2)_2N(CH_3)_2$, —$CH_2CH_2F$ or cyclopropylmethyl;

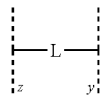

is

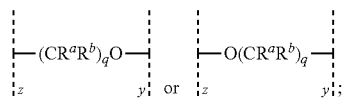

$R^a$ and $R^b$ are F or methyl;

'n' is 1, 2 or 3; and

'q' is 1.

According to yet another embodiment, specifically provided are compounds of formula (IV), in which Ring

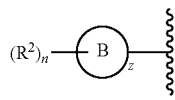

is 4-chlorophenyl, 4-fluorophenyl, 4-(trifluoromethyl)phenyl, 2,4-dichlorophenyl, 3,4-dichlorophenyl, 3,5-dichlorophenyl, 2,4-difluorophenyl, 2,5-difluorophenyl, 3,4-difluorophenyl, 2-chloro-4-fluorophenyl, 4-chloro-2-fluorophenyl, 4-chloro-3-fluoro-phenyl, 3-fluoro-4-trifluoromethyl-phenyl, 2,3,4-trifluorophenyl, 3,4,5-trifluorophenyl, 2,4,6-trifluorophenyl, 2,4,5-trifluorophenyl, 4-chloro-2,6-difluoro-phenyl or 5-chloro-pyridin-2-yl;

$R^4$ is —H, —CH$_3$, —CH$_2$CH$_3$, —CH$_2$CH$_2$CH$_3$, —CH(CH$_3$)$_2$, —CH$_2$CH(CH$_3$)$_2$, —(CH$_2$)$_2$N(CH$_3$)$_2$ or cyclopropylmethyl; and

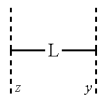

is

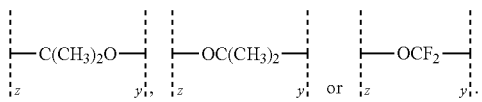

According to an embodiment, specifically provided are compounds of formula (IV) with an IC$_{50}$ value of less than 500 nM, preferably less than 100 nM, more preferably less than 50 nM, with respect to RORγt activity.

Compounds of the present invention include the compounds in Examples 1-145.

It should be understood that the formulas (I), (II), (III) and (IV) structurally encompasses all geometrical isomers, stereoisomers, enantiomers and diastereomers, N-oxides, and pharmaceutically acceptable salts that may be contemplated from the chemical structure of the genera described herein.

The present application also provides a pharmaceutical composition that includes at least one compound described herein and at least one pharmaceutically acceptable excipient (such as a pharmaceutically acceptable carrier or diluent).

Preferably, the pharmaceutical composition comprises a therapeutically effective amount of at least one compound described herein. The compounds described herein may be associated with a pharmaceutically acceptable excipient (such as a carrier or a diluent) or be diluted by a carrier, or enclosed within a carrier which can be in the form of a tablet, capsule, sachet, paper or other container.

The compounds and pharmaceutical compositions of the present invention are useful for inhibiting the activity of RORγt. Thus, the present invention further provides a method of inhibiting RORγt in a subject in need thereof by administering to the subject one or more compounds described herein in the amount effective to cause inhibition of such receptor.

In a further aspect, the present invention relates to a method of treating a disease, disorder or condition modulated by RORγt, such as autoimmune disease, inflammatory disease, respiratory disorders, pain and cancer comprising administering to a subject in need thereof a compound according to any of the embodiments described herein.

In another further aspect, the present invention relates to a method of treating a disease, disorder or condition modulated by RORγt, such as chronic obstructive pulmonary disease (COPD), asthma, cough, pain, inflammatory pain, chronic pain, acute pain, arthritis, osteoarthritis, multiple sclerosis, rheumatoid arthritis, colitis, ulcerative colitis, psoriasis, and inflammatory bowel disease, comprising administering to a subject in need thereof a compound according to any of the embodiments described herein.

DETAILED DESCRIPTION OF THE INVENTION

Definitions

The terms "halogen" or "halo" means fluorine (fluoro), chlorine (chloro), bromine (bromo), or iodine (iodo).

The term "alkyl" refers to a hydrocarbon chain radical that includes solely carbon and hydrogen atoms in the backbone, containing no unsaturation, having from one to eight carbon atoms (i.e. $C_{1-8}$alkyl), and which is attached to the rest of the molecule by a single bond, e.g., methyl, ethyl, n-propyl, 1-methylethyl (isopropyl), n-butyl, n-pentyl, and 1,1-dimethylethyl (t-butyl). The term "$C_{1-6}$ alkyl" refers to an alkyl chain having 1 to 6 carbon atoms. The term "$C_{1-4}$alkyl" refers to an alkyl chain having 1 to 4 carbon atoms. Unless set forth or recited to the contrary, all alkyl groups described or claimed herein may be straight chain or branched.

The term "alkenyl" refers to a hydrocarbon chain containing from 2 to 10 carbon atoms (i.e. $C_{2-10}$alkenyl) and including at least one carbon-carbon double bond. Non-limiting examples of alkenyl groups include ethenyl, 1-propenyl, 2-propenyl (allyl), iso-propenyl, 2-methyl-1-propenyl, 1-butenyl, and 2-butenyl. Unless set forth or recited to the contrary, all alkenyl groups described or claimed herein may be straight chain or branched.

The term "alkynyl" refers to a hydrocarbyl radical having at least one carbon-carbon triple bond, and having 2 to about 12 carbon atoms (with radicals having 2 to about 10 carbon atoms being preferred i.e. $C_{2-10}$alkynyl). Non-limiting examples of alkynyl groups include ethynyl, propynyl, and butynyl. Unless set forth or recited to the contrary, all alkynyl groups described or claimed herein may be straight chain or branched.

The term "alkoxy" denotes an alkyl group attached via an oxygen linkage to the rest of the molecule (i.e. $C_{1-8}$ alkoxy). Representative examples of such groups are —OCH$_3$ and —OC$_2$H$_5$. Unless set forth or recited to the contrary, all alkoxy groups described or claimed herein may be straight chain or branched.

The term "alkoxyalkyl" or "alkyloxyalkyl" refers to an alkoxy or alkyloxy group as defined above directly bonded to an alkyl group as defined above (i.e. $C_{1-8}$alkoxyC$_{1-8}$alkyl or $C_{1-8}$alkyloxyC$_{1-8}$alkyl). Example of such alkoxyalkyl moiety includes, but are not limited to, —CH$_2$OCH$_3$ and —CH$_2$OC$_2$H$_5$. Unless set forth or recited to the contrary, all alkoxyalkyl groups described herein may be straight chain or branched.

The term "haloalkyl" refers to at least one halo group (selected from F, Cl, Br or I), linked to an alkyl group as defined above (i.e. haloC$_{1-8}$alkyl). Examples of such haloalkyl moiety include, but are not limited to, trifluoromethyl, difluoromethyl and fluoromethyl groups. Unless set forth or recited to the contrary, all haloalkyl groups described herein may be straight chain or branched.

The term "haloalkoxy" refers to an alkoxy group substituted with one or more halogen atoms (i.e. halo$C_{1-8}$alkoxy). Examples of "haloalkoxy" include but are not limited to fluoromethoxy, difluoromethoxy, trifluoromethoxy, 2,2,2-trifluoroethoxy, pentafluoroethoxy, pentachloroethoxy, chloromethoxy, dichloromethoxy, trichloromethoxy and 1-bromoethoxy. Unless set forth or recited to the contrary, all haloalkoxy groups described herein may be straight chain or branched.

The term "hydroxyalkyl" refers to an alkyl group as defined above wherein one to three hydrogen atoms on different carbon atoms is/are replaced by hydroxyl groups (i.e. hydroxy$C_{1-8}$alkyl). Examples of hydroxyalkyl moieties include, but are not limited to —$CH_2OH$, —$C_2H_4OH$ and —$CH(OH)C_2H_4OH$.

The term "cycloalkyl" denotes a non-aromatic mono or multicyclic ring system of 3 to about 12 carbon atoms, (i.e. $C_{3-12}$cycloalkyl). Examples of monocyclic cycloalkyl include but are not limited to cyclopropyl, cyclobutyl, cyclopentyl, and cyclohexyl. Examples of multicyclic cycloalkyl groups include, but are not limited to, perhydronaphthyl, adamantyl and norbornyl groups, bridged cyclic groups or spirobicyclic groups, e.g., spiro(4,4)non-2-yl. The term "$C_{3-6}$cycloalkyl" refers to the cyclic ring having 3 to 6 carbon atoms.

The term "cycloalkylalkyl" refers to a cyclic ring-containing radical having 3 to about 6 carbon atoms directly attached to an alkyl group (i.e. $C_{3-6}$cycloalkyl$C_{1-8}$alkyl). The cycloalkylalkyl group may be attached to the main structure at any carbon atom in the alkyl group that results in the creation of a stable structure. Non-limiting examples of such groups include cyclopropylmethyl, cyclobutylethyl, and cyclopentylethyl.

The term "cycloalkenyl" refers to a cyclic ring-containing radical having 3 to about 8 carbon atoms with at least one carbon-carbon double bond, (i.e. $C_{3-8}$cycloalkenyl). Examples of "cycloalkenyl" include but are not limited to cyclopropenyl, cyclobutenyl, and cyclopentenyl.

The term "cycloalkenylalkyl" refers to a cyclic ring-containing radical having 3 to about 8 carbon atoms with at least one carbon-carbon double bond, directly attached to an alkyl group, (i.e. $C_{3-8}$cycloalkenyl$C_{1-8}$alkyl). The cycloalkenylalkyl group may be attached to the main structure at any carbon atom in the alkyl group that results in the creation of a stable structure.

The term "aryl" refers to an aromatic radical having 6 to 14 carbon atoms (i.e. $C_{6-14}$aryl), including monocyclic, bicyclic and tricyclic aromatic systems, such as phenyl, naphthyl, tetrahydronaphthyl, indanyl, and biphenyl.

The term "aryloxy" refers to an aryl group as defined above attached via an oxygen linkage to the rest of the molecule (i.e. $C_{6-14}$aryloxy). Examples of aryloxy moieties include, but are not limited to phenoxy and naphthoxy.

The term "arylalkyl" refers to an aryl group as defined above directly bonded to an alkyl group as defined above, i.e. $C_{6-14}$aryl$C_{1-8}$alkyl, such as —$CH_2C_6H_5$ and —$C_2H_4C_6H_5$.

The term "heterocyclic ring" or "heterocyclyl" unless otherwise specified refers to substituted or unsubstituted non-aromatic 3 to 15 membered ring radical (i.e. 3 to 15 membered heterocyclyl) which consists of carbon atoms and from one to five hetero atoms selected from nitrogen, phosphorus, oxygen and sulfur. The heterocyclic ring radical may be a mono-, bi- or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; also, unless otherwise constrained by the definition the heterocyclic ring or heterocyclyl may optionally contain one or more olefinic bond(s). Examples of such heterocyclic ring radicals include, but are not limited to azepinyl, azetidinyl, benzodioxolyl, benzodioxanyl, chromanyl, dioxolanyl, dioxaphospholanyl, decahydroisoquinolyl, indanyl, indolinyl, isoindolinyl, isochromanyl, isothiazolidinyl, isoxazolidinyl, morpholinyl, oxazolinyl, oxazolidinyl, 2-oxopiperazinyl, 2-oxopiperidinyl, 2-oxopyrrolidinyl, 2-oxoazepinyl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisoquinolyl, tetrahydrofuryl or tetrahydrofuranyl, tetrahydropyranyl, thiazolinyl, thiazolidinyl, thiamorpholinyl, thiamorpholinyl sulfoxide and thiamorpholinyl sulfone. The heterocyclic ring radical may be attached to the main structure at any heteroatom or carbon atom that results in the creation of a stable structure.

The term "heterocyclylalkyl" refers to a heterocyclic ring radical directly bonded to an alkyl group (i.e. 3 to 15 membered heterocyclyl$C_{1-8}$alkyl). The heterocyclylalkyl radical may be attached to the main structure at any carbon atom in the alkyl group that results in the creation of a stable structure.

The term "heteroaryl" unless otherwise specified refers to substituted or unsubstituted 5 to 14 membered aromatic heterocyclic ring radical with one or more heteroatom(s) independently selected from N, O or S (i.e. 5 to 14 membered heteroaryl). The heteroaryl may be a mono-, bi- or tricyclic ring system. The heteroaryl ring radical may be attached to the main structure at any heteroatom or carbon atom that results in the creation of a stable structure. Examples of such heteroaryl ring radicals include, but are not limited to oxazolyl, isoxazolyl, imidazolyl, furyl, indolyl, isoindolyl, pyrrolyl, triazolyl, triazinyl, tetrazoyl, thienyl, oxadiazolyl, thiazolyl, isothiazolyl, pyridyl, pyrimidinyl, pyrazinyl, pyridazinyl, pyrazolyl, benzofuranyl, benzothiazolyl, benzoxazolyl, benzimidazolyl, benzothienyl, benzopyranyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl and phthalazinyl.

The term "heteroarylalkyl" refers to a heteroaryl ring radical directly bonded to an alkyl group (i.e. 5 to 14 membered heterary$lC_{1-8}$alkyl). The heteroarylalkyl radical may be attached to the main structure at any carbon atom in the alkyl group that results in the creation of a stable structure.

The term "pharmaceutically acceptable salt" includes salts prepared from pharmaceutically acceptable bases or acids including inorganic or organic bases and inorganic or organic acids. Examples of such salts include, but are not limited to, acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate, diphosphate, polygalacturonate, salicylate, stearate, sulfate, subacetate, succinate, tannate, tartrate, teoclate, tosylate, triethiodide and valerate. Examples of salts derived from inorganic bases include, but are not limited to, aluminum, ammonium, calcium, copper, ferric, ferrous, lithium, magnesium, manganic, mangamous, potassium, sodium, and zinc.

The term "treating" or "treatment" of a state, disorder or condition includes: (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof; or (c) relieving the disease, i.e., causing regression of the state, disorder or condition or at least one of its clinical or subclinical symptoms.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disorder or condition, is sufficient to effect such treatment. The "therapeutically effective amount" will vary depending on the compound, the disease and its severity and the age, weight, physical condition and responsiveness of the subject to be treated.

Pharmaceutical Compositions

The compounds of the invention are typically administered in the form of a pharmaceutical composition. Such compositions can be prepared using procedures well known in the pharmaceutical art and comprise at least one compound of the invention. The pharmaceutical compositions described herein comprise one or more compounds described herein and one or more pharmaceutically acceptable excipients. Typically, the pharmaceutically acceptable excipients are approved by regulatory authorities or are generally regarded as safe for human or animal use. The pharmaceutically acceptable excipients include, but are not limited to, carriers, diluents, glidants and lubricants, preservatives, buffering agents, chelating agents, polymers, gelling agents, viscosifying agents, solvents and the like.

Examples of suitable carriers include, but are not limited to, water, salt solutions, alcohols, polyethylene glycols, peanut oil, olive oil, gelatin, lactose, terra alba, sucrose, dextrin, magnesium carbonate, sugar, amylose, magnesium stearate, talc, gelatin, agar, pectin, acacia, stearic acid, lower alkyl ethers of cellulose, silicic acid, fatty acids, fatty acid amines, fatty acid monoglycerides and diglycerides, fatty acid esters, and polyoxyethylene.

The pharmaceutical compositions described herein may also include one or more pharmaceutically acceptable auxiliary agents, wetting agents, suspending agents, preserving agents, buffers, sweetening agents, flavouring agents, colorants or any combination of the foregoing.

The pharmaceutical compositions may be in conventional forms, for example, capsules, tablets, solutions, suspensions, injectables or products for topical application. Further, the pharmaceutical composition of the present invention may be formulated so as to provide desired release profile.

Administration of the compounds of the invention, in pure form or in an appropriate pharmaceutical composition, can be carried out using any of the accepted routes of administration of such compounds or pharmaceutical compositions. The route of administration may be any route which effectively transports the active compound of the patent application to the appropriate or desired site of action. Suitable routes of administration include, but are not limited to, oral, nasal, buccal, dermal, intradermal, transdermal, parenteral, rectal, subcutaneous, intravenous, intraurethral, intramuscular, and topical.

Solid oral formulations include, but are not limited to, tablets, capsules (soft or hard gelatin), dragees (containing the active ingredient in powder or pellet form), troches and lozenges.

Liquid formulations include, but are not limited to, syrups, emulsions, and sterile injectable liquids, such as suspensions or solutions.

Topical dosage forms of the compounds include, but are not limited to, ointments, pastes, creams, lotions, powders, solutions, eye or ear drops, impregnated dressings, and may contain appropriate conventional additives such as preservatives, solvents to assist drug penetration.

The pharmaceutical compositions described herein may be prepared by conventional techniques, e.g., as described in *Remington: The Science and Practice of Pharmacy*, 20$^{th}$ Ed., 2003 (Lippincott Williams & Wilkins).

Suitable doses of the compounds for use in treating the diseases and disorders described herein can be determined by those skilled in the relevant art. Therapeutic doses are generally identified through a dose ranging study in humans based on preliminary evidence derived from the animal studies. Doses must be sufficient to result in a desired therapeutic benefit without causing unwanted side effects. Mode of administration, dosage forms, and suitable pharmaceutical excipients can also be well used and adjusted by those skilled in the art. All changes and modifications are envisioned within the scope of the present patent application.

Methods of Treatment

The compounds of the present invention are particularly useful because they inhibit the activity of retinoid-related orphan receptor gamma, particularly retinoid-related orphan receptor gamma t (RORγt), i.e., they prevent, inhibit, or suppress the action of RORγt, and/or may elicit a RORγt modulating effect. Compounds of the invention are therefore useful in the treatment of those conditions in which inhibition of ROR gamma activity, and particularly RORγt, is required.

The compounds of the present patent application are modulators of RORγt and can be useful in the treatment of diseases/disorder mediated by RORγt. Accordingly, the compounds and the pharmaceutical compositions of this invention may be useful in the treatment of inflammatory, metabolic and autoimmune diseases mediated by RORγt.

The term "autoimmune diseases" will be understood by those skilled in the art to refer to a condition that occurs when the immune system mistakenly attacks and destroys healthy body tissue. An autoimmune disorder may result in the destruction of one or more types of body tissue, abnormal growth of an organ, and changes in organ function. An autoimmune disorder may affect one or more organ or tissue types which include, but are not limited to, blood vessels, connective tissues, endocrine glands such as the thyroid or pancreas, joints, muscles, red blood cells, and skin. Examples of autoimmune (or autoimmune-related) disorders include multiple sclerosis, arthritis, rheumatoid arthritis, psoriasis, Crohn's disease, gastrointestinal disorder, inflammatory bowel disease, irritable bowel syndrome, colitis, ulcerative colitis, Sjorgen's syndrome, atopic dermatitis, optic neuritis, respiratory disorder, chronic obstructive pulmonary disease (COPD), asthma, type I diabetes, neuromyelitis optica, Myasthenia Gavis, uveitis, Guillain-Barre syndrome, psoriatic arthritis, Gaves' disease, allergy, osteoarthritis, Kawasaki disease, mucosal leishmaniasis, Hashimoto's thyroiditis, Pernicious anemia, Addison's disease, Systemic lupus erythematosus, Dermatomyositis, Sjogren syndrome, Lupus erythematosus, Myasthenia gravis, Reactive arthritis, Celiac disease—sprue (gluten-sensitive enteropathy), Graves's disease, thymopoiesis and Lupus.

Compounds of the present patent application may also be useful in the treatment of inflammation. The term "inflammation" will be understood by those skilled in the art to include any condition characterized by a localized or a systemic protective response, which may be elicited by physical trauma, infection, chronic diseases, and/or chemical and/or physiological reactions to external stimuli (e.g. as part of an allergic response). Any such response, which may serve to destroy, dilute or sequester both the injurious agent and the injured tissue, may be manifest by, for example, heat, swelling, pain, redness, dilation of blood vessels and/or increased blood flow, invasion of the affected area by white.

The term "inflammation" is also understood to include any inflammatory disease, disorder or condition per se, any condition that has an inflammatory component associated with it, and/or any condition characterized by inflammation as a symptom, including inter alia acute, chronic, ulcerative, specific, allergic, infection by pathogens, immune reactions due to hypersensitivity, entering foreign bodies, physical injury, and necrotic inflammation, and other forms of inflammation known to those skilled in the art. The term thus also includes, for the purposes of this present patent application, inflammatory pain, pain generally and/or fever.

The compounds of the present invention may be used for treatment of arthritis, including, but are not limited to, rheumatoid arthritis, osteoarthritis, psoriatic arthritis, septic arthritis, spondyloarthropathies, gouty arthritis, systemic lupus erythematosus and juvenile arthritis, osteoarthritis, collagen-induced arthritis (CIA) and other arthritic conditions.

The compounds of the present invention may be used for treatment of respiratory disorders including, but are not limited to, chronic obstructive pulmonary disease (COPD), asthma, bronchospasm, and cough.

Other respiratory disorders include, but are not limited to, bronchitis, bronchiolitis, bronchiectasis, acute nasoparyngitis, acute and chronic sinusitis, maxillary sinusitis, pharyngitis, tonsillitis, laryngitis, tracheitis, epiglottis, croup, chronic disease of tonsils and adenoids, hypertrophy of tonsils and adenoids, peritonsillar abscess, rhinitis, abscess or ulcer and nose, pneumonia, viral and bacterial pneumonia, bronchopneumonia, influenza, extrinsic allergic alveolitis, coal workers' pneumoconiosis, asbestosis, pneumoconiosis, pneumonopathy, respiratory conditions due to chemical fumes, vapors and other external agents, emphysema, pleurisy, pneumothorax, abscess of lung and mediastinum, pulmonary congestion and hypostasis, postinflammatory pulmonary fibrosis, other alveolar and parietoalveolar pneumonopathy, idiopathic fibrosing alveolitis, Hamman-Rich syndrome, atelectasis, ARDS, acute respiratory failure, mediastinitis.

The compounds of the present invention may also be used for treatment of pain conditions. The pain can be acute or chronic pain. Thus, the compounds of the present invention may be used for treatment of e.g., inflammatory pain, arthritic pain, neuropathic pain, post-operative pain, surgical pain, visceral pain, dental pain, premenstrual pain, central pain, cancer pain, pain due to burns; migraine or cluster headaches, nerve injury, neuritis, neuralgias, poisoning, ischemic injury, interstitial cystitis, viral, parasitic or bacterial infection, post-traumatic injury, or pain associated with irritable bowel syndrome.

The compounds of the present invention may further be used for treatment of gastrointestinal disorder such as, but not limited to, irritable bowel syndrome, inflammatory bowel disease, colitis, ulcerative colitis, biliary colic and other biliary disorders, renal colic, diarrhea-dominant IBS, and pain associated with gastrointestinal distension.

In addition, the compounds of the present invention may be useful in the treatment of cancer, and pain associated with cancer. Such cancers include, e.g., multiple myeloma and bone disease associated with multiple myeloma, melanoma, medulloblastoma, acute myelogenous leukemia (AML), head and neck squamous cell carcinoma, hepatocellular carcinoma, gastric cancer, bladder carcinoma and colon cancer.

The compounds of the present invention may be useful in a treatment of disease, disorder, syndrome or condition selected from the group consisting of chronic obstructive pulmonary disease (COPD), asthma, cough, pain, inflammatory pain, chronic pain, acute pain, arthritis, osteoarthritis, multiple sclerosis, rheumatoid arthritis, colitis, ulcerative colitis and inflammatory bowel disease.

Any of the methods of treatment described herein comprise administering an effective amount of a compound according to Formula I, (Ia) or (Ib), or a pharmaceutically-acceptable salt thereof, to a subject (particularly a human) in need thereof.

The present inventions further relates to the use of the compounds described herein in the preparation of a medicament for the treatment of diseases mediated by RORγt.

The compounds of the invention are effective both in the therapeutic and/or prophylactic treatment of the above-mentioned conditions. For the above-mentioned therapeutic uses the dosage administered may vary with the compound employed, the mode of administration, the treatment desired and the disorder.

The daily dosage of the compound of the invention administered may be in the range from about 0.05 mg/kg to about 100 mg/kg.

General Methods of Preparation

The compounds of general formulas (IIa)-(IIg), (III), (IV), (V) and specific examples described herein are prepared using techniques known to one skilled in the art through the reaction sequences depicted in synthetic schemes 1-14 and as well as by other methods. Furthermore, in the following schemes, where specific acids, bases, reagents, coupling agents, solvents, etc. are mentioned, it is understood that other suitable reagents may be used and are included within the scope of the present invention. The modifications to reaction conditions, for example, temperature, duration of the reaction or combinations thereof, are envisioned as part of the present invention. The compounds obtained by using the general reaction sequences may be of insufficient purity. These compounds can be purified by using any of the methods for purification of organic compounds known to persons skilled in the art, for example, crystallization or silica gel or alumina column chromatography using different solvents in suitable ratios. All possible geometrical isomers, stereoisomers and tautomers are envisioned within the scope of this invention.

The starting materials for the below reaction schemes are commercially available or can be prepared according to methods known to one skilled in the art or by methods disclosed herein. In general, intermediates and compounds of the present invention may be prepared through the reaction scheme as follows, wherein all symbols are as defined above. In some cases the final product may be further modified, for example, by manipulation of substituents. These manipulations may include, but are not limited to, reduction, oxidation, alkylation, acylation, hydrolysis, and cleavage of protecting groups etc., by following procedures known in the art of organic synthesis.

A general approach for the preparation of compounds of the formula (IIa) (wherein $R^2$, $R^a$, $R^b$, $X^1$ and 'n' are as defined in the general description) is illustrated in Synthetic Scheme 1.

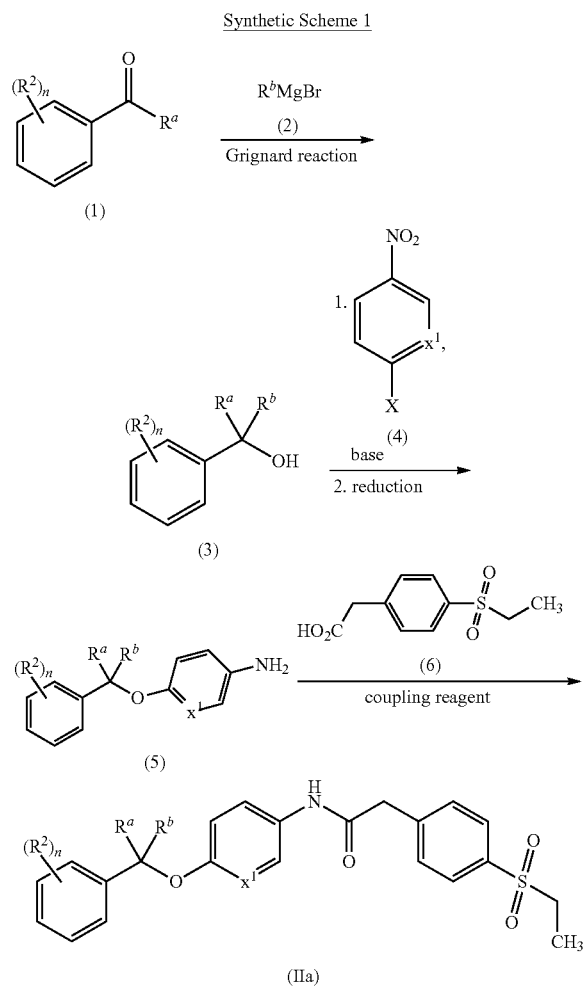

combination thereof. The reaction may also optionally carry out in the presence of suitable base selected from $Et_3N$, DIPEA and DMAP. The reaction may be carried out in a suitable solvent or mixture thereof. The suitable solvent may be selected from dichloromethane, $CHCl_3$, THF and DMF or combination thereof.

A general approach for the preparation of compounds of the formula (IIb) (wherein $R^2$, $R^a$, $R^b$, $X^1$ and 'n' are as defined in the general description) is illustrated in Synthetic Scheme 2.

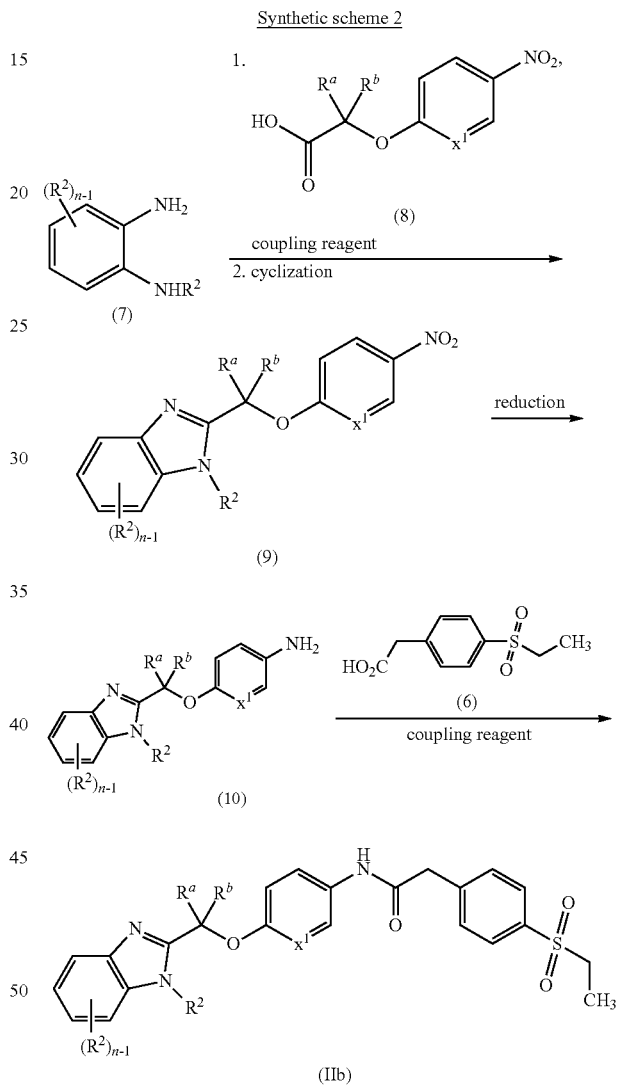

The Grignard reaction of Intermediate (1) with alkyl magnesium bromide of formula (2) affords the tertiary alcohol (3). The aromatic nucleophilic substitution of the alcohol (3) with the compound (4) (wherein X is F, Cl, Br or I) using base such as sodium hydride followed by the reduction of the nitro group yields the amine of formula (5). The reaction of Intermediate (5) with [4-(ethylsulfonyl)phenyl]acetic acid (6) gives final compound of formula (IIa). The intermediate (5) may be reacted with [4-(ethylsulfonyl)phenyl]acetic acid (6) in the presence of a suitable coupling agent. The suitable coupling agent may be selected from EDCI.HCl, HATU, DCC and CDI with or without HOBt or HOEt or in a The o-phenylenediamine compound of formula (7) on coupling reaction with the phenoxy acetic acid intermediate of formula (8) using 1,1'-carbonyldiimidazole (CDI) or other suitable coupling agent gives an amide which in the presence of acetic acid cyclizes to yield benzimidazole compound of formula (9). The reduction of the nitro group of Intermediate (9) yields the corresponding amine intermediate (10). The amine intermediate (10) reacted with [4-(ethylsulfonyl)phenyl]acetic acid (6) to afford the final compound of the formula (IIb). The intermediate (10) may be reacted with [4-(ethylsulfonyl)phenyl]acetic acid (6) in the presence of a suitable coupling agent. The suitable coupling agent may be selected from EDCI.HCl, HATU, DCC and CDI with or without HOBt or HOEt or in a combination thereof. The reaction may also optionally carry out in the presence of suitable base selected from Et₃N, DIPEA and DMAP. The reaction may be carried out in a suitable solvent or mixture thereof. The suitable solvent may be selected from dichloromethane, CHCl₃, THF and DMF or combination thereof.

A general approach for the preparation of compounds of the formula (IIc) (wherein $R^2$, $R^a$, $R^b$, $X^1$ and 'n' are as defined in the general description) is illustrated in Synthetic scheme 3.

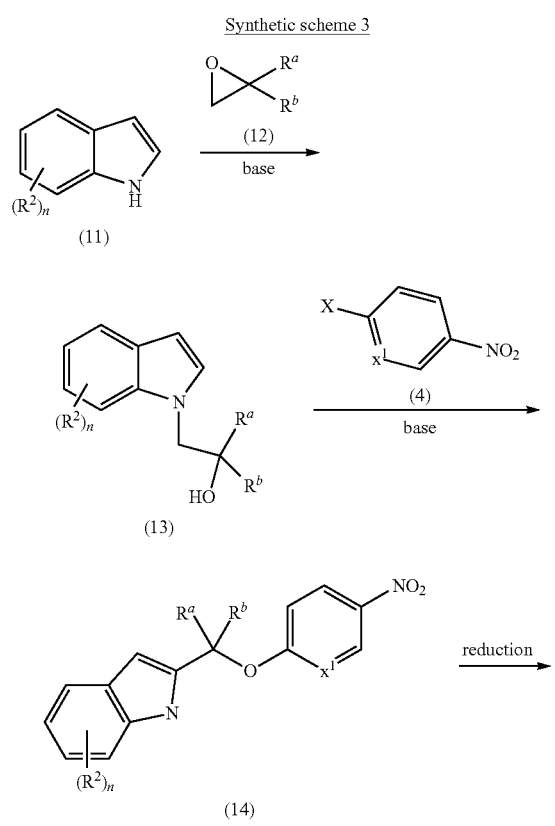

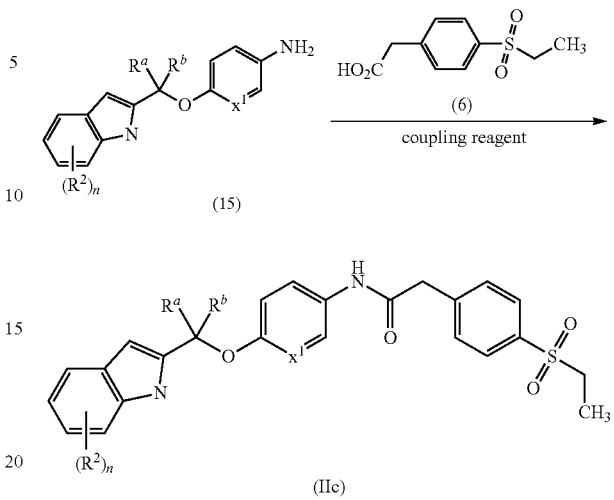

Thus, the substituted indole (11) on reaction with dialkyloxirane (12) using base such as sodium hydride yields the alcohol Intermediate (13). The reaction of the Intermediate (13) with the 4-halo nitro compound of formula (4) (wherein X is F, Cl, Br or I) yields the ether derivative (14). The nitro reduction of the Intermediate (14) gives the corresponding amine compound of formula (15). The coupling of the amine compound of the formula (15) with [4-(ethylsulfonyl)phenyl]acetic acid (6) yields the final compound of the formula (IIc). The amine compound of the formula (15) may be reacted with [4-(ethylsulfonyl)phenyl]acetic acid (6) in the presence of a suitable coupling agent. The suitable coupling agent may be selected from EDCI.HCl, HATU, DCC and CDI with or without HOBt or HOEt or in a combination thereof. The reaction may also optionally carry out in the presence of suitable base selected from triethylamine, DIPEA, diethylamine and DMAP. The reaction may be carried out in a suitable solvent or mixture thereof. The suitable solvent may be selected from dichloromethane, CHCl₃, THF and DMF or combination thereof.

A general approach for the preparation of the compounds of the formula (IId) (wherein $R^2$, $X^1$ and 'n' are as defined in the general description; Y is CH or N; 'v' is 0, 1 or 2; and 'w' is 1, 2 or 3) is illustrated in Synthetic Scheme 4.

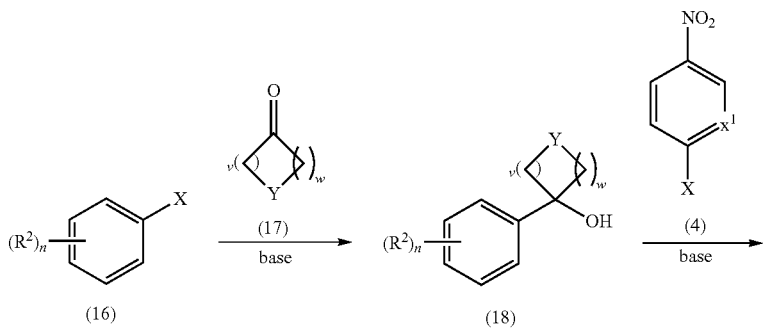

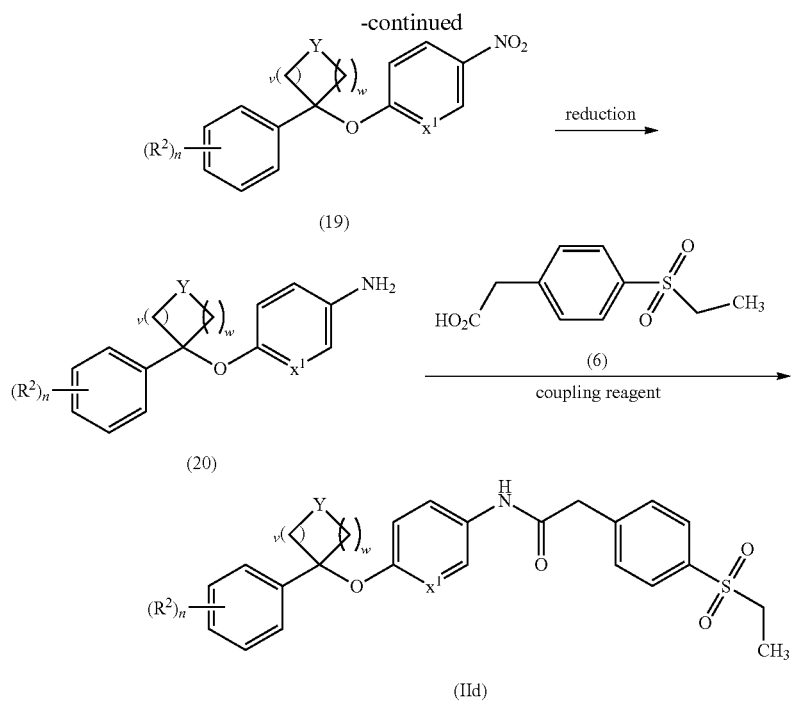

Thus, the metallation of the aryl halide (16) with a suitable base such as n-butyl lithium followed by reaction with an appropriate keto compound of formula (17) affords the alcohol of formula (18). The reaction of Intermediate (18) with 4-halo nitro compound of formula (4) (wherein X is F, Cl, Br or I) yields the compound of formula (19). The reduction of the Intermediate (19) gives the corresponding amine derivative of the formula (20). The reaction of the amine compound of the formula (20) with [4-(ethylsulfonyl)phenyl]acetic acid (6) yields the compound of formula (IId). The amine compound of the formula (20) may be reacted with [4-(ethylsulfonyl)phenyl]acetic acid (6) in the presence of a suitable coupling agent. The suitable coupling agent may be selected from EDCI.HCl, HATU, DCC and CDI with or without HOBt or HOEt or in a combination thereof. The reaction may also optionally carry out in the presence of suitable base selected from $Et_3N$, diethylamine, DIPEA and DMAP. The reaction may be carried out in a suitable solvent or mixture thereof. The suitable solvent may be selected from dichloromethane, $CHCl_3$, THF and DMF or combination thereof.

A general approach for the preparation of compounds of the formula (IIe) (wherein $R^2$, $R^4$ and 'n' are as defined in the general description; Y is CH or N; 'v' is 0, 1 or 2; and 'w' is 1, 2 or 3) is illustrated in Synthetic Scheme 5.

Synthetic scheme 5

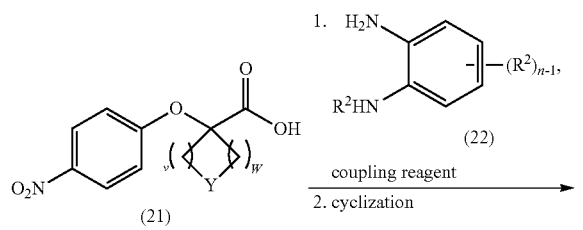

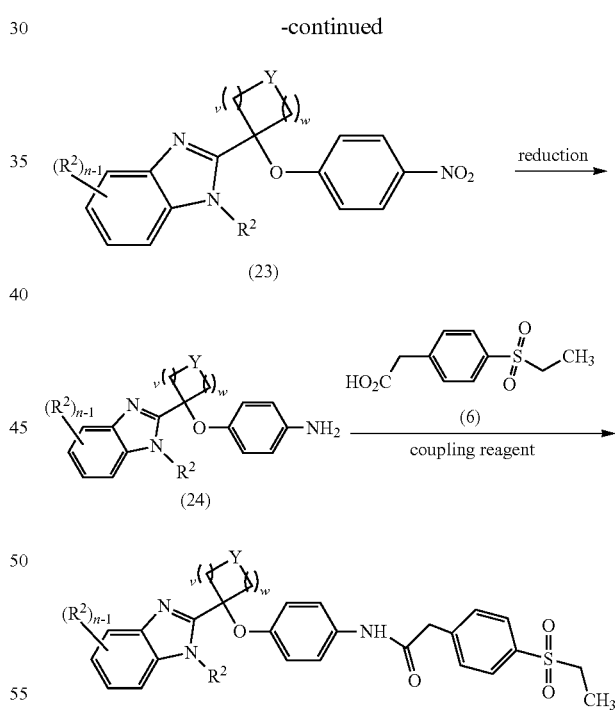

Thus, amide coupling of substituted phenyl acetic acid compound of formula (21) with mono substituted O-phenylenediamine of the formula (22) using suitable coupling agent such as CDI, followed by cyclization in the presence of acetic acid yields substituted 5-nitrobenzimidazole intermediate (23). The reduction of the Intermediate (23) gives the corresponding amine compound of the formula (24). The coupling of the amine compound of the formula (24) with [4-(ethylsulfonyl)phenyl]acetic acid (6) yields the compound of formula (IIe). The amine compound of the formula (24) may be reacted with [4-(ethylsulfonyl)phenyl]acetic acid (6) in the presence of a suitable coupling agent. The suitable coupling agent may be selected from EDCI.HCl, HATU, DCC and CDI with or without HOBt or HOEt or in a combination thereof. The reaction may also optionally carry out in the presence of suitable base selected from Et₃N, diethylamine, DIPEA and DMAP. The reaction may be carried out in a suitable solvent or mixture thereof. The suitable solvent may be selected from dichloromethane, CHCl₃, THF and DMF or combination thereof.

A general approach for the preparation of compounds of the formula (IIf) (wherein R², and 'n' are as defined in the general description, 'v' is 0, 1 or 2, and 'w' is 1, 2 or 3) is illustrated in Synthetic Scheme 6.

Synthetic scheme 6

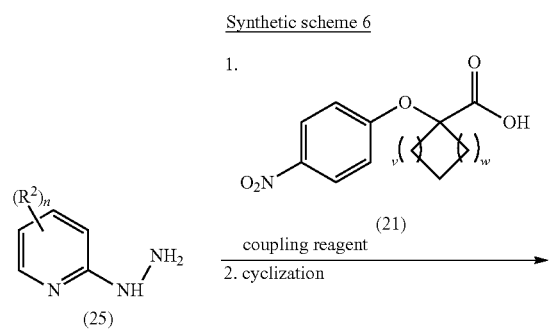

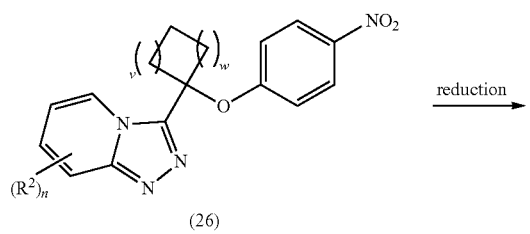

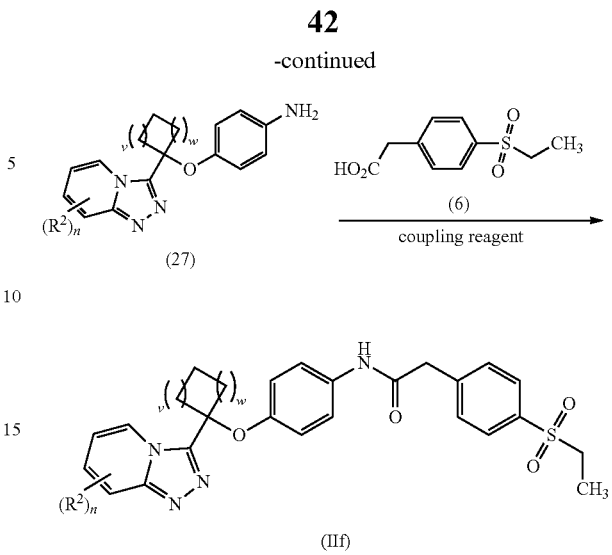

Thus, amide coupling of substituted phenyl acetic acid compound of formula (21) with 2-hydrazinylpyridine compound of the formula (25) using suitable coupling agent such as EDCI, HOBt in the presence of suitable base such as triethylamine, DIPEA followed by cyclization yields substituted 5-nitrophenyl-[1,2,4]triazolo[4,3-a]pyridine intermediate (26). The nitro reduction of the Intermediate (26) gives the corresponding amine compound of the formula (27). The coupling of the amine compound of the formula (27) with [4-(ethylsulfonyl)phenyl]acetic acid (6) yields the compound of formula (IIf). The amine compound of the formula (27) may be reacted with [4-(ethylsulfonyl)phenyl] acetic acid (6) in the presence of a suitable coupling agent. The suitable coupling agent may be selected from EDCI. HCl, HATU, DCC and CDI with or without HOBt or HOEt or in a combination thereof. The reaction may also optionally carry out in the presence of suitable base selected from Et₃N, diethylamine, DIPEA and DMAP. The reaction may be carried out in a suitable solvent or mixture thereof. The suitable solvent may be selected from dichloromethane, CHCl₃, THF and DMF or combination thereof.

A general approach for the preparation of compounds of the formula (IIg) (wherein R², R$^a$, R$^b$ and 'n' are as defined in the general description) is illustrated in Synthetic Scheme 7.

Synthetic scheme 7

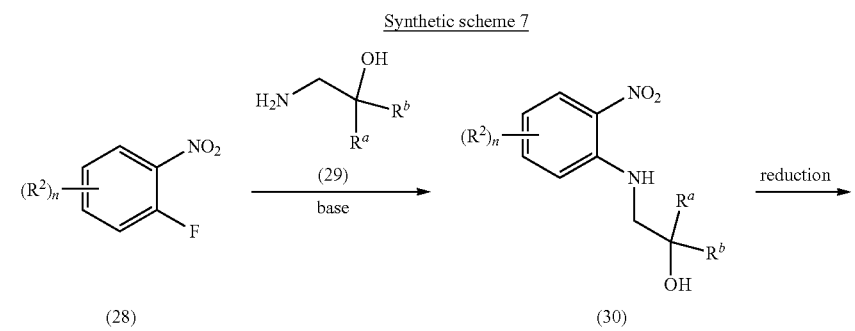

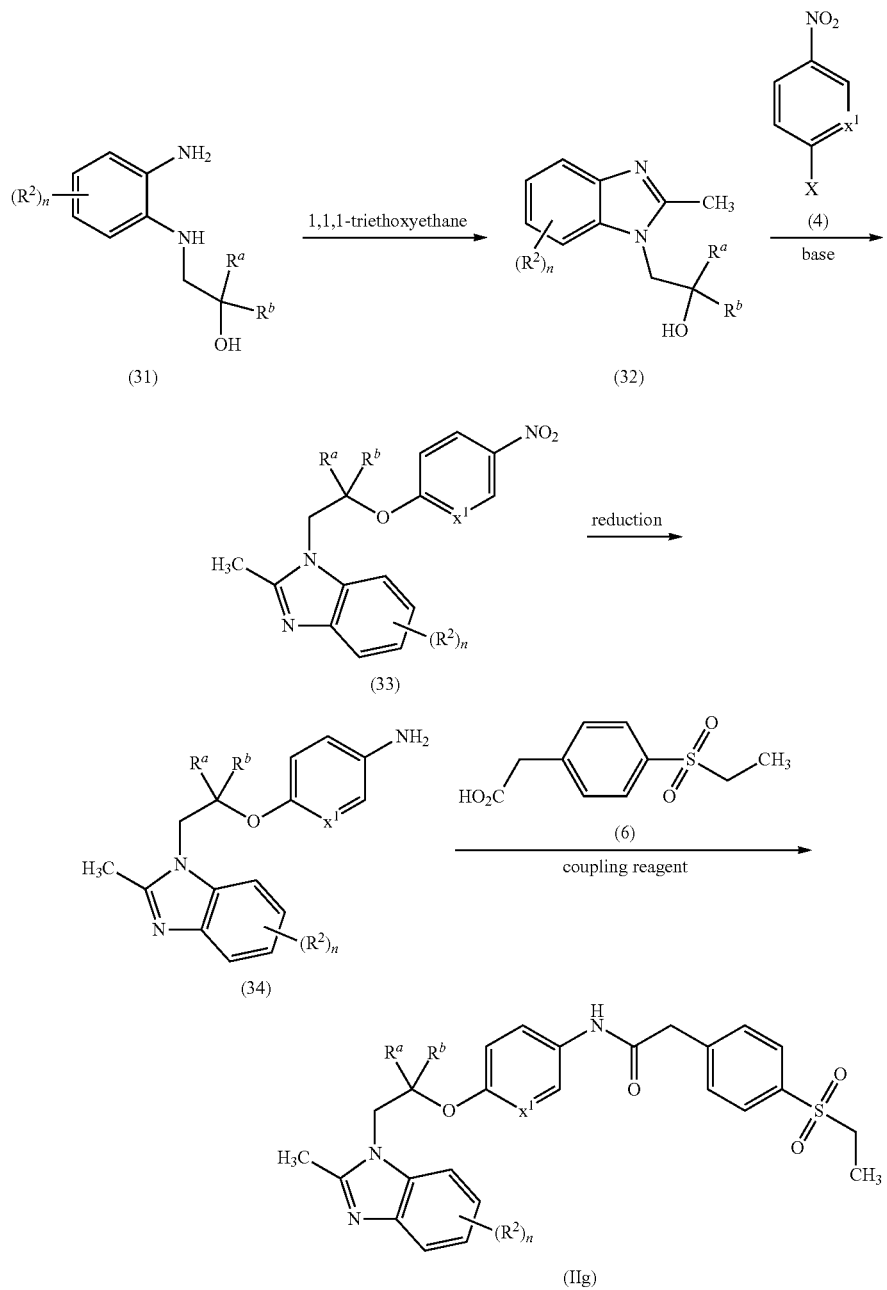

Thus, the substitution of fluoro nitrobenzene compound of the formula (28) with the hydroxyl amine compound of the formula (29) yields the nitro intermediate (30) which on reduction gives the corresponding amine of formula (31). The cyclization of Intermediate (31) with 1,1,1-triethoxyethane gives the hydroxyl substituted benzimidazole compound of formula (32). The reaction of Intermediate (32) with 4-halo nitro compound of the formula (4) (wherein X is F, Cl, Br or I) yields the nitro compound of formula (33). The reduction of the Intermediate (33) gives the amine derivative of the formula (34). The coupling of the amine compound of the formula (34) with [4-(ethylsulfonyl)phenyl]acetic acid (6) yields the compound of formula (IIg). The amine compound of the formula (34) may be reacted with [4-(ethylsulfonyl)phenyl]acetic acid (6) in the presence of a suitable coupling agent. The suitable coupling agent may be selected from EDCI.HCl, HATU, DCC and CDI with or without HOBt or HOEt or in a combination thereof. The reaction may also optionally carry out in the presence of suitable base selected from Et$_3$N, diethylamine, DIPEA and DMAP. The reaction may be carried out in a suitable solvent or mixture thereof. The suitable solvent may be selected from dichloromethane, CHCl$_3$, THF and DMF or combination thereof.

A general approach for the preparation of compounds of the formula (III) (wherein R$^2$, R$^c$, R$^d$, X$^1$ and 'n' are as defined in the general description) is illustrated in Synthetic Scheme 8.

Synthetic scheme 8

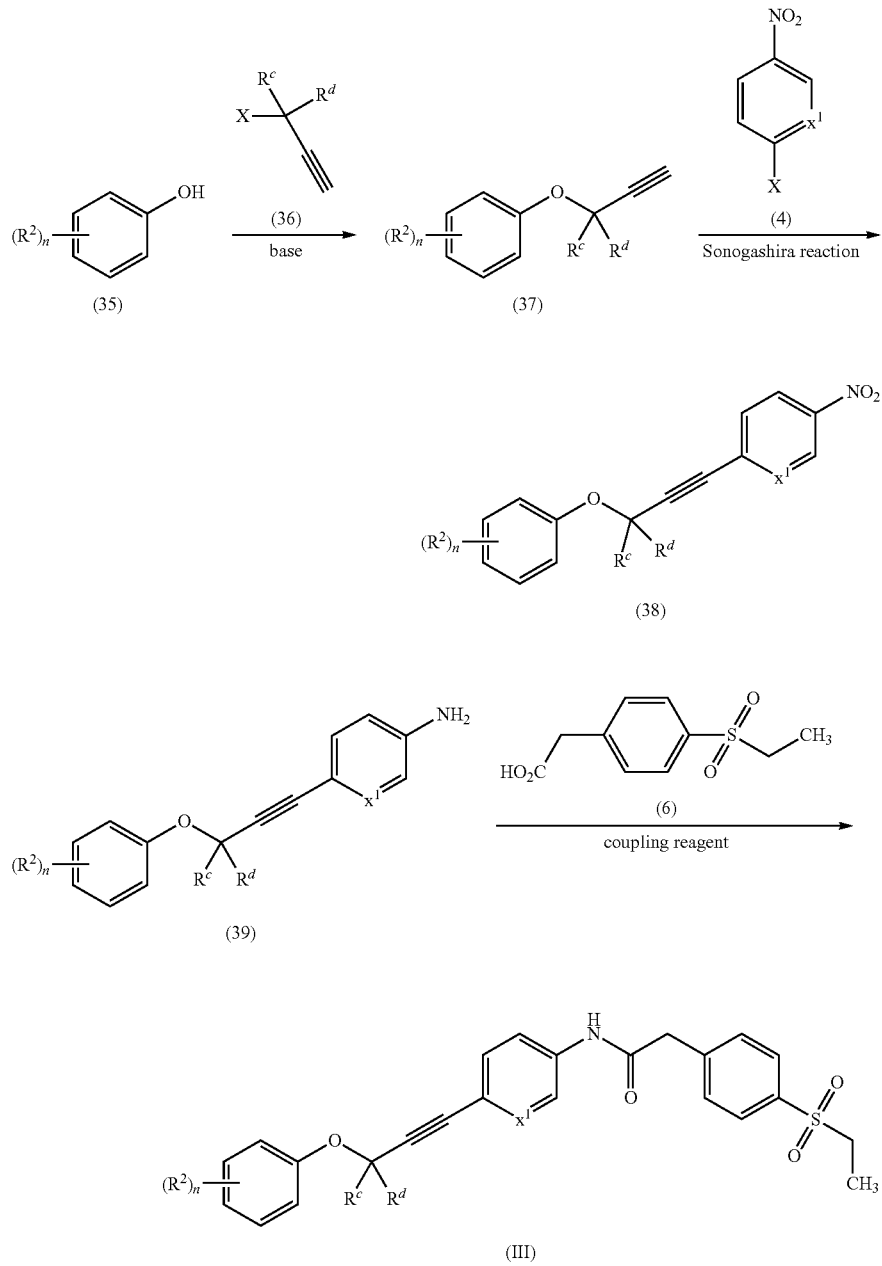

Thus, reaction of the substituted phenol of formula (35) with compound of the formula (36) (wherein X is halogen such as Cl or Br) in the presence of a base such as potassium carbonate gives the acetylene ether Intermediate (37). The Sonogashira coupling reaction of the Intermediate (37) with 4-halonitro compound of formula (4) (wherein X is halogen e.g. Cl or Br) using an appropriate palladium catalyst and copper iodide in presence of a base such as triethylamine gives the Intermediate (38). The reduction of the nitro group Intermediate (38) gives the corresponding amine derivative of the formula (39). The coupling of the amine compound of the formula (39) with [4-(ethylsulfonyl)phenyl]acetic acid (6) yields the compound of formula (III). The amine compound of the formula (39) may be reacted with [4-(ethyl-sulfonyl)phenyl]acetic acid (6) in the presence of a suitable coupling agent. The suitable coupling agent may be selected from EDCI.HCl, HATU, DCC and CDI with or without HOBt or HOEt or in a combination thereof. The reaction may also optionally carry out in the presence of suitable base selected from $Et_3N$, diethylamine, DIPEA and DMAP. The reaction may be carried out in a suitable solvent or mixture thereof. The suitable solvent may be selected from dichloromethane, $CHCl_3$, THF and DMF or combination thereof.

Alternatively, a general approach for the preparation of the compounds of the formula (III), wherein $R^2$, $R^c$, $R^d$, $X^1$ and 'n' are as defined in the general description) is illustrated in synthetic scheme 9.

Synthetic scheme 9

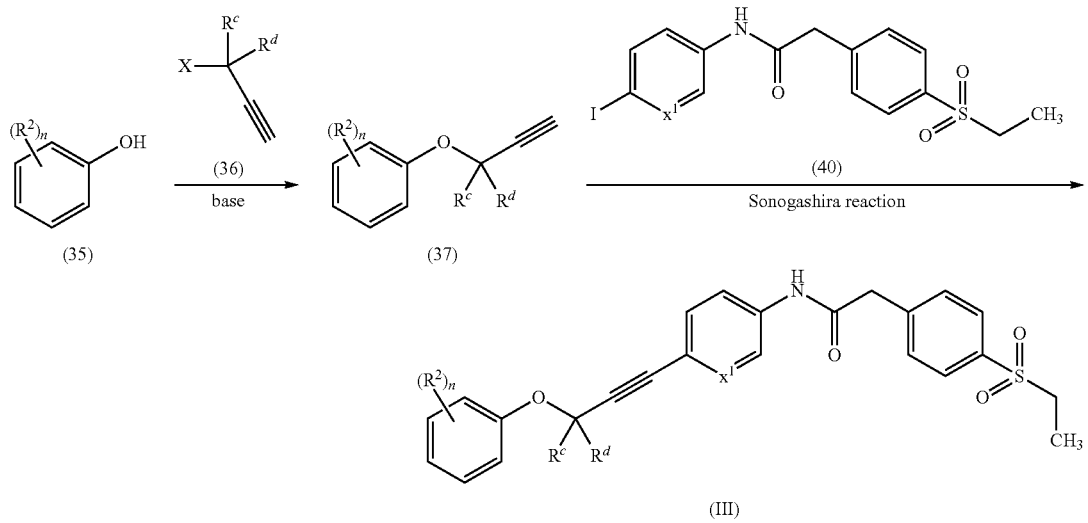

Thus, reaction of the substituted phenol (35) with compound of the formula (36) (wherein X is halogen e.g. Cl or Br) in the presence of base such as potassium carbonate gives the acetylene ether compound of the formula (37). The Sonogashira coupling reaction of the Intermediate (37) with 2-[4-(ethylsulfonyl)phenyl]-N-(4-iodoaryl)acetamide compound of the formula (40) yields the final compound of formula (III). 2-[4-(Ethylsulfonyl)phenyl]-N-(4-iodoaryl) acetamide (40) was prepared by the coupling of an appropriate 4-iodoaryl compound with [4-(ethylsulfonyl)phenyl] acetic acid (6) using coupling agent such as EDCl.HCl in presence of HOBt.

A general approach for the preparation of compounds of the formula (IV) (wherein $R^2$, $R^4$, $R^a$, $R^b$ and 'n' are as defined in the general description) is illustrated in Synthetic Scheme 10.

Synthetic scheme 10

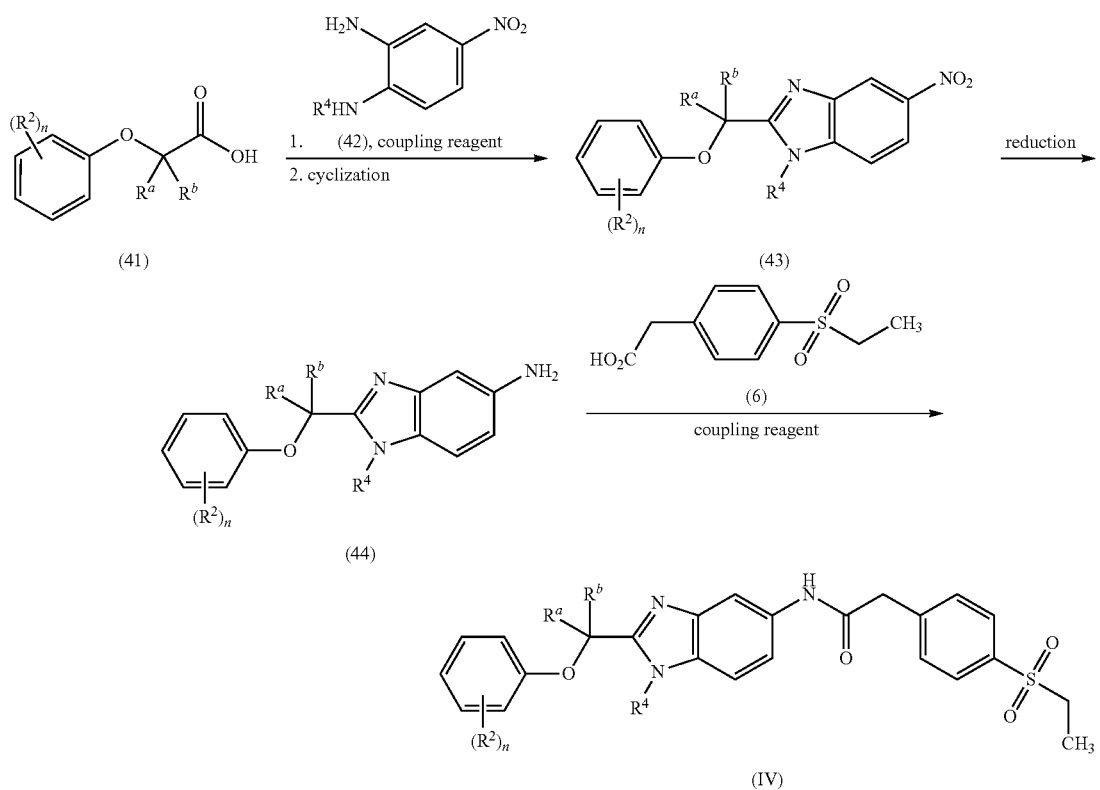

Thus, amide coupling of phenyl acetic acid compound of the formula (41) with O-phenylenediamine of the formula (42) using CDI or other suitable coupling reagent, followed by cyclization in the presence of acetic acid yields substituted 5-nitrobenzimidazole intermediate (43). The reduction of the Intermediate (43) gives the corresponding amine compound of the formula (44). The coupling of the amine compound of the formula (44) with [4-(ethylsulfonyl)phenyl]acetic acid (6) yields the compound of formula (IV). The amine compound of the formula (44) may be reacted with [4-(ethylsulfonyl)phenyl]acetic acid (6) in the presence of a suitable coupling agent. The suitable coupling agent may be selected from EDCI.HCl, HATU, DCC and CDI with or without HOBt or HOEt or in a combination thereof. The reaction may also optionally carry out in the presence of suitable base selected from $Et_3N$, diethylamine, DIPEA and DMAP. The reaction may be carried out in a suitable solvent or mixture thereof. The suitable solvent may be selected from dichloromethane, $CHCl_3$, THF and DMF or combination thereof.

A general approach for the preparation of compounds of the formula (V) (wherein $R^2$, $R^4$, $R^a$, $R^b$, $R^e$ and 'n' are as defined in the general description) is illustrated in Synthetic Scheme 11.

Thus, amide coupling of phenyl acetic acid compound of the formula (8) with substituted aniline compound of the formula (45) using suitable coupling agents, such as EDCI in the presence of HOBt and an appropriate base, such as triethylamine or DIPEA gives the compound of formula (46). The reaction of the compound of formula (46) with suitable halide compound of formula $R^e$—X (wherein X is F, Cl, Br or I) using a suitable base, such as sodium hydride affords compounds of formula (47). The nitro group reduction of the Intermediate (47) gives the corresponding amine compound of the formula (48). The coupling of the amine compound of the formula (48) with [4-(ethylsulfonyl)phenyl]acetic acid (6) yields the compound of formula (V). The amine compound of the formula (48) may be reacted with [4-(ethylsulfonyl)phenyl]acetic acid (6) in the presence of a suitable coupling agent. The suitable coupling agent may be selected from EDCI.HCl, HATU, DCC and CDI with or without HOBt or HOEt or in a combination thereof. The reaction may also optionally carry out in the presence of suitable base selected from $Et_3N$, diethylamine, DIPEA and DMAP. The reaction may be carried out in a suitable solvent or mixture thereof. The suitable solvent may be selected from dichloromethane, $CHCl_3$, THF and DMF or combination thereof.

A general approach for the preparation of compounds of the formula (I) (wherein Ring A, Ring B, L, R, $R^2$, $R^3$, 'p' and 'n' are as defined with respect to a compound of formula (I)) is illustrated in Synthetic Scheme 12.

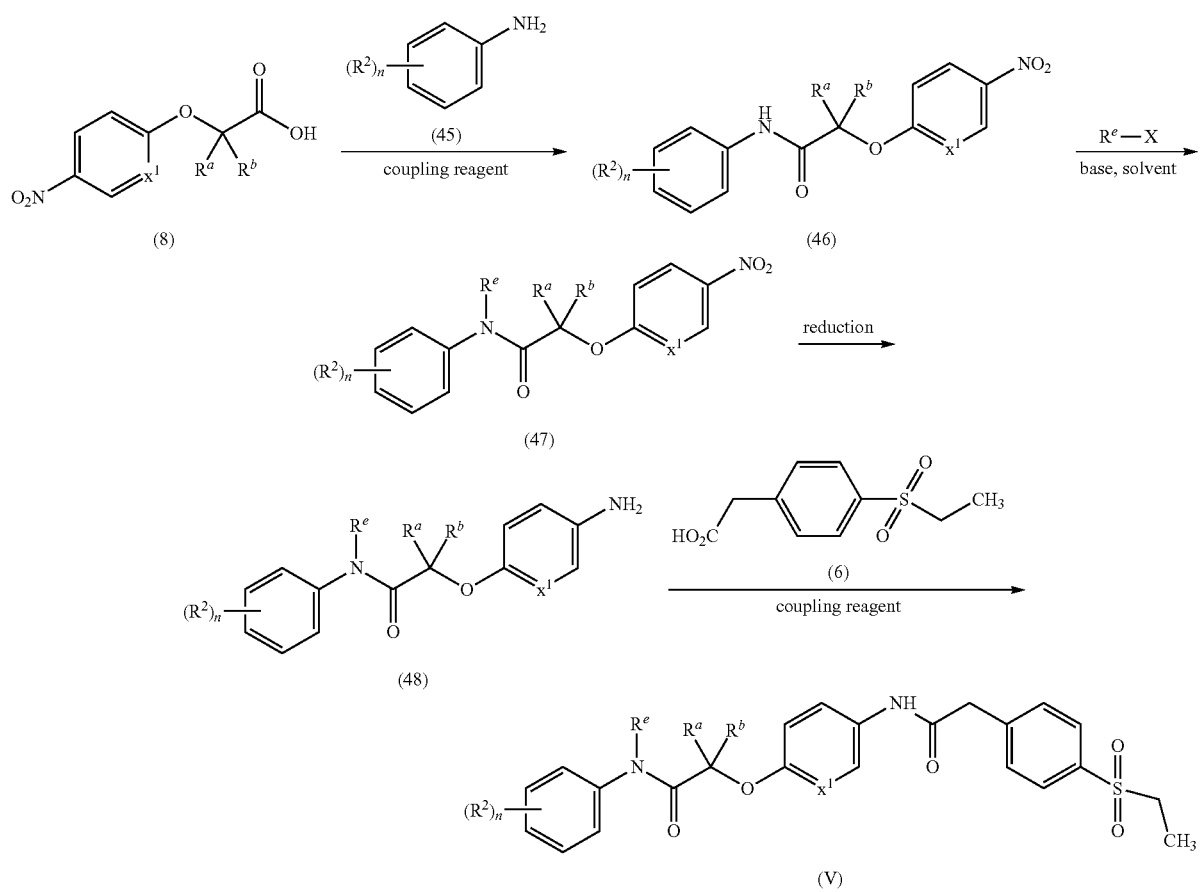

Synthesis scheme 11

Synthetic Scheme 12

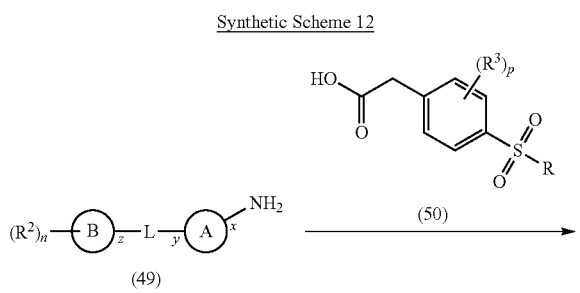

(49)

(50)

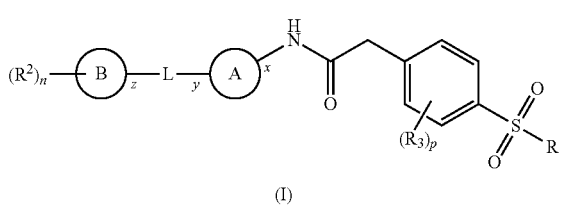

(I)

The process for the preparation of compound of formula (I) or a pharmaceutically acceptable salt thereof, the process comprising:

(i) reacting a compound of formula (49) with a compound of formula (50) to afford a compound of formula (I);

(ii) optionally converting the compound of formula (I) to a pharmaceutically acceptable salt thereof.

In an embodiment, the compound of formula (49) is reacted with compound of formula (50) in the presence of coupling agent. The coupling agent may be selected from EDCI.HCl, HATU, DCC and CDI or combination thereof. The reaction may be carried out optionally in the presence of HOBt or HOEt.

In another embodiment, the compound of formula (49) is reacted with compound of formula (50) in the presence of base selected from Et$_3$N, DIPEA and DMAP or combination thereof.

In yet another embodiment, the compound of formula (49) is reacted with compound of formula (50) in solvent. The solvent may be selected from dichloromethane, CHCl$_3$, THF and DMF or combination thereof.

A general approach for the preparation of compounds of the formula (IV) (wherein Ring B, L, R$^2$, R$^4$ and 'n' are as defined with respect to a compound of formula (IV)) is illustrated in Synthetic Scheme 13.

Synthetic Scheme 13

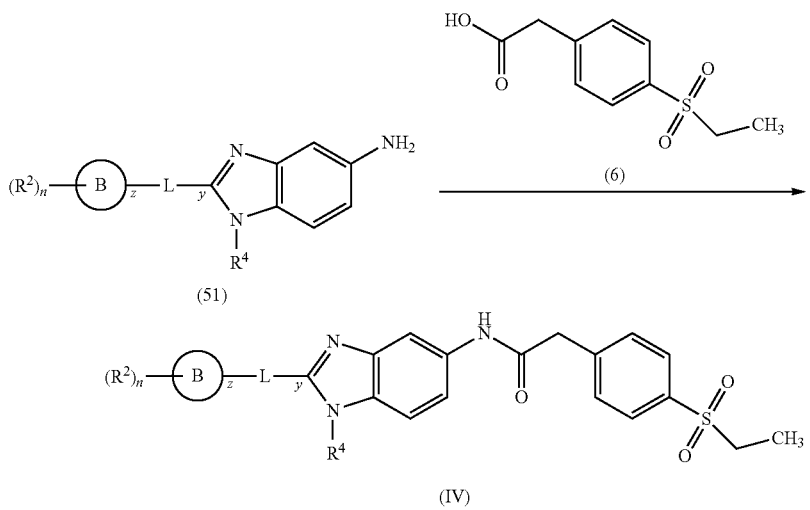

The process for the preparation of compound of formula (IV) or a pharmaceutically acceptable salt thereof, the process comprising:

(i) reacting a compound of formula (51) with a compound of formula (6) to afford a compound of formula (IV);

(ii) optionally converting the compound of formula (IV) to a pharmaceutically acceptable salt thereof.

In an embodiment, the compound of formula (51) is reacted with compound of formula (6) in the presence of coupling agent. The coupling agent may be selected from EDCI.HCl, HATU, DCC and CDI or combination thereof. The reaction may be carried out optionally in the presence of HOBt or HOEt.

In another embodiment, the compound of formula (51) is reacted with compound of formula (6) in the presence of base selected from Et$_3$N, DIPEA and DMAP.

In yet another embodiment, the compound of formula (51) is reacted with compound of formula (6) in solvent. The solvent may be selected from dichloromethane, CHCl$_3$, THF and DMF or combination thereof.

A general approach for the preparation of compounds of the formula (II) (wherein Ring B, L, X$^1$, R$^2$ and 'n' are as defined with respect to a compound of formula (II)) is illustrated in Synthetic Scheme 14.

Synthetic Scheme 14

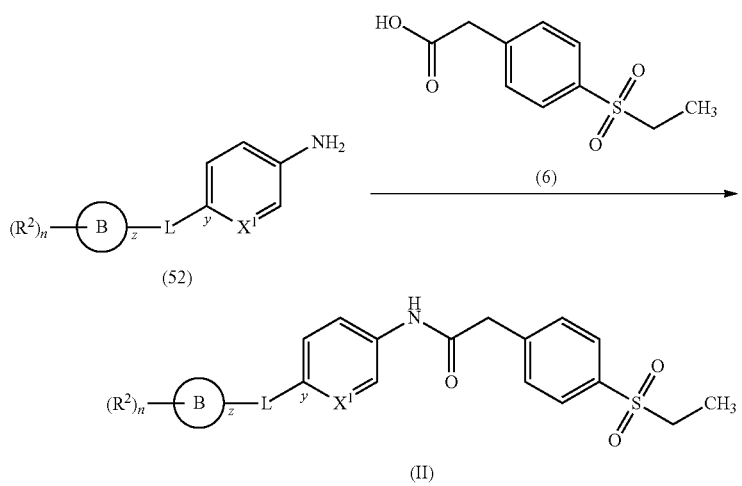

The process for the preparation of compound of formula (II) or a pharmaceutically acceptable salt thereof, the process comprising:

(i) reacting a compound of formula (52) with a compound of formula (6) to afford a compound of formula (II);

(ii) optionally converting the compound of formula (II) to a pharmaceutically acceptable salt thereof.

In an embodiment, the compound of formula (52) is reacted with compound of formula (6) in the presence of coupling agent. The coupling agent may be selected from EDCI.HCl, HATU, DCC and CDI or combination thereof. The reaction may be carried out optionally in the presence of HOBt or HOEt.

In another embodiment, the compound of formula (52) is reacted with compound of formula (6) in the presence of base selected from Et$_3$N, DIPEA and DMAP or combination thereof.

In yet another embodiment, the compound of formula (52) is reacted with compound of formula (6) in solvent. The solvent may be selected from dichloromethane, CHCl$_3$, THF and DMF or combination thereof.

Experimental

The intermediates required for the synthesis are commercially available or alternatively, these intermediates can be prepared using known literature methods. The invention is described in greater detail by way of specific examples.

Unless otherwise stated, work-up includes distribution of the reaction mixture between the organic and aqueous phase indicated within parentheses, separation of layers and drying the organic layer over anhydrous sodium sulfate, filtration and evaporation of the solvent. Purification, unless otherwise mentioned, includes purification by silica gel chromatographic techniques, generally using ethyl acetate/petroleum ether mixture of a suitable polarity as the mobile phase. Use of a different eluent system is indicated within parentheses. The following abbreviations are used in the text: DMSO-d$_6$: Hexadeuterodimethyl sulfoxide; DCM: dichloromethane; DMF: N,N-dimethyl formamide; DIPEA: N,N-diisopropylethylamine; J: Coupling constant in units of Hz; RT or rt: room temperature (22-26° C.); h: hour (s); min: minute (s); Aq.: aqueous; equiv. or eq.: equivalents; DMAP: 4-dimethylaminopyridine; HOBt: Hydroxybenzotriazole; EDCI.HCl: 1-Ethyl-3-(3-dimethylaminopropyl) carbodiimide Hydrochloride; CDI: 1,1'-carbonyldiimidazole; HATU: 1-[Bis(dimethylamino)methylene]-1H-1,2,3-triazolo[4,5-b]pyridinium 3-oxide hexafluorophosphate or N-[(Dimethylamino)-1H-1,2,3-triazolo-[4,5-b]pyridin-1-ylmethylene]-N-methylmethanaminium hexafluorophosphate N-oxide; DCC: N,N'-Dicyclohexylcarbodiimide; LAH: Lithium Aluminum Hydride; THF: Tetrahydrofuran.

The following intermediates required for the synthesis of compounds of the present invention are prepared using the approaches described above in synthetic schemes.

INTERMEDIATES

Intermediate 1

4-{[2-(3,4-Difluorophenyl)propan-2-yl]oxy}aniline

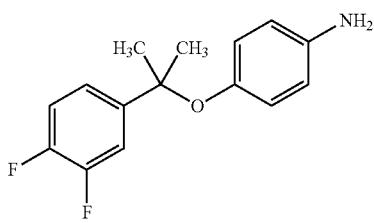 [SMILES: CC(C)(Oc1ccc(N)cc1)c1ccc(F)c(F)c1]

Step 1: 2-(3,4-Difluorophenyl)propan-2-ol

To the stirred and cooled (−78° C.) solution of 3,4-difluoroacetophenone (1 g, 6.404 mmol) in diethyl ether (10 mL) was added methyl magnesium bromide (3M in ether, 1.9 mL, 6.405 mmol). The reaction mixture was allowed to gradually warm up to RT and stirred for 18 h. The reaction mixture was diluted with saturated ammonium chloride solution (50 mL) and extracted with ethyl acetate (2×50 mL). The combined organic layers were washed with water (2×50 mL) and brine (50 mL) and dried over anhydrous sodium sulfate. The solvent was concentrated under reduced pressure and the residue obtained was purified by silica gel column chromatography to yield 542 mg of the title product as semi-solid; $^1$H NMR (300 MHz, DMSO-$d_6$) δ 1.40 (s, 6H), 5.19 (s, 1H), 7.28-7.34 (m, 2H), 7.41-7.48 (m, 1H).

Step 2: 1,2-Difluoro-4-[2-(4-nitrophenoxy)propan-2-yl]benzene

To a stirred and cooled (0° C.) solution of step 1 intermediate (260 mg, 1.510 mmol) in dry DMF (4 mL) was added sodium hydride (60% w/w, 90 mg, 2.265 mmol) and the reaction was stirred at RT for 30 min. 1-Fluoro-4-nitrobenzene (0.16 mL, 1.510 mmol) was added to the reaction mixture and stirred for 2 hours at RT. The mixture was diluted with water (20 mL) and extracted with ethyl acetate (3×20 mL). The combined organic layers were washed with water (2×50 mL), brine (50 mL) and dried over anhydrous sodium sulfate. The solvent was distilled off under reduced pressure and the residue obtained was purified by silica gel column chromatography to yield 163 mg of the title product as a semi-solid. $^1$H NMR (300 MHz, DMSO-$d_6$) δ 1.75 (s, 6H), 6.81 (d, J=8.7 Hz, 2H), 7.27 (br s, 1H), 7.40-7.43 (m, 2H), 8.05 (d, J=8.7 Hz, 2H).

Step 3: 4-{[2-(3,4-Difluorophenyl)propan-2-yl]oxy}aniline

To a stirred solution of step 2 intermediate (150 mg, 0.511 mmol) and nickel chloride (766 mg, 1.022 mmol) in methanol (10 mL) was added sodium borohydride (243 mg, 1.022 mmol) in small portions at RT. The reaction mixture was stirred at RT for 1 h. The mixture was concentrated under reduced pressure to yield a viscous residue. The residue was diluted with water (20 mL) and ethyl acetate (20 mL). The layers were separated and the aqueous layer was extracted with ethyl acetate (2×20 mL). The combined organic layers were washed with water (50 mL), brine (25 mL) and dried over anhydrous sodium sulfate. The solvent was distilled off under reduced pressure and the residue obtained was purified by silica gel column chromatography to yield 134 mg of the title product as a semi-solid. $^1$H NMR (300 MHz, DMSO-$d_6$) δ 1.50 (s, 6H), 4.72 (br s, 2H), 6.37 (d, J=8.4 Hz, 2H), 6.44 (d, J=8.4 Hz, 2H), 7.35-7.44 (m, 2H), 7.48-7.55 (m, 1H); APCI-MS (m/z) 264 (M+H)$^+$.

Intermediate 2

4-{[2-(2,4-Difluorophenyl)propan-2-yl]oxy}aniline

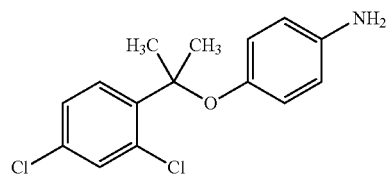

Step 1: 2-(2,4-Difluorophenyl)propan-2-ol

The title compound was prepared by the reaction of methyl 2,4-difluorobenzoate (2.0 g, 13.878 mmol) and methyl magnesium bromide (3M in ether, 11.5 mL) in diethyl ether (20 mL) as per the process described in step 1 of Intermediate 1 to yield 1.25 g of the product as a liquid. $^1$H NMR (300 MHz, DMSO-$d_6$) δ 1.43 (s, 6H), 5.31 (s, 2H), 6.98-7.13 (m, 2H), 7.57-7.65 (m, 1H)

Step 2: 2,4-Difluoro-1-[2-(4-nitrophenoxy)propan-2-yl]benzene

The title compound was synthesized by the reaction of step 1 intermediate (500 mg, 2.904 mmol) with 1-fluoro-4-nitrobenzene (409 mg, 2.904 mmol) using sodium hydride (60% w/w, 174 mg, 4.356 mmol) in DMF (10 mL) as per the process described in step 2 of Intermediate 1 to yield 310 mg of the product as a semi-solid. $^1$H NMR (300 MHz, DMSO-$d_6$) δ 1.81 (s, 6H), 6.86 (d, J=9.3 Hz, 2H), 7.14-7.24 (m, 2H), 7.50-7.54 (m, 1H), 8.06 (d, J=9.3 Hz, 2H).

Step 3: 4-{[2-(2,4-Difluorophenyl)propan-2-yl]oxy}aniline

The title compound was synthesized by the nitro reduction of the step 2 intermediate (300 mg, 1.023 mmol) by using sodium borohydride (154 mg, 4.091 mmol) and nickel chloride (486 mg, 2.045 mmol) in methanol (10 mL) as per the process described in step 3 of Intermediate 1 to yield 251 mg of the product as a liquid. $^1$H NMR (300 MHz, DMSO-$d_6$) δ 1.56 (s, 6H), 4.75 (br s, 2H), 6.37 (d, J=8.7 Hz, 2H), 6.46 (d, J=9.0 Hz, 2H), 7.04 (t, J=9.0 Hz, 1H), 7.22 (t, J=9.3 Hz, 1H), 7.47-7.52 (m, 1H); ESI-MS (m/z) 263 (M+H)$^+$.

Intermediate 3

4-{[2-(2,4-Dichlorophenyl)propan-2-yl]oxy}aniline

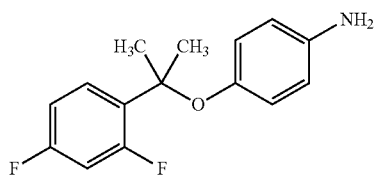 [SMILES: CC(C)(Oc1ccc(N)cc1)c1ccc(F)cc1F]

Step 1: 2-(2,4-Dichlorophenyl)propan-2-ol

To the stirred and cooled (−78° C.) solution of methyl 2,4-dichlorobenzoate (1.0 g, 4.877 mmol) in diethyl ether (20 mL) was added methyl magnesium bromide (3M in ether, 4.0 mL, 12.192 mmol). The reaction mixture was allowed to gradually warm to RT and stirred for 18 hours. The mixture was diluted with saturated ammonium chloride solution (50 mL) and extracted with ethyl acetate (2×50 mL). The combined organic layers were washed with water (2×50 mL) and brine (50 mL) and dried over anhydrous sodium sulfate. The solvent was distilled off under reduced pressure and the residue obtained was purified by silica gel column chromatography to yield 710 mg of the title product as semi-solid. $^1$H NMR (300 MHz, DMSO-$d_6$) δ 1.54 (s, 6H), 5.38 (s, 1H), 7.40 (d, J=9.0 Hz, 1H), 7.47 (s, 1H), 7.82 (d, J=8.1 Hz, 1H); APCI-MS (m/z) 203 (M+H)$^+$.

Step 2: 2,4-Dichloro-1-[2-(4-nitrophenoxy)propan-2-yl]benzene

To a stirred and cooled (0° C.) solution of step 1 intermediate (700 mg, 3.428 mmol) in dry DMF (10 mL) was added sodium hydride (60% w/w, 205 mg, 5.142 mmol) and stirred at RT for 30 minutes. 1-Fluoro-4-nitrobenzene (483 mg, 3.428 mmol) was added to the mixture and further stirred for 2 hours at RT. The reaction mixture was concentrated under reduced pressure. The residue was diluted with water (20 mL) and extracted with ethyl acetate (3×20 mL). The combined organic layers were washed with water (2×50 mL), brine (50 mL) and dried over anhydrous sodium sulfate. The solvent was distilled off under reduced pressure and the residue obtained was purified by silica gel column chromatography to yield 246 mg of the title product as a semi-solid. $^1$H NMR (300 MHz, DMSO-$d_6$) δ 1.87 (s, 6H), 6.81 (d, J=9.3 Hz, 2H), 7.51-7.56 (m, 2H), 7.66 (d, J=8.4 Hz, 1H), 8.05 (d, J=8.7 Hz, 2H).

Step 3: 4-{[2-(2,4-Dichlorophenyl)propan-2-yl]oxy}aniline

To a stirred solution of step 2 intermediate (230 mg, 0.705 mmol) and nickel chloride (335 mg, 1.410 mmol) in methanol (10 mL) was added sodium borohydride (106 mg, 2.820 mmol) in portions. The reaction mixture was stirred at room temperature for 1 hour. The mixture was concentrated under reduced pressure to yield residue. The residue was diluted with water (20 mL) and ethyl acetate (20 mL). The layers were separated and the aqueous layer was extracted with ethyl acetate (2×20 mL). The combined organic layers were washed with water (50 mL) followed by brine (25 mL) and dried over anhydrous sodium sulfate. The solvent was distilled off under reduced pressure and the residue obtained was purified by silica gel column chromatography to yield 224 mg of the title product as a semi-solid. $^1$H NMR (300 MHz, DMSO-$d_6$) δ 1.65 (s, 6H), 4.69 (br s, 2H), 6.36 (d, J=9.0 Hz, 2H), 6.43 (d, J=8.7 Hz, 2H), 7.41 (d, J=8.4 Hz, 1H), 7.58 (d, J=8.4 Hz, 2H); APCI-MS (m/z) 264 (M+H)$^+$.

Intermediate 4

4-{[2-(3,4-Dichlorophenyl)propan-2-yl]oxy}aniline

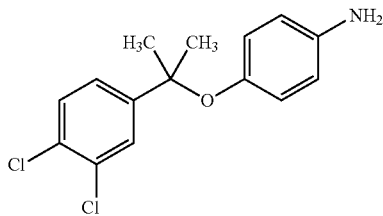 [SMILES: CC(C)(Oc1ccc(N)cc1)c1ccc(Cl)c(Cl)c1]

Step 1: 2-(3,4-Dichlorophenyl)propan-2-ol

The title compound was prepared by the reaction of 3,4-dichloroacetophenone (1.0 g, 5.289 mmol) and methyl magnesium bromide (3M in hexane, 1.76 mL) in THF (15 mL) as per the process described in step 1 of Intermediate 1 to yield 400 mg of the product as a liquid. $^1$H NMR (300 MHz, DMSO-$d_6$) δ 1.40 (s, 6H), 5.26 (s, 1H), 7.44 (d, J=8.7 Hz, 1H), 7.56 (d, J=8.1 Hz, 1H), 7.67 (s, 1H).

Step 2: 3,4-Dichloro-1-[2-(4-nitrophenoxy)propan-2-yl]benzene

The title compound was synthesized by the reaction of step 1 intermediate (100 mg, 0.487 mmol) with 1-fluoro-4-nitrobenzene (52 mg, 0.487 mmol) by using sodium hydride (60% w/w, 29 mg, 0.731 mmol) in DMF (5 mL) as per the process described in step 2 of Intermediate 1 to yield 85 mg of the product as a liquid. $^1$H NMR (300 MHz, DMSO-$d_6$) δ 1.75 (s, 6H), 6.84 (d, J=9.0 Hz, 2H), 7.41 (d, J=9.3 Hz, 1H), 7.66 (d, J=9.9 Hz, 2H), 8.08 (d, J=8.7 Hz, 2H).

Step 3: 4-{[2-(3,4-Dichlorophenyl)propan-2-yl]oxy}aniline

The title compound was synthesized by the nitro reduction of the step 2 intermediate (80 mg, 0.245 mmol) by using sodium borohydride (37 mg, 0.980 mmol) and nickel chloride (116 mg, 0.490 mmol) in methanol (5 mL) as per the process described in step 3 of Intermediate 1 to yield 75 mg of the product as a liquid. $^1$H NMR (300 MHz, DMSO-$d_6$) δ 1.50 (s, 6H), 4.76 (br s, 2H), 6.38 (d, J=8.4 Hz, 2H), 6.45 (d, J=8.7 Hz, 2H), 7.49 (d, J=8.1 Hz, 1H), 7.62 (d, J=7.8 Hz, 1H), 7.69 (br s, 1H); APCI-MS (m/z) 296 (M+H)$^+$.

Intermediate 5

4-{[2-(3,5-Dichlorophenyl)propan-2-yl]oxy}aniline

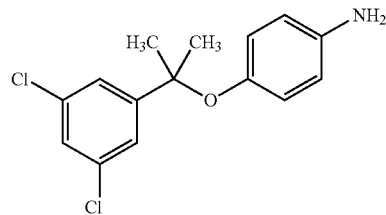 [SMILES: CC(C)(Oc1ccc(N)cc1)c1cc(Cl)cc(Cl)c1]

Step 1: 2-(3,5-Dichlorophenyl)propan-2-ol

The title compound was prepared by the reaction of methyl 3,5-dichlorobenzoate (1.0 g, 4.877 mmol) and methyl magnesium bromide (3M in diethyl ether, 4.0 mL) in diethyl ether (10 mL) as per the process described in step 1 of Intermediate 1 to yield 673 mg of the product as a semi-solid. $^1$H NMR (300 MHz, DMSO-$d_6$) δ 1.40 (s, 6H), 5.30 (s, 1H), 7.42 (s, 1H), 7.47 (s, 2H)

Step 2: 3,5-Dichloro-1-[2-(4-nitrophenoxy)propan-2-yl]benzene

The title compound was synthesized by the reaction of step 1 intermediate (300 mg, 1.462 mmol) with 1-fluoro-4-nitrobenzene (206 mg, 1.462 mmol) by using sodium hydride (60% w/w, 88 mg, 2.194 mmol) in DMF (10 mL) as per the process described in step 2 of Intermediate 1 to yield 377 mg of the product as a liquid. $^1$H NMR (300 MHz, DMSO-$d_6$) δ 1.75 (s, 6H), 6.85 (d, J=8.4 Hz, 2H), 7.45 (s, 2H), 7.58 (s, 1H), 8.09 (d, J=9.3 Hz, 2H).

Step 3: 4-{[2-(3,5-Dichlorophenyl)propan-2-yl]oxy}aniline

The title compound was synthesized by the nitro reduction of the step 2 intermediate (360 mg, 1.103 mmol) using sodium borohydride (167 mg, 4.414 mmol) and nickel chloride (525 mg, 2.207 mmol) in methanol (10 mL) as per the process described in step 3 of Intermediate 1 to yield 270 mg of the product as a semi-solid. $^1$H NMR (300 MHz, DMSO-$d_6$) δ 1.50 (s, 6H), 4.75 (br s, 2H), 6.39 (d, J=7.8 Hz, 2H), 6.47 (d, J=8.4 Hz, 2H), 7.52 (br s, 3H); APCI-MS (m/z) 296 (M+H)$^+$.

Intermediate 6

4-{[2-(4-Chloro-2-fluorophenyl)propan-2-yl]oxy}aniline

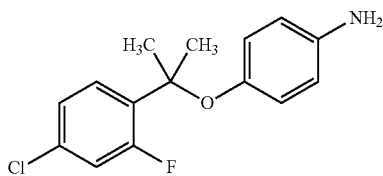 [SMILES: CC(C)(Oc1ccc(N)cc1)c1ccc(Cl)cc1F]

Step 1: 2-(4-Chloro-2-fluorophenyl)propan-2-ol

The title compound was prepared by the reaction of methyl 4-chloro-2-fluorobenzoate (2.0 g, 10.603 mmol) and methyl magnesium bromide (3M in diethyl ether, 8.8 mL) in diethyl ether (40 mL) as per the process described in step 1 of Intermediate 1 to yield 2.01 g of the product as a semi-solid. $^1$H NMR (300 MHz, DMSO-$d_6$) δ 1.45 (s, 6H), 5.38 (s, 1H), 7.24-7.33 (m, 2H), 7.62 (t, J=9.0 Hz, 1H).

Step 2: 2-(4-Chloro-2-fluorophenyl)propan-2-yl 4-nitrophenyl ether

The title compound was synthesized by the reaction of step 1 intermediate (500 mg, 2.650 mmol) with 1-fluoro-4-nitrobenzene (374 mg, 2.650 mmol) by using sodium hydride (60% w/w, 159 mg, 3.976 mmol) in DMF (10 mL) as per the process described in step 2 of Intermediate 1 to yield 668 mg of the product as a semi-solid. $^1$H NMR (300 MHz, DMSO-$d_6$) δ 1.80 (s, 6H), 6.87 (d, J=9.3 Hz, 2H), 7.36 (d, J=8.4 Hz, 1H), 7.41-7.52 (m, 2H), 8.07 (d, J=9.3 Hz, 2H).

Step 3: 4-{[2-(4-Chloro-2-fluorophenyl)propan-2-yl]oxy}aniline

The title compound was synthesized by the nitro reduction of the step 2 intermediate (650 mg, 2.098 mmol) by using sodium borohydride (317 mg, 8.394 mmol) and nickel chloride (998 mg, 4.193 mmol) in methanol (10 mL) as per the process described in step 3 of Intermediate 1 to yield 477 mg of the product as a semi-solid. $^1$H NMR (300 MHz, DMSO-$d_6$) δ 1.56 (s, 6H), 4.74 (br s, 2H), 6.38 (d, J=8.1 Hz, 2H), 6.48 (d, J=8.7 Hz, 2H), 7.26 (t, J=6.3 Hz, 1H), 7.39-7.44 (m, 1H), 7.50 (t, J=9.0 Hz, 1H); APCI-MS (m/z) 279 (M+H)$^+$.

Intermediate 7

4-{[2-(4-Chloro-3-fluorophenyl)propan-2-yl]oxy}aniline

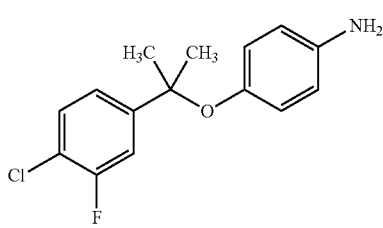 [SMILES: CC(C)(Oc1ccc(N)cc1)c1ccc(Cl)c(F)c1]

Step 1: 2-(4-Chloro-3-fluorophenyl)propan-2-ol

The title compound was prepared by the reaction of methyl 4-chloro-3-fluorobenzoate (1.0 g, 15.302 mmol) and methyl magnesium bromide (3M in diethyl ether, 4.4 mL) in diethyl ether (20 mL) as per the process described in step 1 of Intermediate 1 to yield 380 mg of the product as a semi-solid. $^1$H NMR (300 MHz, DMSO-$d_6$) δ 1.39 (s, 6H), 5.23 (s, 1H), 7.31 (d, J=8.4 Hz, 1H), 7.41-7.51 (m, 2H).

Step 2: 1-Chloro-2-fluoro-4-[2-(4-nitrophenoxy)propan-2-yl]benzene

The title compound was synthesized by the reaction of step 1 intermediate (170 mg, 0.901 mmol) with 1-fluoro-4-nitrobenzene (127 mg, 0.901 mmol) by using sodium hydride (60% w/w, 54 mg, 1.351 mmol) in DMF (4 mL) as per the process described in step 2 of Intermediate 1 to yield 195 mg of the product as a semi-solid. $^1$H NMR (300 MHz, DMSO-$d_6$) δ 1.75 (s, 6H), 6.83 (d, J=9.3 Hz, 2H), 7.29 (d, J=8.7 Hz, 1H), 7.46-7.50 (m, 1H), 7.60 (t, J=8.1 Hz, 1H), 8.07 (d, J=9.3 Hz, 2H).

Step 3: 4-{[2-(4-Chloro-3-fluorophenyl)propan-2-yl]oxy}aniline

The title compound was synthesized by the nitro reduction of the step 2 intermediate (180 mg, 0.581 mmol) by using sodium borohydride (88 mg, 2.324 mmol) and nickel chloride (276 mg, 1.162 mmol) in methanol (5 mL) as per the process described in step 3 of Intermediate 1 to yield 115 mg of the product as a semi-solid. $^1$H NMR (300 MHz, DMSO-$d_6$) δ 1.50 (s, 6H), 4.72 (br s, 2H), 6.44 (dd, J=9.0, 22.8 Hz, 4H), 7.37 (d, J=8.7 Hz, 1H), 7.47-6.59 (m, 2H); ESI-MS (m/z) 279 (M+H)$^+$.

Intermediate 8

4-{[2-(2-Chloro-4-fluorophenyl)propan-2-yl]oxy}aniline

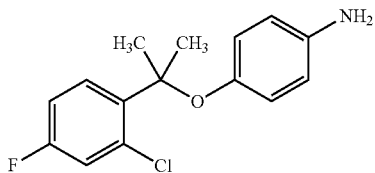 [SMILES: CC(C)(Oc1ccc(N)cc1)c1ccc(F)cc1Cl]

Step 1: 2-(2-Chloro-4-fluorophenyl)propan-2-ol

The title compound was prepared by the reaction of methyl 2-chloro-4-fluorobenzoate (550 mg, 2.916 mmol) and methyl magnesium bromide (3M in diethyl ether, 2.4 mL) in diethyl ether (10 mL) as per the process described in step 1 of Intermediate 1 to yield 513 g of the product as a liquid. $^1$H NMR (300 MHz, DMSO-$d_6$) δ 1.57 (s, 6H), 5.37 (s, 2H), 7.16-7.22 (m, 1H), 7.30-7.38 (m, 1H), 7.81-7.86 (m, 1H)

Step 2: 2-(2-Chloro-4-fluorophenyl)propan-2-yl 4-nitrophenyl ether

The title compound was synthesized by the reaction of step 1 intermediate (500 mg, 2.650 mmol) with 1-fluoro-4- nitrobenzene (374 mg, 2.650 mmol) by using sodium hydride (60% w/w, 159 mg, 3.976 mmol) in DMF (10 mL) as per the process described in step 2 of Intermediate 1 to yield 213 mg of the product as a semi-solid. $^1$H NMR (300 MHz, DMSO-$d_6$) δ 1.88 (s, 6H), 6.80 (d, J=9.3 Hz, 2H), 7.14 (d, J=9.3 Hz, 1H), 7.30-7.41 (m, 2H), 7.66-7.71 (m, 1H), 8.04 (d, J=9.3 Hz, 1H), 8.21 (d, J=9.3 Hz, 1H); APCI-MS (m/z) 309 (M+H)$^+$.

Step 3: 4-{[2-(2-Chloro-4-fluorophenyl)propan-2-yl]oxy}aniline

The title compound was synthesized by the nitro reduction of the step 2 intermediate (200 mg, 0.645 mmol) by using sodium borohydride (96 mg, 2.582 mmol) and nickel chloride (309 mg, 1.291 mmol) in methanol (10 mL) as per the process described in step 3 of Intermediate 1 to yield 131 mg of the product as a solid. $^1$H NMR (300 MHz, DMSO-$d_6$) δ 1.65 (s, 6H), 4.69 (br s, 2H), 6.35 (d, J=8.4 Hz, 2H), 6.43 (d, J=9.0 Hz, 2H), 7.19 (t, J=8.4 Hz, 1H), 7.42 (d, J=8.7 Hz, 1H), 7.56-7.61 (m, 1H); APCI-MS (m/z) 279 (M)$^+$.

Intermediate 9

4-({2-[4-(Trifluoromethyl)phenyl]propan-2-yl}oxy)aniline

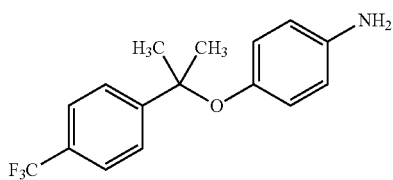 [SMILES: CC(C)(Oc1ccc(N)cc1)c1ccc(C(F)(F)F)cc1]

Step 1: 2-[4-(Trifluoromethyl)phenyl]propan-2-ol

The title compound was prepared by the reaction of methyl 4-(trifluoromethyl)benzoate (1.0 g, 4.901 mmol) and methyl magnesium bromide (3M in diethyl ether, 4.0 mL) in diethyl ether (20 mL) as per the process described in step 1 of Intermediate 1 to yield 163 mg of the product as a semi-solid. $^1$H NMR (300 MHz, DMSO-$d_6$) δ 1.43 (s, 6H), 5.22 (s, 1H), 7.67 (br s, 4H)

Step 2: 1-Nitro-4-({2-[4-(trifluoromethyl)phenyl]propan-2-yl}oxy)benzene

The title compound was synthesized by the reaction of step 1 intermediate (140 mg, 0.685 mmol) with 1-fluoro-4-nitrobenzene (97 mg, 0.685 mmol) by using sodium hydride (60% w/w, 41 mg, 1.028 mmol) in DMF (4 mL) as per the process described in step 2 of Intermediate 1 to yield 141 mg of the product as a semi-solid. $^1$H NMR (300 MHz, DMSO-$d_6$) δ 1.79 (s, 6H), 6.81 (d, J=9.3 Hz, 2H), 7.66 (d, J=8.4 Hz, 2H), 7.77 (d, J=8.4 Hz, 2H), 8.07 (d, J=8.7 Hz, 2H).

Step 3: 4-({2-[4-(Trifluoromethyl)phenyl]propan-2-yl}oxy)aniline

The title compound was synthesized by the nitro reduction of the step 2 intermediate (135 mg, 0.415 mmol) by using sodium borohydride (63 mg, 1.660 mmol) and nickel chloride (198 mg, 0.830 mmol) in methanol (4 mL) as per the process described in step 3 of Intermediate 1 to yield 81 mg of the product as a semi-solid. $^1$H NMR (300 MHz, DMSO-$d_6$) δ 1.53 (s, 6H), 4.70 (br s, 2H), 6.37 (d, J=7.2 Hz, 2H), 6.45 (d, J=8.1 Hz, 2H), 7.72 (br s, 4H); APCI-MS (m/z) 296 (M+H)$^+$.

Intermediate 10

4-({2-[3-Fluoro-4-(trifluoromethyl)phenyl]propan-2-yl}oxy)aniline

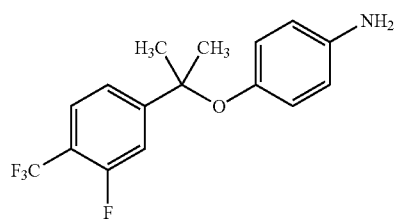 [SMILES: CC(C)(Oc1ccc(N)cc1)c1ccc(C(F)(F)F)c(F)c1]

Step 1: 2-[3-Fluoro-4-(trifluoromethyl)phenyl]propan-2-ol

The title compound was prepared by the reaction of methyl 3-fluoro-4-(trifluoromethyl)benzoate (1.0 g, 4.501 mmol) and methyl magnesium bromide (3M in diethyl ether, 3.7 mL) in diethyl ether (20 mL) as per the process described in step 1 of Intermediate 1 to yield 120 mg of the product as a semi-solid. $^1$H NMR (300 MHz, DMSO-$d_6$) δ 1.43 (s, 6H), 5.37 (s, 1H), 7.47-7.55 (m, 2H), 7.70 (t, J=7.8 Hz, 1H); ESI-MS (m/z) 222 (M+H)$^+$.

Step 2: 2-[3-Fluoro-4-(trifluoromethyl)phenyl]propan-2-yl 4-nitrophenyl ether

The title compound was synthesized by the reaction of step 1 intermediate (100 mg, 0.450 mmol) with 1-fluoro-4-nitrobenzene (63 mg, 0.450 mmol) by using sodium hydride (60% w/w, 27 mg, 0.675 mmol) in DMF (2 mL) as per the process described in step 2 of Intermediate 1 to yield 141 mg of the product as a semi-solid. $^1$H NMR (300 MHz, DMSO-$d_6$) δ 1.78 (s, 6H), 6.85 (d, J=8.7 Hz, 2H), 7.46 (d, J=7.8 Hz, 1H), 7.61 (d, J=11.1 Hz, 1H), 7.77-7.82 (m, 1H), 8.08 (d, J=8.7 Hz, 2H).

Step 3: 4-({2-[3-Fluoro-4-(trifluoromethyl)phenyl]propan-2-yl}oxy)aniline

The title compound was synthesized by the nitro reduction of the step 2 intermediate (100 mg, 0.291 mmol) by using sodium borohydride (44 mg, 1.165 mmol) and nickel chloride (138 mg, 0.582 mmol) in methanol (4 mL) as per the process described in step 3 of Intermediate 1 to yield 78 mg of the product as a semi-solid. $^1$H NMR (300 MHz, DMSO-$d_6$) δ 1.52 (s, 6H), 4.75 (s, 2H), 6.41 (d, J=8.7 Hz, 2H), 6.50 (d, J=8.7 Hz, 2H), 7.54-7.62 (m, 2H), 7.75-7.80 (m, 1H); ESI-MS (m/z) 314 (M+H)$^+$.

Intermediate 11

4-{[2-(3,5-Dichloropyridin-2-yl)propan-2-yl]oxy}aniline

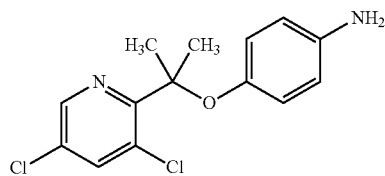 [SMILES: CC(C)(Oc1ccc(N)cc1)c1ncc(Cl)cc1Cl]

Step 1: 2-(3,5-dichloropyridin-2-yl)propan-2-ol

The title compound was prepared by the reaction of methyl 3,5-dichloropyridine-2-carboxylate (1.0 g, 4.854 mmol) and methyl magnesium bromide (1.4M in THF, 10.4 mL) in THF (20 mL) as per the process described in step 1 of Intermediate 1 to yield 800 mg of the product as a liquid. $^1$H NMR (300 MHz, DMSO-$d_6$) δ 1.55 (s, 6H), 8.50 (br s, 1H), 8.53 (br s, 1H)

Step 2: 3,5-Dichloro-2-[2-(4-nitrophenoxy)propan-2-yl]pyridine

The title compound was synthesized by the reaction of step 1 intermediate (200 mg, 0.970 mmol) with 1-fluoro-4-nitrobenzene (150 mg, 1.060 mmol) by using sodium hydride (60% w/w, 42 mg, 1.060 mmol) in DMF (5 mL) as per the process described in step 2 of Intermediate 1 to yield 150 mg of the product as a solid. $^1$H NMR (300 MHz, DMSO-$d_6$) δ 1.88 (s, 6H), 6.70 (d, J=7.2 Hz, 2H), 8.05 (d, J=7.2 Hz, 2H), 8.18 (s, 1H), 8.74 (s, 1H); APCI-MS (m/z) 327 (M)$^+$.

Step 3: 4-{[2-(3,5-Dichloropyridin-2-yl)propan-2-yl]oxy}aniline

The title compound was synthesized by the nitro reduction of the step 2 intermediate (150 mg, 0.458 mmol) by using sodium borohydride (69 mg, 1.833 mmol) and nickel chloride (217 mg, 0.916 mmol) in methanol (5 mL) as per the process described in step 3 of Intermediate 1 to yield 77 mg of the product as a solid. $^1$H NMR (300 MHz, DMSO-$d_6$) δ 1.66 (s, 6H), 4.65 (s, 2H), 6.32 (s, 4H), 8.18 (s, 1H), 5.58 (s, 1H); APCI-MS (m/z) 297 (M)$^+$.

Intermediate 12

4-{[3-(4-Chloro-3-fluorophenyl)pentan-3-yl]oxy}aniline

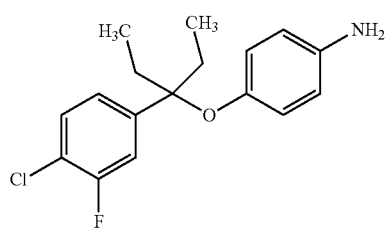 [SMILES: CCC(CC)(Oc1ccc(N)cc1)c1ccc(Cl)c(F)c1]

Step 1: 3-(4-Chloro-3-fluorophenyl)pentan-3-ol

The title compound was prepared by the reaction of methyl 4-chloro-3-fluorobenzoate (1.0 g, 5.302 mmol) and ethyl magnesium bromide (3M in diethyl ether, 4.4 mL) in diethyl ether (20 mL) as per the process described in step 1 of Intermediate 1 to yield 1.1 g of the product as a semi-solid. $^1$H NMR (300 MHz, DMSO-$d_6$) δ 0.62 (t, J=7.5 Hz, 6H), 1.63-1.75 (m, 4H), 4.74 (s, 1H), 7.21 (d, J=7.8 Hz, 1H), 7.36 (d, J=9.9 Hz, 1H), 7.48 (t, J=8.4 Hz, 1H).

Step 2: 1-Chloro-2-fluoro-4-[3-(4-nitrophenoxy)pentan-3-yl]benzene

The title compound was synthesized by the reaction of step 1 intermediate (400 mg, 1.8460 mmol) with 1-fluoro-4-nitrobenzene (260 mg, 1.8460 mmol) by using sodium hydride (60% w/w, 111 mg, 2.769 mmol) in DMF (4 mL) as per the process described in step 2 of Intermediate 1 to yield 417 mg of the product as a solid. $^1$H NMR (300 MHz, DMSO-$d_6$) δ 0.68 (t, J=7.5 Hz, 6H), 2.16 (q, J=7.5 Hz, 4H), 6.90 (d, J=8.7 Hz, 2H), 7.24 (d, J=8.1 Hz, 1H), 7.46 (d, J=10.8 Hz, 1H), 7.60 (t, J=7.8 Hz, 1H), 8.08 (d, J=8.7 Hz, 2H); APCI-MS (m/z) 338 (M+H)$^+$.

Step 3: 4-{[3-(4-Chloro-3-fluorophenyl)pentan-3-yl]oxy}aniline

The title compound was synthesized by the nitro reduction of the step 2 intermediate (405 mg, 1.199 mmol) by using sodium borohydride (181 mg, 4.797 mmol) and nickel chloride (570 mg, 2.398 mmol) in methanol (10 mL) as per the process described in step 3 of Intermediate 1 to yield 298 mg of the product as a solid. $^1$H NMR (300 MHz, DMSO-$d_6$) δ 0.65 (t, J=7.2 Hz, 6H), 1.88 (q, J=7.2 Hz, 4H), 4.69 (s, 2H), 6.42 (d, J=8.7 Hz, 2H), 6.52 (d, J=8.7 Hz, 2H), 7.30 (d, J=8.4 Hz, 1H), 7.45 (d, J=11.1 Hz, 1H), 7.56 (t, J=8.4 Hz, 1H); APCI-MS (m/z) 308 (M+H)$^+$.

Intermediate 13

4-{[3-(2,4-Difluorophenyl)pentan-3-yl]oxy}aniline

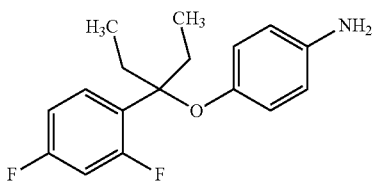 [SMILES: CCC(CC)(Oc1ccc(N)cc1)c1ccc(F)cc1F]

Step 1: 3-(2,4-Difluorophenyl)pentan-3-ol

The title compound was prepared by the reaction of methyl 2,4-difluorobenzoate (1.0 g, 5.809 mmol) and ethyl magnesium bromide (3M in diethyl ether, 4.8 mL) in diethyl ether (20 mL) as per the process described in step 1 of Intermediate 1 to yield 405 mg of the product as a semi-solid. $^1$H NMR (300 MHz, DMSO-$d_6$) δ 0.63 (t, J=7.5 Hz, 6H), 1.65-1.75 (m, 2H), 1.82-1.89 (m, 2H), 4.80 (s, 1H), 7.00-7.12 (m, 2H), 7.54-7.62 (m, 1H).

Step 2: 2,4-Difluoro-1-[3-(4-nitrophenoxy)pentan-3-yl]benzene

The title compound was synthesized by the reaction of step 1 intermediate (370 mg, 1.847 mmol) with 1-fluoro-4- nitrobenzene (260 mg, 1.847 mmol) by using sodium hydride (60% w/w, 110 mg, 2.771 mmol) in DMF (10 mL) as per the process described in step 2 of Intermediate 1 to yield 531 mg of the product as a semi-solid. $^1$H NMR (300 MHz, DMSO-$d_6$) δ 0.71 (t, J=7.5 Hz, 6H), 2.25 (q, J=7.5 Hz, 4H), 6.90 (d, J=8.7 Hz, 2H), 7.11-7.26 (m, 2H), 7.46-7.54 (m, 1H), 8.06 (d, J=8.7 Hz, 2H).

Step 3: 4-{[3-(2,4-Difluorophenyl)pentan-3-yl]oxy}aniline

The title compound was synthesized by the nitro reduction of the step 2 intermediate (250 mg, 0.778 mmol) by using sodium borohydride (118 mg, 3.112 mmol) and nickel chloride (370 mg, 1.556 mmol) in methanol (5 mL) as per the process described in step 3 of Intermediate 1 to yield 192 mg of the product as a solid. $^1$H NMR (300 MHz, DMSO-$d_6$) δ 0.68 (t, J=7.5 Hz, 6H), 1.88 (q, J=7.5 Hz, 4H), 4.74 (s, 2H), 6.42 (d, J=8.7 Hz, 2H), 6.57 (d, J=8.7 Hz, 2H), 7.06-7.22 (m, 2H), 7.58-7.64 (m, 1H); APCI-MS (m/z) 292 (M+H)$^+$.

Intermediate 14

4-{[2-(1-Ethyl-6-fluoro-1H-benzimidazol-2-yl)propan-2-yl]oxy}aniline

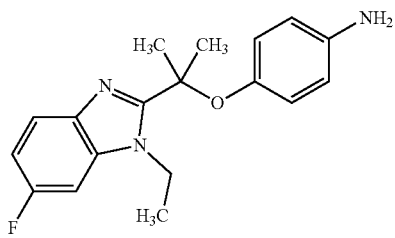 [SMILES: CCn1c(C(C)(C)Oc2ccc(N)cc2)nc2ccc(F)cc21]

Step 1: 1-Ethyl-6-fluoro-2-[2-(4-nitrophenoxy)propan-2-yl]-1H-benzimidazole

To a stirred solution of 2-methyl-2-(4-nitrophenoxy)propanoic acid (400 mg, 1.776 mmol) in THF (5 mL) was added CDI (288 mg, 1.776 mmol) and the reaction was stirred at 50° C. for 30 min. After 30 min, N$^2$-ethyl-4-fluorobenzene-1,2-diamine (273 mg, 1.776 mmol) was added to the reaction mixture and further stirred for 2 h at the same temperature. The reaction mixture was diluted with water (100 mL) and ethyl acetate (100 mL). The layers were separated and the aqueous layer was extracted with ethyl acetate (2×150 mL). The combined organic layers were washed with water (2×100 mL) and dried over anhydrous sodium sulfate. The solvents were distilled off under reduced pressure to yield a gummy residue. The residue was dissolved in acetic acid and refluxed for 1 h. The acetic acid was distilled out under reduced pressure and the residue obtained was diluted with water (100 mL) and ethyl acetate (100 mL). The aqueous layer was extracted with ethyl acetate (3×100 mL). The combined organic layers were washed with water (2×100 mL), brine (100 mL) and dried over anhydrous sodium sulfate. The solvent was recovered under reduced pressure and the residue obtained was purified by silica gel column chromatography to yield 107 mg of the title product as a solid. $^1$H NMR (300 MHz, DMSO-$d_6$) δ 1.08 (t, J=6.6 Hz, 3H), 1.94 (s, 6H), 4.39 (q, J=7.5 Hz, 2H), 6.85 (d, J=9.3 Hz, 2H), 7.06-7.12 (m, 1H), 7.48 (d, J=9.3 Hz, 1H), 7.70-7.76 (m, 1H), 8.08 (d, J=9.3 Hz, 2H).

Step 2: 4-{[2-(1-Ethyl-6-fluoro-1H-benzimidazol-2-yl)propan-2-yl]oxy}aniline

To a stirred solution of step 1 intermediate (100 mg, 0.291 mmol) in a mixture of methanol (10 mL) and water (2 mL) were added iron powder (81 mg, 1.45 mmol) and ammonium chloride (156 mg, 2.91 mmol) at RT. The reaction mixture was heated to 90° C. and stirred for 3 h at the same temperature. The reaction mixture cooled to RT and filtered off the suspended emulsion. The filtrate was concentrated under reduced pressure and diluted with water (10 mL). The aqueous mixture was extracted with ethyl acetate (2×20 mL). The combined organic layers were washed with brine and dried over anhydrous sodium sulfate. The solvents were recovered under reduced pressure and the residue obtained was purified by silica gel column chromatography to 52 mg of the title product as a solid. $^1$H NMR (300 MHz, DMSO-$d_6$) δ 1.11 (t, J=6.9 Hz, 3H), 1.70 (s, 6H), 4.58 (d, J=7.2 Hz, 2H), 4.74 (br s, 2H), 6.39 (d, J=7.8 Hz, 2H), 6.49 (d, J=8.4 Hz, 1H), 6.73 (d, J=8.7 Hz, 1H), 7.05 (d, J=9.3 Hz, 1H), 7.48 (d, J=9.3 Hz, 1H), 7.60-7.66 (m, 1H).

Intermediate 15

4-{[2-(1-Ethyl-5-fluoro-1H-benzimidazol-2-yl)propan-2-yl]oxy}aniline

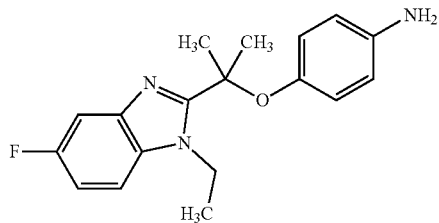 [SMILES: CCn1c(C(C)(C)Oc2ccc(N)cc2)nc2cc(F)ccc21]

Step 1: 1-Ethyl-5-fluoro-2-[2-(4-nitrophenoxy)propan-2-yl]-1H-benzimidazole

The title compound was synthesized by the coupling reaction of 4-fluoro-N$^1$-ethylbenzene-1,2-diamine (340 mg, 2.220 mmol) with 2-methyl-2-(4-nitrophenoxy)propanoic acid (500 mg, 2.220 mmol) in the presence of CDI (360 mg, 2.220 mmol) in THF (5 mL) followed by cyclization in acetic acid (5 mL) as per the process described in step 1 of Intermediate 14 to yield 21 mg of the product as a solid. $^1$H NMR (300 MHz, DMSO-$d_6$) δ 1.09 (t, J=6.9 Hz, 3H), 1.94 (s, 6H), 4.43 (q, J=6.9 Hz, 2H), 6.86 (d, J=8.4 Hz, 2H), 7.10-7.16 (m, 1H), 7.50-7.57 (m, 2H), 8.10 (d, J=9.0 Hz, 2H); ESI-MS (m/z) 344 (M+H)$^+$.

Step 2: 4-{[2-(1-Ethyl-5-fluoro-1H-benzimidazol-2-yl)propan-2-yl]oxy}aniline

The title compound was prepared by the reduction of step 1 intermediate (18 mg, 0.052 mmol) using iron powder (14.6 mg, 0.262 mmol) and ammonium chloride (28 mg, 6.520 mmol) in water (2 mL), methanol (2 mL) and THF (5 mL) as per the process described in step 2 of Intermediate 14 to yield 9 mg of the product as a solid. $^1$H NMR (300 MHz, DMSO-d$_6$) δ 1.14-1.39 (m, 3H), 1.71 (s, 6H), 4.02-4.03 (m, 1H), 4.04-4.25 (m, 2H), 4.56-4.62 (m, 2H), 6.33 (s, 4H), 7.10-7.13 (m, 1H), 7.39-7.45 (m, 1H), 7.58-7.60 (m, 1H); ESI-MS (m/z) 313 (M+H)$^+$.

Intermediate 16

4-{[2-(5-Chloro-1-ethyl-1H-benzimidazol-2-yl)propan-2-yl]oxy}aniline

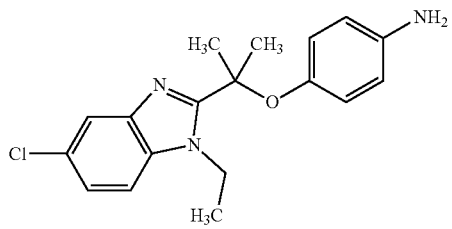 [SMILES: CCn1c(C(C)(C)Oc2ccc(N)cc2)nc2cc(Cl)ccc21]

Step 1: 5-Chloro-1-ethyl-2-[2-(4-nitrophenoxy)propan-2-yl]-1H-benzimidazole

The title compound was synthesized by the coupling reaction of 4-chloro-N$^1$-ethylbenzene-1,2-diamine (400 mg, 2.351 mmol) with 2-methyl-2-(4-nitrophenoxy)propanoic acid (529 mg, 2.351 mmol) in the presence of CDI (381 mg, 2.351 mmol) in THF (5 mL) followed by cyclization in acetic acid (5 mL) as per the process described in step 1 of Intermediate 14 to yield 70 mg of the product as a solid. $^1$H NMR (300 MHz, DMSO-d$_6$) δ 1.07 (t, J=7.2 Hz, 3H), 1.92 (s, 6H), 4.42 (q, J=7.2 Hz, 2H), 6.84 (d, J=9.3 Hz, 2H), 7.27-7.32 (m, 1H), 7.59 (d, J=8.7 Hz, 1H), 7.78 (s, 1H), 8.08 (d, J=9.3 Hz, 2H).

Step 2: 4-{[2-(5-Chloro-1-ethyl-1H-benzimidazol-2-yl)propan-2-yl]oxy}aniline

The title compound was prepared by the reduction of step 1 intermediate (65 mg, 0.180 mmol) using iron powder (50.4 mg, 0.903 mmol) and ammonium chloride (96 mg, 1.806 mmol) in water (3 mL) and THF (5 mL) as per the process described in step 2 of Intermediate 14 to yield 75 mg of the product as a solid. $^1$H NMR (300 MHz, DMSO-d$_6$) δ 1.30 (t, J=6.9 Hz, 3H), 1.71 (s, 6H), 4.61 (d, J=7.2 Hz, 1H), 4.74 (br s, 2H), 6.33 (br s, IH), 7.29 (d, J=7.2 Hz, 1H), 7.62 (d, J=7.6 Hz, 1H), 7.70 (s, 1H).

Intermediate 17

4-{[2-(6-Chloro-1-ethyl-1H-benzimidazol-2-yl)propan-2-yl]oxy}aniline

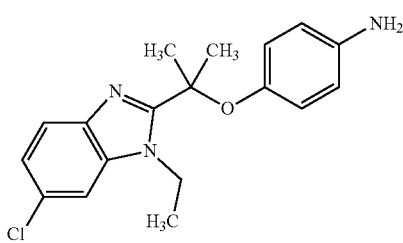 [SMILES: CCn1c(C(C)(C)Oc2ccc(N)cc2)nc2ccc(Cl)cc21]

Step 1: 6-Chloro-1-ethyl-2-[2-(4-nitrophenoxy)propan-2-yl]-1H-benzimidazole

The title compound was synthesized by the coupling reaction of 4-chloro-N$^2$-ethylbenzene-1,2-diamine (226 mg, 1.332 mmol) with 2-methyl-2-(4-nitrophenoxy)propanoic acid (300 mg, 1.332 mmol) using CDI (216 mg, 1.332 mmol) in THF (5 mL) followed by cyclization in the presence of acetic acid (5 mL) as per the process described in step 1 of Intermediate 14 to yield 225 mg of the product as a solid. $^1$H NMR (300 MHz, DMSO-d$_6$) δ 1.00 (t, J=6.9 Hz, 3H), 1.67 (s, 6H), 2.96 (q, J=6.0 Hz, 2H), 6.61 (d, J=7.5 Hz, 1H), 7.02 (d, J=8.4 Hz, 1H), 7.12 (d, J=8.7 Hz, 2H), 8.25 (d, J=8.7 Hz, 2H), 9.47 (s, 1H).

Step 2: 4-{[2-(6-Chloro-1-ethyl-1H-benzimidazol-2-yl)propan-2-yl]oxy}aniline

The title compound was prepared by the reduction of step 1 intermediate (125 mg, 0.347 mmol) using iron powder (97 mg, 1.736 mmol) and ammonium chloride (186 mg, 3.47 mmol) in water (3 mL) and THF (10 mL) as per the process described in step 2 of Intermediate 14 to yield 100 mg of the product as a solid. $^1$H NMR (300 MHz, DMSO-d$_6$) δ 1.30 (t, J=6.9 Hz, 3H), 1.71 (s, 6H), 4.61 (q, J=7.2 Hz, 2H), 4.74 (br s, 2H), 6.33 (br s, 4H), 7.29 (d, J=7.5 Hz, 1H), 7.62 (d, J=8.7 Hz, 1H), 7.70 (s, 1H); APCI-MS (m/z) 330 (M+H)$^+$.

Intermediate 18

4-{[2-(6-Chloro-1-methyl-1H-benzimidazol-2-yl)propan-2-yl]oxy}aniline

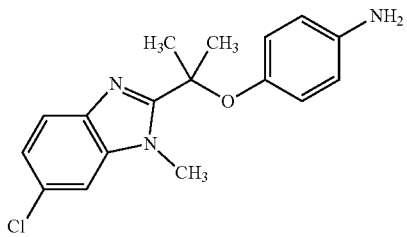 [SMILES: Cn1c(C(C)(C)Oc2ccc(N)cc2)nc2ccc(Cl)cc21]

Step 1: 6-Chloro-1-methyl-2-[2-(4-nitrophenoxy)propan-2-yl]-1H-benzimidazole

The title compound was synthesized by the coupling reaction of 4-chloro-N$^{2-}$methylbenzene-1,2-diamine (277 mg, 1.776 mmol) with 2-methyl-2-(4-nitrophenoxy)propanoic acid (400 mg, 1.776 mmol) in presence of CDI (288 mg, 1.776 mmol) in THF (10 mL) followed by cyclization in acetic acid (5 mL) as per the process described in step 1 of Intermediate 14 to yield 284 mg of the product as a solid. $^1$H NMR (300 MHz, DMSO-d$_6$) δ 1.94 (s, 6H), 3.78 (s, 3H), 6.83 (d, J=7.8 Hz, 2H), 6.94 (d, J=7.8 Hz, 2H), 7.67-7.75 (m, 1H), 8.05-8.13 (m, 2H); ESI-MS (m/z) 345 (M+H)$^+$.

Step 2: 4-{[2-(6-Chloro-1-methyl-1H-benzimidazol-2-yl)propan-2-yl]oxy}aniline

The title compound was prepared by the reduction of step 1 intermediate (280 mg, 0.809 mmol) using iron powder (226 mg, 4.048 mmol) and ammonium chloride (432 mg, 8.090 mmol) in water (5 mL), methanol (5 mL) and THF (10 mL) as per the process described in step 2 of Intermediate 14 to yield 180 mg of the product as a solid. ¹H NMR (300 MHz, DMSO-d₆) δ 1.70 (s, 6H), 4.01 (s, 3H), 4.71 (br s, 2H), 6.27-6.35 (m, 4H), 7.23 (d, J=8.1 Hz, 1H), 7.63 (d, J=8.4 Hz, 1H), 7.72 (s, 1H); ESI-MS (m/z) 315 (M+H)⁺.

Intermediate 19

4-{[2-(7-Chloro-1-ethyl-1H-benzimidazol-2-yl)propan-2-yl]oxy}aniline

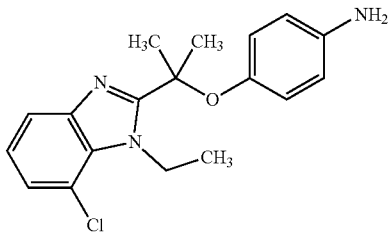 [SMILES: CCn1c(C(C)(C)Oc2ccc(N)cc2)nc2cccc(Cl)c21]

Step 1: 7-Chloro-1-ethyl-2-[2-(4-nitrophenoxy)propan-2-yl]-1H-benzimidazole

The title compound was synthesized by the reaction of 3-chloro-N²-ethylbenzene-1,2-diamine (302 mg, 1.776 mmol) with 2-methyl-2-(4-nitrophenoxy)propanoic acid (400 mg, 1.776 mmol) in presence of CDI (288 mg, 1.776 mmol) in THF (5 mL) followed by cyclization in acetic acid (5 mL) as per the process described in step 1 of Intermediate 14 to yield 451 mg of the product as a solid. ¹H NMR (300 MHz, DMSO-d₆) δ 1.16 (t, J=6.6 Hz, 3H), 1.97 (s, 6H), 4.68 (q, J=6.9 Hz, 2H), 6.89 (d, J=9.3 Hz, 2H), 7.22-7.35 (m, 2H), 7.73 (d, J=7.8 Hz, 1H), 8.12 (d, J=8.7 Hz, 2H); ESI-MS (m/z) 359 (M+H)⁺.

Step 2: 4-{[2-(7-Chloro-1-ethyl-1H-benzimidazol-2-yl)propan-2-yl]oxy}aniline

The title compound was prepared by the reduction of step 1 intermediate (450 mg, 1.250 mmol) using iron powder (349 mg, 6.253 mmol) and ammonium chloride (669 mg, 12.50 mmol) in water (5 mL), methanol (5 mL) and THF (10 mL) as per the process described in step 2 of Intermediate 14 to yield 301 mg of the product as a solid. ¹H NMR (300 MHz, DMSO-d₆) δ 1.38 (t, J=6.9 Hz, 3H), 1.73 (s, 6H), 4.74 (s, 2H), 4.88 (q, J=6.3 Hz, 2H), 6.36 (br s, 4H), 7.20 (t, J=7.8 Hz, 1H), 7.31 (d, J=7.8 Hz, 1H), 7.62 (d, J=7.8 Hz, 1H).

Intermediate 20

4-({2-[5-Fluoro-1-(propan-2-yl)-1H-benzimidazol-2-yl]propan-2-yl}oxy)aniline

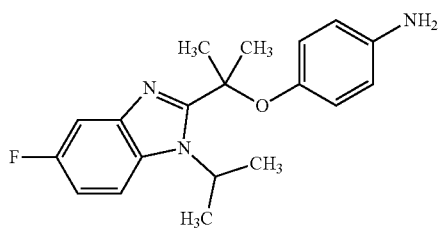 [SMILES: CC(C)n1c(C(C)(C)Oc2ccc(N)cc2)nc2cc(F)ccc21]

Step 1: 5-Fluoro-2-[2-(4-nitrophenoxy)propan-2-yl]-1-(propan-2-yl)-1H-benzimidazole The title compound was synthesized by the coupling reaction of 4-fluoro-N¹-(propan-2-yl)benzene-1,2-diamine (371 mg, 2.220 mmol) with 2-methyl-2-(4-nitrophenoxy)propanoic acid (500 mg, 2.220 mmol) using CDI (360 mg, 2.220 mmol) in THF (5 mL) followed by cyclization in the presence of acetic acid (5 mL) as per the process described in step 1 of Intermediate 14 to yield 104 mg of the product as a solid. ¹H NMR (300 MHz, DMSO-d₆) δ 1.32 (d, J=6.9 Hz, 6H), 1.95 (s, 6H), 5.23-5.27 (m, 1H), 6.86 (d, J=9.3 Hz, 2H), 7.07-7.13 (m, 1H), 7.55 (d, J=7.2 Hz, 1H), 7.71-7.76 (m, 1H), 8.10 (d, J=9.3 Hz, 2H); ESI-MS (m/z) 358 (M+H)⁺.

Step 2: 4-({2-[5-Fluoro-1-(propan-2-yl)-1H-benzimidazol-2-yl]propan-2-yl}oxy)aniline The title compound was prepared by the reduction of step 1 intermediate (100 mg, 0.279 mmol) using iron powder (78 mg, 1.399 mmol) and ammonium chloride (149 mg, 2.790 mmol) in water (3 mL), methanol (3 mL) and THF (7 mL) as per the process described in step 2 of Intermediate 14 to yield 52 mg of the product as a solid. ¹H NMR (300 MHz, DMSO-d₆) δ 1.29-1.47 (m, 6H), 1.73 (s, 6H), 4.67 (br s, 2H), 5.51-5.55 (m, 1H), 6.27-6.32 (m, 4H), 7.07 (t, J=9.3 Hz, 1H), 7.48 (d, J=9.9 Hz, 1H), 7.73-7.78 (m, 1H); ESI-MS (m/z) 328 (M+H)⁺.

Intermediate 21

4-{[2-(5-Chloro-1-ethyl-1H-indol-2-yl)propan-2-yl]oxy}aniline

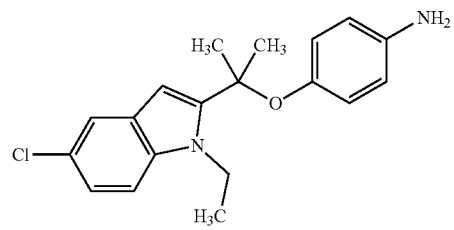 [SMILES: CCn1c(C(C)(C)Oc2ccc(N)cc2)cc2cc(Cl)ccc21]

Step 1: Ethyl 5-chloro-1H-indole-2-carboxylate

To a solution of ethyl 5-chloroindole-2-carboxylate (2.5 g, 11.175 mmol) in DMF (10 mL) was added sodium hydride (60% w/w, 894 mg, 22.351 mmol) and the mixture was stirred at RT for 30 minutes. To the reaction mixture was added ethyl bromide (0.99 mL, 13.410 mmol) and stirred for 16 hours at RT. The reaction mixture was diluted with ethyl acetate (50 mL) and water (50 mL). The layers were separated and the aqueous layer was extracted with ethyl acetate (2×50 mL). The combined organic layers were washed with water (50 mL) followed by brine (50 mL) and dried over anhydrous sodium sulfate. The solvent was distilled off under reduced pressure to obtain 2.63 g of the title compound as a solid. ¹H NMR (300 MHz, DMSO-d₆) δ 1.24-1.35 (m, 6H), 4.29-4.36 (m, 2H), 4.55-4.61 (m, 2H), 7.24 (s, 1H), 7.33 (t, J=9.3 Hz, 1H), 7.66 (d, J=9.0 Hz, 1H), 7.76 (s, 1H); ESI-MS (m/z) 252 (M+H)⁺.

Step 2: 2-(5-Chloro-1-ethyl-1H-indol-2-yl)propan-2-ol

Methyl magnesium bromide (1.4M in THF, 12.8 mL) was added to a stirred and cooled (−78° C.) solution of step 1 intermediate (1.5 g, 6.000 mmol) in anhydrous THF (10 mL). The reaction mixture was allowed to stir at −78° C. for 1 h and then stirred overnight at RT. The reaction mixture was cooled to 0° C. and quenched with saturated aqueous solution of ammonium chloride (50 mL) and stirred for 30 min. The aqueous mixture was extracted with ethyl acetate (2×50 mL). The combined organic layers were washed with water (50 mL) followed by brine (50 mL) and dried over anhydrous sodium sulfate. The solvent was distilled off under reduced pressure to obtain 1.1 g of the title product as a solid. $^1$H NMR (300 MHz, DMSO-$d_6$) δ 1.30 (t, J=6.9 Hz, 3H), 1.58 (s, 6H), 4.51 (q, J=6.9 Hz, 2H), 5.32 (s, 1H), 6.24 (s, 1H), 7.07 (d, J=8.7 Hz, 1H), 7.41 (d, J=8.4 Hz, 1H), 7.50 (s, 1H); APCI-MS (m/z) 237 (M+H)$^+$.

Step 3: 5-Chloro-1-ethyl-2-[2-(4-nitrophenoxy)propan-2-yl]-1H-indole

The title compound was prepared by the reaction of step 2 intermediate (500 mg, 2.104 mmol) with 1-fluoro-4-nitro benzene (327 mg, 2.320 mmol) using sodium hydride (60%, 126 mg, 3.163 mmol) in DMF (5 mL) as per the process described in step 2 of Intermediate 1 to yield 41 mg of the product as a semi-solid. $^1$H NMR (300 MHz, DMSO-$d_6$) δ 1.07 (t, J=6.9 Hz, 3H), 1.89 (s, 6H), 4.40 (q, J=6.9 Hz, 2H), 6.58 (s, 1H), 6.93 (d, J=9.3 Hz, 2H), 7.14-7.18 (m, 1H), 7.44 (d, J=8.7 Hz, 1H), 7.63 (s, 1H), 8.04 (d, J=9.0 Hz, 2H).

Step 4: 4-{[2-(5-Chloro-1-ethyl-1H-indol-2-yl)propan-2-yl]oxy}aniline

The title compound was prepared by the reduction of step 3 intermediate (125 mg, 0.348 mmol) using sodium borohydride (53 mg, 1.393 mmol) and nickel chloride (165 mg, 0.696 mmol) in methanol (5 mL) as per the process described in step 3 of Intermediate 1 to yield 93 mg of the product as a semi-solid. $^1$H NMR (300 MHz, DMSO-$d_6$) δ 1.31 (t, J=6.9 Hz, 3H), 1.66 (s, 6H), 4.60 (q, J=6.9 Hz, 2H), 4.69 (br s, 2H), 6.26-6.33 (m, 5H), 7.14 (d, J=9.0 Hz, 1H), 7.49 (d, J=8.7 Hz, 1H), 7.54 (s, 1H); APCI-MS (m/z) 229 (M+H)$^+$.

Intermediate 22

4-[(5-Chloro-1-ethyl-1H-benzimidazol-2-yl)(difluoro)methoxy]aniline

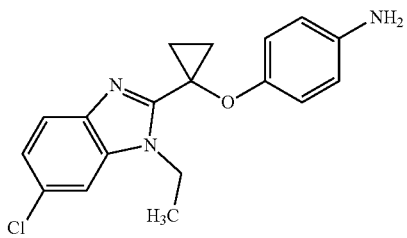

Step 1: 5-Chloro-2-[difluoro(4-nitrophenoxy)methyl]-1-ethyl-1H-benzimidazole The title compound was synthesized by the coupling reaction of 4-chloro-N$^1$-ethylbenzene-1,2-diamine (303 mg, 1.783 mmol) with difluoro(4-nitrophenoxy)acetic acid (400 mg, 1.783 mmol) in the presence of CDI (289 mg, 1.783 mmol) in THF (5 mL) followed by cyclization using acetic acid (5 mL) as per the process described in step 1 of Intermediate 14 to yield 211 mg of the product as a solid. $^1$H NMR (300 MHz, DMSO-$d_6$) δ 1.40 (t, J=7.2 Hz, 3H), 4.56 (q, J=7.5 Hz, 2H), 7.51 (d, J=8.4 Hz, 1H), 7.67 (d, J=8.7 Hz, 2H), 7.84-7.92 (m, 2H), 8.36 (d, J=9.3 Hz, 2H); ESI-MS (m/z) 368 (M+H)$^+$.

Step 2: 4-[(5-Chloro-1-ethyl-1H-benzimidazol-2-yl)(difluoro)methoxy]aniline

The title compound was prepared by the reduction of step 1 intermediate (100 mg, 0.271 mmol) using iron powder (76 mg, 1.359 mmol) and ammonium chloride (145 mg, 2.710 mmol) in water (2 mL), methanol (2 mL) and THF (5 mL) as per the process described in step 2 of Intermediate 14 to yield 43 mg of the product as a solid. $^1$H NMR (300 MHz, DMSO-$d_6$) δ 1.39 (t, J=6.6 Hz, 3H), 4.54 (q, J=7.5 Hz, 2H), 5.19 (br s, 2H), 6.58 (d, J=8.4 Hz, 2H), 7.01 (d, J=7.2 Hz, 2H), 7.47 (d, J=8.1 Hz, 1H), 7.81-7.87 (m, 2H); ESI-MS (m/z) 338 (M+H)$^+$.

Intermediate 23

4-{[1-(6-Chloro-1-ethyl-1H-benzimidazol-2-yl)cyclopropyl]oxy}aniline

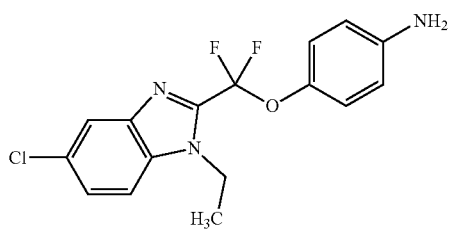 [SMILES: CCn1c(C(F)(F)Oc2ccc(N)cc2)nc2cc(Cl)ccc21]

Step 1: Ethyl 4-bromo-2-(4-nitrophenoxy)butanoate

To a well stirred solution of 4-nitrophenol (10 g, 71.885 mmol) in DMF (40 mL) was added potassium carbonate (10 g, 71.885 mmol) followed by ethyl 2,4-dibromobutanoate (19.7 g, 71.885 mmol) and the reaction mixture was stirred at RT for 16 h. The reaction mixture was diluted with water (300 mL) and extracted with ethyl acetate (3×300 mL). The combined organic layers were washed with water (3×250 mL), brine (250 mL) and dried over anhydrous sodium sulfate. The solvent was recovered under reduced pressure and the residue thus obtained was purified by silica gel column chromatography to yield 8.65 g of the title product as a solid; $^1$H NMR (300 MHz, DMSO-$d_6$) δ 1.19 (d, J=6.9 Hz, 3H), 2.45-2.51 (m, 2H), 3.63-3.70 (m, 2H), 4.14-4.20 (m, 2H), 5.16-5.20 (m, 1H), 7.15 (d, J=9.3 Hz, 2H), 8.21 (d, J=8.7 Hz, 2H).

Step 2: Ethyl 1-(4-nitrophenoxy)cyclopropanecarboxylate

To a stirred solution of step 1 intermediate (1.0 g, 3.010 mmol) in THF (10 mL) was added potassium tert butoxide (367 mg, 3.010 mmol) and the reaction mixture was stirred at RT for 16 h. The reaction mixture was diluted with water (100 mL) and extracted with ethyl acetate (3×150 mL). The combined organic layers were washed with water (2×100 mL), brine (100 mL) and dried over anhydrous sodium sulfate. The solvent was recovered under reduced pressure and the residue obtained was purified by silica gel column chromatography to yield 317 mg of the title product as a solid; $^1$H NMR (300 MHz, DMSO-d$_6$) δ 1.10 (t, J=6.6 Hz, 3H), 1.41 (br s, 2H), 1.61 (br s, 2H), 4.14 (q, J=7.2 Hz, 2H), 7.15 (d, J=9.3 Hz, 2H), 8.21 (d, J=9.3 Hz, 2H); APCI-MS (m/z) 252 (M+H)$^+$.

Step 3: 1-(4-Nitrophenoxy)cyclopropanecarboxylic acid

To a stirred solution of step 2 intermediate (250 mg, 0.995 mmol) in THF (5 mL) was added a solution of lithium hydroxide (165 mg, 3.980 mmol) in water (2 mL) and the reaction mixture was stirred at 80° C. for 16 h. The solvent was distilled off under reduced pressure and the residue obtained was acidified with 1N HCl till pH 3-4. The obtained precipitate was filtered and washed with water to yield 250 mg of the product as a solid; $^1$H NMR (300 MHz, DMSO-d$_6$) δ 1.34 (br s, 2H), 1.58 (br s, 2H), 7.14 (d, J=8.7 Hz, 2H), 8.21 (d, J=9.3 Hz, 2H), 13.24 (br s, 1H); APCI-MS (m/z) 222 (M−H)$^+$.

Step 4: 4-{[1-(6-Chloro-1-ethyl-1H-benzimidazol-2-yl)cyclopropyl]oxy}aniline

The title compound is prepared by coupling of 4-chloro-N$^2$-ethylbenzene-1,2-diamine (190 mg, 1.119 mmol) and step 3 intermediate (250 mg, 1.119 mmol) using CDI (181 mg, 1.119 mmol) in THF (5 mL) followed by cyclization in presence of acetic acid (5 mL). The nitro compound (100 mg, 0.279 mmol) was reduced using iron powder (78 mg, 1.397 mmol) and ammonium chloride (149 mg, 2.79 mmol) in water (2 mL) and THF (5 mL) as per the process described in step 1 and 2 of Intermediate 14 to yield 110 mg of the product as a solid. $^1$H NMR (300 MHz, DMSO-d$_6$) δ 1.21-1.34 (s, 5H), 1.48 (s, 2H), 4.43 (q, J=7.2 Hz, 2H), 4.60 (br s, 2H), 6.38 (d, J=9.0 Hz, 2H), 6.76 (d, J=8.4 Hz, 2H), 7.17 (d, J=8.4 Hz, 1H), 7.58 (d, J=8.7 Hz, 1H), 7.69 (s, 1H); ESI-MS (m/z) 328 (M+H)$^+$.

Intermediate 24

4-{[1-(5-Chloro-1-ethyl-1H-benzimidazol-2-yl)cyclopropyl]oxy}aniline

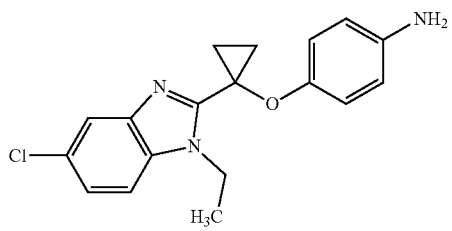 [SMILES: CCn1c(C2(Oc3ccc(N)cc3)CC2)nc2cc(Cl)ccc21]

Step 1: 5-Chloro-1-ethyl-2-[1-(4-nitrophenoxy)cyclopropyl]-1H-benzimidazole

The title compound is prepared by the coupling reaction of 4-chloro-N-ethylbenzene-1,2-diamine (228 mg, 1.343 mmol) and 1-(4-nitrophenoxy)cyclopropanecarboxylic acid (300 mg, 1.343 mmol) using CDI (218 mg, 1.343 mmol) in THF (5 mL) followed by cyclization in the presence of acetic acid (5 mL) as per the process described in step 1 of Intermediate 14 to yield 220 mg of the product as solid. $^1$H NMR (300 MHz, DMSO-d$_6$) δ 1.29 (t, J=7.5 Hz, 3H), 1.57-1.60 (m, 2H), 1.67-1.69 (m, 2H), 4.46 (q, J=7.5 Hz, 2H), 7.28 (d, J=8.7 Hz, 1H), 7.40 (d, J=9.3 Hz, 2H), 7.61 (d, J=8.7 Hz, 1H), 7.73 (s, 1H), 8.19 (d, J=9.3 Hz, 2H).

Step 2: 4-{[1-(5-Chloro-1-ethyl-1H-benzimidazol-2-yl)cyclopropyl]oxy}aniline

Title compound was prepared by the nitro reduction of step 1 intermediate (60 mg, 0.167 mmol) by using iron powder (47 mg, 0.838 mmol) and ammonium chloride (90 mg, 1.637 mmol) in water (2 mL), methanol (2 mL) and THF (5 mL) as per the process described in step 2 of Intermediate 14 to yield 64 mg of the product as a semi-solid. $^1$H NMR (300 MHz, DMSO-d$_6$) δ 1.28 (t, J=7.2 Hz, 3H), 1.29-1.36 (m, 2H), 1.47-1.51 (m, 2H), 4.42 (q, J=6.9 Hz, 2H), 4.62 (br s, 2H), 6.39 (d, J=8.7 Hz, 2H), 6.78 (d, J=8.4 Hz, 2H), 7.22-7.25 (m, 1H), 7.57 (d, J=8.4 Hz, 1H), 7.66 (s, 1H); ESI-MS (m/z) 328 (M+H)$^+$.

Intermediate 25

4-{[1-(5-Chloro-1-methyl-1H-benzimidazol-2-yl)cyclobutyl]oxy}aniline

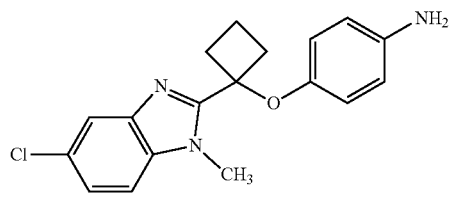 [SMILES: Cn1c(C2(Oc3ccc(N)cc3)CCC2)nc2cc(Cl)ccc21]

Step 1: 1-(4-nitrophenoxy)cyclobutanecarboxylic acid

To a stirred solution of 4-nitrophenol (448 mg, 3.220 mmol) in DMF (5 mL) was added potassium carbonate (890 mg, 6.440 mmol) followed by ethyl bromocyclobutane carboxylate (2.0 mL, 9.660 mmol) and the reaction mixture was stirred at 150° C. for 24 h. The reaction mixture was diluted with water (15 mL) and extracted with ethyl acetate (3×15 mL). The combined organic layers were washed with water (3×25 mL), brine (25 mL) and dried over anhydrous sodium sulfate. The solvent was distilled off under reduced pressure. The compound obtained was subjected to ester hydrolysis using lithium hydroxide (627 mg, 15.094 mmol) in THF (10 mL) and water (5 mL) to yield 700 mg of the title product as a solid which was as such taken forward to the next step without any purification.

Step 2: 5-Chloro-1-methyl-2-[1-(4-nitrophenoxy)cyclobutyl]-1H-benzimidazole

The title compound is prepared by the coupling of 4-chloro-N$^1$-methylbenzene-1,2-diamine (197 mg, 1.265 mmol) and step 1 intermediate (300 mg, 1.265 mmol) in presence of CDI (205 mg, 1.265 mmol) and acetic acid (5 mL) in THF (5 mL) as per the process described in step 1 of Intermediate 14 to yield 16 mg of the product as a solid. $^1$H NMR (300 MHz, DMSO-$d_6$) δ 1.79-1.81 (m, 1H), 1.92-1.98 (m, 1H), 2.69-2.75 (m, 2H), 3.11-3.14 (m, 2H), 3.73 (s, 3H), 7.03 (d, J=9.3 Hz, 2H), 7.27 (d, J=8.7 Hz, 1H), 7.53 (d, J=9.0 Hz, 1H), 7.78 (s, 1H), 8.06 (d, J=9.3 Hz, 2H).

Step 3: 4-{[1-(5-Chloro-1-methyl-1H-benzimidazol-2-yl)cyclobutyl]oxy}aniline

The reduction of step 1 intermediate (15 mg, 0.041 mmol) by using iron powder (12 mg, 0.209 mmol) and ammonium chloride (22 mg, 0.410 mmol) in water (1 mL), methanol (1 mL) and THF (2 mL) as per the process described in step 2 of Intermediate 14 yielded 8 mg of the product as a solid. ESI-MS (m/z) 327 (M)$^+$.

Intermediate 26

4-{[1-(1-Ethyl-5-fluoro-1H-benzimidazol-2-yl)cyclobutyl]oxy}aniline

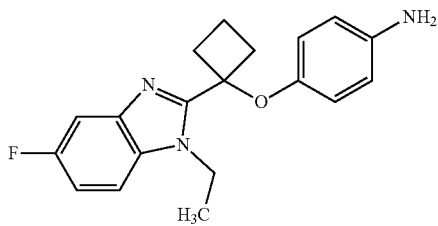 [SMILES: CCn1c(C2(Oc3ccc(N)cc3)CCC2)nc2cc(F)ccc21]

Step 1: 1-Ethyl-5-fluoro-2-[1-(4-nitrophenoxy)cyclobutyl]-1H-benzimidazole

The title compound is prepared by the reaction of N$^1$-ethyl-4-fluorobenzene-1,2-diamine (194 mg, 1.265 mmol) and 1-(4-nitrophenoxy)cyclobutanecarboxylic acid (300 mg, 1.265 mmol) in presence of CDI (205 mg, 1.265 mmol) and acetic acid (5 mL) in THF (5 mL) as per the process described in step 1 of Intermediate 14 to yield 25 mg of the product as a solid. $^1$H NMR (300 MHz, DMSO-$d_6$) δ 1.15 (t, J=6.9 Hz, 3H), 1.80-1.84 (m, 1H), 1.99-2.02 (m, 1H), 2.71-2.75 (m, 2H), 3.10-3.14 (m, 2H), 4.26 (q, J=6.9 Hz, 2H), 7.05 (d, J=9.3 Hz, 2H), 7.12-7.15 (m, 1H), 7.53-7.59 (m, 2H), 8.12 (d, J=8.7 Hz, 2H).

Step 2: 4-{[1-(1-Ethyl-5-fluoro-1H-benzimidazol-2-yl)cyclobutyl]oxy}aniline

The reduction of step 1 intermediate (22 mg, 0.061 mmol) by using iron powder (17 mg, 0.309 mmol) and ammonium chloride (33 mg, 0.610 mmol) in water (2 mL), methanol (2 mL) and THF (5 mL) as per the process described in step 2 of Intermediate 14 to yield 13 mg of the product as off white solid. ESI-MS (m/z) 326 (M+H)$^+$.

Intermediate 27

4-{[1-(6-Chloro[1,2,4]triazolo[4,3-a]pyridin-3-yl)cyclobutyl]oxy}aniline

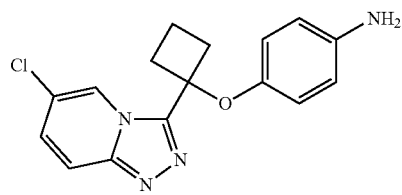 [SMILES: Nc1ccc(OC2(c3nnc4ccc(Cl)cn34)CCC2)cc1]

Step 1: 1-(4-Nitrophenoxy)cyclobutanecarboxylic acid

The title compound was prepared from 4-nitrophenol (448 mg, 3.220 mmol) and ethyl bromo-cyclobutane carboxylate (2 g, 9.660 mmol) in presence of potassium carbonate (890 mg, 6.44 mmol) in DMF (5 mL) as per the process described in step 1 of Intermediate 25 to yield 1.2 g of the product as an oily liquid which was as such taken forward to the next step.

Step 2: N'-(5-Chloropyridin-2-yl)-1-(4-nitrophenoxy)cyclobutanecarbohydrazide

A mixture of step 1 intermediate (250 mg, 1.054 mmol), 5-chloro-2-hydrazinylpyridine (151 mg, 1.054 mmol), EDCI.HCl (242 mg, 1.262 mmol) and HOBt (213 mg, 1.582 mmol) in DCM (10 mL) was stirred at room temperature for 16 h. The reaction mixture was quenched with water (20 mL) and extracted with ethyl acetate (2×20 mL). The combined organic layer was washed with water (2×15 mL), brine (15 mL) and dried over anhydrous sodium sulfate. The solvent was distilled off under reduced pressure and the residue obtained was purified by silica gel column chromatography to yield 127 mg of the title product as a solid. $^1$H NMR (300 MHz, DMSO-$d_6$) δ 1.85-1.91 (m, 2H), 2.34-2.41 (m, 2H), 2.71-2.73 (m, 2H), 6.29 (d, J=9.3 Hz, 1H), 6.93 (d, J=9.3 Hz, 2H), 7.51 (d, J=8.7 Hz, 1H), 8.01 (s, 1H), 8.25 (d, J=9.3 Hz, 2H), 8.53 (s, 1H), 10.1 (s, 1H).

Step 3: 6-chloro-3-[1-(4-nitrophenoxy)cyclobutyl][1,2,4]triazolo[4,3-a]pyridine

To a stirred solution of step 2 intermediate (120 mg, 0.358 mmol) in THF (10 mL) were added triphenylphosphine (188 mg, 0.716 mmol) and triethylamine (0.2 mL, 1.433 mmol) at RT. The reaction mixture was cooled to 0° C. and hexachloroethane (169 mg, 0.716 mmol) was added in two portions at 2 minutes interval. The resulting pale yellow solution was allowed to warm up to RT and stirred for 2 h. The reaction mixture was filtered and filtration bed was washed with THF (20 mL). The combined filtrates were concentrated under reduced pressure and the residue obtained was purified by silica gel column chromatography to obtain 107 mg of the title compound as a solid. APCI-MS (m/z) 345 (M+H)$^+$.

Step 4: 4-{[1-(6-Chloro[1,2,4]triazolo[4,3-a]pyridin-3-yl)cyclobutyl]oxy}aniline The title compound was prepared by the reduction of step 3 intermediate (50 mg, 0.145 mmol) using iron powder (40 mg, 0.725 mmol) and ammonium chloride (77 mg, 1.450 mmol) in a mixture of methanol (5.0 mL and water (5.0 mL) as per the process described in Step 2 of Intermediate 14 to yield 53 mg of the product as a solid. $^1$H NMR (300 MHz, DMSO-$d_6$) δ 1.95-1.99 (m, 2H), 2.67-2.71 (m, 2H), 2.86-6.89 (m, 2H), 4.65 (br s, 2H), 6.28 (d, J=8.1 Hz, 2H), 6.41 d, J=8.7 Hz, 2H), 7.45 (d, J=9.9 Hz, 1H). 7.85 (d, J=9.9 Hz, 1H), 8.43 (s, 1H).

Intermediate 28

4-({2-[5-(4-Chlorophenyl)-1,2,4-oxadiazol-3-yl]propan-2-yl}oxy)aniline

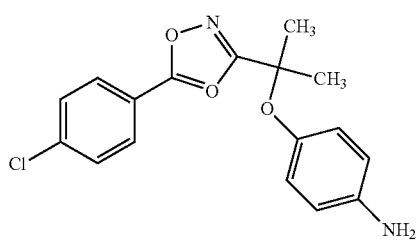

Step 1: {[(4-Chlorophenyl)carbonyl]amino}acetic acid

To a stirred and cooled (15° C.) solution of glycine (5.0 g, 66.602 mmol) in 10% aqueous sodium hydroxide solution (50 mL) was added benzoyl chloride (11.8 mL, 92.57 mmol) in portions. The reaction mixture was stirred at RT for 1.5 h. The reaction mixture was poured in to crushed ice and acidified with conc. HCl till pH 3-4. The obtained precipitate was collected by filtration and dried to yield 11.2 g of the title product as a solid. $^1$H NMR (300 MHz, DMSO-$d_6$) δ 4.08 (s, 2H), 7.49 (d, J=8.7 Hz, 2H), 7.85 (d, J=8.1 Hz, 2H), 8.00 (d, J=8.4 Hz, 1H).

Step 2: 2-(4-Chlorophenyl)-4-[(dimethylamino)methylidene]-1,3-oxazol-5(4H)-one

To an ice cooled solution of step 1 intermediate (3.0 g, 14.00 mmol) in phosphorus oxychloride (3.2 mL, 35.00 mmol) was added DMF (2.3 mL, 32.20 mmol) very slowly. The reaction mixture was heated to 50° C. and stirred for 1 h at the same temperature. The reaction mixture was poured into crushed ice and the precipitate obtained was collected by filtration and purified by silica gel column chromatography to yield 2.8 g of the title product as a solid. $^1$H NMR (300 MHz, DMSO-$d_6$) δ 3.32 (d, J=11.1 Hz, 3H), 3.55 (s, 3H), 7.39 (s, 1H), 7.56 (d, J=8.7 Hz, 2H), 7.84 (d, J=8.7 Hz, 2H).

Step 3: Methyl 5-(4-chlorophenyl)-1,2,4-oxadiazole-3-carboxylate

To a stirred solution of step 2 intermediate (1.5 g, 6.000 mmol) in methanol (10 mL) was added sodium hydroxide (120 mg, 3.000 mmol) and the mixture was refluxed for 30 min. The solvent was recovered under reduced pressure and the residue was suspended in water (5 mL) and aqueous HCl (2 N, 15 mL). The reaction mixture was cooled to 10° C. and to that a precooled solution of sodium nitrite (621 mg, 9.000 mmol) in water (5 mL) was added slowly. The reaction mixture was stirred at RT for 5 h. The precipitate obtained was filtered and washed with water (10 mL). The obtained compound was dried under reduced pressure and purified by silica gel column chromatography to yield 1.01 g of the title product as a solid. $^1$H NMR (300 MHz, CDCl$_3$) δ 4.07 (s, 3H), 7.56 (d, J=8.7 Hz, 2H), 8.17 (d, J=9.0 Hz, 2H); APCI-MS (m/z) 239 (M+H)$^+$.

Step 4: 2-[5-(4-Chlorophenyl)-1,2,4-oxadiazol-3-yl]propan-2-ol

The title compound was prepared by the reaction of step 3 intermediate (500 mg, 2.095 mmol) and methyl magnesium bromide in THF (1.4M, 3.74 mL) in THF (10 mL) as per the process described in step 1 of Intermediate 1 to yield 491 mg of the product as a solid. $^1$H NMR (300 MHz, DMSO-$d_6$) δ 1.54 (s, 6H), 5.56 (s, 1H), 7.72 (d, J=9.0 Hz, 2H), 8.12 (d, J=8.7 Hz, 2H); APCI-MS (m/z) 238 (M+H)$^+$.

Step 5: 5-(4-Chlorophenyl)-3-[2-(4-nitrophenoxy)propan-2-yl]-1,2,4-oxadiazole

To a mixture of step 4 intermediate (200 mg, 0.837 mmol), 4-nitrophenol (116 mg, 0.837 mmol) and triphenylphosphine (329 mg, 1.256 mmol) in THF (5 mL) was slowly added diethyl azadicaboxylate (DIED) (0.21 mL, 1.088 mmol). The reaction mixture was stirred at RT for 16 h. The reaction mixture was diluted with ethyl acetate (20 mL) and water (15 mL). The layers were separated and the organic layer was washed with water (15 mL). The organic layer was dried over anhydrous sodium sulfate, filtered and concentrated under reduced pressure. The residue obtained was purified by silica gel column chromatography to yield 151 mg of the title product as a solid. $^1$H NMR (300 MHz, DMSO-$d_6$) δ 1.85 (s, 6H), 7.01 (d, J=9.3 Hz, 2H), 7.71 (d, J=8.4 Hz, 2H) 8.09-8.14 (m, 4H).

Step 6: 4-({2-[5-(4-Chlorophenyl)-1,2,4-oxadiazol-3-yl]propan-2-yl}oxy)aniline

The title compound was prepared by the reduction of step 5 intermediate (50 mg, 0.139 mmol) using iron powder (39 mg, 0.695 mmol) and ammonium chloride (74 mg, 1.390 mmol) in water (2 mL), methanol (2 mL) and THF (5 mL) as per the process described in step 2 of Intermediate 14 to yield 18 mg of the product as a solid. $^1$H NMR (300 MHz, DMSO-$d_6$) δ 1.90 (s, 6H), 6.37 (d, J=8.1 Hz, 2H), 6.45 (d, J=8.1 Hz, 2H) 7.74 (d, J=9.0 Hz, 2H), 8.17 (d, J=8.4 Hz, 2H); APCI-MS (m/z) 330 (M+H)$^+$.

Intermediate 29

4-{[1-(5-Chloro-1H-indol-1-yl)-2-methylpropan-2-yl]oxy}aniline

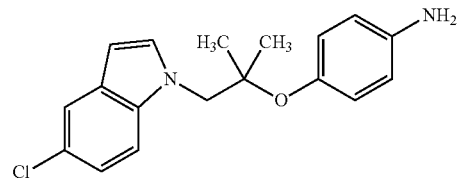 [SMILES: CC(C)(Cn1ccc2cc(Cl)ccc21)Oc1ccc(N)cc1]

Step 1: 1-(5-Chloro-1H-indol-1-yl)-2-methylpropan-2-ol

To a stirred solution of 5-chloro-1H-indole (700 mg, 4.617 mmol) in dry DMF (10 mL) was added of sodium hydride (60% w/w, 277 mg, 6.926 mmol) and the reaction was stirred at RT. After 30 min, 1,2-epoxy-2-methylpropane (0.83 mL, 9.234 mmol) was added to the reaction mixture and it was further stirred for 16 h. The reaction mixture was diluted with water (150 mL) and extracted with ethyl acetate (3×150 mL). The combined organic extracts were washed with water (2×100 mL), brine (100 mL) and dried over anhydrous sodium sulfate. The solvent was distilled off under reduced pressure and the obtained residue was purified by silica gel column chromatography to yield 313 mg of the title product as a viscous oil. $^1$H NMR (300 MHz, CDCl$_3$) δ 1.24 (s, 6H), 4.05 (s, 2H), 6.45 (s, 1H), 7.12-7.18 (m, 2H), 7.31 (d, J=7.2 Hz, 1H), 7.57 (s, 1H); APCI-MS (m/z) 224 (M+H)$^+$.

Step 2: 5-Chloro-1-[2-methyl-2-(4-nitrophenoxy)propyl]-1H-indole

The title compound was prepared by the coupling reaction of step 1 intermediate (300 mg, 1.341 mmol) with 1-fluoro-4-nitrobenzene (0.14 mL, 1.341 mmol) using sodium hydride (60% w/w, 80.4 mg, 2.011 mmol) and DMF (10 mL) as per the process described in step 1 to yield 282 mg of the product as a viscous oil. $^1$H NMR (300 MHz, DMSO-d$_6$) δ 1.37 (s, 6H), 4.48 (s, 2H), 6.48 (s, 1H), 7.14 (d, J=8.7 Hz, 3H), 7.50 (s, 1H), 7.59 (s, 1H), 7.70 (d, J=8.7 Hz, 1H), 8.13 (d, J=8.7 Hz, 2H); APCI-MS (m/z) 345 (M+H)$^+$.

Step 3: 4-{[1-(5-Chloro-1H-indol-1-yl)-2-methylpropan-2-yl]oxy}aniline

The title compound was prepared by the reduction of step 2 intermediate (275 mg, 0.797 mmol) using sodium borohydride (119 mg, 3.190 mmol) and nickel chloride (378 mg, 1.595 mmol) in methanol (10 mL) as per the process described in step 3 of Intermediate 1 to yield 200 mg of the product as an oil. $^1$H NMR (300 MHz, DMSO-d$_6$) δ 1.07 (s, 6H), 4.33 (s, 2H), 4.80 (s, 2H), 6.40 (d, J=7.8 Hz, 2H), 6.46-6.52 (m, 3H), 7.09 (d, J=9.3 Hz, 1H), 7.46 (br s, 1H), 7.58 (s, 1H), 7.62 (d, J=9.0 Hz, 1H); APCI-MS (m/z) 314 (M+H)$^+$.

Intermediate 30

4-{[1-(5-Fluoro-2-methyl-1H-indol-1-yl)-2-methylpropan-2-yl]oxy}aniline

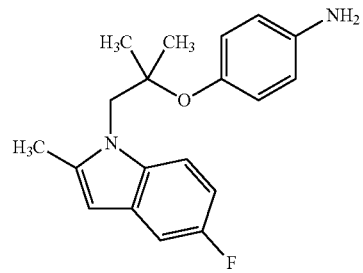 [SMILES: Cc1cc2cc(F)ccc2n1CC(C)(C)Oc1ccc(N)cc1]

Step 1: 1-(5-Fluoro-2-methyl-1H-indol-1-yl)-2-methylpropan-2-ol

The title compound was synthesized by the reaction of 5-fluoro-2-methylindole (700 mg, 4.691 mmol) with 1,2-epoxy-2-methylpropane (0.63 mL, 7.037 mmol) in presence of sodium hydride (60% w/w, 281 mg, 7.037 mmol) dry DMF (10 mL) as per the process described in step 1 of Intermediate 29 to yield 400 mg of the product as a liquid. $^1$H NMR (300 MHz, DMSO-d$_6$) δ 1.11 (s, 6H), 2.42 (s, 3H), 4.00 (s, 2H), 4.61 (s, 1H), 6.18 (s, 1H), 6.78-6.85 (m, 1H), 7.10-7.14 (m, 1H), 7.43-7.48 (m, 1H); APCI-MS (m/z) 222 (M+H)$^+$.

Step 2: 5-Fluoro-2-methyl-1-[2-methyl-2-(4-nitrophenoxy)propyl]-1H-indole

The title compound was prepared by the coupling reaction of step 1 intermediate (400 mg, 1.807 mmol) with 1-fluoro-4-nitrobenzene (0.19 mL, 1.807 mmol) using sodium hydride (60% w/w, 108 mg, 2.711 mmol) and DMF (10 mL) as per the process described in step 2 of Intermediate 1 to yield 500 mg of the product as an oil. $^1$H NMR (300 MHz, DMSO-d$_6$) δ 1.38 (s, 6H), 2.47 (s, 3H), 4.42 (s, 2H), 6.26 (s, 1H), 6.88 (t, J=9.3 Hz, 1H), 7.08 (d, J=9.3 Hz, 2H), 7.15-7.19 (m, 1H), 7.56-7.61 (m, 1H), 8.13 (d, J=9.0 Hz, 2H); APCI-MS (m/z) 343 (M+H)$^+$.

Step 3: 4-{[1-(5-Fluoro-2-methyl-1H-indol-1-yl)-2-methylpropan-2-yl]oxy}aniline The title compound was prepared by the reduction of step 2 intermediate (500 mg, 0.714 mmol) using sodium borohydride (217 mg, 5.841 mmol) and nickel chloride (692 mg, 2.920 mmol) in methanol (10 mL) as per the process described in step 3 of Intermediate 1 to yield 353 mg of the product as an oil. $^1$H NMR (300 MHz, DMSO-d$_6$) δ 1.10 (s, 6H), 2.45 (s, 3H), 4.27 (s, 2H), 4.81 (br s, 2H), 6.23 (s, 1H), 6.38 (d, J=8.7 Hz, 2H), 6.45 (d, J=8.7 Hz, 2H), 6.82 (t, J=8.7 Hz, 2H), 7.15 (d, J=6.0 Hz, 1H), 7.49-7.54 (m, 1H).

Intermediate 31

4-{[1-(4-Chlorophenyl)cyclobutyl]oxy}aniline

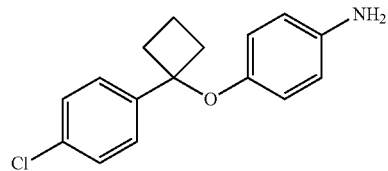 [SMILES: Nc1ccc(OC2(c3ccc(Cl)cc3)CCC2)cc1]

Step 1: 1-(4-chlorophenyl)cyclobutanol

To a stirred solution of 4-bromo-1-chlorobenzene (3 g, 15.669 mmol) in dry THF (10 mL) was added 1.6 M n-butyl lithium (11.7 mL, 18.80 mmol) drop-wise at −78° C. and the reaction mixture was stirred at the same temperature. After 30 minutes a solution of cyclobutanone (1.4 mL, 18.802 mmol) in THF (10 mL) was added to the reaction mixture at −78° C. The cooling bath was removed and the reaction mixture was stirred at room temperature for 4 h. The reaction mixture was diluted with saturated ammonium chloride solution (100 mL) and extracted with ethyl acetate (3×100 mL). The combined organic extracts were washed with water (2×100 mL), brine (100 mL) and dried over anhydrous sodium sulfate. The solvent was distilled under reduced pressure and the residue obtained was purified by silica gel column chromatography to yield 2.21 g of the title product as a semi-solid. $^1$H NMR (300 MHz, DMSO-d$_6$) δ 1.58-1.67 (m, 1H), 1.85-1.95 (m, 1H), 2.20-2.39 (m, 4H), 5.58 (s, 1H), 7.38 (d, J=8.1 Hz, 2H), 7.50 (d, J=8.4 Hz, 2H); ESI-MS (m/z) 183 (M+H)$^+$.

Step 2: 1-(4-chlorophenyl)cyclobutyl 4-nitrophenyl ether

The title compound was prepared by the reaction of step 1 intermediate (1 g, 5.474 mmol) with 1-fluoro-4-nitro benzene (0.58 mL, 5.474 mmol) by using sodium hydride (60% w/w, 328 mg, 8.212 mmol) in DMF (10 mL) as per the process described in step 2 of Intermediate 1 to yield 1.31 g of the product as a viscous oil. $^1$H NMR (300 MHz, DMSO-d$_6$) δ 1.85-2.05 (m, 1H), 2.50 (br s, 3H), 2.61-2.68 (m, 2H), 6.81 (d, J=9.3 Hz, 1H), 7.45 (d, J=8.4 Hz, 1H), 7.54 (d, J=8.7 Hz, 1H), 8.07 (d, J=9.3 Hz, 1H)

Step 3: 4-{[1-(4-chlorophenyl)cyclobutyl]oxy}aniline

The title compound was prepared by the reduction of step 2 intermediate (1.25 g, 4.115 mmol) using sodium borohydride (622 mg, 16.461 mmol) and nickel chloride (1.95 g, 8.230 mmol) in methanol (15 mL) as per the process described in step 3 of Intermediate 1 to yield 1.17 g of the product as a semi-solid. $^1$H NMR (300 MHz, DMSO-d$_6$) δ 1.71-1.78 (m, 1H), 1.88-1.92 (m, 1H), 2.45-2.49 (m, 4H), 4.54 (br s, 2H), 6.26-6.34 (m, 4H), 7.39 (d, J=8.4 Hz, 2H), 7.47 (d, J=8.1 Hz, 2H); ESI-MS (m/z) 273 (M+H)$^+$.

Intermediate 32

4-{[1-(4-Chloro-3-fluorophenyl)cyclobutyl]oxy}aniline

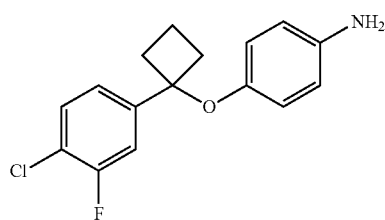

Step 1: 1-(4-Chloro-3-fluorophenyl)cyclobutanol

The title compound was synthesized by the reaction of 4-bromo-1-chloro-2-fluorobenzene (2 mL, 15.759 mmol) and cyclobutanone (1.4 mL, 18.911 mmol) in presence of 1.6 M n-butyl lithium (11.7 mL) in dry THF (10 mL) as per the process described in step 1 of Intermediate 31 to yield 700 mg of the title product as a solid. $^1$H NMR (300 MHz, DMSO-d$_6$) δ 1.60 (br s, 1H), 1.98 (br s, 2H), 2.26 (br s, 3H), 5.66 (s, 1H), 7.17 (t, J=7.8 Hz, 1H), 7.37 (t, J=7.8 Hz, 1H), 7.47 (t, J=6.9 Hz, 1H).

Step 2: 1-(4-Chloro-3-fluorophenyl)cyclobutyl 4-nitrophenyl ether

The title compound was prepared by the reaction of step 1 intermediate (250 mg, 1.246 mmol) with 1-fluoro-4-nitro benzene (0.13 mL, 1.246 mmol) by using sodium hydride (60% w/w, 74 mg, 1.869 mmol) in DMF (10 mL) as per the process described in step 2 of Intermediate 1 to yield 286 mg of the product as a viscous oil. $^1$H NMR (300 MHz, DMSO-d$_6$) δ 1.76 (br s, 1H), 1.99 (br s, 1H), 2.70 (br s, 2H), 2.88 (br s, 2H), 6.91 (d, J=9.0 Hz, 2H), 7.27 (t, J=7.8 Hz, 1H), 7.56 (t, J=7.4 Hz, 1H), 7.76 (t, J=7.4 Hz, 1H), 8.05 (t, J=9.0 Hz, 2H).

Step 3: 4-{[1-(4-Chloro-3-fluorophenyl)cyclobutyl]oxy}aniline

The title compound was prepared by the reduction of step 2 intermediate (278 mg, 0.899 mmol) using sodium borohydride (136 mg, 3.597 mmol) and nickel chloride (426 mg, 1.798 mmol) in methanol (10 mL) as per the process described in step 3 of Intermediate 1 to yield 175 mg of the product as a solid. $^1$H NMR (300 MHz, DMSO-d$_6$) δ 1.60-1.69 (m, 1H), 1.98 (br s, 1H), 2.54-7.62 (m, 4H), 4.63 (br s, 2H), 6.32-6.39 (m, 4H), 7.16 (t, J=7.8 Hz, 1H), 7.40 (t, J=7.5 Hz, 1H), 7.49 (t, J=7.8 Hz, 1H). APCI-MS (m/z) 292 (M+H)$^+$.

Intermediate 33

4-{[1-(4-Chloro-2-fluorophenyl)cyclobutyl]oxy}aniline

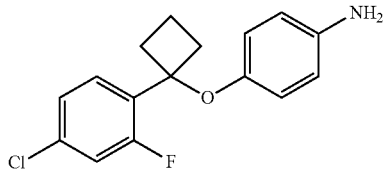 [SMILES: Nc1ccc(OC2(c3ccc(Cl)cc3F)CCC2)cc1]

Step 1: 1-(4-Chloro-2-fluorophenyl)cyclobutanol

The title compound was synthesized from the reaction of 1-bromo-4-chloro-2-fluorobenzene (2.0 mL, 15.756 mmol) and cyclobutanone (1.4 mL, 18.907 mmol) in the presence of n-butyl lithium (1.6M in THF, 11.8 mL) in THF (20 mL) as per the process described in step 1 of Intermediate 31 to obtain 1.62 g of the product as a semi-solid. $^1$H NMR (300 MHz, DMSO-d$_6$) δ 1.59-1.64 (m, 1H), 1.96-2.05 (m, 1H), 2.18-2.28 (m, 2H), 2.46-2.55 (m, 2H), 5.61 (s, 1H), 7.25 (d, J=8.4 Hz, 1H), 7.32-7.45 (m, 2H).

Step 2: 1-(4-Chloro-2-fluorophenyl)cyclobutyl 4-nitrophenyl ether

The title compound was prepared by the reaction of step 1 intermediate (1.2 g, 5.980 mmol) with 1-fluoro-4-nitro benzene (0.63 mL, 5.980 mmol) by using sodium hydride (60% w/w, 358 mg, 8.971 mmol) in DMF (10 mL) as per the process described in step 2 of Intermediate 1 to yield 612 mg of the product as a solid. $^1$H NMR (300 MHz, DMSO-d$_6$) δ

1.89-1.92 (m, 1H), 2.16-2.26 (m, 1H), 2.86-3.02 (m, 4H), 7.00 (d, J=9.3 Hz, 2H), 7.20-7.27 (m, 2H), 7.29-7.41 (m, 1H), 8.13 (d, J=8.7 Hz, 2H).

Step 3: 4-{[1-(4-Chloro-2-fluorophenyl)cyclobutyl]oxy}aniline

The title compound was prepared by the reduction of step 2 intermediate (600 mg, 1.864 mmol) using sodium borohydride (282 mg, 7.459 mmol) and nickel chloride (886 mg, 3.729 mmol) in methanol (10 mL) as per the process described in step 3 of Intermediate 1 to yield 447 mg of the product as a solid. $^1$H NMR (300 MHz, DMSO-$d_6$) δ 1.84 (br s, 1H), 2.22-2.31 (m, 1H), 2.64-2.71 (m, 4H), 4.69 (s, 2H), 6.30 (d, J=8.7 Hz, 2H), 6.36 (t, J=8.7 Hz, 2H), 7.02-7.09 (m, 1H), 7.24 (d, J=7.8 Hz, 1H), 7.28-7.32 (m, 1H).

Intermediate 34

4-{[1-(3,4-Difluorophenyl)cyclobutyl]oxy}aniline

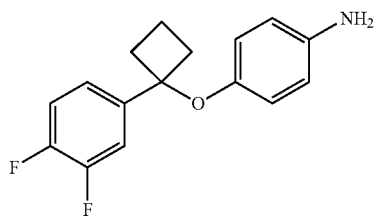 [SMILES: Nc1ccc(OC2(c3ccc(F)c(F)c3)CCC2)cc1]

Step 1: 1-(3,4-Difluorophenyl)cyclobutanol

The title compound was synthesized by the reaction of 4-bromo-1,2-difluorobenzene (1.0 mL, 8.808 mmol) and cyclobutanone (0.79 mL, 10.570 mmol) in the presence of n-butyl lithium (1.6M in THF, 6.6 mL) in THF (10 mL) as per the process described in step 1 of Intermediate 31 to obtain 467 mg of the product as a solid. $^1$H NMR (300 MHz, DMSO-$d_6$) δ 1.60-1.67 (m, 1H), 1.97-2.03 (m, 1H), 2.21-2.31 (m, 3H), 2.55-2.59 (m, 1H), 5.66 (s, 1H), 7.11-7.21 (m, 2H), 7.23-7.36 (m, 1H)

Step 2: 1-(3,4-Difluorophenyl)cyclobutyl 4-nitrophenyl ether

The title compound was prepared by the reaction of step 1 intermediate (250 mg, 1.357 mmol) with 1-fluoro-4-nitrobenzene (0.15 mL, 1.357 mmol) by using sodium hydride (60% w/w, 81 mg, 2.036 mmol) in DMF (4 mL) as per the process described in step 2 of Intermediate 1 to yield 348 mg of the product as a solid. $^1$H NMR (300 MHz, DMSO-$d_6$) δ 1.77-1.83 (m, 1H), 1.99 (br s, 1H), 2.67-2.72 (m, 2H), 2.88 (br s, 2H), 6.93 (d, J=9.3 Hz, 2H), 7.24-7.29 (m, 1H), 7.35-7.43 (m, 1H), 7.57 (t, J=7.8 Hz, 1H), 8.07 (d, J=8.7 Hz, 2H).

Step 3: 4-{[1-(3,4-Difluorophenyl)cyclobutyl]oxy}aniline

The title compound was prepared by the reduction of step 2 intermediate (340 mg, 1.113 mmol) using sodium borohydride (168 mg, 4.454 mmol) and nickel chloride (530 mg, 2.227 mmol) in methanol (10 mL) as per the process described in step 3 of Intermediate 1 to yield 311 mg of the product as a solid. $^1$H NMR (300 MHz, DMSO-$d_6$) δ 1.52 (t, J=6.9 Hz, 1H), 1.98 (br s, 1H), 2.54-2.59 (m, 4H), 4.60 (br s, 2H), 6.28-6.39 (m, 4H), 7.12-7.21 (m, 3H); ESI-MS (m/z) 275 (M+H)$^+$.

Intermediate 35

4-{[4-(3,4-Difluorophenyl)tetrahydro-2H-pyran-4-yl]oxy}aniline

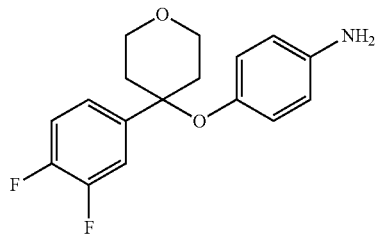 [SMILES: Nc1ccc(OC2(c3ccc(F)c(F)c3)CCOCC2)cc1]

Step 1: 4-(3,4-Difluorophenyl)tetrahydro-2H-pyran-4-ol

The title compound was synthesized from the reaction of 4-bromo-1,2-difluorobenzene (1.70 g, 8.808 mmol) and tetrahydro-4H-pyran-4-one (0.96 mL, 10.570 mmol) using n-butyl lithium (1.6M in THF, 6.6 mL) in THF (10 mL) as per the process described in step 1 of Intermediate 31 to obtain 627 mg of the product as a solid. $^1$H NMR (300 MHz, DMSO-$d_6$) δ 1.56 (d, J=13.2 Hz, 2H), 2.12-2.23 (m, 2H), 3.71-3.82 (m, 4H), 5.44 (s, 1H), 7.16-7.22 (m, 1H), 7.30-7.34 (m, 1H), 7.35-7.45 (m, 1H).

Step 2: 4-(3,4-Difluorophenyl)-4-(4-nitrophenoxy)tetrahydro-2H-pyran

The title compound was prepared by the reaction of step 1 intermediate (250 mg, 1.167 mmol) with 1-fluoro-4-nitro benzene (0.13 mL, 1.167 mmol) by using sodium hydride (60% w/w, 70 mg, 1.750 mmol) in DMF (4 mL) as per the process described in step 2 of Intermediate 1 to yield 346 mg of the product as a solid. $^1$H NMR (300 MHz, DMSO-$d_6$) δ 2.33-2.36 (m, 4H), 3.77 (br s, 4H), 6.92 (d, J=9.0 Hz, 2H), 7.32-7.37 (m, 2H), 7.43-7.48 (m, 1H), 8.08 (d, J=9.3 Hz, 2H).

Step 3: 4-{[4-(3,4-Difluorophenyl)tetrahydro-2H-pyran-4-yl]oxy}aniline

The title compound was prepared by the reduction of step 2 intermediate (330 mg, 0.9841 mmol) using sodium borohydride (149 mg, 3.936 mmol) and nickel chloride (468 mg, 1.968 mmol) in methanol (10 mL) as per the process described in step 3 of Intermediate 1 to yield 332 mg of the product as a solid. $^1$H NMR (300 MHz, DMSO-$d_6$) δ 2.13-2.27 (m, 4H), 3.68-3.71 (m, 2H), 3.78-3.86 (m, 2H), 4.66 (br s, 2H), 6.32-6.40 (m, 4H), 7.20 (br s, 2H), 7.38-7.40 (m, 1H); ESI-MS (m/z) 305 (M+H)$^+$.

Intermediate 36

4-{[4-(4-Chloro-2-fluorophenyl)tetrahydro-2H-pyran-4-yl]oxy}aniline

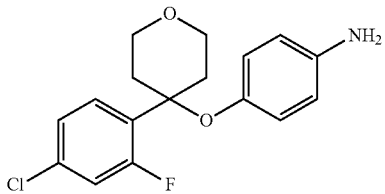 [SMILES: Nc1ccc(OC2(c3ccc(Cl)cc3F)CCOCC2)cc1]

Step 1: 4-(4-Chloro-2-fluorophenyl)tetrahydro-2H-pyran-4-ol

The title compound was synthesized by the reaction of 1-bromo-4-chloro-2-fluorobenzene (2.0 mL, 15.576 mmol) and tetrahydro-4H-pyran-4-one (2.0 mL, 18.907 mmol) using n-butyl lithium (1.6M in THF, 11.8 mL) in THF (20 mL) as per the process described in step 1 of Intermediate 31 to obtain 1.79 g of the product as a semi-solid. $^1$H NMR (300 MHz, DMSO-$d_6$) δ 2.21-2.35 (m, 4H), 3.77-3.87 (m, 4H), 5.42 (s, 1H), 7.10-7.17 (m, 1H), 7.23-7.30 (m, 2H)

Step 2: 4-(4-Chloro-2-fluorophenyl)-4-(4-nitrophenoxy)tetrahydro-2H-pyran

The title compound was prepared by the reaction of step 1 intermediate (700 mg, 3.034 mmol) with 1-fluoro-4-nitro benzene (0.32 mL, 3.034 mmol) by using sodium hydride (60% w/w, 182 mg, 4.552 mmol) in DMF (10 mL) as per the process described in step 2 of Intermediate 1 to yield 306 mg of the product as a solid. $^1$H NMR (300 MHz, DMSO-$d_6$) δ 2.40-2.45 (m, 2H), 2.69 (d, J=13.5 Hz, 2H), 3.76 (br s, 4H), 6.93 (d, J=9.3 Hz, 2H), 7.28-7.47 (m, 3H), 8.11 (t, J=9.3 Hz, 2H).

Step 3: 4-{[4-(4-Chloro-2-fluorophenyl)tetrahydro-2H-pyran-4-yl]oxy}aniline The title compound was prepared by the reduction of step 2 intermediate (300 mg, 0.8528 mmol) using sodium borohydride (129 mg, 3.411 mmol) and nickel chloride (405 mg, 1.705 mmol) in methanol (10 mL) as per the process described in step 3 of Intermediate 1 to yield 282 mg of the product as a solid. $^1$H NMR (300 MHz, DMSO-$d_6$) δ 2.25 (br s, 2H), 2.52-2.58 (m, 2H), 3.34-3.370 (m, 2H), 3.80-3.87 (m, 2H), 4.61 (s, 2H), 6.33 (d, J=9.3 Hz, 2H), 6.38 (t, J=9.3 Hz, 2H), 7.28-7.9 (m, 3H).

Intermediate 37

4-{[4-(4-Chlorophenyl)tetrahydro-2H-pyran-4-yl]oxy}aniline

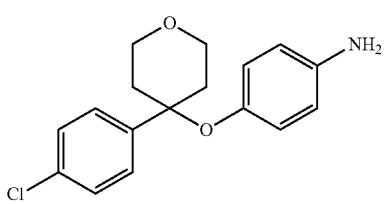 [SMILES: Nc1ccc(OC2(c3ccc(Cl)cc3)CCOCC2)cc1]

Step 1: 4-(4-Chlorophenyl)tetrahydro-2H-pyran-4-ol

The title compound was synthesized from the reaction of 4-bromochlorobenzene (3.0 g, 15.669 mmol), tetrahydro-4H-pyran-4-one (1.7 mL, 18.802 mmol) and n-butyl lithium (1.6M in THF, 11.7 mL) in THF (20 mL) as per the process described in step 1 of Intermediate 31 to obtain 1.95 g of the product as a white solid. $^1$H NMR (300 MHz, DMSO-$d_6$) δ 1.52 (d, J=12.9 Hz, 2H), 1.88-2.01 (m, 2H), 3.70-3.80 (m, 4H), 5.12 (s, 1H), 7.38 (d, J=8.4 Hz, 2H), 7.52 (d, J=9.0 Hz, 2H).

Step 2: 4-(4-Chlorophenyl)-4-(4-nitrophenoxy)tetrahydro-2H-pyran

The title compound was prepared by the reaction of step 1 intermediate (300 mg, 1.410 mmol) with 1-fluoro-4-nitro benzene (0.15 mL, 1.410 mmol) by using sodium hydride (60% w/w, 84 mg, 2.115 mmol) in DMF (4 mL) as per the process described in step 2 of Intermediate 1 to yield 45 mg of the product as a solid. $^1$H NMR (300 MHz, DMSO-$d_6$) δ 2.19 (br s, 4H), 3.69-3.80 (m, 4H), 6.84 (d, J=9.3 Hz, 2H), 7.48 (s, 4H), 8.07 (t, J=9.3 Hz, 2H).

Step 3: 4-{[4-(4-Chlorophenyl)tetrahydro-2H-pyran-4-yl]oxy}aniline

The title compound was prepared by the reduction of step 2 intermediate (400 mg, 1.198 mmol) using sodium borohydride (181 mg, 4.793 mmol) and nickel chloride (570 mg, 2.396 mmol) in methanol (10 mL) as per the process described in step 3 of Intermediate 1 to yield 258 mg of the product as a semi-solid. $^1$H NMR (300 MHz, DMSO-$d_6$) δ 2.04 (br s, 4H), 3.64-3.78 (m, 4H), 4.62 (s, 2H), 6.23-6.33 (m, 4H), 7.39-7.48 (m, 4H)

Intermediate 38

4-{[4-(4-Chloro-3-fluorophenyl)tetrahydro-2H-pyran-4-yl]oxy}aniline

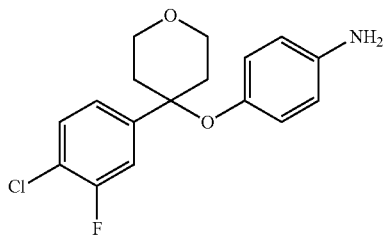

Step 1: 4-(4-Chloro-3-fluorophenyl)tetrahydro-2H-pyran-4-ol

The title compound was synthesized from the reaction of 4-bromo-1-chloro-2-fluorobenzene (1 mL, 8.164 mmol) and tetrahydro-4H-pyran-4-one (0.9 mL, 9.797 mmol) using n-butyl lithium (1.6M, 6.1 mL) in THF (10 mL) as per the process described in step 1 of Intermediate 31 to obtain 732 mg of the product as a semi-solid. $^1$H NMR (300 MHz, DMSO-$d_6$) δ 1.54 (d, J=12.9 Hz, 2H), 2.12-2.24 (m, 2H), 3.71-3.81 (m, 4H), 5.44 (s, 1H), 7.22 (t, J=8.4 Hz, 1H), 7.48 (t, J=6.9 Hz, 1H), 7.58 (t, J=6.9 Hz, 1H).

Step 2: 4-(4-Chloro-3-fluorophenyl)-4-(4-nitrophenoxy)tetrahydro-2H-pyran

The title compound was prepared by the reaction of step 1 intermediate (300 mg, 1.300 mmol) with 1-fluoro-4-nitrobenzene (0.14 mL, 1.300 mmol) by using sodium hydride (60% w/w, 78 mg, 1.950 mmol) in DMF (10 mL) as per the process described in step 2 of Intermediate 1 to yield 241 mg of the product as a semi-solid. $^1$H NMR (300 MHz, DMSO-$d_6$) δ 2.31-2.39 (m, 4H), 3.72-3.77 (m, 4H), 6.91 (d, J=9.3 Hz, 2H), 7.33 (t, J=8.4 Hz, 1H), 7.54 (t, J=6.9 Hz, 1H), 7.63 (t, J=7.4 Hz, 1H), 8.08 (d, J=9.3 Hz, 2H).

Step 3: 4-{[4-(4-Chloro-3-fluorophenyl)tetrahydro-2H-pyran-4-yl]oxy}aniline

The title compound was prepared by the reduction of step 2 intermediate (230 mg, 0.653 mmol) using sodium borohydride (99 mg, 2.615 mmol) and nickel chloride (311 mg, 1.307 mmol) in methanol (10 mL) as per the process described in step 3 of Intermediate 1 to yield 211 mg of the product as a semi-solid. $^1$H NMR (300 MHz, DMSO-$d_6$) δ 2.09-2.26 (m, 4H), 3.69-3.77 (m, 2H), 3.78-3.87 (m, 2H), 4.67 (br s, 2H), 6.31-6.38 (m, 4H), 7.21 (t, J=7.8 Hz, 1H), 7.36 (t, J=6.9 Hz, 1H), 7.56 (t, J=7.2 Hz, 1H); ESI-MS (m/z) 322 (M+H)$^+$.

Intermediate 39

4-{[4-(3,4-Dichlorophenyl)tetrahydro-2H-pyran-4-yl]oxy}aniline

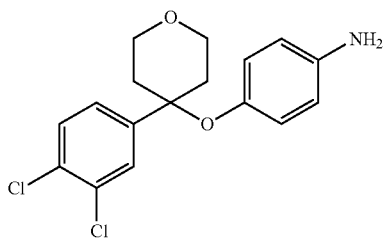 [SMILES: Nc1ccc(OC2(c3ccc(Cl)c(Cl)c3)CCOCC2)cc1]

Step 1: 4-(3,4-Dichlorophenyl)tetrahydro-2H-pyran-4-ol

The title compound was synthesized by the reaction of 1-bromo-3,4-dichlorobenzene (2 mL, 15.582 mmol) with tetrahydro-4H-pyran-4-one (1.7 mL, 18.698 mmol) using n-butyl lithium (1.6M in THF, 11.6 mL) in THF (20 mL) as per the process described in step 1 of Intermediate 31 to obtain 395 mg of the product as a semi-solid. $^1$H NMR (300 MHz, DMSO-$d_6$) δ 1.52 (d, J=12.9 Hz, 2H), 2.51-2.62 (m, 2H), 3.75-3.82 (m, 4H), 5.39 (s, 1H), 7.38 (t, J=7.8 Hz, 1H), 7.58 (d, J=7.8 Hz, 1H), 7.79 (d, J=8.1 Hz, 1H).

Step 2: 4-(3,4-dichlorophenyl)-4-(4-nitrophenoxy)tetrahydro-2H-pyran

The title compound was prepared by the reaction of step 1 intermediate (300 mg, 1.213 mmol) with 1-fluoro-4-nitrobenzene (0.13 mL, 1.213 mmol) by using sodium hydride (60% w/w, 73 mg, 1.820 mmol) in DMF (10 mL) as per the process described in step 2 of Intermediate 1 to yield 382 mg of the product as a solid. $^1$H NMR (300 MHz, DMSO-$d_6$) δ 2.20 (br s, 4H), 3.68-3.79 (m, 4H), 6.87 (d, J=9.3 Hz, 2H), 7.46 (d, J=8.4 Hz, 1H), 7.67-7.72 (m, 2H), 8.09 (d, J=9.3 Hz, 2H).

Step 3: 4-{[4-(3,4-Dichlorophenyl)tetrahydro-2H-pyran-4-yl]oxy}aniline

The title compound was prepared by reduction of step 2 intermediate (200 mg, 0.543 mmol) using sodium borohydride (82 mg, 2.172 mmol) and nickel chloride (258 mg, 1.086 mmol) in methanol (10 mL) as per the process described in step 3 of Intermediate 1 to yield 158 mg of the product as a semi-solid. $^1$H NMR (300 MHz, DMSO-$d_6$) δ 2.05 (br s, 4H), 3.68-3.75 (m, 4H), 4.66 (br s, 2H), 6.27-6.35 (m, 4H), 7.45 (d, J=8.4 Hz, 1H), 7.64 (d, J=4.5 Hz, 2H).

Intermediate 40

4-{[4-(2,4-Dichlorophenyl)tetrahydro-2H-pyran-4-yl]oxy}aniline

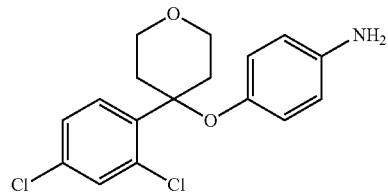 [SMILES: Nc1ccc(OC2(c3ccc(Cl)cc3Cl)CCOCC2)cc1]

Step 1: 4-(2,4-Dichlorophenyl)tetrahydro-2H-pyran-4-ol

To a stirred solution of 1-bromo-2,4-dichlorobenzene (500 mg, 2.213 mmol) in diethyl ether (10 mL) was added n-butyl lithium (1.6M in THF, 1.6 mL) drop-wise at −78° C. under nitrogen atmosphere and the reaction mixture was stirred at the same temperature for 30 minutes. A solution of tetrahydro-4H-pyran-4-one (0.24 mL, 2.656 mmol) in diethyl ether (10 mL) was added to the reaction mixture at −78° C. The cooling bath was removed and the reaction mixture was stirred at room temperature for 18 h. The mixture was diluted with saturated ammonium chloride solution (50 mL) and extracted with ethyl acetate (3×50 mL). The combined organic extracts were washed with water (2×100 mL), brine (100 mL) and dried over anhydrous sodium sulfate. The solvent was distilled under reduced pressure and the residue obtained was purified by silica gel column chromatography to yield 221 g of the title product as a semi-solid. $^1$H NMR (300 MHz, DMSO-$d_6$) δ 1.42 (d, J=13.2 Hz, 2H), 2.48-2.57 (m, 2H), 3.71-3.79 (m, 4H), 5.35 (s, 1H), 7.41-7.51 (m, 2H), 7.78 (d, J=8.7 Hz, 1H).

Step 2: 4-(2,4-dichlorophenyl)-4-(4-nitrophenoxy)tetrahydro-2H-pyran

To a stirred and cooled (0° C.) solution of step 1 intermediate (210 mg, 0.8497 mmol) in dry DMF (4 mL) was added sodium hydride (60% w/w, 51 mg, 1.274 mmol) and the reaction was stirred at RT for 30 min. 1-Fluoro-4-nitrobenzene (0.09 mL, 0.849 mmol) was added to the reaction mixture and stirred for 18 h at RT. The mixture was diluted with water (20 mL) and extracted with ethyl acetate (3×20 mL). The combined organic layers were washed with water (2×50 mL), brine (50 mL) and dried over anhydrous sodium sulfate. The solvent was distilled off under reduced pressure and the residue obtained was purified by silica gel column chromatography to yield 274 mg of the title product as a semi-solid. $^1$H NMR (300 MHz, DMSO-d$_6$) δ 2.24 (br s, 2H), 2.55 (br s, 2H), 3.76-3.79 (m, 4H), 6.82 (d, J=9.0 Hz, 2H), 7.58 (br s, 2H), 7.70-7.73 (m, 1H), 8.05 (d, J=9.3 Hz, 2H).

Step 3: 4-{[4-(2,4-Dichlorophenyl)tetrahydro-2H-pyran-4-yl]oxy}aniline

To a stirred solution of step 2 intermediate (260 mg, 0.7061 mmol) and nickel chloride (335 mg, 1.412 mmol) in methanol (5 mL) was added sodium borohydride (107 mg, 2.824 mmol) in portions. The reaction mixture was stirred at room temperature for 1 h. The mixture was concentrated under reduced pressure to yield a viscous residue. The residue was diluted with water (20 mL) and ethyl acetate (20 mL). The layers were separated and the aqueous layer was extracted with ethyl acetate (2×20 mL). The combined organic layers were washed with water (50 mL) followed by brine (25 mL) and dried over anhydrous sodium sulfate. The solvent was distilled off under reduced pressure and the residue obtained was purified by silica gel column chromatography to yield 204 mg of the title product as a semi-solid. $^1$H NMR (300 MHz, DMSO-d$_6$) δ 2.12-2.16 (m, 2H), 2.33-2.37 (m, 2H), 3.72-3.84 (m, 4H), 4.62 (br s, 2H), 6.32 (s, 4H), 7.44-7.53 (m, 2H), 7.59 (s, 1H)

Intermediate 41

4-({4-[3-Fluoro-4-(trifluoromethyl)phenyl]tetrahydro-2H-pyran-4-yl}oxy)aniline

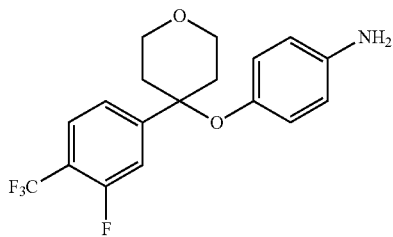 [SMILES: Nc1ccc(OC2(c3ccc(C(F)(F)F)c(F)c3)CCOCC2)cc1]

Step 1: 4-[3-Fluoro-4-(trifluoromethyl)phenyl]tetrahydro-2H-pyran-4-ol

The title compound was synthesized by the reaction of 4-bromo-2-fluorobenzotrifluoride (860 mg, 3.539 mmol) with tetrahydro-4H-pyran-4-one (0.36 mL, 3.893 mmol) using n-butyl lithium (1.6M in THF, 2.4 mL) in THF (20 mL) as per the process described in step 1 of Intermediate 31 to obtain 438 mg of the product as a semi-solid. $^1$H NMR (300 MHz, DMSO-d$_6$) δ 1.52 (d, J=13.2 Hz, 2H), 1.95-2.05 (m, 2H), 3.73-3.81 (m, 4H), 5.41 (s, 1H), 7.52-7.60 (m, 2H), 7.74 (t, J=7.8 Hz, 1H).

Step 2: 4-[3-fluoro-4-(trifluoromethyl)phenyl]-4-(4-nitrophenoxy)tetrahydro-2H-pyran The title compound was prepared by the reaction of step 1 intermediate (210 mg, 0.7947 mmol) with 1-fluoro-4-nitro benzene (0.08 mL, 0.794 mmol) by using sodium hydride (60% w/w, 48 mg, 1.192 mmol) in DMF (5 mL) as per the process described in step 2 of Intermediate 1 to yield 217 mg of the product as a solid. $^1$H NMR (300 MHz, DMSO-d$_6$) δ 2.22 (br s, 4H), 3.69-3.79 (m, 4H), 6.85 (d, J=9.3 Hz, 2H), 7.50 (d, J=8.4 Hz, 1H), 7.66 (d, J=12.6 Hz, 1H), 7.80-7.85 (m, 1H), 8.08 (d, J=9.3 Hz, 2H).

Step 3: 4-({4-[3-Fluoro-4-(trifluoromethyl)phenyl]tetrahydro-2H-pyran-4-yl}oxy)aniline The title compound was prepared by reduction of step 2 intermediate (200 mg, 0.5190 mmol) using sodium borohydride (78 mg, 2.0762 mmol) and nickel chloride (247 mg, 1.038 mmol) in methanol (5 mL) as per the process described in step 3 of Intermediate 1 to yield 135 mg of the product as a semi-solid. $^1$H NMR (300 MHz, DMSO-d$_6$) δ 2.07 (br s, 4H), 3.70-3.75 (m, 4H), 4.67 (br s, 2H), 6.30-6.33 (m, 4H), 7.48-7.59 (m, 2H), 7.79 (t, J=7.8 Hz, 1H).

Intermediate 42

4-({4-[4-Fluoro-3-(trifluoromethyl)phenyl]tetrahydro-2H-pyran-4-yl}oxy)aniline

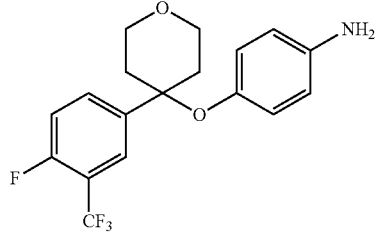 [SMILES: Nc1ccc(OC2(c3ccc(F)c(C(F)(F)F)c3)CCOCC2)cc1]

Step 1: 4-[4-Fluoro-3-(trifluoromethyl)phenyl]tetrahydro-2H-pyran-4-ol

The title compound was synthesized by the reaction of 4-bromo-1-fluoro-2-(trifluoromethyl)benzene (1.0 mL, 7.109 mmol) with tetrahydro-4H-pyran-4-one (0.72 mL, 7.820 mmol) using n-butyl lithium (1.6M in THF, 4.8 mL) in THF (20 mL) as per the process described in step 1 of Intermediate 31 to obtain 803 mg of the product as a semi-solid. $^1$H NMR (300 MHz, DMSO-d$_6$) δ 1.50 (d, J=13.2 Hz, 2H), 1.95-2.03 (m, 2H), 3.75-3.82 (m, 4H), 5.34 (s, 1H), 7.46 (t, J=9.6 Hz, 1H), 7.85 (d, J=6.3 Hz, 2H).

Step 2: 4-[4-fluoro-3-(trifluoromethyl)phenyl]-4-(4-nitrophenoxy)tetrahydro-2H-pyran The title compound was prepared by the reaction of step 1 intermediate (300 mg, 0.135 mmol) with 1-fluoro-4-nitro benzene (0.12 mL, 0.135 mmol) by using sodium hydride (60% w/w, 68 mg, 1.703 mmol) in DMF (10 mL) as per the process described in step 2 of Intermediate 1 to yield 382 mg of the product as a semi-solid. $^1$H NMR (300 MHz, DMSO-d$_6$) δ 2.24 (br s, 4H), 3.66-3.76 (m, 4H), 6.85 (d, J=9.3 Hz, 2H), 7.57 (t, J=9.0 Hz, 1H), 7.77-7.84 (m, 2H), 8.06 (d, J=9.3 Hz, 2H).

Step 3: 4-({4-[4-Fluoro-3-(trifluoromethyl)phenyl]tetrahydro-2H-pyran-4-yl}oxy)aniline The title compound was prepared by reduction of step 2 intermediate (370 mg, 0.9602 mmol) using sodium borohydride (145 mg, 3.8406 mmol) and nickel chloride (456 mg, 1.9205 mmol) in methanol (4 mL) as per the process described in step 3 of Intermediate 1 to yield 261 mg of the product as a semi-solid. $^1$H NMR (300 MHz, DMSO-d$_6$) δ 2.09 (br s, 4H), 3.68-3.75 (m, 4H), 4.67 (br s, 2H), 6.24-6.33 (m, 4H), 7.52 (t, J=9.3 Hz, 1H), 7.70-7.82 (m, 2H).

Intermediate 43

4-{[4-(4-Chloro-3-fluorophenyl)-N-Boc-piperidin-4-yl]oxy}aniline

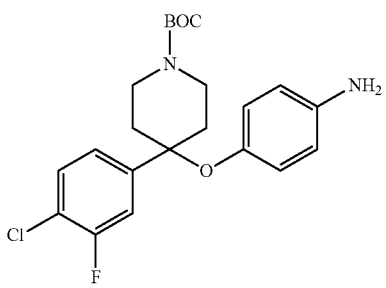 [SMILES: CC(C)(C)OC(=O)N1CCC(Oc2ccc(N)cc2)(c2ccc(Cl)c(F)c2)CC1]

Step 1: tert-Butyl 4-(4-chloro-3-fluorophenyl)-4-hydroxypiperidine-1-carboxylate The title compound was synthesized by the reaction of 4-bromo-1-chloro-2-fluorobenzene (2.0 mL, 15.759 mmol) with tert-butyl 4-oxopiperidine-1-carboxylate (3.76 g, 18.911 mmol) using n-butyl lithium (1.6M in ether, 11.8 mL) in THF (20 mL) as per the process described in step 1 of Intermediate 31 to obtain 1.2 g of the product as a semi-solid. $^1$H NMR (300 MHz, DMSO-d$_6$) δ 1.41 (s, 9H), 1.59 (d, J=12.6 Hz, 2H), 1.98-2.05 (m, 2H), 3.12 (br s, 2H), 3.83 (br s, 2H), 5.52 (s, 1H), 7.22 (t, J=7.5 Hz, 1H), 7.45 (t, J=6.9 Hz, 1H), 7.59 (t, J=7.2 Hz, 1H).

Step 2: 4-(4-Chloro-3-fluorophenyl)-4-(4-nitrophenoxy)-N-Boc-piperidine

The title compound was prepared by the reaction of step 1 intermediate (1.05 g, 3.183 mmol) with 1-fluoro-4-nitro benzene (0.34 mL, 3.183 mmol) by using sodium hydride (60% w/w, 191 mg, 4.775 mmol) in DMF (10 mL) as per the process described in step 2 of Intermediate 1 to yield 955 mg of the product as a solid. $^1$H NMR (300 MHz, DMSO-d$_6$) δ 1.38 (s, 9H), 2.06-2.15 (m, 2H), 2.40-2.48 (m, 2H), 3.07 (br s, 2H), 3.86 (br s, 2H), 6.89 (d, J=9.3 Hz, 2H), 7.29 (t, J=7.8 Hz, 1H), 7.50 (t, J=7.2 Hz, 1H), 7.61 (t, J=7.2 Hz, 1H), 8.06 (d, J=8.7 Hz, 2H); APCI-MS (m/z) 350 (M+H)$^+$.

Step 3: 4-{[4-(4-Chloro-3-fluorophenyl)-N-Boc-piperidin-4-yl]oxy}aniline

The title compound was prepared by the reduction of step 2 intermediate (200 mg, 0.443 mmol) using sodium borohydride (67 mg, 1.774 mmol) and nickel chloride (211 mg, 0.887 mmol) in methanol (5 mL) as per the process described in step 3 of Intermediate 1 to yield 155 mg of the product as a solid. $^1$H NMR (300 MHz, DMSO-d$_6$) δ 1.40 (s, 9H), 1.93-2.01 (m, 2H), 2.23-2.30 (m, 2H), 3.21 (br s, 2H), 3.74-3.80 (m, 2H), 4.67 (s, 2H), 6.31 (d, J=8.7 Hz, 2H), 6.37 (t, J=8.7 Hz, 2H), 7.21 (d, J=7.8 Hz, 1H), 7.38 (t, J=7.2 Hz, 1H), 7.56 (t, J=7.5 Hz, 1H); APCI-MS (m/z) 321 (M+H)$^+$.

Intermediate 44

4-{[4-(4-Chloro-3-fluorophenyl)-1-methylpiperidin-4-yl]oxy}aniline

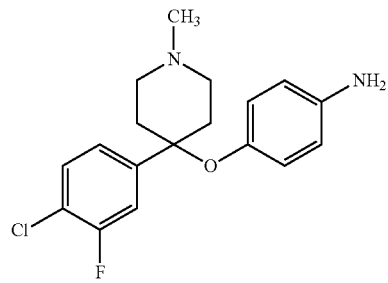 [SMILES: CN1CCC(Oc2ccc(N)cc2)(c2ccc(Cl)c(F)c2)CC1]

Step 1: 4-(4-Chloro-3-fluorophenyl)-1-methylpiperidin-4-ol

The title compound was synthesized by the reaction of 4-bromo-1-chloro-2-fluorobenzene (2.0 mL, 16.233 mmol), N-methylpiperidone (2.3 mL, 19.480 mmol) and n-butyl lithium (1.6M in hexane, 12.2 mL) in THF (40 mL) as per the process described in step 1 of Intermediate 31 to obtain 4.17 g of the product as a semi-solid. $^1$H NMR (300 MHz, CDCl$_3$) δ 1.94 (d, J=13.2 Hz, 2H), 2.46 (br s, 5H), 2.67-2.78 (m, 2H), 2.80-2.89 (m, 2H), 7.08 (t, J=7.8 Hz, 1H), 7.31-7.42 (m, 2H).

Step 2: 4-(4-Chloro-3-fluorophenyl)-1-methyl-4-(4-nitrophenoxy)piperidine

The title compound was prepared by the reaction of step 1 intermediate (300 mg, 1.231 mmol) with 1-fluoro-4-nitro benzene (0.13 mL, 1.231 mmol) by using sodium hydride (60% w/w, 74 mg, 1.846 mmol) in DMF (4 mL) as per the process described in step 2 of Intermediate 1 to yield 392 mg of the product as a semi-solid. $^1$H NMR (300 MHz, DMSO-d$_6$) δ 1.19-2.27 (m, 4H), 2.31-2.45 (m, 5H), 2.63 (br s, 2H), 6.87 (d, J=9.3 Hz, 2H), 7.31 (t, J=7.8 Hz, 1H), 7.52 (t, J=6.9 Hz, 1H), 7.61 (t, J=6.6 Hz, 1H), 8.08 (d, J=9.3 Hz, 2H).

Step 3: 4-{[4-(4-Chloro-3-fluorophenyl)-1-methylpiperidin-4-yl]oxy}aniline

The title compound was prepared by reduction of step 2 intermediate (380 mg, 1.046 mmol) using sodium borohydride (157 mg, 4.166 mmol) and nickel chloride (495 mg, 2.083 mmol) in methanol (5 mL) as per the process described in step 3 of Intermediate 1 to yield 276 mg of the product as a solid. $^1$H NMR (300 MHz, DMSO-d$_6$) δ 2.08-2.55 (m, 11H), 4.66 (br s, 4H), 6.32 (s, 4H), 7.19 (t, J=7.8 Hz, 1H), 7.37 (t, J=6.6 Hz, 1H), 7.55 (t, J=7.8 Hz, 1H); ESI-MS (m/z) 334 (M+H)$^+$.

93

Intermediate 45

4-{[3-(4-Chloro-3-fluorophenyl)oxetan-3-yl]oxy}aniline

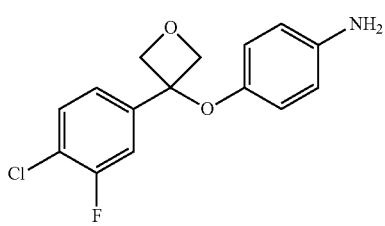 [SMILES: Nc1ccc(OC2(c3ccc(Cl)c(F)c3)COC2)cc1]

Step 1: 3-(4-Chloro-3-fluorophenyl)oxetan-3-ol

The title compound was synthesized from the reaction of 4-bromo-1-chloro-3-fluorobenzene (1 mL, 8.164 mmol), 3-oxetinone (0.62 mL, 9.797 mmol) and n-butyl lithium (1.6M in ether, 6.1 mL) in THF (10 mL) as per the process described in step 1 of Intermediate 31 to obtain 395 mg of the product as a solid. $^1$H NMR (300 MHz, DMSO-$d_6$) δ 4.70 (d, J=6.9 Hz, 2H), 4.97 (d, J=6.6 Hz, 2H), 6.50 (s, 1H), 7.23 (t, J=7.8 Hz, 1H), 7.41 (t, J=6.6 Hz, 1H), 7.55 (t, J=7.2 Hz, 1H).

Step 2: 3-(4-Chloro-3-fluorophenyl)-3-(4-nitrophenoxy)oxetane

The title compound was synthesized by the reaction of step 1 intermediate (180 mg, 0.888 mmol) with 4-fluoro-1-nitrobenzene (125 mg, 0.888 mmol) by using sodium hydride (60% w/w, 53 mg, 1.332 mmol) in DMF (4 mL) as per the process described in step 2 of Intermediate 1 to yield 279 mg of the product as a semi-solid. $^1$H NMR (300 MHz, DMSO-$d_6$) δ 5.06 (d, J=7.8 Hz, 2H), 5.27 (d, J=7.5 Hz, 2H), 6.94 (d, J=9.0 Hz, 2H), 7.28 (t, J=7.8 Hz, 1H), 7.61 (t, J=7.2 Hz, 1H), 7.75 (t, J=7.2 Hz, 1H), 8.10 (d, J=9.3 Hz, 2H).

Step 3: 4-{[3-(4-Chloro-3-fluorophenyl)oxetan-3-yl]oxy}aniline

The title compound was synthesized by the nitro reduction of the step 2 intermediate (396 mg, 1.668 mmol) by using sodium borohydride (126 mg, 3.336 mmol) and nickel chloride (191 mg, 0.8056 mmol) in methanol (4 mL) as per the process described in step 3 of Intermediate 1 to yield 226 mg of the product as a semi-solid. $^1$H NMR (300 MHz, DMSO-$d_6$) δ 4.71 (br s, 2H), 5.00 (d, J=7.2 Hz, 2H), 5.08 (d, J=7.2 Hz, 2H), 6.36 (br s, 4H), 7.19 (t, J=8.7 Hz, 1H), 7.43 (t, J=7.8 Hz, 1H), 0.7.56 (t, J=7.8 Hz, 1H); ESI-MS (m/z) 294 (M+H)$^+$.

94

Intermediate 46

4-{[3-(3,4-Dichlorophenyl)oxetan-3-yl]oxy}aniline

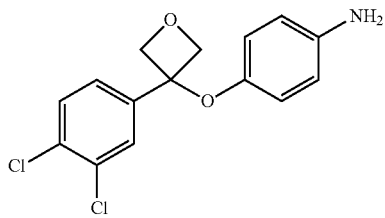 [SMILES: Nc1ccc(OC2(c3ccc(Cl)c(Cl)c3)COC2)cc1]

Step 1: 3-(3,4-Dichlorophenyl)oxetan-3-ol

The title compound was synthesized from the reaction of 1-bromo-3,4-dichlorobenzene (1.25 mL, 9.738 mmol), 3-oxetinone (850 mg, 11.686 mmol) and n-butyl lithium (1.6M in ether, 7.3 mL) in THF (20 mL) as per the process described in step 1 of Intermediate 31 to obtain 985 mg of the product as a semi-solid. $^1$H NMR (300 MHz, DMSO-$d_6$) δ 4.66 (d, J=6.9 Hz, 2H), 4.77 (d, J=6.9 Hz, 2H), 6.61 (s, 1H), 7.59-7.69 (m, 2H), 7.77 (s, 1H).

Step 2: 3-(3,4-Dichlorophenyl)-3-(4-nitrophenoxy)oxetane

The title compound was synthesized by the reaction of step 1 intermediate (100 mg, 0.456 mmol) with 1-fluoro-4-nitrobenzene (64 mg, 0.456 mmol) by using sodium hydride (60% w/w, 22 mg, 0.547 mmol) in DMF (2 mL) as per the process described in step 2 of Intermediate 1 to yield 158 mg of the product as a solid. $^1$H NMR (300 MHz, DMSO-$d_6$) δ 4.97-5.05 (m, 4H), 6.81 (d, J=9.0 Hz, 2H), 7.51 (d, J=8.4 Hz, 1H), 7.71 (d, J=8.7 Hz, 1H), 7.84 (s, 1H), 8.13 (d, J=9.0 Hz, 2H).

Step 3: 4-{[3-(3,4-Dichlorophenyl)oxetan-3-yl]oxy}aniline

The title compound was synthesized by the nitro reduction of the step 2 intermediate (145 mg, 0.426 mmol) by using sodium borohydride (65 mg, 1.705 mmol) and nickel chloride (202 mg, 0.852 mmol) in methanol (4 mL) as per the process described in step 3 of Intermediate 1 to yield 62 mg of the product as a solid. $^1$H NMR (300 MHz, DMSO-$d_6$) δ 4.67 (br s, 2H), 4.88 (br s, 4H), 6.27 (d, J=8.7 Hz, 2H), 6.40 (d, J=8.7 Hz, 2H), 7.49 (d, J=8.4 Hz, 1H), 7.65-7.72 (m, 2H); ESI-MS (m/z) 310 (M+H)$^+$.

Intermediate 47

4-{[3-(2,4-Dichlorophenyl)oxetan-3-yl]oxy}aniline

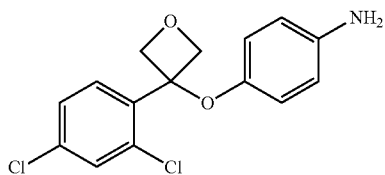 [SMILES: Nc1ccc(OC2(c3ccc(Cl)cc3Cl)COC2)cc1]

Step 1: 3-(2,4-Dichlorophenyl)oxetan-3-ol

The title compound was synthesized from the reaction of 1-bromo-2,4-dichlorobenzene (0.5 mL, 4.183 mmol), 3-oxetinone (331 mg, 4.601 mmol) and n-butyl lithium (1.6M in ether, 2.8 mL) in THF (20 mL) as per the process described in step 1 of Intermediate 31 to obtain 269 mg of the product as a solid. $^1$H NMR (300 MHz, DMSO-$d_6$) δ 4.68 (d, J=6.9 Hz, 2H), 5.02 (d, J=6.9 Hz, 2H), 6.34 (s, 1H), 7.43 (s, 2H), 7.61 (s, 1H).

Step 2: 3-(2,4-Dichlorophenyl)-3-(4-nitrophenoxy)oxetane

The title compound was synthesized by the reaction of step 1 intermediate (125 mg, 0.570 mmol) with 1-fluoro-4-nitrobenzene (80 mg, 0.570 mmol) by using sodium hydride (60% w/w, 34 mg, 0.855 mmol) in DMF (4 mL) as per the process described in step 2 of Intermediate 1 to yield 191 mg of the product as a semi-solid. $^1$H NMR (300 MHz, DMSO-$d_6$) δ 5.12 (d, J=6.9 Hz, 2H), 5.30 (d, J=6.9 Hz, 2H), 6.94 (d, J=8.7 Hz, 2H), 7.52 (d, J=8.4 Hz, 1H), 7.65 (s, 1H), 8.04-8.08 (m, 3H).

Step 3: 4-{[3-(2,4-Dichlorophenyl)oxetan-3-yl]oxy}aniline

The title compound was synthesized by the nitro reduction of the step 2 intermediate (180 mg, 0.529 mmol) by using sodium borohydride (80 mg, 2.116 mmol) and nickel chloride (252 mg, 1.058 mmol) in methanol (4 mL) as per the process described in step 3 of Intermediate 1 to yield 91 mg of the product as a semi-solid. $^1$H NMR (300 MHz, DMSO-$d_6$) δ 4.71 (br s, 2H), 5.02 (d, J=7.8 Hz, 2H), 5.09 (d, J=7.8 Hz, 2H), 6.31 (d, J=8.7 Hz, 2H), 6.40 (d, J=8.7 Hz, 2H), 7.37 (d, J=8.7 Hz, 1H), 7.47 (d, J=8.7 Hz, 1H), 7.63 (s, 1H); ESI-MS (m/z) 310 (M+H)$^+$.

Intermediate 48

4-({3-[3-Fluoro-4-(trifluoromethyl)phenyl]oxetan-3-yl}oxy)aniline

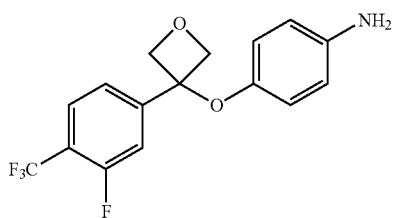 [SMILES: Nc1ccc(OC2(c3ccc(C(F)(F)F)c(F)c3)COC2)cc1]

Step 1: 3-[3-Fluoro-4-(trifluoromethyl)phenyl]oxetan-3-ol

The title compound was synthesized from the reaction of 2-fluoro-4-bromo-benzotrifluoride (0.5 mL, 3.539 mmol), 3-oxetinone (280 mg, 3.893 mmol) and n-butyl lithium (1.6M in ether, 2.4 mL) in THF (20 mL) as per the process described in step 1 of Intermediate 31 to obtain 252 mg of the product as a solid. $^1$H NMR (300 MHz, DMSO-$d_6$) δ 4.67 (d, J=6.9 Hz, 2H), 4.80 (d, J=6.9 Hz, 2H), 6.74 (s, 1H), 7.62-7.69 (m, 2H), 7.80-7.86 (m, 1H).

Step 2: 3-[3-Fluoro-4-(trifluoromethyl)phenyl]-3-(4-nitrophenoxy)oxetane

The title compound was synthesized by the reaction of step 1 intermediate (240 mg, 1.016 mmol) with 1-fluoro-4-nitrobenzene (108 mg, 1.016 mmol) by using sodium hydride (60% w/w, 61 mg, 1.524 mmol) in DMF (10 mL) as per the process described in step 2 of Intermediate 1 to yield 355 mg of the product as yellow solid. $^1$H NMR (300 MHz, DMSO-$d_6$) δ 4.98-5.06 (m, 4H), 6.78 (d, J=9.0 Hz, 2H), 7.53 (d, J=8.4 Hz, 1H), 7.73 (d, J=9.0 Hz, 1H), 7.85 (t, J=7.8 Hz, 1H), 8.10 (d, J=8.7 Hz, 2H).

Step 3: 4-({3-[3-Fluoro-4-(trifluoromethyl)phenyl]oxetan-3-yl}oxy)aniline

The title compound was synthesized by the nitro reduction of the step 2 intermediate (340 mg, 0.9516 mmol) by using sodium borohydride (144 mg, 3.8067 mmol) and nickel chloride (452 mg, 1.9033 mmol) in methanol (10 mL) as per the process described in step 3 of Intermediate 1 to yield 275 mg of the product as off white solid. $^1$H NMR (300 MHz, DMSO-$d_6$) δ 4.68 (s, 2H), 4.91 (br s, 4H), 6.26 (d, J=8.7 Hz, 2H), 6.40 (d, J=8.7 Hz, 2H), 7.55 (d, J=7.8 Hz, 1H), 7.61-7.67 (m, 1H), 7.83 (t, J=8.4 Hz, 1H); ESI-MS (m/z) 328 (M+H)$^+$.

Intermediate 49

4-{[1-(3,4-Dichlorophenyl)cyclopropyl]oxy}aniline

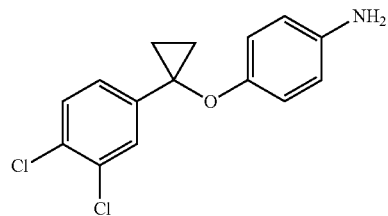 [SMILES: Nc1ccc(OC2(c3ccc(Cl)c(Cl)c3)CC2)cc1]

Step 1: 1-(3,4-Dichlorophenyl)cyclopropanol

To a stirred suspension of magnesium turnings (423 mg, 17.410 mmol) and catalytic amount of iodine in dry diethyl ether (20 mL) was slowly added 1-bromo-3,4-dichlorobenzene (2 mL, 15.139 mmol) and the reaction mixture was refluxed for 2 h. A solution 1,3-dichloroacetone (1.92 g, 15.139 mmol) in diethyl ether (20 mL) was drop-wise added to the reaction mixture and stirred at RT for 1 h. A solution of ferric chloride (49 mg, 0.302 mmol) in diethyl ether (10 mL) and ethyl magnesium bromide (3M in ether, 25 mL) was added simultaneously to the reaction mixture in duration of 1 h. The resulting mixture was stirred at RT for 18 h. The reaction mixture was quenched with saturated ammonium chloride solution (100 mL). The aqueous mixture was extracted with ethyl acetate (2×200 mL). The combined organic layers were washed with brine (150 mL) and dried over anhydrous sodium sulfate. The organic solution was filtered and concentrated under reduced pressure and the residue thus obtained was purified by silica gel column chromatography to yield 827 mg of the product as a solid.

$^1$H NMR (300 MHz, DMSO-d$_6$) δ 0.98-1.02 (m, 2H), 1.11-1.16 (m, 2H), 6.15 (s, 1H), 7.12-7.16 (m, 1H), 7.45-7.53 (m, 2H)

Step 2: 1,2-Dichloro-4-[1-(4-nitrophenoxy)cyclopropyl]benzene

The title compound was synthesized by the reaction of step 1 intermediate (200 mg, 0.984 mmol) with 1-fluoro-4-nitrobenzene (139 mg, 0.984 mmol) by using sodium hydride (60% w/w, 43 mg, 1.083 mmol) in DMF (4 mL) as per the process described in step 2 of Intermediate 1 to yield 134 mg of the product as a semi-solid. $^1$H NMR (300 MHz, DMSO-d$_6$) δ 1.45-1.47 (m, 2H), 1.54-1.57 (m, 2H), 7.14 (d, J=9.3 Hz, 2H), 7.22 (d, J=8.4 Hz, 1H), 7.42 (s, 1H), 7.59 (d, J=8.1 Hz, 1H), 8.18 (d, J=8.7 Hz, 2H).

Step 3: 4-{[1-(3,4-Dichlorophenyl)cyclopropyl]oxy}aniline

The title compound was synthesized by the nitro reduction of the step 2 intermediate (120 mg, 0.370 mmol) by using sodium borohydride (56 mg, 1.480 mmol) and nickel chloride (176 mg, 0.7403 mmol) in methanol (4 mL) as per the process described in step 3 of Intermediate 1 to yield 112 mg of the product as a solid. $^1$H NMR (300 MHz, DMSO-d$_6$) δ 1.20-1.36 (m, 4H), 4.62 (br s, 2H), 6.43 (d, J=8.7 Hz, 2H), 6.56 (d, J=8.7 Hz, 2H), 7.17 (d, J=8.7 Hz, 1H), 7.35 (s, 1H), 7.53 (d, J=9.0 Hz, 1H); ESI-MS (m/z) 294 (M+H)$^+$.

Intermediate 50

4-{[1-(4-Chloro-3-fluorophenyl)cyclopropyl]oxy}aniline

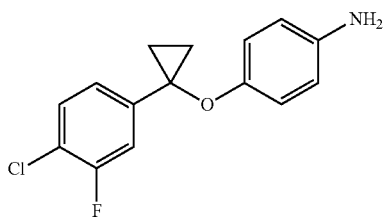

Step 1: 1-(4-Chloro-3-fluorophenyl)cyclopropanol

The title compound was synthesized by the reaction of 4-bromo-1-chloro-2-fluorobenzene (2 mL, 16.329 mmol) with 1,3-dichloroacetone (2.07 g, 16.329 mmol), ferric chloride (52 mg, 0.325 mmol) using magnesium turnings (456 mg, 18.778 mmol) and ethyl magnesium bromide (3M, 27.2 mL) in presence of catalytic amount of iodine in dry diethyl ether (40 mL) as per the process described in step 1 of Intermediate 49 to yield 1.27 g of the product as a semi-solid. $^1$H NMR (300 MHz, DMSO-d$_6$) δ 1.00-1.07 (m, 2H), 1.13-1.20 (m, 2H), 6.12 (br s, 1H), 7.07 (d, J=8.4 Hz, 1H), 7.23 (d J=11.1 Hz, 1H), 7.47 (t, J=7.8 Hz, 1H).

Step 2: 1-(4-Chloro-3-fluorophenyl)cyclopropyl 4-nitrophenyl ether

The title compound was synthesized by the reaction of step 1 intermediate (230 mg, 1.132 mmol) with 1-fluoro-4-nitrobenzene (160 mg, 0.132 mmol) by using sodium hydride (60% w/w, 54 mg, 1.359 mmol) in DMF (4 mL) as per the process described in step 2 of Intermediate 1 to yield 112 mg of the product as a solid. $^1$H NMR (300 MHz, DMSO-d$_6$) δ 1.44-1.57 (m, 4H), 7.06-7.13 (m, 3H), 7.26 (d, J=11.4 Hz, 1H), 7.52 (t, J=8.4 Hz, 1H), 8.17 (d, J=9.3 Hz, 2H).

Step 3: 4-{[1-(4-Chloro-3-fluorophenyl)cyclopropyl]oxy}aniline

The title compound was synthesized by the nitro reduction of the step 2 intermediate (260 mg, 0.8422 mmol) by using sodium borohydride (127 mg, 3.369 mmol) and nickel chloride (400 mg, 1.684 mmol) in methanol (10 mL) as per the process described in step 3 of Intermediate 1 to yield 172 mg of the product as a solid. $^1$H NMR (300 MHz, DMSO-d$_6$) δ 1.31-1.37 (m, 4H), 4.61 (s, 2H), 6.44 (d, J=8.7 Hz, 2H), 6.58 (d, J=8.7 Hz, 2H), 7.06 (d, J=7.8 Hz, 1H), 7.17 (d, J=8.7 Hz, 1H), 7.48 (t, J=7.8 Hz, 1H); ESI-MS (m/z) 278 (M+H)$^+$.

Intermediate 51

4-{[1-(4-Chloro-2-fluorophenyl)cyclopropyl]oxy}aniline

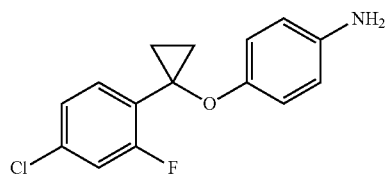 [SMILES: Nc1ccc(OC2(c3ccc(Cl)cc3F)CC2)cc1]

Step 1: 1-(4-chloro-2-fluorophenyl)cyclopropanol

To a stirred and cooled (−78° C.) solution of 1-bromo-4-chloro-2-fluorobenzene (1.0 mL, 8.012 mmol) in diethyl ether (10 mL) was added n-BuLi (1.6 M in ether, 5 mL) and stirred for 30 min. A solution of 1,3-dichloroacetone (1.01 g, 8.012 mmol) in diethyl ether (10 mL) was added to the reaction mixture at −78° C. and stirred at −78° C. to 0° C. for 1 h. To that mixture was added a solution of ferric chloride (26 mg, 0.163 mmol) in diethyl ether (5 mL) followed by ethyl magnesium bromide (13.3 mL, 40.059 mmol) at 0° C. and gradually warmed to RT. The reaction mixture was stirred at RT for 18 h. The reaction mixture was quenched with saturated ammonium chloride solution (50 mL). The aqueous mixture was extracted with ethyl acetate (2×100 mL). The combined organic layers were washed with water (100 mL) and dried over anhydrous sodium sulfate. The solution was filtered, concentrated under reduced pressure and the residue thus obtained was purified by silica gel column chromatography to yield 425 mg of the product as a semi-solid. $^1$H NMR (300 MHz, DMSO-d$_6$) δ 0.96 (d, J=10.2 Hz, 4H), 6.02 (s, 1H), 7.24 (d, J=8.7 Hz, 1H), 7.33 (d J=9.3 Hz, 1H), 7.51 (t, J=8.7 Hz, 1H).

Step 2: 1-(4-chloro-2-fluorophenyl)cyclopropyl 4-nitrophenyl ether

The title compound was synthesized by the reaction of step 1 intermediate (230 mg, 0.747 mmol) with 1-fluoro-4-nitrobenzene (105 mg, 0.747 mmol) by using sodium hydride (60% w/w, 36 mg, 0.896 mmol) in DMF (5 mL) as per the process described in step 2 of Intermediate 1 to yield 118 mg of the product as a semi-solid. $^1$H NMR (300 MHz, DMSO-d$_6$) δ 1.40-1.48 (m, 4H), 7.21-7.30 (m, 3H), 7.43 (d, J=11.1 Hz, 1H), 7.64 (t, J=8.4 Hz, 1H), 8.13 (d, J=9.3 Hz, 2H).

Step 3: 4-{[1-(4-Chloro-2-fluorophenyl)cyclopropyl]oxy}aniline

The title compound was synthesized by the nitro reduction of the step 2 intermediate (110 mg, 0.357 mmol) by using sodium borohydride (54 mg, 1.42 mmol) and nickel chloride (170 mg, 0.714 mmol) in methanol (4 mL) as per the process described in step 3 of Intermediate 1 to yield 69 mg of the product as a semi-solid. $^1$H NMR (300 MHz, DMSO-d$_6$) δ 1.21-1.27 (m, 4H), 4.62 (br s, 2H), 6.39 (d, J=8.4 Hz, 2H), 6.61 (d, J=9.3 Hz, 2H), 7.20 (d, J=7.8 Hz, 1H), 7.37 (d, J=10.5 Hz, 1H), 7.46 (t, J=7.8 Hz, 1H); APCI-MS (m/z) 278 (M+H)$^+$.

Intermediate 52

6-{[1-(4-Chloro-3-fluorophenyl)cyclopropyl]oxy}pyridin-3-amine

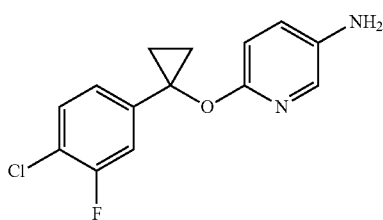

Step 1: 2-{[1-(4-Chloro-3-fluorophenyl)cyclopropyl]oxy}-5-nitropyridine

The title compound was synthesized by the reaction of 1-(4-chloro-3-fluorophenyl)cyclopropanol (100 mg, 0.492 mmol) with 2-bromo-5-nitropyridine (100 mg, 0.492 mmol) by using sodium hydride (60% w/w, 20 mg, 0.492 mmol) in DMF (2 mL) as per the process described in step 2 of Intermediate 1 to yield 109 mg of the product a solid. $^1$H NMR (300 MHz, DMSO-d$_6$) δ 1.51 (d, J=7.8 Hz, 4H), 7.05-7.13 (m, 2H), 7.21-7.25 (m, 1H), 7.49 (t, J=8.1 Hz, 1H), 8.48-8.52 (m, 1H), 9.00 (s, 1H); APCI-MS (m/z) 309 (M+H)$^+$.

Step 2: 6-{[1-(4-Chloro-3-fluorophenyl)cyclopropyl]oxy}pyridin-3-amine

The title compound was synthesized by the nitro reduction of the step 1 intermediate (100 mg, 0.323 mmol) by using sodium borohydride (49 mg, 1.295 mmol) and nickel chloride (154 mg, 0.647 mmol) in methanol (4 mL) as per the process described in step 3 of Intermediate 1 to yield 78 mg of the product as a solid. $^1$H NMR (300 MHz, DMSO-d$_6$) δ 1.35 (d, J=9.0 Hz, 4H), 4.79 (s, 2H), 6.57 (d, J=8.4 Hz, 1H), 6.94-7.03 (m, 2H), 7.14 (d, J=10.1 Hz, 1H), 7.40-7.47 (m, 2H); ESI-MS (m/z) 279 (M+H)$^+$.

Intermediate 53

6-{[1-(3,4-Dichlorophenyl)cyclopropyl]oxy}pyridin-3-amine

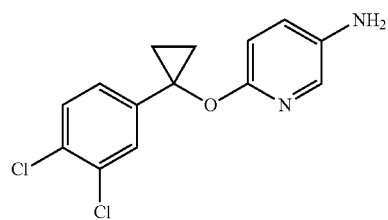 [SMILES: Nc1ccc(OC2(c3ccc(Cl)c(F)c3)CC2)nc1]

Step 1: 2-{[1-(3,4-Dichlorophenyl)cyclopropyl]oxy}-5-nitropyridine

The title compound was synthesized by the reaction of 1-(3,4-dichlorophenyl)cyclopropanol (200 mg, 0.984 mmol) with 2-chloro-5-nitropyridine (156 mg, 0.984 mmol) by using sodium hydride (60% w/w, 43 mg, 1.083 mmol) in DMF (4 mL) as per the process described in step 2 of Intermediate 1 to yield 231 mg of the product as a semi-solid. $^1$H NMR (300 MHz, DMSO-d$_6$) δ 1.45-1.53 (m, 4H), 7.14 (d, J=9.3 Hz, 1H), 7.21 (d, J=8.1 Hz, 1H), 7.42 (s, 1H), 7.55 (d, J=8.1 Hz, 1H), 8.51 (d, J=9.3 Hz, 1H), 9.00 (s, 1H); APCI-MS (m/z) 325 (M+H)$^+$.

Step 2: 6-{[1-(3,4-Dichlorophenyl)cyclopropyl]oxy}pyridin-3-amine

The title compound was synthesized by the nitro reduction of the step 1 intermediate (220 mg, 0.676 mmol) by using sodium borohydride (102 mg, 2.706 mmol) and nickel chloride (322 mg, 1.353 mmol) in methanol (5 mL) as per the process described in step 3 of Intermediate 1 to yield 65 mg of the product as a solid. $^1$H NMR (300 MHz, DMSO-d$_6$) δ 1.31-1.38 (m, 4H), 4.80 (s, 2H), 6.58 (d, J=8.4 Hz, 1H), 6.93-6.97 (m, 1H), 7.12-7.16 (m, 1H), 7.34-7.41 (m, 2H), 7.52 (d, J=8.1 Hz, 1H); ESI-MS (m/z) 295 (M+H)$^+$.

Intermediate 54

6-{[1-(4-Chloro-3-fluorophenyl)cyclobutyl]oxy}pyridin-3-amine

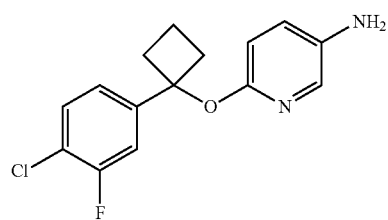 [SMILES: Nc1ccc(OC2(c3ccc(Cl)c(F)c3)CCC2)nc1]

Step 1: 2-{[1-(4-Chloro-3-fluorophenyl)cyclobutyl]oxy}-5-nitropyridine

The title compound was synthesized by the reaction of 1-(4-chloro-3-fluorophenyl) cyclobutanol (200 mg, 0.996 mmol) with 2-chloro-5-nitropyridine (158 mg, 0.9968 mmol) by using sodium hydride (60% w/w, 60 mg, 1.495 mmol) in DMF (4 mL) as per the process described in step 2 of Intermediate 1 to yield 115 mg of the product as a semi-solid. ¹H NMR (300 MHz, DMSO-d₆) δ 1.71-1.78 (m, 1H), 1.98 (br s, 1H), 2.62-2.73 (m, 2H), 2.88 (br s, 2H), 7.04 (d, J=9.0 Hz, 1H), 7.23 (t, J=7.8 Hz, 1H), 7.50 (t, J=8.4 Hz, 1H), 7.75 (t, J=7.8 Hz, 1H), 8.35-8.42 (m, 1H), 8.80 (br s, 1H).

Step 2: 6-{[1-(4-Chloro-3-fluorophenyl)cyclobutyl]oxy}pyridin-3-amine

The title compound was synthesized by the nitro reduction of the step 1 intermediate (130 mg, 0.403 mmol) by using sodium borohydride (61 mg, 1.611 mmol) and nickel chloride (191 mg, 0.806 mmol) in methanol (4 mL) as per the process described in step 3 of Intermediate 1 to yield 121 mg of the product as a semi-solid. ¹H NMR (300 MHz, DMSO-d₆) δ 1.68-1.70 (m, 1H), 1.94-1.97 (m, 1H), 2.51-2.74 (m, 4H), 4.67 (br s, 2H), 6.45 (d, J=8.4 Hz, 1H), 6.89 (d, J=8.4 Hz, 1H), 7.17 (t, J=7.8 Hz, 1H), 7.26 (s, 1H), 7.42 (t, J=7.8 Hz, 1H), 7.56 (t, J=7.8 Hz, 1H); ESI-MS (m/z) 292 (M+H)⁺.

Intermediate 55

6-{[4-(4-Chloro-3-fluorophenyl)tetrahydro-2H-pyran-4-yl]oxy}pyridin-3-amine

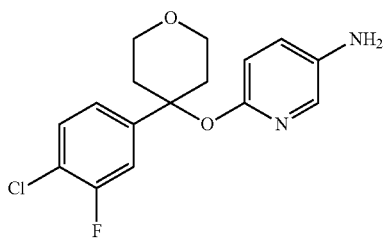 [SMILES: Nc1ccc(OC2(c3ccc(Cl)c(F)c3)CCOCC2)nc1]

Step 1: 2-{[4-(4-Chloro-3-fluorophenyl)tetrahydro-2H-pyran-4-yl]oxy}-5-nitropyridine The title compound was synthesized by the reaction of 4-(4-chloro-3-fluorophenyl)tetrahydro-2H-pyran-4-ol (410 mg, 1.777 mmol) with 2-chloro-5-nitropyridine (281 mg, 1.777 mmol) by using sodium hydride (60% w/w, 78 mg, 1.955 mmol) in DMF (4 mL) as per the process described in step 2 of Intermediate 1 to yield 217 mg of the product as a semi-solid. ¹H NMR (300 MHz, DMSO-d₆) δ 2.26-2.32 (m, 2H), 2.59-2.66 (m, 2H), 3.70-3.79 (m, 4H), 7.15-7.26 (m, 2H), 7.50 (t, J=7.2 Hz, 2H), 8.47 (d, J=6.9 Hz, 1H), 8.68 (s, 1H).

Step 2: 6-{[4-(4-Chloro-3-fluorophenyl)tetrahydro-2H-pyran-4-yl]oxy}pyridin-3-amine The title compound was synthesized by the nitro reduction of the step 1 intermediate (200 mg, 0.566 mmol) by using sodium borohydride (86 mg, 2.267 mmol) and nickel chloride (257 mg, 1.133 mmol) in methanol (4 mL) as per the process described in step 3 of Intermediate 1 to yield 133 mg of the product as a semi-solid. ¹H NMR (300 MHz, DMSO-d₆) δ 2.11-2.14 (m, 2H), 2.51 (s, 2H), 3.74-3.79 (m, 4H), 4.72 (br s, 2H), 6.60 (d, J=8.7 Hz, 1H), 6.90-6.94 (m, 1H), 7.12-7.18 (m, 2H), 7.36-7.47 (m, 2H); ESI-MS (m/z) 322 (M+H)⁺.

Intermediate 56

6-{[2-(4-chloro-2-fluorophenyl)propan-2-yl]oxy}pyridin-3-amine

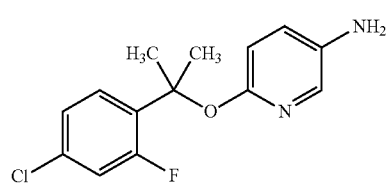 [SMILES: CC(C)(Oc1ccc(N)cn1)c1ccc(Cl)cc1F]

Step 1: 2-{[2-(4-Chloro-2-fluorophenyl)propan-2-yl]oxy}-5-nitropyridine

The title compound was synthesized by the reaction of 2-(4-Chloro-2-fluorophenyl)propan-2-ol (300 mg, 1.590 mmol) with 2-chloro-5-nitropyridine (252 mg, 1.590 mmol) in presence of sodium hydride (60% w/w, 70 mg, 1.749 mmol) and potassium iodide (26 mg, 0.159 mmol) in DMF (10 mL) as per the process described in step 2 of Intermediate 1 to yield 103 mg of the product as a semi-solid. ¹H NMR (300 MHz, DMSO-d₆) δ 1.90 (s, 6H), 7.05 (d, J=9.0 Hz, 1H), 7.24-7.32 (m, 2H), 7.47 (t, J=9.0 Hz, 1H), 8.39-8.43 (m, 1H) 8.75 (s, 1H).

Step 2: 6-{[2-(4-chloro-2-fluorophenyl)propan-2-yl]oxy}pyridin-3-amine

The title compound was synthesized by the nitro reduction of step 1 intermediate (120 mg, 0.386 mmol) by using sodium borohydride (58 mg, 1.544 mmol) and nickel chloride (183 mg, 0.772 mmol) in methanol (5 mL) as per the process described in step 3 of Intermediate 1 to yield 73 mg of the product as a solid. ¹H NMR (300 MHz, DMSO-d₆) δ 1.73 (s, 6H), 4.72 (s, 2H), 6.54 (d, J=8.1 Hz, 1H), 6.90-6.93 (m, 1H), 7.18-7.30 (m, 3H), 7.43 (t, J=8.7 Hz, 1H); APCI-MS (m/z) 281 (M+H)⁺.

Intermediate 57

6-{[2-(2-Chloro-4-fluorophenyl)propan-2-yl]oxy}pyridin-3-amine

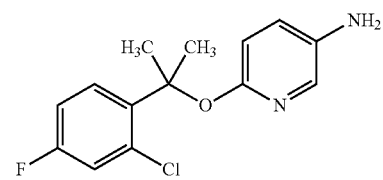 [SMILES: CC(C)(Oc1ccc(N)cn1)c1ccc(F)cc1Cl]

Step 1: 2-{[2-(2-Chloro-4-fluorophenyl)propan-2-yl]oxy}-5-nitropyridine

The title compound was synthesized by the reaction of 2-(2-Chloro-4-fluorophenyl)propan-2-ol (1.0 g, 5.301 mmol) with 2-bromo-5-nitropyridine (1.07 g, 5.301 mmol) by using sodium hydride (60% w/w, 233 mg, 5.831 mmol) in DMF (15 mL) as per the process described in step 2 of Intermediate 1 to yield 260 mg of the product as a solid. $^1$H NMR (300 MHz, DMSO-$d_6$) δ 1.96 (s, 6H), 7.03 (d, J=9.3 Hz, 1H), 7.22-7.27 (m, 2H), 7.62-7.67 (m, 1H), 8.39-8.43 (m, 1H), 8.68 (s, 1H)

Step 2: 6-{[2-(2-Chloro-4-fluorophenyl)propan-2-yl]oxy}pyridin-3-amine

The title compound was synthesized by the reduction of step 1 intermediate (250 mg, 0.804 mmol) in presence of sodium borohydride (121 mg, 3.218 mmol) and nickel chloride (381 mg, 1.609 mmol) in methanol (5 mL) as per the process described in step 3 of Intermediate 1 to yield 113 mg of the product as a solid. $^1$H NMR (300 MHz, DMSO-$d_6$) δ 1.82 (s, 6H), 4.65 (s, 2H), 6.52 (d, J=8.1 Hz, 1H), 6.92 (d, J=8.7 Hz, 1H), 7.13-7.18 (m, 2H), 7.24 (d, J=6.3 Hz, 1H), 7.55-7.62 (m, 1H); APCI-MS (m/z) 281 (M+H)$^+$.

Intermediate 58

6-{[2-(2,4-Dichlorophenyl)propan-2-yl]oxy}pyridin-3-amine

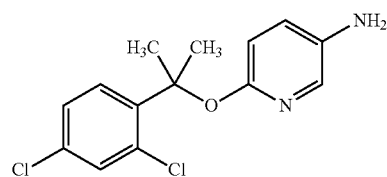 [SMILES: CC(C)(Oc1ccc(N)cn1)c1ccc(Cl)cc1Cl]

Step 1: 2,4-Dichloro-1-[2-(4-nitrophenoxy)propan-2-yl]benzene

The title compound was synthesized by the reaction of 2-(2,4-dichlorophenyl)propan-2-ol (300 mg, 1.462 mmol) with 2-chloro-5-nitropyridine (232 mg, 1.462 mmol) by using sodium hydride (60% w/w, 64 mg, 1.609 mmol) in DMF (10 mL) as per the process described in step 2 of Intermediate 1 to yield 86 mg of the product as a semi-solid. $^1$H NMR (300 MHz, DMSO-$d_6$) δ 1.94 (s, 6H), 7.04 (d, J=9.3 Hz, 1H), 7.46 (d, J=7.8 Hz, 2H), 7.63 (d, J=9.0 Hz, 1H), 8.39-8.44 (m, 1H), 8.67-8.69 (m, 1H).

Step 2: 6-{[2-(2,4-Dichlorophenyl)propan-2-yl]oxy}pyridin-3-amine

The title compound was synthesized by the nitro reduction of the step 1 intermediate (75 mg, 0.229 mmol) by using sodium borohydride (35 mg, 0.916 mmol) and nickel chloride (109 mg, 0.458 mmol) in methanol (4 mL) as per the process described in step 3 of Intermediate 1 to yield 69 mg of the product as a semi-solid. $^1$H NMR (300 MHz, DMSO-$d_6$) δ 1.80 (s, 6H), 4.66 (br s, 2H), 6.51 (d, J=8.1 Hz, 1H), 6.89-6.93 (m, 1H), 7.15 (s, 1H), 7.35-7.41 (m, 2H), 7.56 (d, J=8.1 Hz, 1H); APCI-MS (m/z) 296 (M+H)$^+$.

Intermediate 59

6-{[2-(3,4-Dichlorophenyl)propan-2-yl]oxy}pyridin-3-amine

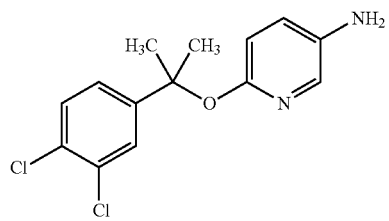 [SMILES: CC(C)(Oc1ccc(N)cn1)c1ccc(Cl)c(Cl)c1]

Step 1: 2-{[2-(3,4-Dichlorophenyl)propan-2-yl]oxy}-5-nitropyridine

The title compound was synthesized by the reaction of 2-(3,4-dichlorophenyl)propan-2-ol (325 mg, 1.584 mmol) with 2-chloro-5-nitropyridine (251 mg, 1.584 mmol) using sodium hydride (60% w/w, 70 mg, 1.743 mmol) and potassium iodide (26 mg, 0.158 mmol) in DMF (5 mL) as per the process described in step 2 of Intermediate 1 to yield 138 mg of the product as a semi-solid. $^1$H NMR (300 MHz, DMSO-$d_6$) δ 1.86 (s, 6H), 7.08 (d, J=9.0 Hz, 1H), 7.36 (d, J=8.7 Hz, 1H), 7.54-7.61 (m, 2H), 8.45 (d, J=8.7 Hz, 1H), 8.07-8.81 (m, 1H).

Step 2: 6-{[2-(3,4-Dichlorophenyl)propan-2-yl]oxy}pyridin-3-amine

The title compound was synthesized by the nitro reduction of the step 1 intermediate (125 mg, 0.3820 mmol) using sodium borohydride (58 mg, 1.528 mmol) and nickel chloride (181 mg, 0.7641 mmol) in methanol (4 mL) as per the process described in step 3 of Intermediate 1 to yield 98 mg of the product as a semi-solid. $^1$H NMR (300 MHz, DMSO-$d_6$) δ 1.68 (s, 6H), 4.73 (br s, 2H), 6.55 (d, J=8.7 Hz, 1H), 6.94 (d, J=10.5 Hz, 1H), 7.26-7.36 (m, 2H), 7.51-7.56 (m, 2H); APCI-MS (m/z) 297 (M+H)$^+$.

Intermediate 60

4-[3-(2,4-Dichlorophenoxy)prop-1-yn-1-yl]aniline

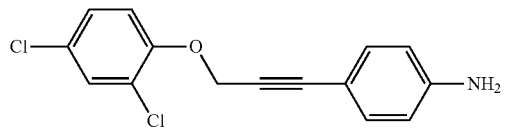

Step 1: 2,4-Dichloro-1-(prop-2-yn-1-yloxy)benzene

To a stirred solution of 2,4-dichlorophenol (1.0 g, 6.134 mmol) in DMF (10 mL) was added potassium carbonate (2.5 g, 18.404 mmol) and the reaction mixture was heated at 60° C. for 30 min. The reaction was cooled to room temperature and 80% solution of propargyl bromide in toluene (0.82 mL, 7.361 mmol) was added to it. The mixture was further stirred for 18 h at room temperature. The reaction mixture was diluted with water (100 mL) and extracted with ethyl acetate (2×200 mL). The combined organic extracts were washed with water (3×100 mL), brine (150 mL) and dried over anhydrous sodium sulfate. The solvent was distilled out under reduced pressure and the residue obtained was purified by silica gel column chromatography to yield 1.31 g of the title product as a solid; $^1$H NMR (300 MHz, DMSO-$d_6$) δ 3.65 (s, 1H), 4.93 (s, 2H), 7.24 (d, J=8.7 Hz, 1H), 7.43 (d, J=9.0 Hz, 2H), 7.60 (s, 1H)

Step 2: 2,4-Dichloro-1-{[3-(4-nitrophenyl)prop-2-yn-1-yl]oxy}benzene

To a stirred and degassed solution of step 1 intermediate (500 mg, 2.486 mmol) in DMSO (10 mL) were added 4-iodo-1-nitrobenzene (619 mg, 2.486 mmol), copper iodide (28 mg, 0.149 mmol), bis(triphenylphosphine)palladium(II) dichloride (175 mg, 0.2486 mmol) and triethylamine (1.74 mL, 12.434 mmol) under inert atmosphere. The reaction mixture was stirred at room temperature for 18 h. The mixture was diluted with ethyl acetate (100 mL) and water (100 mL). The layers were separated and the aqueous layer was extracted with ethyl acetate (2×100 mL). The combined organic extracts were washed with water (2×100 mL), brine (150 mL) and dried over anhydrous sodium sulfate. The solvent was distilled out under reduced pressure and the residue obtained was purified by silica gel column chromatography to yield 340 mg of the title product as a solid. $^1$H NMR (300 MHz, DMSO-$d_6$) δ 5.26 (s, 2H), 7.36 (d, J=8.7 Hz, 1H), 7.45 (d, J=7.8 Hz, 1H), 7.63 (s, 1H), 7.73 (d, J=9.0 Hz, 2H), 8.24 (d, J=8.4 Hz, 2H).

Step 3: 4-[3-(2,4-Dichlorophenoxy)prop-1-yn-1-yl]aniline

The title compound was prepared by the reduction of step 2 intermediate (335 mg, 1.039 mmol) using iron powder (290 mg, 5.199 mmol) and ammonium chloride (556 mg, 10.399 mmol) in a mixture of water (10 mL) and methanol (10 mL) as per the process described in step 2 of Intermediate 14 to yield 70 mg of the product as a solid. $^1$H NMR (300 MHz, DMSO-$d_6$) δ 4.07 (s, 2H), 6.49 (d, J=7.8 Hz, 2H), 7.08 (d, J=7.8 Hz, 2H), 7.29 (d, J=9.3 Hz, 1H), 7.42 (d, J=7.8 Hz, 1H), 7.60 (s, 1H); APCI-MS (m/z) 292 (M+H)$^+$.

Intermediate 61

4-[3-(3,4-Dichlorophenoxy)prop-1-yn-1-yl]aniline

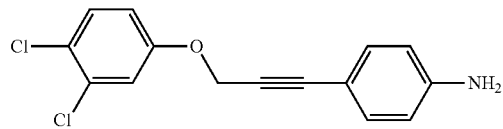 [SMILES: Nc1ccc(C#CCOc2ccc(Cl)c(Cl)c2)cc1]

Step 1: 3,4-Dichloro-1-(prop-2-yn-1-yloxy)benzene

The title compound was synthesized by the reaction of 3,4-dichlorophenol (1.0 g, 6.134 mmol) with 80% solution of propargyl bromide in toluene (0.82 mL, 7.361 mmol) in the presence of potassium carbonate (2.5 g, 18.404 mmol) in DMF (10 mL) as per the process described in step 1 of Intermediate 60 to yield 1.21 g of the product as a semi-solid; $^1$H NMR (300 MHz, DMSO-$d_6$) δ 3.34 (s, 1H), 4.86 (s, 2H), 7.02 (d, J=6.9 Hz, 1H), 7.29 (s, 1H), 7.57 (d, J=8.7 Hz, 1H).

Step 2: 3,4-Dichloro-1-{[3-(4-nitrophenyl)prop-2-yn-1-yl]oxy}benzene

The title compound was synthesized by the reaction of step 1 intermediate (500 mg, 2.486 mmol) with 4-iodo-1-nitrobenzene (619 mg, 2.486 mmol) in the presence of copper iodide (28 mg, 0.149 mmol), bis(triphenylphosphine)palladium(II) dichloride (175 mg, 0.2486 mmol) and triethylamine (1.74 mL, 12.434 mmol) in DMSO (10 mL) as per the process described in step 2 of Intermediate 60 to yield 502 mg of the product as pale yellow solid. $^1$H NMR (300 MHz, DMSO-$d_6$) δ 5.19 (s, 2H), 7.11 (d, J=6.9 Hz, 1H), 7.38 (s, 1H), 7.60 (d, J=9.0 Hz, 1H), 7.73 (d, J=8.1 Hz, 2H), 8.24 (d, J=8.7 Hz, 2H).

Step 3: 4-[3-(3,4-Dichlorophenoxy)prop-1-yn-1-yl]aniline

The title compound was prepared by the reduction of step 2 intermediate (480 mg, 1.4900 mmol) using iron powder (416 mg, 7.450 mmol) and ammonium chloride (797 mg, 14.900 mmol) in a mixture of methanol (10 mL) and water (10 mL) as per the process described in step 2 of Intermediate 14 to yield 191 mg of the product as a solid. $^1$H NMR (300 MHz, DMSO-$d_6$) δ 5.02 (br s, 2H), 5.57 (s, 2H), 6.49 (d, J=8.4 Hz, 2H), 7.02-7.09 (m, 3H), 7.32 (s, 1H), 7.56 (d, J=9.3 Hz, 1H); APCI-MS (m/z) 292 (M+H)$^+$.

Intermediate 62

1,2-Dichloro-4-[(2-methylbut-3-yn-2-yl)oxy]benzene

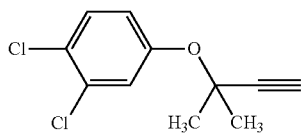

To a stirred solution of 3,4-dichlorophenol (500 mg, 3.067 mmol) in DMF (5 mL) were added 3-chloro-3-methylbut-1-yne (0.69 mL, 6.134 mmol), potassium carbonate (847 mg, 6.134 mmol), copper iodide (11 mg, 0.061 mmol) and potassium iodide (865 mg, 5.214 mmol). The mixture was stirred at 65° C. for 18 h. The mixture was diluted with water (20 mL) and extracted with ethyl acetate (3×20 mL). The combined organic extracts were washed with water (2×50 mL), brine (50 mL) and dried over anhydrous sodium sulfate. The solvent was recovered under reduced pressure and the residue thus obtained was purified by silica gel column chromatography to yield 350 mg of the title product as a liquid. $^1$H NMR (300 MHz, DMSO-$d_6$) δ 1.59 (s, 6H), 3.78 (s, 1H), 7.18 (d, J=8.7 Hz, 1H), 7.39 (s, 1H), 7.57 (d, J=9.0 Hz, 1H).

Intermediate 63

2,4-Dichloro-1-[(2-methylbut-3-yn-2-yl)oxy]benzene

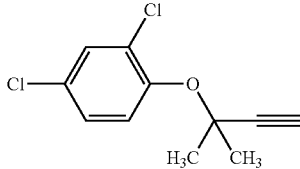

The title compound was synthesized by the reaction of 2,4-dichlorophenol (700 mg, 4.294 mmol) with 3-chloro-3-methylbut-1-yne (0.95 ml, 8.588 mmol) in the presence of potassium carbonate (1.18 g, 8.588 mmol), copper iodide (16 mg, 0.085 mmol) and potassium iodide (1.21 g, 7.300 mmol) in DMF (5 mL) as per the process described in Intermediate 62 to yield 523 mg of the product as a liquid. $^1$H NMR (300 MHz, DMSO-$d_6$) δ 1.63 (s, 6H), 3.76 (s, 1H), 7.37-7.40 (m, 1H), 7.54-7.62 (m, 2H); APCI-MS (m/z) 229 (M+H)$^+$.

Intermediate 64

1-Chloro-4-[(2-methylbut-3-yn-2-yl)oxy]benzene

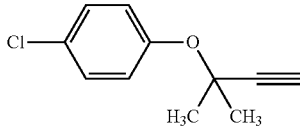

The title compound was synthesized by the reaction of 4-chlorophenol (700 mg, 5.445 mmol) with 3-chloro-3-methylbut-1-yne (0.72 mL, 6.533 mmol) in the presence of potassium carbonate (1.50 g, 10.889 mmol), copper iodide (20 mg, 0.1088 mmol) and potassium iodide (1.53 g, 9.256 mmol) in DMF (10 mL) as per the process described in Intermediate 62 to yield 472 mg of the product as a liquid. $^1$H NMR (300 MHz, DMSO-$d_6$) δ 1.56 (s, 6H), 3.69 (s, 1H), 7.15 (d, J=9.0 Hz, 2H), 7.35 (d, J=8.7 Hz, 2H).

Intermediate 65

4-Chloro-2-fluoro-1-[(2-methylbut-3-yn-2-yl)oxy]benzene

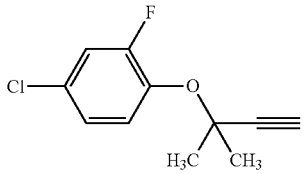

To a stirred solution of 4-chloro-2-fluorophenol (500 mg, 3.411 mmol) in DMF (5 mL) were added 3-chloro-3-methylbut-1-yne (0.45 mL, 4.094 mmol), potassium carbonate (943 mg, 6.823 mmol), copper iodide (12 mg, 0.068 mmol) and potassium iodide (962 mg, 5.800 mmol). The reaction mixture was stirred at 65° C. for 2 hours. The reaction mixture was diluted with water (20 mL) and extracted with ethyl acetate (3×20 mL). The combined organic extracts were washed with water (2×30 mL), brine (30 mL) and dried over anhydrous sodium sulfate. The solvent was recovered under reduced pressure and the residue thus obtained was purified by silica gel column chromatography to yield 332 mg of the title product as a liquid. $^1$H NMR (300 MHz, DMSO-$d_6$) δ 1.59 (s, 6H), 3.69 (s, 1H), 7.22-7.25 (m, 1H), 7.41-7.49 (m, 2H); APCI-MS (m/z) 213 (M+H)$^+$.

Intermediate 66

1-Chloro-2-fluoro-4-[(2-methylbut-3-yn-2-yl)oxy] benzene

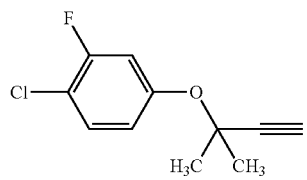

The title compound was synthesized by the reaction of 4-chloro-3-fluorophenol (700 mg, 4.776 mmol) with 3-chloro-3-methylbut-1-yne (0.78 mL, 7.164 mmol) in the presence of potassium carbonate (1.32 g, 9.553 mmol), copper iodide (18 mg, 0.0955 mmol) and potassium iodide (1.34 g, 8.120 mmol) in DMF (10 mL) as per the process described in Intermediate 62 to yield 538 mg of the product as an oil. $^1$H NMR (300 MHz, DMSO-$d_6$) δ 1.58 (s, 6H), 3.75 (s, 1H), 7.02-7.05 (m, 1H), 7.15-7.21 (m, 1H), 7.49 (t, J=8.7 Hz, 1H); APCI-MS (m/z) 213 (M+H)$^+$.

Intermediate 67

2-Chloro-4-fluoro-1-[(2-methylbut-3-yn-2-yl)oxy] benzene

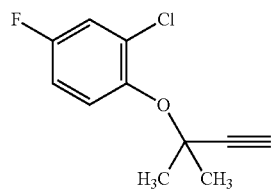

The title compound was synthesized by the reaction of 2-chloro-4-fluorophenol (700 mg, 4.776 mmol) with 3-chloro-3-methylbut-1-yne (0.63 mL, 5.731 mmol) in the presence of potassium carbonate (1.32 g, 9.553 mmol), copper iodide (18 mg, 0.0955 mmol) and potassium iodide (1.35 g, 8.120 mmol) in DMF (10 mL) as per the process described in Intermediate 62 to yield 527 mg of the product as an oily liquid. $^1$H NMR (300 MHz, DMSO-$d_6$) δ 1.60 (s, 6H), 3.71 (s, 1H), 7.16-7.22 (m, 1H), 7.44-7.48 (m, 1H), 7.52-7.57 (m, 1H); APCI-MS (m/z) 213 (M+H)$^+$.

Intermediate 68

2-Chloro-1-fluoro-4-[(2-methylbut-3-yn-2-yl)oxy]benzene

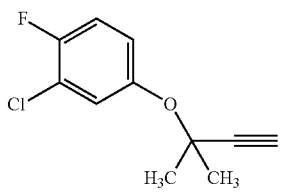

The title compound was synthesized by the reaction of 3-chloro-4-fluorophenol (700 mg, 4.7765 mmol) with 3-chloro-3-methylbut-1-yne (0.63 mL, 5.7318 mmol) in the presence of potassium carbonate (1.32 g, 9.553 mmol), copper iodide (18 mg, 0.0955 mmol) and potassium iodide (1.35 g, 8.120 mmol) in DMF (10 mL) as per the process described in Intermediate 62 to yield 385 mg of the product as a liquid. $^1$H NMR (300 MHz, DMSO-$d_6$) δ 1.56 (s, 6H), 3.74 (s, 1H), 7.13-7.18 (m, 1H), 7.32-7.39 (m, 2H); APCI-MS (m/z) 213 (M+H)$^+$.

Intermediate 69

2,4-Difluoro-1-[(2-methylbut-3-yn-2-yl)oxy]benzene

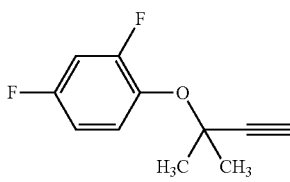

The title compound was synthesized by the reaction of 2,4-difluorophenol (700 mg, 5.380 mmol) with 3-chloro-3-methylbut-1-yne (0.71 mL, 6.456 mmol) in the presence of potassium carbonate (1.48 g, 10.760 mmol), copper iodide (20 mg, 0.1076 mmol) and potassium iodide (1.51 g, 9.146 mmol) in DMF (10 mL) as per the process described in Intermediate 62 to yield 379 mg of the product as an oil. $^1$H NMR (300 MHz, DMSO-$d_6$) δ 1.57 (s, 6H), 3.64 (s, 1H), 7.00-7.06 (m, 1H), 7.27-7.33 (m, 1H), 7.37-7.45 (m, 1H); APCI-MS (m/z) 197 (M+H)$^+$.

Intermediate 70

1,2-Difluoro-4-[(2-methylbut-3-yn-2-yl)oxy]benzene

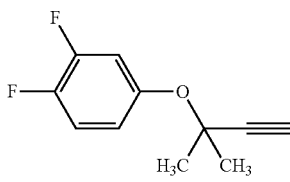

The title compound was synthesized by the reaction of 3,4-difluorophenol (1.0 g, 7.6869 mmol) with 3-chloro-3-methylbut-1-yne (1.27 mL, 11.505 mmol) in the presence of potassium carbonate (2.12 g, 15.373 mmol), copper iodide (73 mg, 0.384 mmol) and potassium iodide (2.16 g, 13.067 mmol) in DMF (10 mL) as per the process described in Intermediate 62 to yield 600 mg of the product as a liquid. $^1$H NMR (300 MHz, DMSO-$d_6$) δ 1.56 (s, 6H), 3.72 (s, 1H), 6.97-7.02 (m, 1H), 7.17-7.24 (m, 1H), 7.32-7.45 (m, 1H); APCI-MS (m/z) 197 (M+H)$^+$.

Intermediate 71

1,2,3-Trifluoro-5-[(2-methylbut-3-yn-2-yl)oxy]benzene

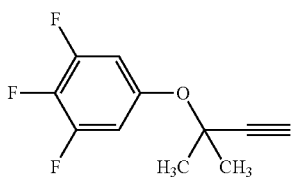

The title compound was synthesized by the reaction of 3,4,5-trifluorophenol (1.0 g, 6.752 mmol) with 3-chloro-3-methylbut-1-yne (1.11 mL, 10.128 mmol) in the presence of potassium carbonate (1.86 g, 13.504 mmol), copper iodide (25 mg, 0.135 mmol) and potassium iodide (1.90 g, 11.478 mmol) in DMF (10 mL) as per the process described in Intermediate 62 to yield 512 mg of the product as a liquid. $^1$H NMR (300 MHz, DMSO-$d_6$) δ 1.59 (s, 6H), 3.80 (s, 1H), 7.09-7.14 (m, 2H); APCI-MS (m/z) 215 (M+H)$^+$.

Intermediate 72

1,2,3-Trifluoro-4-[(2-methylbut-3-yn-2-yl)oxy]benzene

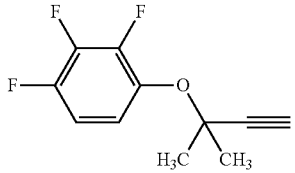

The title compound was synthesized by the reaction of 2,3,4-trifluorophenol (1.0 g, 6.752 mmol) with 3-chloro-3-methylbut-1-yne (1.48 mL, 13.455 mmol) in the presence of potassium carbonate (1.86 g, 13.504 mmol), copper iodide (1.9 g, 11.478 mmol) and potassium iodide (64 mg, 0.337 mmol) in DMF (10 mL) as per the process described in Intermediate 62 to yield 610 mg of the product as an oil. $^1$H NMR (300 MHz, DMSO-$d_6$) δ 1.60 (s, 6H), 3.71 (s, 1H), 7.24-7.28 (m, 2H); APCI-MS (m/z) 197 (M+H)$^+$.

Intermediate 73

1,3,5-Trifluoro-2-[(2-methylbut-3-yn-2-yl)oxy]benzene

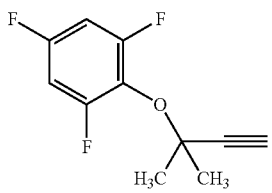

The title compound was synthesized by the reaction of 2,4,6-trifluorophenol (500 mg, 3.376 mmol) with 3-chloro-3-methylbut-1-yne (0.55 mL, 5.0641 mmol) in the presence of potassium carbonate (933 mg, 6.752 mmol), copper iodide (12 mg, 0.062 mmol) and potassium iodide (952 mg, 5.739 mmol) in DMF (10 mL) as per the process described in Intermediate 62 to yield 317 mg of the product as a liquid. $^1$H NMR (300 MHz, DMSO-$d_6$) δ 1.62 (s, 6H), 3.59 (s, 1H), 7.25 (t, J=8.4 Hz, 2H); APCI-MS (m/z) 214 (M)$^+$.

Intermediate 74

1,2,4-Trifluoro-5-[(2-methylbut-3-yn-2-yl)oxy]benzene

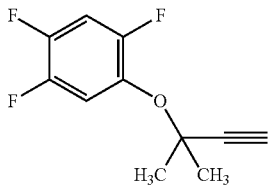

The title compound was synthesized by the reaction of 2,4,5-trifluorophenol (500 mg, 3.376 mmol) with 3-chloro-3-methylbut-1-yne (0.55 mL, 5.064 mmol) in presence of potassium carbonate (933 mg, 6.752 mmol), copper iodide (12 mg, 0.065 mmol) and potassium iodide (952 mg, 5.739 mmol) in DMF (10 mL) as per the process described in Intermediate 62 to yield 318 mg of the product as a liquid. $^1$H NMR (300 MHz, DMSO-$d_6$) δ 1.59 (s, 6H), 3.76 (s, 1H), 7.48-7.52 (m, 1H), 7.63-7.66 (m, 1H)

Intermediate 75

4-Chloro-2,6-difluorophenyl 2-methylbut-3-yn-2-yl ether

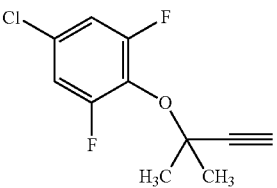

The title compound was synthesized by the reaction of 4-chloro-2,6-difluorophenol (500 mg, 3.0395 mmol) with 3-chloro-3-methylbut-1-yne (0.50 mL, 4.559 mmol) in the presence of potassium carbonate (840 mg, 6.079 mmol), copper iodide (11 mg, 0.060 mmol) and potassium iodide (857 mg, 5.167 mmol) in DMF (10 mL) as per the process described in Intermediate 62 to yield 285 mg of the product as a liquid. $^1$H NMR (300 MHz, DMSO-$d_6$) δ 1.63 (s, 6H), 3.62 (s, 1H), 7.43 (d, J=7.8 Hz, 2H).

Intermediate 76

1-[(2-Methylbut-3-yn-2-yl)oxy]-4-(trifluoromethyl)benzene

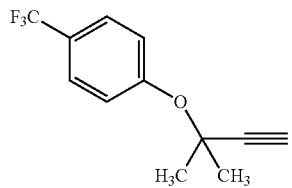

The title compound was synthesized by the reaction of 4-(trifluoromethyl)phenol (700 mg, 4.318 mmol) with 3-chloro-3-methylbut-1-yne (0.57 mL, 5.182 mmol) in the presence of potassium carbonate (1.19 g, 8.363 mmol), copper iodide (16 mg, 0.084 mmol) and potassium iodide (1.21 g, 7.342 mmol) in DMF (10 mL) as per the process described in Intermediate 62 to yield 238 mg of the product as a liquid. $^1$H NMR (300 MHz, DMSO-$d_6$) δ 1.64 (s, 6H), 3.78 (s, 1H), 7.33 (d, J=8.1 Hz, 2H), 7.67 (d, J=8.7 Hz, 2H); APCI-MS (m/z) 229 (M+H)$^+$.

Intermediate 77

1-[(2-Methylbut-3-yn-2-yl)oxy]-4-(trifluoromethoxy)benzene

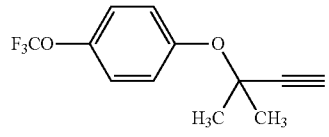

The title compound was synthesized by the reaction of 4-(trifluoromethoxy)phenol (700 mg, 3.930 mmol) with 3-chloro-3-methylbut-1-yne (0.52 mL, 4.716 mmol) in the presence of potassium carbonate (1.08 g, 7.860 mmol), copper iodide (14 mg, 0.078 mmol) and potassium iodide (1.19 g, 6.681 mmol) in DMF (10 mL) as per the process described in Intermediate 62 to yield 321 mg of the product as an oil. $^1$H NMR (300 MHz, DMSO-$d_6$) δ 1.59 (s, 6H), 3.71 (s, 1H), 7.24 (d, J=8.7 Hz, 2H), 7.31 (d, J=8.7 Hz, 2H).

Intermediate 78

1-(Difluoromethoxy)-4-[(2-methylbut-3-yn-2-yl)oxy]benzene

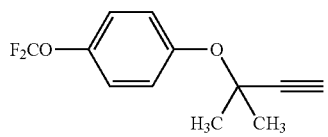

The title compound was synthesized by the reaction of 4-(difluoromethoxy)phenol (1.1 g, 6.869 mmol) with 3-chloro-3-methylbut-1-yne (1.13 mL, 9.750 mmol) in the presence of potassium carbonate (1.89 g, 13.739 mmol), copper iodide (65 mg, 0.343 mmol) and potassium iodide (1.93 g, 11.678 mmol) in DMF (10 mL) as per the process described in Intermediate 62 to yield 450 mg of product as a liquid. $^1$H NMR (300 MHz, DMSO-d$_6$) δ 1.56 (s, 6H), 3.66 (s, 1H), 7.12-7.20 (m, 5H); APCI-MS (m/z) 227 (M+H)$^+$.

Intermediate 79

4-[(2-Methylbut-3-yn-2-yl)oxy]benzonitrile

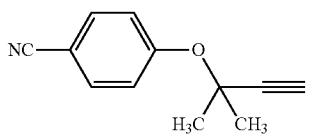

The title compound was synthesized by the reaction of 4-hydroxybenzonitrile (700 mg, 5.8764 mmol) with 3-chloro-3-methylbut-1-yne (0.77 mL, 7.051 mmol) in the presence of potassium carbonate (1.62 g, 11.752 mmol), copper iodide (22 mg, 0.117 mmol) and potassium iodide (1.65 g, 9.989 mmol) in DMF (10 mL) as per the process described in Intermediate 62 to yield 612 mg of product as a liquid. $^1$H NMR (300 MHz, DMSO-d$_6$) δ 1.65 (s, 6H), 3.82 (s, 1H), 7.30 (d, J=9.0 Hz, 2H), 7.78 (d, J=9.0 Hz, 2H); APCI-MS (m/z) 186 (M+H)$^+$.

Intermediate 80

1-Methyl-2-{2-[4-(trifluoromethyl)phenoxy]propan-2-yl}-1H-benzimidazol-5-amine

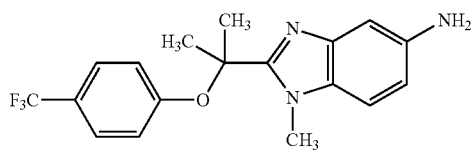

Step 1: 1-Methyl-5-nitro-2-{2-[4-(trifluoromethyl)phenoxy]propan-2-yl}-1H-benzimidazole The title compound was synthesized by the reaction of N$^1$-methyl-4-nitrobenzene-1,2-diamine (235 mg, 1.410 mmol) with 2-methyl-2-[4-(trifluoromethyl)phenoxy]propanoic acid (350 mg, 1.410 mmol) using CDI (228 mg, 1.410 mmol) in THF (5 mL) followed by cyclization in the presence of acetic acid (5 mL) as per the process described in step 1 of Intermediate 14 to yield 175 mg of the product as a solid. $^1$H NMR (300 MHz, DMSO-d$_6$) δ 1.93 (s, 6H), 3.93 (s, 3H), 6.82 (d, J=9.0 Hz, 2H), 7.56 (d, J=8.4 Hz, 2H), 7.81 (d, J=8.7 Hz, 1H), 8.22 (d, J=8.7 Hz, 1H), 8.60 (s, 1H), APCI-MS (m/z) 380 (M+H)$^+$.

Step 2: 1-Methyl-2-{2-[4-(trifluoromethyl)phenoxy]propan-2-yl}-1H-benzimidazol-5-amine The title compound was prepared by the reduction of step 1 intermediate (175 mg, 0.460 mmol) using iron powder (129 mg, 2.301 mmol) and ammonium chloride (246 mg, 4.600 mmol) in a mixture of water (3 mL), methanol (3 mL) and THF (10 mL) as per the process described in step 2 of Intermediate 14 to yield 160 mg of the product as a solid. $^1$H NMR (300 MHz, DMSO-d$_6$) δ 1.86 (s, 6H), 3.68 (s, 3H), 4.80 (br s, 2H), 6.60 (d, J=8.1 Hz, 1H), 6.77 (d, J=8.1 Hz, 3H), 7.13 (d, J=8.7 Hz, 1H), 7.52 (d, J=8.1 Hz, 2H); APCI-MS (m/z) 350 (M+H)$^+$.

Intermediate 81

2-[2-(3,4-Difluorophenoxy)propan-2-yl]-1-methyl-1H-benzimidazol-5-amine

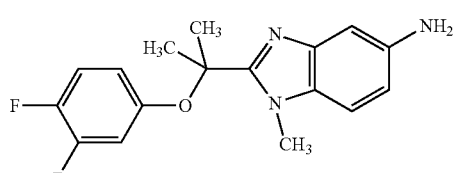

Step 1: 2-[2-(3,4-difluorophenoxy)propan-2-yl]-1-methyl-5-nitro-1H-benzimidazole The title compound was synthesized by the reaction of N$^1$-methyl-4-nitrobenzene-1,2-diamine (308 mg, 1.844 mmol) with 2-(3,4-difluorophenoxy)-2-methylpropanoic acid (400 mg, 1.844 mmol) using CDI (299 mg, 1.844 mmol) in THF (5 mL) followed by cyclization in the presence of acetic acid (5 mL) as per the process described in step 1 of Intermediate 14 to yield 90 mg of the product as a solid. $^1$H NMR (300 MHz, DMSO-d$_6$) δ 1.86 (s, 6H), 4.02 (s, 3H), 6.40 (d, J=8.7 Hz, 1H), 6.81 (br s, 1H), 7.20-7.26 (m, 1H), 7.84 (d, J=9.0 Hz, 1H), 8.24 (d, J=8.4 Hz, 1H), 8.58 (s, 1H); APCI-MS (m/z) 348 (M+H)$^+$.

Step 2: 2-[2-(3,4-Difluorophenoxy)propan-2-yl]-1-methyl-1H-benzimidazol-5-amine The title compound was prepared by reduction of step 1 intermediate (90 mg, 0.259 mmol) using iron powder (72 mg, 1.295 mmol) and ammonium chloride (139 mg, 2.590 mmol) in a mixture of water (2 mL), methanol (2 mL) and THF (5 mL) as per the process described in step 2 of Intermediate 14 to yield 85 mg of the product as a solid. $^1$H NMR (300 MHz, DMSO-d$_6$) δ 1.79 (s, 6H), 3.76 (s, 3H), 4.80 (br s, 2H), 6.33 (br s, 1H), 6.60-6.65 (m, 2H), 6.77 (s, 1H), 7.16-7.27 (m, 2H); APCI-MS (m/z) 318 (M+H)⁺.

Intermediate 82

2-[2-(4-Chloro-2-fluorophenoxy)propan-2-yl]-1-methyl-1H-benzimidazol-5-amine

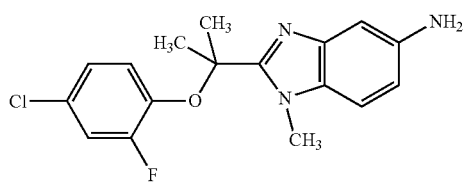 [SMILES: Cn1c(C(C)(C)Oc2ccc(Cl)cc2F)nc2cc(N)ccc21]

Step 1: 2-[2-(4-Chloro-2-fluorophenoxy)propan-2-yl]-1-methyl-5-nitro-1H-benzimidazole The title compound was synthesized by the reaction of N¹-methyl-4-nitrobenzene-1,2-diamine (358 mg, 2.140 mmol) with 2-(4-chloro-2-fluorophenoxy)-2-methylpropanoic acid (500 mg, 2.140 mmol) using CDI (347 mg, 2.140 mmol) in THF (5 mL) followed by cyclization in the presence of acetic acid (5 mL) as per the process described in step 1 of Intermediate 14 to yield 460 mg of the product as a solid. ¹H NMR (300 MHz, DMSO-d₆) δ 1.84 (s, 6H), 4.05 (s, 3H), 6.52 (t, J=8.7 Hz, 1H), 7.03 (d, J=8.7 Hz, 1H), 7.44-7.50 (m, 1H), 7.84 (d, J=9.3 Hz, 1H), 8.17-8.23 (m, 1H), 8.55 (s, 1H); ESI-MS (m/z) 363 (M+H)⁺.

Step 2: 2-[2-(4-Chloro-2-fluorophenoxy)propan-2-yl]-1-methyl-1H-benzimidazol-5-amine The title compound was prepared by the reduction of step 1 intermediate (450 mg, 1.236 mmol) using iron powder (345 mg, 6.184 mmol) and ammonium chloride (661 mg, 12.362 mmol) in a mixture of water (5 mL), methanol (5 mL) and THF (10 mL) as per the process described in step 2 of Intermediate 14 to yield 435 mg of the product as a solid. ¹H NMR (300 MHz, DMSO-d₆) δ 1.79 (s, 6H), 3.79 (s, 3H), 4.76 (br s, 2H), 6.34 (t, J=8.7 Hz 1H), 6.62 (d, J=8.4 Hz, 1H), 6.73 (s, 1H), 6.99 (d, J=8.7 Hz, 1H), 7.18 (d, J=8.4 Hz, 1H), 7.42-7.47 (m, 1H); ESI-MS (m/z) 333 (M+H)⁺.

Intermediate 83

2-[2-(2,4-Dichlorophenoxy)propan-2-yl]-1-methyl-1H-benzimidazol-5-amine

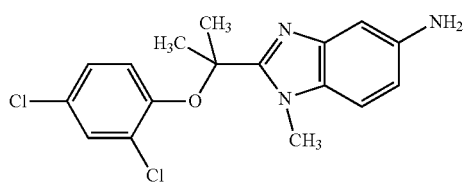 [SMILES: Cn1c(C(C)(C)Oc2ccc(Cl)cc2Cl)nc2cc(N)ccc21]

Step 1: 2-[2-(2,4-Dichlorophenoxy)propan-2-yl]-1-methyl-5-nitro-1H-benzimidazole The title compound was synthesized by the reaction of N¹-methyl-4-nitrobenzene-1,2-diamine (334 mg, 2.00 mmol) with 2-(2,4-dichlorophenoxy)-2-methylpropanoic acid (500 mg, 2.00 mmol) using CDI (325 mg, 2.00 mmol) in THF (5 mL) followed by cyclization in the presence of acetic acid (5 mL) as per the process described in step 1 of Intermediate 14 to yield 225 mg of the product as a solid. ¹H NMR (300 MHz, DMSO-d₆) δ 1.90 (s, 6H), 3.99 (s, 3H), 6.33 (d, J=9.3 Hz, 1H), 7.14 (d, J=8.4 Hz, 1H), 7.65 (s, 1H), 7.84 (d, J=8.7 Hz, 1H), 8.24 (d, J=9.0 Hz, 1H), 8.59 (s, 1H); APCI-MS (m/z) 380 (M+H)⁺.

Step 2: 2-[2-(2,4-Dichlorophenoxy)propan-2-yl]-1-methyl-1H-benzimidazol-5-amine

The title compound was prepared by the reduction of step 1 intermediate (200 mg, 0.526 mmol) using iron powder (147 mg, 2.630 mmol) and ammonium chloride (281 mg, 5.260 mmol) in a mixture of water (3 mL), methanol (3 mL) and THF (10 mL) as per the process described in step 2 of Intermediate 14 to yield 140 mg of the product as a solid. ¹H NMR (300 MHz, DMSO-d₆) δ 1.84 (s, 6H), 3.73 (s, 3H), 4.80 (br s, 2H), 6.25 (d, J=9.3 Hz, 1H), 6.62 (d, J=7.8 Hz, 1H), 6.77 (s, 1H), 7.11 (d, J=8.1 Hz, 1H), 7.16 (d, J=8.4 Hz, 1H), 7.61 (s, 1H); APCI-MS (m/z) 350 (M+H)⁺.

Intermediate 84

2-[2-(3,4-Dichlorophenoxy)propan-2-yl]-1-methyl-1H-benzimidazol-5-amine

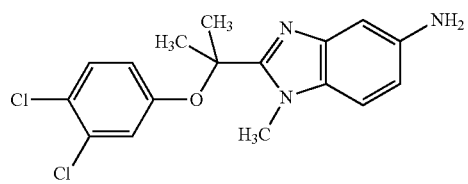 [SMILES: Cn1c(C(C)(C)Oc2ccc(Cl)c(Cl)c2)nc2cc(N)ccc21]

Step 1: 2-[2-(3,4-Dichlorophenoxy)propan-2-yl]-1-methyl-5-nitro-1H-benzimidazole The title compound was synthesized by the reaction of N-methyl-4-nitrobenzene-1,2-diamine (269 mg, 1.605 mmol) with 2-(3,4-dichlorophenoxy)-2-methylpropanoic acid (400 mg, 1.605 mmol) using CDI (260 mg, 1.605 mmol) in THF (5 mL) followed by cyclization in the presence of acetic acid (5 mL) as per the process described in step 1 of Intermediate 14 to yield 150 mg of the product as a solid. ¹H NMR (300 MHz, DMSO-d₆) δ 1.88 (s, 6H), 3.98 (s, 3H), 6.56 (d, J=8.4 Hz, 1H), 7.00 (s, 1H), 7.43 (d, J=9.9 Hz, 1H), 7.83 (d, J=9.3 Hz, 1H), 8.23 (d, J=8.7 Hz, 1H), 8.60 (s, 1H); APCI-MS (m/z) 380 (M)⁺.

Step 2: 2-[2-(3,4-Dichlorophenoxy)propan-2-yl]-1-methyl-1H-benzimidazol-5-amine

The title compound was prepared by the reduction of step 1 intermediate (150 mg, 0.394 mmol) using iron powder (110 mg, 1.972 mmol) and ammonium chloride (210 mg, 3.940 mmol) in a mixture of water (3 mL), methanol (3 mL) and THF (5 mL) as per the process described in step 2 of Intermediate 14 to yield 100 mg of the product as a solid; APCI-MS (m/z) 350 (M+H)⁺.

117

Intermediate 85

2-[2-(4-Chloro-2-fluorophenoxy)propan-2-yl]-1-ethyl-1H-benzimidazol-5-amine

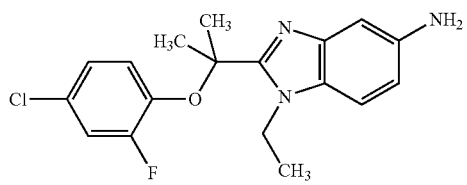 [SMILES: CCn1c(C(C)(C)Oc2ccc(Cl)cc2F)nc2cc(N)ccc21]

Step 1: 2-[2-(4-Chloro-2-fluorophenoxy)propan-2-yl]-1-ethyl-5-nitro-1H-benzimidazole To a stirred solution of 2-(4-chloro-2-fluorophenoxy)-2-methylpropanoic acid (350 mg, 1.500 mmol) in DCM (10 mL) were added catalytic amount of dry DMF and oxalyl chloride (0.65 mL, 7.500 mmol). The reaction mixture was stirred at room temperature for 2 h. The excess of the oxalyl chloride was distilled off under reduced pressure and the residue was dissolved in DCM (10 mL). To that solution were added N-ethyl-4-nitrobenzene-1,2-diamine (325 mg, 1.801 mmol) and triethylamine (0.41 mL, 3.00 mmol) at 0° C. The reaction mixture was stirred at RT for 16 h. The reaction mixture was diluted with ethyl acetate (20 mL) and water (20 mL). The layers were separated and the aqueous layer was extracted with ethyl acetate (2×25 mL). The combined organic extracts were washed with water (20 mL) and brine (20 mL). The solution was dried over anhydrous sodium sulfate, filtered and concentrated under reduced pressure. The residue obtained was refluxed with acetic acid (10 mL) for 2 h. The acetic acid was removed under reduced pressure and the residue obtained was diluted with water (25 mL) and ethyl acetate (50 mL). The organic layer was separated and washed with water (20 mL). The solution was dried over anhydrous sodium sulfate and concentrated under reduced pressure. The residue obtained was purified by silica gel column chromatography to yield 250 mg of the title product as a solid. $^1$H NMR (300 MHz, DMSO-$d_6$) δ 1.31 (t, J=6.6 Hz, 3H), 1.86 (s, 6H), 4.67 (q, J=7.2 Hz, 2H), 6.63 (t, J=8.7 Hz, 1H), 7.08 (d, J=9.3 Hz, 1H), 7.52 (d, J=9.0 Hz, 1H), 7.89 (d, J=9.3 Hz, 1H), 8.23 (d, J=9.0 Hz, 1H), 8.58 (s, 1H); ESI-MS (m/z) 378 (M+H)$^+$.

Step 2: 2-[2-(4-Chloro-2-fluorophenoxy)propan-2-yl]-1-ethyl-1H-benzimidazol-5-amine The title compound was prepared by the reduction of step 1 intermediate (250 mg, 0.0.661 mmol) using iron powder (185 mg, 3.308 mmol) and ammonium chloride (353 mg, 6.610 mmol) in a mixture of water (3 mL), methanol (3 mL) and THF (5 mL) as per the process described in step 2 of Intermediate 14 to yield 220 mg of the product as a solid. $^1$H NMR (300 MHz, DMSO-$d_6$) δ 1.20 (d, J=6.9 Hz, 3H), 1.81 (s, 6H), 4.39 (q, J=6.9 Hz, 2H), 4.79 (br s, 2H), 6.44 (t, J=8.7 Hz, 1H), 6.62 (d, J=8.1 Hz, 1H), 6.77 (s, 1H), 7.01 (d, J=8.7 Hz, 1H), 7.20 (d, J=8.1 Hz, 1H), 7.47 (d, J=8.7 Hz, 1H); ESI-MS (m/z) 348 (M+H)$^+$.

118

Intermediate 86

2-[2-(4-Chloro-3-fluorophenoxy)propan-2-yl]-1-ethyl-1H-benzimidazol-5-amine

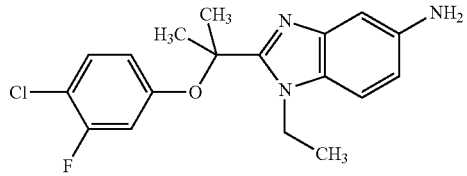 [SMILES: CCn1c(C(C)(C)Oc2ccc(Cl)c(F)c2)nc2cc(N)ccc21]

Step 1: 2-(4-Chloro-3-fluorophenoxy)-N-[2-(ethylamino)-5-nitrophenyl]-2-methylpropanamide To a stirred solution of 2-(4-chloro-3-fluorophenoxy)-2-methylpropanoic acid (400 mg, 1.715 mmol) in dichloromethane (5 mL) were added catalytic amount of dry DMF and oxalyl chloride (745 µL, 8.575 mmol). The reaction mixture was stirred at room temperature for 2 h. The excess of the oxalyl chloride was distilled off under reduced pressure and the residue was dissolved in DCM (5 mL). To the reaction mixture, N$^1$-ethyl-4-nitrobenzene-1,2-diamine (372 mg, 2.058 mmol) and triethylamine (482 µL, 3.430 mmol) were added at 0° C. The reaction mixture was stirred at RT for 16 hours. The reaction mixture was diluted with ethyl acetate (20 mL) and water (20 mL). The layers were separated and the aqueous layer was extracted with ethyl acetate (2×25 mL). The combined organic extracts were washed with water (20 mL) and brine (20 mL). The solution was dried over anhydrous sodium sulfate, filtered and concentrated under reduced pressure. The residue obtained was purified by silica gel column chromatography to yield 413 mg of the title product as a solid. $^1$H NMR (300 MHz, DMSO-$d_6$) δ 1.08 (t, J=6.9 Hz, 3H), 1.72 (s, 6H), 3.17 (q, J=6.9 Hz, 2H), 5.67 (br s, 1H), 6.75 (d, J=9.3 Hz, 1H), 6.86 (d, J=7.2 Hz, 1H), 7.54 (t, J=8.7 Hz, 1H), 7.92 (s, 1H), 8.00 (d, J=6.9 Hz, 1H), 9.64 (s, 1H).

Step 2: 2-[2-(4-Chloro-3-fluorophenoxy)propan-2-yl]-1-ethyl-5-nitro-1H-benzimidazole The step 1 intermediate (400 mg, 1.160 mmol) was refluxed in acetic acid (5 mL) for 16 hours. The reaction mixture was concentrated under reduced pressure and the residue was diluted with ethyl acetate (20 mL) and water (15 mL). The organic layer was separated and washed with water (2×20 mL), dried over anhydrous sodium sulfate and concentrated under reduced pressure. The residue obtained was purified by silica gel column chromatography to yield 325 mg of the title product as a solid. $^1$H NMR (300 MHz, DMSO-$d_6$) δ 1.22 (t, J=6.3 Hz, 3H), 1.89 (s, 6H), 4.59 (q, J=6.6 Hz, 2H), 6.49 (d, J=9.3 Hz, 1H), 6.83 (d, J=11.4 Hz, 1H), 7.38 (t, J=9.3 Hz, 1H), 7.86 (d, J=8.7 Hz, 1H), 8.22 (d, J=8.7 Hz, 1H), 8.60 (s, 1H); APCI-MS (m/z) 378 (M+H)$^+$.

Step 3: 2-[2-(4-Chloro-3-fluorophenoxy)propan-2-yl]-1-ethyl-1H-benzimidazol-5-amine To a stirred solution of step 2 intermediate (100 mg, 0.264 mmol) and nickel chloride (125 mg, 0.528 mmol) in methanol (5 mL) was added sodium borohydride (40 mg, 1.058 mmol) in portions. The reaction mixture was stirred at room temperature for 30 minutes. The reaction mixture was concentrated under reduced pressure to yield residue. The residue was diluted with water (10 mL) and ethyl acetate (10 mL). The layers were separated and the aqueous layer was extracted with ethyl acetate (2×10 mL). The combined organic layers were washed with water (20 mL), brine (20 mL) and dried over anhydrous sodium sulfate. The solvent was distilled off under reduced pressure and the residue obtained was purified by silica gel column chromatography to yield 84 mg of the title product as a semi-solid. $^1$H NMR (300 MHz, DMSO-$d_6$) δ 1.14 (t, J=6.9 Hz, 3H), 1.83 (s, 6H), 4.33 (q, J=6.9 Hz, 2H), 4.80 (br s, 2H), 6.47 (d, J=8.7 Hz, 1H), 6.60-6.69 (m, 2H), 6.79 (s, 1H), 7.19 (d, J=8.7 Hz, 1H), 7.35 (t, J=9.0 Hz, 1H)

Intermediate 87

2-[2-(2,4-Difluorophenoxy)propan-2-yl]-1-ethyl-1H-benzimidazol-5-amine

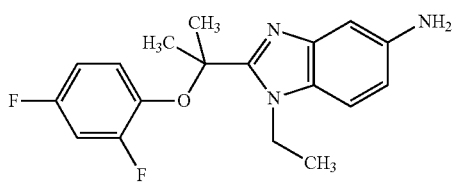 [SMILES: CCn1c(C(C)(C)Oc2ccc(F)cc2F)nc2cc(N)ccc21]

Step 1: 2-[2-(2,4-Difluorophenoxy)propan-2-yl]-1-ethyl-5-nitro-1H-benzimidazole

To a stirred solution of 2-(2,4-difluorophenoxy)-2-methylpropanoic acid (500 mg, 2.321 mmol) in THF (10 mL) was added CDI (376 mg, 2.321 mmol) and the reaction was stirred at 50° C. for 30 min. $N^1$-ethyl-4-nitrobenzene-1,2-diamine (420 mg, 2.321 mmol) was added to the reaction mixture and further stirred for 2 hours at the same temperature. The reaction mixture was diluted with water (50 mL) and ethyl acetate (50 mL). The layers were separated and the aqueous layer was extracted with ethyl acetate (2×50 mL). The combined organic layers were washed with water (2×100 mL) and dried over anhydrous sodium sulfate. The solvents were distilled off under reduced pressure to yield a residue. The residue was dissolved in acetic acid and refluxed for 1.5 hours. The acetic acid was distilled out under reduced pressure and the residue obtained was diluted with water (50 mL) and ethyl acetate (50 mL). The aqueous layer was extracted with ethyl acetate (3×50 mL). The combined organic layers were washed with water (2×100 mL), brine (50 mL) and dried over sodium sulfate. The solvent was recovered under reduced pressure and the residue obtained was purified by silica gel column chromatography to yield 434 mg of the title product as a solid. $^1$H NMR (300 MHz, DMSO-$d_6$) δ 1.36 (t, J=6.9 Hz, 3H), 1.83 (s, 6H), 4.72 (q, J=6.9 Hz, 2H), 6.64-6.70 (m, 1H), 6.85-6.90 (m, 1H), 7.31-7.35 (m, 1H), 7.90 (d, J=8.7 Hz, 1H), 8.23 (d, J=8.7 Hz, 1H), 8.56 (s, 1H); ESI-MS (m/z) 362 (M+H)$^+$.

Step 2: 2-[2-(2,4-Difluorophenoxy)propan-2-yl]-1-ethyl-1H-benzimidazol-5-amine

To a stirred solution of step 1 intermediate (150 mg, 0.417 mmol) in a mixture of methanol (2 mL), THF (5 mL) and water (2 mL) were added iron powder (106 mg, 2.086 mmol) and ammonium chloride (323 mg, 4.170 mmol) at RT. The reaction mixture was heated to 80° C. and it was stirred for 1 hour at the same temperature. The reaction mixture cooled to RT and filtered off the suspended emulsion. The filtrate was concentrated under reduced pressure and diluted with water (10 mL). The aqueous mixture was extracted with ethyl acetate (2×20 mL). The combined organic layers were washed with brine and dried over anhydrous sodium sulfate. The solvents were recovered under reduced pressure and the residue obtained was purified by silica gel column chromatography to 126 mg of the title product as a solid. $^1$H NMR (300 MHz, DMSO-$d_6$) δ 1.25 (t, J=6.9 Hz, 3H), 1.77 (s, 6H), 4.45 (q, J=6.9 Hz, 2H), 4.78 (br s, 2H), 6.40-6.46 (m, 1H), 6.64 (d, J=8.1 Hz, 1H), 6.75 (s, 1H), 6.76-6.84 (m, 1H), 7.23 (d, J=8.7 Hz, 1H), 7.29-7.31 (m, 1H); ESI-MS (m/z) 332 (M+H)$^+$.

Intermediate 88

2-[2-(3,4-Difluorophenoxy)propan-2-yl]-1-ethyl-1H-benzimidazol-5-amine

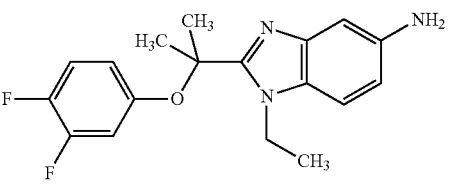 [SMILES: CCn1c(C(C)(C)Oc2ccc(F)c(F)c2)nc2cc(N)ccc21]

Step 1: 2-[2-(3,4-Difluorophenoxy)propan-2-yl]-1-ethyl-5-nitro-1H-benzimidazole

The title compound was synthesized by the coupling reaction of $N^1$-ethyl-4-nitrobenzene-1,2-diamine (400 mg, 2.212 mmol) with 2-(3,4-difluorophenoxy)-2-methylpropanoic acid (400 mg, 1.844 mmol) by using oxalyl chloride (801 μL, 9.220 mmol) and triethylamine (518 μL, 3.688 mmol) in DCM (5 mL) followed by cyclization in the presence of acetic acid (5 mL) as per the process described in step 1 of Intermediate 85 to yield 461 mg of the product as a solid. $^1$H NMR (300 MHz, DMSO-$d_6$) δ 1.27 (t, J=7.5 Hz, 3H), 1.86 (s, 6H), 4.61 (q, J=7.5 Hz, 2H), 6.44 (d, J=8.1 Hz, 1H), 6.82-6.87 (m, 1H), 7.23-7.28 (m, 1H), 7.87 (d, J=8.7 Hz, 1H), 8.19-8.22 (m, 1H), 8.59 (s, 1H); ESI-MS (m/z) 362 (M+H)$^+$.

Step 2: 2-[2-(3,4-Difluorophenoxy)propan-2-yl]-1-ethyl-1H-benzimidazol-5-amine

The title compound was prepared by reduction of step 1 intermediate (100 mg, 0.278 mmol) using sodium borohydride (42 mg, 1.111 mmol) and nickel chloride (132 mg, 0.556 mmol) in methanol (5 mL) as per the process described in step 3 of Intermediate 1 to yield 91 mg of the product as a solid; $^1$H NMR (300 MHz, DMSO-$d_6$) δ 1.16 (t, J=7.2 Hz, 3H), 1.80 (s, 6H), 4.37 (q, J=7.2 Hz, 2H), 4.85 (br s, 2H), 6.40 (d, J=8.4 Hz, 1H), 6.61-6.71 (m, 2H), 6.78 (s, 1H), 7.18-7.27 (m, 2H); ESI-MS (m/z) 332 (M+H)$^+$.

Intermediate 89

1-Ethyl-2-[2-(2,4,6-trifluorophenoxy)propan-2-yl]-1H-benzimidazol-5-amine

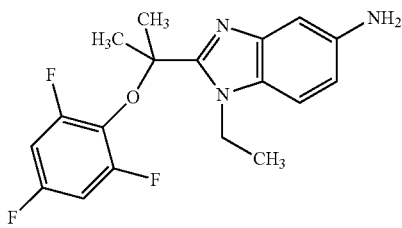 [SMILES: CCn1c(C(C)(C)Oc2c(F)cc(F)cc2F)nc2cc(N)ccc21]

Step 1: 1-Ethyl-5-nitro-2-[2-(2,4,6-trifluorophenoxy)propan-2-yl]-1H-benzimidazole The title compound was synthesized by the coupling reaction of $N^1$-ethyl-4-nitrobenzene-1,2-diamine (325 mg, 1.794 mmol) with 2-methyl-2-(2,4,6-trifluorophenoxy)propanoic acid (350 mg, 1.495 mmol) using oxalyl chloride (649 µL, 7.475 mmol) and triethylamine (420 µL, 2.940 mmol) in DCM (5 mL) followed by cyclization in the presence of acetic acid (5 mL) as per the process described in step 1 of Intermediate 85 to yield 220 mg of the product as a solid. $^1$H NMR (300 MHz, DMSO-$d_6$) δ 1.44 (t, J=6.9 Hz, 3H), 1.82 (s, 6H), 4.73 (q, J=6.9 Hz, 2H), 7.26 (t, J=8.7 Hz, 2H), 7.90 (d, J=9.0 Hz, 1H), 8.23 (d, J=9.3 Hz, 1H), 8.55 (s, 1H); ESI-MS (m/z) 380 (M+H)$^+$.

Step 2: 1-Ethyl-2-[2-(2,4,6-trifluorophenoxy)propan-2-yl]-1H-benzimidazol-5-amine The title compound was prepared by reduction of step 1 intermediate (100 mg, 0.263 mmol) using sodium borohydride (40 mg, 1.055 mmol) and nickel chloride (125 mg, 0.526 mmol) in methanol (5 mL) as per the process described in step 3 of Intermediate 1 to yield 97 mg of the product as a semi-solid; $^1$H NMR (300 MHz, DMSO-$d_6$) δ 1.36 (t, J=7.2 Hz, 3H), 1.73 (s, 6H), 4.50 (q, J=7.2 Hz, 2H), 4.74 (br s, 2H), 6.62 (d, J=8.4 Hz, 1H), 6.73 (s, 1H), 7.24 (t, J=8.1 Hz, 3H); ESI-MS (m/z) 350 (M+H)$^+$.

Intermediate 90

1-Ethyl-2-[2-(2,3,4-trifluorophenoxy)propan-2-yl]-1H-benzimidazol-5-amine

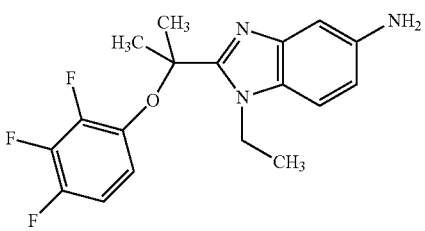 [SMILES: CCn1c(C(C)(C)Oc2ccc(F)c(F)c2F)nc2cc(N)ccc21]

Step 1: 1-Ethyl-5-nitro-2-[2-(2,3,4-trifluorophenoxy)propan-2-yl]-1H-benzimidazole The title compound was synthesized by the coupling reaction of $N^1$-ethyl-4-nitrobenzene-1,2-diamine (510 mg, 2.820 mmol) with 2-methyl-2-(2,3,4-trifluorophenoxy)propanoic acid (550 mg, 2.350 mmol) by using oxalyl chloride (1 mL, 11.75 mmol) and triethylamine (660 µL, 4.70 mmol) in DCM (5 mL) followed by cyclization in the presence of acetic acid (10 mL) as per the process described in step 1 of Intermediate 85 to yield 440 mg of the product as a solid. $^1$H NMR (300 MHz, DMSO-$d_6$) δ 1.36 (t, J=6.9 Hz, 3H), 1.82 (s, 6H), 4.73 (q, J=6.9 Hz, 2H), 6.49 (br s, 1H), 7.10-7.15 (m, 1H), 7.89 (d, J=9.3 Hz, 1H), 8.23 (d, J=8.7 Hz, 1H), 8.57 (s, 1H); APCI-MS (m/z) 380 (M+H)$^+$.

Step 2: 1-Ethyl-2-[2-(2,3,4-trifluorophenoxy)propan-2-yl]-1H-benzimidazol-5-amine The title compound was prepared by reduction of step 1 intermediate (140 mg, 0.369 mmol) using sodium borohydride (56 mg, 1.477 mmol) and nickel chloride (175 mg, 0.738 mmol) in methanol (6 mL) as per the process described in step 3 of Intermediate 1 to yield 125 mg of the product as a semi-solid; $^1$H NMR (300 MHz, DMSO-$d_6$) δ 1.27 (t, J=7.2 Hz, 3H), 1.81 (s, 6H), 4.44 (q, J=7.2 Hz, 2H), 6.26 (br s, 1H), 6.65 (d, J=8.4 Hz, 1H), 6.78 (s, 1H), 7.09 (d, J=10.2 Hz, 1H), 7.24 (d, J=8.7 Hz, 1H); APCI-MS (m/z) 350 (M+H)$^+$.

Intermediate 91

1-Ethyl-2-[2-(2,4,5-trifluorophenoxy)propan-2-yl]-1H-benzimidazol-5-amine

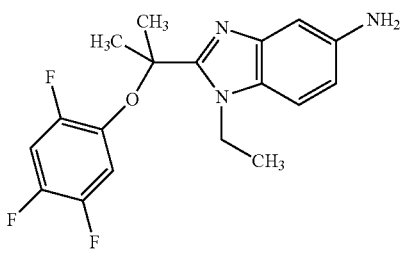 [SMILES: CCn1c(C(C)(C)Oc2cc(F)c(F)cc2F)nc2cc(N)ccc21]

Step 1: 1-Ethyl-5-nitro-2-[2-(2,4,5-trifluorophenoxy)propan-2-yl]-1H-benzimidazole The title compound was synthesized by the coupling reaction of $N^1$-ethyl-4-nitrobenzene-1,2-diamine (742 mg, 4.102 mmol) with 2-methyl-2-(2,4,5-trifluorophenoxy)propanoic acid (800 mg, 3.418 mmol) by using oxalyl chloride (1.48 mL, 17.09 mmol) and triethylamine (960 µL, 6.836 mmol) in DCM (5 mL) followed by cyclization in the presence of acetic acid (10 mL) as per the process described in step 1 of Intermediate 85 to yield 605 mg of the product as a solid. $^1$H NMR (300 MHz, DMSO-$d_6$) δ 1.37 (t, J=6.9 Hz, 3H), 1.84 (s, 6H), 4.68 (q, J=6.9 Hz, 2H), 6.90-6.99 (m, 1H), 7.61-7.68 (m, 1H), 7.87 (d, J=8.7 Hz, 1H), 8.22 (d, J=8.7 Hz, 1H), 8.57 (s, 1H); APCI-MS (m/z) 380 (M+H)$^+$.

Step 2: 1-Ethyl-2-[2-(2,4,5-trifluorophenoxy)propan-2-yl]-1H-benzimidazol-5-amine The title compound was prepared by reduction of step 1 intermediate (150 mg, 0.396 mmol) using sodium borohydride (60 mg, 1.582 mmol) and nickel chloride (187 mg, 0.790 mmol) in methanol (5 mL) as per the process described in step 3 of Intermediate 1 to yield 107 mg of the product as a semi-solid; $^1$H NMR (300 MHz, DMSO-$d_6$) δ 1.26 (t, J=7.2 Hz, 3H), 1.83 (s, 6H), 4.41 (q, J=7.2 Hz, 2H), 6.64 (d, J=8.4 Hz, 2H), 6.78 (s, 1H), 7.23 (d, J=8.4 Hz, 1H), 7.60-7.65 (m, 2H), 7.93 (s, 1H); ESI-MS (m/z) 350 (M+H)$^+$.

Intermediate 92

2-[2-(4-Chlorophenoxy)propan-2-yl]-1-ethyl-1H-benzimidazol-5-amine

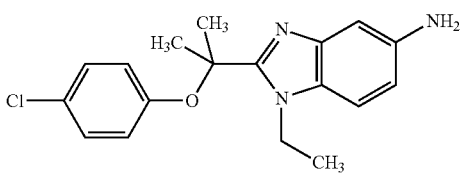

Step 1: 2-[2-(4-Chlorophenoxy)propan-2-yl]-1-ethyl-5-nitro-1H-benzimidazole

The title compound was synthesized by the coupling reaction of N$^1$-ethyl-4-nitrobenzene-1,2-diamine (421 mg, 2.329 mmol) with 2-(4-chlorophenoxy)-2-methylpropanoic acid (500 mg, 2.329 mmol) using CDI (378 mg, 2.329 mmol) in THF (10 mL) followed by cyclization in the presence of acetic acid (5 mL) as per the process described in step 1 of Intermediate 14 to yield 400 mg of the product as a solid. $^1$H NMR (300 MHz, DMSO-$d_6$) δ 1.22 (t, J=7.2 Hz, 3H), 1.87 (s, 6H), 4.59 (q, J=6.9 Hz, 2H), 6.68 (d, J=9.0 Hz, 2H), 7.25 (d, J=8.7 Hz, 2H), 7.86 (d, J=8.7 Hz, 1H), 8.18-8.22 (m, 1H), 8.85 (s, 1H).

Step 2: 2-[2-(4-Chlorophenoxy)propan-2-yl]-1-ethyl-1H-benzimidazol-5-amine

The title compound was prepared by reduction of step 1 intermediate (100 mg, 0.277 mmol) using iron powder (62 mg, 1.111 mmol) and ammonium chloride (149 mg, 2.779 mmol) in a mixture of water (2 mL), methanol (2 mL) and THF (5 mL) as per the process described in step 2 of Intermediate 14 to yield 93 mg of the product as a solid; $^1$H NMR (300 MHz, DMSO-$d_6$) δ 1.11 (t, J=7.5 Hz, 3H), 1.80 (s, 6H), 4.35 (q, J=7.5 Hz, 2H), 4.78 (br s, 2H), 6.63 (d, J=8.7 Hz, 3H), 6.77 (s, 1H), 7.18 (t, J=8.1 Hz, 3H); ESI-MS (m/z) 330 (M+H)$^+$.

Intermediate 93

2-{2-[(5-Chloropyridin-2-yl)oxy]propan-2-yl}-1-ethyl-1H-benzimidazol-5-amine

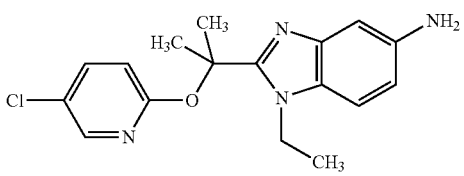 [SMILES: CCn1c(C(C)(C)Oc2ccc(Cl)cn2)nc2cc(N)ccc21]

Step 1: 2-{2-[(5-Chloropyridin-2-yl)oxy]propan-2-yl}-1-ethyl-5-nitro-1H-benzimidazole The title compound was synthesized by the coupling reaction of N$^1$-ethyl-4-nitrobenzene-1,2-diamine (336 mg, 1.548 mmol) with 2-[(5-chloropyridin-2-yl)oxy]-2-methylpropanoic acid (330 mg, 1.715 mmol) using oxalyl chloride (684 μL, 7.930 mmol) and triethylamine (435 μL, 3.097 mmol) in DCM (5 mL) followed by cyclization in the presence of acetic acid (5 mL) as per the process described in step 1 of Intermediate 85 to yield 365 mg of the product as a solid. $^1$H NMR (300 MHz, DMSO-$d_6$) δ 1.00 (t, J=6.9 Hz, 3H), 1.94 (s, 6H), 4.43 (q, J=6.9 Hz, 2H), 7.02 (d, J=8.4 Hz, 1H), 7.74 (d, J=9.3 Hz, 1H), 7.83-7.88 (m, 2H), 8.11-8.16 (m, 1H), 8.53 (s, 1H); APCI-MS (m/z) 361 (M+H)$^+$.

Step 2: 2-{2-[(5-Chloropyridin-2-yl)oxy]propan-2-yl}-1-ethyl-1H-benzimidazol-5-amine The title compound was prepared by the reduction of step 1 intermediate (40 mg, 0.110 mmol) using sodium borohydride (17 mg, 0.443 mmol) and nickel chloride (62 mg, 0.220 mmol) in methanol (5 mL) as per the process described in step 3 of Intermediate 1 to yield 50 mg of the product as a solid. APCI-MS (m/z) 331 (M+H)$^+$.

Intermediate 94

4-{[2-(3,5-Dichloropyridin-2-yl)propan-2-yl]oxy}-3-fluoroaniline

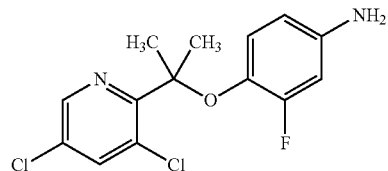 [SMILES: CC(C)(Oc1ccc(N)cc1F)c1ncc(Cl)cc1Cl]

Step 1: 3,5-Dichloro-2-[2-(2-fluoro-4-nitrophenoxy)propan-2-yl]pyridine

The title compound was synthesized by the reaction of 2-(2,4-dichloropyridine)propan-2-ol (150 mg, 0.727 mmol) with 3,4-difluoronitrobenzene (115 mg, 0.727 mmol) using sodium hydride (60% w/w, 43 mg, 1.091 mmol) in DMF (5 mL) as per the process described in step 2 of Intermediate 1 to yield 127 mg of the product as a solid. $^1$H NMR (300 MHz, DMSO-$d_6$) δ 1.90 (s, 6H), 6.43 (t, J=8.7 Hz, 1H), 7.82 (d, J=9.3 Hz, 1H), 8.12-8.22 (m, 2H), 8.74 (s, 1H).

Step 2: 4-{[2-(3,5-Dichloropyridin-2-yl)propan-2-yl]oxy}-3-fluoroaniline

The title compound was synthesized by the nitro reduction of the step 1 intermediate (120 mg, 0.347 mmol) by using sodium borohydride (52 mg, 1.390 mmol) and nickel chloride (164 mg, 0.695 mmol) in methanol (5 mL) as per the process described in step 3 of Intermediate 1 to yield 87 mg of the product as a semi-solid. $^1$H NMR (300 MHz, DMSO-$d_6$) δ 1.65 (s, 6H), 5.03 (s, 2H), 6.07 (d, J=7.8 Hz, 1H), 6.15-6.20 (m, 1H), 6.32 (d, J=13.2 Hz, 1H), 8.23 (s, 1H), 8.56 (s, 1H).

Intermediate 95

4-{[2-(2,4-Dichlorophenyl)propan-2-yl]oxy}-3-fluoroaniline

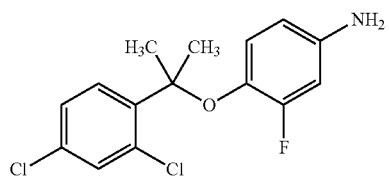 [SMILES: CC(C)(Oc1ccc(N)cc1F)c1ccc(Cl)cc1Cl]

Step 1: 2,4-dichloro-1-[2-(2-fluoro-4-nitrophenoxy)propan-2-yl]benzene

To a stirred and cooled (0° C.) solution of 2-(2,4-dichlorophenyl)propan-2-ol (500 mg, 2.438 mmol) in dry DMF (10 mL) was added sodium hydride (60% w/w, 146 mg, 3.657 mmol) and the reaction was stirred at RT for 30 minutes. 3,4-Difluoronitrobenzene (0.27 mL, 2.438 mmol) was added to the reaction mixture at 0° C. and gradually warmed up to RT. The mixture was stirred at RT for 18 hours. The mixture was diluted with water (20 mL) and extracted with ethyl acetate (3×20 mL). The combined organic layers were washed with water (2×50 mL), brine (50 mL) and dried over anhydrous sodium sulfate. The solvent was distilled off under reduced pressure and the residue obtained was purified by silica gel column chromatography to yield 561 mg of the title product. $^1$H NMR (300 MHz, DMSO-$d_6$) δ 1.90 (s, 6H), 6.65 (t, J=9.3 Hz, 1H), 7.53-7.58 (m, 2H), 7.67 (d, J=8.4 Hz, 1H), 7.79-7.84 (m, 1H), 8.15 (d, J=11.4 Hz, 1H).

Step 2: 4-{[2-(2,4-Dichlorophenyl)propan-2-yl]oxy}-3-fluoroaniline

To a stirred solution of step 1 intermediate (500 mg, 0.453 mmol) and nickel chloride (691 mg, 2.906 mmol) in methanol (10 mL) was added sodium borohydride (220 mg, 5.812 mmol) in small portions. The reaction mixture was stirred at room temperature for 1 hour. The mixture was concentrated under reduced pressure to yield a viscous residue. The residue was diluted with water (20 mL) and ethyl acetate (20 mL). The layers were separated and the aqueous layer was extracted with ethyl acetate (2×20 mL). The combined organic layers were washed with water (50 mL), brine (25 mL) and dried over anhydrous sodium sulfate. The solvent was distilled off under reduced pressure and the residue obtained was purified by silica gel column chromatography to yield 403 mg of the title product as a semi-solid. $^1$H NMR (300 MHz, DMSO-$d_6$) δ 1.64 (s, 6H), 5.07 (br s, 2H), 6.13 (d, J=9.0 Hz, 1H), 6.33-6.44 (m, 2H), 7.42 (d, J=8.4 Hz, 1H), 7.62-6.67 (m, 2H); APCI-MS (m/z) 314 (M+H)$^+$.

Intermediate 96

4-{[2-(2-Chloro-4-fluorophenyl)propan-2-yl]oxy}-3-fluoroaniline

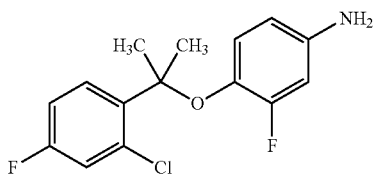 [SMILES: CC(C)(Oc1ccc(N)cc1F)c1ccc(F)cc1Cl]

Step 1: 2-(2-Chloro-4-fluorophenyl)propan-2-yl 2-fluoro-4-nitrophenyl ether

The title compound was synthesized by the reaction of 2-(2-chloro-4-fluorophenyl)propan-2-ol (300 mg, 1.590 mmol) with 3,4-difluoronitrobenzene (253 mg, 1.5904 mmol) by using sodium hydride (60% w/w, 95 mg, 2.3856 mmol) in DMF (5 mL) as per the process described in step 2 of Intermediate 1 to yield 261 mg of the product as a semi-solid. $^1$H NMR (300 MHz, DMSO-$d_6$) δ 1.91 (s, 6H), 6.64 (t, J=9.3 Hz, 1H), 7.34-7.43 (m, 2H), 7.69-7.82 (m, 2H), 8.14 (d, J=11.7 Hz, 1H).

Step 2: 4-{[2-(2-Chloro-4-fluorophenyl)propan-2-yl]oxy}-3-fluoroaniline

The title compound was synthesized by the nitro reduction of the step 1 intermediate (250 mg, 0.763 mmol) by using sodium borohydride (116 mg, 3.051 mmol) and nickel chloride (362 mg, 1.526 mmol) in methanol (5 mL) as per the process described in step 3 of Intermediate 1 to yield 191 mg of the product as a semi-solid. $^1$H NMR (300 MHz, DMSO-$d_6$) δ 1.64 (s, 6H), 5.04 (br s, 2H), 6.12 (d, J=8.1 Hz, 1H), 6.32-6.41 (m, 2H), 7.16-7.23 (m, 1H), 7.42-7.45 (m, 1H), 7.64-7.69 (m, 1H); APCI-MS (m/z) 298 (M+H)$^+$.

Intermediate 97

4-{[2-(4-Chloro-2-fluorophenyl)propan-2-yl]oxy}-3-fluoroaniline

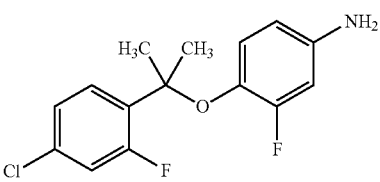 [SMILES: CC(C)(Oc1ccc(N)cc1F)c1ccc(Cl)cc1F]

Step 1: 2-(4-Chloro-2-fluorophenyl)propan-2-yl-2-fluoro-4-nitrophenyl ether

The title compound was synthesized by the reaction of 2-(4-chloro-2-fluorophenyl)propan-2-ol (500 mg, 2.6506 mmol) with 3,4-difluoronitrobenzene (421 mg, 2.6506 mmol) by using sodium hydride (60% w/w, 159 mg, 3.976 mmol) in DMF (10 mL) as per the process described in step 2 of Intermediate 1 to yield 698 mg of the product as a Step 2: 4-{[2-(4-Chloro-2-fluorophenyl)propan-2-yl]oxy}-3-fluoroaniline The title compound was synthesized by the nitro reduction of the step 1 intermediate (690 mg, 2.333 mmol) by using sodium borohydride (353 mg, 9.333 mmol) and nickel chloride (1.1 g, 4.667 mmol) in methanol (10 mL) as per the process described in step 3 of Intermediate 1 to yield 582 mg of the product as a semi-solid. $^1$H NMR (300 MHz, DMSO-$d_6$) δ 1.56 (s, 6H), 5.11 (br s, 2H), 6.17 (d, J=8.7 Hz, 1H), 6.32-6.37 (m, 1H), 6.51 (t, J=8.7 Hz, 1H), 7.28 (d, J=8.4 Hz, 1H), 7.42 (d, J=12.3 Hz, 1H), 7.59 (t, J=9.0 Hz, 1H).

Intermediate 98

4-{[1-(4-Chloro-2-fluorophenyl)cyclopropyl]oxy}-3-fluoroaniline

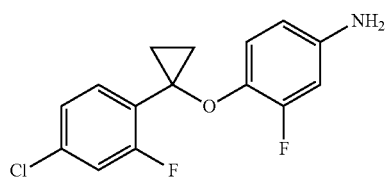 [SMILES: Nc1ccc(OC2(c3ccc(Cl)cc3F)CC2)c(F)c1]

Step 1: 1-(4-Chloro-2-fluorophenyl)cyclopropyl-2-fluoro-4-nitrophenyl ether

The title compound was synthesized by the reaction of 1-(4-chloro-2-fluorophenyl)cyclopropanol (180 mg, 0.965 mmol) with 3,4-difluoronitrobenzene (153 mg, 0.965 mmol) using sodium hydride (60% w/w, 46 mg, 1.157 mmol) in DMF (4 mL) as per the process described in step 2 of Intermediate 1 to yield 205 mg of the product as a semi-solid. $^1$H NMR (300 MHz, DMSO-$d_6$) δ 1.46 (s, 4H), 7.27 (d, J=7.8 Hz, 1H), 7.42-7.56 (m, 2H), 7.65 (t, J=8.4 Hz, 1H), 7.99 (d, J=8.7 Hz, 1H), 8.09-8.13 (m, 1H).

Step 2: 4-{[1-(4-Chloro-2-fluorophenyl)cyclopropyl]oxy}-3-fluoroaniline

The title compound was synthesized by the nitro reduction of the step 1 intermediate (195 mg, 0.598 mmol) by using sodium borohydride (90 mg, 2.395 mmol) and nickel chloride (284 mg, 1.197 mmol) in methanol (4 mL) as per the process described in step 3 of Intermediate 1 to yield 169 mg of the product as a semi-solid. $^1$H NMR (300 MHz, DMSO-$d_6$) δ 1.13 (br s, 2H), 1.34 (br s, 2H), 4.97 (br s, 2H), 6.16 (d, J=7.8 Hz, 1H), 6.24-6.29 (m, 1H), 6.74 (t, J=9.3 Hz, 1H), 7.20 (d, J=8.7 Hz, 1H), 7.36-7.41 (m, 2H).

Intermediate 99

4-{[1-(4-Chloro-3-fluorophenyl)cyclopropyl]oxy}-3-fluoroaniline

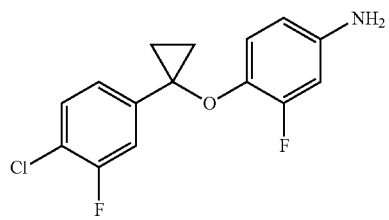 [SMILES: Nc1ccc(OC2(c3ccc(Cl)c(F)c3)CC2)c(F)c1]

Step 1: 1-(4-chloro-3-fluorophenyl)cyclopropyl 2-fluoro-4-nitrophenyl ether

The title compound was synthesized by the reaction of 1-(4-chloro-3-fluorophenyl)cyclopropanol (200 mg, 0.985 mmol) with 3,4-difluoronitrobenzene (156 mg, 0.985 mmol) using sodium hydride (60% w/w, 59 mg, 1.477 mmol) in DMF (4 mL) as per the process described in step 2 of Intermediate 1 to yield 211 mg of the product as a semi-solid. $^1$H NMR (300 MHz, DMSO-$d_6$) δ 1.55 (d, J=8.4 Hz, 4H), 7.09-7.21 (m, 2H), 7.29 (d, J=10.8 Hz, 1H), 7.54 (t, J=7.8 Hz, 1H), 7.98 (d, J=10.2 Hz, 1H), 8.21 (d, J=8.4 Hz, 1H).

Step 2: 4-{[1-(4-Chloro-3-fluorophenyl)cyclopropyl]oxy}-3-fluoroaniline

The title compound was synthesized by the nitro reduction of the step 1 intermediate (200 mg, 0.614 mmol) by using sodium borohydride (93 mg, 2.456 mmol) and nickel chloride (292 mg, 1.228 mmol) in methanol (4 mL) as per the process described in step 3 of Intermediate 1 to yield 151 mg of the product as a solid. $^1$H NMR (300 MHz, DMSO-$d_6$) δ 1.35 (s, 4H), 4.93 (br s, 2H), 6.16 (d, J=8.7 Hz, 1H), 6.36-6.41 (m, 1H), 6.61 (t, J=9.3 Hz, 1H), 7.08 (d, J=8.7 Hz, 1H), 7.21 (d, J=10.8 Hz, 1H), 7.51 (t, J=8.4 Hz, 1H).

Intermediate 100

4-{[3-(2,4-Dichlorophenyl)oxetan-3-yl]oxy}-3-fluoroaniline

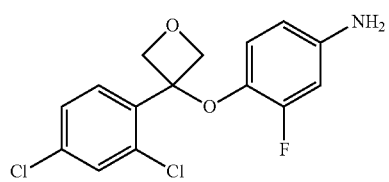 [SMILES: Nc1ccc(OC2(c3ccc(Cl)cc3Cl)COC2)c(F)c1]

Step 1: 3-(2,4-Dichlorophenyl)-3-(2-fluoro-4-nitrophenoxy)oxetane

To a stirred and cooled (0° C.) solution of 3-(2,4-dichlorophenyl)oxetan-3-ol (130 mg, 0.593 mmol) in dry DMF (4 mL) was added sodium hydride (60% w/w, 36 mg, 0.890 mmol) and the reaction was stirred for 30 min at RT.

3,4-Difluoronitrobenzene (94 mg, 0.593 mmol) was added to the mixture and further stirred for 2 h. The mixture was diluted with water (20 mL) and extracted with ethyl acetate (3×20 mL). The combined organic layers were washed with water (2×50 mL), brine (50 mL) and dried over anhydrous sodium sulfate. The solvent was distilled off under reduced pressure and the residue obtained was purified by silica gel column chromatography to yield 176 mg of the title product as a semi-solid. $^1$H NMR (300 MHz, DMSO-$d_6$) δ 5.15 (d, J=8.4 Hz, 2H), 5.30 (d, J=8.4 Hz, 2H), 7.00 (t, J=7.5 Hz, 1H), 7.52 (d, J=8.4 Hz, 1H), 7.67 (br s, 1H), 7.86 (d, J=8.1 Hz, 1H), 8.01 (d, J=8.1 Hz, 1H), 8.14 (d, J=11.1 Hz, 1H).

Step 2: 4-{[3-(2,4-Dichlorophenyl)oxetan-3-yl]oxy}-3-fluoroaniline

To a stirred solution of step 1 intermediate (165 mg, 0.460 mmol) and nickel chloride (219 mg, 0.921 mmol) in methanol (5 mL) was added sodium borohydride (70 mg, 1.843 mmol) in portions. The reaction mixture was stirred at room temperature for 1 h. The mixture was concentrated under reduced pressure to yield a viscous residue. The residue was diluted with water (20 mL) and ethyl acetate (20 mL). The layers were separated and the aqueous layer was extracted with ethyl acetate (2×20 mL). The combined organic layers were washed with water (30 mL), brine (30 mL) and dried over anhydrous sodium sulfate. The solvent was distilled off under reduced pressure and the residue obtained was purified by silica gel column chromatography to yield 112 mg of the title product as a semi-solid. $^1$H NMR (300 MHz, DMSO-$d_6$) δ 4.99-5.08 (m, 6H), 6.07-6.10 (m, 1H), 6.19-6.24 (m, 1H), 6.41-6.46 (m, 1H), 7.36 (br s, 2H), 7.63 (br s, 1H)

Intermediate 101

4-{[3-(4-Chloro-3-fluorophenyl)oxetan-3-yl]oxy}-3-fluoroaniline

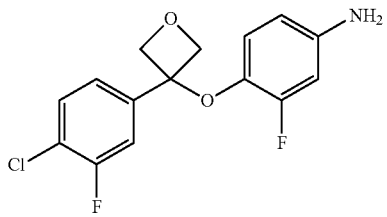 [SMILES: Nc1ccc(OC2(c3ccc(Cl)c(F)c3)COC2)c(F)c1]

Step 1: 3-(4-Chloro-3-fluorophenyl)-3-(2-fluoro-4-nitrophenoxy)oxetane

The title compound was synthesized by the reaction of 3-(4-chloro-3-fluorophenyl)oxetan-3-ol (300 mg, 1.590 mmol) with 3,4-difluoronitrobenzene (253 mg, 1.590 mmol) by using sodium hydride (60% w/w, 95 mg, 2.385 mmol) in DMF (5 mL) as per the process described in step 2 of Intermediate 1 to yield 261 mg of the product as a semi-solid. $^1$H NMR (300 MHz, DMSO-$d_6$) δ 5.01-5.07 (m, 4H), 6.50 (t, J=8.7 Hz, 1H), 7.39 (d, J=8.4 Hz, 1H), 7.67 (t, J=8.1 Hz, 2H), 7.86 (d, J=9.0 Hz, 1H), 8.24 (d, J=10.5 Hz, 1H).

Step 2: 4-{[3-(4-Chloro-3-fluorophenyl)oxetan-3-yl]oxy}-3-fluoroaniline

The title compound was synthesized by the nitro reduction of the step 1 intermediate (128 mg, 0.366 mmol) by using sodium borohydride (56 mg, 1.463 mmol) and nickel chloride (174 mg, 0.732 mmol) in methanol (4 mL) as per the process described in step 3 of Intermediate 1 to yield 84 mg of the product as a semi-solid. $^1$H NMR (300 MHz, DMSO-$d_6$) δ 4.87-4.95 (m, 4H), 5.03 (s, 2H), 6.12-6.24 (m, 2H), 6.35 (d, J=13.8 Hz, 1H), 7.33 (d, J=8.7 Hz, 1H), 7.56 (d, J=12.3 Hz, 1H), 7.62 (t, J=7.8 Hz, 1H).

Intermediate 102

4-{[4-(4-Chloro-3-fluorophenyl)tetrahydro-2H-pyran-4-yl]oxy}-3-fluoroaniline

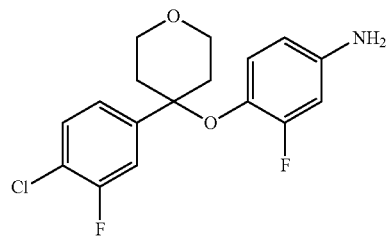

Step 1: 4-(4-Chloro-3-fluorophenyl)-4-(2-fluoro-4-nitrophenoxy)tetrahydro-2H-pyran The title compound was synthesized by the reaction of 4-(4-chloro-3-fluorophenyl)tetrahydro-2H-pyran-4-ol (300 mg, 1.301 mmol) with 3,4-difluoronitrobenzene (207 mg, 1.301 mmol) using sodium hydride (60% w/w, 78 mg, 1.951 mmol) in DMF (4 mL) as per the process described in step 2 of Intermediate 1 to yield 375 mg of the product as a solid. $^1$H NMR (300 MHz, DMSO-$d_6$) δ 2.24 (br s, 4H), 3.63-3.65 (m, 2H), 3.77-3.81 (m, 2H), 6.55-6.61 (m, 1H), 7.35 (d, J=9.9 Hz, 1H), 7.57-7.68 (m, 2H), 7.83 (d, J=9.0 Hz, 1H), 8.16-8.21 (m, 1H).

Step 2: 4-{[4-(4-Chloro-3-fluorophenyl)tetrahydro-2H-pyran-4-yl]oxy}-3-fluoroaniline The title compound was synthesized by the nitro reduction of the step 1 intermediate (200 mg, 0.541 mmol) by using sodium borohydride (82 mg, 2.162 mmol) and nickel chloride (257 mg, 1.082 mmol) in methanol (5 mL) as per the process described in step 3 of Intermediate 1 to yield 136 mg of the product as a solid. $^1$H NMR (300 MHz, DMSO-$d_6$) δ 2.09 (br s, 4H), 3.61-3.65 (m, 2H), 3.72-3.75 (m, 2H), 4.99 (br s, 2H), 6.01-6.09 (m, 2H), 6.30 (d, J=13.5 Hz, 1H), 7.31 (d, J=8.7 Hz, 1H), 7.50 (d, J=11.4 Hz, 1H), 7.56-7.61 (m, 1H).

Intermediate 103

4-{[1-(5-Chloro-1H-indol-1-yl)-2-methylpropan-2-yl]oxy}-3-fluoroaniline

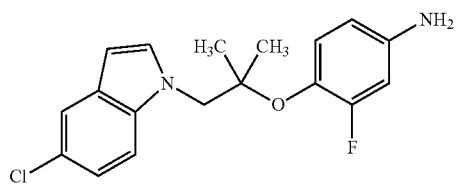 [SMILES: CC(C)(Cn1ccc2cc(Cl)ccc21)Oc1ccc(N)cc1F]

Step 1: 5-Chloro-1-[2-(2-fluoro-4-nitrophenoxy)-2-methylpropyl]-1H-indole

The title compound was prepared by the coupling reaction of 1-(5-chloro-1H-indol-1-yl)-2-methylpropan-2-ol (300 mg, 1.341 mmol) with 3,4-difluoronitrobenzene (0.14 mL, 1.341 mmol) using sodium hydride (80 mg, 2.011 mmol) and DMF (10 mL) as per the process described in step 2 of Intermediate 1 to yield 257 mg of the product as a semi-solid. $^1$H NMR (300 MHz, DMSO-$d_6$) δ 1.34 (s, 6H), 4.51 (s, 2H), 6.48 (s, 1H), 7.12 (d, J=8.7 Hz, 1H), 7.38 (t, J=8.7 Hz, 1H), 7.47 (br s, 1H), 7.59 (br s, 1H), 7.66 (d, J=8.7 Hz, 1H), 8.00 (d, J=9.0 Hz, 1H), 8.15 (d, J=10.2 Hz, 1H); APCI-MS (m/z) 363 (M+H)$^+$.

Step 2: 4-{[1-(5-Chloro-1H-indol-1-yl)-2-methylpropan-2-yl]oxy}-3-fluoroaniline The title compound was prepared by the reduction of step 1 intermediate (250 mg, 0.689 mmol) using sodium borohydride (104 mg, 2.756 mmol) and nickel chloride (327 mg, 1.378 mmol) in methanol (5 mL) as per the process described in step 3 of Intermediate 1 to yield 129 mg of the product as a semi-solid. $^1$H NMR (300 MHz, DMSO-$d_6$) δ 1.09 (s, 6H), 4.35 (s, 2H), 5.10 (s, 2H), 6.20 (d, J=9.0 Hz, 1H), 6.31 (d, J=13.2 Hz, 1H), 6.46 (br s, 1H), 6.59 (t, J=9.3 Hz, 1H), 7.09 (d, J=8.1 Hz, 1H), 7.46 (br s, 1H), 7.58-7.63 (m, 2H); APCI-MS (m/z) 333 (M+H)$^+$.

Intermediate 104

4-{[2-(5-Chloro-1-ethyl-1H-benzimidazol-2-yl)propan-2-yl]oxy}-3-fluoroaniline

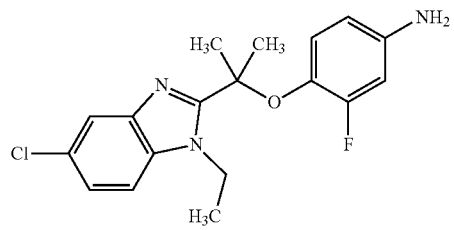 [SMILES: CCn1c(C(C)(C)Oc2ccc(N)cc2F)nc2cc(Cl)ccc21]

Step 1: 5-chloro-1-ethyl-2-[2-(2-fluoro-4-nitrophenoxy)propan-2-yl]-1H-benzimidazole The title compound was synthesized by the coupling reaction of 4-chloro-N$^1$-ethylbenzene-1,2-diamine (500 mg, 2.219 mmol) with 2-(2-fluoro-4-nitrophenoxy)-2-methylpropanoic acid (453 mg, 2.663 mmol) in presence of oxalyl chloride (0.9 mL, 11.095 mmol) and triethylamine (0.6 mL, 4.438 mmol) in DCM (10 mL) followed by cyclization in the presence of acetic acid (5 mL) as per the process described in step 1 of Intermediate 85 to yield 330 mg of the product as a solid. $^1$H NMR (300 MHz, DMSO-$d_6$) δ 1.17 (t, J=6.9 Hz, 3H), 1.96 (s, 6H), 4.46 (q, J=6.9 Hz, 2H), 6.70 (t, J=9.3 Hz, 1H), 7.32 (d, J=8.7 Hz, 1H), 7.63 (d, J=8.7 Hz, 1H), 7.79 (s, 1H), 7.90 (d, J=11.1 Hz, 1H), 8.21 (d, J=8.7 Hz, 1H).

Step 2: 4-{[2-(5-Chloro-1-ethyl-1H-benzimidazol-2-yl)propan-2-yl]oxy}-3-fluoroaniline The title compound was prepared by the reduction of step 1 intermediate (150 mg, 0.397 mmol) using iron powder (111 mg, 1.985 mmol) and ammonium chloride (212 mg, 3.970 mmol) in a mixture of water (5 mL) and THF (10 mL) as per the process described in step 2 of Intermediate 14 to yield 109 mg of the product as a semi-solid. $^1$H NMR (300 MHz, DMSO-$d_6$) δ 1.16 (t, J=7.2 Hz, 3H), 1.70 (s, 6H), 4.65 (q, J=7.2 Hz, 2H), 5.14 (br s, 2H), 6.13 (d, J=9.3 Hz, 1H), 6.25-6.37 (m, 2H), 7.30 (d, J=8.7 Hz, 1H), 7.62-7.69 (m, 2H); APCI-MS (m/z) 348 (M+H)$^+$.

Intermediate 105

2-[4-(Ethylsulfonyl)phenyl]-N-(4-iodophenyl)acetamide

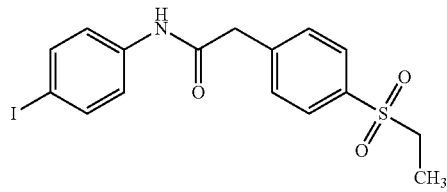 [SMILES: CCS(=O)(=O)c1ccc(CC(=O)Nc2ccc(I)cc2)cc1]

Step 1: [4-(ethylsulfonyl)phenyl]acetic acid

To a solution of ethyl [4-(ethylsulfanyl)phenyl]acetate (9.0 g, 40.121 mmol) in DCM (150 mL) was added m-chloroperbenzoic acid (20.7 g, 120.30 mmol) in portions. The reaction mixture was stirred at RT for 16 h. The reaction mixture was concentrated under reduced pressure and the residue was diluted with ethyl acetate (100 mL) and water (100 mL). The layers were separated and the aqueous layer was extracted with ethyl acetate (2×50 mL). The combined organic extracts were washed with water (100 mL) followed by brine (100 mL) and dried over anhydrous sodium sulfate. The solvent was distilled off under reduced pressure and the residue obtained was purified by silica gel column chromatography. The ester derivative (6.5 g, 25.355 mmol) was subjected to the hydrolysis by using sodium hydroxide (3.65 g, 91.281 mmol) in a mixture of water (80 mL) and ethanol (80 mL) to yield 5.19 g of the title product as a solid. $^1$H NMR (300 MHz, DMSO-$d_6$) δ 1.07 (t, J=7.2 Hz, 3H), 3.24 (q, J=7.2 Hz, 2H), 3.72 (s, 2H), 7.53 (d, J=8.1 Hz, 2H), 7.83 (d, J=8.1 Hz, 2H), 12.53 (s, 1H).

Step 2: 2-[4-(Ethylsulfonyl)phenyl]-N-(4-iodophenyl)acetamide

To a stirred solution of step 1 intermediate (100 mg, 0.438 mmol) in dry DCM (10 mL) were added EDCI.HCl (100 mg, 0.525 mmol) followed by HOBt (88 mg, 0.657 mmol) and the reaction mixture was stirred at RT. After 30 min, 4-iodoaniline (95 mg, 0.438 mmol) was added to the mixture and it was further stirred for 16 h. The reaction mixture was diluted with water (50 mL) and extracted with ethyl acetate (3×50 mL). The combined organic extracts were washed with water (2×25 mL), brine (25 mL) and dried over anhydrous sodium sulfate. The solvent was distilled off under reduced pressure and the residue obtained was purified by silica gel column chromatography to yield 150 mg of the title product as a solid. $^1$H NMR (300 MHz, DMSO-$d_6$) δ 1.09 (t, J=7.8 Hz, 3H), 3.27 (q, J=7.2 Hz, 2H), 3.79 (s, 2H), 7.43 (d, J=7.8 Hz, 2H), 7.57-7.65 (m, 4H), 7.83 (d, J=8.1 Hz, 2H), 10.35 (s, 1H); APCI-MS (m/z) 429 (M+H)$^+$.

Intermediate 106

2-[4-(Ethylsulfonyl)phenyl]-N-(6-iodopyridin-3-yl)acetamide

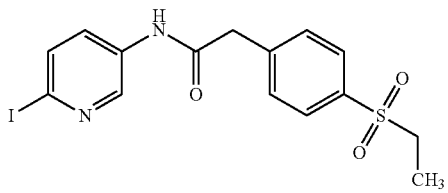

The title compound was synthesized by the reaction of [4-(ethylsulfonyl)phenyl]acetic acid (399 mg, 1.7507 mmol) with 6-iodopyridin-3-amine (350 mg, 1.592 mmol) using EDCI.HCl (610 mg, 3.183 mmol) and HOBt (429 mg, 3.183 mmol) in DCM (10 mL) as per the process described in step 2 of Intermediate 105 to yield 312 mg of the product as a solid. $^1$H NMR (300 MHz, DMSO-$d_6$) δ 1.09 (t, J=7.2 Hz, 3H), 3.27 (q, J=7.2 Hz, 2H), 3.83 (s, 2H), 7.59 (d, J=7.8 Hz, 2H), 7.77 (s, 2H), 7.83 (d, J=8.4 Hz, 2H), 8.58 (s, 1H), 10.57 (s, 1H); APCI-MS (m/z) 430 (M+H)$^+$.

Intermediate 107

2-[4-(Ethylsulfonyl)phenyl]-N-(3-fluoro-4-iodophenyl)acetamide

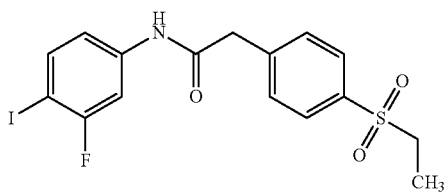 [SMILES: CCS(=O)(=O)c1ccc(CC(=O)Nc2ccc(I)c(F)c2)cc1]

The title compound was synthesized by the reaction of [4-(ethylsulfonyl)phenyl]acetic acid (963 mg, 4.219 mmol) with 3-fluoro-4-iodoaniline (1.0 g, 4.219 mmol) using EDCI.HCl (971 mg, 5.063 mmol) and HOBt (854 mg, 6.329 mmol) in DCM (15 mL) as per the process described in step 2 of Intermediate 105 to yield 1.24 g of the product as off white solid. $^1$H NMR (300 MHz, DMSO-$d_6$) δ 1.09 (t, J=7.2 Hz, 3H), 3.28 (q, J=7.2 Hz, 2H), 3.81 (s, 2H), 7.15 (d, J=6.6 Hz, 1H), 7.58 (d, J=8.4 Hz, 2H), 7.63-7.77 (m, 2H), 7.83 (d, J=7.8 Hz, 2H), 10.57 (br s, 1H).

Intermediate 108

4-{[2-(2,4-difluorophenyl)propan-2-yl]oxy}-3-fluoroaniline

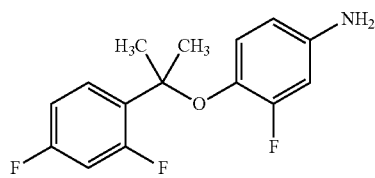 [SMILES: CC(C)(Oc1ccc(N)cc1F)c1ccc(F)cc1F]

Step 1: 1-{[2-(2,4-Difluorophenyl)propan-2-yl]oxy}-2-fluoro-4-nitrobenzene

The title compound was prepared by the reaction of 2-(2,4-difluorophenyl)propan-2-ol (300 mg, 1.742 mmol) with 3,4-difluoronitrobenzene (0.19 mL, 1.742 mmol) using sodium hydride (60% w/w, 104 mg, 2.614 mmol) and DMF (10 mL) as per the process described in step 2 of Intermediate 1 to yield 371 mg of the product as a semi-solid. $^1$H NMR (300 MHz, DMSO-$d_6$) δ 1.83 (s, 6H), 6.80 (t, J=9.0 Hz, 1H), 7.14-7.26 (m, 2H), 7.54-7.59 (m, 1H), 7.85 (d, J=8.4 Hz, 1H), 8.15 (d, J=10.8 Hz, 1H).

Step 2: 4-{[2-(2,4-difluorophenyl)propan-2-yl]oxy}-3-fluoroaniline

The title compound was prepared by the reduction of step 1 intermediate (360 mg, 1.156 mmol) using sodium borohydride (175 mg, 4.626 mmol) and nickel chloride (550 mg, 2.313 mmol) in methanol (10 mL) as per the process described in step 3 of Intermediate 1 to yield 291 mg of the product as a solid. $^1$H NMR (300 MHz, DMSO-$d_6$) δ 1.56 (s, 6H), 5.09 (s, 2H), 6.16 (d, J=7.8 Hz, 1H), 6.34 (d, J=16.2 Hz, 1H), 6.48 (t, J=9.3 Hz, 1H), 7.06 (t, J=6.6 Hz, 1H), 7.23 (t, J=10.2 Hz, 1H), 7.55-7.62 (m, 1H); APCI-MS (m/z) 282 (M+H)$^+$.

Intermediate 109

3-Fluoro-4-{[1-(5-fluoro-2-methyl-1H-indol-1-yl)-2-methylpropan-2-yl]oxy}aniline

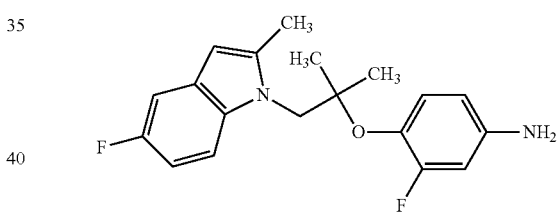

Step 1: 5-Fluoro-1-[2-(2-fluoro-4-nitrophenoxy)-2-methylpropyl]-2-methyl-1H-indole The title compound was prepared by the reaction of 1-(5-fluoro-2-methyl-1H-indol-1-yl)-2-methylpropan-2-ol (300 mg, 1.356 mmol) with 3,4-difluoronitrobenzene (0.15 mL, 1.356 mmol) using sodium hydride (60% w/w, 81 mg, 2.033 mmol) and DMF (10 mL) as per the process described in step 2 of Intermediate 1 to yield 191 mg of the product as a semi-solid. $^1$H NMR (300 MHz, DMSO-$d_6$) δ 1.35 (s, 6H), 2.46 (s, 3H), 4.46 (s, 2H), 6.26 (s, 1H), 6.85 (t, J=8.7 Hz, 1H), 7.17 (d, J=10.2 Hz, 1H), 7.27 (t, J=8.7 Hz, 1H), 7.52-7.55 (m, 1H), 7.98 (d, J=7.2 Hz, 1H), 8.12-8.17 (m, 1H); APCI-MS (m/z) 361 (M+H)$^+$.

Step 2: 3-Fluoro-4-{[1-(5-fluoro-2-methyl-1H-indol-1-yl)-2-methylpropan-2-yl]oxy}aniline The title compound was prepared by the reduction of step 1 intermediate (180 mg, 0.4995 mmol) using sodium borohydride (76 mg, 1.998 mmol) and nickel chloride (238 mg, 0.999 mmol) in methanol (10 mL) as per the process described in step 3 of Intermediate 1 to yield 78 mg of the product as a semi-solid. $^1$H NMR (300 MHz, DMSO-$d_6$) δ 1.13 (s, 6H), 2.45 (s, 3H), 4.31 (s, 2H), 5.09 (s, 2H), 6.17-6.32 (m, 3H), 6.51 (t, J=9.3 Hz, 1H), 6.83 (t, J=9.3 Hz, 1H), 7.15 (d, J=9.9 Hz, 1H), 7.48-7.52 (m, 1H); APCI-MS (m/z) 331 (M+H)$^+$.

Intermediate 110

4-{[2-(2,4-Dichlorophenyl)propan-2-yl]oxy}-3,5-difluoroaniline

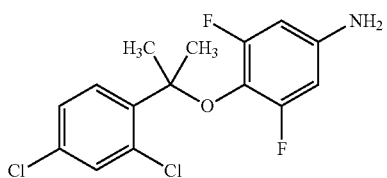 [SMILES: CC(C)(Oc1c(F)cc(N)cc1F)c1ccc(Cl)cc1Cl]

Step 1: 2-{[2-(2,4-Dichlorophenyl)propan-2-yl]oxy}-1,3-difluoro-5-nitrobenzene

The title compound was prepared by the reaction of 2-(2,4-dichlorophenyl)propan-2-ol (200 mg, 0.975 mmol) with 1,2,3-trifluoro-5-nitrobenzene (0.12 mL, 0.975 mmol) using sodium hydride (60% w/w, 59 mg, 1.467 mmol) and DMF (4 mL) as per the process described in step 2 of Intermediate 1 to yield 258 mg of the product as a solid. $^1$H NMR (300 MHz, DMSO-$d_6$) δ 1.79 (s, 6H), 7.47 (d, J=8.1 Hz, 1H), 7.65 (br s, 1H), 7.71 (d, J=8.4 Hz, 1H), 8.14 (d, J=7.8 Hz, 2H).

Step 2: 4-{[2-(2,4-Dichlorophenyl)propan-2-yl]oxy}-3,5-difluoroaniline

The title compound was prepared by the reduction of step 1 intermediate (240 mg, 0.663 mmol) using sodium borohydride (100 mg, 2.651 mmol) and nickel chloride (315 mg, 1.325 mmol) in methanol (10 mL) as per the process described in step 3 of Intermediate 1 to yield 178 mg of the product as a semi-solid. $^1$H NMR (300 MHz, DMSO-$d_6$) δ 1.64 (s, 6H), 5.49 (br s, 2H), 6.20 (d, J=10.8 Hz, 2H), 7.43 (d, J=8.7 Hz, 1H), 7.60 (br s, 1H), 7.80 (d, J=8.7 Hz, 1H); APCI-MS (m/z) 332 (M+H)$^+$.

Intermediate 111

4-{[2-(3,5-Dichloropyridin-2-yl)propan-2-yl]oxy}-3,5-difluoroaniline

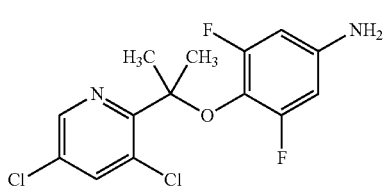 [SMILES: CC(C)(Oc1c(F)cc(N)cc1F)c1ncc(Cl)cc1Cl]

Step 1: 3,5-Dichloro-2-[2-(2,6-difluoro-4-nitrophenoxy)propan-2-yl]pyridine

The title compound was prepared by the reaction of 2-(3,5-dichloropyridin-2-yl)propan-2-ol (200 mg, 0.9705 mmol) with 1,2,3-trifluoro-5-nitrobenzene (0.12 mL, 0.971 mmol) using sodium hydride (60% w/w, 58 mg, 1.456 mmol) and DMF (4 mL) as per the process described in step 2 of Intermediate 1 to yield 159 mg of the product as yellow solid.

Step 2: 4-{[2-(3,5-Dichloropyridin-2-yl)propan-2-yl]oxy}-3,5-difluoroaniline

The title compound was prepared by the reduction of step 1 intermediate (150 mg, 0.450 mmol) using sodium borohydride (68 mg, 1.801 mmol) and nickel chloride (214 mg, 0.900 mmol) in methanol (4 mL) as per the process described in step 3 of Intermediate 1 to yield 122 mg of the product as a semi-solid. $^1$H NMR (300 MHz, DMSO-$d_6$) δ 1.64 (s, 6H), 5.42 (s, 2H), 6.12 (d, J=10.8 Hz, 2H), 8.21 (s, 1H), 8.51 (s, 1H); APCI-MS (m/z) 333 (M+H)$^+$.

Intermediate 112

4-{[2-(1-Ethyl-5-fluoro-1H-benzimidazol-2-yl)propan-2-yl]oxy}-3-fluoroaniline

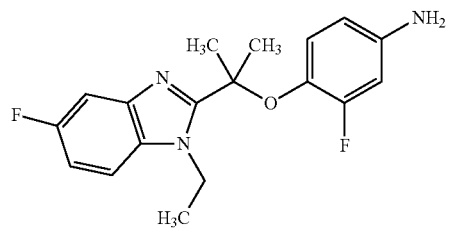 [SMILES: CCn1c(C(C)(C)Oc2ccc(N)cc2F)nc2cc(F)ccc21]

Step 1: 1-Ethyl-5-fluoro-2-[2-(2-fluoro-4-nitrophenoxy)propan-2-yl]-1H-benzimidazole The title compound was synthesized by the coupling reaction of N$^1$-ethyl-4-fluorobenzene-1,2-diamine (410 mg, 2.663 mmol) with 2-(2-fluoro-4-nitrophenoxy)-2-methylpropanoic acid (500 mg, 2.319 mmol) using oxalyl chloride (0.96 mL, 11.09 mmol) and triethylamine (624 μL, 4.438 mmol) in DCM (10 mL) followed by cyclization in the presence of acetic acid (10 mL) as per the process described in step 1 of Intermediate 85 to yield 225 mg of the product as a semi-solid. $^1$H NMR (300 MHz, DMSO-$d_6$) δ 1.17 (t, J=7.2 Hz, 3H), 1.96 (s, 6H), 4.47 (q, J=7.2 Hz, 2H), 6.71 (t, J=9.0 Hz, 1H), 7.17 (t, J=9.9 Hz, 1H), 7.53 (d, J=9.3 Hz, 1H), 7.57-7.64 (m, 1H), 7.90 (d, J=8.7 Hz, 1H), 8.20 (d, J=10.8 Hz, 1H).

Step 2: 4-{[2-(1-Ethyl-5-fluoro-1H-benzimidazol-2-yl)propan-2-yl]oxy}-3-fluoroaniline The title compound was prepared by the reduction of step 1 intermediate (150 mg, 0.415 mmol) using iron powder (116 mg, 2.075 mmol) and ammonium chloride (222 mg, 4.150 mmol) in a mixture of water (3 mL), methanol (3 mL) and THF (7 mL) as per the process described in step 2 of Intermediate 14 to yield 130 mg of the product as a semi-solid. $^1$H NMR (300 MHz, DMSO-$d_6$) δ 1.37 (t, J=6.9 Hz, 3H), 1.70 (s, 6H), 4.64 (q, J=6.9 Hz, 2H), 5.14 (br s, 2H), 6.11 (d, J=8.1 Hz, 1H), 6.27 (d, J=9.3 Hz, 1H), 6.35 (d, J=13.8 Hz, 1H), 7.14 (t, J=9.0 Hz, 1H), 7.43 (d, J=9.9 Hz, 1H), 7.59-7.64 (m, 1H); APCI-MS (m/z) 332 (M+H)$^+$.

Intermediate 113

2-[2-(2,4-Difluorophenoxy)propan-2-yl]-1-methyl-1H-benzimidazol-5-amine

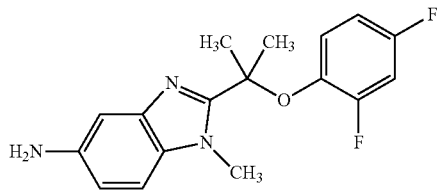 [SMILES: Cn1c(C(C)(C)Oc2ccc(F)cc2F)nc2cc(N)ccc21]

Step 1: 2-[2-(2,4-Difluorophenoxy)propan-2-yl]-1-methyl-5-nitro-1H-benzimidazole The title compound was synthesized by the coupling reaction of $N^1$-methyl-4-nitrobenzene-1,2-diamine (461 mg, 2.762 mmol) with 2-(2,4-difluorophenoxy)-2-methylpropanoic acid (500 mg, 2.302 mmol) using oxalyl chloride (1.00 mL, 11.510 mmol) and triethylamine (647 μL, 4.604 mmol) in DCM (10 mL) followed by cyclization in the presence of acetic acid (10 mL) as per the process described in step 1 of Intermediate 85 to yield 575 mg of the product as a solid. $^1$H NMR (300 MHz, DMSO-$d_6$) δ 1.83 (s, 6H), 4.13 (s, 3H), 6.54-6.69 (m, 1H), 6.82-6.90 (m, 1H), 7.32 (t, J=9.0 Hz, 1H), 7.85 (d, J=8.7 Hz, 1H), 8.23 (d, J=8.7 Hz, 1H), 8.56 (s, 1H); ESI-MS (m/z) 349 (M+H)$^+$.

Step 2: 2-[2-(2,4-Difluorophenoxy)propan-2-yl]-1-methyl-1H-benzimidazol-5-amine The title compound was prepared by the reduction of step 1 intermediate (150 mg, 0.430 mmol) using iron powder (120 mg, 2.152 mmol) and ammonium chloride (230 mg, 4.310 mmol) in a mixture of water (3 mL), methanol (3 mL) and THF (10 mL) as per the process described in step 2 of Intermediate 14 to yield 91 mg of the product as a solid. $^1$H NMR (300 MHz, DMSO-$d_6$) δ 1.77 (s, 6H), 3.86 (s, 3H), 4.83 (br s, 2H), 6.30-6.39 (m, 1H), 6.63 (d, J=8.7 Hz, 1H), 6.73-6.82 (m, 2H), 7.18-7.29 (m, 2H); ESI-MS (m/z) 319 (M+H)$^+$.

Intermediate 114

2-[1-(2,4-Difluoro-phenoxy)-1-methyl-ethyl]-1-(2-dimethylamino-ethyl)-1H-benzoimidazol-5-ylamine

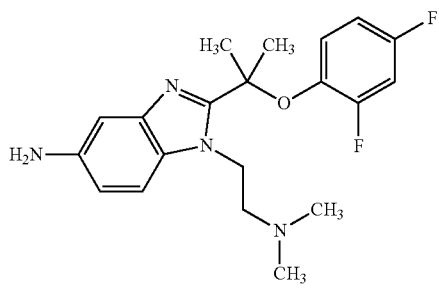 [SMILES: CN(C)CCn1c(C(C)(C)Oc2ccc(F)cc2F)nc2cc(N)ccc21]

Step 1: (2-{2-[1-(2,4-Difluoro-phenoxy)-1-methyl-ethyl]-5-nitro-benzoimidazol-1-yl}-ethyl)-dimethyl-amine The title compound was synthesized by the coupling reaction of $N^1$-[2-(dimethylamino)ethyl]-4-nitrobenzene-1,2-diamine (498 mg, 2.224 mmol) with 2-(2,4-difluorophenoxy)-2-methylpropanoic acid (400 mg, 1.853 mmol) by using oxalyl chloride (0.8 mL, 9.265 mmol) and triethylamine (522 μL, 3.706 mmol) in DCM (5 mL) followed by cyclization in the presence of acetic acid (10 mL) as per the process described in step 1 of Intermediate 85 to yield 400 mg of the product as a solid. $^1$H NMR (300 MHz, DMSO-$d_6$) δ 1.83 (s, 6H), 2.31 (br s, 6H), 2.77 (br s, 2H), 4.79 (br s, 2H), 6.70-6.78 (m, 1H), 6.92 (t, J=6.6 Hz, 1H), 7.35 (t, J=8.4 Hz, 1H), 7.89 (d, J=8.7 Hz, 1H), 8.23 (d, J=8.7 Hz, 1H), 8.57 (s, 1H); ESI-MS (m/z) 404 (M+H)$^+$.

Step 2: 2-[1-(2,4-Difluoro-phenoxy)-1-methyl-ethyl]-1-(2-dimethylamino-ethyl)-1H-benzoimidazol-5-ylamine The title compound was prepared by the reduction of step 1 intermediate (150 mg, 0.371 mmol) using iron powder (103 mg, 1.857 mmol) and ammonium chloride (198 mg, 3.71 mmol) in a mixture of water (3 mL), methanol (3 mL) and THF (10 mL) as per the process described in step 2 of Intermediate 14 to yield 105 mg of the product as a solid. $^1$H NMR (300 MHz, DMSO-$d_6$) δ 1.77 (s, 6H), 2.15 (s, 6H), 2.48 (br s, 2H), 4.46 (br s, 2H), 4.80 (br s, 2H), 6.48-6.53 (m, 1H), 6.62 (d, J=8.4 Hz, 1H), 6.75 (s, 1H), 6.84 (br s, 1H), 7.18 (d, J=8.1 Hz, 1H), 7.31 (d, J=9.3 Hz, 1H); ESI-MS (m/z) 375 (M+H)$^+$.

Intermediate 115

1-(Cyclopropylmethyl)-2-[2-(2,4-difluorophenoxy)propan-2-yl]-1H-benzimidazol-5-amine

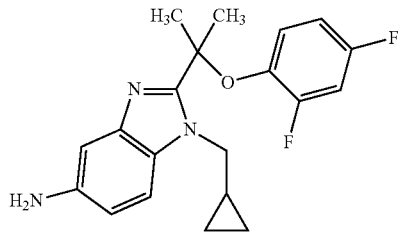 [SMILES: CC(C)(Oc1ccc(F)cc1F)c1nc2cc(N)ccc2n1CC1CC1]

Step 1: 1-(Cyclopropylmethyl)-2-[2-(2,4-difluorophenoxy)propan-2-yl]-5-nitro-1H-benzimidazole The title compound was synthesized by the coupling reaction of $N^1$-(cyclopropylmethyl)-4-nitrobenzene-1,2-diamine (461 mg, 2.224 mmol) with 2-(2,4-difluorophenoxy)-2-methylpropanoic acid (400 mg, 1.853 mmol) using oxalyl chloride (0.8 mL, 9.265 mmol) and triethylamine (522 μL, 3.706 mmol) in DCM (5 mL) followed by cyclization in the presence of acetic acid (10 mL) as per the process described in step 1 of Intermediate 85 to yield 293 mg of the product as a solid. $^1$H NMR (300 MHz, DMSO-$d_6$) δ 0.49 (d, J=6.6 Hz, 4H), 1.20-1.25 (m, 1H), 1.82 (s, 6H), 4.56 (d, J=6.9 Hz, 2H), 6.72-6.79 (m, 1H), 6.80-6.96 (m, 1H), 7.30-7.36 (m, 1H), 7.93 (d, J=8.7 Hz, 1H), 8.21 (d, J=9.3 Hz, 1H), 8.57 (s, 1H); ESI-MS (m/z) 388 (M+H)+.

Step 2: 1-(Cyclopropylmethyl)-2-[2-(2,4-difluorophenoxy)propan-2-yl]-1H-benzimidazol-5-amine The title compound was prepared by the reduction of step 1 intermediate (150 mg, 0.387 mmol) using iron powder (108 mg, 1.937 mmol) and ammonium chloride (207 mg, 3.871 mmol) in a mixture of water (3 mL), methanol (3 mL) and THF (10 mL) as per the process described in step 2 of Intermediate 14 to yield 120 mg of the product as a semi-solid. $^1$H NMR (300 MHz, DMSO-$d_6$) δ 0.43 (d, J=6.6 Hz, 4H), 1.16-1.25 (m, 1H), 1.77 (s, 6H), 4.31 (d, J=6.9 Hz, 2H), 6.53-6.765 (m, 2H), 6.76 (s, 1H), 6.77-7.90 (m, 1H), 7.26-7.32 (m, 2H); ESI-MS (m/z) 358 (M+H)+.

Intermediate 116

2-[2-(2,4-Difluorophenoxy)propan-2-yl]-1-propyl-1H-benzimidazol-5-amine

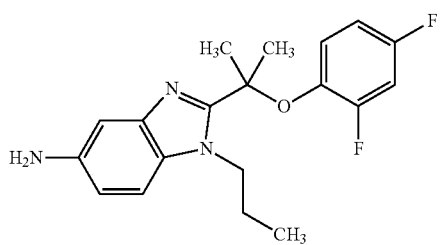 [SMILES: CCCn1c(C(C)(C)Oc2ccc(F)cc2F)nc2cc(N)ccc21]

Step 1: 2-[2-(2,4-Difluorophenoxy)propan-2-yl]-5-nitro-1-propyl-1H-benzimidazole The title compound was synthesized by the reaction of 4-nitro-N$^1$-propylbenzene-1,2-diamine (325 mg, 1.668 mmol) with 2-(2,4-difluorophenoxy)-2-methylpropanoic acid (300 mg, 1.390 mmol) by using oxalyl chloride (0.6 mL, 6.950 mmol) and triethylamine (392 μL, 2.781 mmol) in DCM (5 mL) followed by cyclization in the presence of acetic acid (10 mL) as per the process described in step 1 of Intermediate 85 to yield 210 mg of the product as a solid. $^1$H NMR (300 MHz, DMSO-$d_6$) δ 0.96 (t, J=7.2 Hz, 3H), 1.82 (br s, 8H), 4.59 (t, J=7.8 Hz, 2H), 6.70-6.76 (m, 1H), 6.87-6.95 (m, 1H), 7.32-7.36 (m, 1H), 7.90 (d, J=9.0 Hz, 1H), 8.21 (d, J=9.3 Hz, 1H), 8.57 (s, 1H); APCI-MS (m/z) 376 (M+H)+.

Step 2: 2-[2-(2,4-Difluorophenoxy)propan-2-yl]-1-propyl-1H-benzimidazol-5-amine

The title compound was prepared by the reduction of step 1 intermediate (190 mg, 0.506 mmol) using iron powder (141 mg, 2.532 mmol) and ammonium chloride (271 mg, 5.061 mmol) in a mixture of water (3 mL), methanol (3 mL) and THF (10 mL) as per the process described in step 2 of Intermediate 14 to yield 160 mg of the product as a semi-solid. $^1$H NMR (300 MHz, DMSO-$d_6$) δ 0.87-0.93 (m, 3H), 1.60-1.70 (m, 2H), 1.76 (s, 6H), 4.31 (br s, 2H), 4.89 (br s, 2H), 6.45-6.55 (m, 1H), 6.62 (d, J=8.4 Hz, 1H), 6.75 (s, 1H), 6.76-6.85 (m, 1H), 10.28 (br s, 1H), 7.21 (d, J=8.7 Hz, 1H), 7.27-7.31 (m, 1H); ESI-MS (m/z) 346 (M+H)+.

Intermediate 117

2-[2-(2,4-Difluorophenoxy)propan-2-yl]-1-(2-methylpropyl)-1H-benzimidazol-5-amine

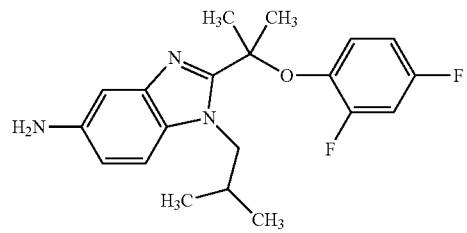 [SMILES: CC(C)Cn1c(C(C)(C)Oc2ccc(F)cc2F)nc2cc(N)ccc21]

Step 1: 2-[2-(2,4-Difluorophenoxy)propan-2-yl]-1-(2-methylpropyl)-5-nitro-1H-benzimidazole The title compound was synthesized by the coupling reaction of N-(2-methylpropyl)-4-nitrobenzene-1,2-diamine (465 mg, 2.224 mmol) with 2-(2,4-difluorophenoxy)-2-methylpropanoic acid (400 mg, 1.853 mmol) using oxalyl chloride (0.8 mL, 9.651 mmol) and triethylamine (522 μL, 3.706 mmol) in DCM (5 mL) followed by cyclization in the presence of acetic acid (10 mL) as per the process described in step 1 of Intermediate 85 to yield 77 mg of the product as a semi-solid. $^1$H NMR (300 MHz, DMSO-$d_6$) δ 0.86 (d, J=6.9 Hz, 6H), 1.80 (s, 6H), 2.38 (br s, 1H), 4.47 (d, J=7.8 Hz, 2H), 6.87-6.97 (m, 2H), 6.30-6.38 (m, 1H), 7.93 (d, J=9.0 Hz, 1H), 8.20 (d, J=8.7 Hz, 1H), 8.56 (s, 1H).

Step 2: 2-[2-(2,4-Difluorophenoxy)propan-2-yl]-1-(2-methylpropyl)-1H-benzimidazol-5-amine The title compound was prepared by the reduction of step 1 intermediate (70 mg, 0.180 mmol) using iron powder (50 mg, 0.900 mmol) and ammonium chloride (96 mg, 1.800 mmol) in a mixture of water (3 mL), methanol (3 mL) and THF (10 mL) as per the process described in step 2 of Intermediate 14 to yield 59 mg of the product as a semi-solid. $^1$H NMR (300 MHz, DMSO-$d_6$) δ 0.82 (d, J=6.3 Hz, 6H), 1.76 (s, 6H), 2.32 (br s, 1H), 4.21 (d, J=7.8 Hz, 2H), 5.16 (s, 2H), 6.60-6.65 (m, 2H), 6.78 (s, 1H), 6.79-6.90 (m, 1H), 7.25-7.35 (m, 2H); ESI-MS (m/z) 360 (M+H)+.

Intermediate 118

2-[2-(2,4-Difluorophenoxy)propan-2-yl]-1-(propan-2-yl)-1H-benzimidazol-5-amine

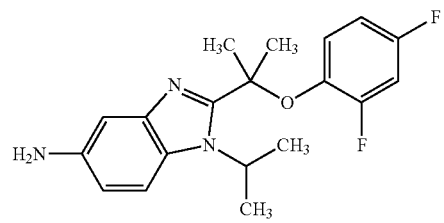 [SMILES: CC(C)n1c(C(C)(C)Oc2ccc(F)cc2F)nc2cc(N)ccc21]

Step 1: 2-[2-(2,4-Difluorophenoxy)propan-2-yl]-5-nitro-1-(propan-2-yl)-1H-benzimidazole The title compound was synthesized by the coupling reaction of 4-nitro-N[1]-(propan-2-yl)benzene-1,2-diamine (434 mg, 2.224 mmol) with 2-(2,4-difluorophenoxy)-2-methylpropanoic acid (400 mg, 1.853 mmol) using oxalyl chloride (0.8 mL, 9.65 mmol) and triethylamine (522 µL, 3.706 mmol) in DCM (5 mL) followed by cyclization in the presence of acetic acid (10 mL) as per the process described in step 1 of Intermediate 85 to yield 161 mg of the product as a solid. $^1$H NMR (300 MHz, DMSO-$d_6$) δ 1.54 (d, J=6.9 Hz, 6H), 1.85 (s, 6H), 6.55 (br s, 1H), 6.86 (br s, 1H), 7.35 (br s, 1H), 8.05-8.15 (m, 2H), 8.58 (s, 1H); ESI-MS (m/z) 376 (M+H)$^+$.

Step 2: 2-[2-(2,4-Difluorophenoxy)propan-2-yl]-1-(propan-2-yl)-1H-benzimidazol-5-amine The title compound was prepared by the reduction of step 1 intermediate (150 mg, 0.399 mmol) using iron powder (111 mg, 1.990 mmol) and ammonium chloride (213 mg, 3.990 mmol) and in a mixture of water (3 mL), methanol (3 mL) and THF (10 mL) as per the process described in step 2 of Intermediate 14 to yield 110 mg of the product as a semi-solid. $^1$H NMR (300 MHz, DMSO-$d_6$) δ 1.40 (d, J=6.9 Hz, 6H), 1.79 (s, 6H), 5.53 (br s, 2H), 6.40-6.45 (m, 1H), 6.63 (d, J=9.0 Hz, 1H), 6.84 (br s, 2H), 7.29-7.39 (m, 1H), 7.41 (d, J=8.7 Hz, 1H); ESI-MS (m/z) 346 (M+H)$^+$.

Intermediate 119

2-[(2,4-Difluorophenoxy)(difluoro)methyl]-1-ethyl-1H-benzimidazol-5-amine

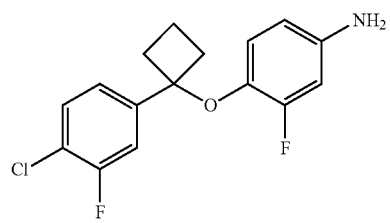

Step 1: 2-[(2,4-Difluorophenoxy)(difluoro)methyl]-1-ethyl-5-nitro-1H-benzimidazole The title compound was synthesized by the reaction of N[1]-ethyl-4-nitrobenzene-1,2-diamine (485 mg, 2.678 mmol) with (2,4-difluorophenoxy)(difluoro)acetic acid (500 mg, 2.230 mmol) using oxalyl chloride (1.0 mL, 11.15 mmol) and triethylamine (626 µL, 4.46 mmol) in DCM (5 mL) followed by cyclization in the presence of acetic acid (10 mL) as per the process described in step 1 of Intermediate 85 to yield 310 mg of the product as a solid. $^1$H NMR (300 MHz, DMSO-$d_6$) δ 1.44 (t, J=7.2 Hz, 3H), 4.67 (q, J=6.9 Hz, 2H), 7.24 (br s, 1H), 7.60-7.73 (m, 2H), 8.07 (d, J=9.3 Hz, 1H), 8.30-8.39 (m, 1H), 8.75 (s, 1H).

Step 2: 2-[(2,4-Difluorophenoxy)(difluoro)methyl]-1-ethyl-1H-benzimidazol-5-amine The title compound was prepared by the reduction of step 1 intermediate (150 mg, 0.406 mmol) using iron powder (113 mg, 2.032 mmol) and ammonium chloride (217 mg, 4.060 mmol) in a mixture of water (3 mL), methanol (3 mL) and THF (10 mL) as per the process described in step 2 of Intermediate 14 to yield 129 mg of the product as a semi-solid. $^1$H NMR (300 MHz, DMSO-$d_6$) δ 1.51 (t, J=6.6 Hz, 3H), 4.59 (q, J=7.2 Hz, 2H), 5.45 (br s, 2H), 6.97 (d, J=8.1 Hz, 1H), 7.02 (s, 1H), 7.35-7.40 (m, 1H), 7.57 (d, J=8.7 Hz, 1H), 7.70-7.80 (m, 2H); ESI-MS (m/z) 340 (M+H)$^+$.

Intermediate 120

4-{[1-(4-Chloro-3-fluorophenyl)cyclobutyl]oxy}-3-fluoroaniline

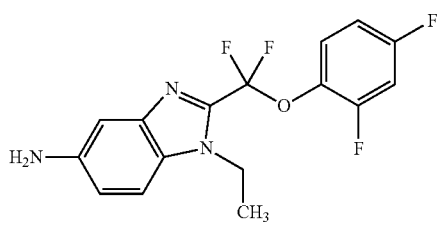 [SMILES: CCn1c(C(F)(F)Oc2ccc(F)cc2F)nc2cc(N)ccc21]

Step 1: 1-(4-Chloro-3-fluorophenyl)cyclobutyl-2-fluoro-4-nitrophenyl ether

The title compound was prepared by the reaction of 1-(4-chloro-3-fluorophenyl)cyclobutanol (300 mg, 1.595 mmol) with 3,4-difluoronitrobenzene (0.16 mL, 1.495 mmol) by using sodium hydride (60% w/w, 90 mg, 2.242 mmol) in DMF (4 mL) as per the process described in step 2 of Intermediate 1 to yield 424 mg of the product as a solid. $^1$H NMR (300 MHz, DMSO-$d_6$) δ 1.75-1.80 (m, 1H), 1.99 (br s, 1H), 2.70-2.76 (m, 2H), 2.89 (br s, 2H), 6.91 (t, J=9.3 Hz, 1H), 7.28 (t, J=7.8 Hz, 1H), 7.61 (t, J=8.1 Hz, 1H), 7.77 (t, J=6.3 Hz, 1H), 7.84-7.89 (m, 1H), 8.10-8.15 (m, 1H).

Step 2: 4-{[1-(4-Chloro-3-fluorophenyl)cyclobutyl]oxy}-3-fluoroaniline

The title compound was prepared by the reduction of step 1 intermediate (400 mg, 0.177 mmol) using sodium borohydride (178 mg, 4.709 mmol) and nickel chloride (560 mg, 2.354 mmol) in methanol (10 mL) as per the process described in step 3 of Intermediate 1 to yield 287 mg of the product as a semi-solid. $^1$H NMR (300 MHz, DMSO-$d_6$) δ 1.62 (br s, 1H), 1.97 (br s, 1H), 2.51-2.59 (m, 4H), 5.00 (br s, 2H), 6.08 (d, J=8.1 Hz, 1H), 6.19-6.36 (m, 2H), 7.13-7.17 (m, 1H), 7.28 (t, J=7.8 Hz, 1H), 7.51 (t, J=7.4 Hz, 1H).

Intermediate 121

4-{[1-(4-Chloro-3-fluorophenyl)cyclopentyl]oxy}aniline

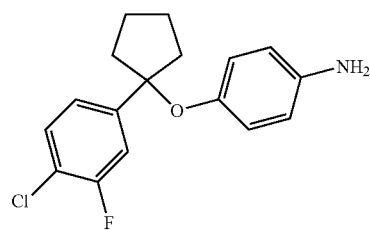 [SMILES: Nc1ccc(OC2(c3ccc(Cl)c(F)c3)CCCC2)cc1]

Step 1: 1-(4-Chloro-3-fluorophenyl)cyclopentanol

The title compound was synthesized by the reaction of 4-bromo-1-chloro-2-fluorobenzene (2.0 g, 9.549 mmol) and cyclopentanone (1.3 mL, 14.324 mmol) using n-butyl lithium (1.6 M in THF, 6.5 mL, 10.504 mmol) in THF (20 mL) as per the process described in step 1 of Intermediate 31 to yield 589 mg of the product as a semi-solid. $^1$H NMR (300 MHz, DMSO-$d_6$) δ 1.73-1.97 (m, 8H), 5.10 (s, 1H), 7.18 (t, J=7.8 Hz, 1H), 7.44 (t, J=7.8 Hz, 1H), 7.57 (t, J=7.8 Hz, 1H).

Step 2: 1-(4-Chloro-3-fluorophenyl)cyclopentyl 4-nitrophenyl ether

The title compound was prepared by the reaction of step 1 intermediate (250 mg, 1.164 mmol) with 1-fluoro-4-nitro benzene (0.13 mL, 1.281 mmol) by using sodium hydride (60% w/w, 70 mg, 1.746 mmol) in DMF (5 mL) as per the process described in step 2 of Intermediate 1 to yield 286 mg of the product as a semi-solid. $^1$H NMR (300 MHz, DMSO-$d_6$) δ 1.80 (br s, 4H), 2.28-2.38 (m, 2H), 2.48 (br s, 2H), 6.86 (d, J=9.3 Hz, 2H), 7.21 (t, J=7.8 Hz, 1H), 7.42 (t, J=7.4 Hz, 1H), 7.55 (t, J=7.4 Hz, 1H), 8.05 (d, J=9.3 Hz, 2H).

Step 3: 4-{[1-(4-Chloro-3-fluorophenyl)cyclopentyl]oxy}aniline

The title compound was prepared by the reduction of step 2 intermediate (270 mg, 0.804 mmol) using sodium borohydride (121 mg, 3.216 mmol) and nickel chloride (382 mg, 1.608 mmol) in methanol (10 mL) as per the process described in step 3 of Intermediate 1 to yield 97 mg of the product as a semi-solid. $^1$H NMR (300 MHz, DMSO-$d_6$) δ 1.75 (br s, 2H), 1.76-1.92 (m, 2H), 2.35 (br s, 2H), 3.07-3.10 (m, 2H), 4.66 (br s, 2H), 6.21 (d, J=9.0 Hz, 2H), 6.30 (d, J=9.0 Hz, 2H), 7.14 (t, J=7.5 Hz, 1H), 7.25-7.28 (m, 1H), 7.50-7.53 (m, 1H); APCI-MS (m/z) 306 (M+H)$^+$.

Intermediate 122

4-{[1-(4-Chloro-3-fluorophenyl)cyclopentyl]oxy}-3-fluoroaniline

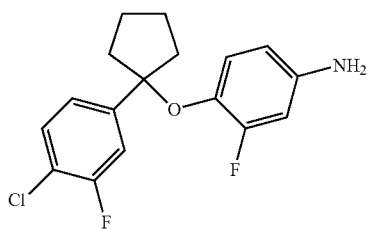 [SMILES: Nc1ccc(OC2(c3ccc(Cl)c(F)c3)CCCC2)c(F)c1]

Step 1: 1-(4-Chloro-3-fluorophenyl)cyclopentyl 2-fluoro-4-nitrophenyl ether

The title compound was prepared by the reaction of 1-(4-chloro-3-fluorophenyl)cyclopentanol (310 mg, 1.444 mmol) with 3,4-difluoronitrobenzene (0.16 mL, 1.444 mmol) by using sodium hydride (60% w/w, 87 mg, 2.166 mmol) in DMF (10 mL) as per the process described in step 2 of Intermediate 1 to yield 258 mg of the product as a semi-solid. $^1$H NMR (300 MHz, DMSO-$d_6$) δ 1.83 (br s, 4H), 2.30-2.40 (m, 2H), 2.43 (br s, 2H), 6.80 (t, J=9.3 Hz, 1H), 7.24 (t, J=8.1 Hz, 1H), 7.46 (t, J=7.2 Hz, 1H), 7.59 (t, J=7.5 Hz, 1H), 7.85 (d, J=9.6 Hz, 1H), 8.14 (d, J=9.0 Hz, 1H).

Step 2: 4-{[1-(4-Chloro-3-fluorophenyl)cyclopentyl]oxy}-3-fluoroaniline

The title compound was prepared by the reduction of step 1 intermediate (240 mg, 0.678 mmol) using sodium borohydride (102 mg, 2.713 mmol) and nickel chloride (322 mg, 0.678 mmol) in methanol (10 mL) as per the process described in step 3 of Intermediate 1 to yield 168 mg of the product as a semi-solid. $^1$H NMR (300 MHz, DMSO-$d_6$) δ 1.74 (br s, 2H), 1.91-1.99 (m, 4H), 2.42 (br s, 2H), 5.00 (br s, 2H), 6.02-6.26 (m, 3H), 7.12 (t, J=7.8 Hz, 1H), 7.26 (t, J=7.5 Hz, 1H), 7.53 (t, J=7.8 Hz, 1H).

Intermediate 123

4-{[1-(4-Chloro-3-fluorophenyl)cyclohexyl]oxy}-3-fluoroaniline

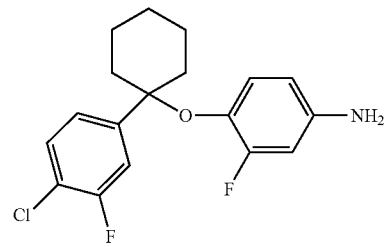 [SMILES: Nc1ccc(OC2(c3ccc(Cl)c(F)c3)CCCCC2)c(F)c1]

Step 1: 1-(4-Chloro-3-fluorophenyl)cyclohexanol

The title compound was synthesized by the reaction of 4-bromo-1-chloro-2-fluorobenzene (4.0 g, 19.099 mmol) and cyclohexanone (2.9 mL, 28.647 mmol) using n-butyl lithium (1.6 M in THF, 13.1 mL, 21.008 mmol) in THF (20 mL) as per the process described in step 1 of Intermediate 31 to yield 1.12 g of the product as a semi-solid. $^1$H NMR (300 MHz, DMSO-$d_6$) δ 1.14-1.98 (m, 10H), 5.09 (s, 1H), 7.19 (t, J=7.8 Hz, 1H), 7.46 (t, J=7.8 Hz, 1H), 7.59 (t, J=7.8 Hz, 1H).

Step 2: 1-(4-Chloro-3-fluorophenyl)cyclohexyl 2-fluoro-4-nitrophenyl ether

The title compound was prepared by the reaction of step 1 intermediate (300 mg, 1.312 mmol) with 3,4-difluoronitrobenzene (0.15 mL, 1.312 mmol) using sodium hydride (60% w/w, 79 mg, 1.967 mmol) in DMF (5 mL) as per the process described in step 2 of Intermediate 1 to yield 138 mg of the product as a semi-solid. $^1$H NMR (300 MHz, DMSO-$d_6$) δ 1.60 (br s, 6H), 1.97-2.10 (m, 4H), 6.64 (t, J=9.0 Hz, 1H), 7.31 (t, J=7.8 Hz, 1H), 7.62 (t, J=7.4 Hz, 1H), 7.84 (d, J=7.4 Hz, 1H), 8.20 (d, J=9.0 Hz, 1H).

Step 3: 4-{[1-(4-Chloro-3-fluorophenyl)cyclohexyl]oxy}-3-fluoroaniline

The title compound was prepared by the reduction of step 2 intermediate (125 mg, 0.339 mmol) using sodium borohydride (52 mg, 1.359 mmol) and nickel chloride (162 mg, 0.679 mmol) in methanol (4 mL) as per the process described in step 3 of Intermediate 1 to yield 86 mg of the product as a semi-solid. $^1$H NMR (300 MHz, DMSO-$d_6$) δ 1.33-1.44 (m, 3H), 1.60-1.70 (m, 3H), 1.96-2.03 (m, 2H), 2.13-2.15 (m, 2H), 4.94 (s, 2H), 6.03-6.07 (m, 1H), 6.12 (t, J=9.3 Hz, 1H), 6.29-6.36 (m, 1H), 7.19-7.25 (m, 1H), 7.42 (t, J=6.9 Hz, 1H), 7.56 (t, J=7.2 Hz, 1H). APCI-MS (m/z) 338 (M+H)$^+$.

Intermediate 124

4-{[1-(2,4-Dichlorophenyl)cyclopentyl]oxy}aniline

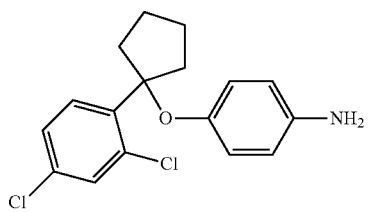 [SMILES: Nc1ccc(OC2(c3ccc(Cl)cc3Cl)CCCC2)cc1]

Step 1: 1-(2,4-Dichlorophenyl)cyclopentanol

To a stirred solution of 1-bromo-2,4-dichlorobenzene (1.0 g, 4.426 mmol) in dry THF (10 mL) was drop-wise added isopropylmagnesium chloride (2M in THF, 3.3 mL) at −10° C. and the mixture was stirred at the same temperature for 1 h. A solution of cyclopentanone (0.58 mL, 6.640 mmol) in THF (10 mL) was added to the reaction mixture and stirred at RT for 18 h. The mixture was quenched with saturated ammonium chloride solution (50 mL) and extracted with ethyl acetate (2×50 mL). The combined organic layers were washed with water (2×100 mL) and dried over anhydrous sodium sulfate. The solvent was distilled off under reduced pressure and the residue obtained was purified by silica gel column chromatography to yield 37 mg of the title product as a semi-solid. $^1$H NMR (300 MHz, DMSO-$d_6$) δ 1.78-2.10 (m, 6H), 2.23 (br s, 2H), 5.07 (s, 1H), 7.40 (d, J=8.7 Hz, 1H), 7.51 (s, 1H), 7.79 (d, J=8.1 Hz, 1H).

Step 2: 1-(2,4-Dichlorophenyl)cyclopentyl 4-nitrophenyl ether

The title compound was prepared by the reaction of step 1 intermediate (210 mg, 0.908 mmol) with 1-fluoro-4-nitro benzene (0.10 mL, 0.908 mmol) by using sodium hydride (60% w/w, 54 mg, 1.362 mmol) in DMF (4 mL) as per the process described in step 2 of Intermediate 1 to yield 159 mg of the product as a semi-solid. $^1$H NMR (300 MHz, DMSO-$d_6$) δ 1.81 (br s, 4H), 2.36 (br s, 2H), 6.83 (d, J=9.3 Hz, 2H), 7.47 (d, J=8.7 Hz, 1H), 7.58 (s, 1H), 7.65 (d, J=8.7 Hz, 1H), 8.03 (d, J=9.3 Hz, 2H).

Step 3: 4-{[1-(2,4-Dichlorophenyl)cyclopentyl]oxy}aniline

The title compound was prepared by the reduction of step 2 intermediate (150 mg, 0.426 mmol) using sodium borohydride (65 mg, 1.704 mmol) and nickel chloride (202 mg, 0.852 mmol) in methanol (5 mL) as per the process described in step 3 of Intermediate 1 to yield 79 mg of the product as a semi-solid. $^1$H NMR (300 MHz, DMSO-$d_6$) δ 1.72 (br s, 2H), 1.85 (br s, 2H), 1.97-2.07 (m, 2H), 2.49 (br s, 2H), 4.64 (br s, 2H), 6.23 (d, J=9.0 Hz, 2H), 6.30 (d, J=8.7 Hz, 2H), 7.33-7.39 (m, 2H), 7.60 (s, 1H); ESI-MS (m/z) 322 (M+H)$^+$.

Intermediate 125

4-{[1-(4-Chloro-3-fluorophenyl)cyclohexyl]oxy}aniline

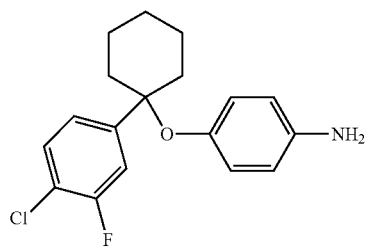 [SMILES: Nc1ccc(OC2(c3ccc(Cl)c(F)c3)CCCCC2)cc1]

Step 1: 1-(4-Chloro-3-fluorophenyl)cyclohexyl 4-nitrophenyl ether

The title compound was prepared by the reaction of 1-(4-chloro-3-fluorophenyl)cyclohexanol (500 mg, 2.186 mmol) with 4-fluoro-1-nitrobenzene (0.23 mL, 2.186 mmol) by using sodium hydride (60% w/w, 131 mg, 3.279 mmol) in DMF (10 mL) as per the process described in step 2 of Intermediate 1 to yield 504 mg of the product as a semi-solid. $^1$H NMR (300 MHz, DMSO-$d_6$) δ 1.58-1.69 (m, 5H), 1.98-2.10 (m, 2H), 2.40-2.49 (m, 3H), 6.85 (d, J=9.3 Hz, 2H), 7.33 (t, J=7.8 Hz, 1H), 7.49 (t, J=7.4 Hz, 1H), 7.60 (t, J=7.4 Hz, 1H), 8.06 (d, J=9.3 Hz, 2H).

Step 2: 4-{[1-(4-Chloro-3-fluorophenyl)cyclohexyl]oxy}aniline

The title compound was prepared by the reduction of step 1 intermediate (250 mg, 0.715 mmol) using iron powder (200 mg, 3.574 mmol) and ammonium chloride (382 mg, 7.147 mmol) in a mixture of water (5 mL) and methanol (5 mL) as per the process described in step 2 of Intermediate 14 to yield 88 mg of the product as a semi-solid. $^1$H NMR (300 MHz, DMSO-$d_6$) δ 1.17-1.33 (m, 2H), 1.40-1.50 (m, 2H), 1.63-1.72 (m, 2H), 1.85-1.97 (m, 2H), 2.20-2.25 (m, 2H), 4.61 (s, 2H), 6.33 (s, 4H), 7.20 (t, J=7.8 Hz, 1H), 7.38 (t, J=7.5 Hz, 1H), 7.53 (t, J=7.8 Hz, 1H). ESI-MS (m/z) 320 (M+H)$^+$.

Intermediate 126

1-Cyclopropyl-2-[2-(2,4-difluorophenoxy)propan-2-yl]-1H-benzimidazol-5-amine

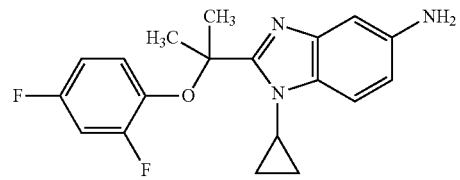 [SMILES: CC(C)(Oc1ccc(F)cc1F)c1nc2cc(N)ccc2n1C1CC1]

Step 1: 1-Cyclopropyl-2-[2-(2,4-difluorophenoxy)propan-2-yl]-5-nitro-1H-benzimidazole The title compound was synthesized by the coupling reaction of $N^1$-cyclopropyl-4-nitrobenzene-1,2-diamine (430 mg, 2.224 mmol) with 2-(2,4-difluorophenoxy)-2-methylpropanoic acid (400 mg, 1.853 mmol) using oxalyl chloride (805 µL, 9.265 mmol) and triethylamine (522 µL, 3.706 mmol) in DCM (10 mL) followed by cyclization in the presence of acetic acid (10 mL) as per the process described in step 1 of Intermediate 85 to yield 89 mg of the product as a semi-solid. $^1$H NMR (300 MHz, DMSO-$d_6$) δ 1.33 (s, 4H), 1.91 (s, 6H), 3.61 (br s, 1H), 6.54-6.86 (m, 1H), 6.80-6.90 (m, 1H), 7.24-7.27 (m, 1H), 7.89 (d, J=8.7 Hz, 1H), 8.22 (d, J=7.2 Hz, 1H), 8.53 (s, 1H); APCI-MS (m/z) 374 (M+H)$^+$.

Step 2: 1-Cyclopropyl-2-[2-(2,4-difluorophenoxy)propan-2-yl]-1H-benzimidazol-5-amine The title compound was prepared by the reduction of step 1 intermediate (80 mg, 0.210 mmol) using iron powder (59 mg, 1.050 mmol) and ammonium chloride (112 mg, 2.100 mmol) in a mixture of water (3 mL), THF (10 mL) and methanol (3 mL) as per the process described in step 2 of Intermediate 14 to yield 91 mg of the product as a semi-solid. $^1$H NMR (300 MHz, DMSO-$d_6$) δ 1.16-1.23 (m, 4H), 1.86 (s, 6H), 6.34-6.38 (m, 1H), 6.75-6.83 (m, 2H), 6.91 (s, 1H), 7.26 (t, J=9.0 Hz, 1H), 7.40 (d, J=8.7 Hz, 1H), 7.95 (s, 1H); APCI-MS (m/z) 344 (M+H)$^+$.

Intermediate 127

2-[2-(2,5-Difluorophenoxy)propan-2-yl]-1-ethyl-1H-benzimidazol-5-amine

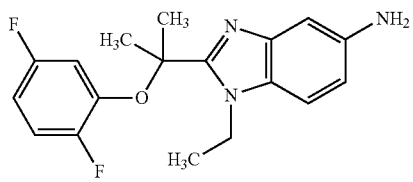 [SMILES: CCn1c(C(C)(C)Oc2cc(F)ccc2F)nc2cc(N)ccc21]

Step 1: 2-[2-(2,5-Difluorophenoxy)propan-2-yl]-1-ethyl-5-nitro-1H-benzimidazole The title compound was synthesized by the coupling reaction of $N^1$-ethyl-4-nitrobenzene-1,2-diamine (503 mg, 2.780 mmol) with 2-(2,5-difluorophenoxy)-2-methylpropanoic acid (500 mg, 2.320 mmol) using oxalyl chloride (1.00 mL, 11.602 mmol) and triethylamine (654 µL, 4.640 mmol) in DCM (10 mL) followed by cyclization in the presence of acetic acid (10 mL) as per the process described in step 1 of Intermediate 85 to yield 457 mg of the product as a solid. $^1$H NMR (300 MHz, DMSO-$d_6$) δ 1.31 (t, J=7.5 Hz, 3H), 1.87 (s, 6H), 4.65 (q, J=7.5 Hz, 2H), 6.49-6.52 (m, 1H), 6.91-6.95 (m, 1H), 7.26-7.36 (m, 1H), 7.84 (d, J=9.3 Hz, 1H), 8.20 (d, J=8.7 Hz, 1H), 8.58 (s, 1H); ESI-MS (m/z) 362 (M+H)$^+$.

Step 2: 2-[2-(2,5-Difluorophenoxy)propan-2-yl]-1-ethyl-1H-benzimidazol-5-amine The title compound was prepared by the reduction of step 1 intermediate (150 mg, 0.415 mmol) using iron powder (116 mg, 2.077 mmol) and ammonium chloride (222 mg, 4.150 mmol) in a mixture of water (3 mL), THF (10 mL) and methanol (3 mL) as per the process described in step 2 of Intermediate 14 to yield 105 mg of the product as a solid; $^1$H NMR (300 MHz, DMSO-$d_6$) δ 1.20 (t, J=7.2 Hz, 3H), 1.84 (s, 6H), 4.41 (q, J=7.2 Hz, 2H), 5.54 (br s, 2H), 6.24-6.27 (m, 1H), 6.70 (d, J=8.7 Hz, 1H), 6.87 (br s, 2H), 7.26 (d, J=8.4 Hz, 2H).

Intermediate 128

2-(4-Aminophenoxy)-N-(4-chlorophenyl)-N-ethyl-2-methylpropanamide

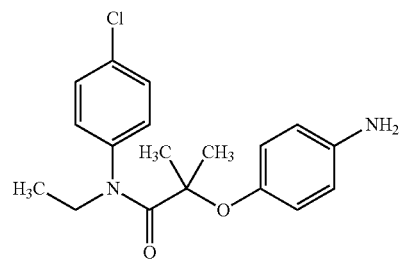 [SMILES: CCN(C(=O)C(C)(C)Oc1ccc(N)cc1)c1ccc(Cl)cc1]

Step 1: N-(4-Chlorophenyl)-2-methyl-2-(4-nitrophenoxy)propanamide

The title compound was synthesized by the reaction of 2-methyl-2-(4-nitrophenoxy)propanoic acid (500 mg, 2.220 mmol) with 4-chloroaniline (340 mg, 2.660 mmol) using EDCI.HCl (510 mg, 2.664 mmol) and HOBt (360 mg, 2.664 mmol) in DCM (10 mL) as per the process described in step 2 of Intermediate 105 to yield 580 mg of the product as a solid. $^1$H NMR (300 MHz, DMSO-$d_6$) δ 1.65 (s, 6H), 7.06 (d, J=9.3 Hz, 2H), 7.35 (d, J=9.0 Hz, 2H), 7.65 (d, J=8.7 Hz, 2H), 8.20 (d, J=9.0 Hz, 2H), 10.17 (s, 1H); APCI-MS (m/z) 333 (M−H)$^-$.

Step 2: N-(4-Chlorophenyl)-N-ethyl-2-methyl-2-(4-nitrophenoxy)propanamide

The title compound was prepared by the reaction of step 1 intermediate (250 mg, 0.748 mmol) with ethyl bromide (0.06 mL, 0.760 mmol) using sodium hydride (60% w/w, 45 mg, 1.122 mmol) in DMF (3 mL) as per the process described in step 2 of Intermediate 1 to yield 208 mg of the product as a solid. $^1$H NMR (300 MHz, DMSO-$d_6$) δ 0.98 (br s, 3H), 1.55 (br s, 6H), 3.60 (br s, 2H), 6.79 (br s, 2H), 6.97 (br s, 2H), 7.35 (br s, 2H), 8.20 (br s, 2H); ESI-MS (m/z) 363 (M+H)$^+$.

Step 3: 2-(4-Aminophenoxy)-N-(4-chlorophenyl)-N-ethyl-2-methylpropanamide

The title compound was prepared by the reduction of step 2 intermediate (100 mg, 0.276 mmol) using iron powder (77 mg, 1.381 mmol) and ammonium chloride (147 mg, 2.760 mmol) in a mixture of water (2 mL), THF (5 mL) and methanol (2 mL) as per the process described in step 2 of Intermediate 14 to yield 60 mg of the product as a semi-solid; $^1$H NMR (300 MHz, DMSO-$d_6$) δ 0.94 (br s, 3H), 1.36

(br s, 6H), 3.71 (br s, 2H), 5.01 (br s, 2H), 6.40-6.48 (m, 4H), 7.12 (d, J=9.0 Hz, 2H), 7.35-7.40 (m, 2H); ESI-MS (m/z) 334 (M+H)+.

Intermediate 129

2-(4-Aminophenoxy)-N-(4-chlorophenyl)-N,2-dimethylpropanamide

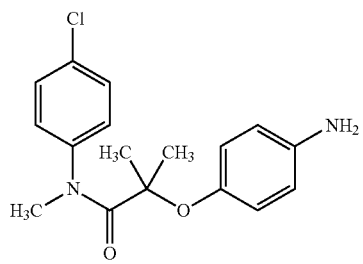 [SMILES: CN(C(=O)C(C)(C)Oc1ccc(N)cc1)c1ccc(Cl)cc1]

Step 1: N-(4-Chlorophenyl)-N,2-dimethyl-2-(4-nitrophenoxy)propanamide

The title compound was prepared by the reaction of N-(4-chlorophenyl)-2-methyl-2-(4-nitrophenoxy)propanamide (300 mg, 0.898 mmol) with methyl iodide (0.08 mL, 1.347 mmol) using sodium hydride (60% w/w, 54 mg, 1.347 mmol) in DMF (3 mL) as per the process described in step 2 of Intermediate 1 to yield 360 mg of the product as a solid. $^1$H NMR (300 MHz, DMSO-$d_6$) δ 1.62 (br s, 6H), 3.21 (br s, 3H), 7.10 (br s, 4H), 7.36 (br s, 2H), 8.22 (d, J=7.8 Hz, 2H).

Step 2: 2-(4-Aminophenoxy)-N-(4-chlorophenyl)-N,2-dimethylpropanamide

The title compound was prepared by the reduction of step 1 intermediate (150 mg, 0.431 mmol) using iron powder (120 mg, 2.155 mmol) and ammonium chloride (230 mg, 4.310 mmol) in a mixture of water (2 mL), THF (5 mL) and methanol (2 mL) as per the process described in step 2 of Intermediate 14 to yield 65 mg of the product as a semi-solid; $^1$H NMR (300 MHz, DMSO-$d_6$) δ 1.41 (br s, 6H), 2.49 (br s, 3H), 4.98 (br s, 2H), 6.49 (br s, 4H), 7.20 (d, J=8.4 Hz, 2H), 7.40 (d, J=8.1 Hz, 2H); ESI-MS (m/z) 319 (M+H)+.

Intermediate 130

2-(4-Aminophenoxy)-N-(2,4-dichlorophenyl)-N-ethyl-2-methylpropanamide

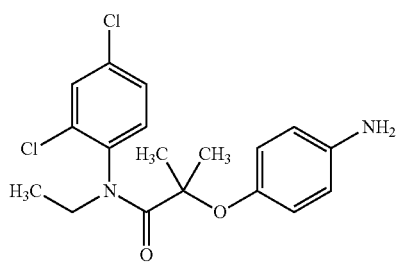 [SMILES: CCN(C(=O)C(C)(C)Oc1ccc(N)cc1)c1ccc(Cl)cc1Cl]

Step 1: N-(2,4-Dichlorophenyl)-2-methyl-2-(4-nitrophenoxy)propanamide

The title compound was synthesized by the reaction of 2-methyl-2-(4-nitrophenoxy)propanoic acid (500 mg, 2.220 mmol) with 2,4-dichloroaniline (432 mg, 2.664 mmol) using EDCI.HCl (510 mg, 2.664 mmol) and HOBt (360 mg, 2.664 mmol) in DCM (10 mL) as per the process described in step 2 of Intermediate 105 to yield 220 mg of the product as a solid. $^1$H NMR (300 MHz, DMSO-$d_6$) δ 1.66 (s, 6H), 6.74-6.78 (m, 1H), 7.10-7.25 (m, 1H), 7.45 (s, 2H), 7.66 (s, 1H), 8.22 (d, J=8.7 Hz, 2H); APCI-MS (m/z) 368 (M+H)+.

Step 2: N-(2,4-Dichlorophenyl)-N-ethyl-2-methyl-2-(4-nitrophenoxy)propanamide

The title compound was prepared by the reaction of step 1 intermediate (220 mg, 0.595 mmol) with ethyl bromide (0.06 mL, 0.893 mmol) using sodium hydride (60% w/w, 36 mg, 0.893 mmol) in DMF (3 mL) as per the process described in step 2 of Intermediate 1 to yield 125 mg of the product as a solid. ESI-MS (m/z) 397 (M)+.

Step 3: 2-(4-Aminophenoxy)-N-(2,4-dichlorophenyl)-N-ethyl-2-methylpropanamide

The title compound was prepared by the reduction of step 2 intermediate (120 mg, 0.302 mmol) using iron powder (84 mg, 1.510 mmol) and ammonium chloride (181 mg, 3.020 mmol) in a mixture of water (2 mL) and THF (5 mL) as per the process described in step 2 of Intermediate 14 to yield 99 mg of the product as a semi-solid. $^1$H NMR (300 MHz, DMSO-$d_6$) δ 1.02 (t, J=6.6 Hz, 3H), 1.15-1.21 (m, 6H), 4.01-4.13 (m, 2H), 4.76 (s, 2H), 6.24 (d, J=7.2 Hz, 1H), 6.35 (d, J=7.2 Hz, 1H), 6.50 (d, J=7.8 Hz, 1H), 6.66 (d, J=8.4 Hz, 1H), 7.26 (d, J=8.4 Hz, 1H), 7.35-7.49 (m, 1H), 7.72 (d, J=9.0 Hz, 1H); APCI-MS (m/z) 367 (M+H)+.

Intermediate 131

2-(4-Aminophenoxy)-N-(4-chloro-3-fluorophenyl)-N-ethyl-2-methylpropanamide

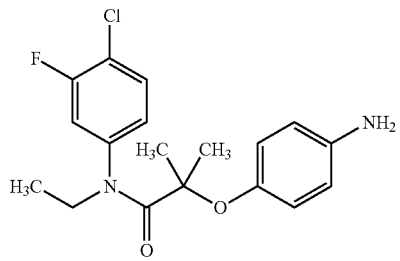 [SMILES: CCN(C(=O)C(C)(C)Oc1ccc(N)cc1)c1ccc(Cl)c(F)c1]

Step 1: N-(4-Chloro-3-fluorophenyl)-2-methyl-2-(4-nitrophenoxy)propanamide

The title compound was synthesized by the reaction of 2-methyl-2-(4-nitrophenoxy)propanoic acid (500 mg, 2.220 mmol) with 4-chloro-3-fluoroaniline (269 mg, 1.850 mmol) using EDCI.HCl (510 mg, 2.664 mmol) and HOBt (360 mg, 2.664 mmol) in DCM (10 mL) as per the process described in step 2 of Intermediate 105 to yield 510 mg of the product as a solid. $^1$H NMR (300 MHz, DMSO-$d_6$) δ 1.65 (s, 6H), 7.05 (d, J=9.0 Hz, 2H), 7.48 (s, 2H), 7.81 (d, J=9.3 Hz, 1H), 8.19 (d, J=9.0 Hz, 2H), 10.37 (s, 1H); ESI-MS (m/z) 346 (M−H)⁻.

Step 2: N-(4-Chloro-3-fluorophenyl)-N-ethyl-2-methyl-2-(4-nitrophenoxy)propanamide The title compound was prepared by the reaction of step 1 intermediate (250 mg, 0.708 mmol) with ethyl bromide (0.07 mL, 1.062 mmol) using sodium hydride (60% w/w, 42 mg, 1.062 mmol) in DMF (3 mL) as per the process described in step 2 of Intermediate 1 to yield 190 mg of the product as a solid. ¹H NMR (300 MHz, DMSO-d₆) δ 0.90 (br s, 3H), 1.60 (s, 6H), 3.71 (br s, 2H), 6.90 (br s, 3H), 7.11 (br s, 1H), 7.53 (br s, 1H), 8.23 (d, J=8.7 Hz, 2H).

Step 3: 2-(4-Aminophenoxy)-N-(4-chloro-3-fluorophenyl)-N-ethyl-2-methylpropanamide The title compound was prepared by the reduction of step 2 intermediate (180 mg, 0.472 mmol) using iron powder (132 mg, 2.363 mmol) and ammonium chloride (252 mg, 4.720 mmol) in water (2 mL), THF (10 mL) and methanol (3 mL) as per the process described in step 2 of Intermediate 14 to yield 47 mg of the product as solid. ¹H NMR (300 MHz, DMSO-d₆) δ 0.94 (t, J=6.9 Hz, 3H), 1.38 (s, 6H), 3.79 (br s, 2H), 4.75 (s, 2H), 6.41-6.46 (m, 4H), 7.04 (d, J=8.4 Hz, 1H), 7.18-7.21 (m, 1H), 7.55 (t, J=8.4 Hz, 1H); APCI-MS (m/z) 351 (M+H)⁺.

Intermediate 132

2-(4-Amino-2-fluorophenoxy)-N-(4-chloro-3-fluorophenyl)-N-ethyl-2-methylpropanamide

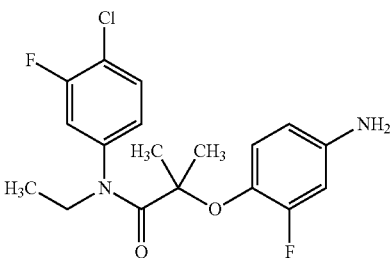 [SMILES: CCN(C(=O)C(C)(C)Oc1ccc(N)cc1F)c1ccc(Cl)c(F)c1]

Step 1: N-(4-Chloro-3-fluorophenyl)-N-ethyl-2-(2-fluoro-4-nitrophenoxy)-2-methylpropanamide To a stirred solution of 2-(2-fluoro-4-nitrophenoxy)-2-methylpropanoic acid (510 mg, 2.071 mmol) in DCM (10 mL) were added catalytic amount of dry DMF and oxalyl chloride (0.9 mL, 10.353 mmol). The reaction mixture was stirred at room temperature for 2 h. The excess of oxalyl chloride was distilled off under reduced pressure and the residue was dissolved in DCM (10 mL). To that solution were added 4-chloro-N-ethyl-3-fluoroaniline (370 mg, 2.071 mmol) and triethylamine (0.58 mL, 4.140 mmol) at 0° C. The reaction mixture was stirred at RT for 16 h. The reaction mixture was diluted with ethyl acetate (15 mL) and water (10 mL). The layers were separated and the aqueous layer was extracted with ethyl acetate (2×15 mL). The combined organic extracts were washed with water (20 mL) and brine (15 mL). The solution was dried over anhydrous sodium sulfate, filtered and concentrated under reduced pressure. The residue obtained was purified by silica gel column chromatography to yield 600 mg of the title compound as solid. ¹H NMR (300 MHz, DMSO-d₆) δ 0.90-0.95 (m, 3H), 1.62 (s, 6H), 3.70 (br s, 2H), 6.90-6.95 (m, 1H), 7.05-7.10 (m, 3H), 7.50-7.54 (m, 1H), 8.12-8.15 (m, 2H); ESI-MS (m/z) 399 (M+H)⁺.

Step 2: 2-(4-Amino-2-fluorophenoxy)-N-(4-chloro-3-fluorophenyl)-N-ethyl-2-methylpropanamide The title compound was prepared by the reduction of step 1 intermediate (200 mg, 0.502 mmol) using iron powder (140 mg, 2.512 mmol) and ammonium chloride (269 mg, 5.020 mmol) in a mixture of water (3 mL), THF (10 mL) and methanol (3 mL) as per the process described in step 2 of Intermediate 14 to yield 115 mg of the product as solid. ¹H NMR (300 MHz, DMSO-d₆) δ 0.98 (t, J=6.9 Hz, 3H), 1.35 (s, 6H), 3.72-3.80 (m, 2H), 5.14 (br s, 2H), 6.24-6.36 (m, 2H), 6.52-6.56 (m, 1H), 7.10 (d, J=8.1 Hz, 1H), 7.29 (d, J=9.6 Hz, 1H), 7.57 (t, J=7.8 Hz, 1H); ESI-MS (m/z) 369 (M+H)⁺.

Intermediate 133

N-(4-Aminophenyl)-2-(2,4-difluorophenoxy)-N-ethyl-2-methylpropanamide

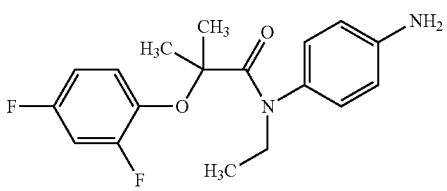 [SMILES: CCN(C(=O)C(C)(C)Oc1ccc(F)cc1F)c1ccc(N)cc1]

Step 1: 2-(2,4-Difluorophenoxy)-2-methyl-N-(4-nitrophenyl)propanamide

The title compound was prepared by the coupling reaction of 2-(2,4-difluorophenoxy)-2-methylpropanoic acid (500 mg, 2.316 mmol) and 4-nitroaniline (384 mg, 2.780 mmol) using oxalyl chloride (1.0 mL, 11.580 mmol) in presence of triethylamine (0.65 mL, 4.630 mmol) in DCM (10 mL) as per the process described in step 1 of Intermediate 132 to yield 365 mg of the product as a semi-solid. ¹H NMR (300 MHz, DMSO-d₆) δ 1.51 (s, 6H), 7.02-7.12 (m, 2H), 7.31-7.35 (m, 1H), 8.04 (d, J=9.3 Hz, 2H), 8.24 (d, J=8.7 Hz, 2H), 10.64 (s, 1H); APCI-MS (m/z) 335 (M−H)⁻.

Step 2: 2-(2,4-Difluorophenoxy)-N-ethyl-2-methyl-N-(4-nitrophenyl)propanamide

The title compound was prepared by the reaction of step 1 intermediate (350 mg, 1.041 mmol) with ethyl bromide (0.12 mL, 1.562 mmol) using sodium hydride (60% w/w, 62 mg, 1.562 mmol) in DMF (3 mL) as per the process described in step 2 of Intermediate 1 to yield 150 mg of the product as a solid. ¹H NMR (300 MHz, DMSO-d₆) δ 0.97 (t, J=7.5 Hz, 3H), 1.48 (s, 6H), 3.86 (q, J=7.2 Hz, 2H), 6.92-7.02 (m, 2H), 7.26-7.29 (m, 1H), 7.44 (d, J=9.0 Hz, 2H), 8.20 (d, J=8.7 Hz, 2H).

Step 3: N-(4-Aminophenyl)-2-(2,4-difluorophenoxy)-N-ethyl-2-methylpropanamide The title compound was prepared by the reduction of step 1 intermediate (150 mg, 0.411 mmol) using iron powder (115 mg, 2.058 mmol) and ammonium chloride (219 mg, 4.112 mmol) in water (3 mL), THF (10 mL) and methanol (3 mL) as per the process described in step 2 of Intermediate 14 to yield 115 mg of the product as a solid. $^1$H NMR (300 MHz, DMSO-$d_6$) δ 1.00 (br s, 3H), 1.35 (m, 6H), 3.52 (br s, 2H), 5.22 (br s, 2H), 6.44 (s, 2H), 6.65 (d, J=8.6 Hz, 2H), 6.85-6.87 (m, 1H), 6.99-7.03 (m, 1H), 7.25-7.28 (m, 1H); ESI-MS (m/z) 335 (M+H)$^+$.

Intermediate 134

4-{[1-(4-Chloro-3-fluorophenyl)cyclohexyl]oxy}aniline

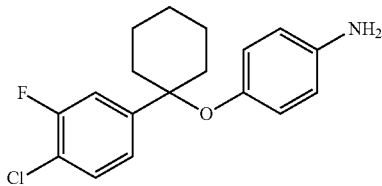 [SMILES: Nc1ccc(OC2(c3ccc(Cl)c(F)c3)CCCCC2)cc1]

Step 1: 1-(4-Chloro-3-fluorophenyl)cyclohexanol

The title compound was synthesized by the reaction of 1-bromo-4-chloro-3-fluorobenzene (4.0 g, 19.098 mmol) and cyclohexanone (2.9 mL, 28.647 mmol) in presence of n-butyl lithium (1.6 M in THF, 20 mL) in dry THF (10 mL) as per the process described in step 1 of Intermediate 31 to yield 1.11 g of the product as a semi solid. $^1$H NMR (300 MHz, DMSO-$d_6$) δ 1.47-1.75 (m, 8H), 1.87-1.98 (m, 2H), 5.09 (s, 1H), 7.19 (t, J=8.4 Hz, 1H), 7.45 (t, J=6.6 Hz, 1H), 7.59 (t, J=7.8 Hz, 1H); APCI-MS (m/z) 228 (M)$^+$.

Step 2: 1-(4-Chloro-3-fluorophenyl)cyclohexyl 4-nitrophenyl ether

The title compound was prepared by the reaction of step 1 intermediate (500 mg, 2.186 mmol) with 4-fluoro-1-nitrobenzene (308 mg, 2.186 mmol) by using sodium hydride (60% w/w, 131 mg, 3.279 mmol) in DMF (10 mL) as per the process described in step 2 of Intermediate 1 to yield 504 mg of the product as a semi-solid. $^1$H NMR (300 MHz, DMSO-$d_6$) δ 1.57-1.66 (m, 6H), 1.96-1.99 (m, 2H), 2.39-2.45 (m, 2H), 6.86 (d, J=8.7 Hz, 2H), 7.30 (t, J=8.1 Hz, 1H), 7.49 (t, J=7.8 Hz, 1H), 7.59 (t, J=7.8 Hz, 1H), 8.05 (d, J=8.7 Hz, 2H).

Step 3: 4-{[1-(4-Chloro-3-fluorophenyl)cyclohexyl]oxy}aniline

The title compound was prepared by the nitro reduction of step 2 intermediate (250 mg, 0.714 mmol) using iron powder (200 mg, 3.573 mmol) and ammonium chloride (382 mg, 7.147 mmol) in a mixture of water (5 mL) and methanol (5 mL) as per the process described in step 2 of Intermediate 14 to yield 88 mg of the product as a semi-solid. $^1$H NMR (300 MHz, DMSO-$d_6$) δ 1.23-1.32 (m, 2H), 1.46-1.50 (m, 2H), 1.64-1.72 (m, 2H), 1.85-1.98 (m, 2H), 2.24 (d, J=6.8 Hz, 2H), 4.61 (s, 2H), 6.33 (s, 4H), 7.20 (t, J=8.2 Hz, 1H), 7.38 (t, J=9.0 Hz, 1H), 7.53 (t, J=9.3 Hz, 1H); ESI-MS (m/z) 320 (M+H)$^+$.

Intermediate 135

4-{[1-(2,4-Dichlorophenyl)cyclohexyl]oxy}aniline

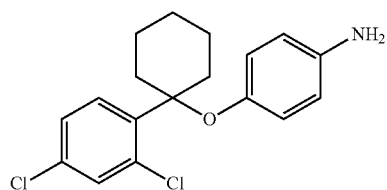 [SMILES: Nc1ccc(OC2(c3ccc(Cl)cc3Cl)CCCCC2)cc1]

Step 1: 1-(2,4-Dichlorophenyl)cyclohexanol

The title compound was synthesized by the reaction of 1-bromo-2,4-dichlorobenzene (2.0 g, 8.853 mmol) and cyclohexanone (1.3 mL, 13.280 mmol) in presence of isopropylmagnesium chloride (2M in THF, 6.6 mL, 13.280 mmol) in dry THF (20 mL) as per the process described in step 1 of Intermediate 124 to yield 458 mg of the product as a solid. $^1$H NMR (300 MHz, DMSO-$d_6$) δ 1.46-1.51 (m, 4H), 1.66-1.74 (m, 4H), 2.24-2.34 (m, 2H), 5.02 (s, 1H), 7.38-7.47 (m, 2H), 7.81 (d, J=8.4 Hz, 1H); ESI-MS (m/z) 336 (M+H)$^+$.

Step 2: 1-(2,4-Dichlorophenyl)cyclohexyl 4-nitrophenyl ether

The title compound was prepared by the reaction of step 1 intermediate (220 mg, 0.951 mmol) with 4-fluoro-1-nitro benzene (148 mg, 1.047 mmol) using sodium hydride (60% w/w, 57 mg, 1.427 mmol) in dry DMF (5.0 mL) as per the process described in step 2 of Intermediate 1 to yield 222 mg of the product as a solid. $^1$H NMR (300 MHz, DMSO-$d_6$) δ 1.24-1.40 (m, 2H), 1.58-1.62 (m, 4H), 1.89-1.92 (m, 2H), 2.61 (d, J=7.4 Hz, 2H), 6.77 (d, J=8.2 Hz, 2H), 7.55 (d, J=9.0 Hz, 2H), 7.69 (d, J=9.3 Hz, 1H), 8.04 (d, J=9.0 Hz, 2H); ESI-MS (m/z) 336 (M+H)$^+$.

Step 3: 4-{[1-(2,4-Dichlorophenyl)cyclohexyl]oxy}aniline

The title compound was prepared by the reduction of step 2 intermediate (210 mg, 0.573 mmol) using iron powder (160 mg, 2.866 mmol) and ammonium chloride (307 mg, 5.733 mmol) in a mixture of water (5 mL) and methanol (5 mL) as per the process described in step 2 of Intermediate 14 to yield 169 mg of the product as a semi-solid. $^1$H NMR (300 MHz, DMSO-$d_6$) δ 1.22-1.24 (m, 2H), 1.38-1.42 (m, 2H), 1.66-1.72 (m, 2H), 1.81-1.85 (m, 2H), 2.32-2.39 (m, 2H), 4.55 (s, 2H), 6.29 (s, 4H), 7.42 (d, J=9.0 Hz, 1H), 7.53 (d, J=9.3 Hz, 1H); ESI-MS (m/z) 336 (M+H)$^+$.

Intermediate 136

4-{[1-(2,4-Dichlorophenyl)cyclohexyl]oxy}-3-fluoroaniline

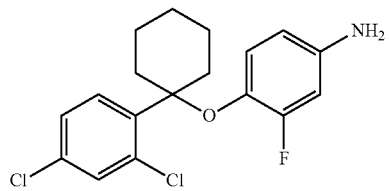 [SMILES: Nc1ccc(OC2(c3ccc(Cl)cc3Cl)CCCCC2)c(F)c1]

Step 1: 1-(2,4-Dichlorophenyl)cyclohexyl 2-fluoro-4-nitrophenyl ether

The title compound was prepared by the reaction of 1-(2,4-dichlorophenyl)cyclohexanol (220 mg, 0.951 mmol) with 3,4-difluoronitrobenzene (116 mg, 1.047 mmol) using sodium hydride (60% w/w, 57 mg, 1.427 mmol) in dry DMF (5.0 mL) as per the process described in step 2 of Intermediate 1 to yield 78 mg of the product as a semi-solid. $^1$H NMR (300 MHz, DMSO-$d_6$) δ 1.36-1.40 (m, 2H), 1.61-1.66 (m, 4H), 1.93-1.97 (m, 2H), 2.57-2.64 (m, 2H), 6.51 (t, J=9.3 Hz, 1H), 7.59 (s, 2H), 7.70 (d, J=9.3 Hz, 1H), 7.81 (d, J=9.3 Hz, 1H), 8.16 (d, J=9.3 Hz, 1H), 7.55 (s, 2H); ESI-MS (m/z) 383 (M)$^+$.

Step 2: 4-{[1-(2,4-Dichlorophenyl)cyclohexyl]oxy}-3-fluoroaniline

The title compound was prepared by the reduction of step 1 intermediate (60 mg, 0.156 mmol) using iron powder (44 mg, 1.561 mmol) and ammonium chloride (84 mg, 1.561 mmol) in a mixture of water (5 mL) and methanol (5 mL) as per the process described in step 2 of Intermediate 14 to yield 26 mg of the product as a semi-solid. $^1$H NMR (300 MHz, DMSO-$d_6$) δ 1.47-1.49 (m, 2H), 1.63-1.66 (m, 3H), 1.94-1.98 (m, 3H), 2.28-2.33 (m, 2H), 4.86 (s, 2H), 5.96 (s, 2H), 6.32-6.38 (m, 1H), 7.44 (d, J=9.3 Hz, 1H), 7.55 (s, 2H); APCI-MS (m/z) 354 (M+H)$^+$.

Intermediate 137

4-{[4-(2,4-Dichlorophenyl)tetrahydro-2H-pyran-4-yl]oxy}-3-fluoroaniline

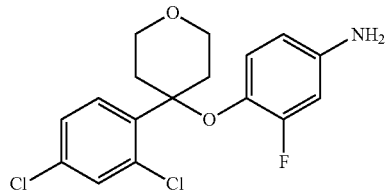 [SMILES: Nc1ccc(OC2(c3ccc(Cl)cc3Cl)CCOCC2)c(F)c1]

Step 1: 4-(2,4-Dichlorophenyl)tetrahydro-2H-pyran-4-ol

To a stirred solution of 1-bromo-2,4-dichlorobenzene (2.0 g, 8.853 mmol) in anhydrous diethyl ether (10 mL) was added n-butyl lithium (1.6 M in ether, 6.0 mL, 9.738 mmol) drop-wise at −78° C. and the reaction mixture was stirred at the same temperature for 1 h. A solution of tetrahydropyrane-4-one (0.9 mL, 9.738 mmol) in THF (10 mL) was added to the reaction mixture at −78° C. The cooling bath was removed and the reaction mixture was stirred at room temperature for 4 h. The mixture was quenched with saturated ammonium chloride solution (50 mL) and extracted with ethyl acetate (3×50 mL). The combined organic extracts were washed with water (2×100 mL), brine (100 mL) and dried over anhydrous sodium sulfate. The solvent was distilled out under reduced pressure and the residue obtained was purified by silica gel column chromatography to yield 685 mg of the title product as a semi-solid. $^1$H NMR (300 MHz, DMSO-$d_6$) δ 1.43 (d, J=9.6 Hz, 2H), 2.49-2.52 (m, 2H), 3.73-3.78 (m, 4H), 5.36 (s, 1H), 7.43-7.52 (m, 2H), 7.82 (d, J=8.7 Hz, 1H); ESI-MS (m/z) 244 (M−H)$^-$.

Step 2: 4-(2,4-Dichlorophenyl)-4-(2-fluoro-4-nitrophenoxy)tetrahydro-2H-pyran To a stirred and cooled (0° C.) solution of step 1 intermediate (300 mg, 1.213 mmol) in dry DMF (10 mL) was added sodium hydride (60% w/w, 58 mg, 1.456 mmol) and the reaction was stirred at RT for 30 min. 3,4-Difluoronitrobenzene (193 mg, 1.213 mmol) was added to the reaction mixture and stirred for 2 h at RT. The mixture was diluted with water (20 mL) and extracted with ethyl acetate (3×20 mL). The combined organic layers were washed with water (2×50 mL), brine (50 mL) and dried over anhydrous sodium sulfate. The solvent was distilled off under reduced pressure and the residue obtained was purified by silica gel column chromatography to yield 292 mg of the title product as a solid. $^1$H NMR (300 MHz, DMSO-$d_6$) δ 2.25-3.32 (m, 2H), 2.53-2.59 (m, 2H), 3.69-3.82 (m, 4H), 6.54 (t, J=7.2 Hz, 1H), 7.60 (s, 2H), 7.72-7.82 (m, 2H), 8.17 (d, J=8.7 Hz, 1H); APCI-MS (m/z) 389 (M+H)$^+$.

Step 3: 4-{[4-(2,4-Dichlorophenyl)tetrahydro-2H-pyran-4-yl]oxy}-3-fluoroaniline To a stirred solution of step 2 intermediate (280 mg, 0.725 mmol) in a mixture of methanol (10 mL) and water (10 mL) were added iron powder (202 mg, 3.625 mmol) and ammonium chloride (388 mg, 7.250 mmol) at RT. The reaction mixture was heated to 90° C. and stirred for 3 h at the same temperature. The reaction mixture cooled to RT and filtered off the suspended emulsion. The filtrate was concentrated under reduced pressure and diluted with water (10 mL). The aqueous mixture was extracted with ethyl acetate (2×20 mL). The combined organic layers were washed with brine and dried over anhydrous sodium sulfate. The solvents were recovered under reduced pressure and the residue obtained was purified by silica gel column chromatography to 224 mg of the title product as a solid. $^1$H NMR (300 MHz, DMSO-$d_6$) δ 2.20-2.33 (m, 4H), 3.69-3.81 (m, 4H), 4.92 (s, 2H), 5.98 (q, J=7.8 Hz, 2H), 6.33-6.39 (m, 1H), 7.46-7.61 (m, 3H); APCI-MS (m/z) 358 (M+H)$^+$.

Intermediate 138

4-{[1-(2,4-Dichlorophenyl)cyclopentyl]oxy}-3-fluoroaniline

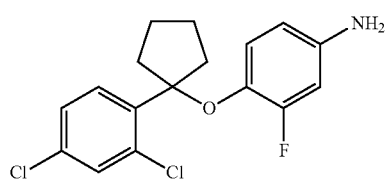 [SMILES: Nc1ccc(OC2(c3ccc(Cl)cc3Cl)CCCC2)c(F)c1]

Step 1: 1-(2,4-Dichlorophenyl)cyclopentyl 2-fluoro-4-nitrophenyl ether

To a stirred and cooled (0° C.) solution of 1-(2,4-dichlorophenyl)cyclopentanol (300 mg, 1.298 mmol) in dry DMF (10 mL) was added sodium hydride (60% w/w, 77 mg, 1.947 mmol) and the reaction was stirred for 30 min at RT. 3,4-Difluoro-1-nitrobenzene (206 mg, 1.298 mmol) was added to the reaction mixture and further stirred at RT for 2 h. The reaction mixture was diluted with water (30 mL) and extracted with ethyl acetate (3×30 mL). The combined organic layers were washed with water (2×50 mL), brine (50 mL) and dried over anhydrous sodium sulfate. The solvent was distilled off under reduced pressure and the residue obtained was purified by silica gel column chromatography to yield 171 mg of the title product as a semi-solid. $^1$H NMR (300 MHz, DMSO-$d_6$) δ 1.81-1.83 (m, 4H), 1.98 (s, 2H), 2.36-2.39 (m, 2H), 2.48-2.52 (m, 2H), 6.68 (t, J=9.3 Hz, 1H), 7.49 (d, J=8.4 Hz, 1H), 7.61 (s, 1H), 7.68 (d, J=8.1 Hz, 1H), 7.81 (d, J=8.4 Hz, 1H), 8.13 (d, J=8.4 Hz, 1H); APCI-MS (m/z) 339 (M)$^+$.

Step 2: 4-{[1-(2,4-Dichlorophenyl)cyclopentyl]oxy}-3-fluoroaniline

To a stirred solution of step 1 intermediate (160 mg, 0.432 mmol) in a mixture of methanol (5 mL) and water (5 mL) were added iron powder (120 mg, 2.160 mmol) and ammonium chloride (231 mg, 4.321 mmol) at RT. The reaction mixture was heated to 90° C. and stirred for 3 h at the same temperature. The reaction mixture cooled to RT and filtered off the suspended emulsion. The filtrate was concentrated under reduced pressure and diluted with water (15 mL). The aqueous mixture was extracted with ethyl acetate (2×20 mL). The combined organic layers were washed with brine and dried over anhydrous sodium sulfate. The solvents were recovered under reduced pressure and the residue obtained was purified by silica gel column chromatography to yield 64 mg of the title product as a solid. $^1$H NMR (300 MHz, DMSO-$d_6$) δ 1.67-1.70 (m, 2H), 1.88-1.90 (m, 2H), 1.98-2.03 (m, 2H), 2.50 (s, 2H), 4.98 (s, 2H), 6.00 (s, 2H), 6.25 (s, 1H), 7.36 (q, J=8.7 Hz, 2H), 7.62 (s, 1H); APCI-MS (m/z) 339 (M)$^+$.

Intermediate 139

4-{[1-(2,4-Dichlorophenyl)cyclopropyl]oxy}-3-fluoroaniline

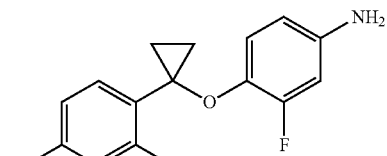

Step 1: 1,3-Dichloro-2-(2,4-dichlorophenyl)propan-2-ol

To a cooled solution of 2,4-dichloro-1-bromobenzene (2.0 mL, 16.733 mmol) in anhydrous THF (20 mL) was slowly added isopropyl magnesium bromide (2M in THF, 12.5 mL, 25.099 mmol) at RT and stirred for 1 h. A solution of 1,3-dichloroacetone (3.1 g, 25.099 mmol) in THF (20 mL) was drop-wise added to the reaction mixture and allowed to stir at RT for 18 h. The reaction mixture was quenched with saturated aqueous ammonium chloride solution (50 mL) and extracted with ethyl acetate (2×50 mL). The combined organic layers were washed with water (50 mL) followed by brine (50 mL) and dried over anhydrous sodium sulfate. The solution was filtered, concentrated and the residue thus obtained was purified by silica gel column chromatography to yield 1.19 g of the title compound as a semi-solid. $^1$H NMR (300 MHz, DMSO-$d_6$) δ 4.00 (d, J=11.7 Hz, 2H), 4.31 (d, J=11.7 Hz, 2H), 6.36 (s, 1H), 7.44-7.49 (m, 1H), 7.58-7.60 (m, 1H), 7.80 (d, J=8.7 Hz, 1H).

Step 2: 1,3-Dichloro-2-(2,4-dichlorophenyl)propan-2-ol

To a solution of step 1 intermediate (1.10 g, 4.015 mmol) in diethyl ether (20 mL) were simultaneously added ethyl magnesium bromide (3M in ether, 6.6 mL, 20.075 mmol) and a solution of ferric chloride (13 mg, 0.080 mmol) in diethyl ether (20 mL) over a period of 1 h. The resultant mixture was stirred at RT for 18 h. The mixture was quenched with saturated aqueous ammonium chloride solution (50 mL) and extracted with ethyl acetate (2×50 mL). The combined organic layers were washed with water (50 mL) followed by brine (50 mL) and dried over anhydrous sodium sulfate. The solution was filtered, concentrated and the residue thus obtained was purified by silica gel column chromatography to yield 1.19 g of the title compound as a semi-solid. $^1$H NMR (300 MHz, DMSO-$d_6$) δ 0.79-0.82 (m, 2H), 0.95-1.01 (m, 2H), 5.79 (br s, 1H), 7.35 (d, J=7.8 Hz, 1H), 7.44 (d, J=8.4 Hz, 1H), 7.54 (s, 1H).

Step 3: 1-(2,4-Dichlorophenyl)cyclopropyl 2-fluoro-4-nitrophenyl ether

To a stirred and cooled (0° C.) solution of step 2 intermediate (350 mg, 1.723 mmol) in dry DMF (10 mL) was added sodium hydride (60% w/w, 69 mg, 1.723 mmol) and the reaction was stirred for 30 min at RT. 3,4-Difluoro-1-nitrobenzene (274 mg, 1.723 mmol) was added to the reaction mixture and further stirred at RT for 2 h. The reaction mixture was diluted with saturated aqueous solution of ammonium chloride (30 mL) and extracted with ethyl acetate (3×30 mL). The combined organic layers were washed with water (2×50 mL), brine (50 mL) and dried over anhydrous sodium sulfate. The solvent was distilled off under reduced pressure and the residue obtained was purified by silica gel column chromatography to yield 393 mg of the title product as a semi-solid. $^1$H NMR (300 MHz, DMSO-$d_6$) δ 1.40-1.43 (m, 2H), 1.49-1.52 (m, 2H), 7.43 (d, J=8.7 Hz, 1H), 7.65-7.72 (m, 2H), 7.86 (d, J=8.4 Hz, 1H), 7.99 (d, J=9.3 Hz, 1H), 8.10 (d, J=8.4 Hz, 1H).

Step 4: 4-{[1-(2,4-Dichlorophenyl)cyclopropyl]oxy}-3-fluoroaniline

To a stirred solution of step 3 intermediate (380 mg, 1.110 mmol) in a mixture of methanol (10 mL) and water (10 mL) were added iron powder (310 mg, 5.553 mmol) and ammonium chloride (594 mg, 11.106 mmol) at RT. The reaction mixture was heated to 80° C. and stirred for 2 h at the same temperature. The reaction mixture cooled to RT and filtered off the suspended emulsion. The filtrate was concentrated under reduced pressure and diluted with water (20 mL). The aqueous mixture was extracted with ethyl acetate (2×20 mL). The combined organic layers were washed with water (30 mL) followed by brine (30 mL) and dried over anhydrous sodium sulfate. The solvents were recovered under reduced pressure and the residue obtained was purified by silica gel column chromatography to yield 283 mg of the title product as a semi-solid. $^1$H NMR (300 MHz, DMSO-$d_6$) δ 1.05 (t, J=6.9 Hz, 2H), 1.39 (t, J=6.9 Hz, 2H), 5.00 (br s, 2H), 6.13-6.25 (m, 2H), 6.71 (t, J=8.7 Hz, 1H), 7.30 (d, J=8.4 Hz, 1H), 7.35 (d, J=8.4 Hz, 1H), 7.61 (s, 1H); APCI-MS (m/z) 339 (M)$^+$.

Intermediate 140

4-{[1-(2,4-Dichlorophenyl)cyclobutyl]oxy}-3-fluoroaniline

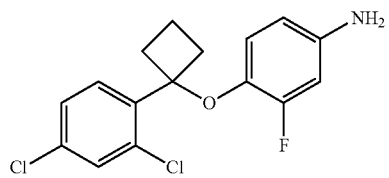 [SMILES: Nc1ccc(OC2(c3ccc(Cl)cc3Cl)CCC2)c(F)c1]

Step 1: 1-(2,4-dichlorophenyl)cyclobutanol

To a stirred solution of 2,4-dichloro-1-bromobenzene (2.0 g, 8.853 mmol) in anhydrous THF (10 mL) was drop-wise added isopropylmagnesium chloride (2M in THF, 6.6 mL, 13.320 mmol) at RT and the mixture was stirred 1 h. A solution of cyclobutanone (1.0 mL, 13.280 mmol) in THF (10 mL) was added to the reaction mixture and stirred at RT for 18 h. The mixture was quenched with saturated ammonium chloride solution (50 mL) and extracted with ethyl acetate (2×50 mL). The combined organic layers were washed with water (2×100 mL) and dried over anhydrous sodium sulfate. The solvent was distilled off under reduced pressure and the residue obtained was purified by silica gel column chromatography to yield 625 mg of the title product as a semi-solid. $^1$H NMR (300 MHz, DMSO-$d_6$) δ: 1.58-1.62 (m, 1H), 1.99-2.06 (m, 1H), 2.28-2.32 (m, 2H), 2.51-2.58 (m, 2H), 5.46 (s, 1H), 7.38-7.45 (m, 2H), 7.51 (s, 1H).

Step 2: 1-(2,4-Dichlorophenyl)cyclobutyl 2-fluoro-4-nitrophenyl ether

To a stirred and cooled (0° C.) solution of step 1 intermediate (250 mg, 1.151 mmol) in dry DMF (5 mL) was added sodium hydride (60% w/w, 46 mg, 1.151 mmol) and the reaction was stirred for 30 min at RT. 3,4-Difluoro-1-nitrobenzene (183 mg, 1.151 mmol) was added to the reaction mixture and further stirred at RT for 18 h. The reaction mixture was diluted with saturated aqueous solution of ammonium chloride (30 mL) and extracted with ethyl acetate (3×30 mL). The combined organic layers were washed with water (2×50 mL), brine (50 mL) and dried over anhydrous sodium sulfate. The solvent was distilled off under reduced pressure and the residue obtained was purified by silica gel column chromatography to yield 283 mg of the title product as a semi-solid. $^1$H NMR (300 MHz, DMSO-$d_6$) δ 1.70-1.78 (m, 1H), 1.98-2.05 (m, 1H), 2.73-2.82 (m, 2H), 2.90-2.95 (m, 2H), 6.88 (t, J=8.7 Hz, 1H), 7.50 (d, J=8.4 Hz, 1H), 7.59-7.61 (m, 1H), 7.83 (d, J=8.7 Hz, 1H), 7.96 (d, J=8.7 Hz, 1H), 8.07-8.13 (m, 1H).

Step 3: 4-{[1-(2,4-Dichlorophenyl)cyclobutyl]oxy}-3-fluoroaniline

To a stirred solution of step 2 intermediate (270 mg, 0.758 mmol) in a mixture of methanol (5 mL) and water (5 mL) were added iron powder (211 mg, 3.790 mmol) and ammonium chloride (405 mg, 7.580 mmol) at RT. The reaction mixture was heated to 80° C. and stirred for 2 h at the same temperature. The reaction mixture cooled to RT and filtered off the suspended emulsion. The filtrate was concentrated under reduced pressure and diluted with water (20 mL). The aqueous mixture was extracted with ethyl acetate (2×20 mL). The combined organic layers were washed with water (30 mL) followed by brine (30 mL) and dried over anhydrous sodium sulfate. The solvents were recovered under reduced pressure and the residue obtained was purified by silica gel column chromatography to yield 198 mg of the title product as a semi-solid. $^1$H NMR (300 MHz, DMSO-$d_6$) δ 1.62-1.65 (m, 1H), 2.04-2.12 (m, 1H), 2.59 (t, J=7.8 Hz, 4H), 5.00 (s, 2H), 6.05 (d, J=8.7 Hz, 1H), 6.17-6.27 (m, 2H), 7.33 (s, 2H), 7.58 (s, 1H); ESI-MS (m/z) 326 (M+H)$^+$.

Intermediate 141

4-{[1-(2,4-Difluorophenyl)cyclohexyl]oxy}-3-fluoroaniline

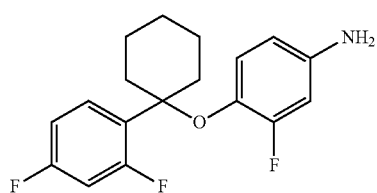 [SMILES: Nc1ccc(OC2(c3ccc(F)cc3F)CCCCC2)c(F)c1]

Step 1: 1-(2,4-Difluorophenyl)cyclohexanol

The title compound was synthesized by the reaction of 1-bromo-2,4-difluorobenzene (3.41 g, 17.700 mmol) and cyclohexanone (2.2 mL, 21.240 mmol) in presence of 1.6 M n-butyl lithium (1.6 M in THF, 6.6 mL) in diethyl ether (20 mL) as per the process described in step 1 of Intermediate 31 to yield 1.61 g of the product as a semi-solid. $^1$H NMR (300 MHz, DMSO-d$_6$) δ 1.22-1.25 (m, 1H), 1.45-1.70 (m, 6H), 1.74-1.89 (m, 2H), 2.24 (t, J=6.9 Hz, 1H), 5.00 (s, 1H), 7.03-7.13 (m, 2H), 7.64 (q, J=7.2 Hz, 1H); ESI-MS (m/z) 212 (M)$^+$.

Step 2: 1-{[1-(2,4-Difluorophenyl)cyclohexyl]oxy}-2-fluoro-4-nitrobenzene

The title compound was prepared by the reaction of step 1 intermediate (500 mg, 2.355 mmol) with 3,4-difluoro-1-nitrobenzene (377 mg, 2.355 mmol) by using sodium hydride (60% w/w, 141 mg, 3.533 mmol) in dry DMF (10 mL) as per the process described in step 2 of Intermediate 1 to yield 708 mg of the product as a solid. $^1$H NMR (300 MHz, DMSO-d$_6$) δ 1.33-1.36 (m, 2H), 1.59-1.62 (m, 4H), 1.63-1.69 (m, 2H), 2.41-2.47 (m, 2H), 6.63 (q, J=7.2 Hz, 1H), 7.17-7.26 (m, 2H), 7.58 (q, J=7.2 Hz, 1H), 7.82 (d, J=8.7 Hz, 1H), 8.14 (d, J=8.1 Hz, 1H); ESI-MS (m/z) 350 (M–H)$^-$.

Step 3: 4-{[1-(2,4-Difluorophenyl)cyclohexyl]oxy}-3-fluoroaniline

The title compound was prepared by the reduction of step 2 intermediate (700 mg, 1.959 mmol) using iron powder (547 mg, 9.795 mmol) and ammonium chloride (1.0 g, 19.590 mmol) in water (10 mL) and methanol (10 mL) as per the process described in step 2 of Intermediate 14 to yield 581 mg of the product as a semi-solid. $^1$H NMR (300 MHz, DMSO-d$_6$) δ 1.35-1.38 (m, 3H), 1.63-1.66 (m, 3H), 1.98-2.11 (m, 4H), 4.93 (s, 2H), 6.03-6.15 (m, 2H), 6.29 (d, J=7.2 Hz, 1H), 7.06 (t, J=7.2 Hz, 1H), 7.20 (t, J=8.7 Hz, 1H), 7.46 (q, J=8.1 Hz, 1H); ESI-MS (m/z) 322 (M+H)$^+$.

Intermediate 142

4-{[1-(2,4-Difluorophenyl)cyclobutyl]oxy}-3-fluoroaniline

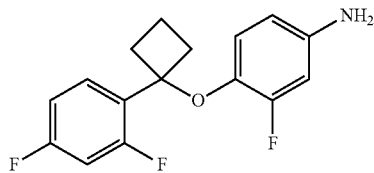 [SMILES: Nc1ccc(OC2(c3ccc(F)cc3F)CCC2)c(F)c1]

Step 1: 1-(2,4-Difluorophenyl)cyclobutanol

The title compound was synthesized by the reaction of 1-bromo-2,4-difluorobenzene (2.5 g, 12.354 mmol) and cyclobutanone (1.36 g, 19.431 mmol) in presence of n-butyl lithium in diethyl ether (1.6 M in THF, 6.5 mL) in diethyl ether (20 mL) as per the process described in step 1 of Intermediate 31 to yield 1.61 g of the product as a liquid. $^1$H NMR (300 MHz, DMSO-d$_6$) δ 1.57-1.60 (m, 1H), 1.94-2.00 (m, 1H), 2.21-2.56 (m, 2H), 5.54 (s, 1H), 7.04 (t, J=9.0 Hz, 1H), 7.15 (t, J=9.3 Hz, 1H), 7.38-7.48 (m, 1H).

Step 2: 1-{[1-(2,4-Difluorophenyl)cyclobutyl]oxy}-2-fluoro-4-nitrobenzene

The title compound was prepared by the reaction of step 1 intermediate (400 mg, 2.173 mmol) with 3,4-difluoro-1-nitrobenzene (346 mg, 2.173 mmol) by using sodium hydride (60% w/w, 195 mg, 3.259 mmol) in dry DMF (10 mL) as per the process described in step 2 of Intermediate 1 to yield 540 mg of the product as a solid. $^1$H NMR (300 MHz, DMSO-d$_6$) δ 1.71-1.76 (m, 1H), 1.95-2.02 (m, 1H), 2.69-2.75 (m, 2H), 2.85-2.90 (m, 2H), 6.91 (t, J=8.7 Hz, 1H), 7.13-7.16 (m, 1H), 7.26 (t, J=9.3 Hz, 1H), 7.82-7.89 (m, 2H), 8.10 (d, J=10.5 Hz, 1H).

Step 3: 4-{[1-(2,4-Difluorophenyl)cyclobutyl]oxy}-3-fluoroaniline

The title compound was prepared by the reduction of step 2 intermediate (520 mg, 1.609 mmol) using iron powder (449 mg, 8.047 mmol) and ammonium chloride (860 mg, 16.095 mmol) in a mixture of water (10 mL) and methanol (10 mL) as per the process described in step 2 of Intermediate 14 to yield 432 mg of the product as a solid. $^1$H NMR (300 MHz, DMSO-d$_6$) δ 1.58-1.63 (m, 1H), 1.95-2.02 (m, 1H), 2.51-2.59 (m, 4H), 5.00 (s, 2H), 6.08 (d, J=8.1 Hz, 1H), 6.21-6.36 (m, 2H), 6.97-7.01 (m, 1H), 7.19 (t, J=9.6 Hz, 1H), 7.32-7.38 (m, 1H); ESI-MS (m/z) 295 (M+H)$^+$.

Intermediate 143

4-{[3-(2,4-Difluorophenyl)oxetan-3-yl]oxy}-3-fluoroaniline

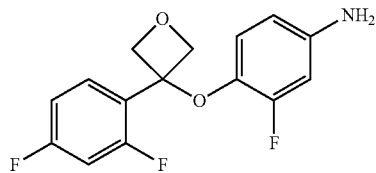 [SMILES: Nc1ccc(OC2(c3ccc(F)cc3F)COC2)c(F)c1]

Step 1: 3-(2,4-Difluorophenyl)oxetan-3-ol

The title compound was synthesized by the reaction of 1-bromo-2,4-difluorobenzene (1.0 mL, 8.808 mmol) and 3-oxetinone (0.67 mL, 10.570 mmol) in presence of n-butyl lithium (1.6 M in THF, 6.6 mL) in diethyl ether (20 mL) as per the process described in step 1 of Intermediate 31 to yield 434 mg of the product as off-white semi solid. $^1$H NMR (300 MHz, DMSO-d$_6$) δ 4.67 (d, J=6.9 Hz, 2H), 4.93 (t, J=6.3 Hz, 2H), 6.40 (s, 1H), 7.11 (t, J=6.3 Hz, 1H), 7.26 (t, J=8.7 Hz, 1H), 7.43-7.50 (m, 1H).

Step 2: 3-(2,4-difluorophenyl)-3-(2-fluoro-4-nitrophenoxy)oxetane

The title compound was prepared by the reaction of step 1 intermediate (200 mg, 1.074 mmol) with 3,4-difluoro-1-nitrobenzene (256 mg, 1.161 mmol) by using sodium hydride (60% w/w, 65 mg, 1.611 mmol) in dry DMF (10 mL) as per the process described in step 2 of Intermediate 1 to yield 304 mg of the product as a solid. $^1$H NMR (300 MHz, DMSO-d$_6$) δ 5.10 (d, J=7.8 Hz, 2H), 4.93 (t, J=7.8 Hz, 2H), 6.92 (t, J=9.0 Hz, 1H), 7.16 (t, J=8.7 Hz, 1H), 7.34 (t, J=9.0 Hz, 1H), 7.86-7.92 (m, 2H), 8.14-8.20 (m, 1H).

Step 3: 4-{[3-(2,4-Difluorophenyl)oxetan-3-yl]oxy}-3-fluoroaniline

The title compound was prepared by the reduction of step 2 intermediate (290 mg, 0.891 mmol) using iron powder (249 mg, 4.458 mmol) and ammonium chloride (477 mg, 8.916 mmol) in a mixture of water (10 mL) and methanol (10 mL) as per the process described in step 2 of Intermediate 14 to yield 234 mg of the product as a semi-solid. $^1$H NMR (300 MHz, DMSO-$d_6$) δ 5.02-5.08 (m, 6H), 6.10 (d, J=8.7 Hz, 1H), 6.20 (d, J=13.2 Hz, 1H), 6.47 (t, J=9.3 Hz, 1H), 7.04 (t, J=9.3 Hz, 1H), 7.25 (t, J=8.7 Hz, 1H).

Intermediate 144

4-{[1-(2,4-Difluorophenyl)cyclopentyl]oxy}-3-fluoroaniline

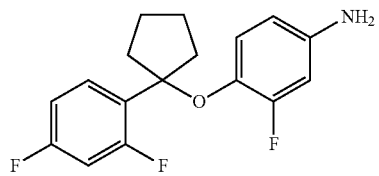 [SMILES: Nc1ccc(OC2(c3ccc(F)cc3F)CCCC2)c(F)c1]

Step 1: 1-(2,4-Difluorophenyl)cyclopentanol

The title compound was synthesized by the reaction of 1-bromo-2,4-difluorobenzene (2.0 mL, 17.700 mmol) and cyclopetanone (1.9 mL, 21.240 mmol) in presence of n-butyl lithium (1.6 M in THF, 13.2 mL) in diethyl ether (20 mL) as per the process described in step 1 of Intermediate 31 to yield 1.58 g of the product as a semi-solid. $^1$H NMR (300 MHz, DMSO-$d_6$) δ 1.71-1.98 (m, 8H), 5.01 (s, 1H), 7.00-7.17 (m, 2H), 7.64 (q, J=7.2 Hz, 1H).

Step 2: 1-{[1-(2,4-Difluorophenyl)cyclopentyl]oxy}-2-fluoro-4-nitrobenzene

The title compound was prepared by the reaction of step 1 intermediate (500 mg, 2.522 mmol) with 3,4-difluoro-1-nitrobenzene (401 mg, 2.522 mmol) by using sodium hydride (60% w/w, 121 mg, 3.027 mmol) in dry DMF (10 mL) as per the process described in step 2 of Intermediate 1 to yield 75 mg of the product as a semi-solid. $^1$H NMR (300 MHz, DMSO-$d_6$) δ 1.79-1.82 (m, 4H), 2.23-2.27 (m, 2H), 2.42-2.49 (m, 1H), 2.65-2.67 (m, 1H), 6.77 (t, J=9.0 Hz, 1H), 7.07-7.12 (m, 1H), 7.24 (t, J=10.5 Hz, 1H), 7.51-7.56 (m, 1H), 7.83 (d, J=9.6 Hz, 1H), 8.10 (d, J=10.5 Hz, 1H).

Step 3: 4-{[1-(2,4-Difluorophenyl)cyclopentyl]oxy}-3-fluoroaniline

The title compound was prepared by the nitro reduction of step 2 intermediate (70 mg, 0.208 mmol) using iron powder (58 mg, 1.037 mmol) and ammonium chloride (111 mg, 2.075 mmol) in a mixture of water (5 mL) and methanol (5 mL) as per the process described in step 2 of Intermediate 14 to yield 16 mg of the product as a semi-solid. $^1$H NMR (300 MHz, DMSO-$d_6$) δ 1.71-1.87 (m, 2H), 1.88-1.92 (m, 4H), 2.42-2.47 (m, 2H), 4.98 (s, 2H), 6.00-6.23 (m, 3H), 6.94-6.97 (m, 1H), 7.12-7.18 (m, 1H), 7.25-7.31 (m, 1H).

Intermediate 145

2-[2-(2,4-Dichlorophenoxy)propan-2-yl]-1-ethyl-1H-benzimidazol-5-amine

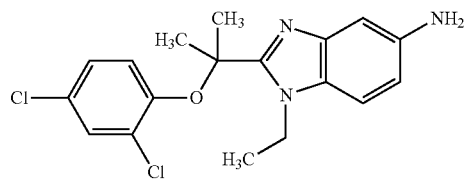 [SMILES: CCn1c(C(C)(C)Oc2ccc(Cl)cc2Cl)nc2cc(N)ccc21]

Step 1: 2-(2,4-Dichlorophenoxy)-N-[2-(ethylamino)-5-nitrophenyl]-2-methylpropanamide The title compound was prepared by the coupling reaction of 2-(2,4-dichlorophenoxy)-2-methylpropanoic acid (500 mg, 2.007 mmol) and $N^1$-ethyl-4-nitrobenzene-1,2-diamine (436 mg, 2.408 mmol) using oxalyl chloride (0.87 mL, 10.035 mmol) in presence of triethylamine (0.56 mL, 4.082 mmol) in DCM (10 mL) as per the process described in step 1 of Intermediate 132 to yield 750 mg of the product as a solid. $^1$H NMR (300 MHz, DMSO-$d_6$) δ 1.12 (t, J=7.2 Hz, 3H), 1.61 (s, 6H), 3.22 (t, J=6.3 Hz, 2H), 5.84 (s, 1H), 6.77 (d, J=9.9 Hz, 1H), 7.10 (d, J=8.7 Hz, 1H), 7.41 (d, J=9.0 Hz, 1H), 7.68 (s, 1H), 8.00 (s, 2H), 9.69 (s, 1H); APCI-MS (m/z) 412 (M+H)$^+$.

Step 2: 2-[2-(2,4-Dichlorophenoxy)propan-2-yl]-1-ethyl-5-nitro-1H-benzimidazole A suspension of step 1 intermediate (750 mg, 18.180 mmol) in acetic acid (20 mL) was heated to 120° C. for 16 h. The excess acetic acid was removed under reduced pressure. The residue was diluted with ethyl acetate (15 mL) and water (10 mL). The organic layer was separated and washed with water (10 mL) followed by brine (10 mL) and dried over anhydrous sodium sulfate. The solvent was distilled off and the residue thus obtained was purified by silica gel column chromatography to yield 360 mg of the title compound as a solid. $^1$H NMR (300 MHz, DMSO-$d_6$) δ 1.24 (t, J=6.9 Hz, 3H), 1.90 (s, 6H), 4.60 (q, J=7.2 Hz, 2H), 6.40 (d, J=8.7 Hz, 1H), 7.15 (d, J=9.3 Hz, 1H), 7.66 (s, 1H), 7.86 (d, J=8.7 Hz, 1H), 8.19-8.21 (m, 1H), 8.60 (s, 1H); ESI-MS (m/z) 394 (M+H)$^+$.

Step 3: 2-[2-(2,4-Dichlorophenoxy)propan-2-yl]-1-ethyl-1H-benzimidazol-5-amine The title compound was prepared by the reduction of step 2 intermediate (140 mg, 0.355 mmol) using iron powder (95 mg, 1.776 mmol) and ammonium chloride (190 mg, 3.550 mmol) in a mixture of water (3 mL), methanol (3 mL) and THF (10 mL) as per the process described in step 2 of Intermediate 14 to yield 115 mg of the product as a semi-solid. ESI-MS (m/z) 363 (M)$^+$.

Intermediate 146

2-[2-(2,4-Difluorophenoxy)propan-2-yl]-1-(2-fluoroethyl)-1H-benzimidazol-5-amine

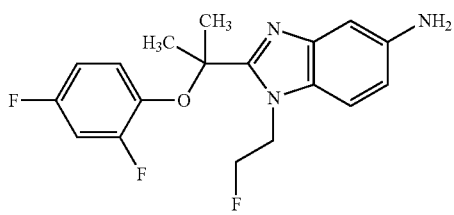 [SMILES: CC(C)(Oc1ccc(F)cc1F)c1nc2cc(N)ccc2n1CCF]

Step 1: 2-(2,4-Difluorophenoxy)-N-{2-[(2-fluoroethyl)amino]-5-nitrophenyl}-2-methylpropanamide To a stirred solution of 2-(2,4-fluorophenoxy)-2-methylpropanoic acid (338 mg, 1.568 mmol) in dichloromethane (10 mL) were added catalytic amount of dry DMF and oxalyl chloride (0.68 mL, 7.840 mmol) at RT. The reaction mixture was stirred at room temperature for 2 h. The excess of oxalyl chloride was distilled off under reduced pressure and the residue was dissolved in DCM (10 mL). To that solution were added $N^1$-(2-fluoroethyl)-4-nitrobenzene-1,2-diamine (375 mg, 1.882 mmol) and triethylamine (0.44 mL, 3.136 mmol) at 0° C. The reaction mixture was stirred at RT for 16 h. The mixture was concentrated under reduced pressure. The residue was diluted with ethyl acetate (25 mL) and water (25 mL). The layers were separated and the aqueous layer was extracted with ethyl acetate (2×25 mL). The combined organic extracts were washed with water (50 mL) and brine (25 mL). The solution was dried over anhydrous sodium sulfate, filtered and concentrated under reduced pressure. The residue obtained was purified by silica gel column chromatography to yield 505 mg of the title compound as a solid. $^1$H NMR (300 MHz, DMSO-$d_6$) δ 1.54 (s, 6H), 3.52-3.57 (m, 1H), 3.60-3.65 (m, 1H), 4.47-4.51 (m, 1H), 4.65-4.68 (m, 1H), 6.15-6.18 (m, 1H), 6.88 (d, J=9.6 Hz, 1H), 7.00-7.10 (m, 1H), 7.20-7.25 (m, 1H), 7.35-7.40 (m, 1H), 8.05 (br s, 2H), 9.72 (s, 1H).

Step 2: 2-[2-(2,4-Difluorophenoxy)propan-2-yl]-1-(2-fluoroethyl)-5-nitro-1H-benzimidazole A suspension of step 1 intermediate (500 mg, 1.258 mmol) in acetic acid (10 mL) was heated to 120° C. for 48 h. The excess acetic acid was removed under reduced pressure. The residue was diluted with ethyl acetate (25 mL) and water (25 mL). The organic layer was separated and washed with water (2×20 mL) followed by brine (20 mL) and dried over anhydrous sodium sulfate. The solvent was distilled off and the residue thus obtained was purified by silica gel column chromatography to yield 250 mg of the title compound as a solid. $^1$H NMR (300 MHz, DMSO-$d_6$) δ 1.80 (s, 6H), 4.75-4.79 (m, 1H), 4.92-5.07 (m, 3H), 6.74-6.78 (m, 1H), 6.88-6.92 (m, 1H), 7.30-7.33 (m, 1H), 7.86 (d, J=9.3 Hz, 1H), 8.22 (d, J=9.0 Hz, 1H), 8.56 (s, 1H).

Step 3: 2-[2-(2,4-Difluorophenoxy)propan-2-yl]-1-(2-fluoroethyl)-1H-benzimidazol-5-amine To a stirred solution of step 2 intermediate (60 mg, 0.158 mmol) in a mixture of THF (10 mL), methanol (3 mL) and water (3 mL) were added iron powder (44 mg, 0.793 mmol) and ammonium chloride (84 mg, 1.582 mmol) at RT. The reaction mixture was heated to 80° C. and stirred for 1 h. The reaction mixture cooled to RT and filtered off the suspended emulsion. The filtrate was concentrated under reduced pressure and diluted with water (20 mL). The aqueous mixture was extracted with ethyl acetate (2×20 mL). The combined organic layers were washed with water (30 mL) followed by brine (30 mL) and dried over anhydrous sodium sulfate. The solvents were recovered under reduced pressure and the residue obtained was purified by silica gel column chromatography to yield 55 mg of the title product as a solid. $^1$H NMR (300 MHz, DMSO-$d_6$) δ 1.76 (s, 6H), 4.68-4.72 (m, 2H), 4.80-4.83 (m, 4H), 6.49-6.52 (m, 1H), 6.63 (d, J=8.7 Hz, 1H), 6.76 (s, 1H), 6.85-6.87 (m, 1H), 7.23-7.32 (m, 2H).

EXAMPLES

Example 1

N-(4-{[2-(3,4-Difluorophenyl)propan-2-yl]oxy}phenyl)-2-[4(ethylsulfonyl)phenyl]acetamide

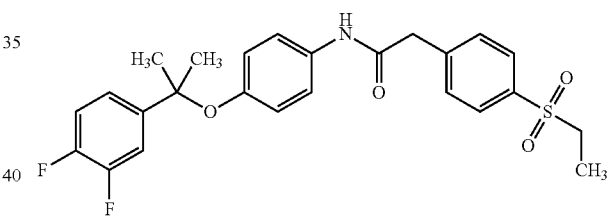

To a well stirred solution of [4-(ethylsulfonyl)phenyl]acetic acid (50 mg, 0.219 mmol) in dry DCM (5 mL) was added EDCI.HCl (50 mg, 0.262 mmol) followed by HOBt (41 mg, 0.306 mmol) and the reaction mixture was stirred at room temperature for 30 min. Intermediate 1 (58 mg, 0.219 mmol) was added to the reaction mixture and stirred at RT for 18 h. The reaction mixture was concentrated under reduced pressure to yield a viscous residue. The residue was diluted with water (10 mL) and extracted with ethyl acetate (3×10 mL). The combined organic extracts were washed with aqueous sodium bicarbonate solution (10 mL), water (2×20 mL) and brine (20 mL). The organic layer was dried over anhydrous sodium sulfate and the solvent was distilled off under reduced pressure. The residue obtained was purified by silica gel column chromatography to yield 47 mg of the title product as a solid. $^1$H NMR (300 MHz, DMSO-$d_6$) δ 1.08 (t, J=7.2 Hz, 3H), 1.59 (s, 6H), 3.26 (q, J=7.2 Hz, 2H), 3.73 (s, 2H), 6.64 (d, J=8.1 Hz, 2H), 7.31 (br s, 1H), 7.38 (d, J=9.0 Hz, 2H), 7.43-7.49 (m, 2H), 7.57 (d, J=7.2 Hz, 2H), 7.82 (d, J=7.8 Hz, 2H), 10.12 (br s, 1H); APCI-MS (m/z) 473 (M+H)$^+$.

Example 2

N-(4-{[2-(2,4-Difluorophenyl)propan-2-yl]oxy}phenyl)-2-[4-(ethylsulfonyl)phenyl]acetamide

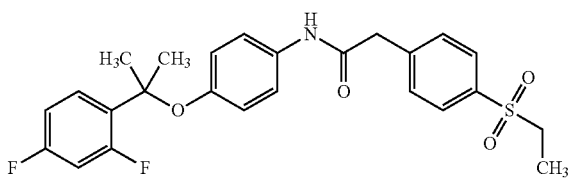 [SMILES: CCS(=O)(=O)c1ccc(CC(=O)Nc2ccc(OC(C)(C)c3ccc(F)cc3F)cc2)cc1]

The title compound was prepared by the reaction of Intermediate 2 (58 mg, 0.219 mmol) with [4-(ethylsulfonyl)phenyl]acetic acid (50 mg, 0.219 mmol) using EDCI.HCl (50 mg, 0.262 mmol) and HOBt (41 mg, 0.306 mmol) in DCM (4 mL) as per the process described in Example 1 to yield 79 mg of the product as a solid. $^1$H NMR (300 MHz, DMSO-$d_6$) δ 1.08 (t, J=7.2 Hz, 3H), 1.65 (s, 6H), 3.26 (q, J=7.2 Hz, 2H), 3.73 (s, 2H), 6.67 (d, J=8.7 Hz, 2H), 7.06 (t, J=8.7 Hz, 1H), 7.23 (t, J=9.3 Hz, 1H), 7.38 (d, J=9.0 Hz, 2H), 7.45-7.51 (m, 1H), 7.57 (d, J=8.1 Hz, 2H), 7.82 (d, J=8.1 Hz, 2H), 10.13 (br s, 1H); APCI-MS (m/z) 473 (M+H)$^+$.

Example 3

N-(4-{[2-(2,4-Dichlorophenyl)propan-2-yl]oxy}phenyl)-2-[4-(ethylsulfonyl)phenyl]acetamide

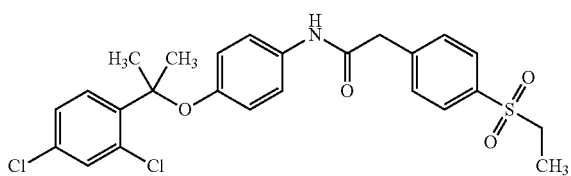 [SMILES: CCS(=O)(=O)c1ccc(CC(=O)Nc2ccc(OC(C)(C)c3ccc(Cl)cc3Cl)cc2)cc1]

To a well stirred solution of [4-(ethylsulfonyl)phenyl]acetic acid (50 mg, 0.219 mmol) in dry DCM (5 mL) was added EDCI.HCl (50 mg, 0.262 mmol) followed by HOBt (41 mg, 0.306 mmol) and the reaction mixture was stirred at room temperature for 30 minutes. Intermediate 3 (65 mg, 0.219 mmol) was added to the reaction mixture and it was further stirred for 18 hours. The reaction mixture was diluted with water (10 mL) and extracted with ethyl acetate (3×10 mL). The combined organic extracts were washed with saturated aqueous sodium bicarbonate solution (20 mL), water (2×20 mL), brine (20 mL). The organic solution was dried over anhydrous sodium sulfate. The solvent was distilled off under reduced pressure and the residue obtained was purified by silica gel column chromatography to yield 63 mg of the title product as a solid. $^1$H NMR (300 MHz, DMSO-$d_6$) δ 1.08 (t, J=7.2 Hz, 3H), 1.73 (s, 6H), 3.25 (q, J=6.9 Hz, 2H), 3.72 (s, 2H), 6.61 (d, J=9.0 Hz, 2H), 7.35 (d, J=9.0 Hz, 2H), 7.44 (t, J=7.8 Hz, 1H), 7.57 (br s, 4H), 7.82 (d, J=7.8 Hz, 2H), 10.09 (br s, 1H); ESI-MS (m/z) 506 (M+H)$^+$.

Example 4

N-(4-{[2-(3,4-Dichlorophenyl)propan-2-yl]oxy}phenyl)-2-[4-(ethylsulfonyl)phenyl]acetamide

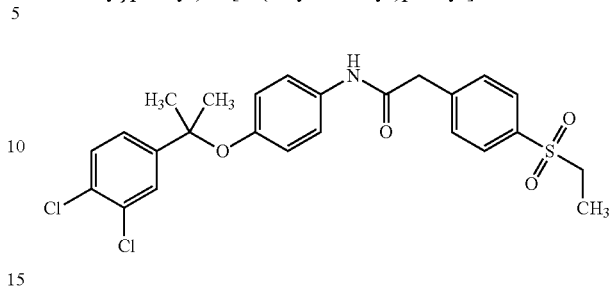

The title compound was prepared by the reaction of Intermediate 4 (70 mg, 0.236 mmol) with [4-(ethylsulfonyl)phenyl]acetic acid (53 mg, 0.236 mmol) using EDCI.HCl (54 mg, 0.283 mmol) and HOBt (38 mg, 0.283 mmol) in DCM (5 mL) as per the process described in Example 1 to yield 19 mg of the product as a solid. $^1$H NMR (300 MHz, DMSO-$d_6$) δ 1.07 (t, J=7.2 Hz, 3H), 1.59 (m, 6H), 3.26 (q, J=7.2 Hz, 2H), 3.73 (s, 2H), 6.65 (d, J=8.7 Hz, 2H), 7.38 (d, J=9.0 Hz, 2H), 7.48 (br s, 1H), 7.56-7.67 (m, 4H), 7.82 (d, J=8.4 Hz, 2H), 10.14 (br s, 1H); APCI-MS (m/z) 506 (M)$^+$.

Example 5

N-(4-{[2-(3,5-Dichlorophenyl)propan-2-yl]oxy}phenyl)-2-[4-(ethylsulfonyl)phenyl]acetamide

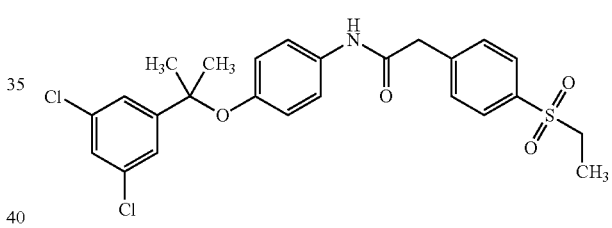

The title compound was prepared by the reaction of Intermediate 5 (65 mg, 0.219 mmol) with [4-(ethylsulfonyl)phenyl]acetic acid (50 mg, 0.219 mmol) using EDCI.HCl (50 mg, 0.262 mmol) and HOBt (41 mg, 0.306 mmol) in DCM (4 mL) as per the process described in Example 1 to yield 71 mg of the product as a solid. $^1$H NMR (300 MHz, DMSO-$d_6$) δ 1.08 (t, J=7.2 Hz, 3H), 1.59 (s, 6H), 3.26 (q, J=7.2 Hz, 2H), 3.74 (s, 2H), 6.67 (d, J=9.0 Hz, 2H), 7.40 (d, J=8.4 Hz, 2H), 7.49 (br s, 2H), 7.53-7.59 (m, 3H), 7.82 (d, J=7.8 Hz, 2H), 10.14 (br s, 1H); APCI-MS (m/z) 506 (M+H)$^+$.

Example 6

N-(4-{[2-(4-Chloro-2-fluorophenyl)propan-2-yl]oxy}phenyl)-2-[4-(ethylsulfonyl)phenyl]acetamide

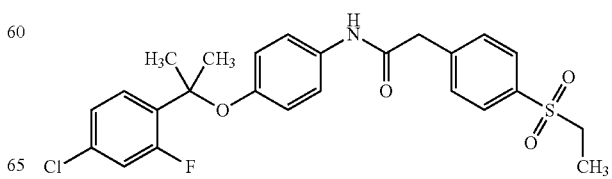

The title compound was prepared by the reaction of Intermediate 6 (61 mg, 0.219 mmol) with [4-(ethylsulfonyl)phenyl]acetic acid (50 mg, 0.219 mmol) using EDCI.HCl (50 mg, 0.262 mmol) and HOBt (41 mg, 0.306 mmol) in DCM (4 mL) as per the process described in Example 1 to yield 64 mg of the product as a solid. $^1$H NMR (300 MHz, DMSO-$d_6$) δ 1.06 (t, J=7.2 Hz, 3H), 1.63 (s, 6H), 3.24 (q, J=7.2 Hz, 2H), 3.71 (s, 2H), 6.66 (d, J=8.7 Hz, 2H), 7.26 (d, J=8.7 Hz, 1H), 7.36 (d, J=8.7 Hz, 2H), 7.42-7.49 (m, 2H), 7.55 (d, J=7.8 Hz, 2H), 7.80 (d, J=8.1 Hz, 2H), 10.12 (br s, 1H); APCI-MS (m/z) 489 (M)$^+$.

Example 7

N-{4-[1-(4-Chloro-3-fluoro-phenyl)-1-methyl-ethoxy]-phenyl}-2-(4-ethanesulfonyl-phenyl)-acetamide

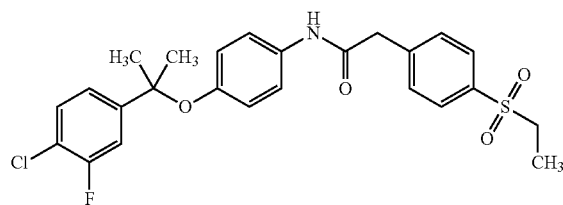 [SMILES: CCS(=O)(=O)c1ccc(CC(=O)Nc2ccc(OC(C)(C)c3ccc(Cl)c(F)c3)cc2)cc1]

The title compound was prepared by the reaction of Intermediate 7 (61 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (4 mL) as per the process described in Example 1 to yield 66 mg of the product as a solid. $^1$H NMR (300 MHz, DMSO-$d_6$) δ 1.08 (t, J=7.2 Hz, 3H), 1.59 (s, 6H), 3.24 (q, J=7.2 Hz, 2H), 3.73 (s, 2H), 6.66 (d, J=8.7 Hz, 2H), 7.31-7.40 (m, 3H), 7.41-7.58 (m, 4H), 7.83 (d, J=8.1 Hz, 2H), 10.12 (br s, 1H); ESI-MS (m/z) 489 (M+H)$^+$.

Example 8

N-(4-{[2-(2-Chloro-4-fluorophenyl)propan-2-yl]oxy}phenyl)-2-[4-(ethylsulfonyl) phenyl]acetamide

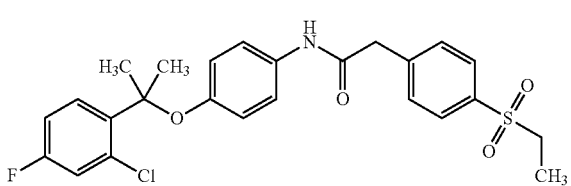

The title compound was prepared by the reaction of Intermediate 8 (50 mg, 0.219 mmol) with [4-(ethylsulfonyl)phenyl]acetic acid (61 mg, 0.219 mmol) using EDCI.HCl (50 mg, 0.262 mmol) and HOBt (39 mg, 0.293 mmol) in DCM (4 mL) as per the process described in Example 1 to yield 46 mg of the product as a solid. $^1$H NMR (300 MHz, DMSO-$d_6$) δ 1.06 (t, J=7.2 Hz, 3H), 1.72 (s, 6H), 3.24 (q, J=7.2 Hz, 2H), 3.70 (s, 2H), 6.58 (d, J=8.7 Hz, 2H), 7.21 (br s, 1H), 7.32 (d, J=8.7 Hz, 2H), 7.35-7.41 (m, 1H), 7.54 (d, J=7.8 Hz, 2H), 7.61 (br s, 1H), 7.80 (d, J=8.4 Hz, 2H), 10.08 (br s, 1H); ESI-MS (m/z) 489 (M)$^+$.

Example 9

2-[4-(Ethylsulfonyl)phenyl]-N-[4-({2-[4-(trifluoromethyl)phenyl]propan-2-yl}oxy) phenyl]acetamide

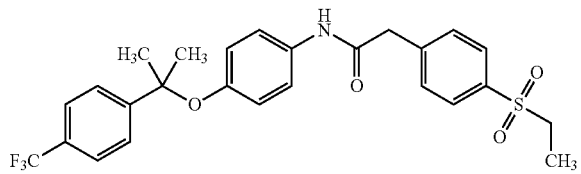 [SMILES: CCS(=O)(=O)c1ccc(CC(=O)Nc2ccc(OC(C)(C)c3ccc(C(F)(F)F)cc3)cc2)cc1]

The title compound was prepared by the reaction of Intermediate 9 (65 mg, 0.219 mmol) with [4-(ethylsulfonyl)phenyl]acetic acid (50 mg, 0.219 mmol) using EDCI.HCl (50 mg, 0.262 mmol) and HOBt (41 mg, 0.306 mmol) in DCM (4 mL) as per the process described in Example 1 to yield 71 mg of the product as a solid. $^1$H NMR (300 MHz, DMSO-$d_6$) δ 1.08 (t, J=7.5 Hz, 3H), 1.63 (s, 6H), 3.26 (q, J=7.2 Hz, 2H), 3.73 (s, 2H), 6.63 (d, J=7.8 Hz, 2H), 7.37 (d, J=7.8 Hz, 2H), 7.57 (d, J=7.2 Hz, 2H), 7.71-7.77 (m, 4H), 7.82 (d, J=7.8 Hz, 2H), 10.11 (br s, 1H); APCI-MS (m/z) 504 (M−H)$^+$.

Example 10

2-(4-Ethanesulfonyl-phenyl)-N-{4-[1-(3-fluoro-4-trifluoromethyl-phenyl)-1-methyl-ethoxy]-phenyl}-acetamide

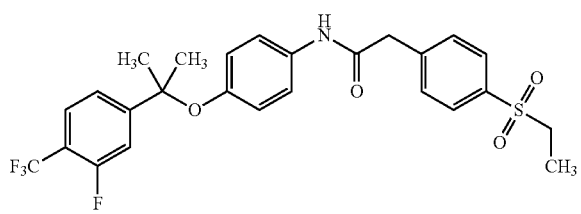 [SMILES: CCS(=O)(=O)c1ccc(CC(=O)Nc2ccc(OC(C)(C)c3ccc(C(F)(F)F)c(F)c3)cc2)cc1]

The title compound was prepared by the reaction of Intermediate 10 (68 mg, 0.219 mmol) with [4-(ethylsulfonyl)phenyl]acetic acid (50 mg, 0.219 mmol) using EDCI.HCl (50 mg, 0.262 mmol) and HOBt (41 mg, 0.306 mmol) in DCM (4 mL) as per the process described in Example 1 to yield 76 mg of the product as a solid. $^1$H NMR (300 MHz, CDCl$_3$) δ 1.28 (t, J=7.2 Hz, 3H), 1.66 (s, 6H), 3.12 (q, J=7.2 Hz, 2H), 3.77 (s, 2H), 6.64 (d, J=8.7 Hz, 2H), 7.12 (s, 1H), 7.24-7.34 (m, 4H), 7.51-7.60 (m, 2H), 7.90 (d, J=8.4 Hz, 2H); ESI-MS (m/z) 524 (M−H)$^+$.

Example 11

N-{4-[1-(3,5-Dichloro-pyridin-2-yl)-1-methyl-ethoxy]-phenyl}-2-(4-ethanesulfonyl-phenyl)-acetamide

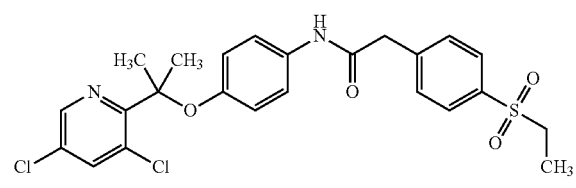

The title compound was prepared by the reaction of Intermediate 11 (65 mg, 0.218 mmol) with [4-(ethylsulfonyl)phenyl]acetic acid (49 mg, 0.218 mmol) using EDCI.HCl (50 mg, 0.262 mmol) and HOBt (44 mg, 0.328 mmol) in DCM (5 mL) as per the process described in Example 1 to yield 40 mg of the product as a solid. $^1$H NMR (300 MHz, DMSO-d$_6$) δ 1.08 (t, J=7.5 Hz, 3H), 1.75 (s, 6H), 3.24 (q, J=7.2 Hz, 2H), 3.71 (s, 2H), 6.50 (d, J=9.3 Hz, 2H), 7.33 (d, J=9.3 Hz, 2H), 7.57 (d, J=7.8 Hz, 2H), 7.83 (d, J=8.4 Hz, 2H), 8.17 (s, 1H), 8.64 (s, 1H), 10.07 (br s, 1H); ESI-MS (m/z) 507 (M+H)$^+$.

Example 12

N-{4-[1-(4-Chloro-3-fluoro-phenyl)-1-ethyl-propoxy]-phenyl}-2-(4-ethanesulfonyl-phenyl)-acetamide

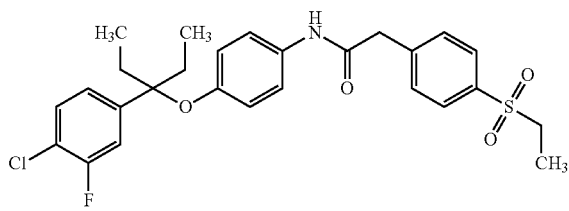 [SMILES: CCC(CC)(Oc1ccc(NC(=O)Cc2ccc(S(=O)(=O)CC)cc2)cc1)c1ccc(Cl)c(F)c1]

The title compound was prepared by the reaction of Intermediate 12 (67 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (5 mL) as per the process described in Example 1 to yield 117 mg of the product as a solid. $^1$H NMR (300 MHz, DMSO-d$_6$) δ 0.66 (t, J=7.5 Hz, 6H), 1.08 (t, J=7.2 Hz, 3H), 2.02 (q, J=7.2 Hz, 4H), 3.24 (q, J=7.2 Hz, 2H), 3.72 (s, 2H), 6.70 (d, J=9.3 Hz, 2H), 7.28 (d, J=7.5 Hz, 1H), 7.37-7.44 (m, 3H), 7.54-7.59 (m, 3H), 7.84 (d, J=8.4 Hz, 2H), 10.12 (s, 1H); ESI-MS (m/z) 515 (M+H)$^+$.

Example 13

N-{4-[1-(2,4-Difluoro-phenyl)-1-ethyl-propoxy]-phenyl}-2-(4-ethanesulfonyl-phenyl)-acetamide

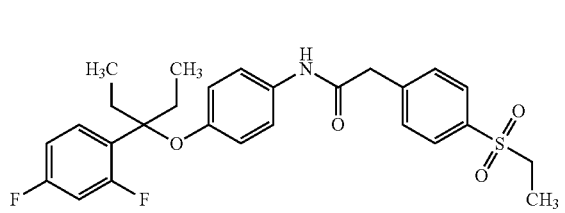 [SMILES: CCC(CC)(Oc1ccc(NC(=O)Cc2ccc(S(=O)(=O)CC)cc2)cc1)c1ccc(F)cc1F]

The title compound was prepared by the reaction of Intermediate 13 (64 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (5 mL) as per the process described in Example 1 to yield 108 mg of the product as a solid. $^1$H NMR (300 MHz, DMSO-d$_6$) δ 0.66 (t, J=7.2 Hz, 6H), 1.06 (t, J=7.2 Hz, 3H), 2.02 (q, J=7.2 Hz, 4H), 3.24 (q, J=7.2 Hz, 2H), 3.32 (s, 2H), 6.73 (d, J=8.7 Hz, 2H), 7.07-7.21 (m, 2H), 7.38 (d, J=9.3 Hz, 2H), 7.55 (d, J=8.4 Hz, 3H), 7.80 (d, J=8.4 Hz, 2H), 10.12 (s, 1H); APCI-MS (m/z) 499 (M+H)$^+$.

Example 14

N-(4-{[2-(1-ethyl-6-fluoro-1H-benzimidazol-2-yl)propan-2-yl]oxy}phenyl)-2-[4-(ethylsulfonyl)phenyl]acetamide

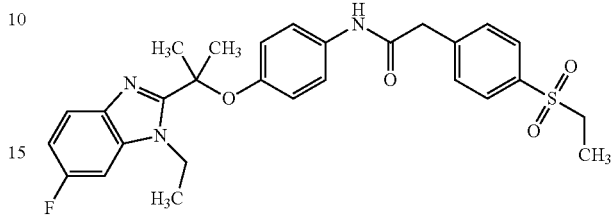

The title compound was prepared by the reaction of Intermediate 14 (50 mg, 0.218 mmol) with [4-(ethylsulfonyl)phenyl]acetic acid (82 mg, 0.262 mmol) using EDCI.HCl (50 mg, 0.261 mmol) and HOBt (36 mg, 0.261 mmol) in DCM (5 mL) as per the process described in Example 1 to yield 42 mg of the product as a solid. $^1$H NMR (300 MHz, DMSO-d$_6$) δ 1.07 (t, J=6.9 Hz, 3H), 1.19 (t, J=6.3 Hz, 3H), 1.79 (s, 6H), 3.25 (q, J=7.8 Hz, 2H), 3.71 (s, 2H), 4.50 (q, J=7.8 Hz, 2H), 6.57 (d, J=8.4 Hz, 2H), 7.07 (br s, 1H), 7.35 (d, J=8.1 Hz, 2H), 7.48 (t, J=9.3 Hz, 1H), 7.55 (d, J=7.8 Hz, 2H), 7.65 (br s, 1H), 7.80 (d, J=7.8 Hz, 2H), 10.12 (br s, 1H).

Example 15

2-(4-Ethanesulfonyl-phenyl)-N-{4-[1-(1-ethyl-5-fluoro-1H-benzoimidazol-2-yl)-1-methyl-ethoxy]-phenyl}-acetamide

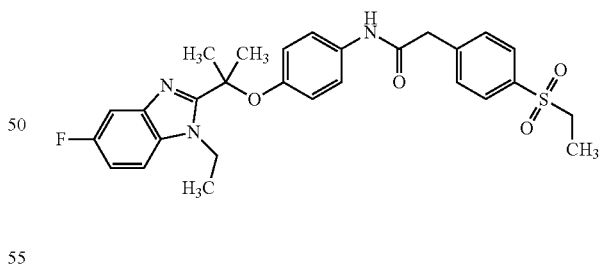

The title compound was prepared by the reaction of Intermediate 15 (15 mg, 0.047 mmol) with [4-(ethylsulfonyl)phenyl]acetic acid (9 mg, 0.039 mmol) using EDCI.HCl (9 mg, 0.047 mmol) and HOBt (6.5 mg, 0.047 mmol) in DCM (3 mL) as per the process described in Example 1 to yield 410 mg of the product as a solid. $^1$H NMR (300 MHz, DMSO-d$_6$) δ 1.07 (t, J=7.2 Hz, 3H), 1.20 (t, J=6.9 Hz, 3H), 1.79 (s, 6H), 3.23 (q, J=7.8 Hz, 2H), 3.70 (s, 2H), 4.51 (q, J=6.9 Hz, 2H), 6.58 (d, J=9.3 Hz, 2H), 7.12-7.14 (m, 2H), 7.36 (d, J=8.4 Hz, 2H), 7.45-7.56 (m, 3H), 7.81 (d, J=7.8 Hz, 2H), 10.14 (s, 1H); ESI-MS (m/z) 524 (M+H)$^+$.

Example 16

N-(4-{[2-(5-Chloro-1-ethyl-1H-benzimidazol-2-yl)propan-2-yl]oxy}phenyl)-2-[4-(ethylsulfonyl)phenyl]acetamide

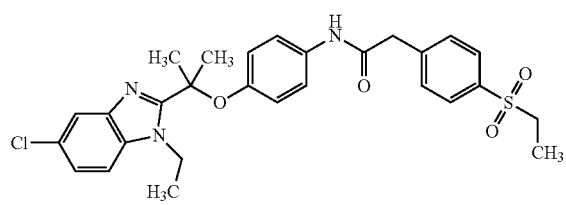 [SMILES: CCn1c(C(C)(C)Oc2ccc(NC(=O)Cc3ccc(S(=O)(=O)CC)cc3)cc2)nc2cc(Cl)ccc21]

The title compound was prepared by the reaction of Intermediate 16 (69 mg, 0.210 mmol) with [4-(ethylsulfonyl)phenyl]acetic acid (40 mg, 0.175 mmol) using EDCI.HCl (40 mg, 0.210 mmol) and HOBt (28 mg, 0.210 mmol) in DCM (5 mL) as per the process described in Example 1 to yield 62 mg of the product as a solid. $^1$H NMR (300 MHz, DMSO-$d_6$) δ 1.07 (t, J=7.2 Hz, 3H), 1.18-1.22 (m, 3H), 1.79 (s, 6H), 3.25 (q, J=7.2 Hz, 2H), 3.71 (s, 2H), 4.53 (d, J=6.9 Hz, 2H), 6.56 (d, J=8.7 Hz, 2H), 7.30 (d, J=8.1 Hz, 1H), 7.35 (t, J=8.7 Hz, 2H), 7.55 (d, J=7.8 Hz, 2H), 7.61 (d, J=8.7 Hz, 1H), 7.73 (s, 1H), 7.81 (d, J=7.8 Hz, 2H), 10.13 (br s, 1H); APCI-MS (m/z) 540 (M)$^+$.

Example 17

N-(4-{[2-(6-Chloro-1-ethyl-1H-benzimidazol-2-yl)propan-2-yl]oxy}phenyl)-2-[4-(ethylsulfonyl)phenyl]acetamide

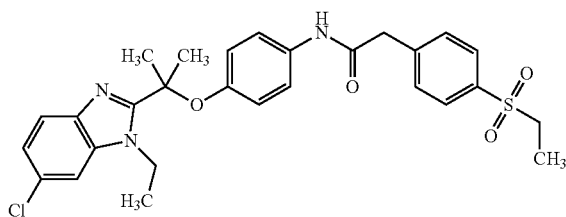 [SMILES: CCn1c(C(C)(C)Oc2ccc(NC(=O)Cc3ccc(S(=O)(=O)CC)cc3)cc2)nc2ccc(Cl)cc21]

The title compound was prepared by the reaction of Intermediate 17 (86 mg, 0.262 mmol) with [4-(ethylsulfonyl)phenyl]acetic acid (50 mg, 0.218 mmol) using EDCI.HCl (50 mg, 0.261 mmol) and HOBt (36 mg, 0.261 mmol) in DCM (5 mL) as per the process described in Example 1 to yield 66 mg of the product as a solid. $^1$H NMR (300 MHz, DMSO-$d_6$) δ 1.07 (br s, 3H), 1.18-1.23 (m, 3H), 1.79 (s, 6H), 3.25 (q, J=7.2 Hz, 2H), 3.71 (s, 2H), 4.53 (d, J=7.2 Hz, 2H), 6.57 (d, J=7.8 Hz, 2H), 7.24 (d, J=9.3 Hz, 1H), 7.35 (t, J=8.4 Hz, 2H), 7.55 (d, J=7.8 Hz, 2H), 7.66 (d, J=9.3 Hz, 1H), 7.71 (s, 1H), 7.81 (d, J=7.2 Hz, 2H), 10.12 (br s, 1H); APCI-MS (m/z) 540 (M)$^+$.

Example 18

N-{4-[1-(6-Chloro-1-methyl-1H-benzoimidazol-2-yl)-1-methyl-ethoxy]-phenyl}-2-(4-ethanesulfonyl-phenyl)-acetamide

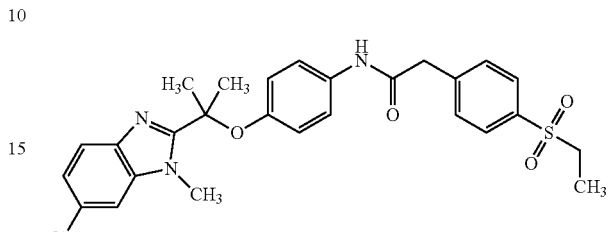

The title compound was prepared by the reaction of Intermediate 18 (83 mg, 0.262 mmol) with [4-(ethylsulfonyl)phenyl]acetic acid (50 mg, 0.218 mmol) using EDCI.HCl (50 mg, 0.261 mmol) and HOBt (36 mg, 0.261 mmol) in DCM (5 mL) as per the process described in Example 1 to yield 81 mg of the product as a solid. $^1$H NMR (300 MHz, DMSO-$d_6$) δ 1.07 (br s, 3H), 1.79 (s, 6H), 3.25 (q, J=7.2 Hz, 2H), 3.70 (s, 2H), 3.91 (s, 3H), 6.55 (d, J=8.7 Hz, 2H), 7.24 (d, J=7.8 Hz, 1H), 7.35 (d, J=8.7 Hz, 2H), 7.56 (d, J=7.8 Hz, 2H), 7.63-7.71 (m, 2H), 7.82 (d, J=7.8 Hz, 2H), 10.12 (br s, 1H); APCI-MS (m/z) 525 (M)$^+$.

Example 19

N-(4-{[2-(7-Chloro-1-ethyl-1H-benzimidazol-2-yl)propan-2-yl]oxy}phenyl)-2-[4-(ethylsulfonyl) phenyl]acetamide

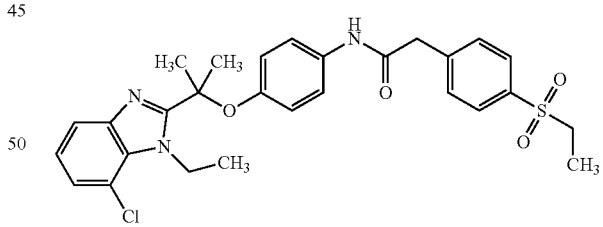

The title compound was prepared by the reaction of Intermediate 19 (86 mg, 0.262 mmol) with [4-(ethylsulfonyl)phenyl]acetic acid (50 mg, 0.218 mmol) using EDCI.HCl (50 mg, 0.262 mmol) and HOBt (35 mg, 0.261 mmol) in DCM (5 mL) as per the process described in Example 1 to yield 106 mg of the product as a solid. $^1$H NMR (300 MHz, DMSO-$d_6$) δ 1.05 (t, J=7.2 Hz, 3H), 1.26 (t, J=6.9 Hz, 3H), 1.80 (s, 6H), 3.23 (q, J=7.5 Hz, 2H), 3.70 (s, 2H), 4.76 (q, J=6.6 Hz, 2H), 6.59 (d, J=9.3 Hz, 2H), 7.20 (t, J=7.8 Hz, 1H), 7.30 (d, J=7.8 Hz, 1H), 7.36 (d, J=8.7 Hz, 2H), 7.53 (d, J=8.1 Hz, 2H), 7.64 (d, J=7.8 Hz, 1H), 7.79 (d, J=8.1 Hz, 2H), 10.12 (br s, 1H).

Example 20

2-(4-Ethanesulfonyl-phenyl)-N-{4-[1-(5-fluoro-1-isopropyl-1H-benzoimidazol-2-yl)-1-methyl-ethoxy]-phenyl}-acetamide

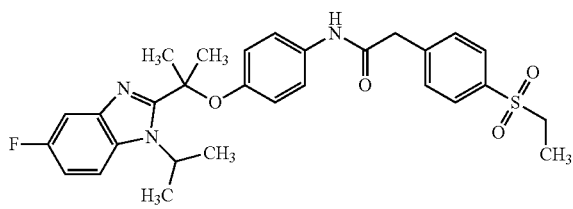

The title compound was prepared by the reaction of Intermediate 20 (86 mg, 0.262 mmol) with [4-(ethylsulfonyl)phenyl]acetic acid (50 mg, 0.218 mmol) using EDCI. HCl (50 mg, 0.262 mmol) and HOBt (35 mg, 0.261 mmol) in DCM (5 mL) as per the process described in Example 1 to yield 77 mg of the product as a solid. $^1$H NMR (300 MHz, DMSO-$d_6$) δ 1.07 (t, J=6.3 Hz, 3H), 1.38 (d, J=6.9 Hz, 6H), 1.82 (s, 6H), 3.66 (q, J=9.0 Hz, 2H), 5.40-5.42 (m, 1H), 6.56 (d, J=9.3 Hz, 2H), 7.08 (t, J=7.5 Hz, 1H), 7.35 (d, J=8.7 Hz, 2H), 7.51-7.56 (m, 3H), 7.71-7.82 (m, 3H), 10.11 (s, 1H); ESI-MS (m/z) 538 (M)$^+$.

Example 21

N-{4-[1-(5-Chloro-1-ethyl-1H-indol-2-yl)-1-methyl-ethoxy]-phenyl}-2-(4-ethanesulfonyl-phenyl)-acetamide

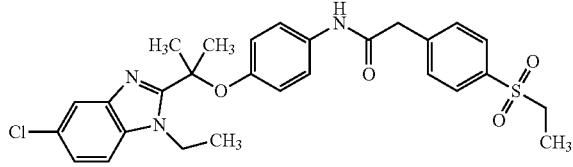 [SMILES: CCn1c(C(C)(C)Oc2ccc(NC(=O)Cc3ccc(S(=O)(=O)CC)cc3)cc2)nc2cc(Cl)ccc21]

The title compound was prepared by the reaction of Intermediate 21 (86 mg, 0.263 mmol) with [4-(ethylsulfonyl)phenyl]acetic acid (50 mg, 0.219 mmol) using EDCI. HCl (50 mg, 0.263 mmol) and HOBt (36 mg, 0.262 mmol) in DCM (5 mL) as per the process described in Example 1 to yield 65 mg of the product as a solid. $^1$H NMR (300 MHz, DMSO-$d_6$) δ 1.07 (t, J=7.5 Hz, 3H), 1.22 (t, J=7.2 Hz, 3H), 1.73 (s, 6H), 3.23 (q, J=7.5 Hz, 2H), 3.70 (s, 2H), 4.53 (q, J=6.6 Hz, 2H), 6.39 (s, 1H), 6.60 (d, J=9.0 Hz, 2H), 7.15 (d, J 8.7 Hz, 1H), 7.33 (d, J=8.7 Hz, 2H), 7.46 (d, J=8.7 Hz, 1H), 7.55 (d, J=8.4 Hz, 3H), 7.80 (d, J=7.8 Hz, 2H), 10.08 (br s, 1H).

Example 22

N-{4-[(5-Chloro-1-ethyl-1H-benzoimidazol-2-yl)-difluoro-methoxy]-phenyl}-2-(4-ethanesulfonyl-phenyl)-acetamide

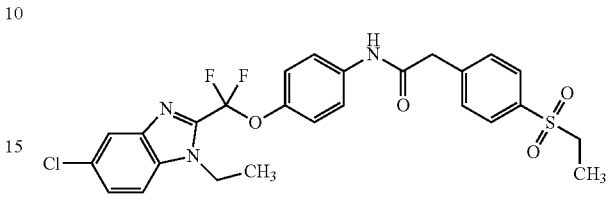

The title compound was prepared by the reaction of Intermediate 22 (84 mg, 0.262 mmol) with [4-(ethylsulfonyl)phenyl]acetic acid (50 mg, 0.218 mmol) using EDCI. HCl (50 mg, 0.262 mmol) and HOBt (36 mg, 0.262 mmol) in DCM (5 mL) as per the process described in Example 1 to yield 97 mg of the product as a solid. $^1$H NMR (300 MHz, DMSO-$d_6$) δ 1.09 (t, J=7.2 Hz, 3H), 1.40 (t, J=6.9 Hz, 3H), 3.26 (q, J=7.8 Hz, 2H), 3.81 (s, 2H), 4.55 (q, J=6.6 Hz, 2H), 7.35 (d, J=9.0 Hz, 2H), 7.49 (d, J=9.3 Hz, 1H), 7.66 (dd, J=9.3, 22.5 Hz, 4H), 7.85-7.89 (m, 4H), 10.42 (br s, 1H); ESI-MS (m/z) 548 (M)$^+$.

Example 23

N-(4-{[1-(6-Chloro-1-ethyl-1H-benzimidazol-2-yl)cyclopropyl]oxy}phenyl)-2-[4-(ethylsulfonyl)phenyl]acetamide

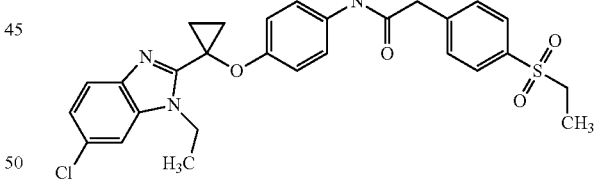

The title compound was prepared by the reaction of Intermediate 23 (86 mg, 0.262 mmol) with [4-(ethylsulfonyl)phenyl]acetic acid (50 mg, 0.218 mmol) using EDCI. HCl (50 mg, 0.262 mmol) and HOBt (36 mg, 0.261 mmol) in DCM (5 mL) as per the process described in Example 1 to yield 103 mg of the product as a solid. $^1$H NMR (300 MHz, DMSO-$d_6$) δ 1.06 (t, J=6.3 Hz, 3H), 1.28 (t, J=6.3 Hz, 3H), 1.42 (br s, 2H), 1.57 (br s, 2H), 3.24 (q, J=6.9 Hz, 2H), 3.70 (s, 2H), 4.44 (q, J=7.2 Hz, 2H), 7.08 (d, J=8.4 Hz, 2H), 7.20 (d, J=8.7 Hz, 1H), 7.42 (d, J=8.7 Hz, 1H), 7.54 (d, J=7.8 Hz, 2H), 7.63 (d, J=8.4 Hz, 2H), 7.79 (s, 1H), 7.80 (d, J=7.2 Hz, 2H), 10.12 (br s, 1H); ESI-MS (m/z) 538 (M+H)$^+$.

Example 24

N-{4-[1-(5-Chloro-1-ethyl-1H-benzoimidazol-2-yl)-cyclopropoxy]-phenyl}-2-(4-ethanesulfonyl-phenyl)-acetamide

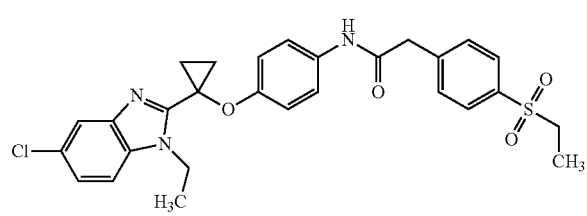 [SMILES: CCn1c(C2(Oc3ccc(NC(=O)Cc4ccc(S(=O)(=O)CC)cc4)cc3)CC2)nc2cc(Cl)ccc21]

The title compound was prepared by the reaction of Intermediate 24 (60 mg, 0.183 mmol) with [4-(ethylsulfonyl)phenyl]acetic acid (35 mg, 0.2153 mmol) using EDCI.HCl (35 mg, 0.183 mmol) and HOBt (25 mg, 0.2183 mmol) in DCM (5 mL) as per the process described in Example 1 to yield 63 mg of the product as a solid. $^1$H NMR (300 MHz, DMSO-$d_6$) δ 1.07 (t, J=7.5 Hz, 3H), 1.28 (t, J=6.3 Hz, 3H), 1.42 (br s, 2H), 1.43 (br s, 2H), 1.58 (br s, 2H), 3.26 (q, J=7.8 Hz, 2H), 3.70 (s, 2H), 4.44 (q, J=6.6 Hz, 2H), 7.09 (d, J=8.7 Hz, 2H), 7.27 (d, J=8.7 Hz, 1H), 7.43 (d, J=8.7 Hz, 2H), 7.53-7.60 (m, 3H), 7.70 (s, 1H), 7.81 (d, J=7.8 Hz, 2H), 10.11 (s, 1H); ESI-MS (m/z) 538 (M+H)$^+$.

Example 25

N-{4-[1-(5-Chloro-1-methyl-1H-benzoimidazol-2-yl)-cyclobutoxy]-phenyl}-2-(4-ethanesulfonyl-phenyl)-acetamide

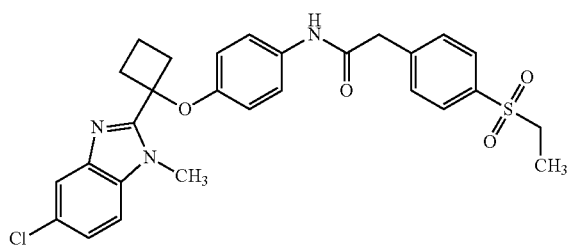 [SMILES: CCS(=O)(=O)c1ccc(CC(=O)Nc2ccc(OC3(c4nc5cc(Cl)ccc5n4C)CCC3)cc2)cc1]

The title compound was prepared by the reaction of Intermediate 25 (12 mg, 0.036 mmol) with [4-(ethylsulfonyl)phenyl]acetic acid (7 mg, 0.030 mmol) using EDCI.HCl (7 mg, 0.036 mmol) and HOBt (5 mg, 0.036 mmol) in DCM (2 mL) as per the process described in Example 1 to yield 11 mg of the product as a solid. $^1$H NMR (300 MHz, DMSO-$d_6$) δ 1.06 (t, J=7.2 Hz, 3H), 1.80-1.85 (m, 1H), 1.91-1.96 (m, 1H), 2.64-2.72 (m, 2H), 3.02-3.05 (m, 2H), 3.23 (q, J=7.2 Hz, 2H), 3.68 (s, 2H), 3.76 (s, 3H), 6.76 (d, J=9.0 Hz, 2H), 7.25-7.34 (m, 3H), 7.54 (d, J=8.7 Hz, 3H), 7.76-7.81 (m, 3H), 10.05 (br s, 1H); ESI-MS (m/z) 538 (M)$^+$.

Example 26

2-(4-Ethanesulfonyl-phenyl)-N-{4-[1-(1-ethyl-5-fluoro-1H-benzoimidazol-2-yl)-cyclobutoxy]-phenyl}-acetamide

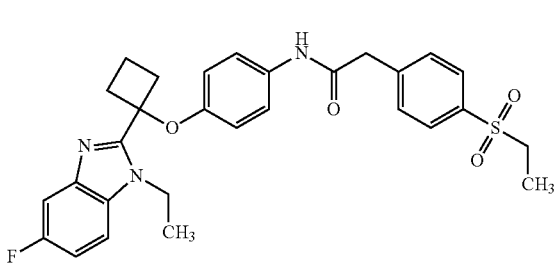 [SMILES: CCn1c(C2(Oc3ccc(NC(=O)Cc4ccc(S(=O)(=O)CC)cc4)cc3)CCC2)nc2cc(F)ccc21]

The title compound was prepared by the reaction of Intermediate 26 (22 mg, 0.068 mmol) with [4-(ethylsulfonyl)phenyl]acetic acid (13 mg, 0.056 mmol) using EDCI.HCl (13 mg, 0.068 mmol) and HOBt (9 mg, 0.068 mmol) in DCM (5 mL) as per the process described in Example 1 to yield 17 mg of the product as a solid. $^1$H NMR (300 MHz, DMSO-$d_6$) δ 1.06 (t, J=7.2 Hz, 3H), 1.17 (t, J=7.2 Hz, 3H), 1.82-1.84 (m, 1H), 1.98-2.00 (m, 1H), 2.61-2.65 (m, 2H), 3.02-3.05 (m, 2H), 3.23 (q, J=7.8 Hz, 2H), 3.69 (s, 2H), 4.29 (d, J=7.5 Hz, 2H), 6.76 (d, J=8.7 Hz, 2H), 7.10-7.12 (m, 1H), 7.36 (d, J=9.3 Hz, 2H), 7.55 (d, J=8.4 Hz, 4H), 7.81 (d, J=8.4 Hz, 2H), 10.05 (s, 1H); ESI-MS (m/z) 536 (M+H)$^+$.

Example 27

N-{4-[1-(6-Chloro-[1,2,4]triazolo[4,3-a]pyridin-3-yl)-cyclobutoxy]-phenyl}-2-(4-ethanesulfonyl-phenyl)-acetamide

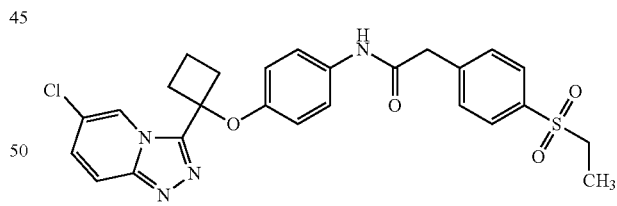

The title compound was prepared by the reaction of Intermediate 27 (50 mg, 0.158 mmol) with [4-(ethylsulfonyl)phenyl]acetic acid (36 mg, 0.158 mmol) using EDCI.HCl (36 mg, 0.190 mmol) and HOBt (32 mg, 0.238 mmol) in DCM (5 mL) as per the process described in Example 1 to yield 8 mg of the product as a solid. $^1$H NMR (300 MHz, DMSO-$d_6$) δ 1.07 (t, J=7.5 Hz, 3H), 1.75-1.78 (m, 1H), 1.89-1.98 (m, 1H), 2.75-2.80 (m, 2H), 2.90-3.02 (m, 2H), 3.23 (q, J=7.5 Hz, 2H), 3.68 (s, 2H), 6.74 (d, J=9.0 Hz, 2H), 7.33 (d, J=8.7 Hz, 2H), 7.45 (d, J=9.9 Hz, 1H), 7.54 (d, J=7.8 Hz, 2H), 7.78-7.87 (m, 3H), 8.45 (s, 1H), 10.07 (s, 1H); ESI-MS (m/z) 525 (M)$^+$.

Example 28

N-(4-{1-[5-(4-Chloro-phenyl)-[1,2,4]oxadiazol-3-yl]-1-methyl-ethoxy}-phenyl)-2-(4-ethanesulfonyl-phenyl)-acetamide

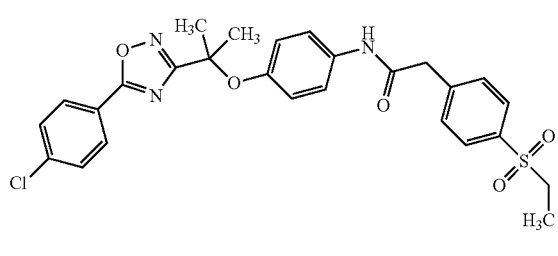 [SMILES: CCS(=O)(=O)c1ccc(CC(=O)Nc2ccc(OC(C)(C)c3noc(-c4ccc(Cl)cc4)n3)cc2)cc1]

The title compound was prepared by the reaction of Intermediate 28 (15 mg, 0.045 mmol) with [4-(ethylsulfonyl)phenyl]acetic acid (8.6 mg, 0.038 mmol) using EDCI.HCl (9 mg, 0.045 mmol) and HOBt (6 mg, 0.045 mmol) in DCM (5 mL) as per the process described in Example 1 to yield 19 mg of the product as a semi-solid. $^1$H NMR (300 MHz, DMSO-$d_6$) δ 1.07 (t, J=7.5 Hz, 3H), 1.70 (s, 6H), 3.26 (q, J=7.5 Hz, 2H), 3.63-3.85 (m, 2H), 6.75 (d, J=8.7 Hz, 2H), 7.43 (d, J=8.7 Hz, 2H), 7.58 (d, J=6.9 Hz, 2H), 7.73 (d, J=7.8 Hz, 2H), 7.82 (t, J=6.6 Hz, 2H), 8.16 (d, J=7.2 Hz, 2H), 10.19 (br s, 1H); APCI-MS (m/z) 541 (M+H)$^+$.

Example 29

N-(4-{[1-(5-Chloro-1H-indol-1-yl)-2-methylpropan-2-yl]oxy}phenyl)-2-[4-(ethylsulfonyl)phenyl]acetamide

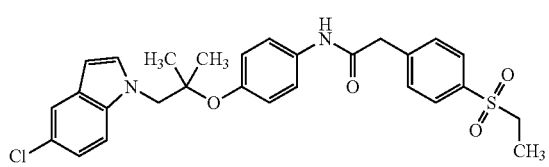 [SMILES: CCS(=O)(=O)c1ccc(CC(=O)Nc2ccc(OC(C)(C)Cn3ccc4cc(Cl)ccc43)cc2)cc1]

The title compound was prepared by the reaction of Intermediate 29 (68 mg, 0.219 mmol) with [4-(ethylsulfonyl)phenyl]acetic acid (50 mg, 0.219 mmol) using EDCI.HCl (50 mg, 0.262 mmol) and HOBt (39 mg, 0.293 mmol) in DCM (5 mL) as per the process described in Example 1 to yield 21 mg of the product as a solid. $^1$H NMR (300 MHz, DMSO-$d_6$) δ 1.08 (br s, 3H), 1.22 (br s, 6H), 3.27 (br s, 2H), 3.74 (s, 2H), 4.38 (br s, 2H), 6.46 (br s, 2H), 6.80 (br s, 2H), 7.11 (br s, 1H), 7.46 (br s, 3H), 7.59 (br s, 3H), 7.81 (br s, 2H), 10.18 (br s, 1H); APCI-MS (m/z) 524 (M+H)$^+$.

Example 30

2-[4-(Ethylsulfonyl)phenyl]-N-(4-{[1-(5-fluoro-2-methyl-1H-indol-1-yl)-2-methylpropan-2-yl]oxy}phenyl)acetamide

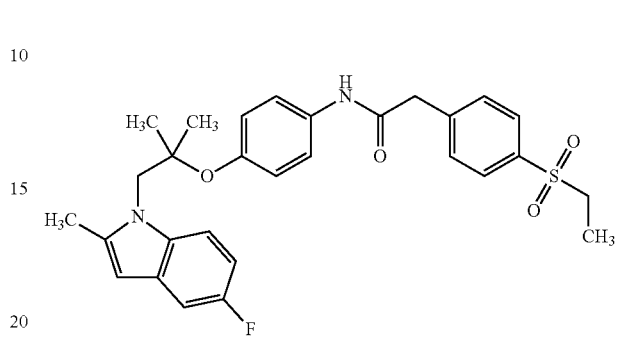

The title compound was prepared by the reaction of Intermediate 30 (68 mg, 0.219 mmol) with [4-(ethylsulfonyl)phenyl]acetic acid (50 mg, 0.219 mmol) using EDCI.HCl (50 mg, 0.262 mmol) and HOBt (44 mg, 0.328 mmol) in DCM (10 mL) as per the process described in Example 1 to yield 41 mg of the product as a solid. $^1$H NMR (300 MHz, DMSO-$d_6$) δ 1.08 (t, J=7.2 Hz, 3H), 1.17 (br s, 6H), 2.46 (s, 3H), 3.26 (q, J=7.2 Hz, 2H), 3.74 (s, 2H), 4.38 (s, 2H), 6.25 (s, 1H), 6.72 (d, J=8.7 Hz, 2H), 6.83 (t, J=7.5 Hz, 1H), 7.16 (d, J=9.6 Hz, 1H), 7.42 (d, J=8.7 Hz, 2H), 7.49-7.54 (m, 1H), 7.57 (d, J=8.1 Hz, 2H), 7.82 (d, J=8.4 Hz, 2H), 10.18 (br s, 1H); APCI-MS (m/z) 523 (M+H)$^+$.

Example 31

N-{4-[1-(4-Chloro-phenyl)-cyclobutoxy]-phenyl}-2-(4-ethanesulfonyl-phenyl)-acetamide

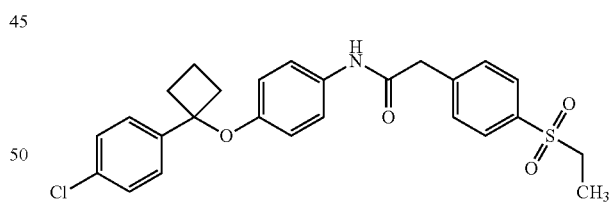

The title compound was prepared by the reaction of Intermediate 31 (60 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (4 mL) as per the process described in Example 1 to yield 87 mg of the product as a solid. $^1$H NMR (300 MHz, DMSO-$d_6$) δ 1.07 (t, J=7.2 Hz, 3H), 1.78-1.82 (m, 1H), 1.83-1.95 (m, 1H), 2.56-2.58 (m, 3H), 3.25 (q, J=7.5 Hz, 2H), 3.70 (s, 2H), 6.53 (d, J=9.0 Hz, 2H), 7.34 (d, J=9.3 Hz, 2H), 7.41 (d, J=8.7 Hz, 2H), 7.50 (d, J=8.7 Hz, 2H), 7.57 (d, J=8.4 Hz, 2H), 7.82 (d, J=8.4 Hz, 2H), 10.04 (br s, 1H)

Example 32

N-(4-{[1-(4-Chloro-3-fluorophenyl)cyclobutyl]oxy}phenyl)-2-[4-(ethylsulfonyl) phenyl]acetamide

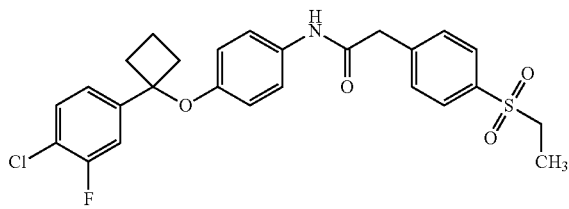

The title compound was prepared by the reaction of Intermediate 32 (60 mg, 0.219 mmol) with [4-(ethylsulfonyl)phenyl]acetic acid (50 mg, 0.219 mmol) using EDCI. HCl (50 mg, 0.262 mmol) and HOBt (44 mg, 0.328 mmol) in DCM (5 mL) as per the process described in Example 1 to yield 42 mg of the product as a solid. $^1$H NMR (300 MHz, DMSO-$d_6$) δ 1.07 (t, J=7.2 Hz, 3H), 1.66-1.71 (m, 1H), 1.95 (br s, 1H), 2.58-2.63 (m, 2H), 2.74 (br s, 2H), 3.25 (q, J=7.5 Hz, 2H), 3.70 (s, 2H), 6.62 (d, J=8.4 Hz, 2H), 7.19 (d, J=8.4 Hz, 1H), 7.34 (d, J=8.4 Hz, 2H), 7.50-7.57 (m, 4H), 7.81 (d, J=7.8 Hz, 2H), 10.07 (br s, 1H); APCI-MS (m/z) 502 (M+H)$^+$.

Example 33

N-(4-{[1-(4-Chloro-2-fluorophenyl)cyclobutyl]oxy}phenyl)-2-[4-(ethylsulfonyl) phenyl]acetamide

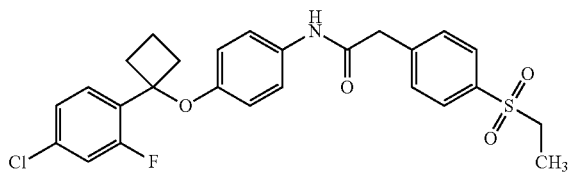 [SMILES: CCS(=O)(=O)c1ccc(CC(=O)Nc2ccc(OC3(c4ccc(Cl)cc4F)CCC3)cc2)cc1]

The title compound was prepared by the reaction of Intermediate 33 (64 mg, 0.219 mmol) with [4-(ethylsulfonyl)phenyl]acetic acid (50 mg, 0.219 mmol) using EDCI. HCl (50 mg, 0.262 mmol) and HOBt (40 mg, 0.306 mmol) in DCM (5 mL) as per the process described in Example 1 to yield 91 mg of the product as a solid. $^1$H NMR (300 MHz, DMSO-$d_6$) δ 1.08 (t, J=7.5 Hz, 3H), 1.84 (br s, 1H), 2.24-2.30 (m, 1H), 2.77 (br s, 4H), 3.26 (q, J=7.2 Hz, 2H), 3.72 (s, 2H), 6.66 (d, J=9.3 Hz, 2H), 7.09-7.15 (m, 1H), 7.23-7.32 (m, 2H), 7.36 (d, J=9.0 Hz, 2H), 7.56 (d, J=7.8 Hz, 2H), 7.82 (d, J=7.8 Hz, 2H), 10.11 (br s, 1H).

Example 34

N-{4-[1-(3,4-Difluoro-phenyl)-cyclobutoxy]-phenyl}-2-(4-ethanesulfonyl-phenyl)-acetamide

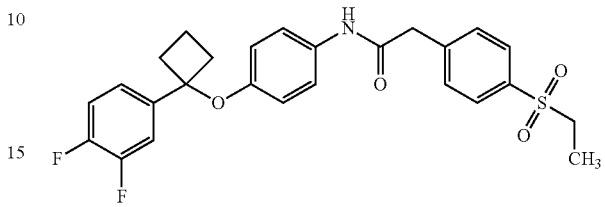

The title compound was prepared by the reaction of Intermediate 34 (60 mg, 0.219 mmol) with [4-(ethylsulfonyl)phenyl]acetic acid (50 mg, 0.219 mmol) using EDCI. HCl (50 mg, 0.262 mmol) and HOBt (40 mg, 0.306 mmol) in DCM (4.0 mL) as per the process described in Example 1 to yield 81 mg of the product as a solid. $^1$H NMR (300 MHz, DMSO-$d_6$) δ 1.08 (t, J=7.5 Hz, 3H), 1.67-1.74 (m, 1H), 1.92-1.98 (m, 1H), 2.60-2.66 (m, 2H), 2.70-2.76 (m, 2H), 3.24 (q, J=7.2 Hz, 2H), 3.71 (s, 2H), 6.64 (d, J=8.4 Hz, 2H), 7.15-7.20 (m, 1H), 7.31-7.41 (m, 4H), 7.57 (d, J=7.8 Hz, 2H), 7.82 (d, J=7.8 Hz, 2H), 10.06 (br s, 1H); ESI-MS (m/z) 485 (M+H)$^+$.

Example 35

N-{4-[4-(3,4-Difluoro-phenyl)-tetrahydro-pyran-4-yloxy]-phenyl}-2-(4-ethanesulfonyl-phenyl)-acetamide

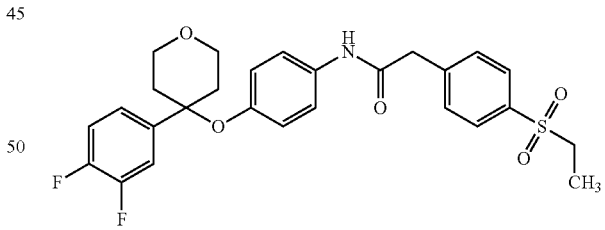

The title compound was prepared by the reaction of Intermediate 35 (67 mg, 0.219 mmol) with [4-(ethylsulfonyl)phenyl]acetic acid (50 mg, 0.219 mmol) using EDCI. HCl (50 mg, 0.262 mmol) and HOBt (40 mg, 0.306 mmol) in DCM (4.0 mL) as per the process described in Example 1 to yield 88 mg of the product as a solid. $^1$H NMR (300 MHz, DMSO-$d_6$) δ 1.07 (t, J=7.5 Hz, 3H), 2.25-2.35 (m, 4H), 3.25 (q, J=7.8 Hz, 2H), 3.70-3.81 (m, 6H), 6.64 (d, J=8.7 Hz, 2H), 7.25-7.41 (m, 5H), 7.57 (d, J=7.8 Hz, 2H), 7.82 (d, J=7.8 Hz, 2H), 10.11 (br s, 1H).

Example 36

N-(4-{[4-(4-Chloro-2-fluorophenyl)tetrahydro-2H-pyran-4-yl]oxy}phenyl)-2-[4-(ethylsulfonyl)phenyl]acetamide

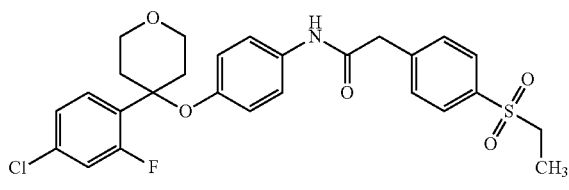 [SMILES: CCS(=O)(=O)c1ccc(CC(=O)Nc2ccc(OC3(c4ccc(Cl)cc4F)CCOCC3)cc2)cc1]

The title compound was prepared by the reaction of Intermediate 36 (71 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (5 mL) as per the process described in Example 1 to yield 81 mg of the product as a solid. $^1$H NMR (300 MHz, DMSO-$d_6$) δ 1.07 (t, J=7.2 Hz, 3H), 2.30 (br s, 2H), 2.57-2.63 (m, 2H), 3.25 (q, J=7.2 Hz, 2H), 3.71 (s, 4H), 3.76-3.81 (m, 2H), 6.63 (d, J=8.7 Hz, 2H), 7.26-7.35 (m, 5H), 7.56 (d, J=7.8 Hz, 2H), 7.81 (d, J=8.1 Hz, 2H), 10.08 (br s, 1H).

Example 37

N-{4-[4-(4-Chlorophenyl)-tetrahydro-pyran-4-yloxy]-phenyl}-2-(4-ethanesulfonyl-phenyl)-acetamide

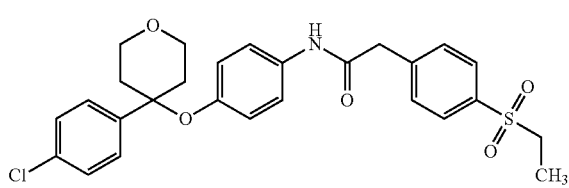 [SMILES: CCS(=O)(=O)c1ccc(CC(=O)Nc2ccc(OC3(c4ccc(Cl)cc4)CCOCC3)cc2)cc1]

The title compound was prepared by the reaction of Intermediate 37 (66 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (4.0 mL) as per the process described in Example 1 to yield 94 mg of the product as a solid. $^1$H NMR (300 MHz, DMSO-$d_6$) δ 1.07 (t, J=7.2 Hz, 3H), 2.09 (br s, 4H), 3.25 (q, J=7.2 Hz, 2H), 3.71 (s, 6H), 6.55 (d, J=8.7 Hz, 2H), 7.33 (d, J=8.4 Hz, 2H), 7.45 (br s, 4H), 7.57 (d, J=8.4 Hz, 2H), 7.83 (d, J=8.4 Hz, 2H), 10.09 (br s, 1H).

Example 38

N-{4-[4-(4-Chloro-3-fluoro-phenyl)-tetrahydro-pyran-4-yloxy]-phenyl}-2-(4-ethanesulfonyl-phenyl)-acetamide

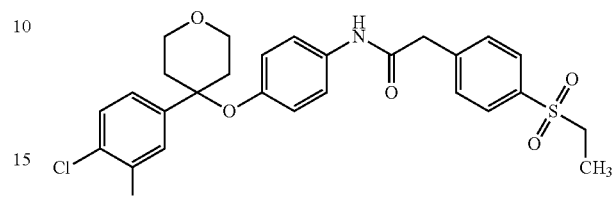

The title compound was prepared by the reaction of Intermediate 38 (70 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (5.0 mL) as per the process described in Example 1 to yield 81 mg of the product as a solid. $^1$H NMR (300 MHz, DMSO-$d_6$) δ 1.07 (t, J=7.2 Hz, 3H), 2.09 (br s, 4H), 3.25 (q, J=7.2 Hz, 2H), 3.71 (br s, 6H), 6.63 (d, J=8.7 Hz, 2H), 7.24-7.26 (m, 1H), 7.36 (d, J=9.0 Hz, 2H), 7.41-7.44 (m, 2H), 7.57 (d, J=8.4 Hz, 2H), 7.82 (d, J=7.8 Hz, 2H), 10.11 (br s, 1H); ESI-MS (m/z) 529 (M−H)⁻.

Example 39

N-{4-[4-(3,4-Dichloro-phenyl)-tetrahydro-pyran-4-yloxy]-phenyl}-2-(4-ethanesulfonyl-phenyl)-acetamide

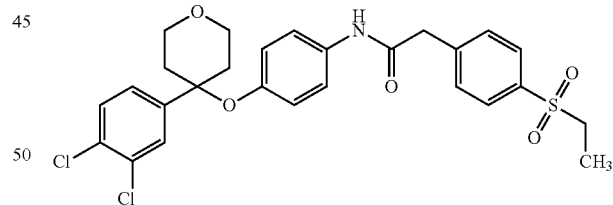

The title compound was prepared by the reaction of Intermediate 39 (148 mg, 0.438 mmol) with [4-(ethylsulfonyl)phenyl]acetic acid (100 mg, 0.438 mmol) using EDCI.HCl (101 mg, 0.525 mmol) and HOBt (83 mg, 0.613 mmol) in DCM (10 mL) as per the process described in Example 1 to yield 148 mg of the product as a solid. $^1$H NMR (300 MHz, DMSO-$d_6$) δ 1.07 (t, J=7.2 Hz, 3H), 2.10 (br s, 4H), 3.25 (q, J=7.2 Hz, 2H), 3.71 (br s, 6H), 6.58 (d, J=8.1 Hz, 2H), 7.36 (d, J=8.1 Hz, 2H), 7.46 (d, J=8.7 Hz, 1H), 7.57 (d, J=7.8 Hz, 2H), 7.67 (d, J=8.7 Hz, 2H), 7.83 (d, J=7.8 Hz, 2H), 10.10 (br s, 1H).

Example 40

N-{4-[4-(2,4-Dichloro-phenyl)-tetrahydro-pyran-4-yloxy]-phenyl}-2-(4-ethanesulfonyl-phenyl)-acetamide

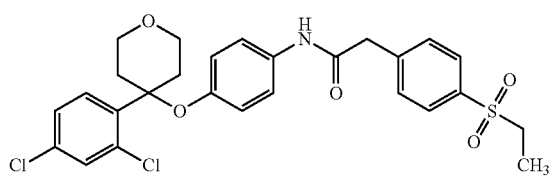 [SMILES: CCS(=O)(=O)c1ccc(CC(=O)Nc2ccc(OC3(c4ccc(Cl)cc4Cl)CCOCC3)cc2)cc1]

To a well stirred solution of [4-(ethylsulfonyl)phenyl]acetic acid (50 mg, 0.219 mmol) in dry DCM (5 mL) was added EDCI.HCl (50 mg, 0.262 mmol) followed by HOBt (41 mg, 0.306 mmol) and the reaction mixture was stirred at room temperature for 30 min. Intermediate 40 (74 mg, 0.219 mmol) was added to the reaction mixture and it was stirred at RT for 24 h. The mixture was diluted with water (10 mL) and extracted with ethyl acetate (3×10 mL). The combined organic extracts were washed with saturated aqueous sodium bicarbonate solution (20 mL), water (2×20 mL) and brine (20 mL). The organic layer was dried over anhydrous sodium sulfate and the solvent was distilled off under reduced pressure. The residue obtained was purified by silica gel column chromatography to yield 53 mg of the title product as a solid. $^1$H NMR (300 MHz, DMSO-$d_6$) δ 1.07 (t, J=7.2 Hz, 3H), 2.10 (br s, 2H), 2.40-2.45 (m, 2H), 3.25 (q, J=7.2 Hz, 2H), 3.71-3.79 (m, 6H), 6.57 (d, J=8.7 Hz, 2H), 7.32 (d, J=9.3 Hz, 2H), 7.49-7.62 (m, 5H), 7.82 (d, J=8.4 Hz, 2H), 10.08 (br s, 1H); APCI-MS (m/z) 545 (M–H)$^-$.

Example 41

2-(4-Ethanesulfonyl-phenyl)-N-{4-[4-(3-fluoro-4-trifluoromethyl-phenyl)-tetrahydro-pyran-4-yloxy]-phenyl}-acetamide

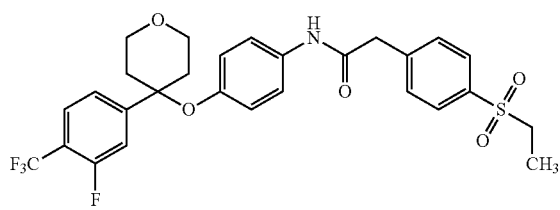 [SMILES: CCS(=O)(=O)c1ccc(CC(=O)Nc2ccc(OC3(c4ccc(C(F)(F)F)c(F)c4)CCOCC3)cc2)cc1]

The title compound was prepared by the reaction of Intermediate 41 (58 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (5 mL) as per the process described in Example 1 to yield 58 mg of the product as a solid. $^1$H NMR (300 MHz, DMSO-$d_6$) δ 1.07 (t, J=7.2 Hz, 3H), 2.13 (br s, 4H), 3.25 (q, J=7.2 Hz, 2H), 3.71 (br s, 6H), 6.57 (d, J=9.0 Hz, 2H), 7.35 (d, J=9.0 Hz, 2H), 7.49-7.57 (m, 4H), 7.80-7.83 (m, 3H), 10.11 (br s, 1H).

Example 42

2-(4-Ethanesulfonyl-phenyl)-N-{4-[4-(4-fluoro-3-trifluoromethyl-phenyl)-tetrahydro-pyran-4-yloxy]-phenyl}-acetamide

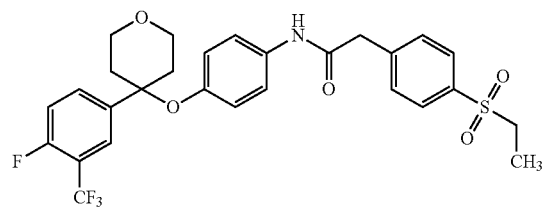 [SMILES: CCS(=O)(=O)c1ccc(CC(=O)Nc2ccc(OC3(c4ccc(F)c(C(F)(F)F)c4)CCOCC3)cc2)cc1]

The title compound was prepared by the reaction of Intermediate 42 (78 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (5 mL) as per the process described in Example 1 to yield 90 mg of the product as a solid. $^1$H NMR (300 MHz, DMSO-$d_6$) δ 1.07 (t, J=7.2 Hz, 3H), 2.14 (br s, 4H), 3.25 (q, J=7.2 Hz, 2H), 3.71 (br s, 6H), 6.54 (d, J=9.0 Hz, 2H), 7.35 (d, J=8.7 Hz, 2H), 7.56 (d, J=8.1 Hz, 3H), 7.76 (br s, 1H), 7.81 (d, J=8.4 Hz, 3H), 10.10 (br s, 1H).

Example 43

N-(4-{[4-(4-Chloro-3-fluorophenyl)piperidin-4-yl]oxy}phenyl)-2-[4-(ethylsulfonyl)phenyl]acetamide

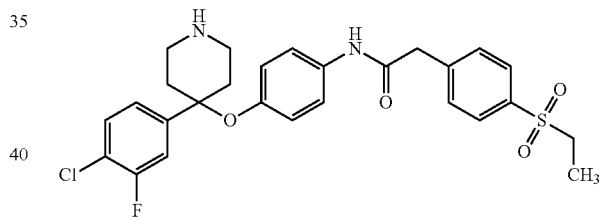

Step 1: tert-Butyl 4-(4-chloro-3-fluorophenyl)-4-(4-(2-(4-(ethylsulfonyl)phenyl)acetamido) phenoxy)piperidine-1-carboxylate The title compound was prepared by the reaction of Intermediate 43 (92 mg, 0.219 mmol) with [4-(ethylsulfonyl)phenyl]acetic acid (50 mg, 0.219 mmol) using EDCI.HCl (50 mg, 0.262 mmol) and HOBt (41 mg, 0.306 mmol) in DCM (4 mL) as per the process described in Example 1 to yield 75 mg of the product as a solid. $^1$H NMR (300 MHz, DMSO-$d_6$) δ 1.07 (t, J=7.2 Hz, 3H), 1.39 (s, 9H), 2.02 (br s, 2H), 2.31-2.37 (m, 2H), 3.16 (br s, 2H), 3.25 (q, J=7.8 Hz, 2H), 3.71 (s, 2H), 3.80 (br s, 2H), 6.62 (d, J=8.7 Hz, 2H), 7.24 (t, J=7.8 Hz, 1H), 7.34 (d, J=8.7 Hz, 2H), 7.43 (t, J=7.2 Hz, 1H), 7.56 (d, J=7.8 Hz, 3H), 7.81 (d, J=7.8 Hz, 2H), 10.11 (br s, 1H).

Step 2: N-(4-{[4-(4-Chloro-3-fluorophenyl)piperidin-4-yl]oxy}phenyl)-2-[4-(ethylsulfonyl) phenyl]acetamide To a stirred solution of 70% trifluoroacetic acid in DCM (4 mL) was added step 1 intermediate (68 mg, 0.108 mmol)

at 0° C. and the reaction mixture was stirred at the same temperature for 1 h. The reaction mixture was concentrated under reduced pressure and residue obtained was diluted with water (20 mL) and ethyl acetate (20 mL). The layers were separated and the aqueous layer was extracted with ethyl acetate (2×30 mL). The combined organic extracts were washed with water (2×25 mL), brine (20 mL) and dried over anhydrous sodium sulfate. The solvent was distilled off under reduced pressure and the residue obtained was purified by recrystallized from diethyl ether to yield 55 mg of the title product as a solid. $^1$H NMR (300 MHz, DMSO-d$_6$) δ 1.07 (t, J=7.5 Hz, 3H), 2.02-2.07 (m, 2H), 2.22-2.29 (m, 2H), 2.76-2.80 (m, 2H), 2.88-2.92 (m, 2H), 3.25 (q, J=7.2 Hz, 2H), 3.71 (s, 2H), 6.59 (d, J=8.7 Hz, 2H), 7.24 (t, J=7.8 Hz, 1H), 7.34 (d, J=8.7 Hz, 2H), 7.42 (t, J=7.2 Hz, 1H), 7.56 (d, J=8.4 Hz, 3H), 7.81 (d, J=8.4 Hz, 2H), 10.12 (br s, 1H); APCI-MS (m/z) 531 (M+H)$^+$.

Example 44

N-{4-[4-(4-Chloro-3-fluoro-phenyl)-1-methyl-piperidin-4-yloxy]-phenyl}-2-(4-ethanesulfonyl-phenyl)-acetamide

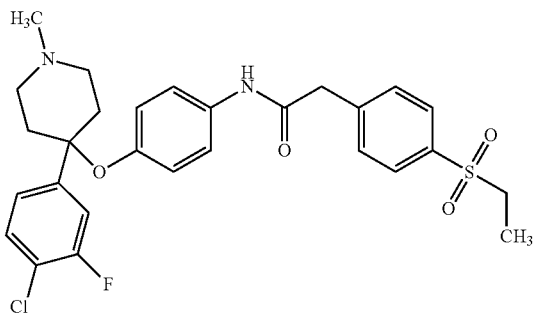 [SMILES: CCS(=O)(=O)c1ccc(CC(=O)Nc2ccc(OC3(c4ccc(Cl)c(F)c4)CCN(C)CC3)cc2)cc1]

The title compound was prepared by the reaction of Intermediate 44 (73 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (5 mL) as per the process described in Example 1 to yield 89 mg of the product as a solid. $^1$H NMR (300 MHz, DMSO-d$_6$) δ 1.07 (t, J=7.2 Hz, 3H), 2.10-2.35 (m, 5H), 2.36-2.49 (m, 4H), 2.58 (br s, 2H), 3.24 (q, J=7.2 Hz, 2H), 3.71 (s, 2H), 6.60 (d, J=9.0 Hz, 2H), 7.23 (t, J=6.9 Hz, 1H), 6.35 (d, J=8.4 Hz, 2H), 7.43 (t, J=7.2 Hz, 1H), 7.57 (d, J=7.8 Hz, 3H), 7.82 (d, J=7.8 Hz, 2H), 10.11 (br s, 1H); ESI-MS (m/z) 545 (M+H)$^+$.

Example 45

N-{4-[3-(4-Chloro-3-fluoro-phenyl)-oxetan-3-yloxy]-phenyl}-2-(4-ethanesulfonyl-phenyl)-acetamide

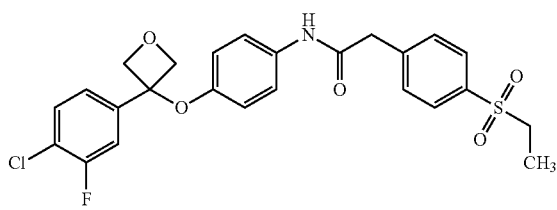 [SMILES: CCS(=O)(=O)c1ccc(CC(=O)Nc2ccc(OC3(c4ccc(Cl)c(F)c4)COC3)cc2)cc1]

The title compound was prepared by the reaction of Intermediate 45 (64 mg, 0.219 mmol) with [4-(ethylsulfonyl)phenyl]acetic acid (50 mg, 0.219 mmol) using EDCI.HCl (50 mg, 0.262 mmol) and HOBt (44 mg, 0.328 mmol) in DCM (5.0 mL) as per the process described in Example 1 to yield 80 mg of the product as a solid. $^1$H NMR (300 MHz, DMSO-d$_6$) δ 1.07 (t, J=7.2 Hz, 3H), 3.24 (q, J=7.2 Hz, 2H), 3.71 (s, 2H), 5.02 (d, J=7.5 Hz, 2H), 5.16 (d, J=7.5 Hz, 2H), 6.65 (d, J=8.7 Hz, 2H), 7.21 (t, J=7.8 Hz, 1H), 7.40 (d, J=8.7 Hz, 2H), 7.53-7.61 (m, 4H), 7.83 (d, J=8.4 Hz, 2H), 10.12 (br s, 1H); APCI-MS (m/z) 503 (M+H)$^+$.

Example 46

N-{4-[3-(3,4-Dichlorophenyl)-oxetan-3-yloxy]-phenyl}-2-(4-ethanesulfonyl-phenyl)-acetamide

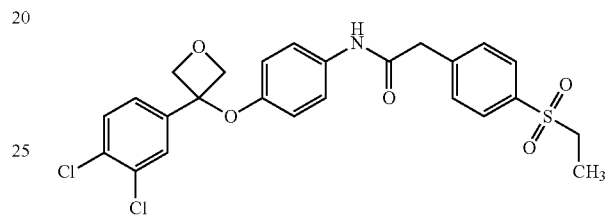

The title compound was prepared by the reaction of Intermediate 46 (55 mg, 0.177 mmol) with [4-(ethylsulfonyl)phenyl]acetic acid (41 mg, 0.177 mmol) using EDCI.HCl (41 mg, 0.212 mmol) and HOBt (34 mg, 0.248 mmol) in DCM (4 mL) as per the process described in Example 1 to yield 49 mg of the product as a solid. $^1$H NMR (300 MHz, DMSO-d$_6$) δ 1.07 (t, J=7.2 Hz, 3H), 3.24 (q, J=7.2 Hz, 2H), 3.72 (s, 2H), 3.92 (br s, 4H), 6.52 (d, J=9.3 Hz, 2H), 7.42 (d, J=9.3 Hz, 2H), 7.50 (d, J=8.4 Hz, 1H), 7.57 (t, J=7.8 Hz, 2H), 7.68 (d, J=8.7 Hz, 1H), 7.76-7.83 (m, 3H), 10.12 (br s, 1H); APCI-MS (m/z) 520 (M)$^+$.

Example 47

N-{4-[3-(2,4-Dichlorophenyl)-oxetan-3-yloxy]-phenyl}-2-(4-ethanesulfonyl-phenyl)-acetamide

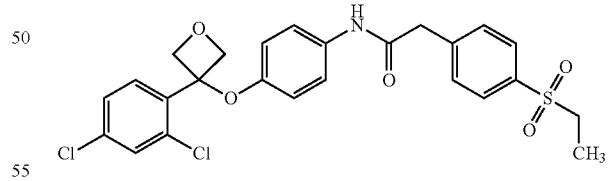

The title compound was prepared by the reaction of Intermediate 47 (68 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.307 mmol) in DCM (4 mL) as per the process described in Example 1 to yield 74 mg of the product as a solid. $^1$H NMR (300 MHz, DMSO-d$_6$) δ 1.07 (t, J=7.2 Hz, 3H), 3.24-3.34 (m, 3H), 3.71 (s, 2H), 5.06 (d, J=7.8 Hz, 2H), 5.19 (d, J=7.8 Hz, 2H), 6.67 (d, J=8.7 Hz, 2H), 7.35-7.43 (m, 3H), 7.54-7.62 (m, 3H), 7.74-7.82 (m, 3H), 10.11 (br s, 1H); APCI-MS (m/z) 519 (M+H)$^+$.

Example 48

(4-Ethanesulfonyl-phenyl)-N-{4-[3-(3-fluoro-4-trifluoromethyl-phenyl)-oxetan-3-yloxy]-phenyl}-acetamide

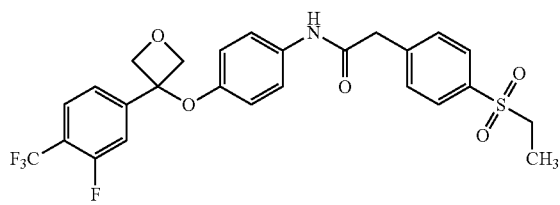 [SMILES: CCS(=O)(=O)c1ccc(CC(=O)Nc2ccc(OC3(c4ccc(C(F)(F)F)c(F)c4)COC3)cc2)cc1]

The title compound was prepared by the reaction of Intermediate 48 (72 mg, 0.219 mmol) with [4-(ethylsulfonyl)phenyl]acetic acid (50 mg, 0.219 mmol) using EDCI. HCl (50 mg, 0.262 mmol) and HOBt (40 mg, 0.307 mmol) in DCM (5 mL) as per the process described in Example 1 to yield 79 mg of the product as a solid. $^1$H NMR (300 MHz, DMSO-$d_6$) δ 1.07 (t, J=7.2 Hz, 3H), 3.24 (q, J=7.2 Hz, 2H), 3.72 (s, 2H), 4.96 (br s, 4H), 6.50 (d, J=9.3 Hz, 2H), 7.41 (d, J=9.0 Hz, 2H), 7.56 (d, J=7.2 Hz, 3H), 7.66 (d, J=11.1 Hz, 1H), 7.82 (d, J=8.1 Hz, 3H), 10.14 (br s, 1H); APCI-MS (m/z) 537 (M+H)$^+$.

Example 49

N-{4-[1-(3,4-Dichloro-phenyl)-cyclopropoxy]-phenyl}-2-(4-ethanesulfonyl-phenyl)-acetamide

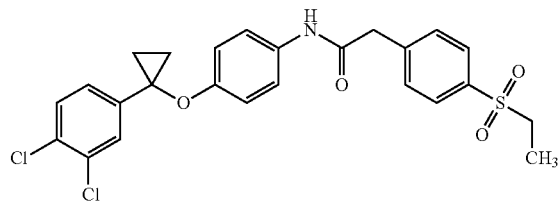 [SMILES: CCS(=O)(=O)c1ccc(CC(=O)Nc2ccc(OC3(c4ccc(Cl)c(Cl)c4)CC3)cc2)cc1]

The title compound was prepared by the reaction of Intermediate 49 (64 mg, 0.219 mmol) with [4-(ethylsulfonyl)phenyl]acetic acid (50 mg, 0.219 mmol) using EDCI. HCl (50 mg, 0.262 mmol) and HOBt (40 mg, 0.306 mmol) in DCM (10 mL) as per the process described in Example 1 to yield 71 mg of the product as a solid. $^1$H NMR (300 MHz, DMSO-$d_6$) δ 1.08 (t, J=7.5 Hz, 3H), 1.36 (br s, 2H), 1.45 (br s, 2H), 3.24 (q, J=7.5 Hz, 2H), 3.73 (s, 2H), 6.84 (d, J=8.4 Hz, 2H), 7.18 (d, J=7.8 Hz, 1H), 7.37-7.44 (m, 3H), 7.56-7.58 (m, 3H), 7.83 (d, J=8.4 Hz, 2H), 10.12 (br s, 1H); APCI-MS (m/z) 504 (M)$^+$.

Example 50

N-{4-[1-(4-Chloro-3-fluoro-phenyl)-cyclopropoxy]-phenyl}-2-(4-ethanesulfonyl-phenyl)-acetamide

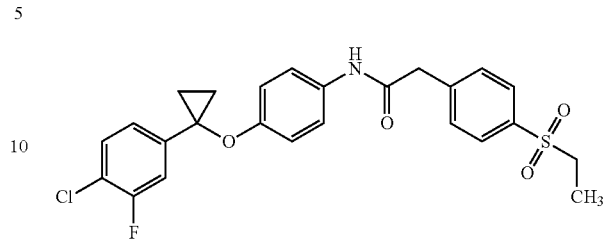

The title compound was prepared by the reaction of Intermediate 50 (61 mg, 0.219 mmol) with [4-(ethylsulfonyl)phenyl]acetic acid (50 mg, 0.219 mmol) using EDCI. HCl (50 mg, 0.262 mmol) and HOBt (40 mg, 0.306 mmol) in DCM (4 mL) as per the process described in Example 1 to yield 98 mg of the product as a solid. $^1$H NMR (300 MHz, DMSO-$d_6$) δ 1.08 (t, J=7.2 Hz, 3H), 1.37-1.44 (m, 4H), 3.25 (q, J=7.2 Hz, 2H), 3.73 (s, 2H), 6.84 (d, J=8.7 Hz, 2H), 7.07 (d, J=8.4 Hz, 1H), 7.19 (d, J=9.0 Hz, 1H), 7.42-7.52 (m, 3H), 7.58 (d, J=8.4 Hz, 2H), 7.84 (d, J=8.4 Hz, 2H), 10.12 (br s, 1H); APCI-MS (m/z) 488 (M+H)$^+$.

Example 51

N-{4-[1-(4-Chloro-2-fluoro-phenyl)-cyclopropoxy]-phenyl}-2-(4-ethanesulfonyl-phenyl)-acetamide

The title compound was prepared by the reaction of Intermediate 51 (61 mg, 0.219 mmol) with [4-(ethylsulfonyl)phenyl]acetic acid (50 mg, 0.219 mmol) using EDCI. HCl (50 mg, 0.262 mmol) and HOBt (42 mg, 0.306 mmol) in DCM (5 mL) as per the process described in Example 1 to yield 59 mg of the product as a solid. $^1$H NMR (300 MHz, DMSO-$d_6$) δ 1.08 (t, J=7.2 Hz, 3H), 1.30-1.36 (m, 4H), 3.25 (q, J=7.2 Hz, 2H), 3.72 (s, 2H), 6.90 (d, J=8.7 Hz, 2H), 7.22 (d, J=6.9 Hz, 1H), 7.36-7.44 (m, 3H), 7.51-7.59 (m, 3H), 7.81 (d, J=7.8 Hz, 2H), 10.10 (br s, 1H); APCI-MS (m/z) 489 (M+H)$^+$.

Example 52

N-{6-[1-(4-Chloro-3-fluoro-phenyl)-cyclopropoxy]-pyridin-3-yl}-2-(4-ethanesulfonyl-phenyl)-acetamide

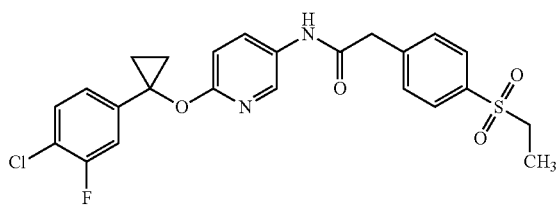

The title compound was prepared by the reaction of Intermediate 52 (61 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (5 mL) as per the process described in Example 1 to yield 47 mg of the product as a solid. $^1$H NMR (300 MHz, DMSO-$d_6$) δ 1.08 (t, J=7.2 Hz, 3H), 1.36-1.43 (m, 4H), 3.25 (q, J=7.2 Hz, 2H), 3.77 (s, 2H), 6.86 (d, J=8.7 Hz, 1H), 7.03 (d, J=7.8 Hz, 1H), 7.17 (d, J=10.8 Hz, 1H), 7.46 (t, J=7.8 Hz, 1H), 7.59 (d, J=8.4 Hz, 2H), 7.84 (d, J=8.4 Hz, 2H), 7.91 (d, J=9.3 Hz, 1H), 8.24 (s, 1H), 10.29 (br s, 1H); APCI-MS (m/z) 489 (M+H)$^+$.

Example 53

N-{6-[1-(3,4-Dichloro-phenyl)-cyclopropoxy]-pyridin-3-yl}-2-(4-ethanesulfonyl-phenyl)-acetamide

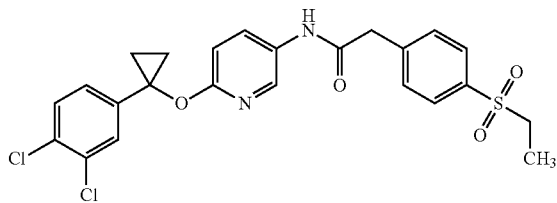 [SMILES: CCS(=O)(=O)c1ccc(CC(=O)Nc2ccc(OC3(c4ccc(Cl)c(F)c4)CC3)nc2)cc1]

The title compound was prepared by the reaction of Intermediate 53 (64 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (4 mL) as per the process described in Example 1 to yield 69 mg of the product as a solid. $^1$H NMR (300 MHz, DMSO-$d_6$) δ 1.08 (t, J=7.2 Hz, 3H), 1.34-1.43 (m, 4H), 3.25 (q, J=7.2 Hz, 2H), 3.77 (s, 2H), 6.86 (d, J=8.7 Hz, 1H), 7.17 (d, J=8.7 Hz, 1H), 7.26 (s, 1H), 7.50-7.59 (m, 3H), 7.84 (d, J=7.8 Hz, 2H), 7.92 (d, J=8.7 Hz, 1H), 8.25 (s, 1H), 10.29 (br s, 1H); APCI-MS (m/z) 505 (M+H)$^+$.

Example 54

N-{6-[1-(4-Chloro-3-fluoro-phenyl)-cyclobutoxy]-pyridin-3-yl}-2-(4-ethanesulfonyl-phenyl)-acetamide

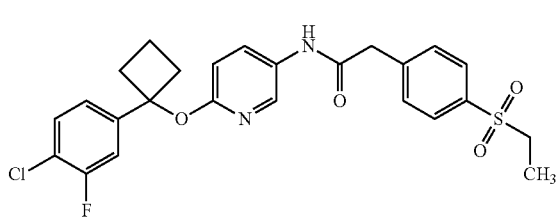 [SMILES: CCS(=O)(=O)c1ccc(CC(=O)Nc2ccc(OC3(c4ccc(Cl)c(F)c4)CCC3)nc2)cc1]

The title compound was prepared by the reaction of Intermediate 54 (64 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (10 mL) as per the process described in Example 1 to yield 73 mg of the product as a solid. $^1$H NMR (300 MHz, DMSO-$d_6$) δ 1.07 (t, J=7.2 Hz, 3H), 1.71-1.73 (m, 1H), 1.93-1.95 (m, 1H), 2.51-2.65 (m, 2H), 2.78-2.80 (m, 2H), 3.25 (q, J=6.9 Hz, 2H), 3.74 (s, 2H), 6.76 (d, J=8.7 Hz, 1H), 7.17 (t, J=7.8 Hz, 1H), 7.43-7.46 (m, 1H), 7.57 (d, J=7.2 Hz, 2H), 7.66-7.68 (m, 1H), 7.73-7.83 (m, 3H), 8.14 (br s, 1H), 10.18 (br s, 1H)

Example 55

N-{6-[4-(4-Chloro-3-fluoro-phenyl)-tetrahydro-pyran-4-yloxy]-pyridin-3-yl}-2-(4-ethanesulfonyl-phenyl)-acetamide

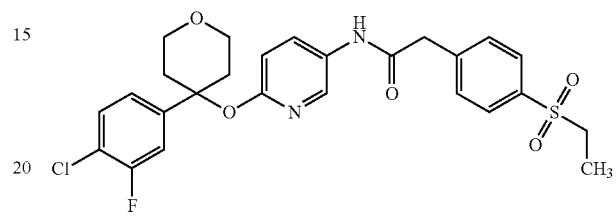

The title compound was prepared by the reaction of Intermediate 55 (71 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (5 mL) as per the process described in Example 1 to yield 62 mg of the product as a solid. $^1$H NMR (300 MHz, DMSO-$d_6$) δ 1.05 (t, J=7.2 Hz, 3H), 2.18-2.20 (m, 2H), 2.48-2.58 (m, 3H), 3.25 (q, J=7.2 Hz, 2H), 3.71 (br s, 5H), 6.88 (d, J=8.7 Hz, 1H), 7.15 (t, J=8.4 Hz, 1H), 7.42-7.46 (m, 2H), 7.55 (d, J=8.4 Hz, 2H), 7.76-7.82 (m, 3H), 7.98 (br s, 1H), 10.18 (br s, 1H); ESI-MS (m/z) 530 (M+H)$^+$.

Example 56

N-{6-[1-(4-Chloro-2-fluoro-phenyl)-1-methyl-ethoxy]-pyridin-3-yl}-2-(4-ethanesulfonyl-phenyl)-acetamide

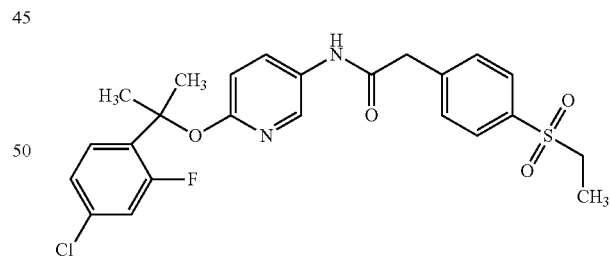

The title compound was prepared by the reaction of Intermediate 56 (61 mg, 0.219 mmol) with [4-(ethylsulfonyl)phenyl]acetic acid (50 mg, 0.219 mmol) using EDCI.HCl (50 mg, 0.262 mmol) and HOBt (44 mg, 0.328 mmol) in DCM (10 mL) as per the process described in Example 1 to yield 17 mg of the product as a solid. $^1$H NMR (300 MHz, DMSO-$d_6$) δ 1.08 (t, J=7.2 Hz, 3H), 1.81 (s, 6H), 3.25 (q, J=6.9 Hz, 2H), 3.74 (s, 2H), 6.80 (d, J=8.7 Hz, 1H), 7.19-7.29 (m, 2H), 7.42 (t, J=8.7 Hz, 1H), 7.58 (d, J=7.8 Hz, 2H), 7.83 (d, J=8.4 Hz, 3H), 8.04 (br s, 1H), 10.19 (br s, 1H); APCI-MS (m/z) 489 (M−H)$^-$.

Example 57

N-{6-[1-(2-Chloro-4-fluoro-phenyl)-1-methyl-ethoxy]-pyridin-3-yl}-2-(4-ethanesulfonyl-phenyl)-acetamide

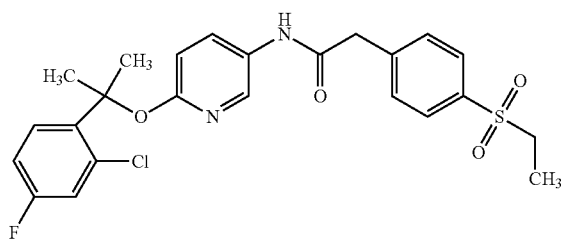 [SMILES: CCS(=O)(=O)c1ccc(CC(=O)Nc2ccc(OC(C)(C)c3ccc(F)cc3Cl)nc2)cc1]

The title compound was prepared by the reaction of Intermediate 57 (100 mg, 0.356 mmol) with [4-(ethylsulfonyl)phenyl]acetic acid (81 mg, 0.356 mmol) using EDCI.HCl (82 mg, 0.427 mmol) and HOBt (72 mg, 0.534 mmol) in DCM (10 mL) as per the process described in Example 1 to yield 40 mg of the product as a solid. $^1$H NMR (300 MHz, DMSO-$d_6$) δ 1.08 (t, J=7.5 Hz, 3H), 1.88 (br s, 6H), 3.25 (q, J=6.9 Hz, 2H), 3.73 (s, 2H), 6.78 (d, J=8.7 Hz, 1H), 7.18-7.23 (m, 2H), 7.55-7.58 (m, 3H), 7.79-7.84 (m, 3H), 7.97 (br s, 1H), 10.15 (br s, 1H); APCI-MS (m/z) 490 (M)$^+$.

Example 58

N-(6-{[2-(2,4-Dichlorophenyl)propan-2-yl]oxy}pyridin-3-yl)-2-[4-(ethylsulfonyl) phenyl]acetamide

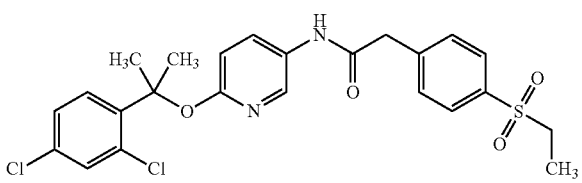 [SMILES: CCS(=O)(=O)c1ccc(CC(=O)Nc2ccc(OC(C)(C)c3ccc(Cl)cc3Cl)nc2)cc1]

The title compound was prepared by the reaction of Intermediate 58 (65 mg, 0.219 mmol) with [4-(ethylsulfonyl)phenyl]acetic acid (50 mg, 0.219 mmol) using EDCI.HCl (50 mg, 0.262 mmol) and HOBt (41 mg, 0.306 mmol) in DCM (4 mL) as per the process described in Example 1 to yield 48 mg of the product as a solid. $^1$H NMR (300 MHz, DMSO-$d_6$) δ 1.07 (t, J=7.5 Hz, 3H), 1.86 (s, 6H), 3.26 (q, J=7.5 Hz, 2H), 3.73 (s, 2H), 6.77 (d, J=9.3 Hz, 1H), 7.39 (br s, 2H), 7.56 (d, J=7.2 Hz, 3H), 7.81 (d, J=7.8 Hz, 3H), 7.96 (br s, 1H), 10.17 (br s, 1H); ESI-MS (m/z) 506 (M)$^+$.

Example 59

N-{6-[1-(3,4-Dichloro-phenyl)-1-methyl-ethoxy]-pyridin-3-yl}-2-(4-ethanesulfonyl-phenyl)-acetamide

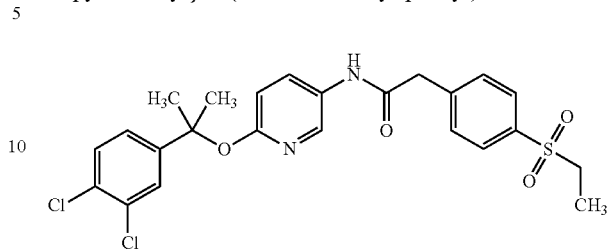

The title compound was prepared by the reaction of Intermediate 59 (65 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (4 mL) as per the process described in Example 1 to yield 42 mg of the product as a solid. $^1$H NMR (300 MHz, DMSO-$d_6$) δ 1.08 (t, J=7.5 Hz, 3H), 1.77 (s, 6H), 3.26 (q, J=7.5 Hz, 2H), 3.75 (s, 2H), 6.81 (d, J=8.7 Hz, 1H), 7.37 (br s, 1H), 7.51-7.58 (m, 4H), 7.81-7.83 (m, 3H), 8.05 (br s, 1H), 10.20 (br s, 1H); ESI-MS (m/z) 505 (M−H)$^−$.

Example 60

N-{4-[3-(2,4-Dichlorophenoxy)prop-1-yn-1-yl]phenyl}-2-[4-(ethylsulfonyl)phenyl]acetamide

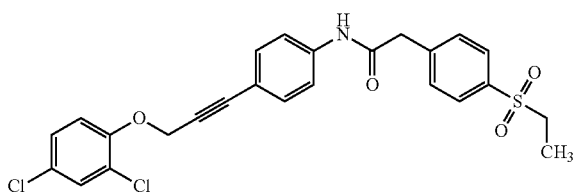 [SMILES: CCS(=O)(=O)c1ccc(CC(=O)Nc2ccc(C#CCOc3ccc(Cl)cc3Cl)cc2)cc1]

The title compound was prepared by the reaction of Intermediate 60 (50 mg, 0.219 mmol) with [4-(ethylsulfonyl)phenyl]acetic acid (64 mg, 0.219 mmol) using EDCI.HCl (50 mg, 0.262 mmol) and HOBt (40 mg, 0.295 mmol) in DCM (4 mL) as per the process described in Example 1 to yield 63 mg of the product as a solid. $^1$H NMR (300 MHz, DMSO-$d_6$) δ 1.08 (t, J=7.8 Hz, 3H), 3.27 (q, J=7.2 Hz, 2H), 3.81 (s, 2H), 5.16 (s, 2H), 7.31 (d, J=8.7 Hz, 1H), 7.37-7.42 (m, 3H), 7.60 (br s, 5H), 7.84 (d, J=7.8 Hz, 2H), 10.45 (br s, 1H); APCI-MS (m/z) 502 (M+H)$^+$.

Example 61

N-{4-[3-(3,4-Dichlorophenoxy)prop-1-yn-1-yl]phenyl}-2-[4-(ethylsulfonyl)phenyl]acetamide

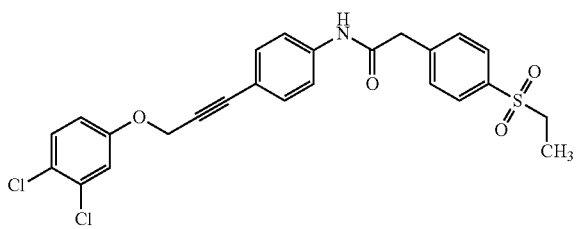 [SMILES: CCS(=O)(=O)c1ccc(CC(=O)Nc2ccc(C#CCOc3ccc(Cl)c(Cl)c3)cc2)cc1]

The title compound was prepared by the reaction of Intermediate 61 (64 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.295 mmol) in DCM (4 mL) as per the process described in Example 1 to yield 42 mg of the product as a solid; $^1$H NMR (300 MHz, DMSO-$d_6$) δ 1.08 (t, J=6.9 Hz, 3H), 3.27 (q, J=7.5 Hz, 2H), 3.81 (s, 2H), 5.08 (s, 2H), 7.15 (d, J=8.4 Hz, 1H), 7.35-7.41 (m, 3H), 7.56-7.63 (m, 5H), 7.84 (d, J=7.8 Hz, 2H), 10.46 (br s, 1H); APCI-MS (m/z) 502 (M+H)$^+$.

Example 62

N-{4-[3-(3,4-Dichlorophenoxy)-3-methylbut-1-yn-1-yl]phenyl}-2-[4-(ethylsulfonyl)phenyl]acetamide

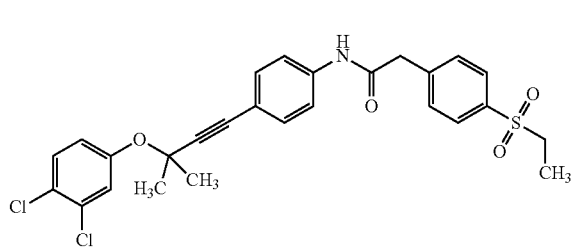 [SMILES: CCS(=O)(=O)c1ccc(CC(=O)Nc2ccc(C#CC(C)(C)Oc3ccc(Cl)c(Cl)c3)cc2)cc1]

To a degassed solution of Intermediate 105 (50 mg, 0.116 mmol) in DMSO (5 mL) were added Intermediate 62 (53 mg, 0.232 mmol), copper iodide (3 mg, 0.013 mmol), triethylamine (0.08 ml, 0.582 mmol) and bis(triphenylphosphine)palladium(II) dichloride (8 mg, 0.011 mmol) and the mixture was stirred at RT for 16 h. The reaction mixture was diluted with ethyl acetate (15 mL) and water (10 mL). The layers were separated and the aqueous layer was extracted with ethyl acetate (2×15 mL). The combined organic extracts were washed with water (20 mL) and brine (20 mL). The solution was dried over anhydrous sodium sulfate, filtered and concentrated under reduced pressure. The residue obtained was purified by silica gel column chromatography to yield 8 mg the title product as a solid; $^1$H NMR (300 MHz, DMSO-$d_6$) δ 1.09 (t, J=7.5 Hz, 3H), 1.68 (s, 6H), 3.27 (q, J=8.4 Hz, 2H), 3.81 (s, 2H), 7.24 (d, J=8.1 Hz, 1H), 7.35 (d, J=7.2 Hz, 2H), 7.45 (s, 1H), 7.54-7.62 (m, 5H), 7.84 (d, J=7.2 Hz, 2H), 10.44 (br s, 1H); APCI-MS (m/z) 530 (M+H)$^+$.

Example 63

N-{4-[3-(2,4-Dichloro-phenoxy)-3-methyl-but-1-yn-1-yl]-phenyl}-2-(4-ethanesulfonyl-phenyl)-acetamide

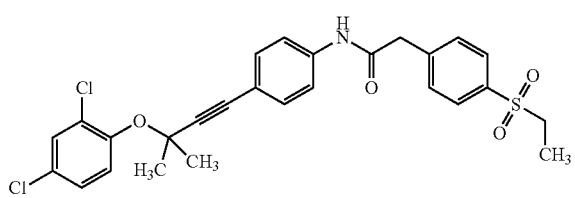 [SMILES: CCS(=O)(=O)c1ccc(CC(=O)Nc2ccc(C#CC(C)(C)Oc3ccc(Cl)cc3Cl)cc2)cc1]

The title compound was prepared by the reaction of Intermediate 63 (192 mg, 0.8386 mmol) and Intermediate 105 (300 mg, 0.698 mmol) using copper iodide (13 mg, 0.069 mmol) and bis(triphenylphosphine)palladium(II) dichloride (98 mg, 0.1397 mmol) in excess of diethylamine (15 mL) as per the process described in Example 62 to yield 50 mg the product as a solid; $^1$H NMR (300 MHz, DMSO-$d_6$) δ 1.07 (t, J=7.5 Hz, 3H), 1.70 (s, 6H), 3.25 (q, J=7.2 Hz, 2H), 3.79 (s, 2H), 7.31 (d, J=7.8 Hz, 2H), 7.39 (d, J=8.4 Hz, 1H), 7.58 (d, J=6.9 Hz, 6H), 7.82 (d, J=7.2 Hz, 2H), 10.42 (br s, 1H); APCI-MS (m/z) 530 (M+H)$^+$.

Example 64

N-{4-[3-(4-Chloro-phenoxy)-3-methyl-but-1-yn-1-yl]-phenyl}-2-(4-ethanesulfonyl-phenyl)-acetamide

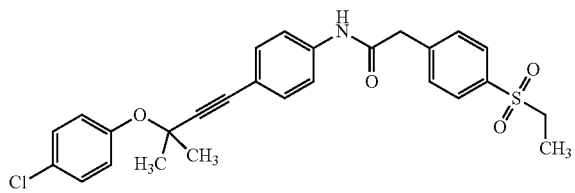 [SMILES: CCS(=O)(=O)c1ccc(CC(=O)Nc2ccc(C#CC(C)(C)Oc3ccc(Cl)cc3)cc2)cc1]

The title compound was prepared by the reaction of Intermediate 64 (181 mg, 0.9318 mmol) and Intermediate 105 (200 mg, 0.4659 mmol) using copper iodide (17 mg, 0.093 mmol), bis(triphenylphosphine)palladium(II) dichloride (65 mg, 0.0932 mmol) and triphenylphosphine (2 mg, 0.0092 mmol) in excess of diethylamine (10 mL) as per the process described in Example 62 to yield 148 mg the product as a solid; $^1$H NMR (300 MHz, DMSO-$d_6$) δ 1.09 (t, J=7.2 Hz, 3H), 1.66 (s, 6H), 3.26 (q, J=7.2 Hz, 2H), 3.81 (s, 2H), 7.20 (d, J=8.7 Hz, 2H), 7.33-7.38 (m, 4H), 7.59-7.62 (m, 4H), 7.84 (d, J=7.8 Hz, 2H), 10.43 (br s, 1H); APCI-MS (m/z) 496 (M)$^+$.

Example 65

N-{4-[3-(4-Chloro-2-fluoro-phenoxy)-3-methyl-but-1-yn-1-yl]-phenyl}-2-(4-ethanesulfonyl-phenyl)-acetamide

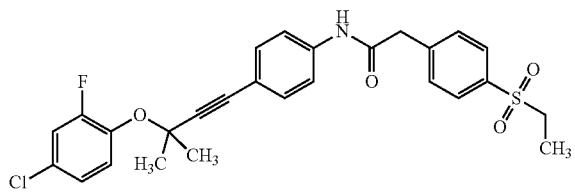 [SMILES: CCS(=O)(=O)c1ccc(CC(=O)Nc2ccc(C#CC(C)(C)Oc3ccc(Cl)cc3F)cc2)cc1]

To a stirred solution of Intermediate 105 (300 mg, 0.698 mmol) in diethylamine (15 mL) was added Intermediate 65 (178 mg, 0.838 mmol). The mixture was purged with nitrogen for 15 minutes. Copper iodide (13 mg, 0.069 mmol) and bis(triphenylphosphine)palladium(II) dichloride (98 mg, 0.139 mmol) were added to the mixture and stirred at RT for 16 hours. The reaction mixture was diluted with ethyl acetate (20 mL) and water (10 mL). The layers were separated and the aqueous layer was extracted with ethyl acetate (2×20 mL). The combined organic extracts were washed with water (30 mL) and brine (30 mL). The solution was dried over anhydrous sodium sulfate, filtered and concentrated under reduced pressure. The residue obtained was purified by silica gel column chromatography to yield 21 mg the title product as a solid. ¹H NMR (300 MHz, DMSO-d₆) δ 1.09 (t, J=7.2 Hz, 3H), 1.68 (s, 6H), 3.25 (q, J=7.8 Hz, 2H), 3.81 (s, 2H), 7.27-7.32 (m, 3H), 7.45-7.51 (m, 2H), 7.59 (d, J=6.3 Hz, 4H), 7.83 (d, J=8.4 Hz, 2H), 10.42 (br s, 1H); APCI-MS (m/z) 514 (M+H)⁺.

Example 66

N-{4-[3-(4-Chloro-3-fluoro-phenoxy)-3-methyl-but-1-yn-1-yl]-phenyl}-2-(4-ethanesulfonyl-phenyl)-acetamide

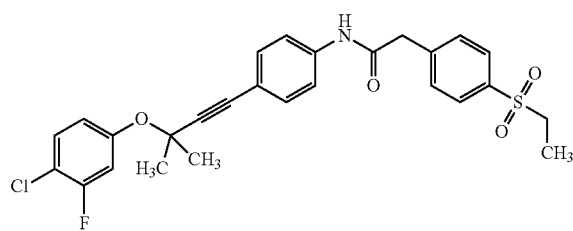 [SMILES: CCS(=O)(=O)c1ccc(CC(=O)Nc2ccc(C#CC(C)(C)Oc3ccc(Cl)c(F)c3)cc2)cc1]

The title compound was prepared by the reaction of Intermediate 105 (300 mg, 0.698 mmol) and Intermediate 66 (178 mg, 0.8386 mmol) using copper iodide (13 mg, 0.069 mmol) and bis(triphenylphosphine)palladium(II) dichloride (98 mg, 0.1397 mmol) in excess of diethylamine (15 mL) as per the process described in Example 62 to yield 69 mg the product as a solid; ¹H NMR (300 MHz, DMSO-d₆) δ 1.09 (t, J=7.2 Hz, 3H), 1.69 (s, 6H), 3.26 (q, J=7.2 Hz, 2H), 3.81 (s, 2H), 7.13 (d, J=9.0 Hz, 1H), 7.26 (d, J=13.5 Hz, 1H), 7.37 (d, J=8.4 Hz, 2H), 7.50-7.63 (m, 5H), 7.85 (d, J=8.4 Hz, 2H), 10.44 (br s, 1H); APCI-MS (m/z) 514 (M+H)⁺.

Example 67

N-{4-[3-(2-Chloro-4-fluoro-phenoxy)-3-methyl-but-1-yn-1-yl]-phenyl}-2-(4-ethanesulfonyl-phenyl)-acetamide

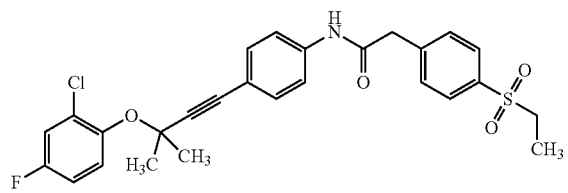 [SMILES: CCS(=O)(=O)c1ccc(CC(=O)Nc2ccc(C#CC(C)(C)Oc3ccc(F)cc3Cl)cc2)cc1]

The title compound was prepared by the reaction of Intermediate 67 (178 mg, 0.8386 mmol) and Intermediate 105 (300 mg, 0.6988 mmol) using copper iodide (13 mg, 0.0698 mmol) and bis(triphenylphosphine)palladium(II) dichloride (98 mg, 0.1397 mmol) in excess of triethylamine (10 mL) as per the process described in Example 62 to yield 71 mg the product as a solid; ¹H NMR (300 MHz, DMSO-d₆) δ 1.07 (t, J=7.2 Hz, 3H), 1.68 (s, 6H), 3.25 (q, J=7.2 Hz, 2H), 3.79 (s, 2H), 7.18-7.20 (m, 1H), 7.30 (d, J=8.4 Hz, 2H), 7.44-7.48 (m, 1H), 7.56-7.60 (m, 5H), 7.82 (d, J=8.1 Hz, 2H), 10.41 (br s, 1H); APCI-MS (m/z) 514 (M+H)⁺.

Example 68

N-{4-[3-(3-Chloro-4-fluoro-phenoxy)-3-methyl-but-1-yn-1-yl]-phenyl}-2-(4-ethanesulfonyl-phenyl)-acetamide

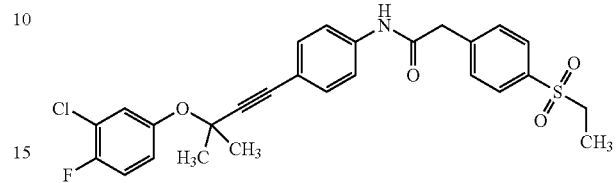

The title compound was prepared by the reaction of Intermediate 68 (178 mg, 0.8386 mmol) and Intermediate 105 (300 mg, 0.6988 mmol) using copper iodide (13 mg, 0.0698 mmol) and bis(triphenylphosphine)palladium(II) dichloride (98 mg, 0.1397 mmol) in excess of triethylamine (10 mL) as per the process described in Example 62 to yield 82 mg the product as a solid; ¹H NMR (300 MHz, DMSO-d₆) δ 1.09 (t, J=7.2 Hz, 3H), 1.65 (s, 6H), 3.26 (q, J=7.2 Hz, 2H), 3.81 (s, 2H), 7.22 (br s, 1H), 7.33-7.39 (m, 4H), 7.57-7.7.62 (m, 4H), 7.83 (d, J=8.4 Hz, 2H), 10.43 (br s, 1H); APCI-MS (m/z) 514 (M+H)⁺.

Example 69

N-{4-[3-(2,4-Difluoro-phenoxy)-3-methyl-but-1-yn-1-yl]-phenyl}-2-(4-ethanesulfonyl-phenyl)-acetamide

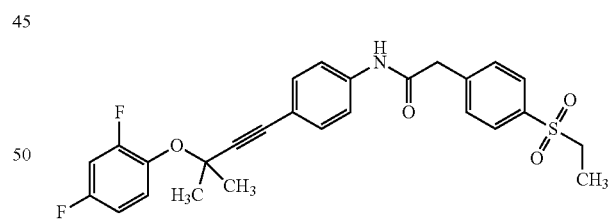

The title compound was prepared by the reaction of Intermediate 105 (300 mg, 0.698 mmol) and Intermediate 69 (178 mg, 0.8386 mmol) using copper iodide (13 mg, 0.069 mmol) and bis(triphenylphosphine)palladium(II) dichloride (98 mg, 0.1397 mmol) in excess of diethylamine (15 mL) as per the process described in Example 62 to yield 41 mg the product as a solid; ¹H NMR (300 MHz, DMSO-d₆) δ 1.09 (t, J=7.5 Hz, 3H), 1.66 (s, 6H), 3.28 (q, J=7.2 Hz, 2H), 3.81 (s, 2H), 7.03-7.07 (m, 1H), 7.31 (d, J=10.8 Hz, 3H), 7.41-7.46 (m, 1H), 7.61 (d, J=7.8 Hz, 4H), 7.85 (d, J=8.1 Hz, 2H), 10.42 (br s, 1H); APCI-MS (m/z) 498 (M+H)⁺.

Example 70

N-{4-[3-(3,4-Difluoro-phenoxy)-3-methyl-but-1-yn-1-yl]-phenyl}-2-(4-ethanesulfonyl-phenyl)-acetamide

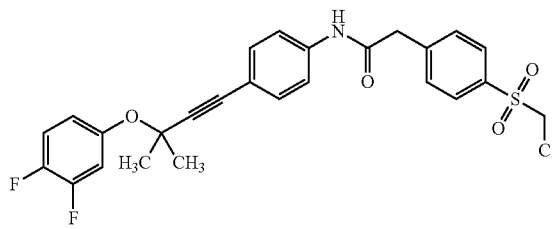

The title compound was prepared by the reaction of Intermediate 105 (250 mg, 0.5823 mmol) and Intermediate 70 (342 mg, 1.7471 mmol) using copper iodide (44 mg, 0.2322 mmol), bis(triphenylphosphine)palladium(II) dichloride (163 mg, 0.2322 mmol) and triphenylphosphine (7 mg, 0.0291 mmol) in excess of diethylamine (15 mL) as per the process described in Example 62 to yield 168 mg the product as a solid; $^1$H NMR (300 MHz, DMSO-$d_6$) δ 1.09 (t, J=7.5 Hz, 3H), 1.65 (s, 6H), 3.24 (q, J=7.5 Hz, 2H), 3.81 (br s, 2H), 7.07 (br s, 1H), 7.21-7.45 (m, 4H), 7.60-7.65 (m, 4H), 7.84 (d, J=7.8 Hz, 2H), 10.44 (br s, 1H); APCI-MS (m/z) 498 (M+H)$^+$.

Example 71

2-(4-Ethanesulfonyl-phenyl)-N-{4-[3-methyl-3-(3,4,5-trifluoro-phenoxy)-but-1-yn-1-yl]-phenyl}-acetamide

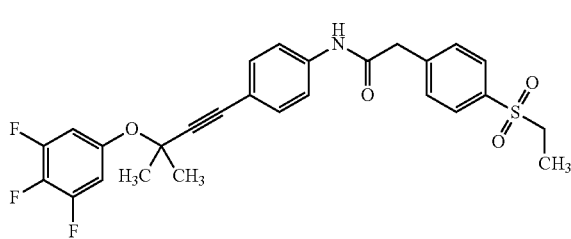 [SMILES: CCS(=O)(=O)c1ccc(CC(=O)Nc2ccc(C#CC(C)(C)Oc3cc(F)c(F)c(F)c3)cc2)cc1]

The title compound was prepared by the reaction of Intermediate 71 (449 mg, 2.0965 mmol) and Intermediate 105 (300 mg, 0.6988 mmol) using copper iodide (53 mg, 0.2795 mmol), bis(triphenylphosphine)palladium(II) dichloride (196 mg, 0.2795 mmol) and triphenylphosphine (3 mg, 0.0139 mmol) in excess of diethylamine (15 mL) as per the process described in Example 62 to yield 207 mg the product as a solid; $^1$H NMR (300 MHz, DMSO-$d_6$) δ 1.09 (t, J=7.2 Hz, 3H), 1.68 (s, 6H), 3.25 (q, J=7.2 Hz, 2H), 3.81 (s, 2H), 7.13-7.19 (m, 2H), 7.36 (d, J=8.7 Hz, 2H), 7.61 (t, J=7.8 Hz, 4H), 7.83 (d, J=8.4 Hz, 2H), 10.44 (br s, 1H); APCI-MS (m/z) 516 (M+H)$^+$.

Example 72

2-(4-Ethanesulfonyl-phenyl)-N-{4-[3-methyl-3-(2,3,4-trifluoro-phenoxy)-but-1-yn-1-yl]-phenyl}-acetamide

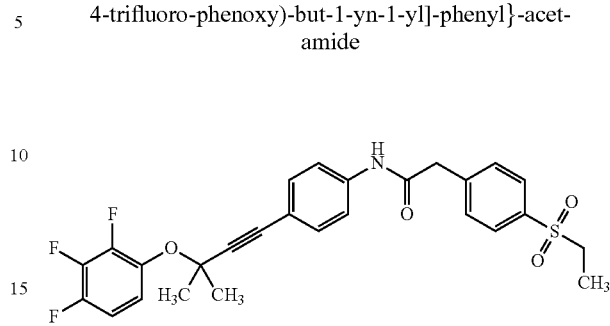

The title compound was prepared by the reaction of Intermediate 72 (449 mg, 2.0965 mmol) and Intermediate 105 (300 mg, 0.6988 mmol) using copper iodide (53 mg, 0.2795 mmol), bis(triphenylphosphine)palladium(II) dichloride (196 mg, 0.2795 mmol) and triphenylphosphine (9 mg, 0.0340 mmol) in excess of diethylamine (15 mL) as per the process described in Example 62 to yield 150 mg the product as a solid; $^1$H NMR (300 MHz, DMSO-$d_6$) δ 1.09 (t, J=7.2 Hz, 3H), 1.68 (s, 6H), 3.25 (q, J=7.2 Hz, 2H), 3.81 (s, 2H), 7.28-7.35 (m, 4H), 7.57-7.63 (m, 4H), 7.83 (d, J=7.8 Hz, 2H), 10.43 (br s, 1H); APCI-MS (m/z) 516 (M+H)$^+$.

Example 73

2-(4-Ethanesulfonyl-phenyl)-N-{4-[3-methyl-3-(2,4,6-trifluoro-phenoxy)-but-1-yn-1-yl]-phenyl}-acetamide

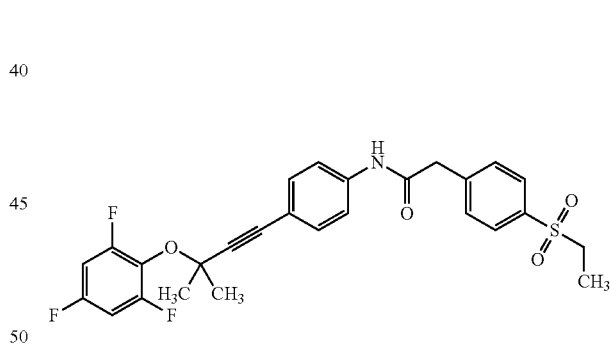

The title compound was prepared by the reaction of Intermediate 73 (299 mg, 1.3977 mmol) and Intermediate 105 (200 mg, 0.4659 mmol) using copper iodide (35 mg, 0.1863 mmol), bis(triphenylphosphine)palladium(II) dichloride (130 mg, 0.1863 mmol) and triphenylphosphine (2 mg, 0.0091 mmol) in excess of diethylamine (10 mL) as per the process described in Example 62 to yield 82 mg the product as a solid; $^1$H NMR (300 MHz, DMSO-$d_6$) δ 1.09 (t, J=7.2 Hz, 3H), 1.70 (s, 6H), 3.26 (q, J=7.2 Hz, 2H), 3.80 (s, 2H), 7.20 (d, J=8.1 Hz, 2H), 7.27 (t, J=8.7 Hz, 2H), 7.58 (d, J=7.8 Hz, 4H), 7.83 (d, J=8.1 Hz, 2H), 10.42 (br s, 1H); APCI-MS (m/z) 516 (M+H)$^+$.

Example 74

2-(4-Ethanesulfonyl-phenyl)-N-{4-[3-methyl-3-(2,4,5-trifluoro-phenoxy)-but-1-yn-1-yl]-phenyl}-acetamide

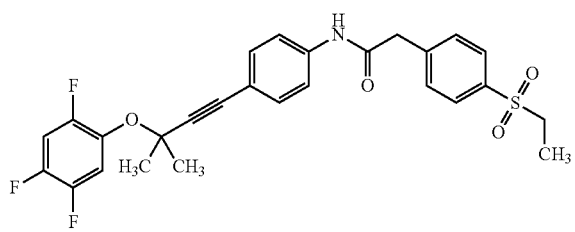 [SMILES: CCS(=O)(=O)c1ccc(CC(=O)Nc2ccc(C#CC(C)(C)Oc3cc(F)c(F)cc3F)cc2)cc1]

The title compound was prepared by the reaction of Intermediate 74 (299 mg, 1.3977 mmol) and Intermediate 105 (200 mg, 0.4659 mmol) using copper iodide (35 mg, 0.1863 mmol), bis(triphenylphosphine)palladium(II) dichloride (130 mg, 0.1863 mmol) and triphenylphosphine (2.0 mg, 0.0091 mmol) in excess of diethylamine (10 mL) as per the process described in Example 62 to yield 115 mg the product as a solid; $^1$H NMR (300 MHz, DMSO-$d_6$) δ 1.09 (t, J=7.2 Hz, 3H), 1.68 (s, 6H), 3.26 (q, J=7.2 Hz, 2H), 3.81 (s, 2H), 7.31 (d, J=8.1 Hz, 2H), 7.58-7.62 (m, 6H), 7.84 (d, J=8.4 Hz, 2H), 10.44 (br s, 1H); APCI-MS (m/z) 538 (M+H+Na)$^+$.

Example 75

N-{4-[3-(4-Chloro-2,6-difluoro-phenoxy)-3-methyl-but-1-yn-1-yl]-phenyl}-2-(4-ethanesulfonyl-phenyl)-acetamide

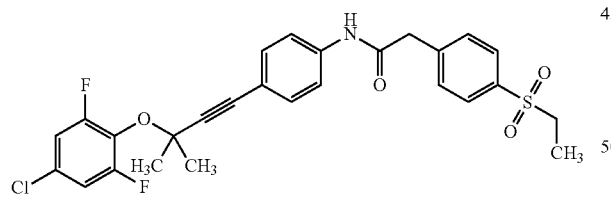

The title compound was prepared by the reaction of Intermediate 75 (268 mg, 1.1647 mmol) and Intermediate 105 (200 mg, 0.4659 mmol) using copper iodide (35 mg, 0.1863 mmol), bis(triphenylphosphine)palladium(II) dichloride (130 mg, 0.1863 mmol) and triphenylphosphine (2 mg, 0.0091 mmol) in excess of diethylamine (10 mL) as per the process described in Example 62 to yield 45 mg the product as a solid; $^1$H NMR (300 MHz, DMSO-$d_6$) δ 1.08 (t, J=7.2 Hz, 3H), 1.71 (s, 6H), 3.25 (q, J=7.2 Hz, 2H), 3.80 (s, 2H), 7.19 (d, J=8.1 Hz, 2H), 7.45 (d, J=7.5 Hz, 2H), 7.58 (d, J=7.8 Hz, 4H), 7.83 (d, J=7.8 Hz, 2H), 10.42 (br s, 1H).

Example 76

2-(4-Ethanesulfonyl-phenyl)-N-{4-[3-methyl-3-(4-trifluoromethyl-phenoxy)-but-1-yn-1-yl]-phenyl}-acetamide

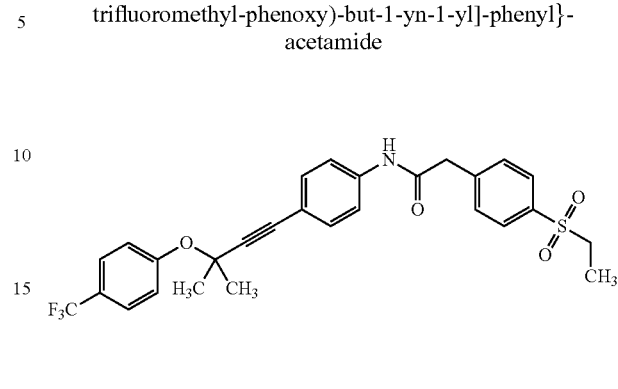

The title compound was prepared by the reaction of Intermediate 76 (239 mg, 1.0482 mmol) and Intermediate 105 (150 mg, 0.3494 mmol) using copper iodide (26 mg, 0.1397 mmol), bis(triphenylphosphine)palladium(II) dichloride (98 mg, 0.1397 mmol) and triphenylphosphine (2 mg, 0.0069 mmol) in excess of diethylamine (10 mL) as per the process described in Example 62 to yield 37 mg the product as a solid; $^1$H NMR (300 MHz, DMSO-$d_6$) δ 1.09 (t, J=7.2 Hz, 3H), 1.73 (s, 6H), 3.25 (q, J=7.2 Hz, 2H), 3.81 (s, 2H), 7.38 (t, J=8.4 Hz, 4H), 7.60 (br s, 4H), 7.69 (d, J=7.8 Hz, 2H), 7.83 (d, J=8.1 Hz, 2H), 10.43 (br s, 1H); APCI-MS (m/z) 530 (M+H)$^+$.

Example 77

2-(4-Ethanesulfonyl-phenyl)-N-{4-[3-methyl-3-(4-trifluoromethoxy-phenoxy)-but-1-yn-1-yl]-phenyl}-acetamide

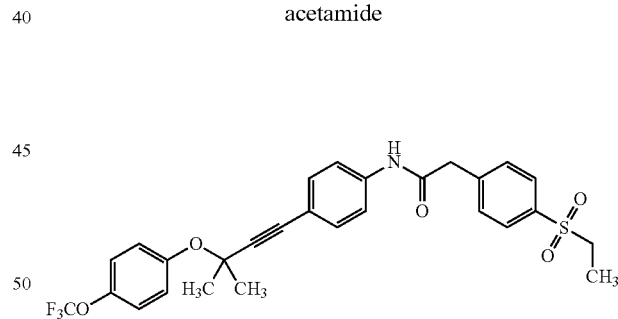

The title compound was prepared by the reaction of Intermediate 77 (205 mg, 0.8386 mmol) and Intermediate 105 (300 mg, 0.6988 mmol) using copper iodide (13 mg, 0.0698 mmol) and bis(triphenylphosphine)palladium(II) dichloride (98 mg, 0.1397 mmol) in excess of triethylamine (10 mL) as per the process described in Example 62 to yield 78 mg the product as a solid; $^1$H NMR (300 MHz, DMSO-$d_6$) δ 1.09 (t, J=7.2 Hz, 3H), 1.67 (s, 6H), 3.26 (q, J=7.2 Hz, 2H), 3.81 (s, 2H), 7.27-7.35 (m, 6H), 7.60 (d, J=6.3 Hz, 4H), 7.83 (d, J=7.8 Hz, 2H), 10.43 (br s, 1H); APCI-MS (m/z) 546 (M+H)$^+$.

Example 78

N-{4-[3-(4-Difluoromethoxy-phenoxy)-3-methyl-but-1-yn-1-yl]-phenyl}-2-(4-ethanesulfonyl-phenyl)-acetamide

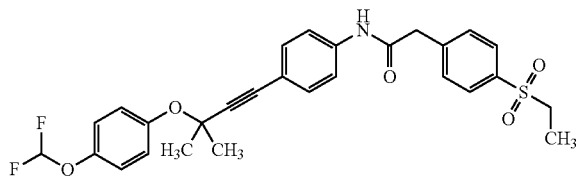 [SMILES: CCS(=O)(=O)c1ccc(CC(=O)Nc2ccc(C#CC(C)(C)Oc3ccc(OC(F)F)cc3)cc2)cc1]

The title compound was prepared by the reaction of Intermediate 78 (470 mg, 2.0965 mmol) and Intermediate 105 (300 mg, 0.6988 mmol) using copper iodide (53 mg, 0.2795 mmol), bis(triphenylphosphine)palladium(II) dichloride (196 mg, 0.2795 mmol) and triphenylphosphine (9 mg, 0.0349 mmol) in excess of diethylamine (15 mL) as per the process described in Example 62 to yield 153 mg the product as a solid; $^1$H NMR (300 MHz, DMSO-$d_6$) δ 1.08 (t, J=7.2 Hz, 3H), 1.64 (s, 6H), 3.26 (q, J=7.2 Hz, 2H), 3.81 (br s, 2H), 7.13 (d, J=7.8 Hz, 2H), 7.23 (d, J=8.7 Hz, 2H), 7.31-7.39 (m, 3H), 7.58 (br s, 4H), 7.83 (d, J=7.8 Hz, 2H), 10.42 (br s, 1H); APCI-MS (m/z) 528 (M+H)$^+$.

Example 79

N-{4-[3-(4-Cyano-phenoxy)-3-methyl-but-1-yn-1-yl]-phenyl}-2-(4-ethanesulfonyl-phenyl)-acetamide

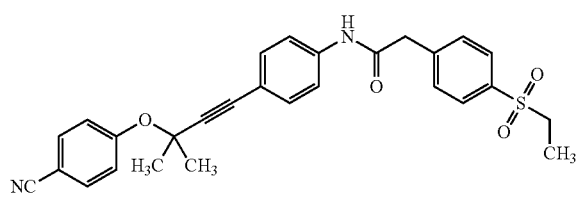 [SMILES: CCS(=O)(=O)c1ccc(CC(=O)Nc2ccc(C#CC(C)(C)Oc3ccc(C#N)cc3)cc2)cc1]

The title compound was prepared by the reaction of Intermediate 79 (323 mg, 1.747 mmol) and Intermediate 105 (250 mg, 0.5823 mmol) using copper iodide (44 mg, 0.2329 mmol) and bis(triphenylphosphine)palladium(II) dichloride (163 mg, 0.2329 mmol) in excess of diethylamine (15 mL) as per the process described in Example 62 to yield 141 mg the product as a solid; $^1$H NMR (300 MHz, DMSO-$d_6$) δ 1.09 (t, J=7.2 Hz, 3H), 1.74 (s, 6H), 3.26 (q, J=7.2 Hz, 2H), 3.81 (s, 2H), 7.36 (d, J=9.0 Hz, 4H), 7.60-7.63 (m, 4H), 7.78-7.85 (m, 4H), 10.43 (br s, 1H); APCI-MS (m/z) 487 (M+H)$^+$.

Example 80

N-{6-[3-(4-Chloro-2-fluoro-phenoxy)-3-methyl-but-1-yn-1-yl]-pyridin-3-yl}-2-(4-ethanesulfonyl-phenyl)-acetamide

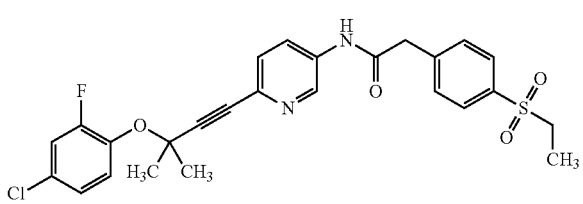 [SMILES: CCS(=O)(=O)c1ccc(CC(=O)Nc2ccc(C#CC(C)(C)Oc3ccc(Cl)cc3F)nc2)cc1]

The title compound was prepared by the reaction of Intermediate 106 (300 mg, 0.697 mmol) and Intermediate 65 (444 mg, 2.091 mmol) using copper iodide (53 mg, 0.2788 mmol), bis(triphenylphosphine)palladium(II) dichloride (195 mg, 0.2788 mmol) and triphenylphosphine (3 mg, 0.0139 mmol) in excess of diethylamine (15 mL) as per the process described in Example 62 to yield 81 mg the product as a solid; $^1$H NMR (300 MHz, DMSO-$d_6$) δ 1.11 (t, J=7.5 Hz, 3H), 1.69 (s, 6H), 3.25 (q, J=7.5 Hz, 2H), 3.85 (s, 2H), 7.25-7.30 (m, 1H), 7.41-7.53 (m, 3H), 7.59 (d, J=8.4 Hz, 2H), 7.85 (d, J=8.4 Hz, 2H), 8.05 (br s, 1H), 8.70 (br s, 1H), 10.65 (br s, 1H); APCI-MS (m/z) 515 (M+H)$^+$.

Example 81

2-[4-(Ethylsulfonyl)phenyl]-N-(1-methyl-2-{2-[4-(trifluoromethyl) phenoxy]propan-2-yl}-1H-benzimidazol-5-yl)acetamide

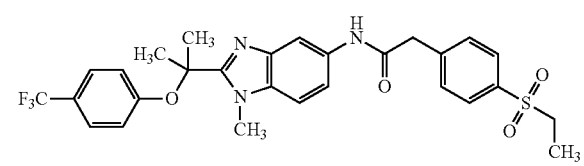 [SMILES: CCS(=O)(=O)c1ccc(CC(=O)Nc2ccc3c(c2)nc(C(C)(C)Oc2ccc(C(F)(F)F)cc2)n3C)cc1]

The title compound was prepared by the reaction of Intermediate 80 (73 mg, 0.210 mmol) with [4-(ethylsulfonyl)phenyl]acetic acid (40 mg, 0.175 mmol) using EDCI.HCl (40 mg, 0.210 mmol) and HOBt (29 mg, 0.210 mmol) in DCM (5 mL) as per the process described in Example 1 to yield 72 mg of the product as a solid. $^1$H NMR (300 MHz, DMSO-$d_6$) δ 1.08 (t, J=6.9 Hz, 3H), 1.88 (br s, 6H), 3.26 (q, J=6.9 Hz, 2H), 3.76 (s, 3H), 3.80 (s, 2H), 6.75 (d, J=8.4 Hz, 2H), 7.37-7.43 (m, 2H), 7.50 (d, J=8.1 Hz, 2H), 7.61 (d, J=7.8 Hz, 2H), 7.84 (d, J=7.8 Hz, 2H), 7.99 (s, 1H), 10.27 (br s, 1H); APCI-MS (m/z) 560 (M+H)$^+$.

Example 82

N-{2-[2-(3,4-Difluorophenoxy)propan-2-yl]-1-methyl-1H-benzimidazol-5-yl}-2-[4-(ethylsulfonyl)phenyl]acetamide

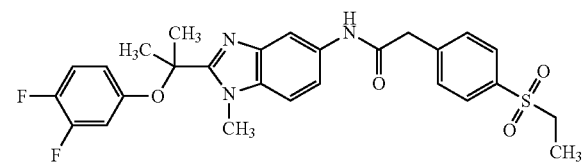 [SMILES: CCS(=O)(=O)c1ccc(CC(=O)Nc2ccc3c(c2)nc(C(C)(C)Oc2ccc(F)c(F)c2)n3C)cc1]

The title compound was prepared by the reaction of Intermediate 81 (83 mg, 0.262 mmol) with [4-(ethylsulfonyl)phenyl]acetic acid (50 mg, 0.218 mmol) using EDCI.HCl (50 mg, 0.262 mmol) and HOBt (36 mg, 0.261 mmol) in DCM (5 mL) as per the process described in Example 1 to yield 73 mg of the product as a solid. $^1$H NMR (300 MHz, DMSO-$d_6$) δ 1.09 (t, J=7.2 Hz, 3H), 1.82 (br s, 6H), 3.26 (q, J=7.2 Hz, 2H), 3.82 (s, 2H), 3.87 (s, 3H), 6.34 (br s, 1H), 6.69 (br s, 1H), 7.18-7.24 (m, 1H), 7.43-7.50 (m, 2H), 7.63 (d, J=7.8 Hz, 2H), 7.85 (d, J=7.8 Hz, 2H), 7.98 (s, 1H), 10.28 (br s, 1H); APCI-MS (m/z) 528 (M+H)$^+$.

Example 83

N-{2-[1-(4-Chloro-2-fluoro-phenoxy)-1-methyl-ethyl]-1-methyl-1H-benzoimidazol-5-yl}-2-(4-ethanesulfonyl-phenyl)-acetamide

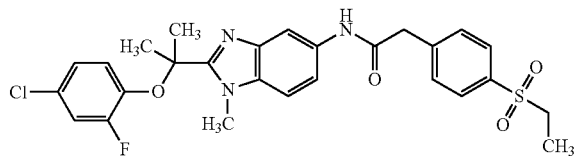 [SMILES: CCS(=O)(=O)c1ccc(CC(=O)Nc2ccc3c(c2)nc(C(C)(C)Oc2ccc(Cl)cc2F)n3C)cc1]

The title compound was prepared by the reaction of Intermediate 82 (88 mg, 0.262 mmol) with [4-(ethylsulfonyl)phenyl]acetic acid (50 mg, 0.218 mmol) using EDCI.HCl (50 mg, 0.262 mmol) and HOBt (36 mg, 0.261 mmol) in DCM (5 mL) as per the process described in Example 1 to yield 124 mg of the product as a solid. $^1$H NMR (300 MHz, DMSO-$d_6$) δ 1.10 (t, J=7.2 Hz, 3H), 1.83 (s, 6H), 3.26 (q, J=7.5 Hz, 2H), 3.82 (s, 2H), 3.91 (s, 3H), 6.39 (t, J=8.7 Hz, 1H), 7.00 (d, J=8.7 Hz, 1H), 7.41-7.51 (m, 3H), 7.64 (d, J=7.8 Hz, 2H), 7.87 (d, J=8.4 Hz, 2H), 7.96 (s, 1H), 10.27 (br s, 1H); APCI-MS (m/z) 544 (M+H)$^+$.

Example 84

N-{2-[2-(2,4-Dichlorophenoxy)propan-2-yl]-1-methyl-1H-benzimidazol-5-yl}-2-[4-(ethylsulfonyl)phenyl]acetamide

The title compound was prepared by the reaction of Intermediate 83 (73 mg, 0.210 mmol) with [4-(ethylsulfonyl)phenyl]acetic acid (40 mg, 0.175 mmol) using EDCI.HCl (40 mg, 0.210 mmol) and HOBt (28 mg, 0.210 mmol) in DCM (5 mL) as per the process described in Example 1 to yield 66 mg of the product as a solid. $^1$H NMR (300 MHz, DMSO-$d_6$) δ 1.09 (t, J=7.2 Hz, 3H), 1.87 (br s, 6H), 3.28 (q, J=6.9 Hz, 2H), 3.83 (s, 5H), 6.24 (d, J=9.0 Hz, 1H), 7.10 (d, J=8.7 Hz, 1H), 7.41 (d, J=8.4 Hz, 1H), 7.48 (d, J=9.0 Hz, 1H), 7.64 (br s, 3H), 7.85 (d, J=7.8 Hz, 2H), 7.99 (s, 1H), 10.29 (br s, 1H); APCI-MS (m/z) 560 (M+H)$^+$.

Example 85

N-{2-[2-(3,4-Dichlorophenoxy)propan-2-yl]-1-methyl-1H-benzimidazol-5-yl}-2-[4-(ethylsulfonyl)phenyl]acetamide

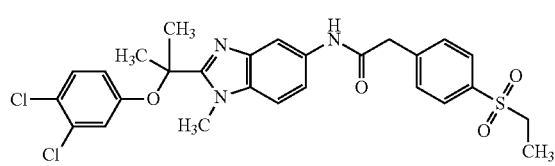 [SMILES: CCS(=O)(=O)c1ccc(CC(=O)Nc2ccc3c(c2)nc(C(C)(C)Oc2ccc(Cl)c(Cl)c2)n3C)cc1]

The title compound was prepared by the reaction of Intermediate 84 (92 mg, 0.262 mmol) with [4-(ethylsulfonyl)phenyl]acetic acid (50 mg, 0.218 mmol) using EDCI.HCl (50 mg, 0.262 mmol) and HOBt (42 mg, 0.313 mmol) in DCM (5 mL) as per the process described in Example 1 to yield 87 mg of the product as a solid. $^1$H NMR (300 MHz, DMSO-$d_6$) δ 1.10 (t, J=6.9 Hz, 3H), 1.85 (br s, 6H), 3.28 (q, J=6.9 Hz, 2H), 3.83 (s, 5H), 6.52 (d, J=8.7 Hz, 1H), 6.90 (s, 1H), 7.37-7.45 (m, 3H), 7.63 (d, J=7.8 Hz, 2H), 7.85 (d, J=7.8 Hz, 2H), 7.99 (s, 1H), 10.28 (br s, 1H); APCI-MS (m/z) 560 (M+H)$^+$.

Example 86

N-{2-[2-(4-Chloro-2-fluorophenoxy)propan-2-yl]-1-ethyl-1H-benzimidazol-5-yl}-2-[4-(ethylsulfonyl)phenyl]acetamide

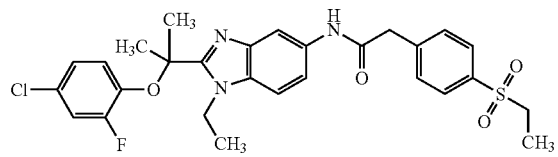 [SMILES: CCn1c(C(C)(C)Oc2ccc(Cl)cc2F)nc2cc(NC(=O)Cc3ccc(S(=O)(=O)CC)cc3)ccc21]

The title compound was prepared by the reaction of Intermediate 85 (91 mg, 0.262 mmol) with [4-(ethylsulfonyl)phenyl]acetic acid (50 mg, 0.218 mmol) using EDCI.HCl (50 mg, 0.262 mmol) and HOBt (35 mg, 0.262 mmol) in DCM (5 mL) as per the process described in Example 1 to yield 104 mg of the product as a solid. $^1$H NMR (300 MHz, DMSO-$d_6$) δ 1.10 (t, J=7.2 Hz, 3H), 1.24 (t, J=7.2 Hz, 3H), 1.83 (br s, 6H), 3.28 (q, J=7.5 Hz, 2H), 3.82 (s, 2H), 4.50 (q, J=7.2 Hz, 2H), 6.46 (t, J=8.7 Hz, 1H), 7.02 (d, J=9.0 Hz, 1H), 7.43 (t, J=7.8 Hz, 2H), 7.52 (d, J=8.7 Hz, 1H), 7.63 (d, J=8.4 Hz, 2H), 7.85 (d, J=8.1 Hz, 2H), 7.98 (s, 1H), 10.28 (br s, 1H); ESI-MS (m/z) 557 (M+H)$^+$.

Example 87

N-{2-[1-(4-Chloro-3-fluoro-phenoxy)-1-methyl-ethyl]-1-ethyl-1H-benzoimidazol-5-yl}-2-(4-ethanesulfonyl-phenyl)-acetamide

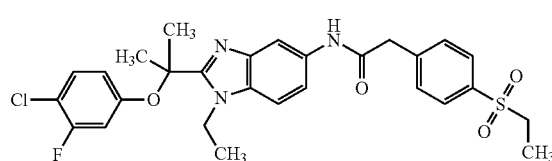

To a stirred solution of [4-(ethylsulfonyl)phenyl]acetic acid (50 mg, 0.218 mmol) in dry DCM (5 mL) was added EDCI.HCl (50 mg, 0.262 mmol) followed by HOBt (35 mg, 0.262 mmol) and the reaction mixture was stirred at RT for 30 min. Intermediate 86 (91 mg, 0.262 mmol) was added to the reaction mixture and it was further stirred for 16 hours at RT. The mixture was diluted with water (10 mL) and extracted with ethyl acetate (3×10 mL). The combined organic extracts were washed with saturated aqueous sodium bicarbonate solution (20 mL), water (2×25 mL), brine (25 mL) and dried over anhydrous sodium sulfate. The solvent was distilled off under reduced pressure and the residue obtained was purified by silica gel column chromatography to yield 95 mg of the title product as a solid. $^1$H NMR (300 MHz, DMSO-d$_6$) δ 1.10 (t, J=7.5 Hz, 3H), 1.16 (t, J=6.6 Hz, 3H), 1.86 (s, 6H), 3.26 (q, J=7.2 Hz, 2H), 3.82 (s, 2H), 4.44 (q, J=7.5 Hz, 2H), 6.45 (d, J=8.1 Hz, 1H), 6.73 (d, J=11.4 Hz, 1H), 7.32-7.50 (m, 3H), 7.64 (d, J=7.8 Hz, 2H), 7.87 (d, J=8.4 Hz, 2H), 8.00 (s, 1H), 10.28 (br s, 1H); APCI-MS (m/z) 559 (M)$^+$.

Example 88

N-{2-[1-(2,4-Difluoro-phenoxy)-1-methyl-ethyl]-1-ethyl-1H-benzoimidazol-5-yl}-2-(4-ethanesulfonyl-phenyl)-acetamide

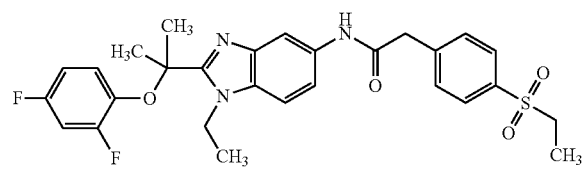 [SMILES: CCn1c(C(C)(C)Oc2ccc(F)cc2F)nc2cc(NC(=O)Cc3ccc(S(=O)(=O)CC)cc3)ccc21]

To a stirred solution of [4-(ethylsulfonyl)phenyl]acetic acid (50 mg, 0.218 mmol) in dry DCM (5 mL) was added EDCI.HCl (50 mg, 0.262 mmol) followed by HOBt (35 mg, 0.262 mmol) and the reaction mixture was stirred at RT for 30 minutes. Intermediate 87 (86 mg, 0.262 mmol) was added to the mixture and it was further stirred for at RT 16 hours. The reaction mixture was diluted with water (50 mL) and extracted with ethyl acetate (3×50 mL). The combined organic extracts were washed with saturated aqueous sodium bicarbonate solution (20 mL), water (2×25 mL) and brine (25 mL). The solution was dried over anhydrous sodium sulfate. The solvent was distilled off under reduced pressure and the residue obtained was purified by silica gel column chromatography to yield 97 mg of the title product as a solid. $^1$H NMR (300 MHz, DMSO-d$_6$) δ 1.09 (t, J=7.2 Hz, 3H), 1.31 (t, J=6.3 Hz, 3H), 1.80 (s, 6H), 3.26 (q, J=7.2 Hz, 2H), 3.81 (s, 2H), 4.54 (q, J=7.5 Hz, 2H), 6.46-6.50 (m, 1H), 6.80-6.85 (m, 1H), 7.30-7.32 (m, 1H), 7.44 (d, J=8.4 Hz, 1H), 7.54 (d, J=8.7 Hz, 1H), 7.64 (d, J=8.4 Hz, 2H), 7.87 (d, J=8.4 Hz, 2H), 7.96 (s, 1H), 10.27 (br s, 1H); ESI-MS (m/z) 542 (M+H)$^+$.

Example 89

N-{2-[1-(3,4-Difluoro-phenoxy)-1-methyl-ethyl]-1-ethyl-1H-benzoimidazol-5-yl}-2-(4-ethanesulfonyl-phenyl)-acetamide

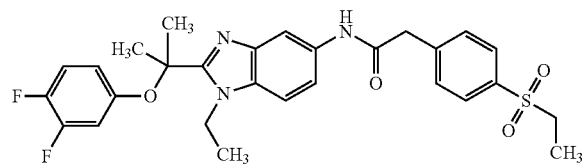 [SMILES: CCn1c(C(C)(C)Oc2ccc(F)c(F)c2)nc2cc(NC(=O)Cc3ccc(S(=O)(=O)CC)cc3)ccc21]

The title compound was prepared by the reaction of Intermediate 88 (87 mg, 0.262 mmol) with [4-(ethylsulfonyl)phenyl]acetic acid (50 mg, 0.218 mmol) using EDCI.HCl (50 mg, 0.261 mmol) and HOBt (35 mg, 0.261 mmol) in DCM (5 mL) as per the process described in Example 1 to yield 89 mg of the product as a solid. $^1$H NMR (300 MHz, DMSO-d$_6$) δ 1.10 (t, J=7.5 Hz, 3H), 1.20 (t, J=6.9 Hz, 3H), 1.83 (s, 6H), 3.28 (q, J=7.2 Hz, 2H), 3.82 (s, 2H), 4.48 (q, J=6.9 Hz, 2H), 6.35 (br s, 1H), 7.02 (br s, 1H), 7.24 (d, J=7.2 Hz, 1H), 7.43 (d, J=9.0 Hz, 1H), 7.52 (d, J=9.0 Hz, 1H), 7.64 (d, J=7.8 Hz, 2H), 7.87 (d, J=8.4 Hz, 2H), 7.98 (s, 1H), 10.27 (s, 1H); ESI-MS (m/z) 542 (M+H)$^+$.

Example 90

2-(4-Ethanesulfonyl-phenyl)-N-{1-ethyl-2-[1-methyl-1-(2,4,6-trifluoro-phenoxy)-ethyl]-1H-benzoimidazol-5-yl}-acetamide

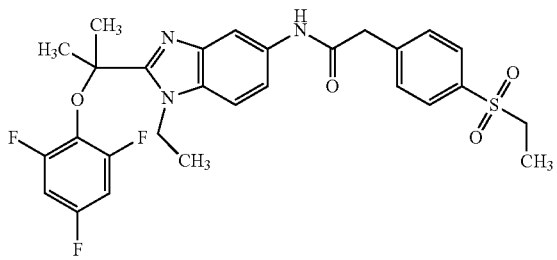 [SMILES: CCn1c(C(C)(C)Oc2c(F)cc(F)cc2F)nc2cc(NC(=O)Cc3ccc(S(=O)(=O)CC)cc3)ccc21]

The title compound was prepared by the reaction of Intermediate 89 (92 mg, 0.262 mmol) with [4-(ethylsulfonyl)phenyl]acetic acid (50 mg, 0.218 mmol) using EDCI.HCl (50 mg, 0.262 mmol) and HOBt (35 mg, 0.262 mmol) in DCM (5 mL) as per the process described in Example 1 to yield 111 mg of the product as a solid. $^1$H NMR (300 MHz, DMSO-d$_6$) δ 1.09 (t, J=7.2 Hz, 3H), 1.42 (t, J=6.9 Hz, 3H), 1.76 (s, 6H), 3.26 (q, J=7.2 Hz, 2H), 3.81 (s, 2H), 4.60 (q, J=6.9 Hz, 2H), 7.24 (t, J=9.0 Hz, 2H), 7.43 (d, J=9.9 Hz, 1H), 7.53 (d, J=8.1 Hz, 1H), 7.63 (d, J=9.9 Hz, 2H), 7.85 (d, J=8.1 Hz, 2H), 7.92 (s, 1H), 10.25 (br s, 1H).

Example 91

2-(4-Ethanesulfonyl-phenyl)-N-{1-ethyl-2-[1-methyl-1-(2,3,4-trifluoro-phenoxy)-ethyl]-1H-benzoimidazol-5-yl}-acetamide

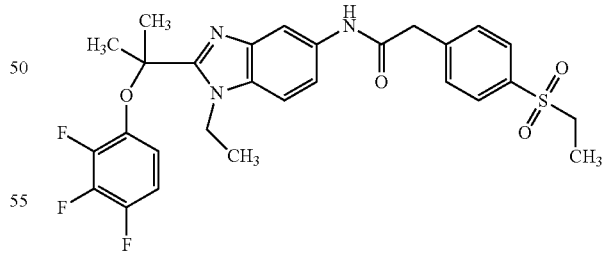

The title compound was prepared by the reaction of Intermediate 90 (93 mg, 0.263 mmol) with [4-(ethylsulfonyl)phenyl]acetic acid (50 mg, 0.219 mmol) using EDCI.HCl (50 mg, 0.262 mmol) and HOBt (36 mg, 0.262 mmol) in DCM (5 mL) as per the process described in Example 1 to yield 111 mg of the product as a solid. $^1$H NMR (300 MHz, DMSO-d$_6$) δ 1.09 (t, J=7.2 Hz, 3H), 1.29 (t, J=6.9 Hz, 3H), 1.83 (s, 6H), 3.29 (q, J=7.2 Hz, 2H), 3.81 (s, 2H), 4.53 (q, J=6.9 Hz, 2H), 6.28 (br s, 1H), 7.06-7.12 (m, 1H), 7.44

(d, J=8.7 Hz, 1H), 7.53 (d, J=8.7 Hz, 1H), 7.63 (d, J=7.8 Hz, 2H), 7.85 (d, J=8.4 Hz, 2H), 7.97 (s, 1H), 10.27 (br s, 1H); APCI-MS (m/z) 560 (M+H)+.

Example 92

2-(4-Ethanesulfonyl-phenyl)-N-{1-ethyl-2-[1-methyl-1-(2,4,5-trifluoro-phenoxy)-ethyl]-1H-benzoimidazol-5-yl}-acetamide

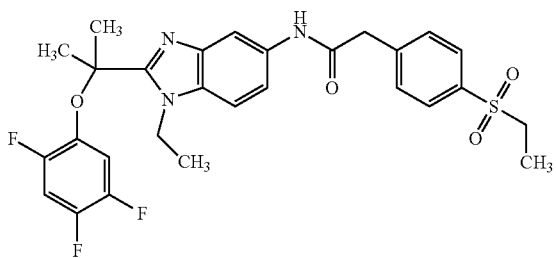 [SMILES: CCn1c(C(C)(C)Oc2cc(F)c(F)cc2F)nc2cc(NC(=O)Cc3ccc(S(=O)(=O)CC)cc3)ccc21]

The title compound was prepared by the reaction of Intermediate 91 (92 mg, 0.263 mmol) with [4-(ethylsulfonyl)phenyl]acetic acid (50 mg, 0.219 mmol) using EDCI.HCl (50 mg, 0.262 mmol) and HOBt (36 mg, 0.262 mmol) in DCM (5 mL) as per the process described in Example 1 to yield 67 mg of the product as a solid. $^1$H NMR (300 MHz, DMSO-$d_6$) δ 1.01 (t, J=7.2 Hz, 3H), 1.30 (t, J=6.9 Hz, 3H), 1.82 (s, 6H), 3.29 (q, J=7.2 Hz, 2H), 3.82 (s, 2H), 4.53 (q, J=6.9 Hz, 2H), 6.68 (br s, 1H), 7.45 (d, J=9.0 Hz, 2H), 7.53 (d, J=9.0 Hz, 3H), 7.85 (d, J=8.4 Hz, 2H), 7.98 (s, 1H), 10.27 (br s, 1H); APCI-MS (m/z) 560 (M+H)+.

Example 93

N-{2-[1-(4-Chloro-phenoxy)-1-methyl-ethyl]-1-ethyl-1H-benzoimidazol-5-yl}-2-(4-ethanesulfonyl-phenyl)-acetamide

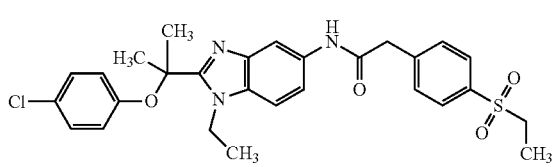

The title compound was prepared by the reaction of Intermediate 92 (87 mg, 0.262 mmol) with [4-(ethylsulfonyl)phenyl]acetic acid (50 mg, 0.218 mmol) using EDCI.HCl (50 mg, 0.262 mmol) and HOBt (36 mg, 0.261 mmol) in DCM (5 mL) as per the process described in Example 1 to yield 114 mg of the product as a solid. $^1$H NMR (300 MHz, DMSO-$d_6$) δ 1.10 (t, J=7.2 Hz, 3H), 1.24 (t, J=6.6 Hz, 3H), 1.83 (s, 6H), 3.28 (q, J=6.9 Hz, 2H), 3.82 (s, 2H), 4.46 (q, J=7.5 Hz, 2H), 6.63 (d, J=8.7 Hz, 2H), 7.21 (d, J=8.7 Hz, 2H), 7.41 (d, J=8.7 Hz, 1H), 7.50 (d, J=8.7 Hz, 1H), 7.64 (d, J=7.8 Hz, 2H), 7.87 (d, J=7.8 Hz, 2H), 7.98 (s, 1H), 10.27 (br s, 1H); ESI-MS (m/z) 540 (M)+.

Example 94

N-{2-[1-(5-Chloro-pyridin-2-yloxy)-1-methyl-ethyl]-1-ethyl-1H-benzoimidazol-5-yl}-2-(4-ethanesulfonyl-phenyl)-acetamide

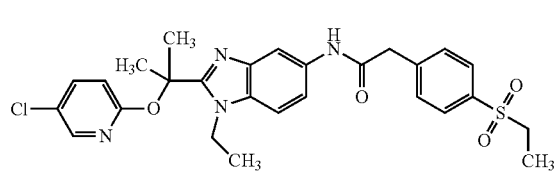

The title compound was prepared by the reaction of Intermediate 93 (45 mg, 0.131 mmol) with [4-(ethylsulfonyl)phenyl]acetic acid (25 mg, 0.109 mmol) using EDCI.HCl (25 mg, 0.130 mmol) and HOBt (18 mg, 0.130 mmol) in DCM (5 mL) as per the process described in Example 1 to yield 29 mg of the product as a solid. $^1$H NMR (300 MHz, DMSO-$d_6$) δ 0.98 (t, J=6.9 Hz, 3H), 1.10 (t, J=7.2 Hz, 3H), 1.92 (s, 6H), 3.25 (q, J=6.9 Hz, 2H), 3.81 (s, 2H), 4.33 (q, J=6.9 Hz, 2H), 6.95 (d, J=8.7 Hz, 1H), 7.36-7.38 (m, 2H), 7.64 (d, J=8.4 Hz, 2H), 7.80-7.90 (m, 5H), 10.22 (br s, 1H).

Example 95

N-{4-[1-(3,5-Dichloro-pyridin-2-yl)-1-methyl-ethoxy]-3-fluoro-phenyl}-2-(4-ethanesulfonyl-phenyl)-acetamide

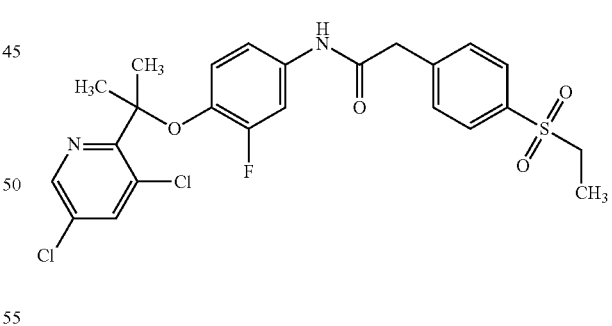

The title compound was prepared by the reaction of Intermediate 94 (80 mg, 0.253 mmol) with [4-(ethylsulfonyl)phenyl]acetic acid (57 mg, 0.253 mmol) using EDCI.HCl (58 mg, 0.304 mmol) and HOBt (51 mg, 0.380 mmol) in DCM (10 mL) as per the process described in Example 1 to yield 41 mg of the product as a solid. $^1$H NMR (300 MHz, DMSO-$d_6$) δ 1.08 (t, J=7.5 Hz, 3H), 1.74 (s, 6H), 3.25 (q, J=7.5 Hz, 2H), 3.74 (s, 2H), 6.33-6.39 (m, 1H), 6.95 (br s, 1H), 7.54-7.58 (m, 3H), 7.82 (d, J=7.8 Hz, 2H), 8.22 (s, 1H), 8.63 (s, 1H), 10.29 (br s, 1H); APCI-MS (m/z) 526 (M+H)+.

Example 96

N-{4-[1-(2,4-Dichloro-phenyl)-1-methyl-ethoxy]-3-fluoro-phenyl}-2-(4-ethanesulfonyl-phenyl)-acetamide

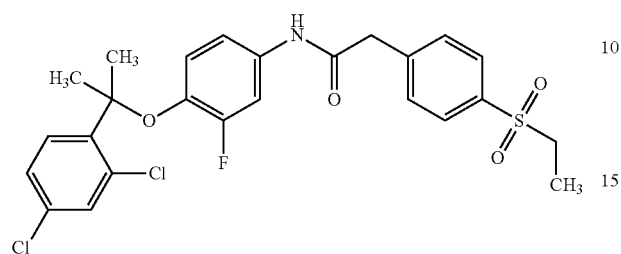

To a stirred solution of [4-(ethylsulfonyl)phenyl]acetic acid (50 mg, 0.219 mmol) and HOBt (40 mg, 0.306 mmol) in anhydrous dichloromethane (5 mL) was added EDCI.HCl (50 mg, 0.262 mmol) at RT. The reaction mixture was stirred at room temperature for 30 minutes. A solution of Intermediate 95 (69 mg, 0.219 mmol) in dichloromethane (5 mL) was added to the mixture and stirred at RT for 18 h. The reaction mixture was concentrated under reduced pressure. The residue obtained was diluted with water (10 mL) and extracted with ethyl acetate (3×10 mL). The combined organic extracts were washed with water (2×20 mL), brine (20 mL) and dried over anhydrous sodium sulfate. The solvent was distilled off under reduced pressure and the residue obtained was purified by silica gel column chromatography to yield 71 mg of the title product as a solid. $^1$H NMR (300 MHz, DMSO-$d_6$) δ 1.08 (t, J=7.2 Hz, 3H), 1.73 (s, 6H), 3.24 (q, J=7.2 Hz, 2H), 3.75 (s, 2H), 6.59 (t, J=8.7 Hz, 1H), 7.01 (d, J=7.8 Hz, 1H), 7.45 (d, J=8.7 Hz, 1H), 7.56-7.66 (m, 5H), 7.82 (d, J=8.4 Hz, 2H), 10.32 (br s, 1H).

Example 97

N-{4-[1-(2-Chloro-4-fluoro-phenyl)-1-methyl-ethoxy]-3-fluoro-phenyl}-2-(4-ethanesulfonyl-phenyl)-acetamide

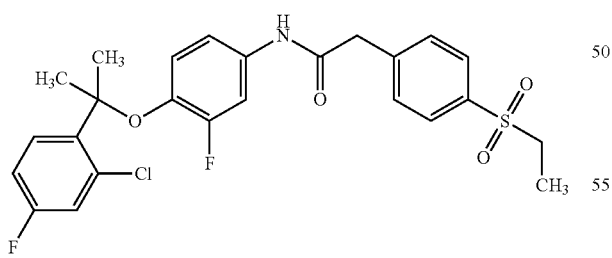

The title compound was prepared by the reaction of Intermediate 96 (65 mg, 0.219 mmol) with [4-(ethylsulfonyl)phenyl]acetic acid (50 mg, 0.219 mmol) using EDCI. HCl (50 mg, 0.262 mmol) and HOBt (42 mg, 0.307 mmol) in DCM (4 mL) as per the process described in Example 1 to yield 92 mg of the product as a solid. $^1$H NMR (300 MHz, DMSO-$d_6$) δ 1.08 (t, J=7.2 Hz, 3H), 1.73 (s, 6H), 3.25 (q, J=7.2 Hz, 2H), 3.75 (s, 2H), 6.57 (t, J=9.3 Hz, 1H), 7.01 (br s, 1H), 7.24 (br s, 1H), 7.45 (br s, 1H), 7.55-7.65 (m, 4H), 7.82 (d, J=8.1 Hz, 2H), 10.31 (br s, 1H); APCI-MS (m/z) 520 (M)$^+$.

Example 98

N-{4-[1-(4-Chloro-2-fluoro-phenyl)-1-methyl-ethoxy]-3-fluoro-phenyl}-2-(4-ethanesulfonyl-phenyl)-acetamide

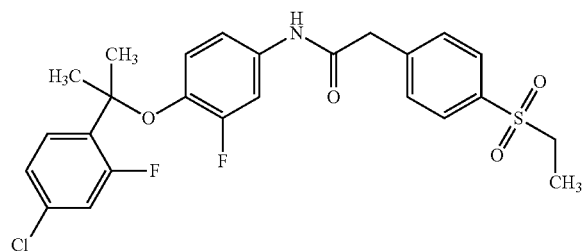 [SMILES: CCS(=O)(=O)c1ccc(CC(=O)Nc2ccc(OC(C)(C)c3ccc(Cl)cc3F)c(F)c2)cc1]

The title compound was prepared by the reaction of Intermediate 97 (66 mg, 0.219 mmol) with [4-(ethylsulfonyl)phenyl]acetic acid (50 mg, 0.219 mmol) using EDCI. HCl (50 mg, 0.262 mmol) and HOBt (40 mg, 0.307 mmol) in DCM (4 mL) as per the process described in Example 1 to yield 116 mg of the product as a solid. $^1$H NMR (300 MHz, DMSO-$d_6$) δ 1.08 (t, J=7.2 Hz, 3H), 1.63 (s, 6H), 3.25 (q, J=7.2 Hz, 2H), 3.76 (s, 2H), 6.76 (t, J=9.0 Hz, 1H), 7.07 (d, J=7.5 Hz, 1H), 7.29 (d, J=7.8 Hz, 1H), 7.43 (d, J=12.0 Hz, 1H), 7.56-7.63 (m, 4H), 7.83 (d, J=8.4 Hz, 2H), 10.34 (br s, 1H).

Example 99

N-{4-[1-(4-Chloro-2-fluoro-phenyl)-cyclopropoxy]-3-fluoro-phenyl}-2-(4-ethanesulfonyl-phenyl)-acetamide

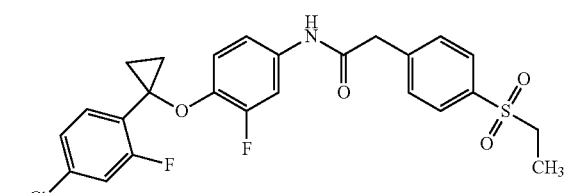

The title compound was prepared by the reaction of Intermediate 98 (72 mg, 0.219 mmol) with [4-(ethylsulfonyl)phenyl]acetic acid (50 mg, 0.219 mmol) using EDCI. HCl (50 mg, 0.262 mmol) and HOBt (40 mg, 0.307 mmol) in DCM (4 mL) as per the process described in Example 1 to yield 75 mg of the product as a solid. $^1$H NMR (300 MHz, DMSO-$d_6$) δ 1.07 (t, J=7.2 Hz, 3H), 1.27-1.38 (m, 4H), 3.24 (q, J=7.2 Hz, 2H), 3.72 (s, 2H), 7.12-7.23 (m, 3H), 7.40 (d, J=10.2 Hz, 1H), 7.49-7.57 (m, 4H), 7.80 (d, J=8.4 Hz, 2H), 10.27 (br s, 1H); APCI-MS (m/z) 506 (M+H)$^+$.

Example 100

N-{4-[1-(4-Chloro-3-fluoro-phenyl)-cyclopropoxy]-3-fluoro-phenyl}-2-(4-ethanesulfonyl-phenyl)-acetamide

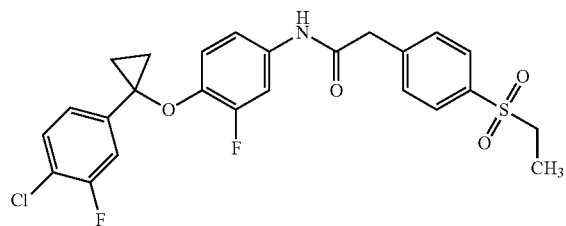 [SMILES: CCS(=O)(=O)c1ccc(CC(=O)Nc2ccc(OC3(c4ccc(Cl)c(F)c4)CC3)c(F)c2)cc1]

The title compound was prepared by the reaction of Intermediate 99 (65 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.307 mmol) in DCM (4 mL) as per the process described in Example 1 to yield 61 mg of the product as a solid. $^1$H NMR (300 MHz, DMSO-$d_6$) δ 1.08 (t, J=7.2 Hz, 3H), 1.43 (d, J=7.5 Hz, 4H), 3.24 (q, J=7.2 Hz, 2H), 3.74 (s, 2H), 6.88 (t, J=9.3 Hz, 1H), 7.08 (d, J=8.7 Hz, 2H), 7.20 (d, J=10.8 Hz, 1H), 7.49-7.65 (m, 4H), 7.82 (d, J=8.4 Hz, 2H), 10.30 (br s, 1H); APCI-MS (m/z) 506 (M+H)$^+$.

Example 101

N-{4-[3-(2,4-Dichloro-phenyl)-oxetan-3-yloxy]-3-fluoro-phenyl}-2-(4-ethanesulfonyl-phenyl)-acetamide

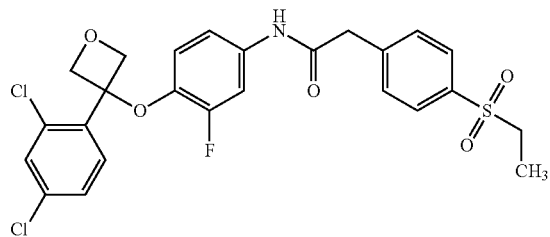 [SMILES: CCS(=O)(=O)c1ccc(CC(=O)Nc2ccc(OC3(c4ccc(Cl)cc4Cl)COC3)c(F)c2)cc1]

To a stirred solution of [4-(ethylsulfonyl)phenyl]acetic acid (50 mg, 0.219 mmol) in dry DCM (5 mL) was added EDCI.HCl (50 mg, 0.262 mmol) followed by HOBt (41 mg, 0.306 mmol) and the reaction mixture was stirred at room temperature for 30 min. Intermediate 100 (72 mg, 0.219 mmol) was added to the reaction mixture and it was further stirred for 18 h. The reaction mixture was diluted with water (10 mL) and extracted with ethyl acetate (3×10 mL). The combined organic extracts were washed with saturated aqueous sodium bicarbonate solution (20 mL), water (2×20 mL) and brine (20 mL). The organic layer was dried over anhydrous sodium sulfate and the solvent was distilled off under reduced pressure. The residue obtained was purified by silica gel column chromatography to yield 29 mg of the title product as a solid. $^1$H NMR (300 MHz, DMSO-$d_6$) δ 1.08 (t, J=7.2 Hz, 3H), 3.24 (q, J=7.2 Hz, 2H), 3.73 (s, 2H), 5.07 (d, J=8.4 Hz, 2H), 5.18 (d, J=8.4 Hz, 2H), 6.76-6.82 (m, 1H), 7.04 (br s, 1H), 7.42-7.63 (m, 6H), 7.82 (d, J=7.8 Hz, 2H), 10.30 (br s, 1H); APCI-MS (m/z) 537 (M+H)$^+$.

Example 102

N-{4-[3-(4-Chloro-3-fluoro-phenyl)-oxetan-3-yloxy]-3-fluoro-phenyl}-2-(4-ethanesulfonyl-phenyl)-acetamide

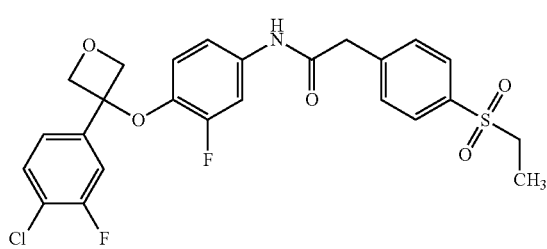 [SMILES: CCS(=O)(=O)c1ccc(CC(=O)Nc2ccc(OC3(c4ccc(Cl)c(F)c4)COC3)c(F)c2)cc1]

The title compound was prepared by the reaction of Intermediate 101 (68 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.307 mmol) in DCM (4 mL) as per the process described in Example 1 to yield 68 mg of the product as a solid. $^1$H NMR (300 MHz, DMSO-$d_6$) δ 1.08 (t, J=7.2 Hz, 3H), 3.24 (q, J=7.2 Hz, 2H), 3.73 (s, 2H), 4.97 (br s, 4H), 6.32-6.38 (m, 1H), 7.02 (d, J=8.4 Hz, 1H), 7.34 (d, J=6.9 Hz, 1H), 7.54-7.63 (m, 5H), 7.81 (d, J=8.4 Hz, 2H), 10.30 (br s, 1H); APCI-MS (m/z) 522 (M+H)$^+$.

Example 103

N-{4-[4-(4-Chloro-3-fluoro-phenyl)-tetrahydro-pyran-4-yloxy]-3-fluoro-phenyl}-2-(4-ethanesulfonyl-phenyl)-acetamide

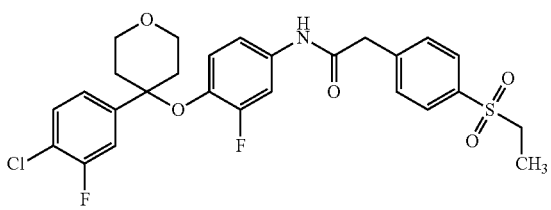 [SMILES: CCS(=O)(=O)c1ccc(CC(=O)Nc2ccc(OC3(c4ccc(Cl)c(F)c4)CCOCC3)c(F)c2)cc1]

The title compound was prepared by the reaction of Intermediate 102 (75 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.307 mmol) in DCM (4 mL) as per the process described in Example 1 to yield 68 mg of the product as a solid. $^1$H NMR (300 MHz, DMSO-$d_6$) δ 1.08 (t, J=7.2 Hz, 3H), 2.14 (br s, 4H), 3.24 (q, J=7.2 Hz, 2H), 3.69-3.73 (m, 6H), 6.37 (t, J=9.3 Hz, 1H), 6.92 (br s, 1H), 7.33 (d, J=8.1 Hz, 1H), 7.51-7.61 (m, 5H), 7.82 (d, J=7.8 Hz, 2H), 10.29 (br s, 1H); APCI-MS (m/z) 548 (M−H)$^-$.

Example 104

N-{4-[2-(5-Chloro-indol-1-yl)-1,1-dimethyl-ethoxy]-3-fluoro-phenyl}-2-(4-ethanesulfonyl-phenyl)-acetamide

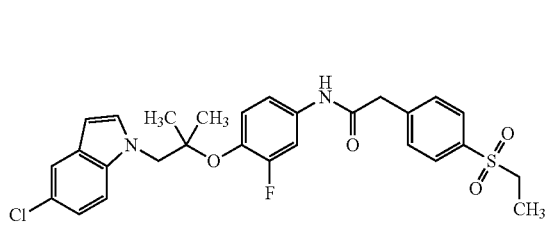 [SMILES: CCS(=O)(=O)c1ccc(CC(=O)Nc2ccc(OC(C)(C)Cn3ccc4cc(Cl)ccc43)c(F)c2)cc1]

The title compound was prepared by the reaction of Intermediate 103 (73 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.307 mmol) in DCM (4 mL) as per the process described in Example 1 to yield 91 mg of the product as a solid. $^1$H NMR (300 MHz, DMSO-$d_6$) δ 1.08 (t, J=7.2 Hz, 3H), 1.15 (br s, 6H), 3.26 (q, J=7.2 Hz, 2H), 3.77 (s, 2H), 4.42 (s, 2H), 6.47 (br s, 1H), 6.95 (t, J=8.1 Hz, 1H), 7.09-7.18 (m, 2H), 7.47 (br s, 1H), 7.55-7.65 (m, 5H), 7.83 (d, J=8.4 Hz, 2H), 10.37 (br s, 1H); APCI-MS (m/z) 542 (M+H)$^+$.

Example 105

N-{4-[1-(5-Chloro-1-ethyl-1H-benzoimidazol-2-yl)-1-methyl-ethoxy]-3-fluoro-phenyl}-2-(4-ethanesulfonyl-phenyl)-acetamide

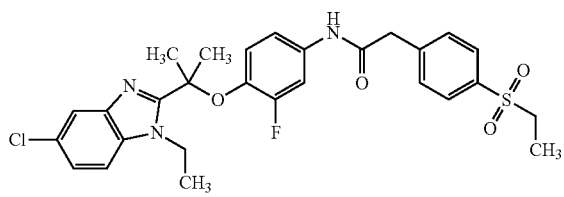 [SMILES: CCn1c(C(C)(C)Oc2ccc(NC(=O)Cc3ccc(S(=O)(=O)CC)cc3)cc2F)nc2cc(Cl)ccc21]

The title compound was prepared by the reaction of Intermediate 104 (91 mg, 0.262 mmol) with [4-(ethylsulfonyl)phenyl]acetic acid (50 mg, 0.218 mmol) using EDCI.HCl (50 mg, 0.262 mmol) and HOBt (36 mg, 0.262 mmol) in DCM (5 mL) as per the process described in Example 1 to yield 149 mg of the product as a solid. $^1$H NMR (300 MHz, DMSO-$d_6$) δ 1.08 (t, J=7.2 Hz, 3H), 1.31 (t, J=6.9 Hz, 3H), 1.78 (s, 6H), 3.22-3.39 (m, 4H), 3.75 (s, 2H), 4.61 (q, J=6.9 Hz, 2H), 6.53 (t, J=8.7 Hz, 1H), 7.00 (d, J=9.0 Hz, 1H), 7.31 (d, J=7.8 Hz, 1H), 7.55-7.72 (m, 5H), 7.82 (d, J=7.8 Hz, 2H), 10.35 (br s, 1H); APCI-MS (m/z) 558 (M+H)$^+$.

Example 106

N-{4-[3-(4-Chloro-3-fluoro-phenoxy)-3-methyl-but-1-ynyl]-3-fluoro-phenyl}-2-(4-ethanesulfonyl-phenyl)-acetamide

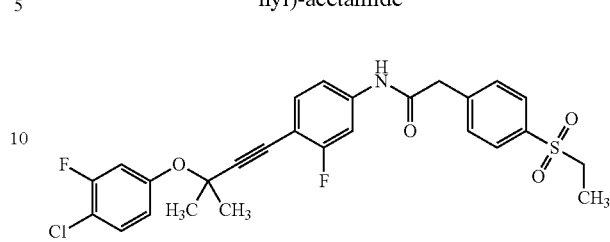

The title compound was prepared by the reaction of Intermediate 107 (300 mg, 0.670 mmol) and Intermediate 66 (446 mg, 2.012 mmol) using copper iodide (51 mg, 0.268 mmol), bis(triphenylphosphine)palladium(II) dichloride (188 mg, 0.268 mmol) and triphenylphosphine (3 mg, 0.013 mmol) in excess of diethylamine (15 mL) as per the process described in Example 62 to yield 232 mg the product as a solid; $^1$H NMR (300 MHz, DMSO-$d_6$) δ 1.09 (t, J=7.2 Hz, 3H), 1.69 (s, 6H), 3.25 (q, J=7.2 Hz, 2H), 3.83 (s, 2H), 7.10 (d, J=9.3 Hz, 1H), 7.24-7.41 (m, 2H), 7.43-7.69 (m, 5H), 7.84 (d, J=7.8 Hz, 2H), 10.64 (br s, 1H).

Example 107

N-{4-[1-(2,4-Difluoro-phenyl)-1-methyl-ethoxy]-3-fluoro-phenyl}-2-(4-ethanesulfonyl-phenyl)-acetamide

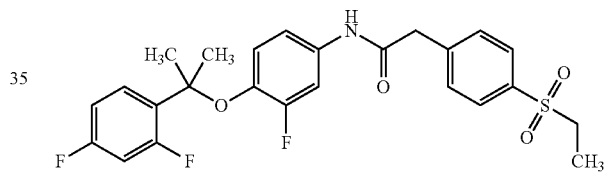

The title compound was prepared by the reaction of Intermediate 108 (62 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (4 mL) as per the process described in Example 1 to yield 93 mg of the product as a solid. $^1$H NMR (300 MHz, DMSO-$d_6$) δ 1.08 (t, J=7.2 Hz, 3H), 1.64 (s, 6H), 3.25 (q, J=7.2 Hz, 2H), 3.76 (s, 2H), 7.72 (t, J=9.3 Hz, 1H), 7.06 (d, J=8.4 Hz, 2H), 7.25 (t, J=12.0 Hz, 1H), 7.54-7.63 (m, 4H), 7.83 (d, J=8.4 Hz, 2H), 10.34 (br s, 1H).

Example 108

2-(4-Ethanesulfonyl-phenyl)-N-{3-fluoro-4-[2-(5-fluoro-2-methyl-indol-1-yl)-1,1-dimethyl-ethoxy]-phenyl}-acetamide

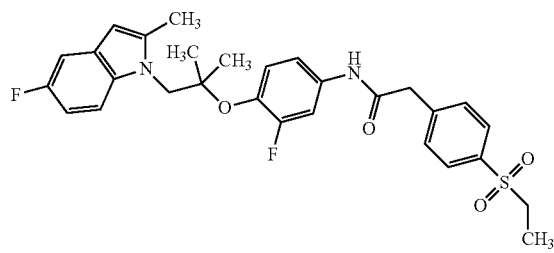 [SMILES: CCS(=O)(=O)c1ccc(CC(=O)Nc2ccc(OC(C)(C)Cn3c(C)cc4cc(F)ccc43)c(F)c2)cc1]

The title compound was prepared by the reaction of Intermediate 109 (72 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (4 mL) as per the process described in Example 1 to yield 45 mg of the product as a solid. $^1$H NMR (300 MHz, DMSO-d$_6$) δ 1.08 (t, J=7.5 Hz, 3H), 1.19 (s, 6H), 2.45 (s, 3H), 3.26 (q, J=7.5 Hz, 2H), 3.76 (s, 2H), 4.37 (s, 2H), 6.24 (s, 1H), 6.80-6.87 (m, 2H), 7.15 (t, J=9.3 Hz, 2H), 7.54-7.59 (m, 4H), 7.83 (d, J=8.1 Hz, 2H), 10.36 (br s, 1H); APCI-MS (m/z) 541 (M+H)$^+$.

Example 109

N-{4-[1-(2,4-Dichloro-phenyl)-1-methyl-ethoxy]-3,5-difluoro-phenyl}-2-(4-ethanesulfonyl-phenyl)-acetamide

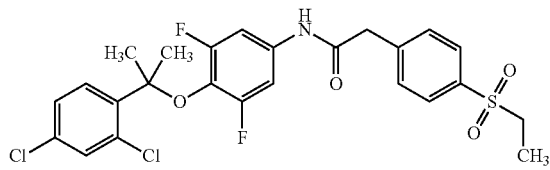 [SMILES: CCS(=O)(=O)c1ccc(CC(=O)Nc2cc(F)c(OC(C)(C)c3ccc(Cl)cc3Cl)c(F)c2)cc1]

The title compound was prepared by the reaction of Intermediate 110 (73 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (4 mL) as per the process described in Example 1 to yield 56 mg of the product as a solid. $^1$H NMR (300 MHz, DMSO-d$_6$) δ 1.09 (t, J=7.2 Hz, 3H), 1.69 (s, 6H), 3.26 (q, J=7.2 Hz, 2H), 3.80 (s, 2H), 7.35 (d, J=10.2 Hz, 2H), 7.45 (d, J=8.4 Hz, 1H), 7.60 (t, J=8.4 Hz, 3H), 7.76 (d, J=9.0 Hz, 1H), 7.84 (d, J=8.4 Hz, 2H), 10.56 (br s, 1H).

Example 110

N-{4-[1-(3,5-Dichloro-pyridin-2-yl)-1-methyl-ethoxy]-3,5-difluoro-phenyl}-2-(4-ethanesulfonyl-phenyl)-acetamide

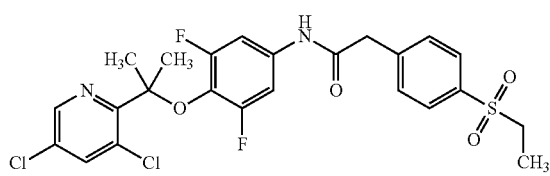 [SMILES: CCS(=O)(=O)c1ccc(CC(=O)Nc2cc(F)c(OC(C)(C)c3ncc(Cl)cc3Cl)c(F)c2)cc1]

The title compound was prepared by the reaction of Intermediate 111 (73 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.3066 mmol) in DCM (4 mL) as per the process described in Example 1 to yield 34 mg of the product as a solid. $^1$H NMR (300 MHz, DMSO-d$_6$) δ 1.08 (t, J=7.2 Hz, 3H), 1.70 (s, 6H), 3.25 (q, J=7.2 Hz, 2H), 3.78 (s, 2H), 7.28 (d, J=10.2 Hz, 2H), 7.57 (d, J=6.6 Hz, 2H), 7.83 (d, J=7.8 Hz, 2H), 8.26 (s, 1H), 8.55 (s, 1H), 10.52 (br s, 1H); APCI-MS (m/z) 543 (M+H)$^+$.

Example 111

2-(4-Ethanesulfonyl-phenyl)-N-{4-[1-(1-ethyl-5-fluoro-1H-benzoimidazol-2-yl)-1-methyl-ethoxy]-3-fluoro-phenyl}-acetamide

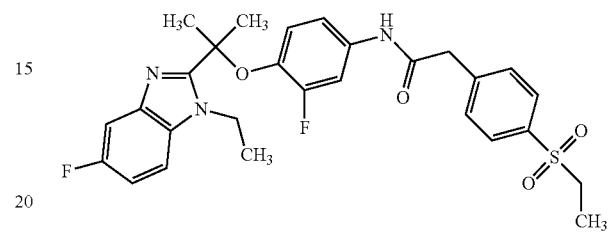

The title compound was prepared by the reaction of Intermediate 112 (128 mg, 0.367 mmol) with [4-(ethylsulfonyl)phenyl]acetic acid (70 mg, 0.306 mmol) using EDCI.HCl (70 mg, 0.367 mmol) and HOBt (50 mg, 0.367 mmol) in DCM (5 mL) as per the process described in Example 1 to yield 110 mg of the product as a solid. $^1$H NMR (300 MHz, DMSO-d$_6$) δ 1.08 (t, J=7.5 Hz, 3H), 1.31 (br s, 3H), 1.78 (s, 6H), 3.25 (q, J=7.5 Hz, 2H), 3.75 (s, 2H), 4.59 (br s, 2H), 6.53 (t, J=7.8 Hz, 1H), 7.00 (d, J=9.6 Hz, 1H), 7.16 (br s, 1H), 7.46 (d, J=10.2 Hz, 1H), 7.55-7.68 (m, 4H), 7.82 (d, J=7.8 Hz, 2H), 10.35 (br s, 1H); ESI-MS (m/z) 542 (M+H)$^+$.

Example 112

N-{2-[1-(2,4-Difluoro-phenoxy)-1-methyl-ethyl]-1-methyl-1H-benzoimidazol-5-yl}-2-(4-ethanesulfonyl-phenyl)-acetamide

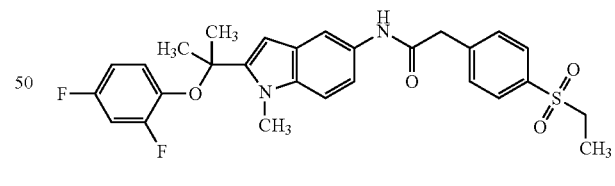

The title compound was prepared by the reaction of Intermediate 113 (83 mg, 0.262 mmol) with [4-(ethylsulfonyl)phenyl]acetic acid (50 mg, 0.218 mmol) using EDCI.HCl (50 mg, 0.261 mmol) and HOBt (35 mg, 0.261 mmol) in DCM (10 mL) as per the process described in Example 1 to yield 126 mg of the product as a solid. $^1$H NMR (300 MHz, DMSO-d$_6$) δ 1.09 (t, J=7.2 Hz, 3H), 1.79 (s, 6H), 3.28 (q, J=7.2 Hz, 2H), 3.81 (s, 2H), 3.96 (s, 3H), 6.41 (br s, 1H), 6.80 (br s, 1H), 7.29 (t, J=11.4 Hz, 1H), 7.41-7.53 (m, 2H), 7.63 (d, J=7.8 Hz, 2H), 7.85 (d, J=8.1 Hz, 2H), 7.94 (s, 1H), 10.24 (br s, 1H); ESI-MS (m/z) 529 (M+H)$^+$.

Example 113

N-[2-[1-(2,4-Difluoro-phenoxy)-1-methyl-ethyl]-1-(2-dimethylamino-ethyl)-1H-benzoimidazol-5-yl]-2-(4-ethanesulfonyl-phenyl)-acetamide

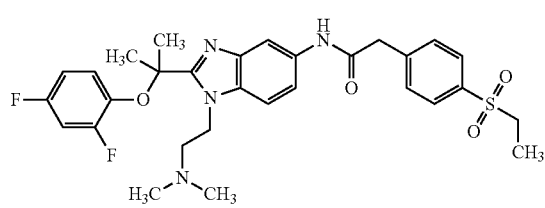 [SMILES: CCS(=O)(=O)c1ccc(CC(=O)Nc2ccc3c(c2)nc(C(C)(C)Oc2ccc(F)cc2F)n3CCN(C)C)cc1]

The title compound was prepared by the reaction of Intermediate 114 (98 mg, 0.262 mmol) with [4-(ethylsulfonyl)phenyl]acetic acid (50 mg, 0.218 mmol) using EDCI.HCl (50 mg, 0.261 mmol) and HOBt (36 mg, 0.262 mmol) in DCM (10 mL) as per the process described in Example 1 to yield 101 mg of the product as a solid. $^1$H NMR (300 MHz, DMSO-$d_6$) δ 1.10 (t, J=7.2 Hz, 3H), 1.81 (s, 6H), 2.25 (s, 6H), 2.64 (br s, 2H), 3.27 (q, J=7.2 Hz, 2H), 3.82 (s, 2H), 4.61 (br s, 2H), 6.58 (br s, 1H), 6.87 (br s, 1H), 7.33-7.53 (m, 3H), 7.63 (d, J=7.2 Hz, 2H), 7.85 (d, J=8.4 Hz, 2H), 7.97 (s, 1H), 10.28 (br s, 1H); ESI-MS (m/z) 585 (M+H)$^+$.

Example 114

N-{1-Cyclopropylmethyl-2-[1-(2,4-difluoro-phenoxy)-1-methyl-ethyl]-1H-benzoimidazol-5-yl}-2-(4-ethanesulfonyl-phenyl)-acetamide

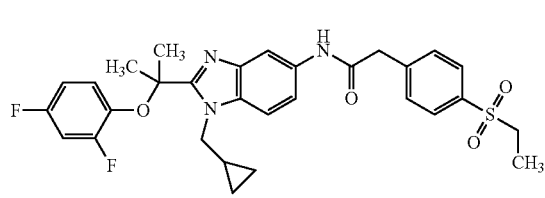 [SMILES: CCS(=O)(=O)c1ccc(CC(=O)Nc2ccc3c(c2)nc(C(C)(C)Oc2ccc(F)cc2F)n3CC2CC2)cc1]

The title compound was prepared by the reaction of Intermediate 115 (94 mg, 0.262 mmol) with [4-(ethylsulfonyl)phenyl]acetic acid (50 mg, 0.218 mmol) using EDCI.HCl (50 mg, 0.261 mmol) and HOBt (36 mg, 0.262 mmol) in DCM (5 mL) as per the process described in Example 1 to yield 102 mg of the product as a solid. $^1$H NMR (300 MHz, DMSO-$d_6$) δ 0.44 (br s, 4H), 0.95-1.31 (m, 4H), 1.80 (s, 6H), 3.27 (q, J=7.8 Hz, 2H), 3.82 (s, 2H), 4.43 (br s, 2H), 6.55-6.65 (m, 1H), 6.80-6.90 (m, 1H), 7.30-7.45 (m, 2H), 7.56-7.66 (m, 3H), 7.85 (d, J=7.8 Hz, 2H), 7.96 (s, 1H), 10.28 (br s, 1H); APCI-MS (m/z) 568 (M+H)$^+$.

Example 115

N-{2-[1-(2,4-Difluoro-phenoxy)-1-methyl-ethyl]-1-propyl-1H-benzoimidazol-5-yl}-2-(4-ethanesulfonyl-phenyl)-acetamide

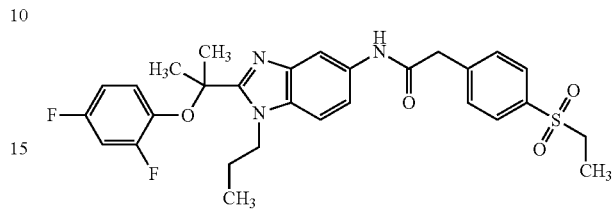

The title compound was prepared by the reaction of Intermediate 116 (90 mg, 0.262 mmol) with [4-(ethylsulfonyl)phenyl]acetic acid (50 mg, 0.218 mmol) using EDCI.HCl (50 mg, 0.261 mmol) and HOBt (35 mg, 0.261 mmol) in DCM (5 mL) as per the process described in Example 1 to yield 101 mg of the product as a solid. $^1$H NMR (300 MHz, DMSO-$d_6$) δ 0.93 (br s, 3H), 1.07-1.13 (m, 3H), 1.70-1.80 (m, 8H), 3.27-3.32 (m, 2H), 3.82 (br s, 2H), 4.43 (br s, 2H), 6.55-6.65 (m, 1H), 6.80-6.90 (m, 1H), 7.30-7.45 (m, 2H), 7.56-7.66 (m, 3H), 7.85 (d, J=8.1 Hz, 2H), 7.96 (s, 1H), 10.28 (br s, 1H).

Example 116

N-{2-[1-(2,4-Difluoro-phenoxy)-1-methyl-ethyl]-1-isobutyl-1H-benzoimidazol-5-yl}-2-(4-ethanesulfonyl-phenyl)-acetamide

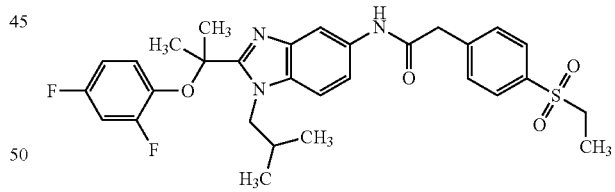

The title compound was prepared by the reaction of Intermediate 117 (79 mg, 0.220 mmol) with [4-(ethylsulfonyl)phenyl]acetic acid (40 mg, 0.180 mmol) using EDCI.HCl (42 mg, 0.220 mmol) and HOBt (30 mg, 0.220 mmol) in DCM (5 mL) as per the process described in Example 1 to yield 45 mg of the product as a solid. $^1$H NMR (300 MHz, DMSO-$d_6$) δ 0.84 (d, J=5.7 Hz, 6H), 1.10 (t, J=6.9 Hz, 3H), 1.70 (s, 6H), 2.48 (br s, 1H), 3.28 (q, J=7.2 Hz, 2H), 3.82 (s, 2H), 4.33 (d, J=7.8 Hz, 2H), 6.72 (br s, 1H), 6.90-6.95 (m, 1H), 7.34-7.45 (m, 2H), 7.57-7.64 (m, 3H), 7.85 (d, J=7.5 Hz, 2H), 7.97 (s, 1H), 10.29 (br s, 1H); APCI-MS (m/z) 570 (M+H)$^+$.

Example 117

N-{2-[1-(2,4-Difluoro-phenoxy)-1-methyl-ethyl]-1-isopropyl-1H-benzoimidazol-5-yl}-2-(4-ethanesulfonyl-phenyl)-acetamide

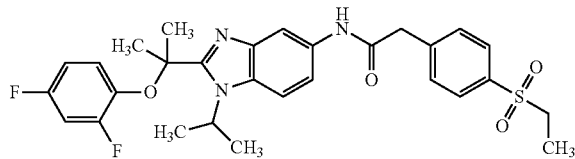

The title compound was prepared by the reaction of Intermediate 118 (90 mg, 0.262 mmol) with [4-(ethylsulfonyl)phenyl]acetic acid (50 mg, 0.218 mmol) using EDCI.HCl (50 mg, 0.261 mmol) and HOBt (35 mg, 0.261 mmol) in DCM (5 mL) as per the process described in Example 1 to yield 102 mg of the product as a solid. $^1$H NMR (300 MHz, DMSO-$d_6$) δ 1.09 (t, J=7.8 Hz, 3H), 1.45 (d, J=6.6 Hz, 6H), 1.83 (s, 6H), 3.27 (q, J=7.5 Hz, 2H), 3.38 (br s, 1H), 3.82 (s, 2H), 6.40-6.45 (m, 1H), 6.80-6.85 (m, 1H), 7.25-7.89 (m, 2H), 7.62 (d, J=7.8 Hz, 2H), 7.70 (d, J=9.0 Hz, 1H), 7.85 (d, J=7.8 Hz, 2H), 8.00 (s, 1H), 10.29 (s, 1H).

Example 118

N-{2-[(2,4-Difluoro-phenoxy)-difluoromethyl]-1-ethyl-1H-benzoimidazol-5-yl}-2-(4-ethanesulfonyl-phenyl)-acetamide

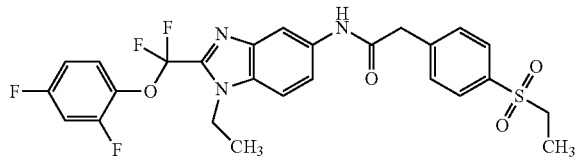 [SMILES: CCn1c(C(F)(F)Oc2ccc(F)cc2F)nc2cc(NC(=O)Cc3ccc(S(=O)(=O)CC)cc3)ccc21]

The title compound was prepared by the reaction of Intermediate 119 (89 mg, 0.262 mmol) with [4-(ethylsulfonyl)phenyl]acetic acid (50 mg, 0.218 mmol) using EDCI.HCl (50 mg, 0.261 mmol) and HOBt (35 mg, 0.261 mmol) in DCM (5 mL) as per the process described in Example 1 to yield 85 mg of the product as a solid. $^1$H NMR (300 MHz, DMSO-$d_6$) δ 1.10 (t, J=7.2 Hz, 3H), 1.40 (t, J=6.9 Hz, 3H), 3.26 (q, J=7.2 Hz, 2H), 3.84 (s, 2H), 4.54 (q, J=6.9 Hz, 2H), 7.20-7.30 (m, 1H), 7.57-7.75 (m, 6H), 7.85 (d, J=8.1 Hz, 2H), 8.14 (s, 1H), 10.40 (s, 1H); ESI-MS (m/z) 550 (M+H)$^+$.

Example 119

N-{4-[1-(4-Chloro-3-fluorophenyl)-cyclobutoxy]-3-fluoro-phenyl}-2-(4-ethanesulfonyl-phenyl)-acetamide

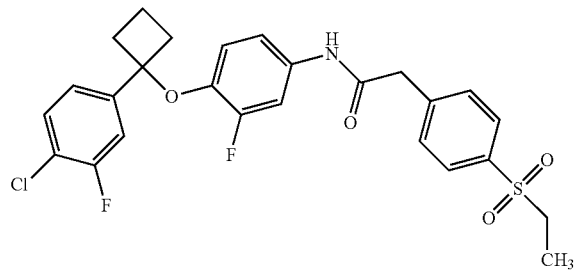 [SMILES: CCS(=O)(=O)c1ccc(CC(=O)Nc2ccc(OC3(c4ccc(Cl)c(F)c4)CCC3)c(F)c2)cc1]

The title compound was prepared by the reaction of Intermediate 120 (68 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (4 mL) as per the process described in Example 1 to yield 86 mg of the product as a solid. $^1$H NMR (300 MHz, DMSO-$d_6$) δ 1.08 (t, J=7.2 Hz, 3H), 1.67-1.70 (m, 1H), 1.99 (br s, 1H), 2.64-2.72 (m, 4H), 3.26 (q, J=7.2 Hz, 2H), 3.73 (s, 2H), 6.65-6.67 (m, 1H), 7.04-7.06 (m, 1H), 7.18 (t, J=8.1 Hz, 1H), 7.47-7.58 (m, 5H), 7.83 (d, J=8.4 Hz, 2H), 10.28 (br s, 1H); APCI-MS (m/z) 517 (M+H)$^+$.

Example 120

N-{4-[1-(4-Chloro-3-fluorophenyl)-cyclopentyloxy]-phenyl}-2-(4-ethanesulfonyl-phenyl)-acetamide

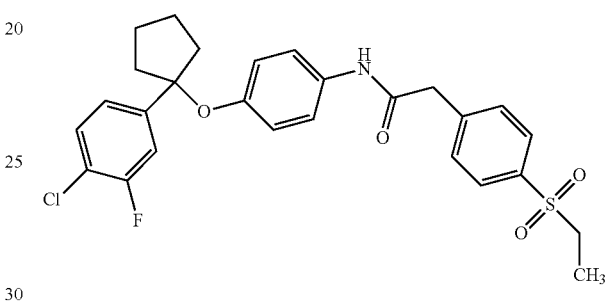

The title compound was prepared by the reaction of Intermediate 121 (67 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (10 mL) as per the process described in Example 1 to yield 81 mg of the product as a solid. $^1$H NMR (300 MHz, DMSO-$d_6$) δ 1.08 (t, J=7.8 Hz, 3H), 1.79 (br s, 4H), 2.08 (br s, 2H), 2.33-2.36 (m, 2H), 3.25 (q, J=7.8 Hz, 2H), 3.72 (s, 2H), 6.53 (d, J=9.0 Hz, 2H), 7.17 (t, J=8.4 Hz, 1H), 7.35 (d, J=9.0 Hz, 3H), 7.54-7.59 (m, 3H), 7.82 (d, J=8.4 Hz, 2H), 10.10 (br s, 1H); ESI-MS (m/z) 514 (M–H)$^-$.

Example 121

N-{4-[1-(4-Chloro-3-fluorophenyl)-cyclopentyloxy]-3-fluorophenyl}-2-(4-ethanesulfonyl-phenyl)-acetamide

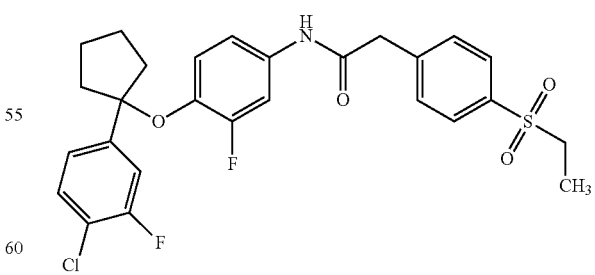

The title compound was prepared by the reaction of Intermediate 122 (71 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (5 mL) as per the process described in Example 1 to yield 78 mg of the product as a solid. ¹H NMR (300 MHz, DMSO-d₆) δ 1.08 (t, J=7.2 Hz, 3H), 176-1.88 (m, 4H), 2.07 (br s, 2H), 2.49 (br s, 2H), 3.25 (q, J=7.2 Hz, 2H), 3.74 (s, 2H), 6.48 (t, J=9.0 Hz, 1H), 7.00 (d, J=8.7 Hz, 1H), 7.16 (t, J=7.8 Hz, 1H), 7.30 (t, J=6.9 Hz, 1H), 7.49-7.58 (m, 4H), 7.82 (d, J=7.8 Hz, 2H), 10.30 (br s, 1H); ESI-MS (m/z) 533 (M−H)⁻.

Example 122

N-{4-[1-(4-Chloro-3-fluorophenyl)-cyclohexyloxy]-3-fluorophenyl}-2-(4-ethanesulfonyl-phenyl)-acetamide

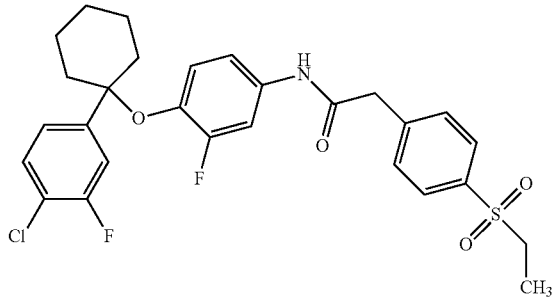 [SMILES: CCS(=O)(=O)c1ccc(CC(=O)Nc2ccc(OC3(c4ccc(Cl)c(F)c4)CCCCC3)c(F)c2)cc1]

The title compound was prepared by the reaction of Intermediate 123 (74 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (10 mL) as per the process described in Example 1 to yield 58 mg of the product as a solid. ¹H NMR (300 MHz, DMSO-d₆) δ 1.08 (t, J=7.2 Hz, 3H), 1.49-1.51 (m, 2H), 1.52-1.62 (m, 2H), 1.98-1.21 (m, 2H), 2.24-2.26 (m, 2H), 3.25 (q, J=7.2 Hz, 2H), 3.73 (s, 2H), 6.39 (t, J=9.3 Hz, 1H), 6.90-6.92 (m, 1H), 7.24-7.27 (m, 1H), 7.44-7.50 (m, 1H), 7.55-7.62 (m, 4H), 7.82 (d, J=8.4 Hz, 2H), 10.27 (br s, 1H); ESI-MS (m/z) 565 (M+H+18)⁺.

Example 123

N-{4-[1-(2,4-Dichlorophenyl)-cyclopentyloxy]-phenyl}-2-(4-ethanesulfonyl-phenyl)-acetamide

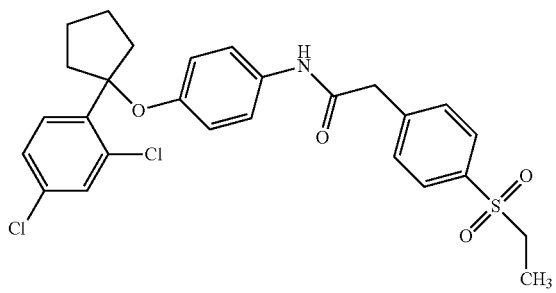 [SMILES: CCS(=O)(=O)c1ccc(CC(=O)Nc2ccc(OC3(c4ccc(Cl)cc4Cl)CCCC3)cc2)cc1]

The title compound was prepared by the reaction of Intermediate 124 (71 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (5 mL) as per the process described in Example 1 to yield 52 mg of the product as a solid. ¹H NMR (300 MHz, DMSO-d₆) δ 1.07 (t, J=7.2 Hz, 3H), 1.81-1.83 (4H), 2.17 (br s, 2H), 2.49 (br s, 2H), 3.25 (q, J=7.2 Hz, 2H), 3.71 (s, 2H), 6.52 (d, J=9.0 Hz, 2H), 7.30-7.40 (m, 3H), 7.47-7.58 (m, 4H), 7.82 (d, J=8.4 Hz, 2H), 10.08 (br s, 1H).

Example 124

N-{4-[1-(4-Chloro-3-fluorophenyl)-cyclohexyloxy]-phenyl}-2-(4-ethanesulfonyl-phenyl)-acetamide

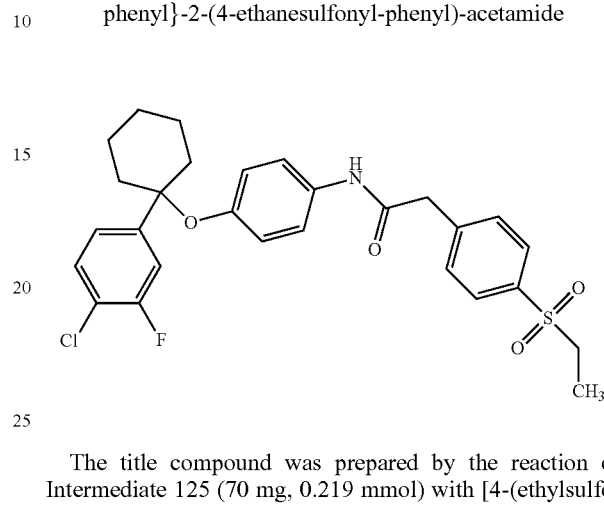

The title compound was prepared by the reaction of Intermediate 125 (70 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (10 mL) as per the process described in Example 1 to yield 78 mg of the product as a solid. ¹H NMR (300 MHz, DMSO-d₆) δ 1.08 (t, J=7.2 Hz, 3H), 1.32-1.36 (m, 2H), 1.51-1.54 (m, 2H), 1.63-1.88 (m, 2H), 1.90-1.93 (m, 2H), 2.27-2.34 (m, 2H), 3.25 (q, J=7.2 Hz, 2H), 3.71 (s, 2H), 6.59 (d, J=8.7 Hz, 2H), 7.26 (t, J=7.8 Hz, 1H), 7.33 (d, J=8.7 Hz, 2H), 7.40-7.44 (m, 1H), 7.54-7.58 (m, 3H), 7.82 (d, J=7.8 Hz, 2H), 10.09 (br s, 1H).

Example 125

N-{1-Cyclopropyl-2-[1-(2,4-difluorophenoxy)-1-methylethyl]-1H-benzoimidazol-5-yl}-2-(4-ethanesulfonyl-phenyl)-acetamide

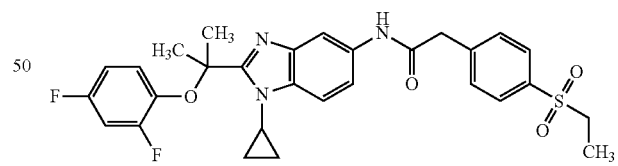

The title compound was prepared by the reaction of Intermediate 126 (82 mg, 0.240 mmol) with [4-(ethylsulfonyl)phenyl]acetic acid (45 mg, 0.200 mmol) using EDCI.HCl (46 mg, 0.240 mmol) and HOBt (32 mg, 0.240 mmol) in DCM (5 mL) as per the process described in Example 1 to yield 45 mg of the product as a solid. ¹H NMR (300 MHz, DMSO-d₆) δ 1.09 (t, J=7.5 Hz, 3H), 1.25 (br s, 4H), 1.88 (s, 6H), 3.25 (q, J=7.5 Hz, 2H), 3.37 (s, 1H), 3.81 (s, 2H), 6.35-6.42 (m, 1H), 6.80-6.85 (m, 1H), 7.20-7.30 (m, 1H), 7.43 (d, J=8.7 Hz, 1H), 7.58-7.65 (m, 3H), 7.85 (d, J=7.5 Hz, 2H), 7.95 (s, 1H), 10.31 (br s, 1H); ESI-MS (m/z) 554 (M+H)⁺.

Example 126

N-{2-[1-(2,5-Difluorophenoxy)-1-methylethyl]-1-ethyl-1H-benzoimidazol-5-yl}-2-(4-ethanesulfonyl-phenyl)-acetamide

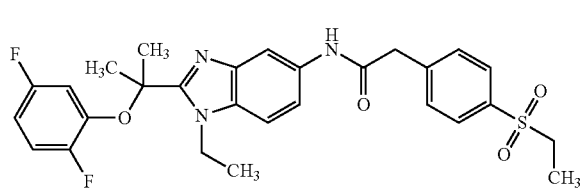 [SMILES: CCn1c(C(C)(C)Oc2cc(F)ccc2F)nc2cc(NC(=O)Cc3ccc(S(=O)(=O)CC)cc3)ccc21]

The title compound was prepared by the reaction of Intermediate 127 (86 mg, 0.262 mmol) with [4-(ethylsulfonyl)phenyl]acetic acid (50 mg, 0.218 mmol) using EDCI.HCl (50 mg, 0.262 mmol) and HOBt (35 mg, 0.261 mmol) in DCM (5 mL) as per the process described in Example 1 to yield 110 mg of the product as a solid. $^1$H NMR (300 MHz, DMSO-$d_6$) δ 1.10 (t, J=7.5 Hz, 3H), 1.25 (t, J=7.5 Hz, 3H), 1.86 (s, 6H), 3.29 (q, J=7.5 Hz, 2H), 3.82 (s, 2H), 4.50 (q, J=7.5 Hz, 2H), 6.30-6.35 (m, 1H), 6.85-6.87 (m, 1H), 7.32 (br s, 1H), 7.46 (d, J=9.0 Hz, 1H), 7.54 (t, J=9.0 Hz, 1H), 7.63 (d, J=8.4 Hz, 2H), 7.85 (d, J=8.4 Hz, 2H), 8.01 (s, 1H), 10.30 (br s, 1H); APCI-MS (m/z) 543 (M+H)$^+$.

Example 127

N-(4-Chlorophenyl)-2-{4-[2-(4-ethanesulfonylphenyl) acetylamino]-phenoxy}-N-ethyl-2-methylpropionamide

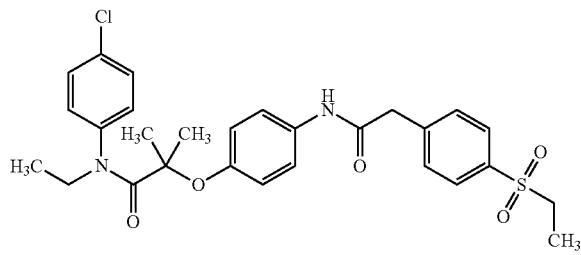 [SMILES: CCN(C(=O)C(C)(C)Oc1ccc(NC(=O)Cc2ccc(S(=O)(=O)CC)cc2)cc1)c1ccc(Cl)cc1]

The title compound was prepared by the reaction of Intermediate 128 (50 mg, 0.150 mmol) with [4-(ethylsulfonyl)phenyl]acetic acid (29 mg, 0.125 mmol) using EDCI.HCl (29 mg, 0.150 mmol) and HOBt (21 mg, 0.150 mmol) in DCM (5 mL) as per the process described in Example 1 to yield 55 mg of the product as a solid. $^1$H NMR (300 MHz, DMSO-$d_6$) δ 0.96 (t, J=7.2 Hz, 3H), 1.09 (t, J=6.9 Hz, 3H), 1.45 (s, 6H), 3.28 (q, J=6.9 Hz, 2H), 3.76 (s, 4H), 6.58 (br s, 2H), 7.06 (br s, 2H), 7.35 (br s, 2H), 7.48 (br s, 2H), 7.61 (d, J=7.8 Hz, 2H), 7.85 (d, J=7.2 Hz, 2H), 10.19 (br s, 1H); ESI-MS (m/z) 543 (M+H)$^+$.

Example 128

N-(4-Chlorophenyl)-2-{4-[2-(4-ethanesulfonylphenyl) acetylamino]-phenoxy}-2-N-dimethylpropionamide

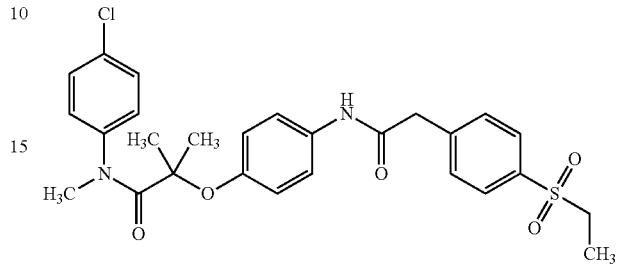

The title compound was prepared by the reaction of Intermediate 129 (60 mg, 0.188 mmol) with [4-(ethylsulfonyl)phenyl]acetic acid (36 mg, 0.157 mmol) using EDCI.HCl (36 mg, 0.188 mmol) and HOBt (25 mg, 0.188 mmol) in DCM (5 mL) as per the process described in Example 1 to yield 50 mg of the product as a solid. $^1$H NMR (300 MHz, DMSO-$d_6$) δ 1.09 (t, J=7.2 Hz, 3H), 1.49 (s, 6H), 3.27-3.32 (m, 5H), 3.76 (s, 2H), 6.72 (br s, 2H), 7.15 (br s, 2H), 7.37 (br s, 2H), 7.48-7.50 (m, 2H), 7.60-7.65 (m, 2H), 7.82-7.85 (m, 2H), 10.20 (br s, 1H); ESI-MS (m/z) 529 (M+H)$^+$.

Example 129

N-(2,4-Dichlorophenyl)-N-ethyl-2-(4-(2-(4-(ethylsulfonyl)phenyl)acetamido)phenoxy)-2-methylpropanamide

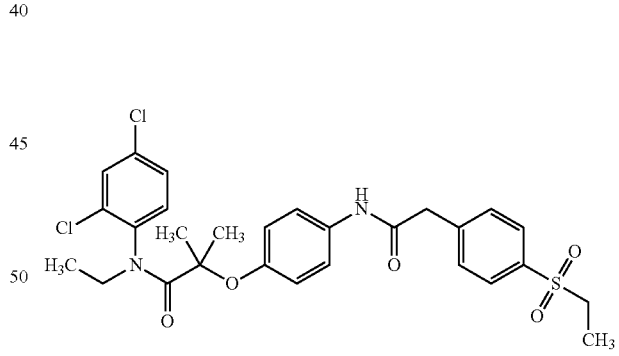

The title compound was prepared by the reaction of Intermediate 130 (96 mg, 0.262 mmol) with [4-(ethylsulfonyl)phenyl]acetic acid (50 mg, 0.218 mmol) using EDCI.HCl (50 mg, 0.262 mmol) and HOBt (35 mg, 0.261 mmol) in DCM (5 mL) as per the process described in Example 1 to yield 55 mg of the product as a solid. $^1$H NMR (300 MHz, DMSO-$d_6$) δ 1.17 (t, J=6.9 Hz, 6H), 1.23-135 (m, 3H) (rotamer), 1.53-1.65 (m, 3H) (rotamer), 3.26 (q, J=6.9 Hz, 2H), 3.76 (s, 2H), 4.02 (q, J=6.9 Hz, 2H), 6.53-6.55 (m, 1H), 6.90-6.94 (m, 1H), 7.20-6.30 (m, 1H), 7.52-7.61 (m, 3H), 7.83 (d, J=7.8 Hz, 2H), 10.20 (br s, 1H).

Example 130

N-(4-Chloro-3-fluorophenyl)-N-ethyl-2-(4-(2-(4-(ethylsulfonyl)phenyl)acetamido)phenoxy)-2-methylpropanamide

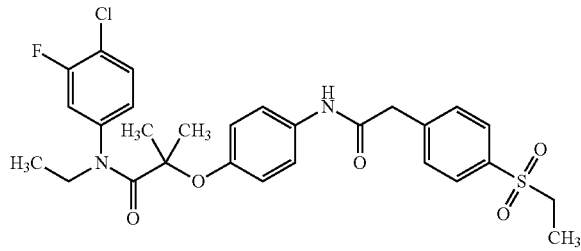 [SMILES: CCN(C(=O)C(C)(C)Oc1ccc(NC(=O)Cc2ccc(S(=O)(=O)CC)cc2)cc1)c1ccc(Cl)c(F)c1]

The title compound was prepared by the reaction of Intermediate 131 (92 mg, 0.262 mmol) with [4-(ethylsulfonyl)phenyl]acetic acid (50 mg, 0.218 mmol) using EDCI.HCl (49 mg, 0.262 mmol) and HOBt (35 mg, 0.262 mmol) in DCM (5 mL) as per the process described in Example 1 to yield 118 mg of the product as a solid. $^1$H NMR (300 MHz, DMSO-$d_6$) δ 0.86-0.89 (m, 3H), 1.09 (t, J=7.2 Hz, 3H), 1.47 (s, 6H), 3.26 (q, J=7.2 Hz, 2H), 3.76 (s, 2H), 6.62-6.65 (m, 2H), 6.96-7.10 (m, 2H), 7.48-7.61 (m, 5H), 7.84 (d, J=8.7 Hz, 2H), 10.19 (s, 1H); APCI-MS (m/z) 561 (M+H)$^+$.

Example 131

N-(4-Chloro-3-fluorophenyl)-N-ethyl-2-(4-(2-(4-(ethylsulfonyl)phenyl)acetamido)-2-fluorophenoxy)-2-methylpropanamide

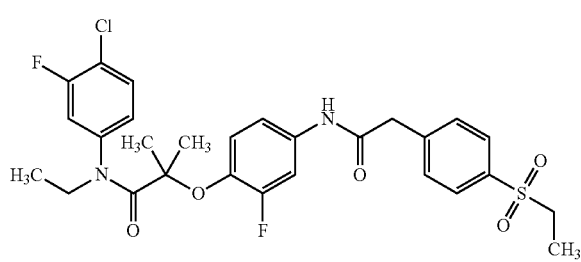 [SMILES: CCN(C(=O)C(C)(C)Oc1ccc(NC(=O)Cc2ccc(S(=O)(=O)CC)cc2)cc1F)c1ccc(Cl)c(F)c1]

The title compound was prepared by the reaction of Intermediate 132 (97 mg, 0.262 mmol) with [4-(ethylsulfonyl)phenyl]acetic acid (50 mg, 0.218 mmol) using EDCI.HCl (49 mg, 0.262 mmol) and HOBt (35 mg, 0.262 mmol) in DCM (5 mL) as per the process described in Example 1 to yield 61 mg of the product as a solid. $^1$H NMR (300 MHz, DMSO-$d_6$) δ 0.93-0.96 (m, 3H), 1.09 (t, J=7.2 Hz, 3H), 1.45 (s, 6H), 3.26 (q, J=7.2 Hz, 2H), 3.78 (s, 4H), 6.82-6.85 (m, 1H), 7.04 (d, J=8.7 Hz, 1H), 7.20-7.22 (m, 2H), 7.52-7.60 (m, 4H), 7.84 (d, J=8.7 Hz, 2H), 10.38 (s, 1H); ESI-MS (m/z) 577 (M−H)$^-$.

Example 132

2-(2,4-Difluorophenoxy)-N-ethyl-N-(4-(2-(4-(ethylsulfonyl)phenyl)acetamido)phenyl)-2-methylpropanamide

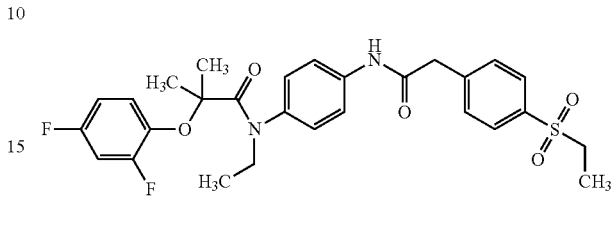

The title compound was prepared by the reaction of Intermediate 133 (88 mg, 0.262 mmol) with [4-(ethylsulfonyl)phenyl]acetic acid (50 mg, 0.218 mmol) using EDCI.HCl (49 mg, 0.262 mmol) and HOBt (35 mg, 0.262 mmol) in DCM (5 mL) as per the process described in Example 1 to yield 44 mg of the product as a solid. $^1$H NMR (300 MHz, DMSO-$d_6$) δ 1.09 (t, J=6.9 Hz, 3H), 1.39-1.42 (m, 6H), 3.26 (q, J=7.2 Hz, 2H), 3.79 (s, 2H), 7.02 (br s, 3H), 7.26 (br s, 2H), 7.54-7.61 (m, 4H), 7.84 (d, J=8.1 Hz, 2H), 10.35 (s, 1H); ESI-MS (m/z) 545 (M+H)$^+$.

Example 133

N-(4-((1-(4-Chloro-3-fluorophenyl)cyclohexyl)oxy)phenyl)-2-(4-(ethylsulfonyl)phenyl)acetamide

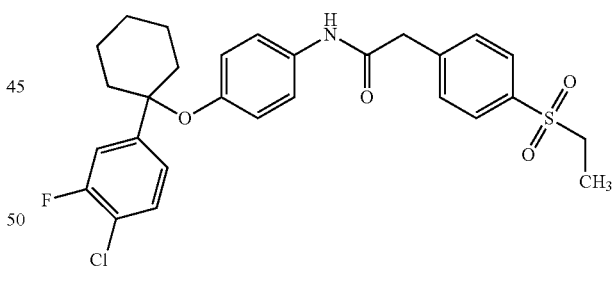

The title compound was prepared by the reaction of Intermediate 134 (70 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (10 mL) as per the process described in Example 1 to yield 78 mg of the product as a solid. $^1$H NMR (300 MHz, DMSO-$d_6$) δ 1.08 (t, J=7.2 Hz, 3H), 1.31-1.34 (m, 2H), 1.52-1.55 (m, 2H), 1.63-1.69 (m, 2H), 1.90-1.94 (m, 2H), 2.28-2.33 (m, 2H), 3.26 (q, J=7.2 Hz, 2H), 3.71 (s, 2H), 6.58 (d, J=8.7 Hz, 2H), 7.25 (t, J=8.7 Hz, 1H), 7.34 (d, J=9.3 Hz, 2H), 7.42 (t, J=9.0 Hz, 1H), 7.56 (d, J=8.1 Hz, 3H), 7.82 (d, J=8.1 Hz, 2H), 10.09 (s, 1H).

Example 134

N-(4-((1-(2,4-Dichlorophenyl)cyclohexyl)oxy)phenyl)-2-(4-(ethylsulfonyl)phenyl)acetamide

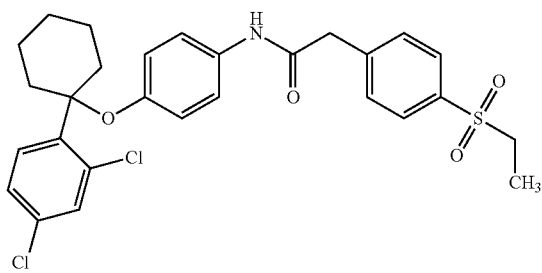 [SMILES: CCS(=O)(=O)c1ccc(CC(=O)Nc2ccc(OC3(c4ccc(Cl)cc4Cl)CCCCC3)cc2)cc1]

The title compound was prepared by reaction of Intermediate 135 (74 mg, 0.219 mmol) with [4-(ethylsulfonyl)phenyl]acetic acid (50 mg, 0.219 mmol) using EDCI.HCl (50 mg, 0.262 mmol) and HOBt (42 mg, 0.306 mmol) in DCM (5.0 mL) as per the procedure described in Example 1 to yield 73 mg of the product as a solid. $^1$H NMR (300 MHz, DMSO-$d_6$) δ 1.08 (t, J=7.2 Hz, 3H), 1.54 (br s, 2H), 1.64-1.67 (m, 3H), 1.83-1.87 (m, 2H), 2.49 (s, 2H), 3.26 (q, J=7.2 Hz, 2H), 3.71 (s, 2H), 6.52 (d, J=8.7 Hz, 2H), 7.29 (d, J=8.7 Hz, 2H), 7.46-7.61 (m, 5H), 7.81 (d, J=8.1 Hz, 2H), 10.05 (s, 1H); APCI-MS (m/z) 543 (M−H)$^-$.

Example 135

N-(4-((1-(2,4-Dichlorophenyl)cyclohexyl)oxy)-3-fluorophenyl)-2-(4-(ethylsulfonyl)phenyl)acetamide

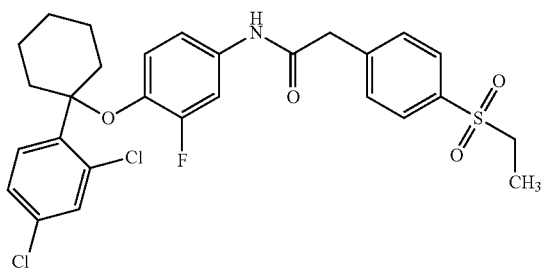 [SMILES: CCS(=O)(=O)c1ccc(CC(=O)Nc2ccc(OC3(c4ccc(Cl)cc4Cl)CCCCC3)c(F)c2)cc1]

The title compound was prepared by reaction of Intermediate 136 (20 mg, 0.056 mmol) with [4-(ethylsulfonyl)phenyl]acetic acid (13 mg, 0.056 mmol) using EDCI.HCl (13 mg, 0.067 mmol) and HOBt (11 mg, 0.079 mmol) in DCM (4.0 mL) as per the procedure described in Example 1 to yield 16 mg of the desired product as a solid. $^1$H NMR (300 MHz, DMSO-$d_6$) δ 1.07 (t, J=6.3 Hz, 3H), 1.22-1.25 (m, 2H), 1.52-1.63 (m, 4H), 1.89-1.92 (m, 2H), 2.40-2.49 (m, 2H), 3.26 (q, J=7.2 Hz, 2H), 3.72 (s, 2H), 6.22 (t, J=9.3 Hz, 1H), 6.86 (d, J=7.8 Hz, 1H), 7.50-7.60 (m, 6H), 7.80 (d, J=7.8 Hz, 2H), 10.23 (s, 1H); APCI-MS (m/z) 561 (M−H)$^-$.

Example 136

N-(4-((4-(2,4-Dichlorophenyl)tetrahydro-2H-pyran-4-yl)oxy)-3-fluorophenyl)-2-(4-(ethylsulfonyl)phenyl)acetamide

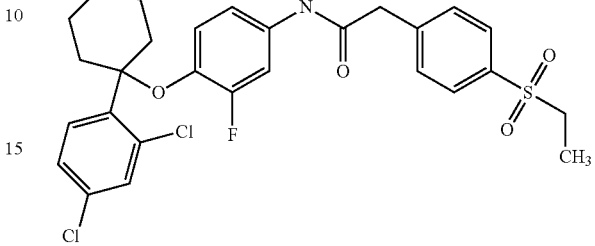

To a stirred solution of [4-(ethylsulfonyl)phenyl]acetic acid (50 mg, 0.219 mmol) in dry DCM (5 mL) was added EDCI.HCl (50 mg, 0.262 mmol) followed by HOBt (40 mg, 0.306 mmol) and the reaction mixture was stirred at room temperature for 30 min. Intermediate 137 (78 mg, 0.219 mmol) was added to the mixture and it was further stirred for 18 h at RT. The mixture was diluted with water (10 mL) and extracted with ethyl acetate (3×10 mL). The combined organic extracts were washed with saturated aqueous sodium bicarbonate solution (20 mL), water (2×20 mL) and brine (20 mL). The organic layer was dried over anhydrous sodium sulfate and the solvent was distilled off under reduced pressure. The residue obtained was purified by silica gel column chromatography to yield 73 mg of the title product as a solid. $^1$H NMR (300 MHz, DMSO-$d_6$) δ 1.08 (t, J=7.2 Hz, 3H), 2.23-2.25 (m, 2H), 2.42-2.47 (m, 2H), 3.26 (q, J=7.2 Hz, 2H), 3.73 (s, 4H), 6.22-6.26 (m, 1H), 6.86-6.89 (m, 1H), 7.54-7.61 (m, 6H), 7.82 (d, J=8.7 Hz, 2H), 10.26 (s, 1H); ESI-MS (m/z) 566 (M)$^+$.

Example 137

N-(4-((1-(2,4-Dichlorophenyl)cyclopentyl)oxy)-3-fluorophenyl)-2-(4-(ethylsulfonyl)phenyl)acetamide

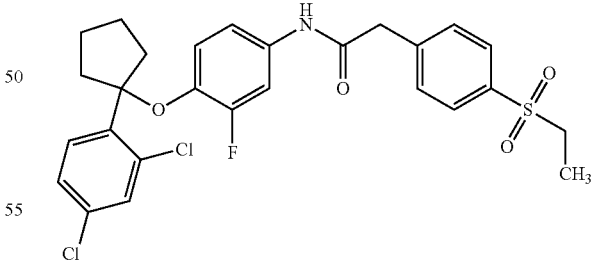

To a well stirred solution of [4-(ethylsulfonyl)phenyl]acetic acid (50 mg, 0.219 mmol) in dry DCM (5 mL) was added EDCI.HCl (50 mg, 0.262 mmol) followed by HOBt (40 mg, 0.306 mmol) and the reaction mixture was stirred at room temperature for 30 min. Intermediate 138 (71 mg, 0.219 mmol) was added to the reaction mixture and it was further stirred for 18 h. The reaction mixture was diluted with water (10 mL) and extracted with ethyl acetate (3×10 mL). The combined organic extracts were washed with saturated aqueous sodium bicarbonate solution (20 mL), water (2×20 mL) and brine (20 mL). The organic layer was dried over anhydrous sodium sulfate and the solvent was distilled off under reduced pressure. The residue obtained was purified by silica gel column chromatography to yield 57 mg of the title product as a solid. $^1$H NMR (300 MHz, DMSO-$d_6$) δ 1.08 (t, J=7.2 Hz, 3H), 1.73-1.86 (m, 6H), 2.19 (br s, 2H), 3.26 (q, J=7.2 Hz, 2H), 3.73 (s, 2H), 6.32-6.35 (m, 1H), 6.91 (d, J=8.7 Hz, 1H), 7.39-7.49 (m, 1H), 7.54-7.61 (m, 5H), 7.81 (d, J=8.1 Hz, 2H), 10.27 (s, 1H).

Example 138

N-(4-((1-(2,4-Dichlorophenyl)cyclopropyl)oxy)-3-fluorophenyl)-2-(4-(ethylsulfonyl)phenyl)acetamide

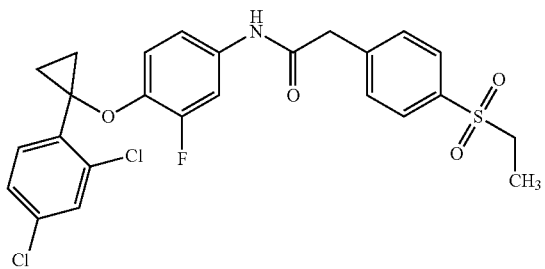 [SMILES: CCS(=O)(=O)c1ccc(CC(=O)Nc2ccc(OC3(c4ccc(Cl)cc4Cl)CC3)c(F)c2)cc1]

To a stirred solution of [4-(ethylsulfonyl)phenyl]acetic acid (50 mg, 0.219 mmol) in dry DCM (5 mL) was added EDCI.HCl (50 mg, 0.262 mmol) followed by HOBt (40 mg, 0.306 mmol) and the reaction mixture was stirred at room temperature for 30 min. Intermediate 139 (68 mg, 0.219 mmol) was added to the mixture and it was further stirred for 18 hours at RT. The mixture was diluted with water (10 mL) and extracted with ethyl acetate (3×10 mL). The combined organic extracts were washed with saturated aqueous sodium bicarbonate solution (20 mL), water (2×20 mL) and brine (20 mL). The organic layer was dried over anhydrous sodium sulfate and the solvent was distilled off under reduced pressure. The residue obtained was purified by silica gel column chromatography to yield 73 mg of the title product as a solid. $^1$H NMR (300 MHz, DMSO-$d_6$) δ 1.08 (t, J=7.5 Hz, 3H), 1.19-1.22 (m, 2H), 1.40-1.45 (m, 2H), 3.25 (q, J=7.5 Hz, 2H), 3.74 (s, 2H), 7.13-7.16 (m, 1H), 7.21 (d, J=9.3 Hz, 1H), 7.35 (d, J=8.4 Hz, 1H), 7.46-7.61 (m, 5H), 7.82 (d, J=8.1 Hz, 2H), 10.28 (s, 1H).

Example 139

N-(4-((1-(2,4-Dichlorophenyl)cyclobutyl)oxy)-3-fluorophenyl)-2-(4-(ethylsulfonyl)phenyl)acetamide

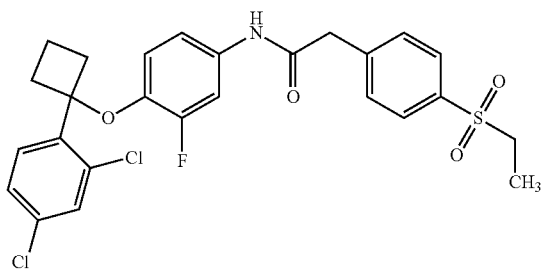

To a stirred solution of [4-(ethylsulfonyl)phenyl]acetic acid (50 mg, 0.219 mmol) in dry DCM (5 mL) was added EDCI.HCl (50 mg, 0.262 mmol) followed by HOBt (40 mg, 0.306 mmol) and the reaction mixture was stirred at room temperature for 30 min. Intermediate 140 (72 mg, 0.219 mmol) was added to the mixture and it was further stirred for 18 h at RT. The mixture was diluted with water (10 mL) and extracted with ethyl acetate (3×10 mL). The combined organic extracts were washed with saturated aqueous sodium bicarbonate solution (20 mL), water (2×20 mL) and brine (20 mL). The organic layer was dried over anhydrous sodium sulfate and the solvent was distilled off under reduced pressure. The residue obtained was purified by silica gel column chromatography to yield 57 mg of the title product as a solid. $^1$H NMR (300 MHz, DMSO-$d_6$) δ 1.08 (t, J=7.2 Hz, 3H), 1.73-1.86 (m, 1H), 2.00-2.06 (m, 1H), 2.65-2.80 (m, 4H), 3.26 (q, J=7.2 Hz, 2H), 3.73 (s, 2H), 6.57 (t, J=9.3 Hz, 1H), 7.00 (d, J=7.8 Hz, 1H), 7.40 (d, J=8.4 Hz, 1H), 7.54-7.61 (m, 5H), 7.82 (d, J=8.1 Hz, 2H), 10.25 (s, 1H).

Example 140

N-(4-((1-(2,4-Difluorophenyl)cyclohexyl)oxy)-3-fluorophenyl)-2-(4-(ethylsulfonyl)phenyl)acetamide

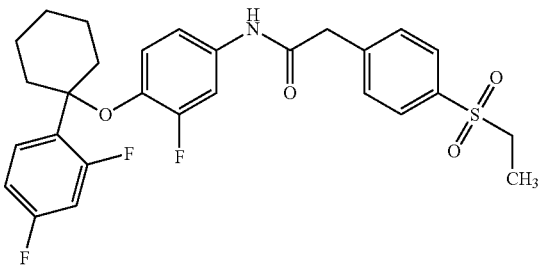 [SMILES: CCS(=O)(=O)c1ccc(CC(=O)Nc2ccc(OC3(c4ccc(F)cc4F)CCCCC3)c(F)c2)cc1]

The title compound was prepared by reaction of Intermediate 141 (71 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (4.0 mL) as per the procedure described in Example 1 to yield 57 mg of the product as a solid. $^1$H NMR (300 MHz, DMSO-$d_6$) δ 1.08 (t, J=7.2 Hz, 3H), 1.32-1.35 (m, 1H), 1.46-1.49 (m, 2H), 1.60-1.63 (m, 3H), 1.96-2.20 (m, 2H), 3.25 (q, J=7.2 Hz, 2H), 3.73 (s, 2H), 6.38 (t, J=8.7 Hz, 1H), 6.90 (d, J=8.7 Hz, 1H), 7.10-7.25 (m, 2H), 7.46-7.60 (m, 4H), 7.82 (d, J=8.1 Hz, 2H), 10.26 (s, 1H); ESI-MS (m/z) 529 (M−H)$^-$.

Example 141

N-(4-(1-(2,4-Difluorophenyl)cyclobutoxy)-3-fluorophenyl)-2-(4-(ethylsulfonyl)phenyl)acetamide

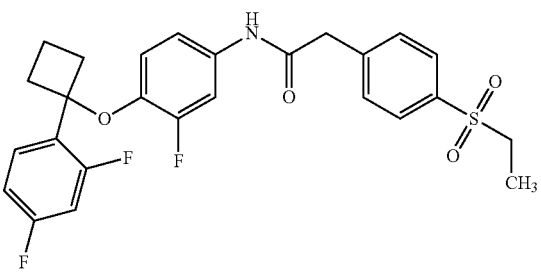 [SMILES: CCS(=O)(=O)c1ccc(CC(=O)Nc2ccc(OC3(c4ccc(F)cc4F)CCC3)c(F)c2)cc1]

The title compound was prepared by the reaction of Intermediate 142 (64 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (5 mL) as per the process described in Example 1 to yield 92 mg of the product as a solid. $^1$H NMR (300 MHz, DMSO-$d_6$) δ 1.08 (t, J=7.2 Hz, 3H), 1.60-1.67 (m, 1H), 1.95-2.02 (m, 1H), 1.60-1.63 (m, 3H), 2.59-2.67 (m, 4H), 3.25 (q, J=7.2 Hz, 2H), 3.73 (s, 2H), 6.65 (t, J=8.7 Hz, 1H), 7.02 (d, J=8.1 Hz, 2H), 7.15-7.25 (m, 1H), 7.46-7.58 (m, 4H), 7.82 (d, J=8.1 Hz, 2H), 10.26 (s, 1H); ESI-MS (m/z) 529 (M−H)⁻.

Example 142

N-(4-((3-(2,4-Difluorophenyl)oxetan-3-yl)oxy)-3-fluorophenyl)-2-(4-(ethylsulfonyl)phenyl)acetamide

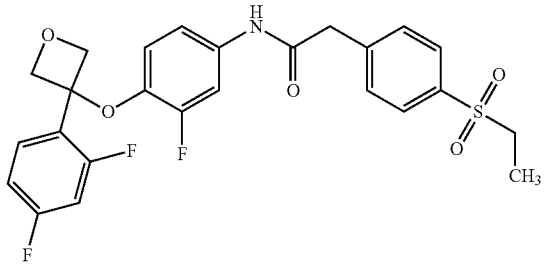 [SMILES: CCS(=O)(=O)c1ccc(CC(=O)Nc2ccc(OC3(c4ccc(F)cc4F)COC3)c(F)c2)cc1]

The title compound was prepared by the reaction of Intermediate 143 (64 mg, 0.219 mmol) with [4-(ethylsulfonyl)phenyl]acetic acid (50 mg, 0.219 mmol) using EDCI.HCl (50 mg, 0.262 mmol) and HOBt (40 mg, 0.306 mmol) in DCM (5 mL) as per the process described in Example 1 to yield 92 mg of the product as a solid. $^1$H NMR (300 MHz, DMSO-$d_6$) δ 1.06 (t, J=6.9 Hz, 3H), 3.24 (q, J=6.9 Hz, 2H), 3.72 (s, 2H), 5.04-5.07 (m, 4H), 6.73-6.75 (m, 1H), 7.03-7.06 (m, 2H), 7.23-7.27 (m, 1H), 7.44-7.57 (m, 4H), 7.80 (d, J=8.4 Hz, 2H), 10.28 (s, 1H).

Example 143

N-(4-((1-(2,4-Difluorophenyl)cyclopentyl)oxy)-3-fluorophenyl)-2-(4-(ethylsulfonyl)phenyl)acetamide

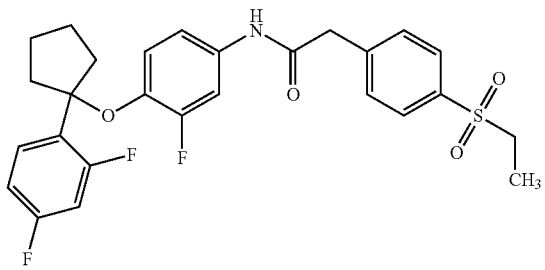 [SMILES: CCS(=O)(=O)c1ccc(CC(=O)Nc2ccc(OC3(c4ccc(F)cc4F)CCCC3)c(F)c2)cc1]

The title compound was prepared by the reaction of Intermediate 144 (14 mg, 0.045 mmol) with [4-(ethylsulfonyl)phenyl]acetic acid (10 mg, 0.045 mmol) using EDCI.HCl (10 mg, 0.0055 mmol) and HOBt (9 mg, 0.0064 mmol) in DCM (5 mL) as per the process described in Example 1 to yield 4.0 mg of the product as a solid. $^1$H NMR (300 MHz, DMSO-$d_6$) δ 1.08 (t, J=7.2 Hz, 3H), 1.75-2.04 (m, 6H), 2.44-2.49 (m, 2H), 3.23 (q, J=7.2 Hz, 2H), 3.73 (s, 2H), 6.45 (t, J=8.7 Hz, 1H), 6.98 (d, J=8.7 Hz, 2H), 7.20-7.35 (m, 1H), 7.36-7.49 (m, 1H), 7.56 (d, J=8.1 Hz, 3H), 7.82 (d, J=7.8 Hz, 2H), 10.27 (s, 1H).

Example 144

N-(2-(2-(2,4-Dichlorophenoxy)propan-2-yl)-1-ethyl-1H-benzo[d]imidazol-5-yl)-2-(4-(ethylsulfonyl)phenyl)acetamide

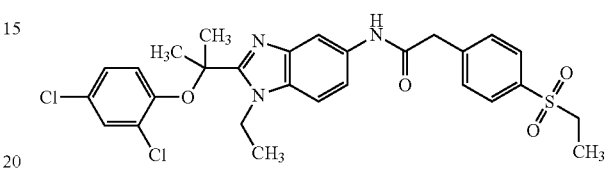

The title compound was prepared by the reaction of Intermediate 145 (95 mg, 0.262 mmol) with [4-(ethylsulfonyl)phenyl]acetic acid (50 mg, 0.218 mmol) using EDCI.HCl (49 mg, 0.262 mmol) and HOBt (35 mg, 0.262 mmol) in DCM (5 mL) as per the process described in Example 1 to yield 125 mg of the product as a solid. $^1$H NMR (300 MHz, DMSO-$d_6$) δ 1.07-1.18 (m, 6H), 1.87 (s, 6H), 3.24-3.36 (m, 2H), 3.82 (s, 2H), 4.44 (q, J=7.2 Hz, 2H), 6.31 (d, J=7.0 Hz, 1H), 7.12 (d, J=8.7 Hz, 1H), 7.40 (d, J=8.7 Hz, 2H), 7.51 (d, J=9.3 Hz, 3H), 7.86 (d, J=9.0 Hz, 2H), 8.00 (s, 1H), 10.28 (s, 1H); ESI-MS (m/z) 574 (M+H)⁺.

Example 145

N-(2-(2-(2,4-Difluorophenoxy)propan-2-yl)-1-(2-fluoroethyl)-1H-benzo[d]imidazol-5-yl)-2-(4-(ethylsulfonyl)phenyl)acetamide

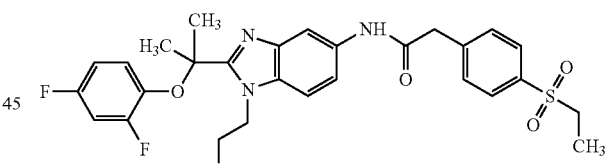

To a well stirred solution of [4-(ethylsulfonyl)phenyl]acetic acid (28 mg, 0.114 mmol) in dry DCM (5 mL) was added EDCI.HCl (26 mg, 0.136 mmol) followed by HOBt (41 mg, 0.306 mmol) and the reaction mixture was stirred at room temperature for 30 minutes. Intermediate 146 (48 mg, 0.137 mmol) was added to the mixture and stirred for 16 hours at RT. The reaction mixture was diluted with water (10 mL) and extracted with ethyl acetate (3×10 mL). The combined organic extracts were washed with saturated aqueous sodium bicarbonate solution (20 mL), water (2×20 mL) and brine (20 mL). The organic layer was dried over anhydrous sodium sulfate and the solvent was distilled off under reduced pressure. The residue obtained was purified by silica gel column chromatography to yield 51 mg of the title product as a solid. $^1$H NMR (300 MHz, DMSO-$d_6$) δ 1.09 (d, J=7.8 Hz, 3H), 1.79 (s, 6H), 3.26 (q, J=7.8 Hz, 2H), 3.82 (s, 2H), 4.70-4.90 (m, 4H), 6.55-6.60 (m, 1H), 6.85-6.89 (m, 1H), 7.32-7.39 (m, 1H), 7.42 (d, J=8.4 Hz, 1H), 7.56 (d, J=8.4 Hz, 1H), 7.63 (d, J=8.4 Hz, 2H), 7.85 (d, J=8.4 Hz, 2H), 7.97 (s, 1H), 10.29 (s, 1H); ESI-MS (m/z) 560 (M+H)$^+$.

Pharmacological Activity

Biological Assay

The compounds described herein were screened for ROR gamma modulator activity using the TR-FRET assay by Lantha Screen as described in *JBC* 2011, 286, 26: 22707-10; and *Drug Metabolism and Disposition* 2009, 37, 10: 2069-78.

TR-FRET Assay for ROR Gamma

The assay is based on the principle that binding of the agonist to the ROR gamma causes a conformational change around helix 12 in the ligand binding domain, resulting in higher affinity for the co-activator peptide. ROR gamma being constitutively active, the Fluorescein-D22 co-activator peptide used in the assay is recruited in the absence of a ligand. Binding of the co-activator peptide, causes an increase in the TR-FRET signal while binding of an antagonist decreases the recruitment of the co-activator peptide, causing a decrease in the TR-FRET signal compared to control with no compound. The assay was performed using a two-step procedure, pre-incubation step with the compound followed by the detection step on addition of the anti-GST tagged terbium (Tb) and fluorescein tagged fluorophores as the acceptor.

Test compounds or reference compounds such as T0901317 (Calbiochem) were dissolved in dimethylsulfoxide (DMSO) to prepare 10.0 mM stock solutions and diluted to the desired concentration. The final concentration of DMSO in the reaction was 4% (v/v). The assay mixture was prepared by mixing 10 nM of the GST-tagged ROR gamma ligand binding domain (LBD) in the assay buffer containing 25 mM HEPES (pH 7.4), 100 mM NaCl, 5 mM DTT and 0.01% BSA with or without the desired concentration of the compound. The reaction was incubated at 22° C. for 1 hour. The pre-incubation step was terminated by addition of the detection mixture containing 300 nM Fluorescein-D22 co-activator peptide and 10 nM lantha screen Tb-anti GST antibody into the reaction mixture. After shaking for 5 minutes the reaction was further incubated for 1 hour at room temperature and read at 4° C. on an Infinite F500 reader as per the kit instructions (Invitrogen). The inhibition of test compound was calculated based on the TR-FRET ratio of 520/495. The activity was calculated as a percent of control reaction. IC$_{50}$ values were calculated from dose response curve by nonlinear regression analysis using GraphPad Prism software.

The compounds prepared were tested using the above assay procedure and the results obtained are given in Table 1. Percentage inhibition at concentrations of 1.0 μM and 10.0 μM are given in the table along with IC$_{50}$ (nM) details for selected examples. The compounds were found to have IC$_{50}$ less than 500 nM, preferably less than 100 nM, more preferably less than 50 nM.

The IC$_{50}$ (nM) values are set forth in Table 1 wherein "A" refers to an IC$_{50}$ value of less than 50 nM, "B" refers to IC$_{50}$ value in range of 50.01 to 100.0 nM and "C" refers to IC$_{50}$ values more than 100 nM.

TABLE 1

In-vitro screening results

| Sr. No | Example | % Inhibition at 1 μM | % Inhibition at 10 μM | IC$_{50}$ value (nM) |
|---|---|---|---|---|
| 1. | Example 1 | 47.67 | 74.30 | — |
| 2. | Example 2 | 66.92 | 77.96 | — |
| 3. | Example 3 | 81.34 | 83.44 | A |
| 4. | Example 4 | 80.48 | 86.36 | A |
| 5. | Example 5 | 58.23 | 66.89 | — |
| 6. | Example 6 | 77.45 | 83.10 | — |
| 7. | Example 7 | 74.42 | 85.11 | — |
| 8. | Example 8 | 85.02 | 87.81 | A |
| 9. | Example 9 | 86.52 | 88.95 | A |
| 10. | Example 10 | 70.93 | 81.47 | — |
| 11. | Example 11 | 84.28 | 89.05 | A |
| 12. | Example 12 | 73.89 | 85.43 | B |
| 13. | Example 13 | 56.2 | 68.8 | — |
| 14. | Example 14 | 88.91 | 93.35 | A |
| 15. | Example 15 | 83.05 | 85.21 | A |
| 16. | Example 16 | 88.59 | 94.33 | A |
| 17. | Example 17 | 88.73 | 94.35 | A |
| 18. | Example 18 | 78.61 | 91.03 | C |
| 19. | Example 19 | 85.55 | 88.86 | B |
| 20. | Example 20 | 79.75 | 85.17 | C |
| 21. | Example 21 | 82.6 | 84.1 | A |
| 22. | Example 22 | 74.36 | 82.76 | — |
| 23. | Example 23 | 69.57 | 85.95 | C |
| 24. | Example 24 | 65.72 | 85.64 | C |
| 25. | Example 25 | 85.28 | 94.16 | B |
| 26. | Example 26 | 80.51 | 90.94 | B |
| 27. | Example 27 | 69.72 | 89.97 | B |
| 28. | Example 28 | 61.08 | 84.42 | — |
| 29. | Example 29 | 80.34 | 82.75 | A |
| 30. | Example 30 | 67.66 | 70.67 | — |
| 31. | Example 31 | 81.90 | 89.13 | B |
| 32. | Example 32 | 83.70 | 88.55 | A |
| 33. | Example 33 | 76.65 | 81.81 | — |
| 34. | Example 34 | 86.64 | 89.68 | A |
| 35. | Example 35 | 79.51 | 86.68 | B |
| 36. | Example 36 | 69.88 | 74.72 | — |
| 37. | Example 37 | 80.84 | 83.20 | C |
| 38. | Example 38 | 85.75 | 87.77 | A |
| 39. | Example 39 | 87.66 | 94.78 | B |
| 40. | Example 40 | 77.4 | 81.9 | A |
| 41. | Example 41 | 77.98 | 87.17 | C |
| 42. | Example 42 | 65.9 | 86.0 | — |
| 43. | Example 43 | 27.29 | 54.99 | — |
| 44. | Example 44 | 44.65 | 69.99 | — |
| 45. | Example 45 | 76.85 | 85.74 | A |
| 46. | Example 46 | 68.10 | 86.26 | C |
| 47. | Example 47 | 90.3 | 93.2 | A |
| 48. | Example 48 | 60.3 | 77.4 | — |
| 49. | Example 49 | 69.09 | 79.99 | B |
| 50. | Example 50 | 81.30 | 87.92 | A |
| 51. | Example 51 | 85.89 | 87.73 | A |
| 52. | Example 52 | 63.72 | 83.85 | — |
| 53. | Example 53 | 52.65 | 76.52 | — |
| 54. | Example 54 | 91.99 | 93.7 | A |
| 55. | Example 55 | 75.45 | 80.34 | — |
| 56. | Example 56 | 83.07 | 91.34 | A |
| 57. | Example 57 | 78.03 | 91.35 | B |
| 58. | Example 58 | 83.65 | 86.73 | A |
| 59. | Example 59 | 71.81 | 86.65 | A |
| 60. | Example 60 | 92.64 | 90.43 | C |
| 61. | Example 61 | 85.49 | 92.93 | C |
| 62. | Example 62 | 86.28 | 90.16 | A |
| 63. | Example 63 | 80.52 | 84.51 | A |
| 64. | Example 64 | 82.2 | 84.2 | A |
| 65. | Example 65 | 83.87 | 88.23 | A |
| 66. | Example 66 | 84.32 | 87.54 | A |
| 67. | Example 67 | 70.5 | 75.7 | — |
| 68. | Example 68 | 70.7 | 79.9 | — |
| 69. | Example 69 | 71.56 | 81.85 | B |
| 70. | Example 70 | 77.73 | 81.29 | A |
| 71. | Example 71 | 75.89 | 79.91 | A |
| 72. | Example 72 | 76.2 | 79.7 | A |
| 73. | Example 73 | 75.4 | 78.6 | A |
| 74. | Example 74 | 73.6 | 78.8 | A |

TABLE 1-continued

In-vitro screening results

| Sr. No | Example | % Inhibition at 1 μM | % Inhibition at 10 μM | IC$_{50}$ value (nM) |
|---|---|---|---|---|
| 75. | Example 75 | 83.2 | 84.0 | A |
| 76. | Example 76 | 82.2 | 86.2 | A |
| 77. | Example 77 | 82.82 | 87.06 | A |
| 78. | Example 78 | 85.2 | 87.4 | A |
| 79. | Example 79 | 79.87 | 86.13 | A |
| 80. | Example 80 | 50.24 | 62.43 | — |
| 81. | Example 81 | 76.05 | 88.89 | C |
| 82. | Example 82 | 82.04 | 88.38 | B |
| 83. | Example 83 | 83.29 | 91.95 | B |
| 84. | Example 84 | 89.69 | 90.16 | A |
| 85. | Example 85 | 87.07 | 91.20 | A |
| 86. | Example 86 | 92.84 | 93.83 | A |
| 87. | Example 87 | 90.81 | 94.78 | A |
| 88. | Example 88 | 86.15 | 96.13 | A |
| 89. | Example 89 | 86.52 | 95.49 | A |
| 90. | Example 90 | 87.3 | 88.8 | A |
| 91. | Example 91 | 90.03 | 90.62 | A |
| 92. | Example 92 | 91.53 | 93.11 | A |
| 93. | Example 93 | 83.39 | 87.43 | A |
| 94. | Example 94 | 78.00 | 90.13 | C |
| 95. | Example 95 | 75.72 | 77.64 | A |
| 96. | Example 96 | 79.3 | 79.85 | A |
| 97. | Example 97 | 80.8 | 82.1 | A |
| 98. | Example 98 | 55.01 | 49.57 | — |
| 99. | Example 99 | 81.71 | 81.13 | A |
| 100. | Example 100 | 79.4 | 87.2 | A |
| 101. | Example 101 | 86.6 | 82.3 | A |
| 102. | Example 102 | 81.7 | 84.0 | A |
| 103. | Example 103 | 73.6 | 80.2 | A |
| 104. | Example 104 | 74.47 | 79.19 | B |
| 105. | Example 105 | 83.59 | 84.60 | A |
| 106. | Example 106 | 81.92 | 85.91 | A |
| 107. | Example 107 | 59.03 | 59.46 | — |
| 108. | Example 108 | 9.67 | 61.40 | — |
| 109. | Example 109 | 16.61 | 17.19 | — |
| 110. | Example 110 | 23.66 | 47.63 | — |
| 111. | Example 111 | 88.03 | 86.78 | A |
| 112. | Example 112 | 82.41 | 87.38 | B |
| 113. | Example 113 | 15.63 | 52.38 | — |
| 114. | Example 114 | 78.90 | 82.62 | A |
| 115. | Example 115 | 82.44 | 88.31 | A |
| 116. | Example 116 | 79.10 | 84.52 | C |
| 117. | Example 117 | 82.7 | 86.69 | C |
| 118. | Example 118 | 5.43 | 9.14 | — |
| 119. | Example 119 | 84.9 | 84.52 | A |
| 120. | Example 120 | 84.83 | 89.63 | A |
| 121. | Example 121 | 86.83 | 90.18 | A |
| 122. | Example 122 | 77.34 | 81.23 | A |
| 123. | Example 123 | 81.97 | 87.21 | A |
| 124. | Example 124 | 82.24 | 84.78 | A |
| 125. | Example 125 | 89.2 | 90.4 | A |
| 126. | Example 126 | 85.9 | 89.53 | A |
| 127. | Example 127 | 67.99 | 75.84 | — |
| 128. | Example 128 | 64.2 | 79.76 | — |
| 129. | Example 129 | 2.49 | 8.35 | — |
| 130. | Example 130 | 73 | 85.18 | C |
| 131. | Example 131 | 69.79 | 72.87 | B |
| 132. | Example 132 | 52.92 | 60.92 | — |
| 133. | Example 133 | 82.24 | 84.78 | A |
| 134. | Example 134 | 77.32 | 81.07 | A |
| 135. | Example 135 | 73.2 | 76.95 | B |
| 136. | Example 136 | 71.61 | 79.33 | A |
| 137. | Example 137 | 79.96 | 86.5 | A |
| 138. | Example 138 | 86.85 | 83.58 | A |
| 139. | Example 139 | 86.34 | 82.56 | A |
| 140. | Example 140 | 69.06 | 72.81 | A |
| 141. | Example 141 | 81.37 | 75.22 | A |
| 142. | Example 142 | 81.1 | 81.48 | A |
| 143. | Example 144 | 90.62 | 92.55 | A |
| 144. | Example 145 | 79.7 | 85.8 | A |

(—): Not determined

What is claimed is:

1. A compound of formula (I)

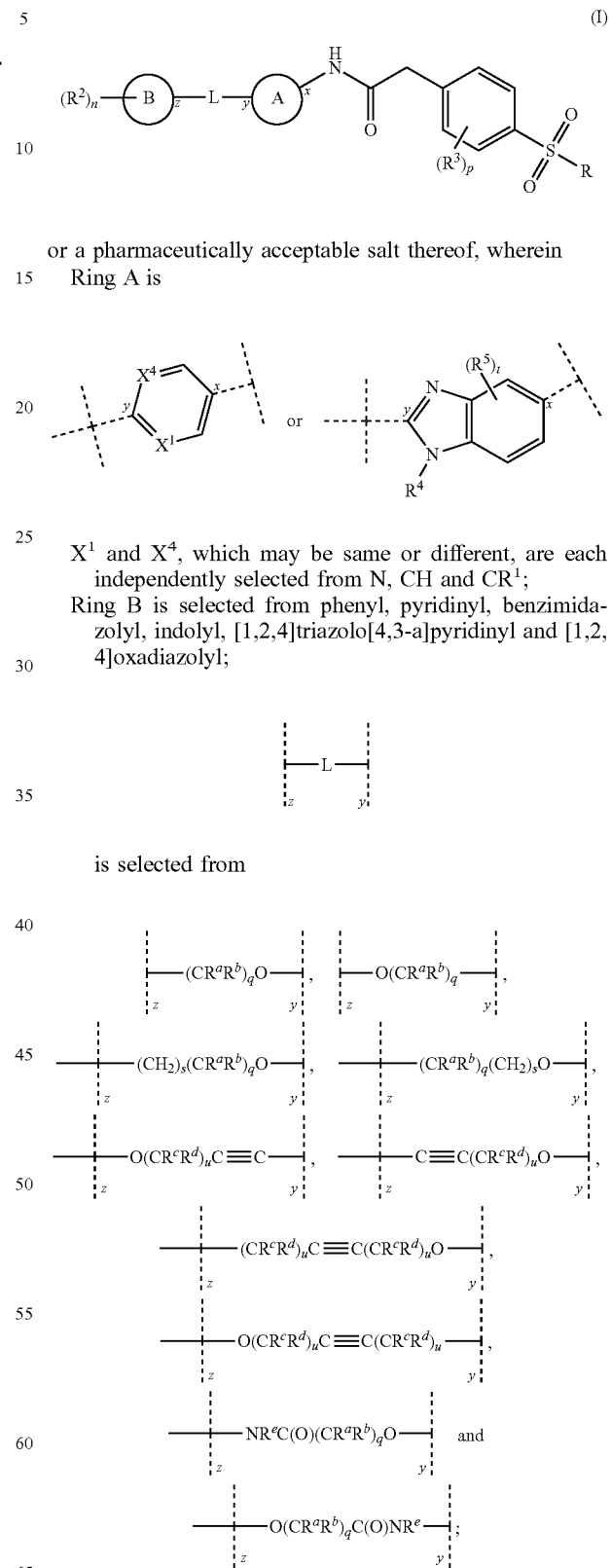

or a pharmaceutically acceptable salt thereof, wherein
Ring A is $X^1$ and $X^4$, which may be same or different, are each independently selected from N, CH and $CR^1$;

Ring B is selected from phenyl, pyridinyl, benzimidazolyl, indolyl, [1,2,4]triazolo[4,3-a]pyridinyl and [1,2,4]oxadiazolyl;

is selected from each of x, y and z represents a point of attachment;

R is selected from $C_{1-8}$alkyl and halo$C_{1-8}$alkyl;

each occurrence of W is independently selected from halogen, cyano, hydroxyl and $C_{1-8}$alkyl;

each occurrence of $R^2$ is independently selected from halogen, cyano, hydroxyl, $C_{1-8}$alkyl, $C_{1-8}$alkoxy, halo$C_{1-8}$alkyl, halo$C_{1-8}$alkoxy, hydroxy$C_{1-8}$alkyl, $C_{3-6}$cycloalkyl, $C_{3-6}$cycloalkyl$C_{1-8}$alkyl and 4-chlorophenyl;

each occurrence of $R^3$ is independently selected from halogen, cyano, hydroxyl and $C_{1-4}$alkyl;

$R^4$ is selected from hydrogen, $-(CH_2)_2N(CH_3)_2$, $C_{1-8}$alkyl, halo$C_{1-8}$alkyl, $C_{3-6}$cycloalkyl and $C_{3-6}$cycloalkyl$C_{1-8}$alkyl;

each occurrence of $R^5$ is independently selected from halogen, cyano, hydroxyl and $C_{1-8}$alkyl;

$R^a$ and $R^b$, which may be same or different, are each independently selected from halogen, $C_{1-8}$alkyl, halo$C_{1-8}$alkyl and $C_{1-8}$alkoxy; or $R^a$ and $R^b$ together with the carbon atom to which they are attached, form a cyclopropyl, cyclobutyl, cyclopentyl, cyclohexyl, tetrahydro-2H-pyran-4-yl, oxetan-3-yl, N-methyl-piperidin-4-yl or piperidin-4-yl ring;

$R^c$ and $R^d$, which may be same or different, are each independently selected from hydrogen, $C_{1-8}$alkyl, halo$C_{1-8}$alkyl and $C_{1-8}$alkoxy; or $R^c$ and $R^d$ together with the carbon atom to which they are attached, form a $C_{3-6}$cycloalkyl ring;

$R^e$ is selected from $C_{1-8}$alkyl, halo$C_{1-8}$alkyl and $C_{3-6}$cycloalkyl;

'n' is 0, 1, 2 or 3;
'p' is 0, 1 or 2;
'q' is 1 or 2;
's' is 1, 2 or 3;
't' is 0, 1 or 2; and
'u' is 1 or 2.

2. The compound according to claim 1, wherein R is $-C_2H_5$.

3. The compound according to claim 1, wherein 'p' is 0.

4. The compound according to claim 1, wherein

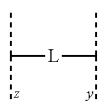

is

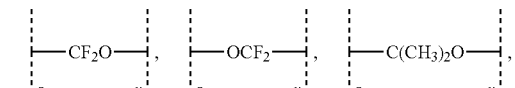

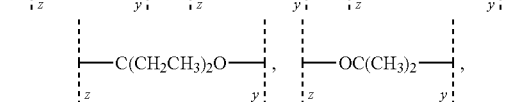

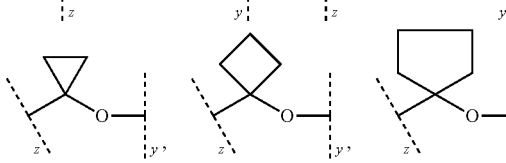

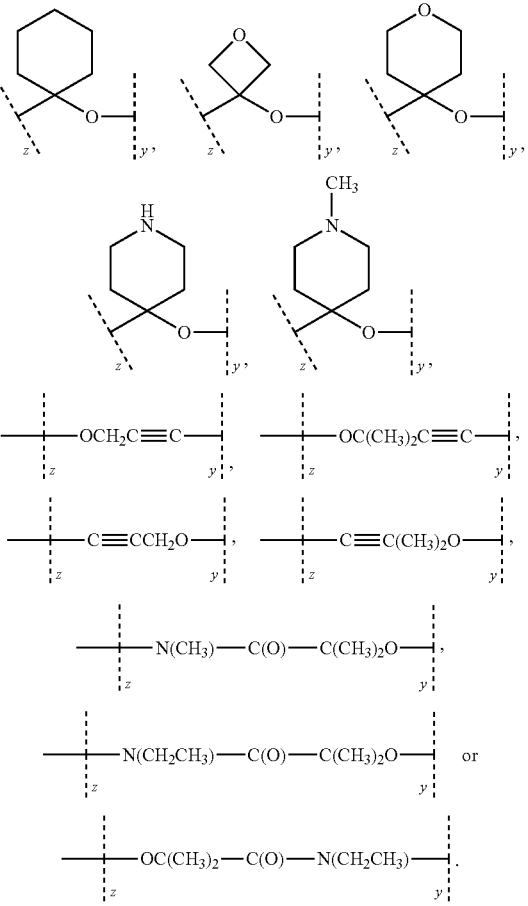

5. The compound according to claim 1, wherein ring A is

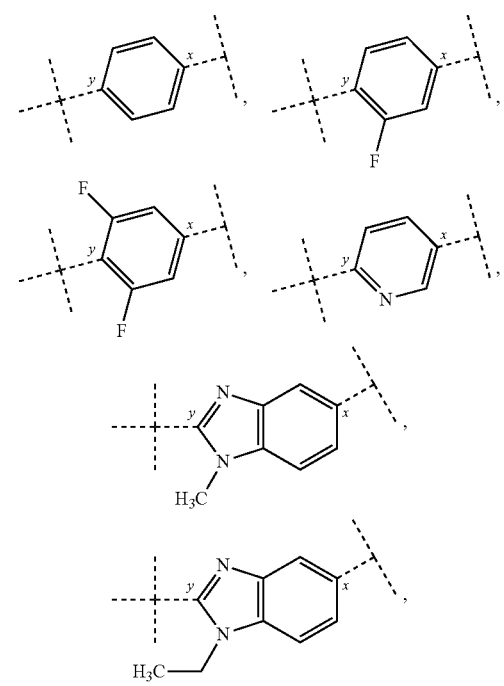

-continued

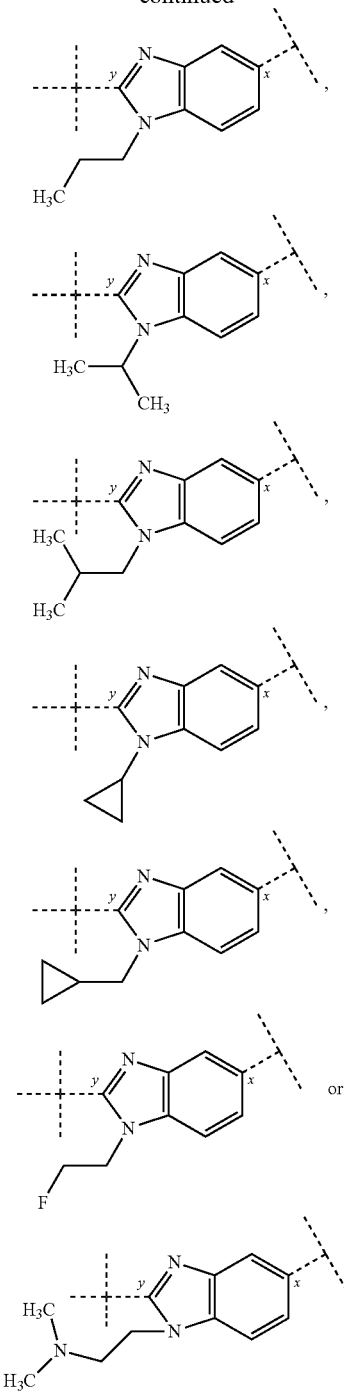

6. The compound according to claim 1, wherein R² is —F, —CH₃, —CH₂CH₃, —CH(CH₃)₂, —CF₃, —OCF₂, —OCF₃, —CN or 4-chlorophenyl; and 'n' is 1, 2 or 3.

7. The compound according to claim 1, wherein Ring

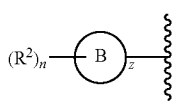

is 4-chlorophenyl, 4-fluorophenyl, 4-(trifluoromethyl)phenyl, 4-trifluoromethoxy-phenyl, 4-difluoromethoxy-phenyl, 4-cyano-phenyl, 2,4-dichlorophenyl, 3,4-dichlorophenyl, 3,5-dichlorophenyl, 2,4-difluorophenyl, 2,5-difluorophenyl, 3,4-difluorophenyl, 2-chloro-4-fluorophenyl, 3-chloro-4-fluorophenyl, 4-chloro-2-fluorophenyl, 4-chloro-3-fluorophenyl, 3-fluoro-4-trifluoromethyl-phenyl, 4-fluoro-3-trifluoromethyl-phenyl, 2,3,4-trifluorophenyl, 3,4,5-trifluorophenyl, 2,4,6-trifluorophenyl, 2,4,5-trifluorophenyl, 4-chloro-2,6-difluoro-phenyl, 5-chloro-pyridin-2-yl, 3,5-dichloro-pyridin-2-yl, 1-ethyl-6-fluoro-1H-benzimidazol-2-yl, 1-ethyl-5-fluoro-1H-benzoimidazol-2-yl, 5-chloro-1-ethyl-1H-benzimidazol-2-yl, 5-chloro-1-methyl-1H-benzimidazol-2-yl, 6-chloro-1-ethyl-1H-benzimidazol-2-yl, 6-chloro-1-methyl-1H-benzoimidazol-2-yl, 7-chloro-1-ethyl-1H-benzimidazol-2-yl, 5-fluoro-1-isopropyl-1H-benzoimidazol-2-yl, 6-chloro-[1,2,4]triazolo[4,3-a]pyridin-3-yl, 5-chloro-1H-indol-1-yl, 5-chloro-1-ethyl-1H-indol-2-yl, 5-fluoro-2-methyl-1H-indol-1-yl, or 4-chloro-phenyl-[1,2,4]oxadiazol-3-yl.

8. The compound according to claim 1, wherein Ring A is

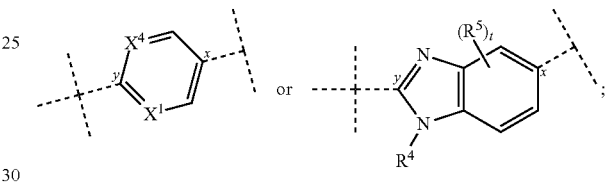

$X^1$ is N, CH or $CR^1$;
$X^4$ is CH or $CR^1$;
Ring B is phenyl, pyridin-2-yl, benzimidazol-2-yl, indol-1-yl, [1,2,4]triazolo[4,3-a]pyridin-3-yl or [1,2,4]oxadiazol-3-yl;
$R^1$ is F;
$R^2$ is —F, —Cl, —CH₃, —CH₂CH₃, —CH(CH₃)₂, —CF₃, —OCF₂, —OCF₃, —CN or 4-chlorophenyl;
$R^4$ is —H, —CH₃, —CH₂CH₃, —CH₂CH₂CH₃, —CH(CH₃)₂, —CH₂CH(CH₃)₂, —(CH₂)₂N(CH₃)₂, —CH₂CH₂F, cyclopropyl or cyclopropylmethyl;

is

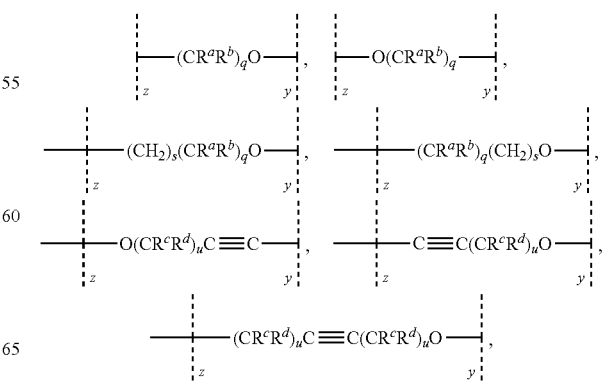

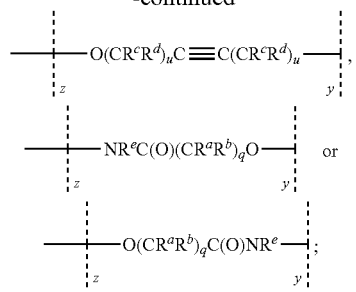

$R^a$ and $R^b$ are independently selected from fluoro, methyl and ethyl; or $R^a$ and $R^b$ together with the carbon atom to which they are attached, form a cyclopropyl, cyclobutyl, cyclopentyl, cyclohexyl, tetrahydro-2H-pyran-4-yl, oxetan-3-yl, N-methyl-piperidin-4-yl or piperidin-4-yl ring;

$R^c$ and $R^d$ are independently selected from hydrogen and methyl;

$R^e$ is selected from methyl and ethyl;

's' is 1;
'q' is 1;
'u' is 1;
'n' is 1, 2 or 3;
'p' is 0; 't' is 0; and
R is $C_2H_5$.

9. The compound according to claim 1, wherein Ring A is

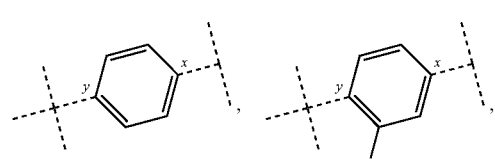

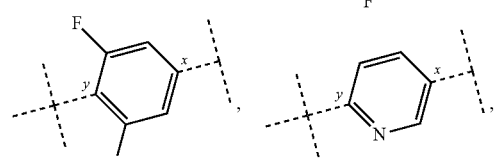

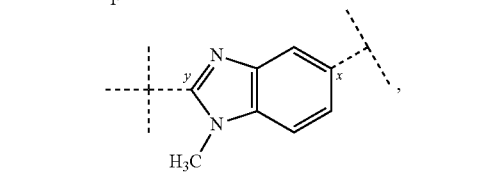

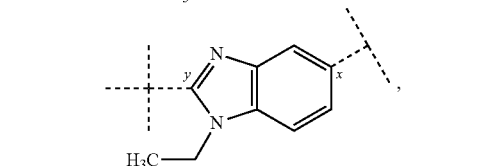

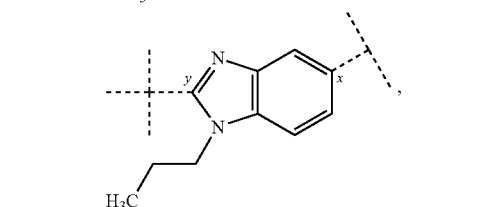

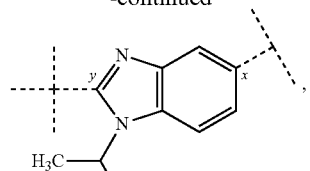

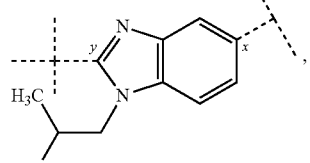

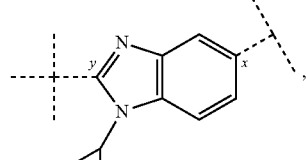

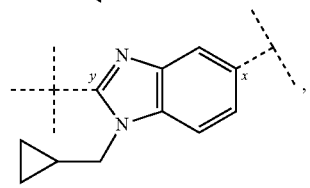

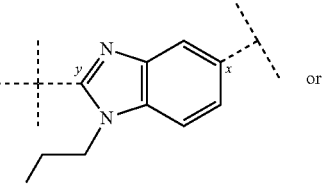

or

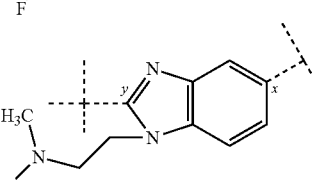

Ring

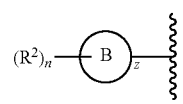

is 4-chlorophenyl, 4-fluorophenyl, 4-(trifluoromethyl)phenyl, 4-trifluoromethoxy-phenyl, 4-difluoromethoxy-phenyl, 4-cyano-phenyl, 2,4-dichlorophenyl, 3,4-dichlorophenyl, 3,5-dichlorophenyl, 2,4-difluorophenyl, 2,5-difluorophenyl, 3,4-difluorophenyl, 2-chloro-4-fluorophenyl, 3-chloro-4-fluorophenyl, 4-chloro-2-fluorophenyl, 4-chloro-3-fluorophenyl, 3-fluoro-4-trifluoromethyl-phenyl, 4-fluoro-3-trifluoromethyl-phenyl, 2,3,4-trifluorophenyl, 3,4,5-trifluorophenyl, 2,4,6-trifluorophenyl, 2,4,5-trifluorophenyl, 4-chloro-2,6-difluoro-phenyl, 5-chloro-pyridin-2-yl, 3,5-dichloro-pyridin-2-yl, 1-ethyl-6-fluoro-1H-benzimidazol-2-yl, 1-ethyl-5-fluoro-1H-benzoimidazol-2-yl, 5-chloro-1-ethyl-1H-benzimidazol-2-yl, 5-chloro-1-methyl-1H-benzimidazol-2-yl, 6-chloro-1-ethyl-1H-benzoimidazol-2-yl, 6-chloro-1-methyl-1H-benzoimidazol-2-yl, 7-chloro-1-ethyl-1H-benzimidazol-2-yl, 5-fluoro-1-isopropyl-1H-benzimidazol-2-yl, 6-chloro-[1,2,4]triazolo[4,3-a]pyridin-3-yl, 5-chloro-1H-indol-1-yl, 5-chloro-1-ethyl-1H-indol-2-yl, 5-fluoro-2-methyl-1H-indol-1-yl, or 4-chloro-phenyl-[1,2,4]oxadiazol-3-yl;

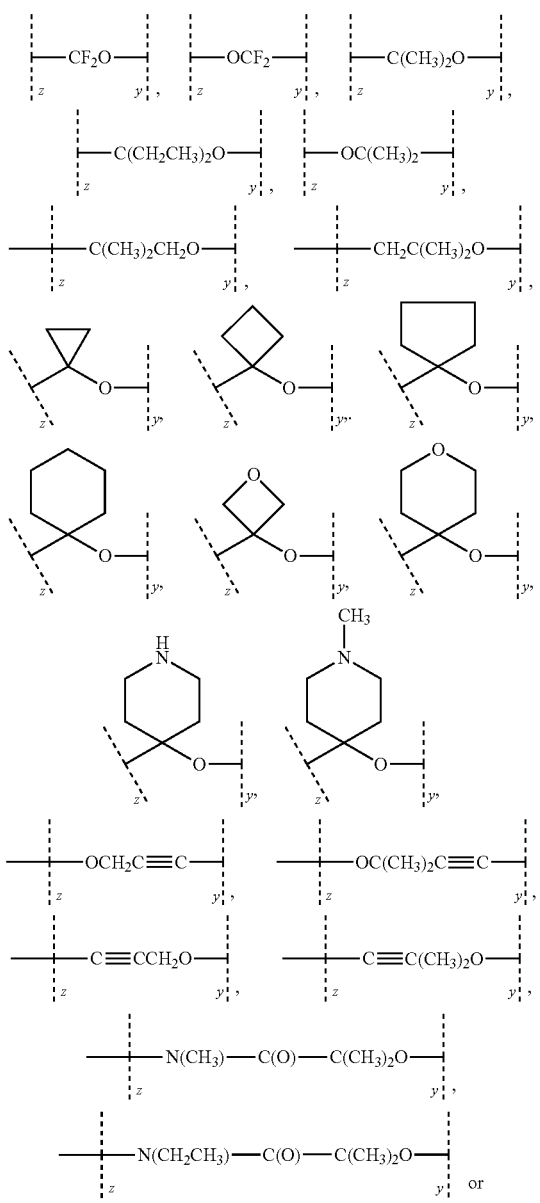

is

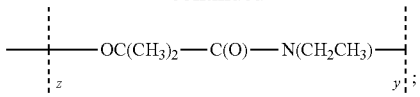

'p' is 0; and
R is $C_2H_5$.

10. The compound according to claim 1, represented by formula (IV)

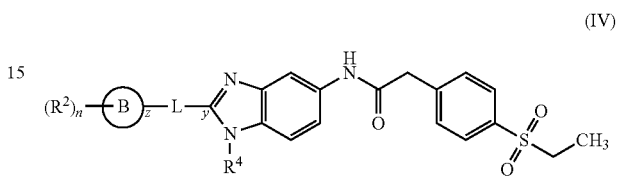

or a pharmaceutically acceptable salt thereof, wherein
Ring B is selected from phenyl and pyridinyl;

is selected from

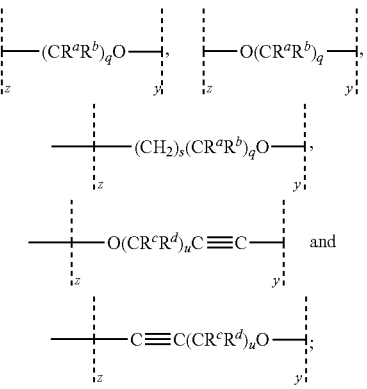

each of y and z represents a point of attachment;
each occurrence of $R^2$ is independently selected from halogen, cyano, hydroxyl, $C_{1-8}$alkyl, $C_{1-8}$alkoxy, halo$C_{1-8}$alkyl, halo$C_{1-8}$alkoxy, hydroxy$C_{1-8}$alkyl and $C_{3-6}$cycloalkyl;
$R^4$ is selected from hydrogen, —$(CH_2)_2N(CH_3)_2$, $C_{1-8}$alkyl, halo$C_{1-8}$alkyl, $C_{3-6}$cycloalkyl and $C_{3-6}$cycloalkyl$C_{1-8}$alkyl;
$R^a$ and $R^b$, which may be same or different, are each independently selected from halogen, $C_{1-8}$alkyl, halo$C_{1-8}$alkyl and $C_{1-8}$alkoxy; or $R^a$ and $R^b$ together with the carbon atom to which they are attached, form a cyclopropyl, cyclobutyl, cyclopentyl, or cyclohexyl ring;
$R^c$ and $R^d$, which may be same or different, are each independently selected from hydrogen, $C_{1-8}$alkyl, halo$C_{1-8}$alkyl and $C_{1-8}$alkoxy; or $R^c$ and $R^d$ together with the carbon atom to which they are attached, form a $C_{3-6}$cycloalkyl ring;

'n' is 0, 1, 2 or 3;
'q' is 1 or 2;
's' is 1, 2 or 3; and
'u' is 1.

11. The compound according to claim 10, wherein
Ring B is phenyl or pyridin-2-yl;
$R^2$ is F, Cl or $CF_3$;
$R^4$ is —H, —$CH_3$, —$CH_2CH_3$, —$CH_2CH_2CH_3$, —CH($CH_3$)$_2$, —$CH_2CH(CH_3)_2$, —$(CH_2)_2N(CH_3)_2$, —$CH_2CH_2F$ or cyclopropylmethyl;

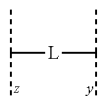

is

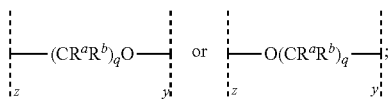

$R^a$ and $R^b$ are F or methyl;
'n' is 1, 2 or 3; and
'q' is 1.

12. The compound according to claim 10, wherein
Ring

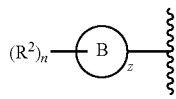

is 4-chlorophenyl, 4-fluorophenyl, 4-(trifluoromethyl)phenyl, 2,4-dichlorophenyl, 3,4-dichlorophenyl, 3,5-dichlorophenyl, 2,4-difluorophenyl, 2,5-difluorophenyl, 3,4-difluorophenyl, 2-chloro-4-fluorophenyl, 4-chloro-2-fluorophenyl, 4-chloro-3-fluoro-phenyl, 3-fluoro-4-trifluoromethyl-phenyl, 2,3,4-trifluorophenyl, 3,4,5-trifluorophenyl, 2,4,6-trifluorophenyl, 2,4,5-trifluorophenyl, 4-chloro-2,6-difluoro-phenyl or 5-chloro-pyridin-2-yl;
$R^4$ is —H, —$CH_3$, —$CH_2CH_3$, —$CH_2CH_2CH_3$, —CH($CH_3$)$_2$, —$CH_2CH(CH_3)_2$, —$(CH_2)_2N(CH_3)_2$ or cyclopropylmethyl; and

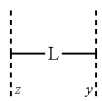

is

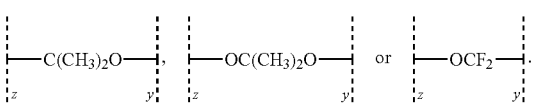

13. The compound according to claim 1, represented by formula (II)

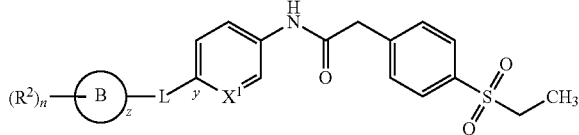

or a pharmaceutically acceptable salt thereof, wherein
$X^1$ is selected from N, CH and $CR^1$;
Ring B is selected from phenyl, pyridinyl, benzimidazolyl, indolyl, [1,2,4]triazolo[4,3-a]pyridinyl and [1,2,4]oxadiazolyl;

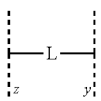

is selected from

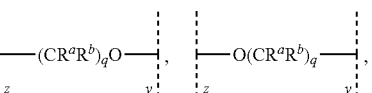

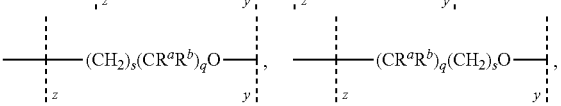

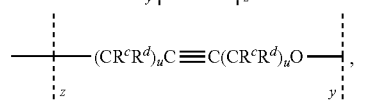

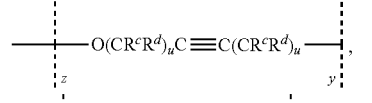

each of y and z represents a point of attachment;
$R^1$ is independently selected from halogen, cyano, hydroxyl and $C_{1-8}$alkyl;
each occurrence of $R^2$ is independently selected from halogen, cyano, hydroxyl, $C_{1-8}$alkyl, $C_1$-8alkoxy, halo$C_{1-8}$alkyl, halo$C_{1-8}$alkoxy, hydroxy$C_{1-8}$alkyl, $C_{3-6}$cycloalkyl, $C_{3-6}$cycloalkyl$C_1$-8alkyl and 4-chlorophenyl;
$R^a$ and $R^b$, which may be same or different, are each independently selected from halogen, $C_{1-8}$alkyl, halo$C_{1-8}$alkyl and $C_{1-8}$ alkoxy; or $R^a$ and $R^b$ together with the carbon atom to which they are attached, form a cyclopropyl, cyclobutyl, cyclopentyl, cyclohexyl, tetrahydro-2H-pyran-4-yl, oxetan-3-yl, N-methyl-piperidin-4-yl or piperidin-4-yl ring;
$R^c$ and $R^d$, which may be same or different, are each independently selected from hydrogen, $C_{1-8}$alkyl, haloC$_{1-8}$alkyl and C$_{1-8}$alkoxy; or R$^c$ and R$^d$ together with the carbon atom to which they are attached, form a C$_{3-6}$cycloalkyl ring;

R$^e$ is selected from C$_{1-8}$alkyl, haloC$_{1-8}$alkyl and C$_{3-6}$cycloalkyl;

'n' is 0, 1, 2 or 3;
'q' is 1 or 2;
's' is 1, 2 or 3; and
'u' is 1.

14. The compound according to claim 13, wherein R$^2$ is —F, —Cl, —CH$_3$, —CH$_2$CH$_3$, —CH(CH$_3$)$_2$, —CF$_3$, —OCF$_2$, —OCF$_3$, —CN or 4-chlorophenyl; and 'n' is 1, 2 or 3.

15. The compound according to claim 13, wherein
X$^1$ is N, CH or CF;
Ring

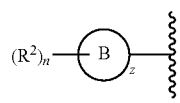

is 4-chlorophenyl, 4-fluorophenyl, 4-(trifluoromethyl)phenyl, 4-trifluoromethoxy-phenyl, 4-difluoromethoxy-phenyl, 4-cyano-phenyl, 2,4-dichlorophenyl, 3,4-dichlorophenyl, 3,5-dichlorophenyl, 2,4-difluorophenyl, 2,5-difluorophenyl, 3,4-difluorophenyl, 2-chloro-4-fluorophenyl, 3-chloro-4-fluorophenyl, 4-chloro-2-fluorophenyl, 4-chloro-3-fluorophenyl, 3-fluoro-4-trifluoromethyl-phenyl, 4-fluoro-3-trifluoromethyl-phenyl, 2,3,4-trifluorophenyl, 3,4,5-trifluorophenyl, 2,4,6-trifluorophenyl, 2,4,5-trifluorophenyl, 4-chloro-2,6-difluoro-phenyl, 5-chloro-pyridin-2-yl, 3,5-dichloro-pyridin-2-yl, 1-ethyl-6-fluoro-1H-benzimidazol-2-yl, 1-ethyl-5-fluoro-1H-benzoimidazol-2-yl, 5-chloro-1-ethyl-1H-benzimidazol-2-yl, 5-chloro-1-methyl-1H-benzimidazol-2-yl, 6-chloro-1-ethyl-1H-benzimidazol-2-yl, 6-chloro-1-methyl-1H-benzoimidazol-2-yl, 7-chloro-1-ethyl-1H-benzimidazol-2-yl, 5-fluoro-1-isopropyl-1H-benzoimidazol-2-yl, 6-chloro-[1,2,4]triazolo[4,3-a]pyridin-3-yl, 5-chloro-1H-indol-1-yl, 5-chloro-1-ethyl-1H-indol-2-yl, 5-fluoro-2-methyl-1H-indol-1-yl, or 4-chloro-phenyl-[1,2,4]oxadiazol-3-yl; and

is

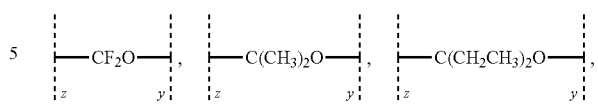

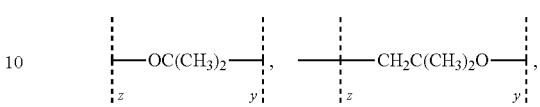

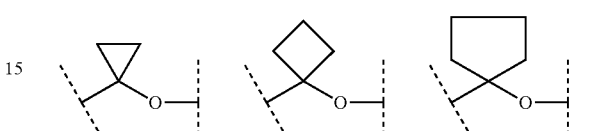

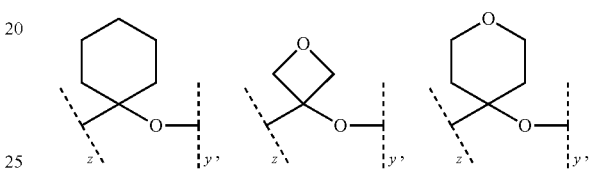

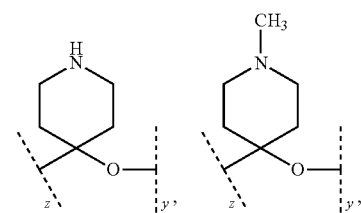

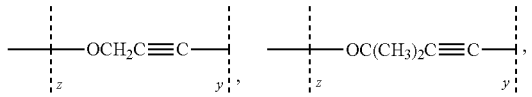

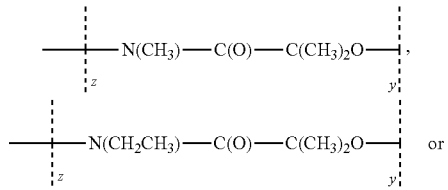

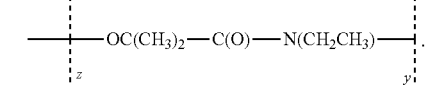

16. The compound according to claim 1, represented by formula (III)

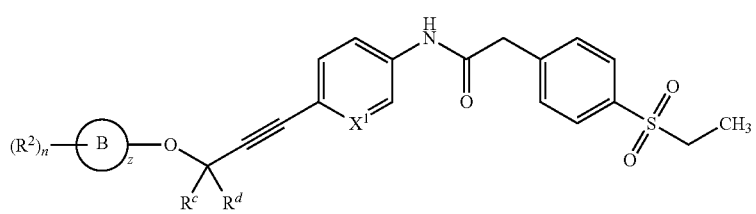

or a pharmaceutically acceptable salt thereof, wherein
X¹ is selected from N, CH and CR¹;
Ring B is selected from phenyl and pyridinyl;
R¹ is independently selected from halogen, cyano, hydroxyl and $C_{1-8}$alkyl;
each occurrence of R² is independently selected from halogen, cyano, hydroxyl, $C_{1-8}$alkyl, $C_{1-8}$alkoxy, halo$C_{1-8}$alkyl, halo$C_{1-8}$alkoxy, hydroxy$C_{1-8}$alkyl and $C_{3-6}$cycloalkyl;
$R^c$ and $R^d$, which may be same or different, are each independently selected from hydrogen, $C_{1-8}$alkyl, halo$C_{1-8}$alkyl and $C_{1-8}$alkoxy; or $R^c$ and $R^d$ together with the carbon atom to which they are attached, form a $C_{3-6}$cycloalkyl ring;
z represents a point of attachment; and
'n' is 0, 1, 2 or 3.

17. The compound according to claim 16, wherein
X¹ is N, CH or CF;
Ring B is phenyl;
R² is —F, —Cl, —CF₃, —OCF₂, —OCF₃ or CN;
'n' is 1, 2 or 3; and
$R^c$ and $R^d$ are independently selected from hydrogen and methyl.

18. The compound according to claim 16, wherein
X¹ is N, CH or CF;
Ring

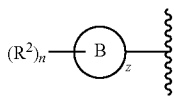

is 4-chlorophenyl, 4-fluorophenyl, 4-(trifluoromethyl) phenyl, 2,4-dichlorophenyl, 3,4-dichlorophenyl, 3,5-dichlorophenyl, 2,4-difluorophenyl, 2,5-difluorophenyl, 3,4-difluorophenyl, 2-chloro-4-fluorophenyl, 3-chloro-4-fluorophenyl, 4-chloro-2-fluorophenyl, 4-chloro-3-fluoro-phenyl, 3-fluoro-4-trifluoromethyl-phenyl, 2,3,4-trifluorophenyl, 3,4,5-trifluorophenyl, 2,4,6-trifluorophenyl, 2,4,5-trifluorophenyl or 4-chloro-2,6-difluoro-phenyl; and
$R^c$ and $R^d$ are independently selected from hydrogen and methyl.

19. The compound according to claim 1, selected from
2-[4-(Ethylsulfonyl)phenyl]-N-(1-methyl-2-{2-[4-(trifluoromethyl) phenoxy]propan-2-yl}-1H-benzimidazol-5-yl)acetamide;
N-{2-[2-(3,4-Difluorophenoxy)propan-2-yl]-1-methyl-1H-benzimidazol-5-yl}-2-[4-(ethylsulfonyl)phenyl]acetamide;
N-{2-[1-(4-Chloro-2-fluoro-phenoxy)-1-methyl-ethyl]-1-methyl-1H-benzoimidazol-5-yl}-2-(4-ethanesulfonylphenyl)-acetamide;
N-{2-[2-(2,4-Dichlorophenoxy)propan-2-yl]-1-methyl-1H-benzimidazol-5-yl}-2-[4-(ethylsulfonyl)phenyl]acetamide;
N-{2-[2-(3,4-Dichlorophenoxy)propan-2-yl]-1-methyl-1H-benzimidazol-5-yl}-2-[4-(ethylsulfonyl)phenyl]acetamide;
N-{2-[2-(4-Chloro-2-fluorophenoxy)propan-2-yl]-1-ethyl-1H-benzimidazol-5-yl}-2-[4-(ethylsulfonyl)phenyl]acetamide;
N-{2-[1-(4-Chloro-3-fluoro-phenoxy)-1-methyl-ethyl]-1-ethyl-1H-benzoimidazol-5-yl}-2-(4-ethanesulfonylphenyl)-acetamide;
N-{2-[1-(2,4-Difluoro-phenoxy)-1-methyl-ethyl]-1-ethyl-1H-benzoimidazol-5-yl}-2-(4-ethanesulfonylphenyl)-acetamide;
N-{2-[1-(3,4-Difluoro-phenoxy)-1-methyl-ethyl]-1-ethyl-1H-benzoimidazol-5-yl}-2-(4-ethanesulfonylphenyl)-acetamide;
2-(4-Ethanesulfonyl-phenyl)-N-{1-ethyl-2-[1-methyl-1-(2,4,6-trifluoro-phenoxy)-ethyl]-1H-benzoimidazol-5-yl}-acetamide;
2-(4-Ethanesulfonyl-phenyl)-N-{1-ethyl-2-[1-methyl-1-(2,3,4-trifluoro-phenoxy)-ethyl]-1H-benzoimidazol-5-yl}-acetamide;
2-(4-Ethanesulfonyl-phenyl)-N-{1-ethyl-2-[1-methyl-1-(2,4,5-trifluoro-phenoxy)-ethyl]-1H-benzoimidazol-5-yl}-acetamide;
N-{2-[1-(4-Chloro-phenoxy)-1-methyl-ethyl]-1-ethyl-1H-benzoimidazol-5-yl}-2-(4-ethanesulfonyl-phenyl)-acetamide;
N-{2-[1-(5-Chloro-pyridin-2-yloxy)-1-methyl-ethyl]-1-ethyl-1H-benzoimidazol-5-yl}-2-(4-ethanesulfonylphenyl)-acetamide;
N-{2-[1-(2,4-Difluoro-phenoxy)-1-methyl-ethyl]-1-methyl-1H-benzoimidazol-5-yl}-2-(4-ethanesulfonylphenyl)-acetamide;
N-[2-[1-(2,4-Difluoro-phenoxy)-1-methyl-ethyl]-1-(2-dimethylamino-ethyl)-1H-benzoimidazol-5-yl]-2-(4-ethanesulfonyl-phenyl)-acetamide;
N-{1-Cyclopropylmethyl-2-[1-(2,4-difluoro-phenoxy)-1-methyl-ethyl]-1H-benzoimidazol-5-yl}-2-(4-ethanesulfonyl-phenyl)-acetamide;
N-{2-[1-(2,4-Difluoro-phenoxy)-1-methyl-ethyl]-1-propyl-1H-benzoimidazol-5-yl}-2-(4-ethanesulfonyl-phenyl)-acetamide;
N-{2-[1-(2,4-Difluoro-phenoxy)-1-methyl-ethyl]-1-isobutyl-1H-benzoimidazol-5-yl}-2-(4-ethanesulfonylphenyl)-acetamide;
N-{2-[1-(2,4-Difluoro-phenoxy)-1-methyl-ethyl]-1-isopropyl-1H-benzoimidazol-5-yl}-2-(4-ethanesulfonylphenyl)-acetamide;
N-{2-[(2,4-Difluoro-phenoxy)-difluoromethyl]-1-ethyl-1H-benzoimidazol-5-yl}-2-(4-ethanesulfonyl-phenyl)-acetamide;
N-{1-Cyclopropyl-2-[1-(2,4-difluorophenoxy)-1-methyl-ethyl]-1H-benzoimidazol-5-yl}-2-(4-ethanesulfonylphenyl)-acetamide;
N-{2-[1-(2,5-Difluorophenoxy)-1-methylethyl]-1-ethyl-1H-benzoimidazol-5-yl}-2-(4-ethanesulfonylphenyl)-acetamide;
N-(2-(2-(2,4-Dichlorophenoxy)propan-2-yl)-1-ethyl-1H-benzo[d]imidazol-5-yl)-2-(4-(ethylsulfonyl)phenyl)acetamide;
N-(2-(2-(2,4-Difluorophenoxy)propan-2-yl)-1-(2-fluoroethyl)-1H-benzo[d]imidazol-5-yl)-2-(4-(ethylsulfonyl) phenyl)acetamide;
and pharmaceutically acceptable salt thereof.

20. The compound according to claim 1, selected from
N-(4-{[2-(3,4-Difluorophenyl)propan-2-yl]oxy}phenyl)-2-[4(ethylsulfonyl)phenyl]acetamide;
N-(4-{[2-(2,4-Difluorophenyl)propan-2-yl]oxy}phenyl)-2-[4-(ethylsulfonyl)phenyl]acetamide;
N-(4-{[2-(2,4-Dichlorophenyl)propan-2-yl]oxy}phenyl)-2-[4-(ethylsulfonyl)phenyl]acetamide;
N-(4-{[2-(3,4-Dichlorophenyl)propan-2-yl]oxy}phenyl)-2-[4-(ethylsulfonyl)phenyl]acetamide;
N-(4-{[2-(3,5-Dichlorophenyl)propan-2-yl]oxy}phenyl)-2-[4-(ethylsulfonyl)phenyl]acetamide;

N-(4-{[2-(4-Chloro-2-fluorophenyl)propan-2-yl]oxy}phenyl)-2-[4-(ethylsulfonyl) phenyl]acetamide;
N-{4-[1-(4-Chloro-3-fluoro-phenyl)-1-methyl-ethoxy]-phenyl}-2-(4-ethanesulfonyl-phenyl)-acetamide;
N-(4-{[2-(2-Chloro-4-fluorophenyl)propan-2-yl]oxy}phenyl)-2-[4-(ethylsulfonyl) phenyl]acetamide;
2-[4-(Ethylsulfonyl)phenyl]-N-[4-({2-[4-(trifluoromethyl)phenyl]propan-2-yl}oxy) phenyl]acetamide;
2-(4-Ethanesulfonyl-phenyl)-N-{4-[1-(3-fluoro-4-trifluoromethyl-phenyl)-1-methyl-ethoxy]-phenyl}-acetamide;
N-{4-[1-(3,5-Dichloro-pyridin-2-yl)-1-methyl-ethoxy]-phenyl}-2-(4-ethanesulfonyl-phenyl)-acetamide;
N-{4-[1-(4-Chloro-3-fluoro-phenyl)-1-ethyl-propoxy]-phenyl}-2-(4-ethanesulfonyl-phenyl)-acetamide;
N-{4-[1-(2,4-Difluoro-phenyl)-1-ethyl-propoxy]-phenyl}-2-(4-ethanesulfonyl-phenyl)-acetamide;
N-(4-{[2-(1-ethyl-6-fluoro-1H-benzimidazol-2-yl)propan-2-yl]oxy}phenyl)-2-[4-(ethylsulfonyl)phenyl]acetamide;
2-(4-Ethanesulfonyl-phenyl)-N-{4-[1-(1-ethyl-5-fluoro-1H-benzoimidazol-2-yl)-1-methyl-ethoxy]-phenyl}-acetamide;
N-(4-{[2-(5-Chloro-1-ethyl-1H-benzimidazol-2-yl)propan-2-yl]oxy}phenyl)-2-[4-(ethylsulfonyl)phenyl]acetamide;
N-(4-{[2-(6-Chloro-1-ethyl-1H-benzimidazol-2-yl)propan-2-yl]oxy}phenyl)-2-[4-(ethylsulfonyl)phenyl]acetamide;
N-{4-[1-(6-Chloro-1-methyl-1H-benzoimidazol-2-yl)-1-methyl-ethoxy]-phenyl}-2-(4-ethanesulfonyl-phenyl)-acetamide;
N-(4-{[2-(7-Chloro-1-ethyl-1H-benzimidazol-2-yl)propan-2-yl]oxy}phenyl)-2-[4-(ethylsulfonyl) phenyl]acetamide;
2-(4-Ethanesulfonyl-phenyl)-N-{4-[1-(5-fluoro-1-isopropyl-1H-benzoimidazol-2-yl)-1-methyl-ethoxy]-phenyl}-acetamide;
N-{4-[1-(5-Chloro-1-ethyl-1H-indol-2-yl)-1-methyl-ethoxy]-phenyl}-2-(4-ethanesulfonyl-phenyl)-acetamide;
N-{4-[(5-Chloro-1-ethyl-1H-benzoimidazol-2-yl)-difluoro-methoxy]-phenyl}-2-(4-ethanesulfonyl-phenyl)-acetamide;
N-(4-{[1-(6-Chloro-1-ethyl-1H-benzimidazol-2-yl)cyclopropyl]oxy}phenyl)-2-[4-(ethylsulfonyl) phenyl]acetamide;
N-{4-[1-(5-Chloro-1-ethyl-1H-benzoimidazol-2-yl)-cyclopropoxy]-phenyl}-2-(4-ethanesulfonyl-phenyl)-acetamide;
N-{4-[1-(5-Chloro-1-methyl-1H-benzoimidazol-2-yl)-cyclobutoxy]-phenyl}-2-(4-ethanesulfonyl-phenyl)-acetamide;
2-(4-Ethanesulfonyl-phenyl)-N-{4-[1-(1-ethyl-5-fluoro-1H-benzoimidazol-2-yl)-cyclobutoxy]-phenyl}-acetamide;
N-{4-[1-(6-Chloro-[1,2,4]triazolo[4,3-a]pyridin-3-yl)-cyclobutoxy]-phenyl}-2-(4-ethanesulfonyl-phenyl)-acetamide;
N-(4-{1-[5-(4-Chloro-phenyl)-[1,2,4]oxadiazol-3-yl]-1-methyl-ethoxy}-phenyl)-2-(4-ethanesulfonyl-phenyl)-acetamide;
N-(4-{[1-(5-Chloro-1H-indol-1-yl)-2-methylpropan-2-yl]oxy}phenyl)-2-[4-(ethylsulfonyl)phenyl]acetamide;
2-[4-(Ethylsulfonyl)phenyl]-N-(4-{[1-(5-fluoro-2-methyl-1H-indol-1-yl)-2-methylpropan-2-yl]oxy}phenyl)acetamide;
N-{4-[1-(4-Chloro-phenyl)-cyclobutoxy]-phenyl}-2-(4-ethanesulfonyl-phenyl)-acetamide;
N-(4-{[1-(4-Chloro-3-fluorophenyl)cyclobutyl]oxy}phenyl)-2-[4-(ethylsulfonyl) phenyl]acetamide;
N-(4-{[1-(4-Chloro-2-fluorophenyl)cyclobutyl]oxy}phenyl)-2-[4-(ethylsulfonyl) phenyl]acetamide;
N-{4-[1-(3,4-Difluoro-phenyl)-cyclobutoxy]-phenyl}-2-(4-ethanesulfonyl-phenyl)-acetamide;
N-{4-[4-(3,4-Difluoro-phenyl)-tetrahydro-pyran-4-yloxy]-phenyl}-2-(4-ethanesulfonyl-phenyl)-acetamide;
N-(4-{[4-(4-Chloro-2-fluorophenyl)tetrahydro-2H-pyran-4-yl]oxy}phenyl)-2-[4-(ethylsulfonyl)phenyl]acetamide;
N-{4-[4-(4-Chlorophenyl)-tetrahydro-pyran-4-yloxy]-phenyl}-2-(4-ethanesulfonyl-phenyl)-acetamide;
N-{4-[4-(4-Chloro-3-fluoro-phenyl)-tetrahydro-pyran-4-yloxy]-phenyl}-2-(4-ethanesulfonyl-phenyl)-acetamide;
N-{4-[4-(3,4-Dichloro-phenyl)-tetrahydro-pyran-4-yloxy]-phenyl}-2-(4-ethanesulfonyl-phenyl)-acetamide;
N-{4-[4-(2,4-Dichloro-phenyl)-tetrahydro-pyran-4-yloxy]-phenyl}-2-(4-ethanesulfonyl-phenyl)-acetamide;
2-(4-Ethanesulfonyl-phenyl)-N-{4-[4-(3-fluoro-4-trifluoromethyl-phenyl)-tetrahydro-pyran-4-yloxy]-phenyl}-acetamide;
2-(4-Ethanesulfonyl-phenyl)-N-{4-[4-(4-fluoro-3-trifluoromethyl-phenyl)-tetrahydro-pyran-4-yloxy]-phenyl}-acetamide;
N-(4-{[4-(4-Chloro-3-fluorophenyl)piperidin-4-yl]oxy}phenyl)-2-[4-(ethylsulfonyl)phenyl]acetamide;
N-{4-[4-(4-Chloro-3-fluoro-phenyl)-1-methyl-piperidin-4-yloxy]-phenyl}-2-(4-ethanesulfonyl-phenyl)-acetamide;
N-{4-[3-(4-Chloro-3-fluoro-phenyl)-oxetan-3-yloxy]-phenyl}-2-(4-ethanesulfonyl-phenyl)-acetamide;
N-{4-[3-(3,4-Dichlorophenyl)-oxetan-3-yloxy]-phenyl}-2-(4-ethanesulfonyl-phenyl)-acetamide;
N-{4-[3-(2,4-Dichlorophenyl)-oxetan-3-yloxy]-phenyl}-2-(4-ethanesulfonyl-phenyl)-acetamide;
(4-Ethanesulfonyl-phenyl)-N-{4-[3-(3-fluoro-4-trifluoromethyl-phenyl)-oxetan-3-yloxy]-phenyl}-acetamide;
N-{4-[1-(3,4-Dichloro-phenyl)-cyclopropoxy]-phenyl}-2-(4-ethanesulfonyl-phenyl)-acetamide;
N-{4-[1-(4-Chloro-3-fluoro-phenyl)-cyclopropoxy]-phenyl}-2-(4-ethanesulfonyl-phenyl)-acetamide;
N-{4-[1-(4-Chloro-2-fluoro-phenyl)-cyclopropoxy]-phenyl}-2-(4-ethanesulfonyl-phenyl)-acetamide;
N-{6-[1-(4-Chloro-3-fluoro-phenyl)-cyclopropoxy]-pyridin-3-yl}-2-(4-ethanesulfonyl-phenyl)-acetamide;
N-{6-[1-(3,4-Dichloro-phenyl)-cyclopropoxy]-pyridin-3-yl}-2-(4-ethanesulfonyl-phenyl)-acetamide;
N-{6-[1-(4-Chloro-3-fluoro-phenyl)-cyclobutoxy]-pyridin-3-yl}-2-(4-ethanesulfonyl-phenyl)-acetamide;
N-{6-[4-(4-Chloro-3-fluoro-phenyl)-tetrahydro-pyran-4-yloxy]-pyridin-3-yl}-2-(4-ethanesulfonyl-phenyl)-acetamide;
N-{6-[1-(4-Chloro-2-fluoro-phenyl)-1-methyl-ethoxy]-pyridin-3-yl}-2-(4-ethanesulfonyl-phenyl)-acetamide;
N-{6-[1-(2-Chloro-4-fluoro-phenyl)-1-methyl-ethoxy]-pyridin-3-yl}-2-(4-ethanesulfonyl-phenyl)-acetamide;
N-(6-{[2-(2,4-Dichlorophenyl)propan-2-yl]oxy}pyridin-3-yl)-2-[4-(ethylsulfonyl) phenyl]acetamide;
N-{6-[1-(3,4-Dichloro-phenyl)-1-methyl-ethoxy]-pyridin-3-yl}-2-(4-ethanesulfonyl-phenyl)-acetamide;

N-{4-[3-(2,4-Dichlorophenoxy)prop-1-yn-1-yl]phenyl}-2-[4-(ethylsulfonyl)phenyl]acetamide;
N-{4-[3-(3,4-Dichlorophenoxy)prop-1-yn-1-yl]phenyl}-2-[4-(ethylsulfonyl)phenyl]acetamide;
N-{4-[3-(3,4-Dichlorophenoxy)-3-methylbut-1-yn-1-yl]phenyl}-2-[4-(ethylsulfonyl)phenyl]acetamide;
N-{4-[3-(2,4-Dichloro-phenoxy)-3-methyl-but-1-yn-1-yl]-phenyl}-2-(4-ethanesulfonyl-phenyl)-acetamide;
N-{4-[3-(4-Chloro-phenoxy)-3-methyl-but-1-yn-1-yl]-phenyl}-2-(4-ethanesulfonyl-phenyl)-acetamide;
N-{4-[3-(4-Chloro-2-fluoro-phenoxy)-3-methyl-but-1-yn-1-yl]-phenyl}-2-(4-ethanesulfonyl-phenyl)-acetamide;
N-{4-[3-(4-Chloro-3-fluoro-phenoxy)-3-methyl-but-1-yn-1-yl]-phenyl}-2-(4-ethanesulfonyl-phenyl)-acetamide;
N-{4-[3-(2-Chloro-4-fluoro-phenoxy)-3-methyl-but-1-yn-1-yl]-phenyl}-2-(4-ethanesulfonyl-phenyl)-acetamide;
N-{4-[3-(3-Chloro-4-fluoro-phenoxy)-3-methyl-but-1-yn-1-yl]-phenyl}-2-(4-ethanesulfonyl-phenyl)-acetamide;
N-{4-[3-(2,4-Difluoro-phenoxy)-3-methyl-but-1-yn-1-yl]-phenyl}-2-(4-ethanesulfonyl-phenyl)-acetamide;
N-{4-[3-(3,4-Difluoro-phenoxy)-3-methyl-but-1-yn-1-yl]-phenyl}-2-(4-ethanesulfonyl-phenyl)-acetamide;
2-(4-Ethanesulfonyl-phenyl)-N-{4-[3-methyl-3-(3,4,5-trifluoro-phenoxy)-but-1-yn-1-yl]-phenyl}-acetamide;
2-(4-Ethanesulfonyl-phenyl)-N-{4-[3-methyl-3-(2,3,4-trifluoro-phenoxy)-but-1-yn-1-yl]-phenyl}-acetamide;
2-(4-Ethanesulfonyl-phenyl)-N-{4-[3-methyl-3-(2,4,6-trifluoro-phenoxy)-but-1-yn-1-yl]-phenyl}-acetamide;
2-(4-Ethanesulfonyl-phenyl)-N-{4-[3-methyl-3-(2,4,5-trifluoro-phenoxy)-but-1-yn-1-yl]-phenyl}-acetamide;
N-{4-[3-(4-Chloro-2,6-difluoro-phenoxy)-3-methyl-but-1-yn-1-yl]-phenyl}-2-(4-ethanesulfonyl-phenyl)-acetamide;
2-(4-Ethanesulfonyl-phenyl)-N-{4-[3-methyl-3-(4-trifluoromethyl-phenoxy)-but-1-yn-1-yl]-phenyl}-acetamide;
2-(4-Ethanesulfonyl-phenyl)-N-{4-[3-methyl-3-(4-trifluoromethoxy-phenoxy)-but-1-yn-1-yl]-phenyl}-acetamide;
N-{4-[3-(4-Difluoromethoxy-phenoxy)-3-methyl-but-1-yn-1-yl]-phenyl}-2-(4-ethanesulfonyl-phenyl)-acetamide;
N-{4-[3-(4-Cyano-phenoxy)-3-methyl-but-1-yn-1-yl]-phenyl}-2-(4-ethanesulfonyl-phenyl)-acetamide;
N-{6-[3-(4-Chloro-2-fluoro-phenoxy)-3-methyl-but-1-yn-1-yl]-pyridin-3-yl}-2-(4-ethanesulfonyl-phenyl)-acetamide;
N-{4-[1-(3,5-Dichloro-pyridin-2-yl)-1-methyl-ethoxy]-3-fluoro-phenyl}-2-(4-ethanesulfonyl-phenyl)-acetamide;
N-{4-[1-(2,4-Dichloro-phenyl)-1-methyl-ethoxy]-3-fluoro-phenyl}-2-(4-ethanesulfonyl-phenyl)-acetamide;
N-{4-[1-(2-Chloro-4-fluoro-phenyl)-1-methyl-ethoxy]-3-fluoro-phenyl}-2-(4-ethanesulfonyl-phenyl)-acetamide;
N-{4-[1-(4-Chloro-2-fluoro-phenyl)-1-methyl-ethoxy]-3-fluoro-phenyl}-2-(4-ethanesulfonyl-phenyl)-acetamide;
N-{4-[1-(4-Chloro-2-fluoro-phenyl)-cyclopropoxy]-3-fluoro-phenyl}-2-(4-ethanesulfonyl-phenyl)-acetamide;
N-{4-[1-(4-Chloro-3-fluoro-phenyl)-cyclopropoxy]-3-fluoro-phenyl}-2-(4-ethanesulfonyl-phenyl)-acetamide;
N-{4-[3-(2,4-Dichloro-phenyl)-oxetan-3-yloxy]-3-fluoro-phenyl}-2-(4-ethanesulfonyl-phenyl)-acetamide;
N-{4-[3-(4-Chloro-3-fluoro-phenyl)-oxetan-3-yloxy]-3-fluoro-phenyl}-2-(4-ethanesulfonyl-phenyl)-acetamide;
N-{4-[4-(4-Chloro-3-fluoro-phenyl)-tetrahydro-pyran-4-yloxy]-3-fluoro-phenyl}-2-(4-ethanesulfonyl-phenyl)-acetamide;
N-{4-[2-(5-Chloro-indol-1-yl)-1,1-dimethyl-ethoxy]-3-fluoro-phenyl}-2-(4-ethanesulfonyl-phenyl)-acetamide;
N-{4-[1-(5-Chloro-1-ethyl-1H-benzoimidazol-2-yl)-1-methyl-ethoxy]-3-fluoro-phenyl}-2-(4-ethanesulfonyl-phenyl)-acetamide;
N-{4-[3-(4-Chloro-3-fluoro-phenoxy)-3-methyl-but-1-ynyl]-3-fluoro-phenyl}-2-(4-ethanesulfonyl-phenyl)-acetamide;
N-{4-[1-(2,4-Difluoro-phenyl)-1-methyl-ethoxy]-3-fluoro-phenyl}-2-(4-ethanesulfonyl-phenyl)-acetamide;
2-(4-Ethanesulfonyl-phenyl)-N-{3-fluoro-4-[2-(5-fluoro-2-methyl-indol-1-yl)-1,1-dimethyl-ethoxy]-phenyl}-acetamide;
N-{4-[1-(2,4-Dichloro-phenyl)-1-methyl-ethoxy]-3,5-difluoro-phenyl}-2-(4-ethanesulfonyl-phenyl)-acetamide;
N-{4-[1-(3,5-Dichloro-pyridin-2-yl)-1-methyl-ethoxy]-3,5-difluoro-phenyl}-2-(4-ethanesulfonyl-phenyl)-acetamide;
2-(4-Ethanesulfonyl-phenyl)-N-{4-[1-(1-ethyl-5-fluoro-1H-benzoimidazol-2-yl)-1-methyl-ethoxy]-3-fluoro-phenyl}-acetamide;
N-{4-[1-(4-Chloro-3-fluorophenyl)-cyclobutoxy]-3-fluoro-phenyl}-2-(4-ethanesulfonyl-phenyl)-acetamide;
N-{4-[1-(4-Chloro-3-fluorophenyl)-cyclopentyloxy]-phenyl}-2-(4-ethanesulfonyl-phenyl)-acetamide;
N-{4-[1-(4-Chloro-3-fluorophenyl)-cyclopentyloxy]-3-fluorophenyl}-2-(4-ethanesulfonyl-phenyl)-acetamide;
N-{4-[1-(4-Chloro-3-fluorophenyl)-cyclohexyloxy]-3-fluorophenyl}-2-(4-ethanesulfonyl-phenyl)-acetamide;
N-{4-[1-(2,4-Dichlorophenyl)-cyclopentyloxy]-phenyl}-2-(4-ethanesulfonyl-phenyl)-acetamide;
N-{4-[1-(4-Chloro-3-fluorophenyl)-cyclohexyloxy]-phenyl}-2-(4-ethanesulfonyl-phenyl)-acetamide;
N-(4-Chlorophenyl)-2-{4-[2-(4-ethanesulfonylphenyl)acetylamino]-phenoxy}-N-ethyl-2-methylpropionamide;
N-(4-Chlorophenyl)-2-{4-[2-(4-ethanesulfonylphenyl)acetylamino]-phenoxy}-2-N-dimethylpropionamide;
N-(2,4-Dichlorophenyl)-N-ethyl-2-(4-(2-(4-(ethylsulfonyl)phenyl)acetamido)phenoxy)-2-methylpropanamide;
N-(4-Chloro-3-fluorophenyl)-N-ethyl-2-(4-(2-(4-(ethylsulfonyl)phenyl)acetamido)phenoxy)-2-methylpropanamide;
N-(4-Chloro-3-fluorophenyl)-N-ethyl-2-(4-(2-(4-(ethylsulfonyl)phenyl)acetamido)-2-fluorophenoxy)-2-methylpropanamide;
2-(2,4-Difluorophenoxy)-N-ethyl-N-(4-(2-(4-(ethylsulfonyl)phenyl)acetamido)phenyl)-2-methylpropanamide;

N-(4-((1-(4-Chloro-3-fluorophenyl)cyclohexyl)oxy)phenyl)-2-(4-(ethylsulfonyl)phenyl)acetamide;
N-(4-((1-(2,4-Dichlorophenyl)cyclohexyl)oxy)phenyl)-2-(4-(ethylsulfonyl)phenyl)acetamide;
N-(4-((1-(2,4-Dichlorophenyl)cyclohexyl)oxy)-3-fluorophenyl)-2-(4-(ethylsulfonyl)phenyl)acetamide;
N-(4-((4-(2,4-Dichlorophenyl)tetrahydro-2H-pyran-4-yl)oxy)-3-fluorophenyl)-2-(4-(ethylsulfonyl)phenyl)acetamide;
N-(4-((1-(2,4-Dichlorophenyl)cyclopentyl)oxy)-3-fluorophenyl)-2-(4-(ethylsulfonyl)phenyl)acetamide;
N-(4-((1-(2,4-Dichlorophenyl)cyclopropyl)oxy)-3-fluorophenyl)-2-(4-(ethylsulfonyl)phenyl)acetamide;
N-(4-((1-(2,4-Dichlorophenyl)cyclobutyl)oxy)-3-fluorophenyl)-2-(4-(ethylsulfonyl)phenyl)acetamide;
N-(4-((1-(2,4-Difluorophenyl)cyclohexyl)oxy)-3-fluorophenyl)-2-(4-(ethylsulfonyl)phenyl)acetamide;
N-(4-(1-(2,4-Difluorophenyl)cyclobutoxy)-3-fluorophenyl)-2-(4-(ethylsulfonyl)phenyl)acetamide;
N-(4-((3-(2,4-Difluorophenyl)oxetan-3-yl)oxy)-3-fluorophenyl)-2-(4-(ethylsulfonyl)phenyl)acetamide;
N-(4-((1-(2,4-Difluorophenyl)cyclopentyl)oxy)-3-fluorophenyl)-2-(4-(ethylsulfonyl)phenyl)acetamide;
and pharmaceutically acceptable salt thereof.

21. The compound according to claim 1, having the formula

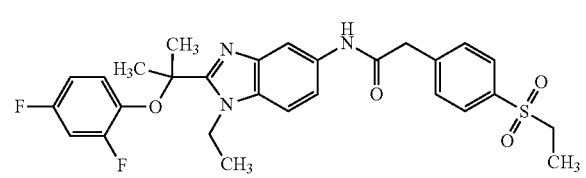 [SMILES: CCn1c(C(C)(C)Oc2ccc(F)cc2F)nc2cc(NC(=O)Cc3ccc(S(=O)(=O)CC)cc3)ccc21]

or a pharmaceutically acceptable salt thereof.

22. The compound according to claim 1, having the formula

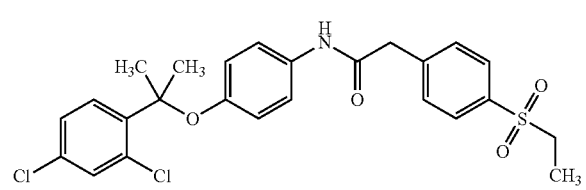

or a pharmaceutically acceptable salt thereof.

23. The compound according to claim 1, having the formula

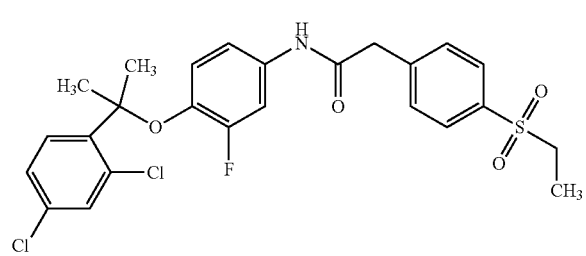 [SMILES: CCS(=O)(=O)c1ccc(CC(=O)Nc2ccc(OC(C)(C)c3ccc(Cl)cc3Cl)c(F)c2)cc1]

or a pharmaceutically acceptable salt thereof.

24. The compound according to claim 1, having the formula

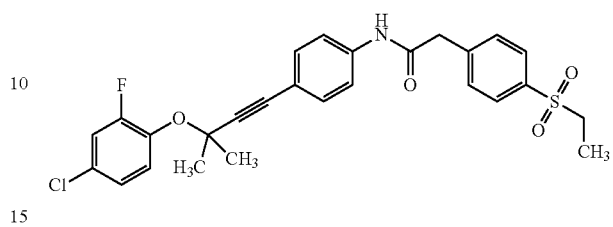

or a pharmaceutically acceptable salt thereof.

25. The compound according to claim 1, having the formula

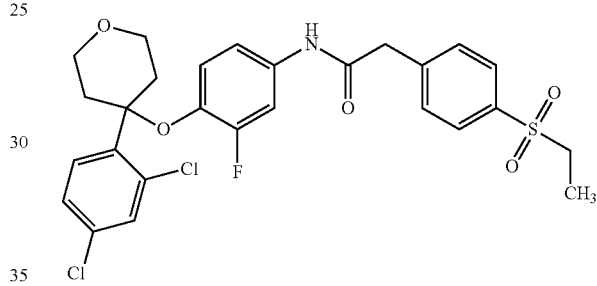

or a pharmaceutically acceptable salt thereof.

26. The compound according to claim 1, having the formula

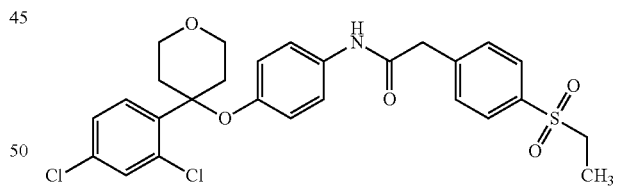

or a pharmaceutically acceptable salt thereof.

27. A pharmaceutical composition comprising a compound according to claim 1 and a pharmaceutically acceptable excipient.

28. The pharmaceutical composition according to claim 27, wherein the pharmaceutically acceptable excipient is a carrier or diluent.

* * * * *